United States Patent
Lanier et al.

(10) Patent No.: US 11,970,452 B2
(45) Date of Patent: Apr. 30, 2024

(54) MODULATORS OF MAS-RELATED G-PROTEIN RECEPTOR X2 AND RELATED PRODUCTS AND METHODS

(71) Applicant: Escient Pharmaceuticals, Inc., San Diego, CA (US)

(72) Inventors: Marion Lanier, San Diego, CA (US); Marcus Boehm, San Diego, CA (US); Liming Huang, San Diego, CA (US); Esther Martinborough, San Diego, CA (US); Marcos Sainz, San Diego, CA (US); Brandon Selfridge, San Diego, CA (US); Adam Yeager, San Diego, CA (US)

(73) Assignee: Escient Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 17/506,447

(22) Filed: Oct. 20, 2021

(65) Prior Publication Data
US 2022/0177434 A1   Jun. 9, 2022

Related U.S. Application Data

(60) Provisional application No. 63/094,864, filed on Oct. 21, 2020.

(51) Int. Cl.
| | |
|---|---|
| *C07D 215/44* | (2006.01) |
| *C07D 239/94* | (2006.01) |
| *C07D 401/12* | (2006.01) |
| *C07D 401/14* | (2006.01) |
| *C07D 405/12* | (2006.01) |
| *C07D 409/12* | (2006.01) |
| *C07D 413/14* | (2006.01) |
| *C07D 417/12* | (2006.01) |
| *C07D 471/04* | (2006.01) |
| *C07D 487/04* | (2006.01) |

(52) U.S. Cl.
CPC ......... *C07D 215/44* (2013.01); *C07D 239/94* (2013.01); *C07D 401/12* (2013.01); *C07D 401/14* (2013.01); *C07D 405/12* (2013.01); *C07D 409/12* (2013.01); *C07D 413/14* (2013.01); *C07D 417/12* (2013.01); *C07D 471/04* (2013.01); *C07D 487/04* (2013.01)

(58) Field of Classification Search
CPC .. C07D 215/44; C07D 405/12; C07D 471/04; C07D 239/94; C07D 401/12; C07D 401/14; C07D 409/12; C07D 413/14; C07D 417/12; C07D 487/04
See application file for complete search history.

(56) References Cited

U.S. PATENT DOCUMENTS

| | | | | |
|---|---|---|---|---|
| 6,818,772 B2 * | 11/2004 | Kym | ............ | C07D 215/46 546/160 |
| 2023/0065217 A1 * | 3/2023 | Lanier | ............ | C07D 401/12 |

FOREIGN PATENT DOCUMENTS

| | | | | |
|---|---|---|---|---|
| WO | 03/070244 A1 | 8/2003 | | |
| WO | WO-03070244 A1 * | 8/2003 | ........... | C07D 215/46 |
| WO | 2016/053769 A1 | 4/2016 | | |

OTHER PUBLICATIONS

International Immunopharmacology 70 (2019) 417-427 (Year: 2019).*
Iwaki et al., "Discovery and SAR of a novel series of Natriuretic Peptide Receptor-A (NPR-A) agonists", Bioorganic & Medicinal Chemistry Letters, 27, 2017, pp. 4904-4907.

* cited by examiner

*Primary Examiner* — D Margaret M Seaman
(74) *Attorney, Agent, or Firm* — Seed IP Law Group LLP

(57) ABSTRACT

Methods are provided for modulating MRGPRX2 or a MRGPRX2 ortholog generally, or for treating a MRGPRX2 or a MRGPRX2 ortholog dependent condition more specifically, by contacting the MRGPRX2 or the MRGPRX2 ortholog by administering to a subject in need thereof, respectively, an effective amount of a compound having structure (I):

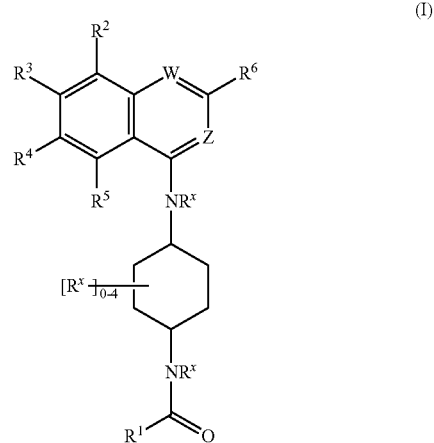

or a pharmaceutically acceptable salt, isomer, hydrate, solvate or isotope thereof, wherein W, Z, $R^1$, $R^2$, $R^3$, $R^4$, $R^5$, $R^6$ and $R^x$ are as defined herein. Pharmaceutical compositions containing such compounds, as well as the compounds themselves, are also provided.

4 Claims, No Drawings

MODULATORS OF MAS-RELATED G-PROTEIN RECEPTOR X2 AND RELATED PRODUCTS AND METHODS

BACKGROUND

Technical Field

The invention relates to modulators of the Mas-related G-protein coupled receptor X2, to products containing the same, as well as to methods of their use and preparation.

Description of the Related Art

Mas-related G-protein receptors (MRGPRs) are a group of orphan receptors with limited expression in very specialized tissues. Very little is known about the function of most of these receptors. There are eight related receptors in this class expressed in humans, only four of which have readily identifiable orthologs in other species (i.e., MRGPR D, E, F and G). Some of the other four receptors (MRGPR X1, X2, X3 and X4) have counterparts in higher species including dogs and horses, but they do not have a single corresponding ortholog in rodents.

BRIEF SUMMARY

This invention is based, in part, on the identification of MRGPRX2 or MRGPRX2 ortholog modulator compounds. MRGPRX2 corresponds functionally to mouse mrgprb2 and dog MRGPRX2 in mast cells. MRGPRX2 and its ortholog receptors mediate disorders including pseudo-allergic reactions including pseudo-allergic drug reactions, chronic itch (e.g., pruritus), inflammation disorders, pain disorders, skin disorders, wound healing, cardiovascular disease, and lung inflammation/COPD. In one embodiment, both mrgprb2 and MRGPRX2 expression is largely restricted to mast cells. Mast cells are innate immune cells that primarily reside at sites exposed to the external environment, such as the skin, oral/gastrointestinal mucosa and respiratory tract. Mast cells express numerous receptors that respond to mechanical and chemical stimuli. Upon activation, classically by IgE, mast cells release pre-formed mediators from granules (e.g., histamine, proteases, and heparin) and newly synthesized mediators (e.g., thromboxane, prostaglandin D2, leukotriene C4, tumor necrosis factor alpha, eosinol chemotactor factor, and platelet-activating factor) that elicit allergic and inflammatory responses. Histamine dilates post-capillary venules, activates the endothelium, and increases blood vessel permeability. This causes local edema, warmth, redness, and chemotaxis of other inflammatory cells to the site of release. Histamine also contributes to neuronal sensitization that leads to pain or itch. MRGPRX2 and mrgprb2 mediate immunoglobulin E (IgE) independent activation of mast cells. MRGPRX2 and mrgprb2 are receptors for (or sensitive to activation by) various ligands, including basic secretagogues (small cationic molecules), certain drugs (e.g., cationic peptidergic drugs), neuropeptides, and antimicrobial peptides, and thus are important for non-IgE mediated pseudo-allergic reactions, inflammation, pain, and itch conditions. Mast cells may also contribute to the progression of autoimmune disorders by promoting chronic inflammation in the local tissue microenvironment and ultimately polarizing toward a $T_H17$ immune response. Thus, modulating MRGPRX2 or MRGPRX2 ortholog allows for treatment of autoimmune diseases, pseudo-allergic drug reactions, pain, itch, and inflammatory disorders such as inflammatory bowel disease, urticaria, sinusitis, asthma, rosacea, endometriosis, and other MRGPRX2 or MRGPRX2 ortholog dependent conditions as explained in more detail below.

In one embodiment is provided, a method of treating a MRGPRX2 or a MRGPRX2 ortholog dependent condition by administering to a subject in need thereof an effective amount of the pharmaceutical composition of the modulator compounds of the present invention.

Accordingly, in an embodiment, methods are provided for modulating a MRGPRX2 by contacting the MRGPRX2 with an effective amount of a compound having structure (I):

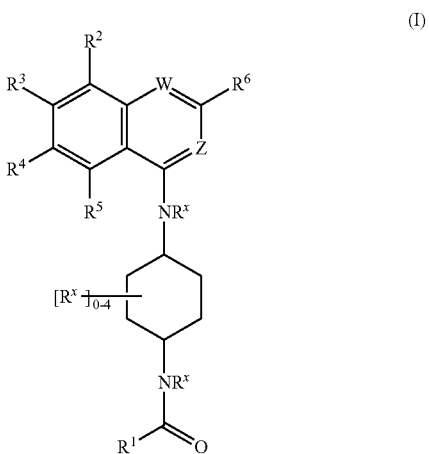

or a pharmaceutically acceptable salt, isomer, hydrate, solvate or isotope thereof, wherein W, Z, $R^1$, $R^2$, $R^3$, $R^4$, $R^5$, $R^6$ and $R^x$ are as defined herein.

In another embodiment, methods are provided for treating an MRGPRX2 or MRGPRX2 ortholog dependent condition by administering to a subject in need thereof an effective amount of a compound having structure (I) or a pharmaceutically acceptable salt, isomer, hydrate, solvate or isotope thereof.

In one embodiment, the methods of treating the MRGPRX2 or MRGPRX2 ortholog dependent condition are provided which comprise administering an effective amount of a compound of structure (I) with formula (1A), (1B) or (1C) as defined herein, or a pharmaceutically acceptable salt, isomer, hydrate, solvate or isotope thereof.

In yet other embodiments, pharmaceutical compositions are provided comprising a carrier or excipient and a compound having formula (1A), (1B) or (1C) or a pharmaceutically acceptable salt, isomer, hydrate, solvate or isotope thereof.

In another embodiment, compounds are provided having formula (1A), (1B) or (1C) as defined herein, or a pharmaceutically acceptable salt, isomer, hydrate, solvate or isotope thereof.

In another embodiment, compounds are provided having one or more of the structures disclosed herein, or a pharmaceutically acceptable salt, isomer, hydrate, solvate or isotope thereof.

DETAILED DESCRIPTION

As mentioned above, the invention relates to modulators of the MRGPRX2, to products containing the same, as well as to methods of their use and preparation. This invention is based, in part, on the identification MRGPRX2 modulator compounds. Both mrgprb2 and MRGPRX2 are expressed in mast cells and dorsal root ganglia. Both MRGPRX2 and mrgprb2 are receptors for (or sensitive to activation by) a diverse group of ligands, including basic secretagogues, certain drugs, neuropeptides, antimicrobial peptides, and thus are important for pseudo-allergic reactions, itch, pain, or inflammatory disorders upon exposure.

MRGPRs appear to be sensory receptors that recognize their external environment to exogenous or endogenous signals/chemicals. These receptors likely respond to multiple chemical ligands/agonists. For example, MRGPRX2 recognizes Compound 48/80, Substance P, mastoparan, icatibant, ciprofloxacin, and tracurium, as agonist signals. In certain embodiments, molecules of this invention modulate MRGPRX2 by functioning as inverse agonists that are capable of blocking multiple chemical entities, and/or as competitive antagonists that can specifically block individual ligands. In one embodiment, such modulations are selective against other MRGPRs, such as MRGPRX1, X3 and/or X4.

Definitions

As used herein, the following terms have the meaning defined below, unless the context indicates otherwise.

"Modulating" MRGPRX2 means that the compound interacts with the MRGPRX2 in a manner such that it functions as an inverse agonist to the receptor, and/or as a competitive antagonist to the receptor. In one embodiment, such modulation is partially or fully selective against other MRGPRs, such as MRGPRX1, X3 and/or X4.

"MRGPR" refers to one or more of the Mas-related G protein coupled receptors, which are a group of orphan receptors with limited expression in very specialized tissues (e.g., in mast cells and dorsal root ganglia) and barrier tissues. There are eight related receptors in this class expressed in humans, only 4 of which have readily identifiable orthologs in other species (i.e., MRGPRD, E, F and G). Some of the other four receptors (MRGPRX1, X2, X3 and X4) have counterparts in higher species including dogs and horses, but they do not have a single corresponding ortholog in rodents.

"MRGPRX2," also referred to as "MRGX2," or "MGRG3," refers to a member of the MRGPR family that is expressed on mast cells and capable of mediating IgE independent activation (e.g., mast cell degranulation) in response to ligand binding. An exemplary human MRGPRX2 amino acid sequence is set forth in Uniprot Q96LB1.

MRGPRX2 ortholog refers to genes in non-human species including dogs and horses that have evolved through speciation events.

"Effective amount" refers to a quantity of a specified agent sufficient to achieve a desired effect in a subject being treated with that agent. Ideally, an effective amount of an agent is an amount sufficient to inhibit or treat the disease without causing substantial toxicity in the subject. The effective amount of an agent will be dependent on the subject being treated, the severity of the affliction, and the manner of administration of the pharmaceutical composition. Methods of determining an effective amount of the disclosed compound sufficient to achieve a desired effect in a subject will be understood by those of skill in the art in light of this disclosure.

"Alkyl" means a saturated or unsaturated straight chain or branched alkyl group having from 1 to 8 carbon atoms, in some embodiments from 1 to 6 carbon atoms, in some embodiments from 1 to 4 carbon atoms, and in some embodiments from 1 to 3 carbon atoms. Examples of saturated straight chain alkyl groups include, but are not limited to, methyl, ethyl, n-propyl, n-butyl, n-pentyl-, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. An unsaturated alkyl includes alkenyl and alkynyl as defined below.

"Alkenyl" means a straight chain or branched alkenyl group having from 2 to 8 carbon atoms, in some embodiments from 2 to 6 carbon atoms, in some embodiments from 2 to 4 carbon atoms, and in some embodiments from 2 to 3 carbon atoms. Alkenyl groups are unsaturated hydrocarbons that contain at least one carbon-carbon double bond. Examples of lower alkenyl groups include, but are not limited to, vinyl, propenyl, butenyl, pentenyl, and hexenyl.

"Alkynyl" means a straight chain or branched alkynyl group having from 2 to 8 carbon atoms, in some embodiments from 2 to 6 carbon atoms, in some embodiments from 2 to 4 carbon atoms, and in some embodiments from 2 to 3 carbon atoms. Alkynyl groups are unsaturated hydrocarbons that contain at least one carbon-carbon triple bond. Examples of alkynyl groups include, but are not limited to, ethynyl, propynyl, butynyl, pentynyl, and hexynyl.

"Halo" or "halogen" refers to fluorine, chlorine, bromine, and iodine.

"Hydroxy" refers to —OH.

"Cyano" refers to —CN.

Amino refers to —NH$_2$, —NHalkyl or N(alkyl)$_2$, wherein alkyl is as defined above. Examples of amino include, but are not limited to —NH$_2$, —NHCH$_3$, —N(CH$_3$)$_2$, and the like.

"Haloalkyl" refers to alkyl as defined above with one or more hydrogen atoms replaced with halogen. Examples of lower haloalkyl groups include, but are not limited to, —CF$_3$, —CHF$_2$, and the like.

"Alkoxy" refers to alkyl as defined above joined by way of an oxygen atom (i.e., —O-alkyl). Examples of alkoxy groups include, but are not limited to, methoxy, ethoxy, n-propoxy, n-butoxy, isopropoxy, sec-butoxy, tert-butoxy, and the like.

"Haloalkoxy" refers to haloalkyl as defined above joined by way of an oxygen atom (i.e., —O-haloalkyl). Examples of lower haloalkoxy groups include, but are not limited to, —OCF$_3$, and the like.

"Cycloalkyl" refers to alkyl groups forming a ring structure, which can be substituted or unsubstituted, wherein the ring is either completely saturated, partially unsaturated, or fully unsaturated, wherein if there is unsaturation, the conjugation of the pi-electrons in the ring do not give rise to aromaticity. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

"Aryl" groups are cyclic aromatic hydrocarbons that do not contain heteroatoms. Representative aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The terms "aryl" and "aryl groups" include fused rings wherein at least one ring, but not necessarily all rings, are aromatic, such as fused aromatic-aliphatic ring systems (e.g., indanyl, tetrahydronaphthyl, and the like). In one embodiment, aryl is phenyl or naphthyl, and in another embodiment aryl is phenyl.

"Carbocycle" refers to alkyl groups forming a ring structure, which can be substituted or unsubstituted, wherein the ring is either completely saturated, partially unsaturated, or fully unsaturated, wherein if there is unsaturation, the conjugation of the pi-electrons in the ring may give rise to aromaticity. In one embodiment, carbocycle includes cycloalkyl as defined above. In another embodiment, carbocycle includes aryl as defined above.

"Heterocycle" refers to aromatic and non-aromatic ring moieties containing 3 or more ring members, of which one or more is a heteroatom such as, but not limited to, N, O, S, or P. In some embodiments, heterocyclyl include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein.

Heterocyclyl groups also include fused ring species including those having fused aromatic and non-aromatic groups. A heterocyclyl group also includes polycyclic ring systems containing a heteroatom such as, but not limited to, quinuclidyl, and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups.

In one embodiment, heterocyclyl includes heteroaryl.

"Heteroaryl" refers to aromatic ring moieties containing 5 or more ring members, of which, one or more is a heteroatom such as, but not limited to, N, O, and S. Heteroaryl groups include, but are not limited to, groups such as pyrrolyl, pyrazolyl, pyridinyl, pyridazinyl, pyrimidyl, pyrazyl, pyrazinyl, pyrimidinyl, thienyl, triazolyl, tetrazolyl, triazinyl, thiazolyl, thiophenyl, oxazolyl, isoxazolyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl, and 2,3-dihydro indolyl.

"Isomer" is used herein to encompass all chiral, diastereomeric or racemic forms of a structure (also referred to as a stereoisomer, as opposed to a structural or positional isomer), unless a particular stereochemistry or isomeric form is specifically indicated. Such compounds can be enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention. The isomers resulting from the presence of a chiral center comprise a pair of nonsuperimposable-isomers that are called "enantiomers." Single enantiomers of a pure compound are optically active (i.e., they are capable of rotating the plane of plane polarized light and designated R or S).

"Isolated optical isomer" means a compound which has been substantially purified from the corresponding optical isomer(s) of the same formula. For example, the isolated isomer may be at least about 80%, at least 80% or at least 85% pure by weight. In other embodiments, the isolated isomer is at least 90% pure or at least 98% pure, or at least 99% pure by weight.

"Substantially enantiomerically or diastereomerically" pure means a level of enantiomeric or diastereomeric enrichment of one enantiomer with respect to the other enantiomer or diastereomer of at least about 80%, and more specifically in excess of 80%, 85%, 90%, 95%, 98%, 99%, 99.5% or 99.9%.

The terms "racemate" and "racemic mixture" refer to an equal mixture of two enantiomers. A racemate is labeled "(±)" because it is not optically active (i.e., will not rotate plane-polarized light in either direction since its constituent enantiomers cancel each other out). All compounds with an asterisk (*) adjacent to a tertiary or quaternary carbon are optically active isomers, which may be purified from the respective racemate and/or synthesized by appropriate chiral synthesis.

A "hydrate" is a compound that exists in combination with water molecules. The combination can include water in stoichiometric quantities, such as a monohydrate or a dihydrate, or can include water in random amounts. As the term is used herein a "hydrate" refers to a solid form; that is, a compound in a water solution, while it may be hydrated, is not a hydrate as the term is used herein.

A "solvate" is similar to a hydrate except that a solvent other that water is present. For example, methanol or ethanol can form an "alcoholate", which can again be stoichiometric or non-stoichiometric. As the term is used herein a "solvate" refers to a solid form; that is, a compound in a solvent solution, while it may be solvated, is not a solvate as the term is used herein.

"Isotope" refers to atoms with the same number of protons but a different number of neutrons, and an isotope of a compound of structure (I) includes any such compound wherein one or more atoms are replaced by an isotope of that atom. For example, carbon 12, the most common form of carbon, has six protons and six neutrons, whereas carbon 13 has six protons and seven neutrons, and carbon 14 has six protons and eight neutrons. Hydrogen has two stable isotopes, deuterium (one proton and one neutron) and tritium (one proton and two neutrons). While fluorine has a number of isotopes, fluorine-19 is longest-lived. Thus, an isotope of a compound having the structure of structure (I) includes, but not limited to, compounds of structure (I) wherein one or more carbon 12 atoms are replaced by carbon-13 and/or carbon-14 atoms, wherein one or more hydrogen atoms are replaced with deuterium and/or tritium, and/or wherein one or more fluorine atoms are replaced by fluorine-19.

"Salt" generally refers to an organic compound, such as a carboxylic acid or an amine, in ionic form, in combination with a counter ion. For example, salts formed between acids in their anionic form and cations are referred to as "acid addition salts". Conversely, salts formed between bases in the cationic form and anions are referred to as "base addition salts."

The term "pharmaceutically acceptable" refers an agent that has been approved for human consumption and is generally non-toxic. For example, the term "pharmaceutically acceptable salt" refers to nontoxic inorganic or organic acid and/or base addition salts (see, e.g., Lit et al., Salt Selection for Basic Drugs, Int. J. Pharm., 33, 201-217, 1986) (incorporated by reference herein).

Pharmaceutically acceptable base addition salts of compounds of the invention include, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N'dibenzylethylenediamine, chloroprocaine, choline, diethanolamine, ethylenediamine, meglumine (N-methylglucamine), and procaine.

Pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aromatic aliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, hippuric, malonic, oxalic, embonic (pamoic), methanesulfonic, ethanesulfonic, benzenesulfonic, panthothenic, trifluoromethanesulfonic, 2-hydroxyethanesulfonic, p-toluenesulfonic, sulfanilic, cyclohexylaminosulfonic, stearic, alginic, βhydroxybutyric, salicylic, -galactaric, and galacturonic acid.

The compounds of the disclosure (i.e., compounds of structure (I) and embodiments thereof), or their pharmaceutically acceptable salts may contain one or more centers of geometric asymmetry and may thus give rise to enantiomers, diastereomers, and other stereoisomeric forms that are defined, in terms of absolute stereochemistry, as (R)- or (S)- or, as (D)- or (L)- for amino acids. Embodiments thus include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also included.

Although pharmaceutically unacceptable salts are not generally useful as medicaments, such salts may be useful, for example as intermediates in the synthesis of compounds having the structure of Formula I, for example in their purification by recrystallization.

As used herein, the phrase "MRGPRX2 or MRGPRX2 ortholog dependent condition" means a condition where the activation, over sensitization, or desensitization of MRGPRX2 or its ortholog by a natural or synthetic ligand initiates, mediates, sustains, or augments a pathological condition. For example, it is known that some cationic peptidergic drugs cause pseudo-allergic reactions in patients. MRGPRX2 is sensitive to (or activated by) secretagogues, cationic peptidergic drugs, including icatibant, leuprolide, or ganirelix, neutral and anionic peptidergic drugs (e.g., exenatide, glucagon, liraglutide, enfuviritide, colistimethate), non-steroidal agonist (atracurium mivacurium), non-steroidal antagonist drugs, neuropeptides, and antimicrobial peptides. Moreover, overexpression of MRGPRX2 and/or overactivity MRGPRX2 may also render mast cells more susceptible to activation by endogenous and/or exogenous ligands. Without limited by theory, it is to be understood that by modulating MRGPRX2, pseudo-allergic reactions, itch, pain, inflammatory or autoimmune disorders can be eased.

In some embodiments, the MRGPRX2 dependent condition is a condition that is caused by IgE independent activation of MRGPRX2. IgE independent activation of MRGPRX2 is capable of inducing mast cell degranulation. For example, IgE independent mast cell activation associated with some cases of chronic urticaria and other mast cell mediated conditions, which are not responsive to current anti-IgE or antihistamine therapies. Thus, the compounds of the present disclosure may be used for treating an MRGPRX2 dependent condition caused by IgE independent activation of MRGPRX2 and that would benefit from modulating MRGPRX2.

In some embodiments, the MRGPRX2 dependent condition is an itch associated condition, a pain associated condition, a pseudo-allergic reaction, or an autoimmune or inflammatory disorder.

As used herein the phrase "pseudo-allergic reaction" refers to an IgE-independent allergic reaction, characterized by histamine release, inflammation, airway contraction, or any combination thereof. A pseudo-allergic reaction may be an analphylactic reaction. A pseudo-allergic reaction may be caused by a range of cationic substances, collectively called basic secretagogues, including inflammatory peptides and drugs associated with allergic-type reactions. Thus, in one embodiment, the method of present invention is provided to treat a pseudo-allergic reaction, such as pseudo-allergic reactions caused by secretagogues, cationic peptidergic drugs, anionic peptidergic drugs, neutral peptidergic drugs, non-steroidal antagonist drugs, neuropeptides, and antimicrobial peptides. In one embodiment, the pseudo-allergic reaction is caused by MCD peptide, Substance P, VIP, PACAP, dynorphin, somatostatin, Compound 48/80, cortistatin-14, mastoparan, melettin, cathelicidin peptides, ciprofloxacin, vancomycin, leuprolide, goserelin, histrelin, triptorelin, cetrorelix, ganirelix, degarelix, octreotide, lanreotide, pasireotide, sermorelin, tesamorelin, icatibant, glatiramer acetate, teriparatide, pramlintide, bleomycin, exenatide, glucagon, liraglutide, enfuvirtide, colistimethate, succinylcholine, tubocurarine, atracurium, mivacurium, and rocuronium.

As used herein, the phrase "itch associated condition" means pruritus (including acute and chronic pruritus) associated with any condition. The itch sensation can originate, e.g., from the peripheral nervous system (e.g., dermal or neuropathic itch) or from the central nervous system (e.g., neuropathic, neurogenic or psychogenic itch). Thus, in one embodiment, the method of present invention is provided to treat an itch associated condition, such as chronic itch; contact dermatitis; Allergic blepharitis; Anaphylaxis; Anaphylactoid drug reactions; Anaphylactic shock; Anemia; Atopic dermatitis; Bullous pemphigoid; Candidiasis; Chicken pox; end-stage renal failure; hemodialysis; Cholestatic pruritis; Chronic urticaria; Contact dermatitis, Atopic Dermatitis; Dermatitis herpetiformis; Diabetes; Drug allergy, Dry skin; Dyshidrotic dermatitis; Ectopic eczema; Eosinophilic fasciitis; Epidermolysis bullosa; Erythrasma; Food allergy; Folliculitis; Fungal skin infection; Hemorrhoids; Herpes; HIV infection; Hodgkin's disease; Hyperthyroidism; Iodinated contrast dye allergy; Iron deficiency anemia; Kidney disease; Leukemia, Porphyrias; Lymphoma; Mast cell activation syndrome; Malignancy; Mastocystosis; Multiple myeloma; Neurodermatitis; Onchocerciasis; Paget's disease; Pediculosis; Polycythemia rubra vera; Prurigo nodularis; Lichen Planus; Lichen Sclerosis; Pruritus ani; Pseudo-allergic reactions; Pseudorabies; Psoriasis; Rectal prolapse; Sarcoidosis granulomas; Scabies; Schistosomiasis; Scleroderma, Severe stress, Stasia dermatitis; Swimmer's itch; Thyroid disease; Tinea cruris; Uremic Pruritus; Rosacea; Cutaneous amyloidosis; Scleroderma; Acne; wound healing; burn healing; ocular itch; and Urticaria.

As used herein, the phrase "pain associated condition" means any pain due to a medical condition. Thus, in one embodiment, the method of present invention is provided to treat a pain associated condition, such as Acute Pain, Advanced Prostate Cancer, AIDS-Related Pain, Ankylosing Spondylitis, Arachnoiditis, Arthritis, Arthrofibrosis, Ataxic Cerebral Palsy, Autoimmune Atrophic Gastritis, Avascular Necrosis, Back Pain, Behcet's Disease (Syndrome), Burning Mouth Syndrome, Bursitis, Cancer Pain, Carpal Tunnel, Cauda Equina Syndrome, Central Pain Syndrome, Cerebral Palsy, Cervical Stenosis, Charcot-Marie-Tooth (CMT) Disease, Chronic Fatigue Syndrome (CFS), Chronic Functional Abdominal Pain (CFAP), Chronic Pain, Chronic Pancreatitis, Chronic Pelvic Pain Syndrome, Collapsed Lung (Pneumothorax), Complex Regional Pain Syndrome (RSD), Corneal Neuropathic Pain, Crohn's Disease, Degenerative Disc Disease, Dental Pain, Dercum's Disease, Dermatomyositis, Diabetic Peripheral Neuropathy (DPN), Dystonia, Ehlers-Danlos Syndrome (EDS), Endometriosis, Eosinophilia-Myalgia Syndrome (EMS), Erythromelalgia, Fibromyalgia, Gout, Headaches, Herniated disc, Hydrocephalus, Intercostal Neuraligia, Interstitial Cystitis, Irritable Bowel syndrome (IBS), Juvenile Dermatositis (Dermatomyositis), Knee Injury, Leg Pain, Loin Pain-Haematuria Syndrome, Lupus, Lyme Disease, Medullary Sponge Kidney (MSK), Meralgia Paresthetica, Mesothelioma, Migraine, Musculoskeletal pain, Myofascial Pain, Myositis, Neck Pain, Neuropathic Pain, Occipital Neuralgia, Osteoarthritis, Paget's Disease, Parsonage Turner Syndrome, Pelvic Pain, Periodontitis Pain, Peripheral Neuropathy, Phantom Limb Pain, Pinched Nerve, Polycystic Kidney Disease, Polymyalgia Rhuematica, Polymyositis, Porphyria, Post Herniorraphy Pain Syndrome, Post Mastectomy, Postoperative Pain, Pain Syndrome, Post Stroke Pain, Post Thorocotomy Pain Syndrome, Postherpetic Neuralgia (Shingles), Post-Polio Syndrome, Primary Lateral Sclerosis, Psoriatic Arthritis, Pudendal Neuralgia, Radiculopathy, Raynaud's Disease, Rheumatoid Arthritis (RA), Sacroiliac Joint Dysfunction, Sarcoidosi, Scheuemann's Kyphosis Disease, Sciatica, Scoliosis, Shingles (Herpes Zoster), Sjogren's Syndrome, Spasmodic Torticollis, Sphincter of Oddi Dysfunction, Spinal Cerebellum Ataxia (SCA Ataxia), Spinal Cord Injury, Spinal Stenosis, Syringomyelia, Tarlov Cysts, Transverse Myelitis, Trigeminal Neuralgia, Neuropathic Pain, Ulcerative Colitis, Vascular Pain and Vulvodynia.

As used herein, the term "autoimmune disorder", or "inflammatory disorder" means a disease or disorder arising from and/or directed against an individual's own tissues or organs, or a co-segregate or manifestation thereof, or resulting condition therefrom. Typically, various clinical and laboratory markers of autoimmune diseases may exist including, but not limited to, hypergammaglobulinemia, high levels of autoantibodies, antigen-antibody complex deposits in tissues, clinical benefit from corticosteroid or immunosuppressive treatments, and lymphoid cell aggregates in affected tissues. Thus, in one embodiment, the method of present invention is provided to treat an autoimmune disorder, such as chronic inflammation, mast cell activation syndrome, Multiple Sclerosis, Steven Johnson's Syndrome, Toxic Epidermal Necrolysis, appendicitis, bursitis, cutaneous lupus, colitis, cystitis, dermatitis, phlebitis, reflex sympathetic dystrophy/complex regional pain syndrome (rsd/crps), rhinitis, tendonitis, tonsillitis, acne vulgaris, sinusitis, rosacea, psoriasis, graft-versus-host disease, reactive airway disorder, asthma, airway infection, allergic rhinitis, autoinflammatory disease, celiac disease, chronic prostatitis, diverticulitis, glomerulonephritis, hidradenitis suppurativa, hypersensitivities, intestinal disorder, epithelial intestinal disorder, inflammatory bowel disease, irritable bowel syndrome, Crohn's Disease, ulcerative colitis, lupus erythematous, interstitial cystitis, otitis, pelvic inflammatory disease, endometrial pain, reperfusion injury, rheumatic fever, rheumatoid arthritis, sarcoidosis, transplant rejection, psoriasis, lung inflammation, chronic obstructive pulmonary disease, permanent sputum eosiniophilia, eosinophilic leukemia, eosinophilic esophagitis, eosinophilic gastritis, mast cell gastrointestinal disease, hypereosinophilic syndrome, aspirin-exacerbated respiratory disease, nasal polyposis, chronic rhinosinusitis, antibody-dependent cell-mediated cytotoxicity, neurofibromatosis, swannamatoisis, tubulointerstitial nephritis, glomerulonephritis, diabetic nephropathy, allograft rejection, amyloidosis, renovascular ischemia, reflux nephropathy, polycystic kidney disease, liver fibrosis/cirrhosis, autoimmune liver disease, Biliary atresia, acute and chronic Hepatitis B and C virus, Liver tumors and cancer, Alcoholic liver disease, Polycystic liver disease, Liver cholangiocarcinoma, neuromyelitis optica spectum disorder, cardiovascular disease, and vasculitis.

As used herein the phrase "cancer associated condition" means any disease arising from the proliferation of malignant cancerous cells. Thus, in one embodiment, the method of present invention is provided to treat a cancer/tumor associated condition, such as adenoid cystic carcinoma, adrenal gland tumor, amyloidosis, anal cancer, appendix cancer, astrocytoma, ataxia-telangiectasia, beckwith-wiedemann syndrome, cholangiocarcinoma, birt-hogg-dube syndrome, bone cancer, brain stem glioma, brain tumor, breast cancer (inflammatory, metastatic, male), prostrate, basal cell, melanoma, colon, colorectal, bladder, kidney cancer, lacrimal gland cancer, laryngeal and hypopharyngeal cancer, lung cancer (non-small cell, small cell), leukemia (acute lymphoblastic, acute lymphocytic, acute myeloid, B cell prolymphocytic, chronic lymphocytic, chronic myeloid, chronic T cell lymphocytic, eosinophilic), Liver Cancer, Li-Fraumei syndrome, lymphoma (Hodgkin and non-hodgkin), lynch syndrome, mastocytosis, medulloblastoma, meningioma, mesothelioma, multiple endocrine neoplasia, multiple myeloma, MUTYH-associated polyposis, myelodyspastic syndrome, nasal cavity and paranasal sinus cancer, neurobastoma, neuroendocrine tyymors, neurofibromatosis, penile cancer, parathyroid cancer, ovarian fallopian tube and peritoneal cancer, osteosarcoma, pituitary gland tumor, pleupulmonary blastoma, oral and oropharyngeal, thyroid, uterine, pancreatic, carney complex, brain and spinal cord cancer, cervical cancer, cowden syndrome, craniopharyngioma, desmoid tumor, desmoplatic infantile ganglioglioma, ependymoma, esophageal cancer, ewing sarcoma, eye cancer, eyelid cancer, familial adenomatous polyposis, familial GIST, familial malignant melanoma, familial pancreatic cancer, gallbladder cancer, gastrointestinal stromal tumor, germ cell tumor, gestational trophoblastic disease, head and neck cancer, hereditary breast and ovarian cancer, hereditary diffuse gastric cancer, hereditary, leiomyomastosis and renal cell cancer, hereditary pancreatitis, herediatary papillary renal carcinoma, hereditary mixed polyposis syndrome, HIV/AIDS related cancers, retinoblastoma, rhabdomyosarcoma, salivary glanc cancer, Kaposi sarcoma, small bowel cancer, stomach cancer, testicular cancer, thymoma and thymic carcinoma, thyroid cancer, vaginal cancer, culver cancer, werner syndrome and Xeroderma pigmentosum.

As used herein, the term "administration" refers to providing a compound, or a pharmaceutical composition comprising the compound as described herein. The compound or composition can be administered by another person to the subject or it can be self-administered by the subject. Non-limiting examples of routes of administration are oral, parenteral (e.g., intravenous), or topical.

As used herein, the term "treatment" refers to an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

As used herein, the term "subject" refers to an animal (e.g., a mammal, such as a human, dog or horse). A subject to be treated according to the methods described herein may be one who has been diagnosed with a MRGPRX2 dependent condition or MRGPRX2 orthologB2 dependent condition, such as a pseudo-allergic reaction, an itch associated condition, a pain associated condition, inflammatory or an autoimmune disorder. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition. The term "patient" may be used interchangeably with the term "subject." A subject may refer to an adult or pediatric subject.

The Federal Food, Drug, and Cosmetic Act defines "pediatric" as a subject aged 21 or younger at the time of their diagnosis or treatment. Pediatric subpopulations are further characterized as: (i) neonates—from birth through the first 28 days of life; (ii) infants—from 29 days to less than 2 years; (iii) children—2 years to less than 12 years; and (iv) adolescents—aged 12 through 21. Despite the definition, depending on the susceptible patient population and clinical trial evaluation, an approved regulatory label may include phrasing that specifically modifies the range of a pediatric population, such as, for example, pediatric patients up to 22 years of age.

In another embodiment, the method of treating a subject having a MRGPRX2 dependent condition (e.g., an itch associated condition, a pain associated condition, a pseudo-allergic reaction, or an inflammatory or autoimmune disorder) described herein further comprises administering to the subject a pharmaceutically effective amount of a second therapeutic agent. In one embodiment, the itch associated condition is a pseudo-allergic condition.

In one embodiment, the second therapeutic agent is an antihistamine, such as an H1 receptor antagonist or an H2 receptor antagonist. In one embodiment, the second therapeutic agent is an H1 receptor antagonist antihistamine, such as levocetirizine, loratadine, fexofenadine, cetirizine, desloratadine, olopatadine, diphenhydramine, cyproheptadine or hydroxyzine pamoate. In one embodiment, the second therapeutic agent is a H2 receptor antagonist, such as cimetidine, nizatidine, ranitidine or famotidine. In one embodiment, the second therapeutic agent is a leukotriene receptor antagonist or leukotriene synthesis inhibitor, such as montelukast, zafirlukast, pranlukast, or 5-lipoxygenase inhibitor (e.g., zileuton, hypericum perforatum). In one embodiment, the second therapeutic agent is an immunomodulatory agent such as Omalizumab or immunoglobulin therapy. In one embodiment, the second therapeutic agent is a corticosteroid, such as hydrocortisone, cortisone, ethamethasoneb, triamcinolone, prednisone, prednisolone, or fludrocortisone. In one embodiment, the second therapeutic agent is a tricylic antidepressant that can relieve itch such as doxepin, amitriptyline or nortriptyline. In one embodiment, the second therapeutic agent is an anti-inflammatory drug such as dapsone, sulfasalazine, hydroxycholoroquine or colchicine. In one embodiment, the second therapeutic agent is an immunosuppressant such as cyclosporine, methotrexate, mycophenolic acid or tacromilus.

The second therapeutic agent may be administered simultaneously, separately, or sequentially with the compounds of the present disclosure. If administered simultaneously, the second therapeutic agent and compound of the present disclosure may be administered in separate dosage forms or in the same dosage form.

In another embodiment, a method of treating a subject having an itch associated condition is provided, the method comprising administering to the subject a pharmaceutically effective amount of a compound having structure (I) or a pharmaceutically acceptable salt, isomer, hydrate, solvate or isotope thereof, or a pharmaceutical composition thereof. In one embodiment, the itch associated condition is urticaria, pruritus, atopic dermatitis, dry skin, psoriasis, contact dermatitis, or eczema. In another embodiment, a method of treating a subject having an inflammation or autoimmune associated condition is provided, the method comprising administering to the subject a pharmaceutically effective amount of a compound having structure (I) or a pharmaceutically acceptable salt, isomer, hydrate, solvate or isotope thereof, or a pharmaceutical composition thereof. In one embodiment, the inflammation or autoimmune associated condition is sinusitis, asthma, rosacea, or endometriosis.

In another embodiment, a method of treating a subject having a pain associated condition is provided, the method comprising administering to the subject a pharmaceutically effective amount of a compound having structure (I) or a pharmaceutically acceptable salt, isomer, hydrate, solvate or isotope thereof, or a pharmaceutical composition thereof. In one embodiment, the pain associated condition is chronic pelvic pain syndrome, endometriosis pain, fibromyalgia, migraine or postoperative pain.

Methods

One embodiment provides a method of modulating a Mas-Related G-Protein Receptor (MRGPR) X2 or a MRGPRX2 ortholog by contacting the MRGPRX2 or MRGPRX2 ortholog with an effective amount of a compound having structure (1):

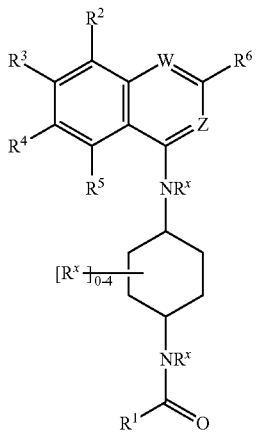

(I)

or a pharmaceutically acceptable salt, isomer, hydrate, solvate or isotope thereof, wherein:

$R^1$ is cycloalkyl, aryl, heterocyclyl, —$(CH_2)_nQ$, —CHQR, or —$CQ(R)_2$ where Q is $C_{1-6}$ alkyl, aryl, cycloalkyl, heterocyclyl, —OR, —$CH_2C(O)OR$, —C(O)OR, —C(O)NHR, —OC(O)R, —$CX_3$, —$CX_2H$, —$C(X)H_2$, —CN, —$N(R)_2$, —N(R)C(O)R, —N(R)C(O)OR, or —$N(R)S(O)_2R$, where $R^1$ and/or Q is optionally substituted with one or more $R^q$;

each R is independently H, $C_{1-6}$ alkyl, $C_{2-6}$ alkenyl, $C_{2-6}$ alkynyl, alkylamino, —$(CH_2)_nR'$, X, aryl, cycloalkyl, heteroaryl, or heterocyclyl, or two R groups together with the atom to which it is attached forms a carbocycle;

each $R^q$ is independently $C_{1-6}$ alkyl, $C_{2-6}$ alkenyl, $C_{2-6}$ alkynyl, aryl, cycloalkyl, heteroaryl, heterocyclyl, —OR, —$O(CH_2)_nR$, —$OX_3$, —$OX_2H$, —$O(X)H_2$, —C(O)OR, —C(O)R, —OC(O)R, X, —$CX_3$, —$CX_2H$, —$C(X)H_2$, —CN, —$N(R)_2$, —N(R)C(O)R, —$N(R)S(O)_2R$, $S(O)_2R$, —C(H)Q'R, or —$(CH_2)_nQ'$ where Q' is selected from $C_{1-6}$ alkyl, aryl, cycloalkyl, heterocyclyl, OR', —C(O)OR', —OC(O)R', —$CX_3$, —$CX_2H$, —$C(X)H_2$, —CN, —$N(R')_2$, —N(R')C(O)R', and —$N(R')S(O)_2R'$;

$R^2$, $R^4$, and $R^6$ are at each occurrence, independently H, $C_{1-6}$ alkyl, $C_{2-6}$ alkenyl, $C_{2-6}$ alkynyl, aryl, cycloalkyl, heteroaryl, heterocyclyl, —OR, —C(O)OR, —OC(O)R, X, —$CX_3$, —$CX_2H$, —$C(X)H_2$, $C(X)_2R$, —$C(X)(R)_2$, —CN, —$N(R)_2$, —N(R)C(O)R, —$N(R)S(O)_2R$, or $S(O)_2R$;

$R^3$ is at each occurrence, independently $C_{1-6}$ alkyl, $C_{2-6}$ alkenyl, H, OH, F, Br, I, —$N(R)_2$, —N(R)C(O)R, —N(R)C(O)OR, or —$N(R)S(O)_2R$;

$R^6$ is at each occurrence, independently H, $C_{1-6}$ alkyl, $C_{2-6}$ alkenyl, X, —$CF_3$, —$CF_2H$, —$C(F)H_2$, $C(F)_2R$, or —$C(F)(R)_2$;

each $R^x$ is independently H, $C_{1-6}$ alkyl, $C_{2-6}$ alkenyl, $C_{2-6}$ alkynyl, aryl, cycloalkyl, heteroaryl, heterocyclyl, —OR, —C(O)OR, —OC(O)R, X, —$CX_3$, —$CX_2H$, —$C(X)H_2$, —CN, —$N(R)_2$, —N(R)C(O)R, —$N(R)S(O)_2R$, and $S(O)_2R$;

each R' is independently H, $C_{1-6}$ alkyl, $C_{2-6}$ alkenyl, $C_{2-6}$ alkynyl, aryl, cycloalkyl, heteroaryl, or heterocyclyl;

W is N or $CR^w$;

Z is N or $CR^z$;

$R^w$ is $C_{1-6}$ alkyl, $C_{2-6}$ alkenyl, $C_{2-6}$ alkynyl, H, aryl, cycloalkyl, heteroaryl, or heterocyclyl;

$R^z$ is $C_{1-6}$ alkyl, $C_{2-6}$ alkenyl, H, OH, F, Br, I, —$N(R)_2$, —N(R)C(O)R, —N(R)C(O)OR, or —$N(R)S(O)_2R$;

each X is independently F, Cl, Br, and I; and n is independently 0, 1, 2, 3, 4 and 5.

In another embodiment, a method of treating an MRGPRX2 or a MRGPRX2 ortholog dependent condition is provided, by administering to a subject in need thereof an effective amount of a compound having structure (I):

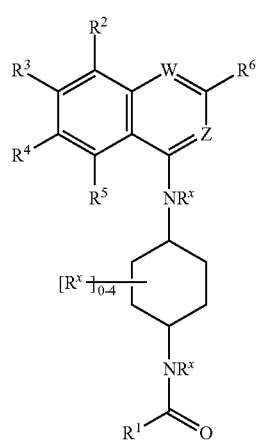

(I)

or a pharmaceutically acceptable salt, isomer, hydrate, solvate or isotope thereof, wherein:

$R^1$ is cycloalkyl, aryl, heterocyclyl, —$(CH_2)_nQ$, —CHQR, or —$CQ(R)_2$ where Q is $C_{1-6}$ alkyl, aryl, cycloalkyl, heterocyclyl, —OR, —$CH_2C(O)OR$, —C(O)OR, —C(O)NHR, —OC(O)R, —$CX_3$, —$CX_2H$, —$C(X)H_2$, —CN, —$N(R)_2$, —N(R)C(O)R, —N(R)C(O)OR, or —$N(R)S(O)_2R$, where R' and/or Q is optionally substituted with one or more $R^q$;

each R is independently H, $C_{1-6}$ alkyl, $C_{2-6}$ alkenyl, $C_{2-6}$ alkynyl, alkylamino, —$(CH_2)_nR'$, X, aryl, cycloalkyl, heteroaryl, or heterocyclyl, or two R groups together with the atom to which it is attached forms a carbocycle;

each $R^q$ is independently $C_{1-6}$ alkyl, $C_{2-6}$ alkenyl, $C_{2-6}$ alkynyl, aryl, cycloalkyl, heteroaryl, heterocyclyl, —OR, —$O(CH_2)_nR$, —$OX_3$, —$OX_2H$, —$O(X)H_2$, —C(O)OR, —C(O)R, —OC(O)R, X, —$CX_3$, —$CX_2H$, —$C(X)H_2$, —CN, —$N(R)_2$, —N(R)C(O)R, —$N(R)S(O)_2R$, $S(O)_2R$, —C(H)Q'R, or —$(CH_2)_nQ'$ where Q' is selected from $C_{1-6}$ alkyl, aryl, cycloalkyl, heterocyclyl, OR', —C(O)OR', —OC(O)R', —CX$_3$, —CX$_2$H, —C(X)H$_2$, —CN, —N(R')$_2$, —N(R')C(O)R', and —N(R')S(O)$_2$R';

R$^2$, R$^4$, and R$^6$ are at each occurrence, independently H, C$_{1-6}$ alkyl, C$_{2-6}$ alkenyl, C$_{2-6}$ alkynyl, aryl, cycloalkyl, heteroaryl, heterocyclyl, —OR, —C(O)OR, —OC(O)R, X, —CX$_3$, —CX$_2$H, —C(X)H$_2$, C(X)$_2$R, —C(X)(R)$_2$, —CN, —N(R)$_2$, —N(R)C(O)R, —N(R)S(O)$_2$R, or S(O)$_2$R;

R$^3$ is at each occurrence, independently C$_{1-6}$ alkyl, C$_{2-6}$ alkenyl, H, OH, F, Br, I, —N(R)$_2$, —N(R)C(O)R, —N(R)C(O)OR, or —N(R)S(O)$_2$R;

R$^6$ is at each occurrence, independently H, C$_{1-6}$ alkyl, C$_{2-6}$ alkenyl, X, —CF$_3$, —CF$_2$H, —C(F)H$_2$, C(F)$_2$R, or —C(F)(R)$_2$;

each R$^x$ is independently H, C$_{1-6}$ alkyl, C$_{2-6}$ alkenyl, C$_{2-6}$ alkynyl, aryl, cycloalkyl, heteroaryl, heterocyclyl, —OR, —C(O)OR, —OC(O)R, X, —CX$_3$, —CX$_2$H, —C(X)H$_2$, —CN, —N(R)$_2$, —N(R)C(O)R, —N(R)S(O)$_2$R, and S(O)$_2$R;

each R' is independently H, C$_{1-6}$ alkyl, C$_{2-6}$ alkenyl, C$_{2-6}$ alkynyl, aryl, cycloalkyl, heteroaryl, or heterocyclyl;

W is N or CR$^w$;

Z is N or CR$^z$;

R$^w$ is C$_{1-6}$ alkyl, C$_{2-6}$ alkenyl, C$_{2-6}$ alkynyl, H, aryl, cycloalkyl, heteroaryl, or heterocyclyl;

R$^z$ is C$_{1-6}$ alkyl, C$_{2-6}$ alkenyl, H, OH, F, Br, I, —N(R)$_2$, —N(R)C(O)R, —N(R)C(O)OR, or —N(R)S(O)$_2$R;

each X is independently F, Cl, Br, and I; and n is independently 0, 1, 2, 3, 4 and 5.

In yet another embodiment, the MRGPRX2 or the MRGPRX2 ortholog dependent condition is a pseudo-allergic reaction, an itch associated condition, a pain associated condition, or an inflammatory or autoimmune disorder.

In one embodiment, the itch associated condition is chronic itch; contact dermatitis; Allergic blepharitis; Anemia; Atopic dermatitis; Bullous pemphigoid; Candidiasis; Chicken pox; end-stage renal failure; hemodialysis; Chronic urticaria; Contact dermatitis, Atopic Dermatitis; Dermatitis herpetiformis; Diabetes; Drug allergy, Dry skin; Dyshidrotic dermatitis; Ectopic eczema; Eosinophilic fasciitis; Epidermolysis bullosa; Erythrasma; Food allergy; Folliculitis; Fungal skin infection; Hemorrhoids; Herpes; HIV infection; Hodgkin's disease; Hyperthyroidism; Iodinated contrast dye allergy; Iron deficiency anemia; Kidney disease; Leukemia; porphyrias; Lymphoma; Malignancy; Mastocystosis; Multiple myeloma; Neurodermatitis; Onchocerciasis; Paget's disease; Pediculosis; Polycythemia rubra vera; Prurigo nodularis; Lichen Planus; Lichen Sclerosis; Pruritus ani; Pseudorabies; Psoriasis; Rectal prolapse; Sarcoidosis granulomas; Scabies; Schistosomiasis; Scleroderma, Severe stress, Stasia dermatitis; Swimmer's itch; Thyroid disease; Tinea cruris; Rosacea; Cutaneous amyloidosis; Scleroderma; Acne; wound healing; burn healing; ocular itch; or Urticaria.

In a specific embodiment, the itch associated condition is urticaria, pruritus, atopic dermatitis, dry skin, psoriasis, contact dermatitis, or eczema.

In one embodiment, the pain associated condition is Acute Pain, Advanced Prostate Cancer, AIDS-Related Pain, Ankylosing Spondylitis, Arachnoiditis, Arthritis, Arthrofibrosis, Ataxic Cerebral Palsy, Autoimmune Atrophic Gastritis, Avascular Necrosis, Back Pain, Behcet's Disease (Syndrome), Burning Mouth Syndrome, Bursitis, Cancer Pain, Carpal Tunnel, Cauda Equina Syndrome, Central Pain Syndrome, Cerebral Palsy, Cervical Stenosis, Charcot-Marie-Tooth (CMT) Disease, Chronic Fatigue Syndrome (CFS), Chronic Functional Abdominal Pain (CFAP), Chronic Pain, Chronic Pancreatitis, Chronic Pelvic Pain Syndrome, Collapsed Lung (Pneumothorax), Complex Regional Pain Syndrome (RSD), Corneal Neuropathic Pain, Crohn's Disease, Degenerative Disc Disease, Dental Pain, Dercum's Disease, Dermatomyositis, Diabetic Peripheral Neuropathy (DPN), Dystonia, Ehlers-Danlos Syndrome (EDS), Endometriosis, Eosinophilia-Myalgia Syndrome (EMS), Erythromelalgia, Fibromyalgia, Gout, Headaches, Herniated disc, Hydrocephalus, Intercostal Neuraligia, Interstitial Cystitis, Irritable Bowel syndrome (IBS), Juvenile Dermatositis (Dermatomyositis), Knee Injury, Leg Pain, Loin Pain-Haematuria Syndrome, Lupus, Lyme Disease, Medullary Sponge Kidney (MSK), Meralgia Paresthetica, Mesothelioma, Migraine, Musculoskeletal pain, Myofascial Pain, Myositis, Neck Pain, Neuropathic Pain, Occipital Neuralgia, Osteoarthritis, Paget's Disease, Parsonage Turner Syndrome, Pelvic Pain, Periodontitis Pain, Peripheral Neuropathy, Phantom Limb Pain, Pinched Nerve, Polycystic Kidney Disease, Polymyalgia Rhuematica, Polymyositis, Porphyria, Post Herniorraphy Pain Syndrome, Post Mastectomy, Postoperative Pain, Pain Syndrome, Post Stroke Pain, Post Thorocotomy Pain Syndrome, Postherpetic Neuralgia (Shingles), Post-Polio Syndrome, Primary Lateral Sclerosis, Psoriatic Arthritis, Pudendal Neuralgia, Radiculopathy, Raynaud's Disease, Rheumatoid Arthritis (RA), Sacroiliac Joint Dysfunction, Sarcoidosi, Scheuemann's Kyphosis Disease, Sciatica, Scoliosis, Shingles (Herpes Zoster), Sjogren's Syndrome, Spasmodic Torticollis, Sphincter of Oddi Dysfunction, Spinal Cerebellum Ataxia (SCA Ataxia), Spinal Cord Injury, Spinal Stenosis, Syringomyelia, Tarlov Cysts, Transverse Myelitis, Trigeminal Neuralgia, Neuropathic Pain, Ulcerative Colitis, Vascular Pain or Vulvodynia.

In yet another embodiment, the inflammatory or autoimmune disorder provided is chronic inflammation, mast cell activation syndrome, Multiple Sclerosis, Steven Johnson's Syndrome, Toxic Epidermal Necrolysis, appendicitis, bursitis, cutaneous lupus, colitis, cystitis, dermatitis, phlebitis, reflex sympathetic dystrophy/complex regional pain syndrome (rsd/crps), rhinitis, tendonitis, tonsillitis, acne vulgaris, sinusitis, rosacea, psoriasis, graft-versus-host disease, reactive airway disorder, asthma, airway infection, autoinflammatory disease, celiac disease, chronic prostatitis, diverticulitis, glomerulonephritis, hidradenitis suppurativa, hypersensitivities, intestinal disorder, epithelial intestinal disorder, inflammatory bowel disease, irritable bowel syndrome, Crohn's Disease, ulcerative colitis, lupus erythematous, interstitial cystitis, otitis, pelvic inflammatory disease, endometrial pain, reperfusion injury, rheumatic fever, rheumatoid arthritis, sarcoidosis, transplant rejection, psoriasis, lung inflammation, chronic obstructive pulmonary disease, cardiovascular disease, or vasculitis.

In one embodiment is provided, methods of modulating MRGPRX2 or a MRGPRX2 ortholog with structures having formula (IA), (IB) or (IC) or a pharmaceutically acceptable salt, isomer, hydrate, solvate or isotope.

In another embodiment is provided, methods of treating an MRGPRX2 condition or a MRGPRX2 ortholog dependent condition by administering to a subject in need thereof a compound having formula (IA), (IB) or (IC) or a pharmaceutically acceptable salt, isomer, hydrate, solvate or isotope.

Another embodiment provides a method where the compound of structure (I) is formula (IA):

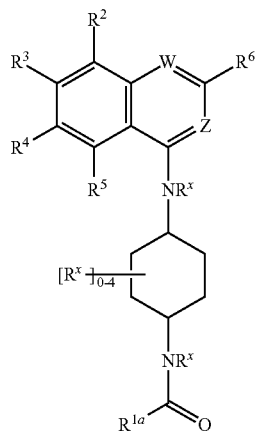

(IA)

or a pharmaceutically acceptable salt, isomer, hydrate, solvate or isotope thereof, wherein:

$R^{1a}$ is cycloalkyl, —(CH$_2$)$_n$Q, —CHQR, or —CQ(R)$_2$,

Q is cycloalkyl, —OR, —CH$_2$C(O)OR, —C(O)OR, —C(O)NHR, —OC(O)R, —CX$_3$, —CX$_2$H, —C(X)H$_2$, —CN, —N(R)$_2$, —N(R)C(O)R, —N(R)C(O)OR, or —N(R)S(O)$_2$R, and where $R^{1a}$ and/or Q is optionally substituted with one or more $R^q$.

In yet another embodiment, is provided a method where the compound of structure (I) is formula (IB):

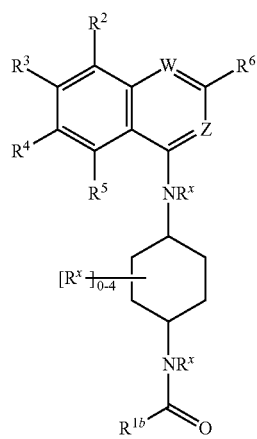

(IB)

or a pharmaceutically acceptable salt, isomer, hydrate, solvate or isotope thereof, wherein:

$R^{1b}$ is aryl, —(CH$_2$)$_n$Q, —CHQR, or —CQ(R)$_2$,

Q is aryl, —OR, —CH$_2$C(O)OR, —C(O)OR, —C(O)NHR, —OC(O)R, —CX$_3$, —CX$_2$H, —C(X)H$_2$, —CN, —N(R)$_2$, —N(R)C(O)R, —N(R)C(O)OR, or —N(R)S(O)$_2$R, and where $R^{1b}$ and/or Q is optionally substituted with one or more $R^q$.

In another embodiment, is provided a method where the compound of structure (I) is formula (IC):

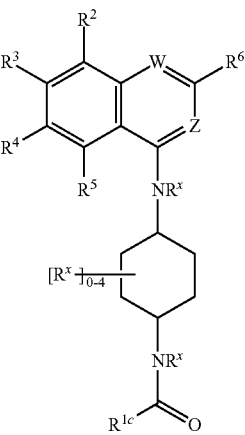

(IC)

or a pharmaceutically acceptable salt, isomer, hydrate, solvate or isotope thereof, wherein:

$R^{1c}$ is heterocyclyl, —(CH$_2$)$_n$Q, —CHQR, or —CQ(R)$_2$,

Q is heterocyclyl, —OR, —CH$_2$C(O)OR, —C(O)OR, —C(O)NHR, —OC(O)R, —CX$_3$, —CX$_2$H, —C(X)H$_2$, —CN, —N(R)$_2$, —N(R)C(O)R, —N(R)C(O)OR, or —N(R)S(O)$_2$R, and where $R^{1c}$ and/or Q is optionally substituted with one or more $R^q$.

Pharmaceutical Compositions

One embodiment provides a pharmaceutical composition comprising a carrier or excipient having a compound of structure (IA):

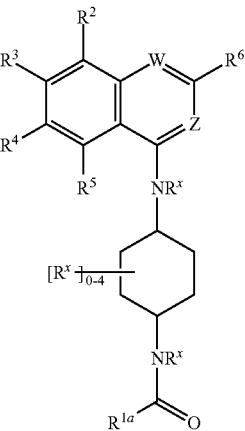

(IA)

or a pharmaceutically acceptable salt, isomer, hydrate, solvate or isotope thereof, wherein:

$R^{1a}$ is cycloalkyl, —(CH$_2$)$_n$Q, —CHQR, or —CQ(R)$_2$;

Q is cycloalkyl, —OR, —CH$_2$C(O)OR, —C(O)OR, —C(O)NHR, —OC(O)R, —CX$_3$, —CX$_2$H, —C(X)H$_2$, —CN, —N(R)$_2$, —N(R)C(O)R, —N(R)C(O)OR, or —N(R)S(O)$_2$R, where $R^{1a}$ and/or Q is optionally substituted with one or more $R^q$;

each R is independently H, C$_{1-6}$ alkyl, C$_{2-6}$ alkenyl, C$_{2-6}$ alkynyl, alkylamino, —(CH$_2$)$_n$R', X, aryl, cycloalkyl, heteroaryl, or heterocyclyl, or two R groups together with the atom to which it is attached forms a carbocycle;

each $R^q$ is independently $C_{1-6}$ alkyl, $C_{2-6}$ alkenyl, $C_{2-6}$ alkynyl, aryl, cycloalkyl, heteroaryl, heterocyclyl, —OR, —O(CH$_2$)$_n$R, —OX$_3$, —OX$_2$H, —O(X)H$_2$, —C(O)OR, —C(O)R, —OC(O)R, X, —CX$_3$, —CX$_2$H, —C(X)H$_2$, —CN, —N(R)$_2$, —N(R)C(O)R, —N(R)S(O)$_2$R, S(O)$_2$R, —C(H)Q'R, or —(CH$_2$)$_n$Q' where Q' is selected from $C_{1-6}$ alkyl, aryl, cycloalkyl, heterocyclyl, OR', —C(O)OR', —OC(O)R', —CX$_3$, —CX$_2$H, —C(X)H$_2$, —CN, —N(R')$_2$, —N(R')C(O)R', and —N(R')S(O)$_2$R';

$R^2$, $R^4$, and $R^6$ are at each occurrence, independently H, $C_{1-6}$ alkyl, $C_{2-6}$ alkenyl, $C_{2-6}$ alkynyl, aryl, cycloalkyl, heteroaryl, heterocyclyl, —OR, —C(O)OR, —OC(O)R, X, —CX$_3$, —CX$_2$H, —C(X)H$_2$, C(X)$_2$R, —C(X)(R)$_2$, —CN, —N(R)$_2$, —N(R)C(O)R, —N(R)S(O)$_2$R, or S(O)$_2$R;

$R^3$ is at each occurrence, independently $C_{1-6}$ alkyl, $C_{2-6}$ alkenyl, H, OH, F, Br, I, —N(R)$_2$, —N(R)C(O)R, —N(R)C(O)OR, or —N(R)S(O)$_2$R;

$R^6$ is at each occurrence, independently H, $C_{1-6}$ alkyl, $C_{2-6}$ alkenyl, X, —CF$_3$, —CF$_2$H, —C(F)H$_2$, C(F)$_2$R, or —C(F)(R)$_2$;

each $R^x$ is independently H, $C_{1-6}$ alkyl, $C_{2-6}$ alkenyl, $C_{2-6}$ alkynyl, aryl, cycloalkyl, heteroaryl, heterocyclyl, —OR, —C(O)OR, —OC(O)R, X, —CX$_3$, —CX$_2$H, —C(X)H$_2$, —CN, —N(R)$_2$, —N(R)C(O)R, —N(R)S(O)$_2$R, and S(O)$_2$R;

each R' is independently H, $C_{1-6}$ alkyl, $C_{2-6}$ alkenyl, $C_{2-6}$ alkynyl, aryl, cycloalkyl, heteroaryl, or heterocyclyl;

W is N or CR$^w$;

Z is N or CR$^z$;

$R^w$ is $C_{1-6}$ alkyl, $C_{2-6}$ alkenyl, $C_{2-6}$ alkynyl, H, aryl, cycloalkyl, heteroaryl, or heterocyclyl;

$R^z$ is $C_{1-6}$ alkyl, $C_{2-6}$ alkenyl, H, OH, F, Br, I, —N(R)$_2$, —N(R)C(O)R, —N(R)C(O)OR, or —N(R)S(O)$_2$R;

each X is independently F, Cl, Br, and I; and n is independently 0, 1, 2, 3, 4 and 5.

Another embodiment provides a pharmaceutical composition comprising a carrier or excipient having a compound of structure (IB):

(IB)

or a pharmaceutically acceptable salt, isomer, hydrate, solvate or isotope thereof, wherein:

$R^{1b}$ is aryl, —(CH$_2$)$_n$Q, —CHQR, or —CQ(R)$_2$,

Q is aryl, —OR, —CH$_2$C(O)OR, —C(O)OR, —C(O)NHR, —OC(O)R, —CX$_3$, —CX$_2$H, —C(X)H$_2$, —CN, —N(R)$_2$, —N(R)C(O)R, —N(R)C(O)OR, or —N(R)S(O)$_2$R, where $R^{1b}$ and/or Q is optionally substituted with one or more $R^q$;

each R is independently H, $C_{1-6}$ alkyl, $C_{2-6}$ alkenyl, $C_{2-6}$ alkynyl, alkylamino, —(CH$_2$)$_n$R', X, aryl, cycloalkyl, heteroaryl, or heterocyclyl, or two R groups together with the atom to which it is attached forms a carbocycle;

each $R^q$ is independently $C_{1-6}$ alkyl, $C_{2-6}$ alkenyl, $C_{2-6}$ alkynyl, aryl, cycloalkyl, heteroaryl, heterocyclyl, —OR, —O(CH$_2$)$_n$R, —OX$_3$, —OX$_2$H, —O(X)H$_2$, —C(O)OR, —C(O)R, —OC(O)R, X, —CX$_3$, —CX$_2$H, —C(X)H$_2$, —CN, —N(R)$_2$, —N(R)C(O)R, —N(R)S(O)$_2$R, S(O)$_2$R, —C(H)Q'R, or —(CH$_2$)$_n$Q' where Q' is selected from $C_{1-6}$ alkyl, aryl, cycloalkyl, heterocyclyl, OR', —C(O)OR', —OC(O)R', —CX$_3$, —CX$_2$H, —C(X)H$_2$, —CN, —N(R')$_2$, —N(R')C(O)R', and —N(R')S(O)$_2$R';

$R^2$, $R^4$, and $R^6$ are at each occurrence, independently H, $C_{1-6}$ alkyl, $C_{2-6}$ alkenyl, $C_{2-6}$ alkynyl, aryl, cycloalkyl, heteroaryl, heterocyclyl, —OR, —C(O)OR, —OC(O)R, X, —CX$_3$, —CX$_2$H, —C(X)H$_2$, C(X)$_2$R, —C(X)(R)$_2$, —CN, —N(R)$_2$, —N(R)C(O)R, —N(R)S(O)$_2$R, or S(O)$_2$R;

$R^3$ is at each occurrence, independently $C_{1-6}$ alkyl, $C_{2-6}$ alkenyl, H, OH, F, Br, I, —N(R)$_2$, —N(R)C(O)R, —N(R)C(O)OR, or —N(R)S(O)$_2$R;

$R^6$ is at each occurrence, independently H, $C_{1-6}$ alkyl, $C_{2-6}$ alkenyl, X, —CF$_3$, —CF$_2$H, —C(F)H$_2$, C(F)$_2$R, or —C(F)(R)$_2$;

each $R^x$ is independently H, $C_{1-6}$ alkyl, $C_{2-6}$ alkenyl, $C_{2-6}$ alkynyl, aryl, cycloalkyl, heteroaryl, heterocyclyl, —OR, —C(O)OR, —OC(O)R, X, —CX$_3$, —CX$_2$H, —C(X)H$_2$, —CN, —N(R)$_2$, —N(R)C(O)R, —N(R)S(O)$_2$R, and S(O)$_2$R;

each R' is independently H, $C_{1-6}$ alkyl, $C_{2-6}$ alkenyl, $C_{2-6}$ alkynyl, aryl, cycloalkyl, heteroaryl, or heterocyclyl;

W is N or CR$^w$;

Z is N or CR$^z$;

$R^w$ is $C_{1-6}$ alkyl, $C_{2-6}$ alkenyl, $C_{2-6}$ alkynyl, H, aryl, cycloalkyl, heteroaryl, or heterocyclyl;

$R^z$ is $C_{1-6}$ alkyl, $C_{2-6}$ alkenyl, H, OH, F, Br, I, —N(R)$_2$, —N(R)C(O)R, —N(R)C(O)OR, or —N(R)S(O)$_2$R;

each X is independently F, Cl, Br, and I;

n is independently 0, 1, 2, 3, 4 and 5;

with the proviso that when $R^z$ is —NH$_2$, then $R^x$ is not —CH$_2$CN;

with the proviso that when $R^6$ is Cl, then $R^{1b}$ is not 3,4-difluorophenyl;

with the proviso that when $R^6$ is H, then $R^{1b}$ is not 3,5-difluorophenyl; and with the proviso that when $R^6$ is —CF$_3$, then $R^{1b}$ is not 3,5-difluorophenyl.

Yet another embodiment, provides a pharmaceutical composition comprising a carrier or excipient having a compound of structure (IC):

(IC)

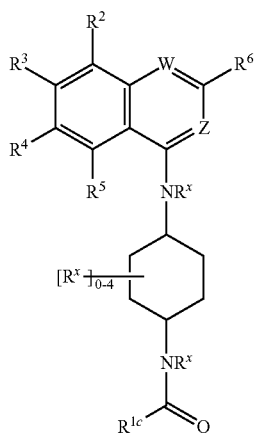

or a pharmaceutically acceptable salt, isomer, hydrate, solvate or isotope thereof, wherein:

$R^{1c}$ is heterocyclyl, —$(CH_2)_nQ$, —CHQR, or —CQ(R)$_2$,

Q is heterocyclyl, —OR, —CH$_2$C(O)OR, —C(O)OR, —C(O)NHR, —OC(O)R, —CX$_3$, —CX$_2$H, —C(X)H$_2$, —CN, —N(R)$_2$, —N(R)C(O)R, —N(R)C(O)OR, or —N(R)S(O)$_2$R, where $R^{1c}$ and/or Q is optionally substituted with one or more $R^q$;

each R is independently H, C$_{1-6}$ alkyl, C$_{2-6}$ alkenyl, C$_{2-6}$ alkynyl, alkylamino, —$(CH_2)_nR'$, X, aryl, cycloalkyl, heteroaryl, or heterocyclyl, or two R groups together with the atom to which it is attached forms a carbocycle;

each $R^q$ is independently C$_{1-6}$ alkyl, C$_{2-6}$ alkenyl, C$_{2-6}$ alkynyl, aryl, cycloalkyl, heteroaryl, heterocyclyl, —OR, —O(CH$_2$)$_n$R, —OX$_3$, —OX$_2$H, —O(X)H$_2$, —C(O)OR, —C(O)R, —OC(O)R, X, —CX$_3$, —CX$_2$H, —C(X)H$_2$, —CN, —N(R)$_2$, —N(R)C(O)R, —N(R)S(O)$_2$R, S(O)$_2$R, —C(H)Q'R, or —(CH$_2$)$_n$Q' where Q' is selected from C$_{1-6}$ alkyl, aryl, cycloalkyl, heterocyclyl, OR', —C(O)OR', —OC(O)R', —CX$_3$, —CX$_2$H, —C(X)H$_2$, —CN, —N(R')$_2$, —N(R')C(O)R', and —N(R')S(O)$_2$R';

$R^2$, $R^4$, and $R^6$ are at each occurrence, independently H, C$_{1-6}$ alkyl, C$_{2-6}$ alkenyl, C$_{2-6}$ alkynyl, aryl, cycloalkyl, heteroaryl, heterocyclyl, —OR, —C(O)OR, —OC(O)R, X, —CX$_3$, —CX$_2$H, —C(X)H$_2$, C(X)$_2$R, —C(X)(R)$_2$, —CN, —N(R)$_2$, —N(R)C(O)R, —N(R)S(O)$_2$R, or S(O)$_2$R;

$R^3$ is at each occurrence, independently C$_{1-6}$ alkyl, C$_{2-6}$ alkenyl, H, OH, F, Br, I, —N(R)$_2$, —N(R)C(O)R, —N(R)C(O)OR, or —N(R)S(O)$_2$R;

$R^6$ is at each occurrence, independently H, C$_{1-6}$ alkyl, C$_{2-6}$ alkenyl, X, —CF$_3$, —CF$_2$H, —C(F)H$_2$, C(F)$_2$R, or —C(F)(R)$_2$;

each $R^x$ is independently H, C$_{1-6}$ alkyl, C$_{2-6}$ alkenyl, C$_{2-6}$ alkynyl, aryl, cycloalkyl, heteroaryl, heterocyclyl, —OR, —C(O)OR, —OC(O)R, X, —CX$_3$, —CX$_2$H, —C(X)H$_2$, —CN, —N(R)$_2$, —N(R)C(O)R, —N(R)S(O)$_2$R, and S(O)$_2$R;

each R' is independently H, C$_{1-6}$ alkyl, C$_{2-6}$ alkynyl, aryl, cycloalkyl, heteroaryl, or heterocyclyl;

W is N or CR$^w$;

Z is N or CR$^z$;

$R^w$ is C$_{1-6}$ alkyl, C$_{2-6}$ alkenyl, C$_{2-6}$ alkynyl, H, aryl, cycloalkyl, heteroaryl, or heterocyclyl;

$R^z$ is C$_{1-6}$ alkyl, C$_{2-6}$ alkenyl, H, OH, F, Br, I, —N(R)$_2$, —N(R)C(O)R, —N(R)C(O)OR, or —N(R)S(O)$_2$R;

each X is independently F, Cl, Br, and I;

n is independently 0, 1, 2, 3, 4 and 5; and with the proviso that when $R^6$ is Cl, then $R^{1b}$ is not 2-phenoxy pyridine.

Compounds

One embodiment provides a compound having formula (IA):

(IA)

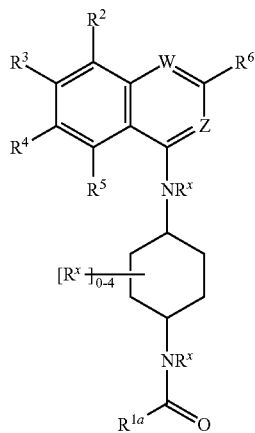

or a pharmaceutically acceptable salt, isomer, hydrate, solvate or isotope thereof, wherein:

$R^{1a}$ is cycloalkyl, —(CH$_2$)$_n$Q, —CHQR, or —CQ(R)$_2$;

Q is cycloalkyl, —OR, —CH$_2$C(O)OR, —C(O)OR, —C(O)NHR, —OC(O)R, —CX$_3$, —CX$_2$H, —C(X)H$_2$, —CN, —N(R)$_2$, —N(R)C(O)R, —N(R)C(O)OR, or —N(R)S(O)$_2$R, where $R^{1a}$ and/or Q is optionally substituted with one or more $R^q$;

each R is independently H, C$_{1-6}$ alkyl, C$_{2-6}$ alkenyl, C$_{2-6}$ alkynyl, alkylamino, —(CH$_2$)$_n$R', X, aryl, cycloalkyl, heteroaryl, or heterocyclyl, or two R groups together with the atom to which it is attached forms a carbocycle;

each $R^q$ is independently C$_{1-6}$ alkyl, C$_{2-6}$ alkenyl, C$_{2-6}$ alkynyl, aryl, cycloalkyl, heteroaryl, heterocyclyl, —OR, —O(CH$_2$)$_n$R, —OX$_3$, —OX$_2$H, —O(X)H$_2$, —C(O)OR, —C(O)R, —OC(O)R, X, —CX$_3$, —CX$_2$H, —C(X)H$_2$, —CN, —N(R)$_2$, —N(R)C(O)R, —N(R)S(O)$_2$R, S(O)$_2$R, —C(H)Q'R, or —(CH$_2$)$_n$Q' where Q' is selected from C$_{1-6}$ alkyl, aryl, cycloalkyl, heterocyclyl, OR', —C(O)OR', —OC(O)R', —CX$_3$, —CX$_2$H, —C(X)H$_2$, —CN, —N(R')$_2$, —N(R')C(O)R', and —N(R')S(O)$_2$R';

$R^2$, $R^4$, and $R^6$ are at each occurrence, independently H, C$_{1-6}$ alkyl, C$_{2-6}$ alkenyl, C$_{2-6}$ alkynyl, aryl, cycloalkyl, heteroaryl, heterocyclyl, —OR, —C(O)OR, —OC(O)R, X, —CX$_3$, —CX$_2$H, —C(X)H$_2$, C(X)$_2$R, —C(X)(R)$_2$, —CN, —N(R)$_2$, —N(R)C(O)R, —N(R)S(O)$_2$R, or S(O)$_2$R;

$R^3$ is at each occurrence, independently C$_{1-6}$ alkyl, C$_{2-6}$ alkenyl, H, OH, F, Br, I, —N(R)$_2$, —N(R)C(O)R, —N(R)C(O)OR, or —N(R)S(O)$_2$R;

$R^6$ is at each occurrence, independently H, C$_{1-6}$ alkyl, C$_{2-6}$ alkenyl, X, —CF$_3$, —CF$_2$H, —C(F)H$_2$, C(F)$_2$R, or —C(F)(R)$_2$;

each $R^x$ is independently H, C$_{1-6}$ alkyl, C$_{2-6}$ alkenyl, C$_{2-6}$ alkynyl, aryl, cycloalkyl, heteroaryl, heterocyclyl, —OR, —C(O)OR, —OC(O)R, X, —CX₃, —CX₂H, —C(X)H₂, —CN, —N(R)₂, —N(R)C(O)R, —N(R)S(O)₂R, and S(O)₂R;

each R' is independently H, $C_{1-6}$ alkyl, $C_{2-6}$ alkenyl, $C_{2-6}$ alkynyl, aryl, cycloalkyl, heteroaryl, or heterocyclyl;

W is N or $CR^w$;

Z is N or $CR^z$;

$R^w$ is $C_{1-6}$ alkyl, $C_{2-6}$ alkenyl, $C_{2-6}$ alkynyl, H, aryl, cycloalkyl, heteroaryl, or heterocyclyl;

$R^z$ is $C_{1-6}$ alkyl, $C_{2-6}$ alkenyl, H, OH, F, Br, I, —N(R)₂, —N(R)C(O)R, —N(R)C(O)OR, or —N(R)S(O)₂R;

each X is independently F, Cl, Br, and I; and n is independently 0, 1, 2, 3, 4 and 5.

Another embodiment provides a compound having formula (IB):

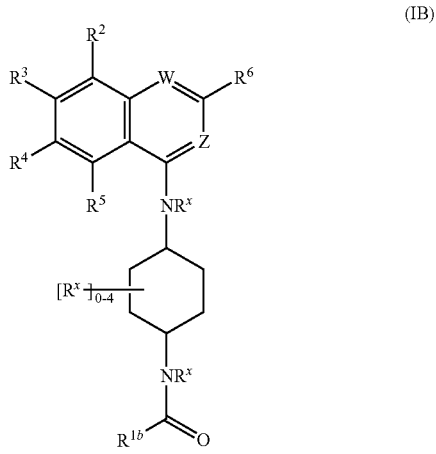

(IB)

or a pharmaceutically acceptable salt, isomer, hydrate, solvate or isotope thereof, wherein:

$R^{1b}$ is aryl, —(CH₂)ₙQ, —CHQR, or —CQ(R)₂;

Q is aryl, —OR, —CH₂C(O)OR, —C(O)OR, —C(O)NHR, —OC(O)R, —CX₃, —CX₂H, —C(X)H₂, —CN, —N(R)₂, —N(R)C(O)R, —N(R)C(O)OR, or —N(R)S(O)₂R, where $R^{1b}$ and/or Q is optionally substituted with one or more $R^q$;

each R is independently H, $C_{1-6}$ alkyl, $C_{2-6}$ alkenyl, $C_{2-6}$ alkynyl, alkylamino, —(CH₂)ₙR', X, aryl, cycloalkyl, heteroaryl, or heterocyclyl, or two R groups together with the atom to which it is attached forms a carbocycle;

each $R^q$ is independently $C_{1-6}$ alkyl, $C_{2-6}$ alkenyl, $C_{2-6}$ alkynyl, aryl, cycloalkyl, heteroaryl, heterocyclyl, —OR, —O(CH₂)ₙR, —OX₃, —OX₂H, —O(X)H₂, —C(O)OR, —C(O)R, —OC(O)R, X, —CX₃, —CX₂H, —C(X)H₂, —CN, —N(R)₂, —N(R)C(O)R, —N(R)S(O)₂R, S(O)₂R, —C(H)Q'R, or —(CH₂)ₙQ' where Q' is selected from $C_{1-6}$ alkyl, aryl, cycloalkyl, heterocyclyl, OR', —C(O)OR', —OC(O)R', —CX₃, —CX₂H, —C(X)H₂, —CN, —N(R')₂, —N(R')C(O)R', and —N(R')S(O)₂R';

$R^2$, $R^4$, and $R^6$ are at each occurrence, independently H, $C_{1-6}$ alkyl, $C_{2-6}$ alkenyl, $C_{2-6}$ alkynyl, aryl, cycloalkyl, heteroaryl, heterocyclyl, —OR, —C(O)OR, —OC(O)R, X, —CX₃, —CX₂H, —C(X)H₂, C(X)₂R, —C(X)(R)₂, —CN, —N(R)₂, —N(R)C(O)R, —N(R)S(O)₂R, or S(O)₂R;

$R^3$ is at each occurrence, independently $C_{1-6}$ alkyl, $C_{2-6}$ alkenyl, H, OH, F, Br, I, —N(R)₂, —N(R)C(O)R, —N(R)C(O)OR, or —N(R)S(O)₂R;

$R^6$ is at each occurrence, independently H, $C_{1-6}$ alkyl, $C_{2-6}$ alkenyl, X, —CF₃, —CF₂H, —C(F)H₂, C(F)₂R, or —C(F)(R)₂;

each $R^x$ is independently H, $C_{1-6}$ alkyl, $C_{2-6}$ alkenyl, $C_{2-6}$ alkynyl, aryl, cycloalkyl, heteroaryl, heterocyclyl, —OR, —C(O)OR, —OC(O)R, X, —CX₃, —CX₂H, —C(X)H₂, —CN, —N(R)₂, —N(R)C(O)R, —N(R)S(O)₂R, and S(O)₂R;

each R' is independently H, $C_{1-6}$ alkyl, $C_{2-6}$ alkenyl, $C_{2-6}$ alkynyl, aryl, cycloalkyl, heteroaryl, or heterocyclyl;

W is N or $CR^w$;

Z is N or $CR^z$;

$R^w$ is $C_{1-6}$ alkyl, $C_{2-6}$ alkenyl, $C_{2-6}$ alkynyl, H, aryl, cycloalkyl, heteroaryl, or heterocyclyl;

$R^z$ is $C_{1-6}$ alkyl, $C_{2-6}$ alkenyl, H, OH, F, Br, I, —N(R)₂, —N(R)C(O)R, —N(R)C(O)OR, or —N(R)S(O)₂R;

each X is independently F, Cl, Br, and I;

n is independently 0, 1, 2, 3, 4 and 5;

with the proviso that when $R^z$ is —NH₂, then $R^x$ is not —CH₂CN;

with the proviso that when $R^6$ is Cl, then $R^{1b}$ is not 3,4-difluorophenyl;

with the proviso that when $R^6$ is H, then $R^{1b}$ is not 3,5-difluorophenyl; and with the proviso that when $R^6$ is —CF₃, then $R^{1b}$ is not 3,5-difluorophenyl.

Yet another embodiment provides a compound having formula (IC):

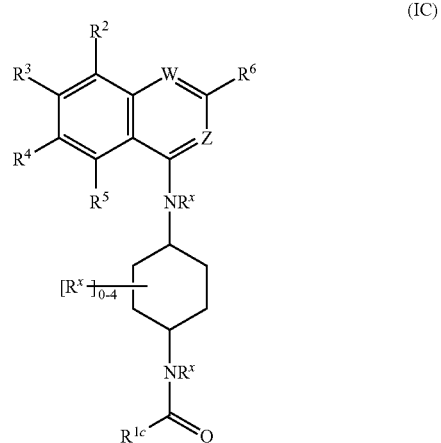

(IC)

or a pharmaceutically acceptable salt, isomer, hydrate, solvate or isotope thereof, wherein:

$R^{1c}$ is heterocyclyl, —(CH₂)ₙQ, —CHQR, or —CQ(R)₂;

Q is heterocyclyl, —OR, —CH₂C(O)OR, —C(O)OR, —C(O)NHR, —OC(O)R, —CX₃, —CX₂H, —C(X)H₂, —CN, —N(R)₂, —N(R)C(O)R, —N(R)C(O)OR, or —N(R)S(O)₂R, where $R^{1c}$ and/or Q is optionally substituted with one or more $R^q$;

each R is independently H, $C_{1-6}$ alkyl, $C_{2-6}$ alkenyl, $C_{2-6}$ alkynyl, alkylamino, —(CH₂)ₙR', X, aryl, cycloalkyl, heteroaryl, or heterocyclyl, or two R groups together with the atom to which it is attached forms a carbocycle;

each $R^q$ is independently $C_{1-6}$ alkyl, $C_{2-6}$ alkenyl, $C_{2-6}$ alkynyl, aryl, cycloalkyl, heteroaryl, heterocyclyl, —OR, —O(CH₂)ₙR, —OX₃, —OX₂H, —O(X)H₂, —C(O)OR, —C(O)R, —OC(O)R, X, —CX₃, —CX₂H, —C(X)H₂, —CN, —N(R)₂, —N(R)C(O)R, —N(R)S(O)₂R, S(O)₂R, —C(H)Q'R, or —(CH₂)ₙQ' where Q' is selected from C_{1-6} alkyl, aryl, cycloalkyl, heterocyclyl, OR', —C(O)OR', —OC(O)R', —CX₃, —CX₂H, —C(X)H₂, —CN, —N(R')₂, —N(R')C(O)R', and —N(R')S(O)₂R';

R², R⁴, and R⁶ are at each occurrence, independently H, C_{1-6} alkyl, C_{2-6} alkenyl, C_{2-6} alkynyl, aryl, cycloalkyl, heteroaryl, heterocyclyl, —OR, —C(O)OR, —OC(O)R, X, —CX₃, —CX₂H, —C(X)H₂, C(X)₂R, —C(X)(R)₂, —CN, —N(R)₂, —N(R)C(O)R, —N(R)S(O)₂R, or S(O)₂R;

R³ is at each occurrence, independently C_{1-6} alkyl, C_{2-6} alkenyl, H, OH, F, Br, I, —N(R)₂, —N(R)C(O)R, —N(R)C(O)OR, or —N(R)S(O)₂R;

R⁶ is at each occurrence, independently H, C_{1-6} alkyl, C_{2-6} alkenyl, X, —CF₃, —CF₂H, —C(F)H₂, C(F)₂R, or —C(F)(R)₂;

each R^x is independently H, C_{1-6} alkyl, C_{2-6} alkenyl, C_{2-6} alkynyl, aryl, cycloalkyl, heteroaryl, heterocyclyl, —OR, —C(O)OR, —OC(O)R, X, —CX₃, —CX₂H, —C(X)H₂, —CN, —N(R)₂, —N(R)C(O)R, —N(R)S(O)₂R, and S(O)₂R;

each R' is independently H, C_{1-6} alkyl, C_{2-6} alkenyl, C_{2-6} alkynyl, aryl, cycloalkyl, heteroaryl, or heterocyclyl;

W is N or CR^w;

Z is N or CR^z;

R^w is C_{1-6} alkyl, C_{2-6} alkenyl, C_{2-6} alkynyl, H, aryl, cycloalkyl, heteroaryl, or heterocyclyl;

R^z is C_{1-6} alkyl, C_{2-6} alkenyl, H, OH, F, Br, I, —N(R)₂, —N(R)C(O)R, —N(R)C(O)OR, or —N(R)S(O)₂R;

each X is independently F, Cl, Br, and I;

n is independently 0, 1, 2, 3, 4 and 5; and 4 with the proviso that when R⁶ is Cl, then R^{1b} is not 2-phenoxy pyridine.

In one embodiment, a compound is selected from any one of the compounds listed in Table I, or a pharmaceutically acceptable salt, isomer, hydrate, solvate or isotope thereof.

TABLE I

Representative compounds having Structure (I)

| Structure | Cpd No. |
|---|---|

1-1

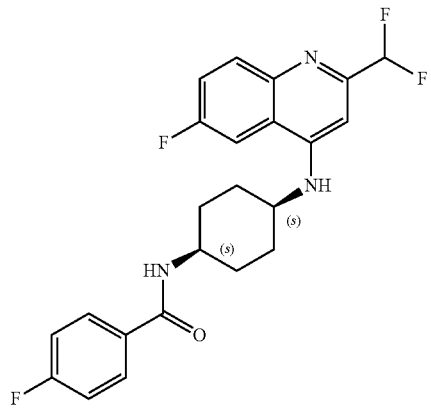 [SMILES: O=C(N[C@H]1CC[C@@H](Nc2cc(C(F)F)nc3ccc(F)cc23)CC1)c1ccc(F)cc1]

1-2

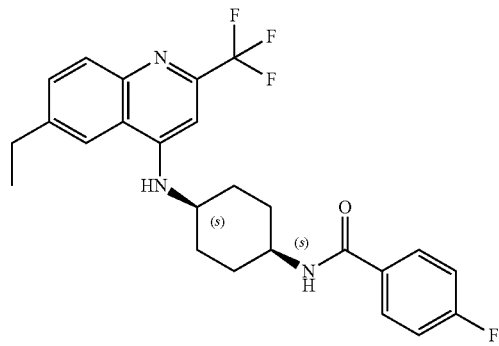 [SMILES: CCc1ccc2nc(C(F)(F)F)cc(N[C@H]3CC[C@@H](NC(=O)c4ccc(F)cc4)CC3)c2c1]

TABLE I-continued
Representative compounds having Structure (I)
| Structure | Cpd No. |
|---|---|
| 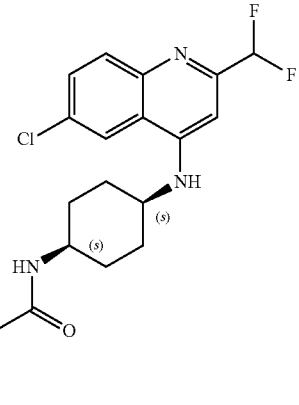 | 1-3 |
| 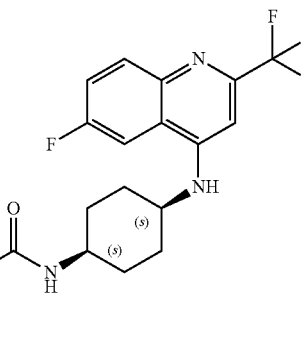 | 1-4 |
| 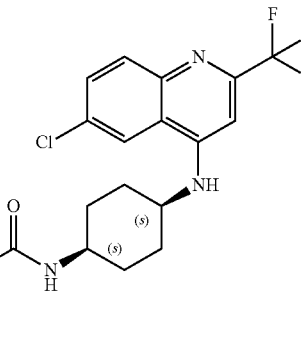 | 1-5 |
| 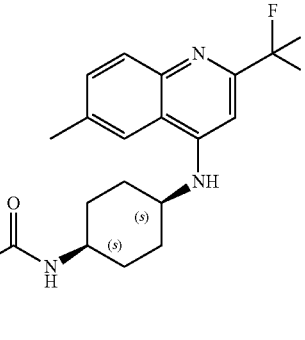 | 1-6 |

TABLE I-continued

Representative compounds having Structure (I)

| Structure | Cpd No. |
|---|---|
| 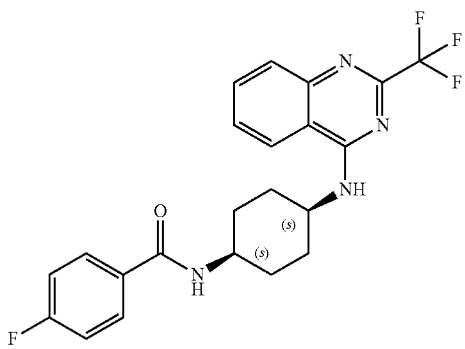 [SMILES: O=C(N[C@H]1CC[C@@H](Nc2nc(C(F)(F)F)nc3ccccc23)CC1)c1ccc(F)cc1] | 1-7 |
| 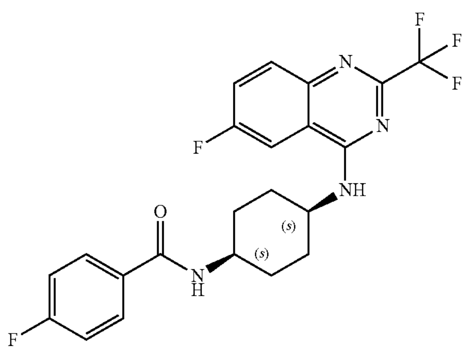 [SMILES: O=C(N[C@H]1CC[C@@H](Nc2nc(C(F)(F)F)nc3ccc(F)cc23)CC1)c1ccc(F)cc1] | 1-8 |
| 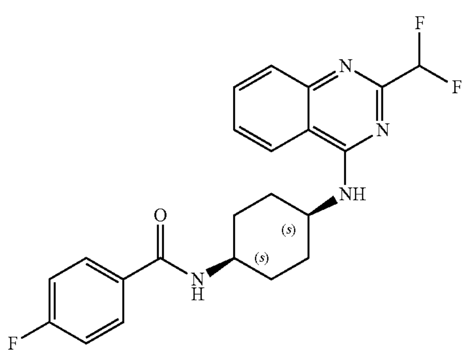 [SMILES: O=C(N[C@H]1CC[C@@H](Nc2nc(C(F)F)nc3ccccc23)CC1)c1ccc(F)cc1] | 1-9 |
| 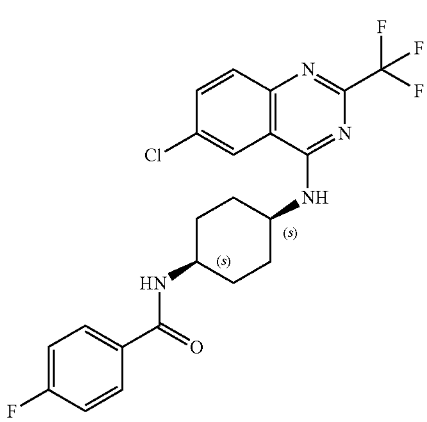 [SMILES: O=C(N[C@H]1CC[C@@H](Nc2nc(C(F)(F)F)nc3ccc(Cl)cc23)CC1)c1ccc(F)cc1] | 2-1 |

TABLE I-continued

Representative compounds having Structure (I)

| Structure | Cpd No. |
|---|---|
| 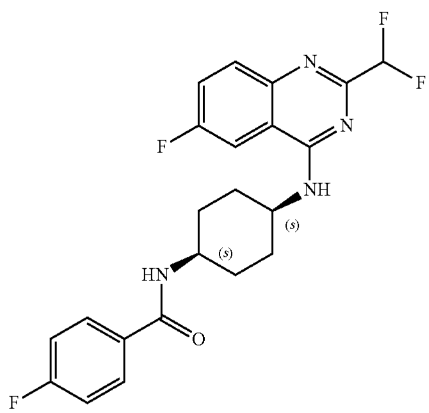 [SMILES: O=C(N[C@H]1CC[C@@H](Nc2nc(C(F)F)nc3ccc(F)cc23)CC1)c1ccc(F)cc1] | 2-2 |
| 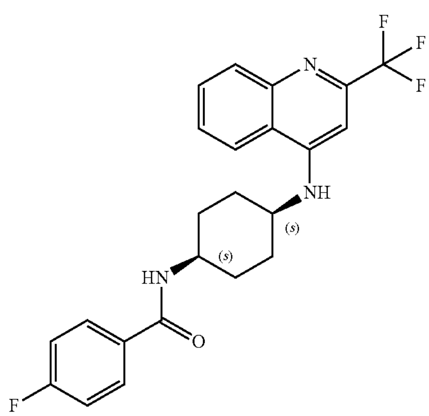 [SMILES: O=C(N[C@H]1CC[C@@H](Nc2cc(C(F)(F)F)nc3ccccc23)CC1)c1ccc(F)cc1] | 3-1 |
| 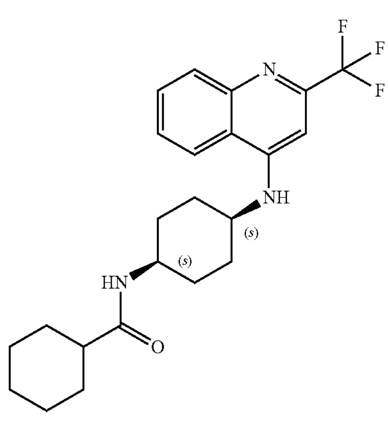 [SMILES: O=C(N[C@H]1CC[C@@H](Nc2cc(C(F)(F)F)nc3ccccc23)CC1)C1CCCCC1] | 3-2 |

TABLE I-continued
Representative compounds having Structure (I)
| Structure | Cpd No. |
|---|---|
| 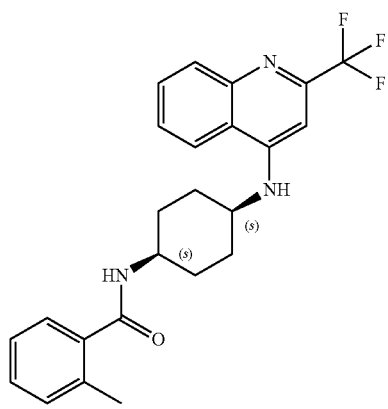 [SMILES: Cc1ccccc1C(=O)N[C@H]1CC[C@@H](Nc2cc(C(F)(F)F)nc3ccccc23)CC1] | 3-3 |
| 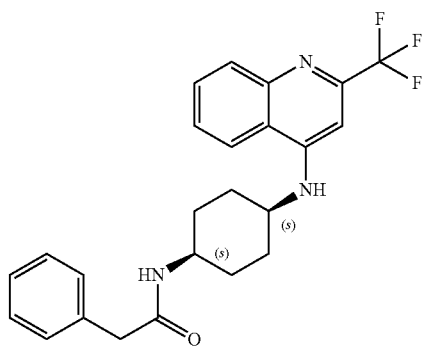 [SMILES: O=C(Cc1ccccc1)N[C@H]1CC[C@@H](Nc2cc(C(F)(F)F)nc3ccccc23)CC1] | 3-4 |
| 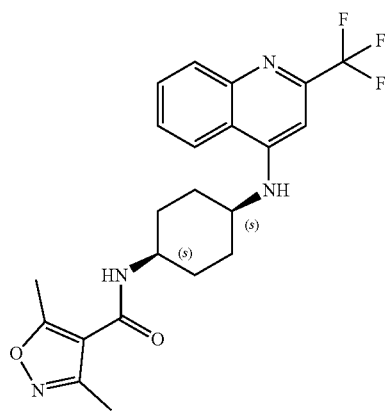 [SMILES: Cc1noc(C)c1C(=O)N[C@H]1CC[C@@H](Nc2cc(C(F)(F)F)nc3ccccc23)CC1] | 3-5 |

TABLE I-continued

Representative compounds having Structure (I)

| Structure | Cpd No. |
|---|---|
| 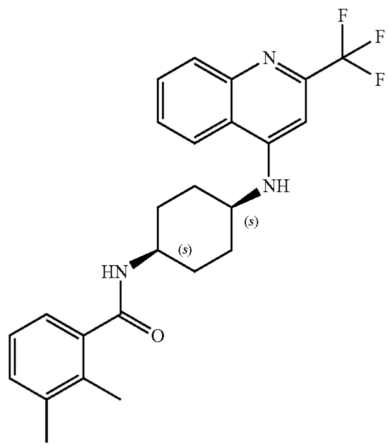 [SMILES: Cc1cccc(C(=O)N[C@H]2CC[C@@H](Nc3cc(C(F)(F)F)nc4ccccc34)CC2)c1C] | 3-6 |
| 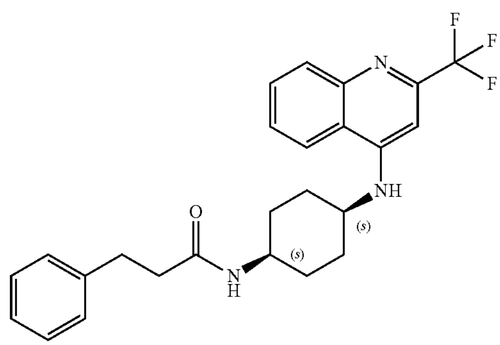 [SMILES: O=C(CCc1ccccc1)N[C@H]1CC[C@@H](Nc2cc(C(F)(F)F)nc3ccccc23)CC1] | 3-7 |
| 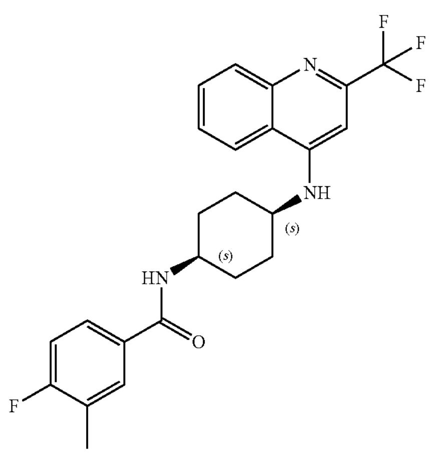 [SMILES: Cc1cc(C(=O)N[C@H]2CC[C@@H](Nc3cc(C(F)(F)F)nc4ccccc34)CC2)ccc1F] | 3-8 |
| 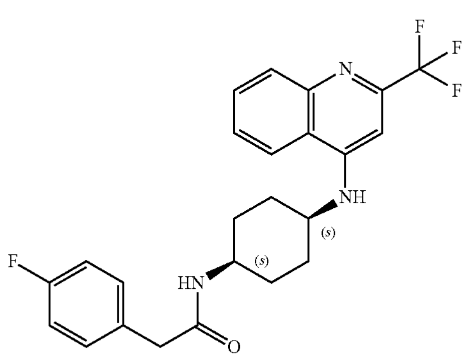 [SMILES: O=C(Cc1ccc(F)cc1)N[C@H]1CC[C@@H](Nc2cc(C(F)(F)F)nc3ccccc23)CC1] | 3-9 |

TABLE I-continued
Representative compounds having Structure (I)
| Structure | Cpd No. |
|---|---|
| 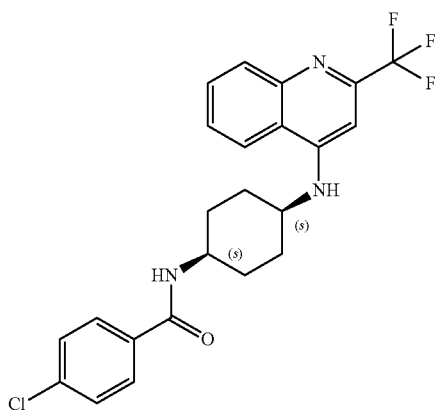 [SMILES: O=C(N[C@H]1CC[C@@H](Nc2cc(C(F)(F)F)nc3ccccc23)CC1)c1ccc(Cl)cc1] | 3-10 |
| 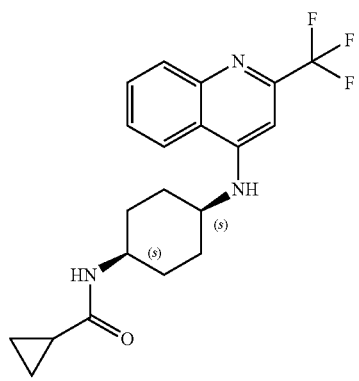 [SMILES: O=C(N[C@H]1CC[C@@H](Nc2cc(C(F)(F)F)nc3ccccc23)CC1)C1CC1] | 3-11 |
| 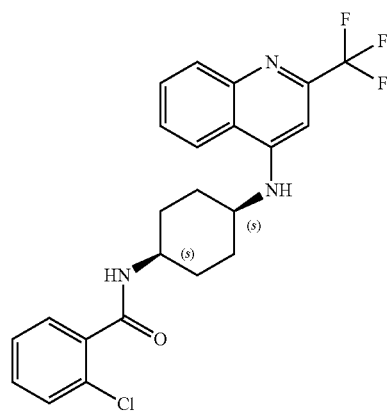 [SMILES: O=C(N[C@H]1CC[C@@H](Nc2cc(C(F)(F)F)nc3ccccc23)CC1)c1ccccc1Cl] | 3-12 |

TABLE I-continued
Representative compounds having Structure (I)
| Structure | Cpd No. |
|---|---|
| 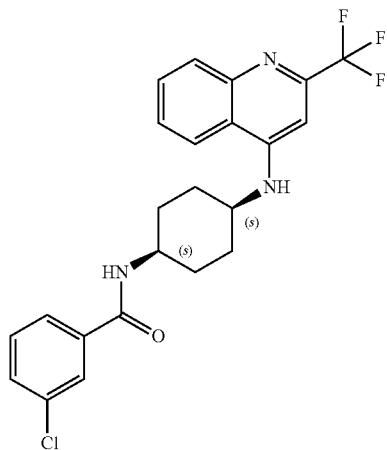 [SMILES: O=C(N[C@H]1CC[C@@H](Nc2cc(C(F)(F)F)nc3ccccc23)CC1)c1cccc(Cl)c1] | 3-13 |
| 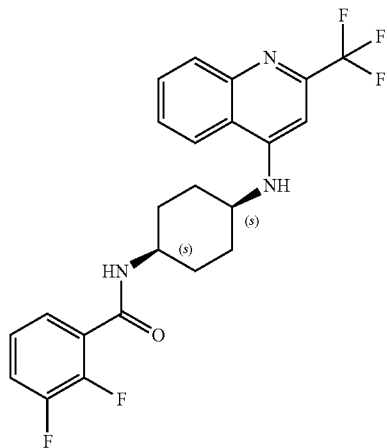 [SMILES: O=C(N[C@H]1CC[C@@H](Nc2cc(C(F)(F)F)nc3ccccc23)CC1)c1cccc(F)c1F] | 3-14 |
| 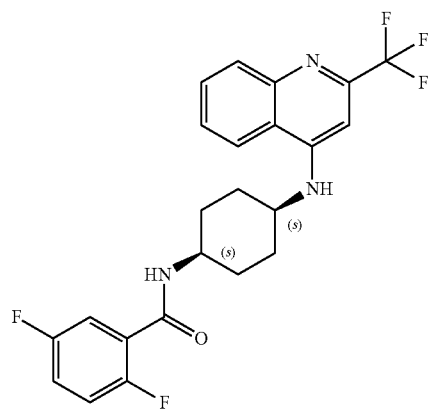 [SMILES: O=C(N[C@H]1CC[C@@H](Nc2cc(C(F)(F)F)nc3ccccc23)CC1)c1cc(F)ccc1F] | 3-15 |

TABLE I-continued
Representative compounds having Structure (I)
| Structure | Cpd No. |
|---|---|
| 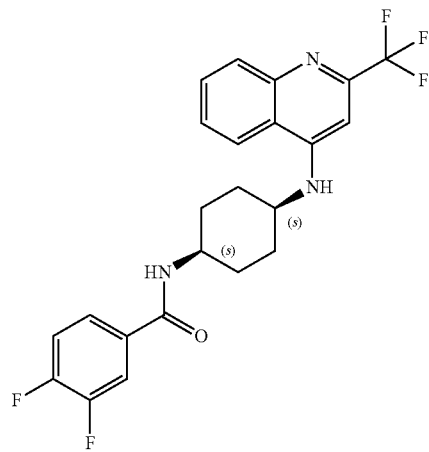 [SMILES: O=C(N[C@H]1CC[C@@H](Nc2cc(C(F)(F)F)nc3ccccc23)CC1)c1ccc(F)c(F)c1] | 3-16 |
| 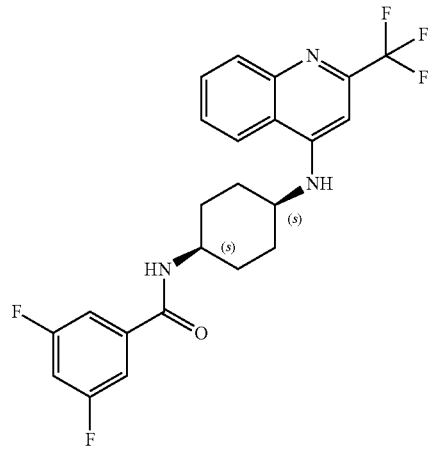 [SMILES: O=C(N[C@H]1CC[C@@H](Nc2cc(C(F)(F)F)nc3ccccc23)CC1)c1cc(F)cc(F)c1] | 3-17 |
| 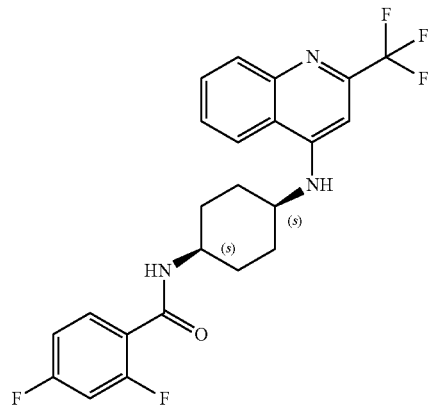 [SMILES: O=C(N[C@H]1CC[C@@H](Nc2cc(C(F)(F)F)nc3ccccc23)CC1)c1ccc(F)cc1F] | 3-18 |

TABLE I-continued

Representative compounds having Structure (I)

| Structure | Cpd No. |
|---|---|
| 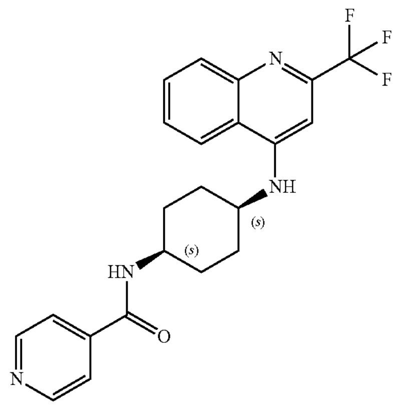 [SMILES: O=C(N[C@H]1CC[C@@H](Nc2cc(C(F)(F)F)nc3ccccc23)CC1)c1ccncc1] | 3-19 |
| 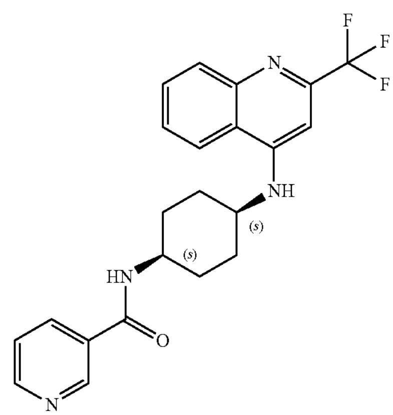 [SMILES: O=C(N[C@H]1CC[C@@H](Nc2cc(C(F)(F)F)nc3ccccc23)CC1)c1cccnc1] | 3-20 |
| 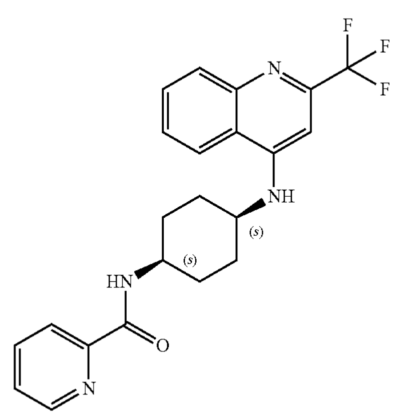 [SMILES: O=C(N[C@H]1CC[C@@H](Nc2cc(C(F)(F)F)nc3ccccc23)CC1)c1ccccn1] | 3-21 |

TABLE I-continued
Representative compounds having Structure (I)
| Structure | Cpd No. |
|---|---|
| 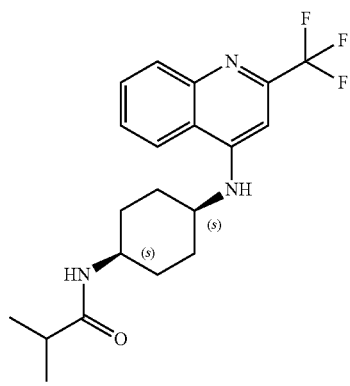 [SMILES: CC(C)C(=O)N[C@H]1CC[C@@H](Nc2cc(C(F)(F)F)nc3ccccc23)CC1] | 3-22 |
| 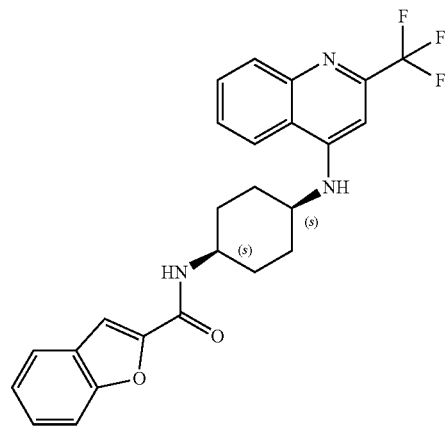 [SMILES: O=C(N[C@H]1CC[C@@H](Nc2cc(C(F)(F)F)nc3ccccc23)CC1)c1cc2ccccc2o1] | 3-23 |
| 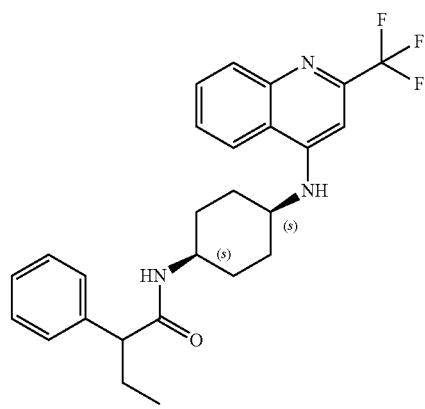 [SMILES: CCC(C(=O)N[C@H]1CC[C@@H](Nc2cc(C(F)(F)F)nc3ccccc23)CC1)c1ccccc1] | 3-24 |

TABLE I-continued
Representative compounds having Structure (I)
| Structure | Cpd No. |
|---|---|
| 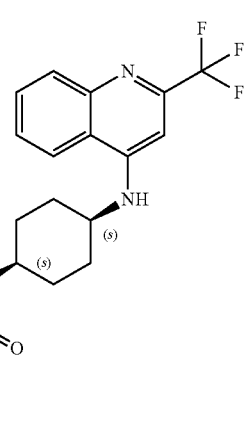 | 3-25 |
| 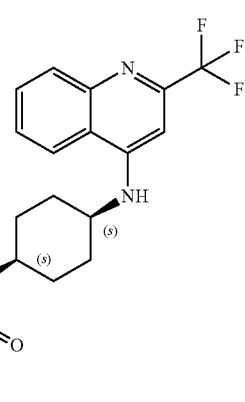 | 3-26 |
| 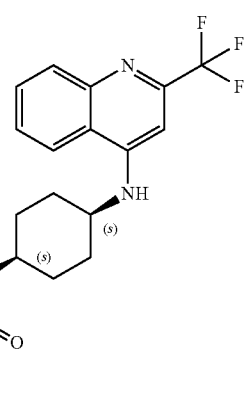 | 3-27 |

TABLE I-continued
Representative compounds having Structure (I)
| Structure | Cpd No. |
|---|---|
| 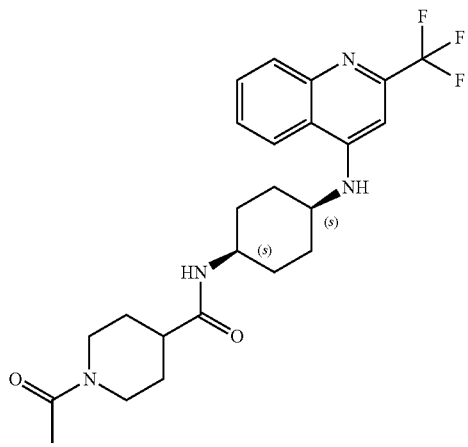 [SMILES: CC(=O)N1CCC(C(=O)N[C@H]2CC[C@@H](Nc3cc(C(F)(F)F)nc4ccccc34)CC2)CC1] | 3-28 |
| 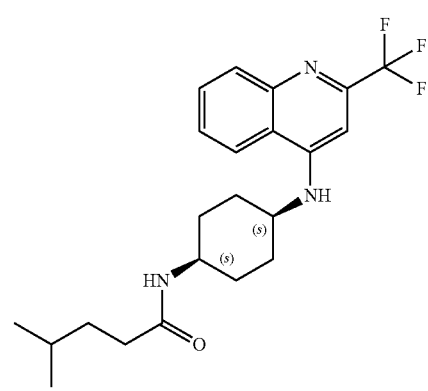 [SMILES: CC(C)CCC(=O)N[C@H]1CC[C@@H](Nc2cc(C(F)(F)F)nc3ccccc23)CC1] | 3-29 |
| 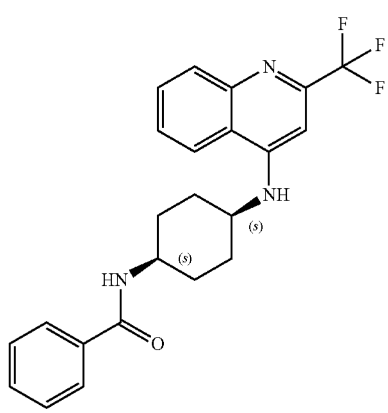 [SMILES: O=C(N[C@H]1CC[C@@H](Nc2cc(C(F)(F)F)nc3ccccc23)CC1)c1ccccc1] | 3-30 |

TABLE I-continued

Representative compounds having Structure (I)

| Structure | Cpd No. |
|---|---|
| 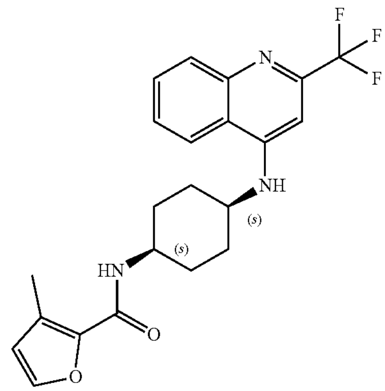 [SMILES: Cc1ccoc1C(=O)N[C@H]1CC[C@@H](Nc2cc(C(F)(F)F)nc3ccccc23)CC1] | 3-31 |
| 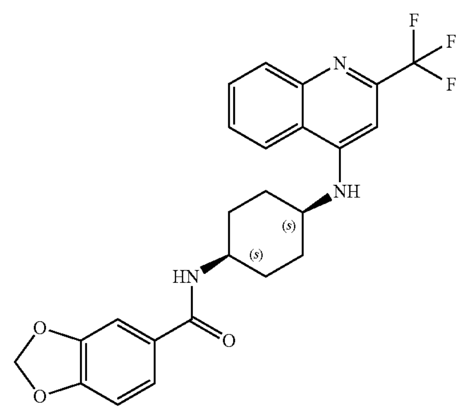 [SMILES: O=C(N[C@H]1CC[C@@H](Nc2cc(C(F)(F)F)nc3ccccc23)CC1)c1ccc2c(c1)OCO2] | 3-32 |
| 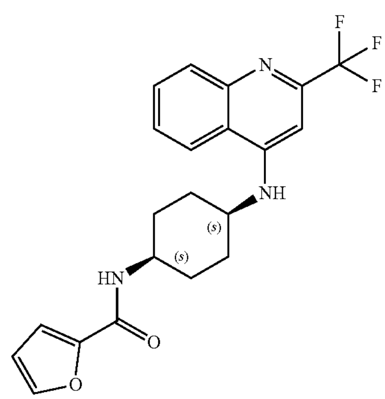 [SMILES: O=C(N[C@H]1CC[C@@H](Nc2cc(C(F)(F)F)nc3ccccc23)CC1)c1ccco1] | 3-33 |
| 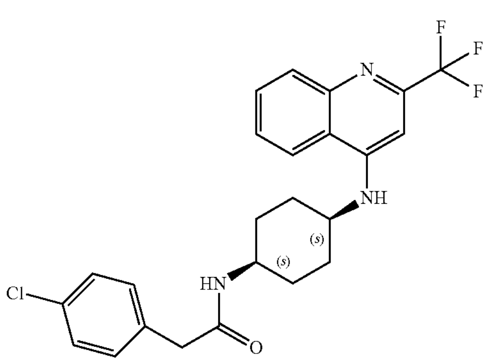 [SMILES: O=C(Cc1ccc(Cl)cc1)N[C@H]1CC[C@@H](Nc2cc(C(F)(F)F)nc3ccccc23)CC1] | 3-34 |

TABLE I-continued

Representative compounds having Structure (I)

| Structure | Cpd No. |
|---|---|
| 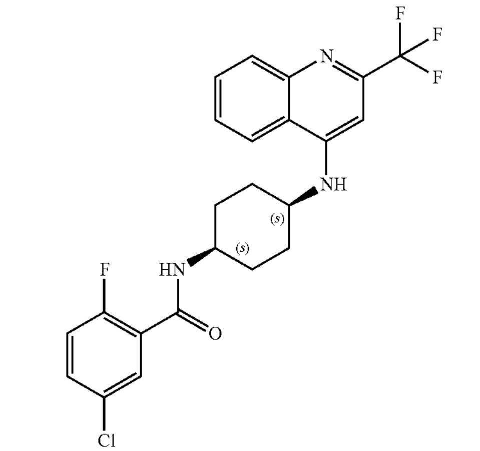 [SMILES: O=C(N[C@H]1CC[C@@H](Nc2cc(C(F)(F)F)nc3ccccc23)CC1)c1cc(Cl)ccc1F] | 3-35 |
| 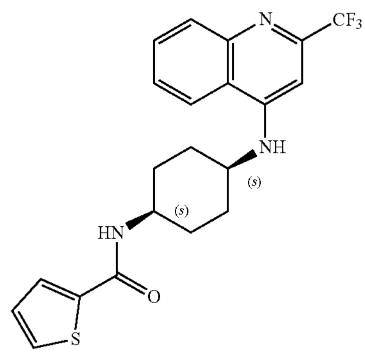 [SMILES: O=C(N[C@H]1CC[C@@H](Nc2cc(C(F)(F)F)nc3ccccc23)CC1)c1cccs1] | 3-36 |
| 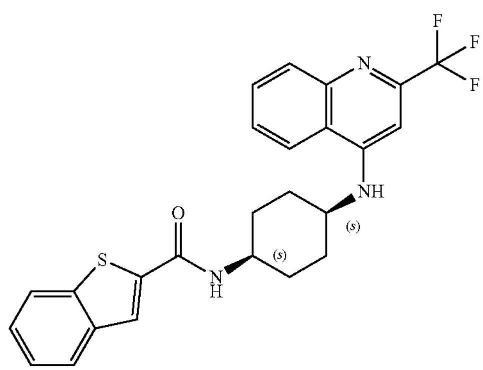 [SMILES: O=C(N[C@H]1CC[C@@H](Nc2cc(C(F)(F)F)nc3ccccc23)CC1)c1cc2ccccc2s1] | 3-37 |
| 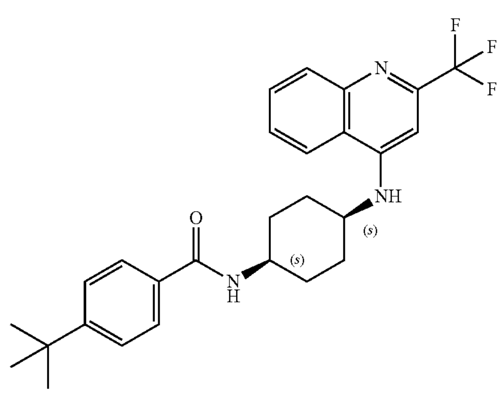 [SMILES: CC(C)(C)c1ccc(C(=O)N[C@H]2CC[C@@H](Nc3cc(C(F)(F)F)nc4ccccc34)CC2)cc1] | 3-38 |

TABLE I-continued

Representative compounds having Structure (I)

| Structure | Cpd No. |
|---|---|
| (structure) | 3-39 |
| (structure) | 3-40 |
| (structure) | 3-41 |
| (structure) | 3-42 |

TABLE I-continued

Representative compounds having Structure (I)

| Structure | Cpd No. |
|---|---|
| 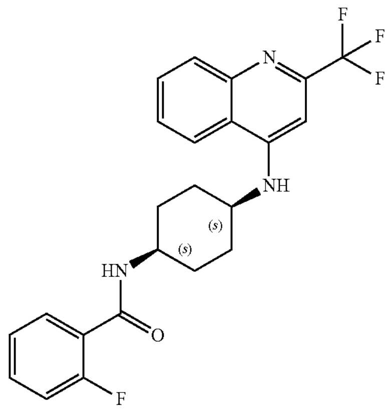 [SMILES: O=C(N[C@H]1CC[C@@H](Nc2cc(C(F)(F)F)nc3ccccc23)CC1)c1ccccc1F] | 3-43 |
| 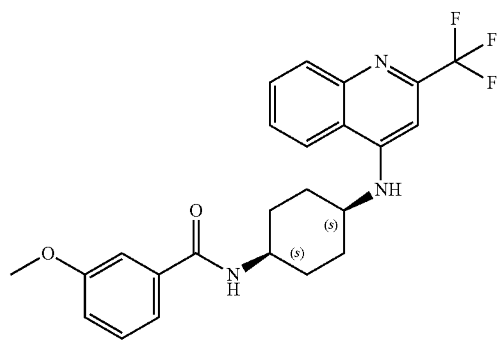 [SMILES: COc1cccc(C(=O)N[C@H]2CC[C@@H](Nc3cc(C(F)(F)F)nc4ccccc34)CC2)c1] | 3-44 |
| 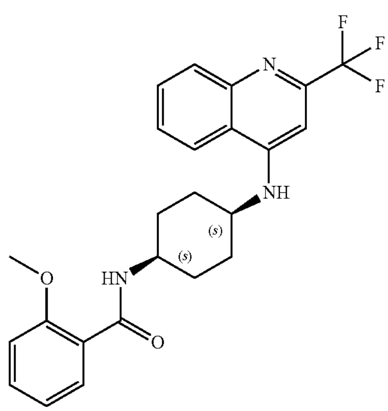 [SMILES: COc1ccccc1C(=O)N[C@H]1CC[C@@H](Nc2cc(C(F)(F)F)nc3ccccc23)CC1] | 3-45 |
| 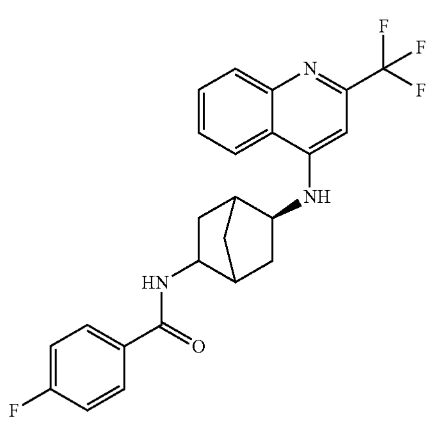 [SMILES: O=C(NC1CC2CC1C[C@@H]2Nc1cc(C(F)(F)F)nc2ccccc12)c1ccc(F)cc1] | 3-46 |

TABLE I-continued
Representative compounds having Structure (I)
| Structure | Cpd No. |
|---|---|
| 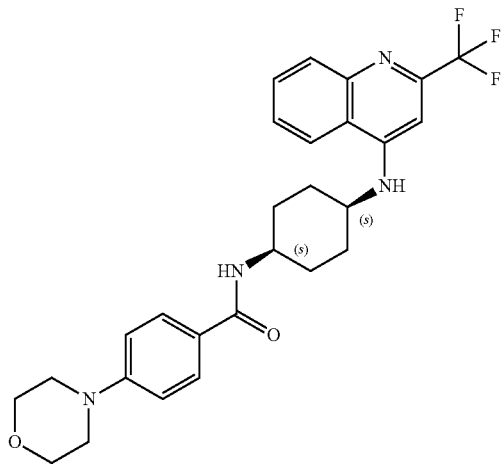 [SMILES: O=C(N[C@H]1CC[C@@H](Nc2cc(C(F)(F)F)nc3ccccc23)CC1)c1ccc(N2CCOCC2)cc1] | 4-1 |
| 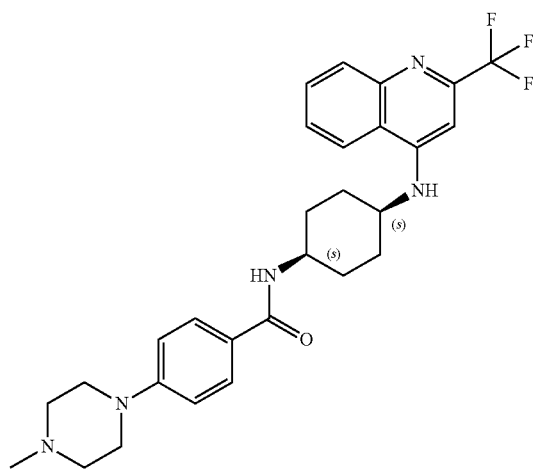 [SMILES: CN1CCN(c2ccc(C(=O)N[C@H]3CC[C@@H](Nc4cc(C(F)(F)F)nc5ccccc45)CC3)cc2)CC1] | 4-2 |
| 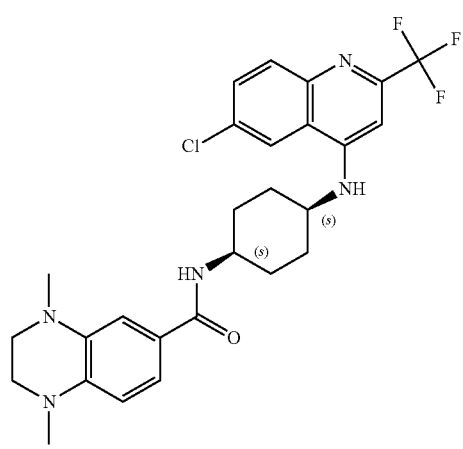 [SMILES: CN1CCN(C)c2cc(C(=O)N[C@H]3CC[C@@H](Nc4cc(C(F)(F)F)nc5ccc(Cl)cc45)CC3)ccc21] | 4-3 |

TABLE I-continued
Representative compounds having Structure (I)
| Structure | Cpd No. |
|---|---|
| 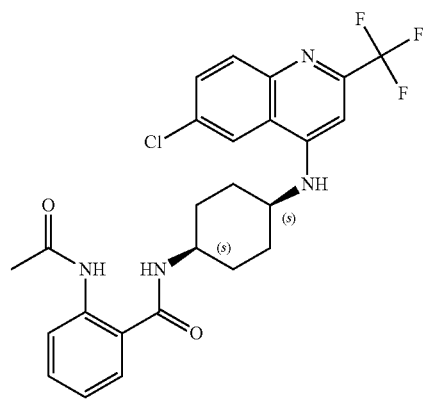 [SMILES: CC(=O)Nc1ccccc1C(=O)N[C@H]1CC[C@@H](Nc2cc(C(F)(F)F)nc3ccc(Cl)cc23)CC1] | 4-4 |
| 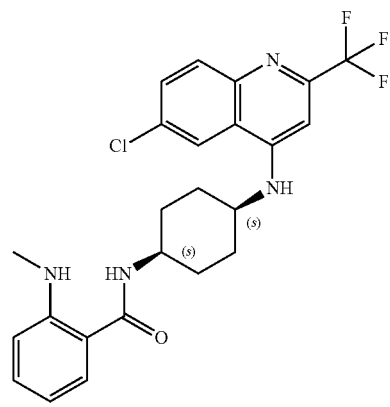 [SMILES: CNc1ccccc1C(=O)N[C@H]1CC[C@@H](Nc2cc(C(F)(F)F)nc3ccc(Cl)cc23)CC1] | 4-5 |
| 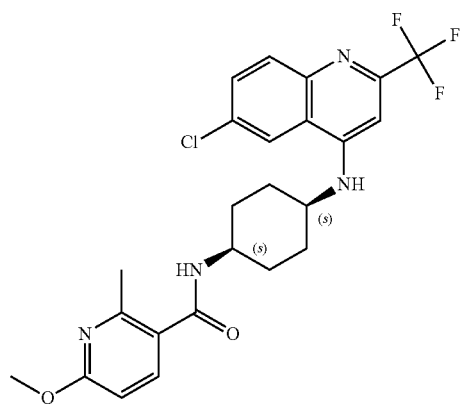 [SMILES: COc1ccc(C(=O)N[C@H]2CC[C@@H](Nc3cc(C(F)(F)F)nc4ccc(Cl)cc34)CC2)c(C)n1] | 4-6 |

TABLE I-continued

Representative compounds having Structure (I)

| Structure | Cpd No. |
|---|---|
| 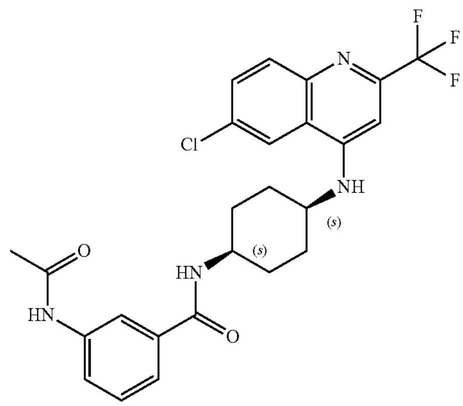 [SMILES: CC(=O)Nc1cccc(C(=O)N[C@H]2CC[C@@H](Nc3cc(C(F)(F)F)nc4ccc(Cl)cc34)CC2)c1] | 4-7 |
| 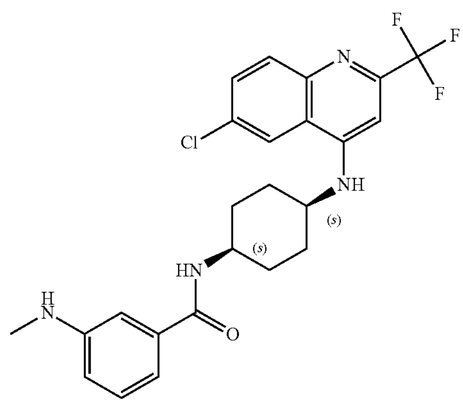 [SMILES: CNc1cccc(C(=O)N[C@H]2CC[C@@H](Nc3cc(C(F)(F)F)nc4ccc(Cl)cc34)CC2)c1] | 4-8 |
| 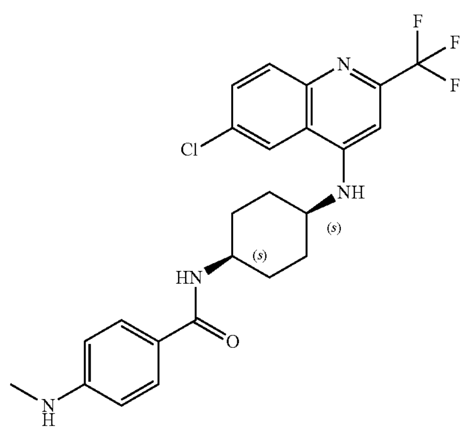 [SMILES: CNc1ccc(C(=O)N[C@H]2CC[C@@H](Nc3cc(C(F)(F)F)nc4ccc(Cl)cc34)CC2)cc1] | 4-9 |
| 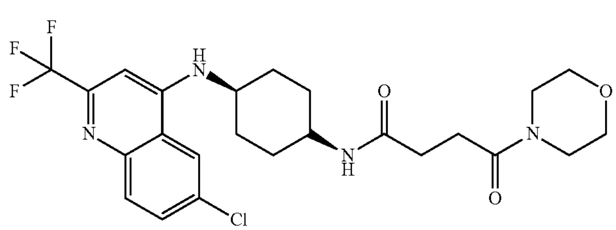 | 4-10 |

TABLE I-continued

Representative compounds having Structure (I)

| Structure | Cpd No. |
|---|---|
| 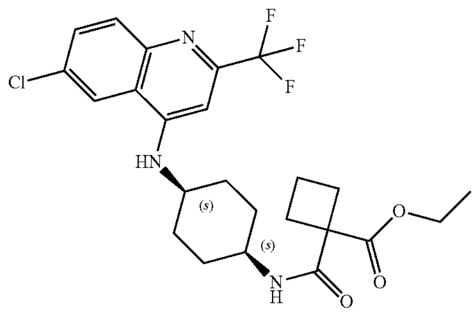 [SMILES: CCOC(=O)C1(C(=O)N[C@H]2CC[C@@H](Nc3cc(C(F)(F)F)nc4ccc(Cl)cc34)CC2)CCC1] | 4-11 |
| 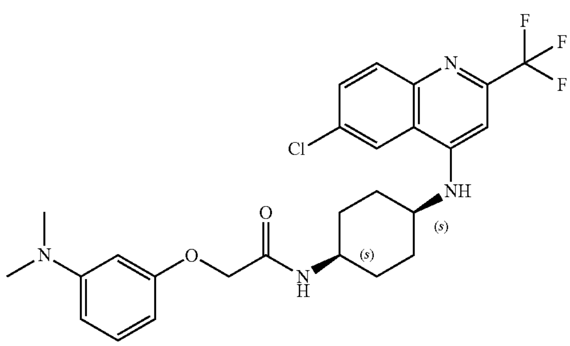 [SMILES: CN(C)c1cccc(OCC(=O)N[C@H]2CC[C@@H](Nc3cc(C(F)(F)F)nc4ccc(Cl)cc34)CC2)c1] | 4-12 |
| 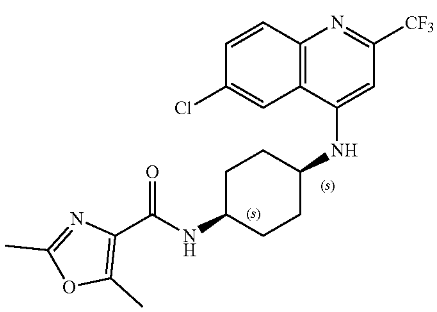 [SMILES: Cc1nc(C(=O)N[C@H]2CC[C@@H](Nc3cc(C(F)(F)F)nc4ccc(Cl)cc34)CC2)c(C)o1] | 4-13 |
| 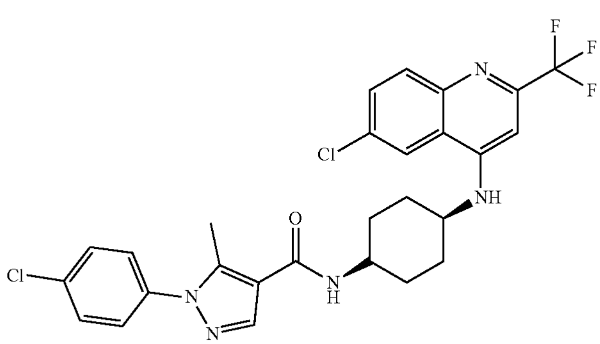 | 4-14 |

TABLE I-continued
Representative compounds having Structure (I)
| Structure | Cpd No. |
|---|---|
| 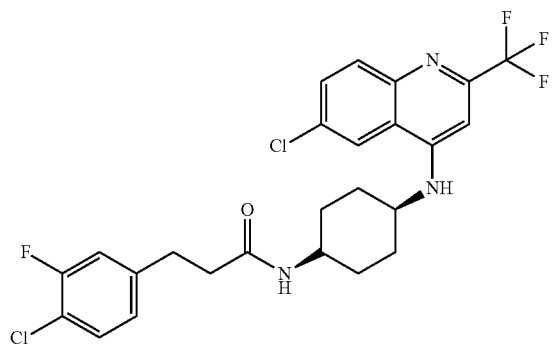 | 4-15 |
| 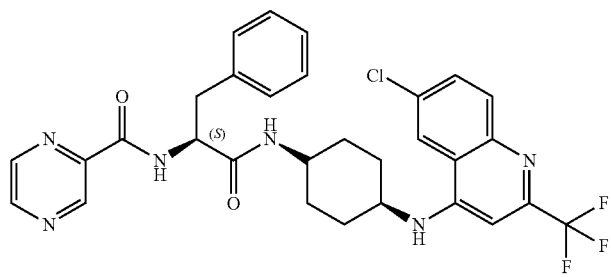 | 4-16 |
| 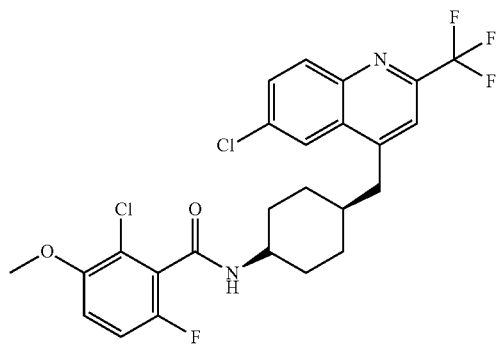 | 4-17 |
| 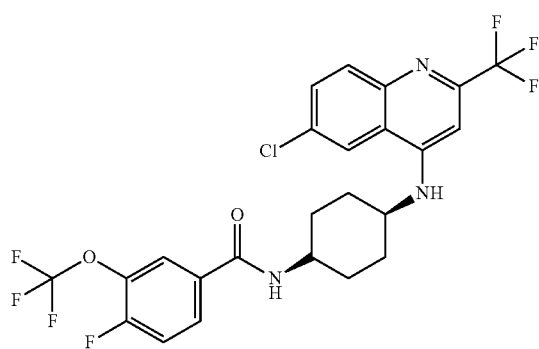 | 4-18 |

TABLE I-continued

Representative compounds having Structure (I)

| Structure | Cpd No. |
|---|---|
| 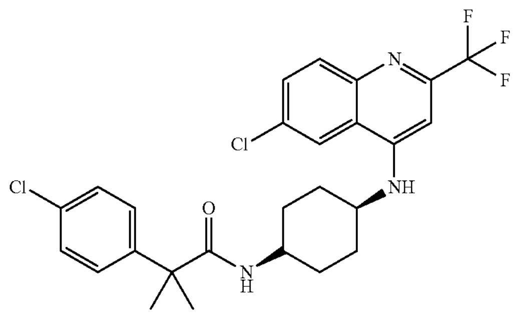 | 4-19 |
| 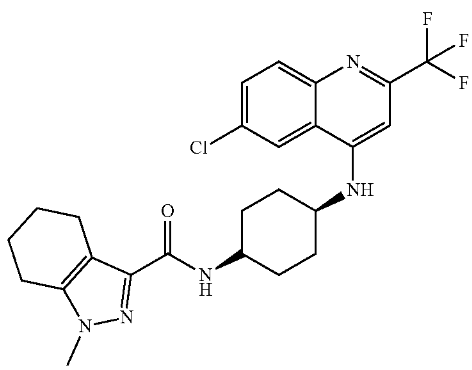 | 4-20 |
| 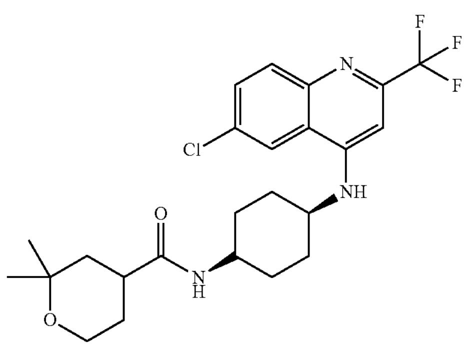 | 4-21 |
| 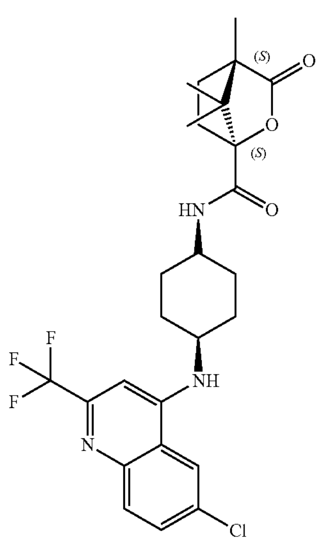 | 4-22 |

TABLE I-continued
Representative compounds having Structure (I)
| Structure | Cpd No. |
|---|---|
| 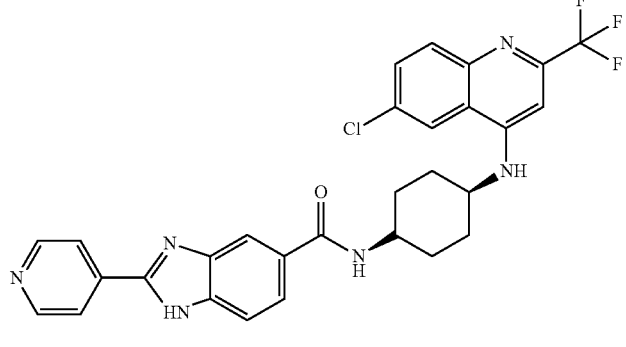 | 4-23 |
| 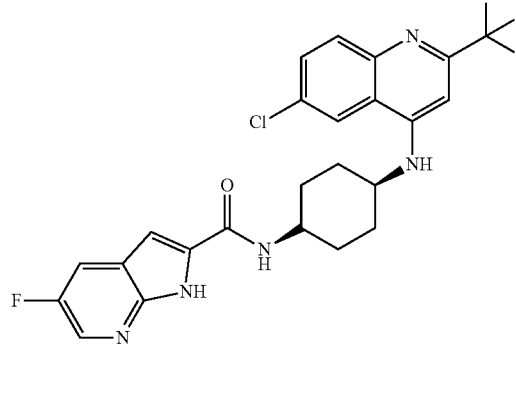 | 4-24 |
| 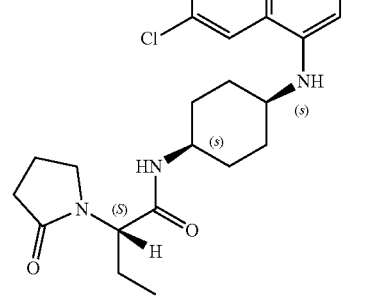 | 4-25 |

TABLE I-continued

Representative compounds having Structure (I)

| Structure | Cpd No. |
|---|---|
| 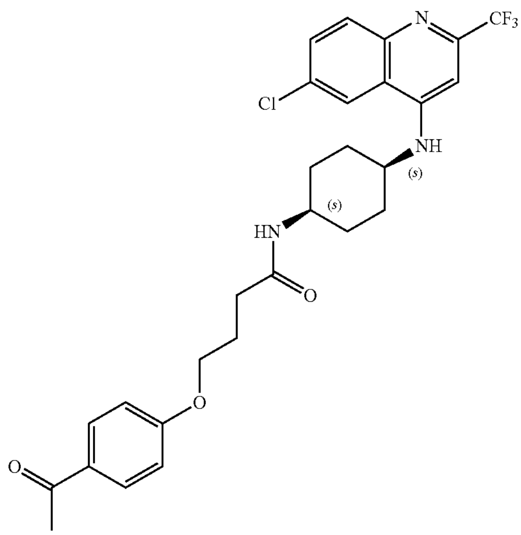 [SMILES: CC(=O)c1ccc(OCCCC(=O)N[C@H]2CC[C@@H](Nc3cc(C(F)(F)F)nc4ccc(Cl)cc34)CC2)cc1] | 4-26 |
| 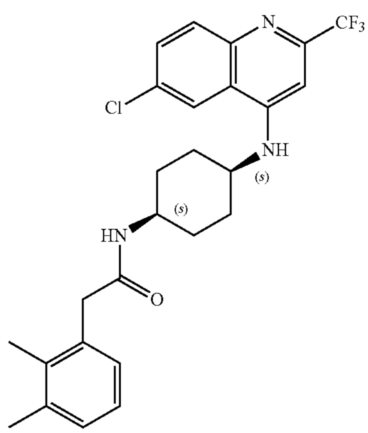 [SMILES: Cc1cccc(CC(=O)N[C@H]2CC[C@@H](Nc3cc(C(F)(F)F)nc4ccc(Cl)cc34)CC2)c1C] | 4-27 |
| 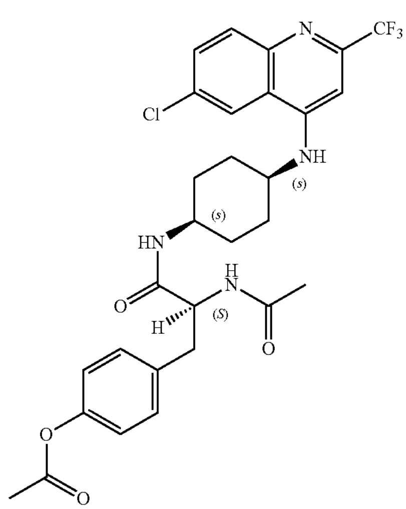 | 4-28 |

TABLE I-continued

Representative compounds having Structure (I)

| Structure | Cpd No. |
|---|---|
| 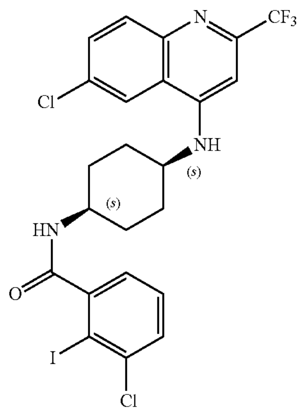 [SMILES: O=C(N[C@H]1CC[C@@H](Nc2cc(C(F)(F)F)nc3ccc(Cl)cc23)CC1)c1cccc(Cl)c1I] | 4-29 |
| 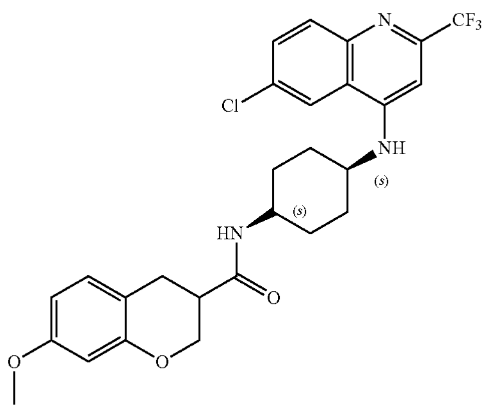 | 4-30 |
| 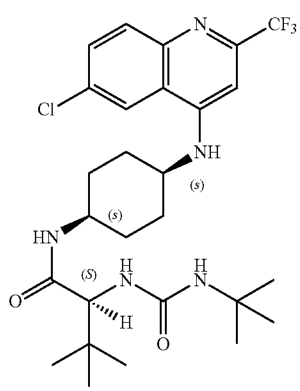 | 4-31 |
| 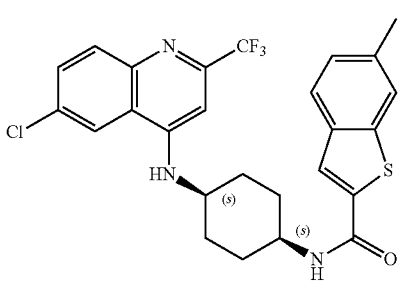 [SMILES: Cc1ccc2cc(C(=O)N[C@H]3CC[C@@H](Nc4cc(C(F)(F)F)nc5ccc(Cl)cc45)CC3)sc2c1] | 4-32 |

TABLE I-continued

Representative compounds having Structure (I)

| Structure | Cpd No. |
|---|---|
| 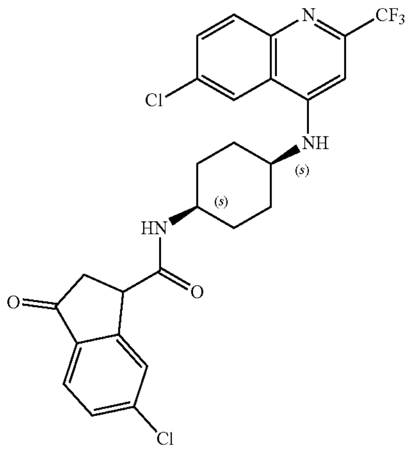 [SMILES: O=C1CC(C(=O)N[C@H]2CC[C@@H](Nc3cc(C(F)(F)F)nc4ccc(Cl)cc34)CC2)c2cc(Cl)ccc21] | 4-33 |
| 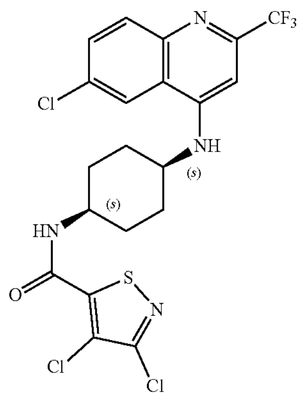 [SMILES: O=C(N[C@H]1CC[C@@H](Nc2cc(C(F)(F)F)nc3ccc(Cl)cc23)CC1)c1snc(Cl)c1Cl] | 4-34 |
| 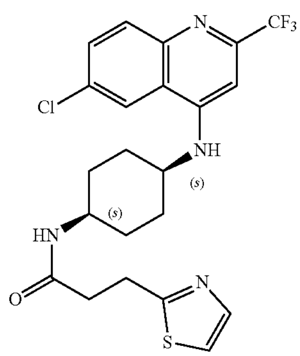 [SMILES: O=C(CCc1nccs1)N[C@H]1CC[C@@H](Nc2cc(C(F)(F)F)nc3ccc(Cl)cc23)CC1] | 4-35 |
| 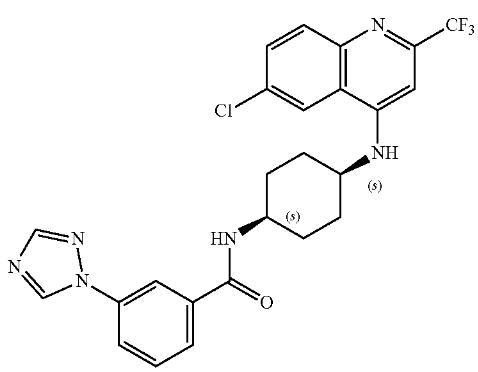 [SMILES: O=C(N[C@H]1CC[C@@H](Nc2cc(C(F)(F)F)nc3ccc(Cl)cc23)CC1)c1cccc(-n2cncn2)c1] | 4-36 |

TABLE I-continued
Representative compounds having Structure (I)
| Structure | Cpd No. |
|---|---|
| 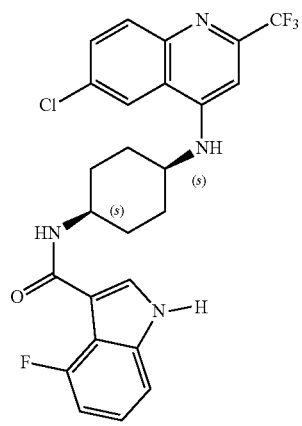 [SMILES: O=C(N[C@H]1CC[C@@H](Nc2cc(C(F)(F)F)nc3ccc(Cl)cc23)CC1)c1c[nH]c2cccc(F)c12] | 4-37 |
| 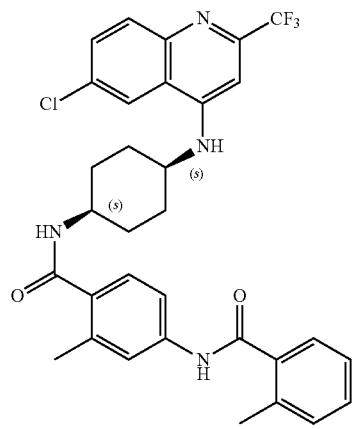 [SMILES: Cc1ccccc1C(=O)Nc1ccc(C(=O)N[C@H]2CC[C@@H](Nc3cc(C(F)(F)F)nc4ccc(Cl)cc34)CC2)c(C)c1] | 4-38 |
| 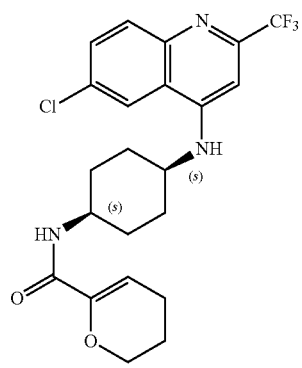 [SMILES: O=C(N[C@H]1CC[C@@H](Nc2cc(C(F)(F)F)nc3ccc(Cl)cc23)CC1)C1=CCCCO1] | 4-39 |

TABLE I-continued
Representative compounds having Structure (I)
| Structure | Cpd No. |
| --- | --- |
| 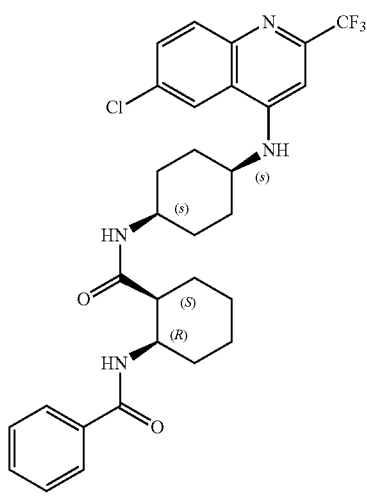 | 4-40 |
| 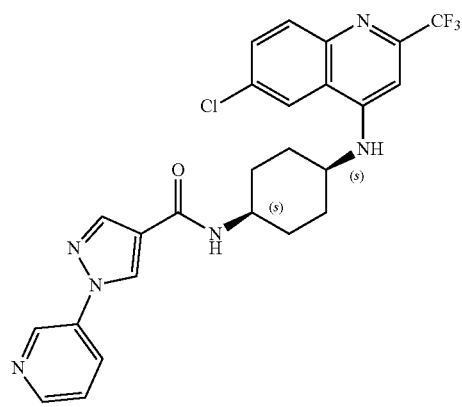 [SMILES: O=C(N[C@H]1CC[C@@H](Nc2cc(C(F)(F)F)nc3ccc(Cl)cc23)CC1)c1cnn(-c2cccnc2)c1] | 4-41 |
| 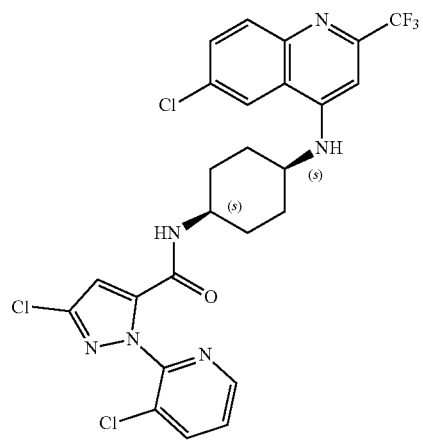 [SMILES: O=C(N[C@H]1CC[C@@H](Nc2cc(C(F)(F)F)nc3ccc(Cl)cc23)CC1)c1cc(Cl)nn1-c1ncccc1Cl] | 4-42 |

TABLE I-continued

Representative compounds having Structure (I)

| Structure | Cpd No. |
|---|---|
| 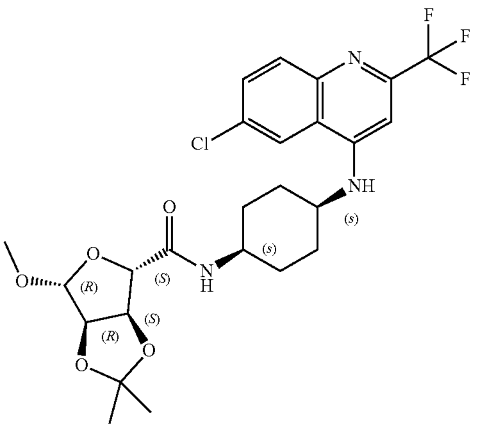 | 4-43 |
| 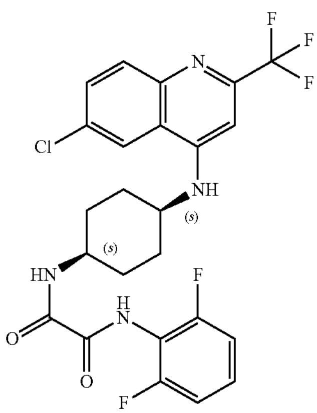 [SMILES: O=C(Nc1c(F)cccc1F)C(=O)N[C@H]1CC[C@@H](Nc2cc(C(F)(F)F)nc3ccc(Cl)cc23)CC1] | 4-44 |
| 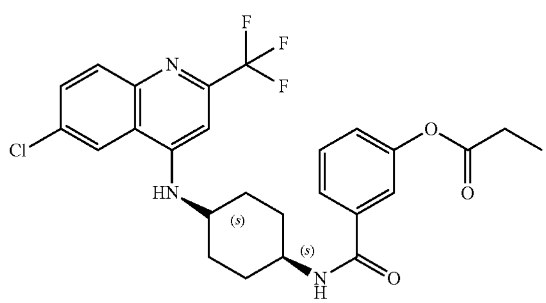 | 4-45 |
| 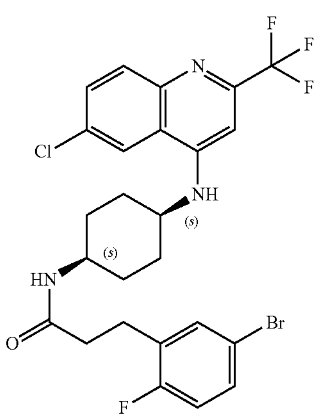 [SMILES: O=C(CCc1cc(Br)ccc1F)N[C@H]1CC[C@@H](Nc2cc(C(F)(F)F)nc3ccc(Cl)cc23)CC1] | 4-46 |

TABLE I-continued
Representative compounds having Structure (I)
| Structure | Cpd No. |
|---|---|
| 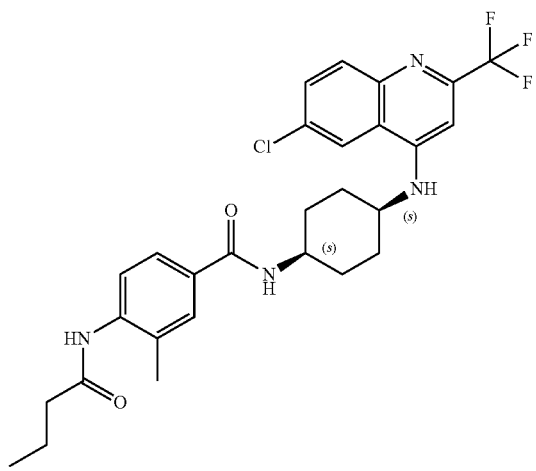 [SMILES: CCCC(=O)Nc1ccc(C(=O)N[C@H]2CC[C@@H](Nc3cc(C(F)(F)F)nc4ccc(Cl)cc34)CC2)cc1C] | 4-47 |
| 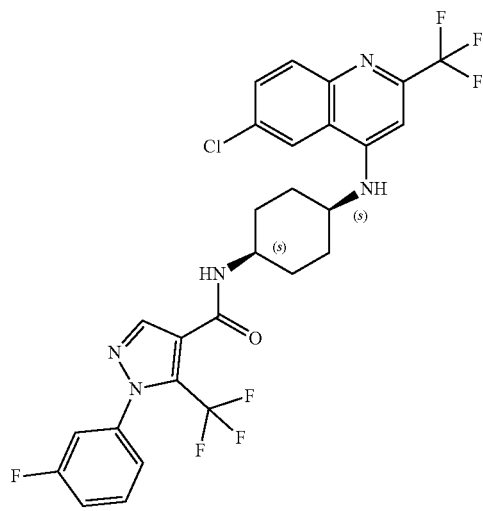 [SMILES: O=C(N[C@H]1CC[C@@H](Nc2cc(C(F)(F)F)nc3ccc(Cl)cc23)CC1)c1cnn(-c2cccc(F)c2)c1C(F)(F)F] | 4-48 |
| 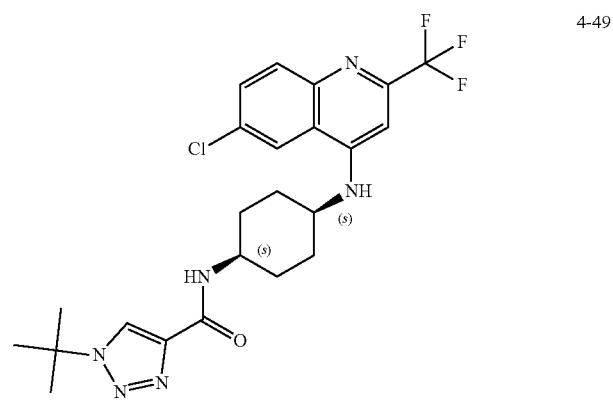 | 4-49 |

TABLE I-continued

Representative compounds having Structure (I)

| Structure | Cpd No. |
|---|---|
| 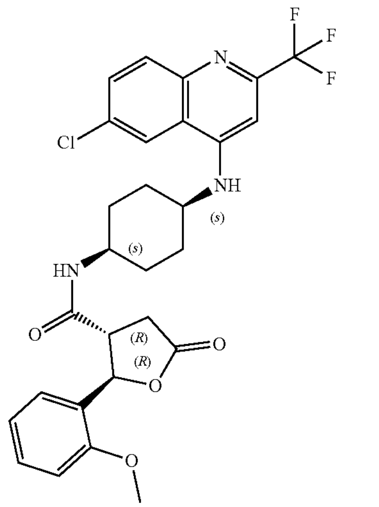 | 4-50 |
| 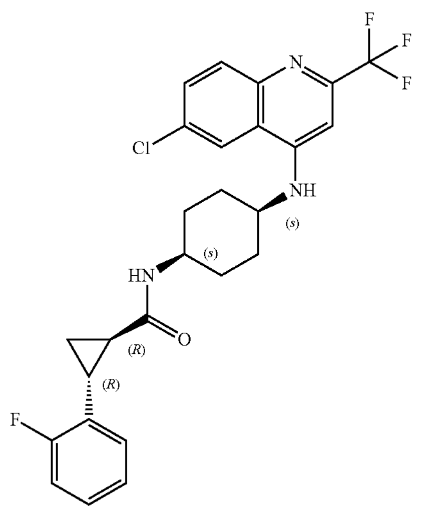 | 4-51 |
| 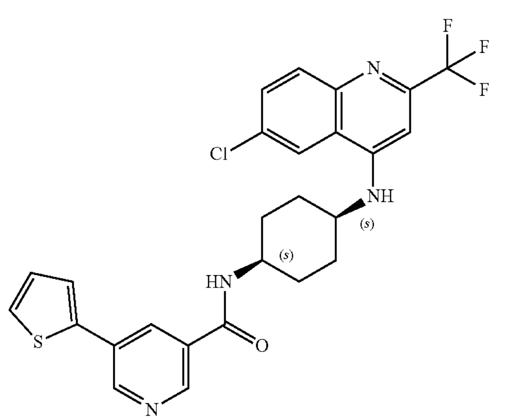 [SMILES: O=C(N[C@H]1CC[C@@H](Nc2cc(C(F)(F)F)nc3ccc(Cl)cc23)CC1)c1cncc(-c2cccs2)c1] | 4-52 |

TABLE I-continued

Representative compounds having Structure (I)

| Structure | Cpd No. |
|---|---|
| 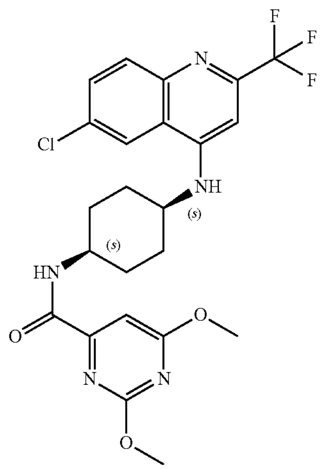 [SMILES: COc1cc(C(=O)N[C@H]2CC[C@@H](Nc3cc(C(F)(F)F)nc4ccc(Cl)cc34)CC2)nc(OC)n1] | 4-53 |
| 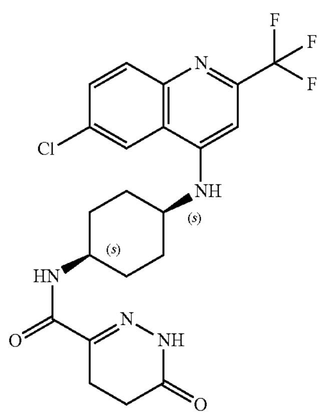 [SMILES: O=C1CCC(C(=O)N[C@H]2CC[C@@H](Nc3cc(C(F)(F)F)nc4ccc(Cl)cc34)CC2)=NN1] | 4-54 |
| 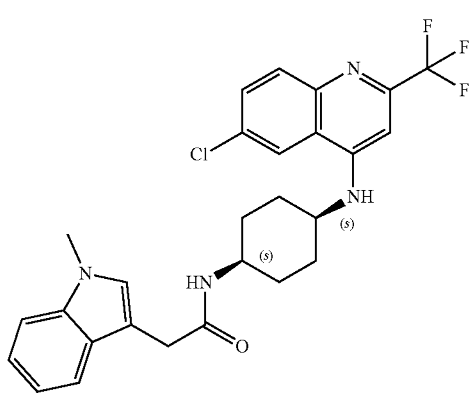 [SMILES: Cn1cc(CC(=O)N[C@H]2CC[C@@H](Nc3cc(C(F)(F)F)nc4ccc(Cl)cc34)CC2)c2ccccc21] | 4-55 |

TABLE I-continued
Representative compounds having Structure (I)
| Structure | Cpd No. |
|---|---|
| 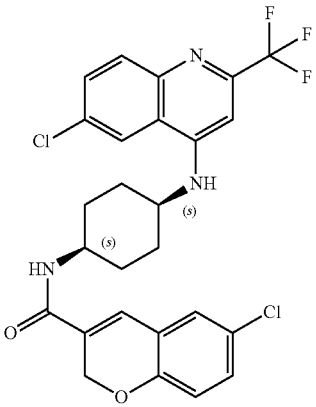 [SMILES: O=C(N[C@H]1CC[C@@H](Nc2cc(C(F)(F)F)nc3ccc(Cl)cc23)CC1)C1=Cc2cc(Cl)ccc2OC1] | 4-56 |
| 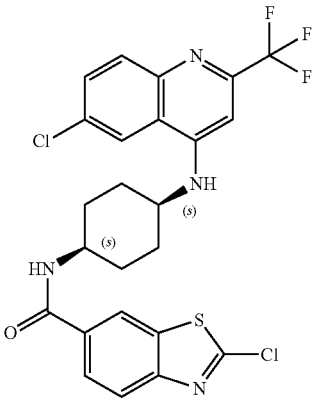 [SMILES: O=C(N[C@H]1CC[C@@H](Nc2cc(C(F)(F)F)nc3ccc(Cl)cc23)CC1)c1ccc2nc(Cl)sc2c1] | 4-57 |
| 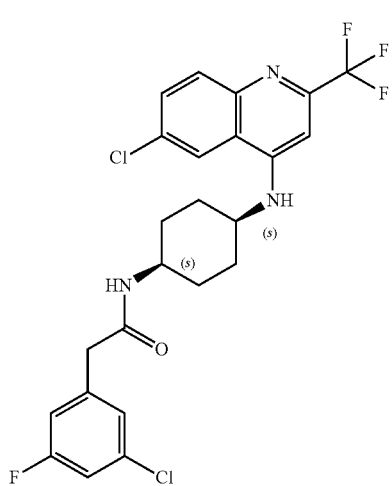 [SMILES: O=C(Cc1cc(F)cc(Cl)c1)N[C@H]1CC[C@@H](Nc2cc(C(F)(F)F)nc3ccc(Cl)cc23)CC1] | 4-58 |

TABLE I-continued
Representative compounds having Structure (I)
| Structure | Cpd No. |
|---|---|
| 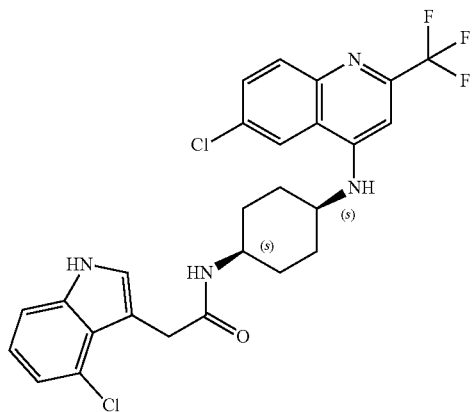 [SMILES: O=C(Cc1c[nH]c2cccc(Cl)c12)N[C@H]1CC[C@@H](Nc2cc(C(F)(F)F)nc3ccc(Cl)cc23)CC1] | 4-59 |
| 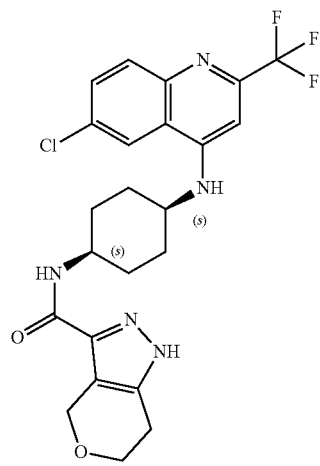 [SMILES: O=C(N[C@H]1CC[C@@H](Nc2cc(C(F)(F)F)nc3ccc(Cl)cc23)CC1)c1n[nH]c2c1COCC2] | 4-60 |
| 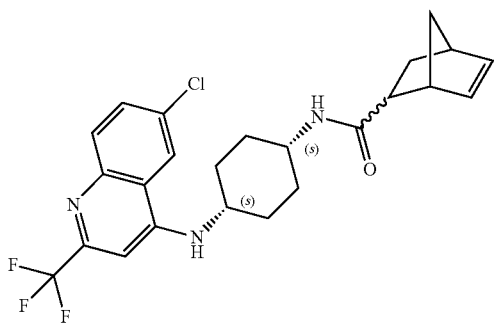 [SMILES: O=C(N[C@H]1CC[C@@H](Nc2cc(C(F)(F)F)nc3ccc(Cl)cc23)CC1)C1CC2C=CC1C2] | 4-61 |

TABLE I-continued
Representative compounds having Structure (I)
| Structure | Cpd No. |
|---|---|
| 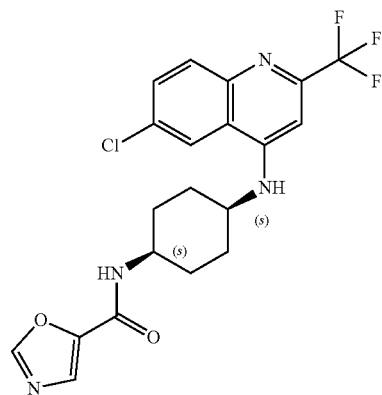 [SMILES: O=C(N[C@H]1CC[C@@H](Nc2cc(C(F)(F)F)nc3ccc(Cl)cc23)CC1)c1cnco1] | 4-62 |
| 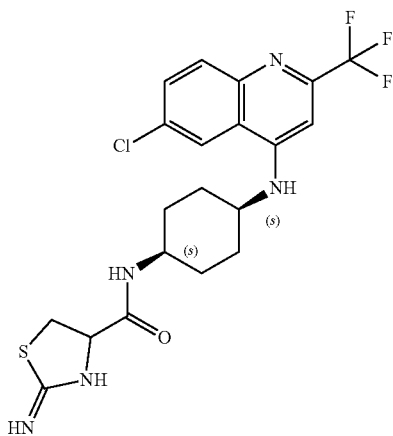 [SMILES: N=C1NC(C(=O)N[C@H]2CC[C@@H](Nc3cc(C(F)(F)F)nc4ccc(Cl)cc34)CC2)CS1] | 4-63 |
| 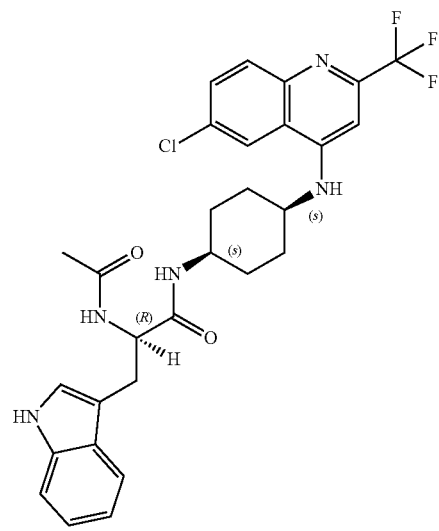 | 4-64 |

TABLE I-continued

Representative compounds having Structure (I)

| Structure | Cpd No. |
|---|---|
| 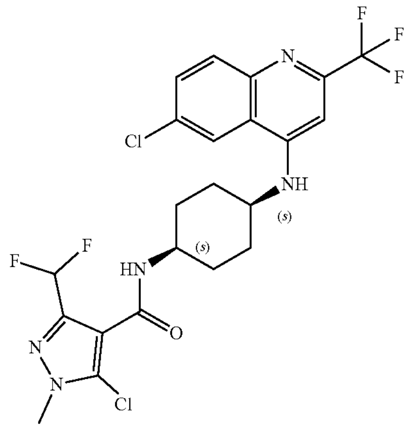 [SMILES: Cn1nc(C(F)F)c(C(=O)N[C@H]2CC[C@@H](Nc3cc(C(F)(F)F)nc4ccc(Cl)cc34)CC2)c1Cl] | 4-65 |
| 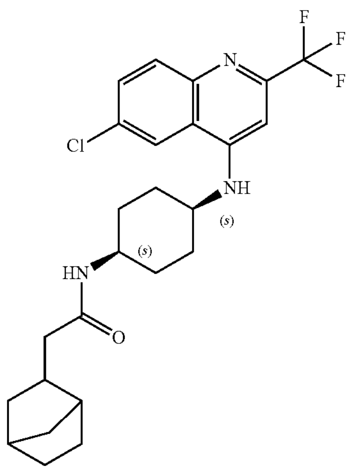 [SMILES: O=C(CC1CC2CCC1C2)N[C@H]1CC[C@@H](Nc2cc(C(F)(F)F)nc3ccc(Cl)cc23)CC1] | 4-66 |
| 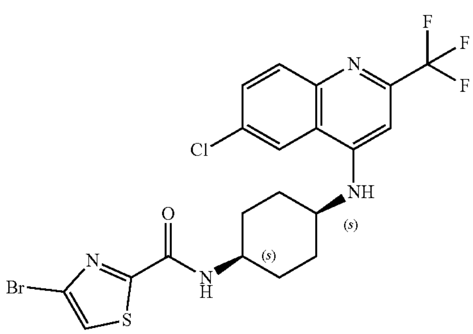 [SMILES: O=C(N[C@H]1CC[C@@H](Nc2cc(C(F)(F)F)nc3ccc(Cl)cc23)CC1)c1nc(Br)cs1] | 4-67 |
| 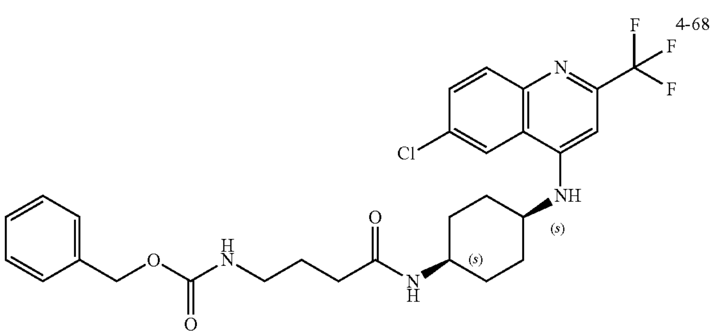 | 4-68 |

TABLE I-continued

Representative compounds having Structure (I)

| Structure | Cpd No. |
|---|---|
| 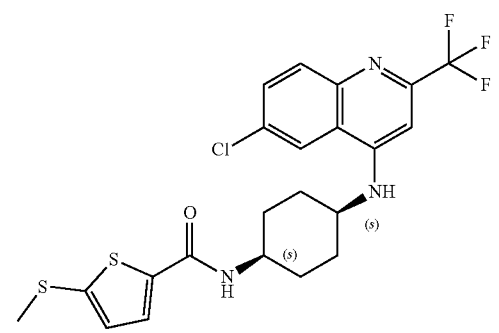 [SMILES: CSc1ccc(C(=O)N[C@H]2CC[C@@H](Nc3cc(C(F)(F)F)nc4ccc(Cl)cc34)CC2)s1] | 4-69 |
| 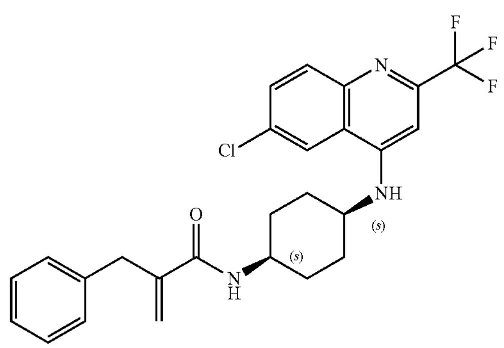 [SMILES: C=C(Cc1ccccc1)C(=O)N[C@H]1CC[C@@H](Nc2cc(C(F)(F)F)nc3ccc(Cl)cc23)CC1] | 4-70 |
| 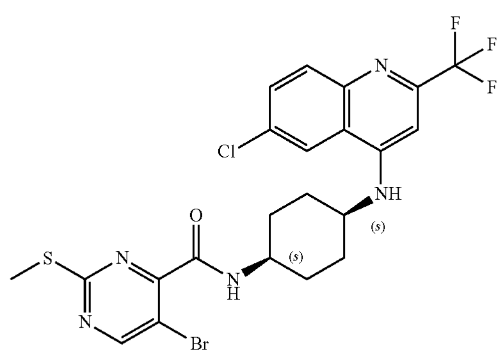 [SMILES: CSc1ncc(Br)c(C(=O)N[C@H]2CC[C@@H](Nc3cc(C(F)(F)F)nc4ccc(Cl)cc34)CC2)n1] | 4-71 |
| 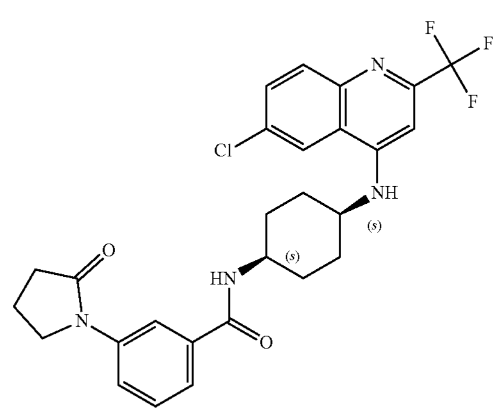 [SMILES: O=C(N[C@H]1CC[C@@H](Nc2cc(C(F)(F)F)nc3ccc(Cl)cc23)CC1)c1cccc(N2CCCC2=O)c1] | 4-72 |

TABLE I-continued

Representative compounds having Structure (I)

| Structure | Cpd No. |
|---|---|
| 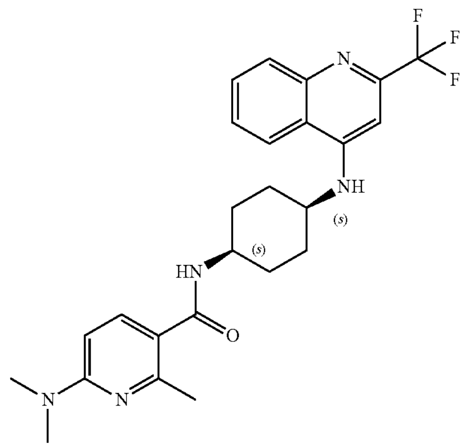 [SMILES: Cc1nc(N(C)C)ccc1C(=O)N[C@H]1CC[C@@H](Nc2cc(C(F)(F)F)nc3ccccc23)CC1] | 4-73 |
| 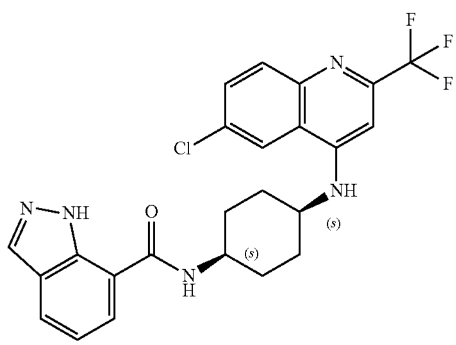 [SMILES: O=C(N[C@H]1CC[C@@H](Nc2cc(C(F)(F)F)nc3ccc(Cl)cc23)CC1)c1cccc2cn[nH]c12] | 4-74 |
| 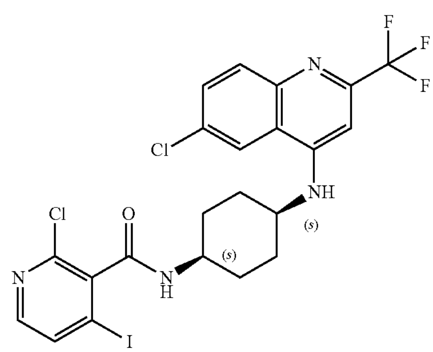 [SMILES: O=C(N[C@H]1CC[C@@H](Nc2cc(C(F)(F)F)nc3ccc(Cl)cc23)CC1)c1c(I)ccnc1Cl] | 4-75 |
| 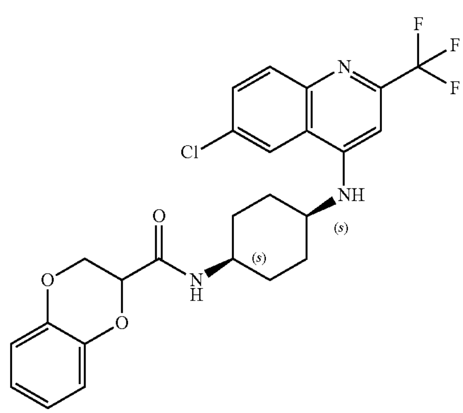 [SMILES: O=C(N[C@H]1CC[C@@H](Nc2cc(C(F)(F)F)nc3ccc(Cl)cc23)CC1)C1COc2ccccc2O1] | 4-76 |

TABLE I-continued

Representative compounds having Structure (I)

| Structure | Cpd No. |
|---|---|
| 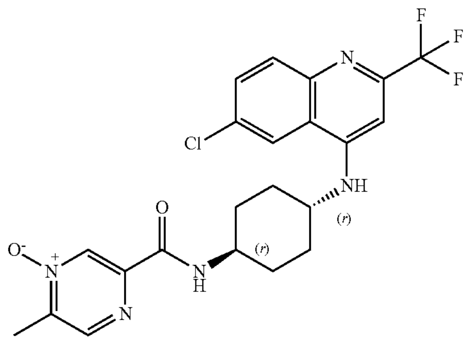 | 4-77 |
| 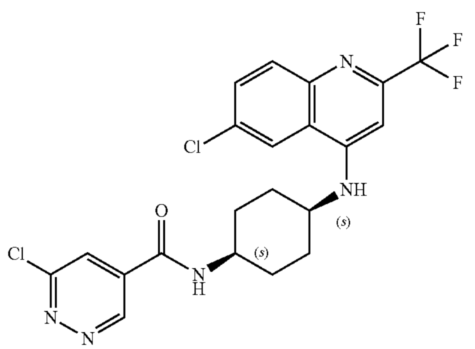 [SMILES: O=C(N[C@H]1CC[C@@H](Nc2cc(C(F)(F)F)nc3ccc(Cl)cc23)CC1)c1cnnc(Cl)c1] | 4-78 |
| 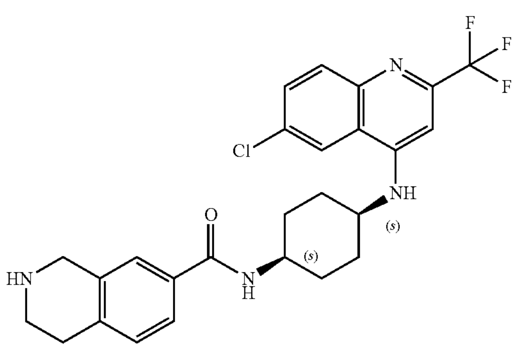 [SMILES: O=C(N[C@H]1CC[C@@H](Nc2cc(C(F)(F)F)nc3ccc(Cl)cc23)CC1)c1ccc2c(c1)CNCC2] | 4-79 |
| 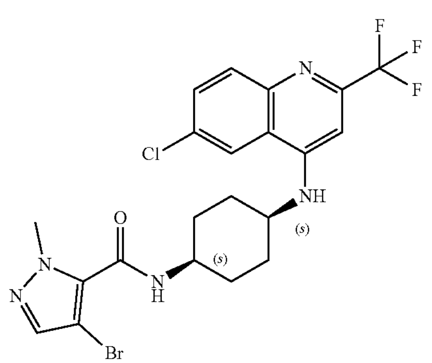 [SMILES: Cn1ncc(Br)c1C(=O)N[C@H]1CC[C@@H](Nc2cc(C(F)(F)F)nc3ccc(Cl)cc23)CC1] | 4-80 |

TABLE I-continued

Representative compounds having Structure (I)

| Structure | Cpd No. |
|---|---|
| 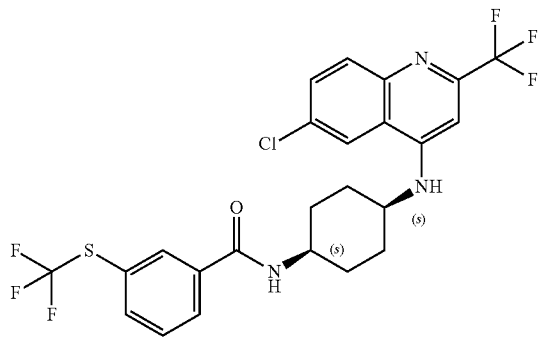 [SMILES: O=C(N[C@H]1CC[C@@H](Nc2cc(C(F)(F)F)nc3ccc(Cl)cc23)CC1)c1cccc(SC(F)(F)F)c1] | 4-81 |
| 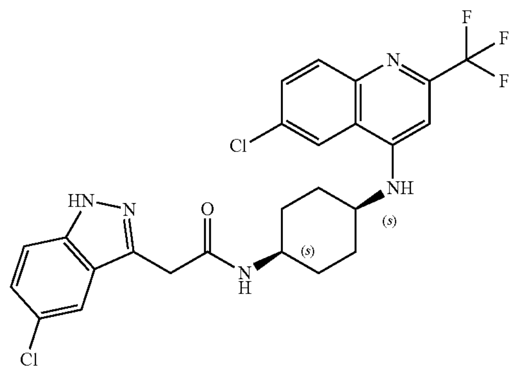 [SMILES: O=C(Cc1n[nH]c2ccc(Cl)cc12)N[C@H]1CC[C@@H](Nc2cc(C(F)(F)F)nc3ccc(Cl)cc23)CC1] | 4-82 |
| 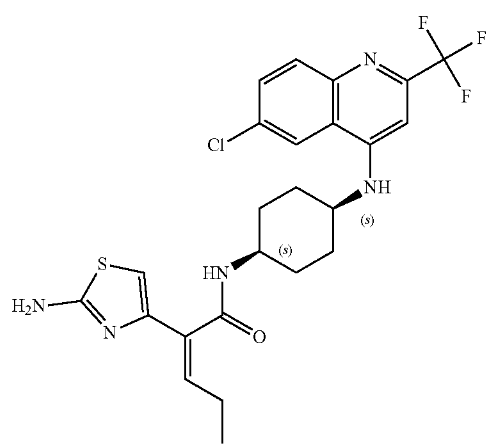 [SMILES: CC/C=C(\C(=O)N[C@H]1CC[C@@H](Nc2cc(C(F)(F)F)nc3ccc(Cl)cc23)CC1)c1csc(N)n1] | 4-83 |
| 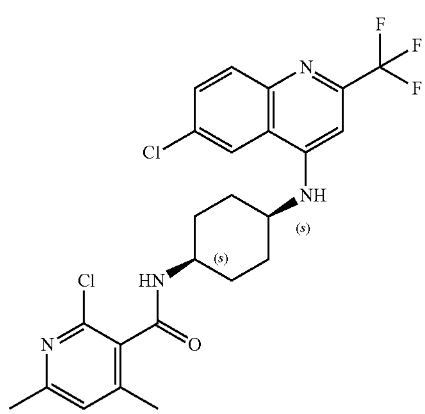 [SMILES: Cc1cc(C)c(C(=O)N[C@H]2CC[C@@H](Nc3cc(C(F)(F)F)nc4ccc(Cl)cc34)CC2)c(Cl)n1] | 4-84 |

TABLE I-continued
| Representative compounds having Structure (I) | |
|---|---|
| Structure | Cpd No. |
| | 4-85 |
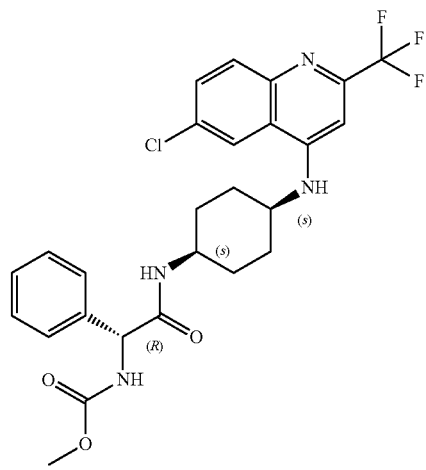
| | 4-86 |
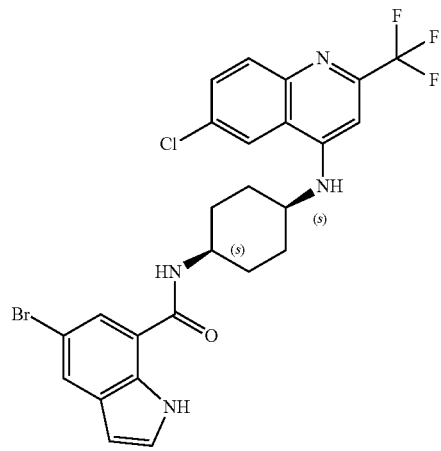 [SMILES: O=C(N[C@H]1CC[C@@H](Nc2cc(C(F)(F)F)nc3ccc(Cl)cc23)CC1)c1cc(Br)cc2cc[nH]c12]
| | 4-87 |
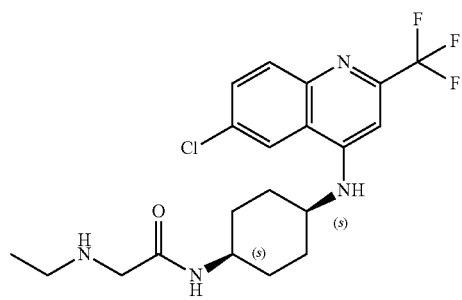 [SMILES: CCNCC(=O)N[C@H]1CC[C@@H](Nc2cc(C(F)(F)F)nc3ccc(Cl)cc23)CC1]

TABLE I-continued

Representative compounds having Structure (I)

| Structure | Cpd No. |
|---|---|
| 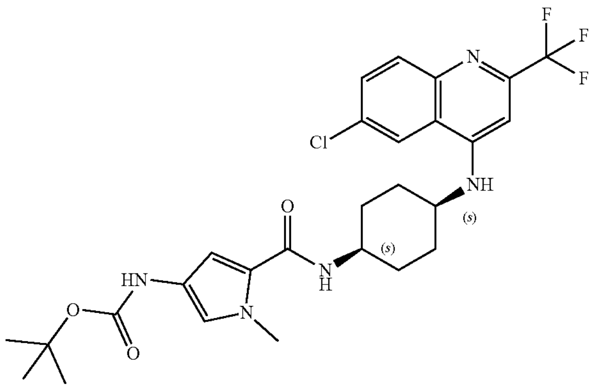 [SMILES: Cn1cc(NC(=O)OC(C)(C)C)cc1C(=O)N[C@H]1CC[C@@H](Nc2cc(C(F)(F)F)nc3ccc(Cl)cc23)CC1] | 4-88 |
| 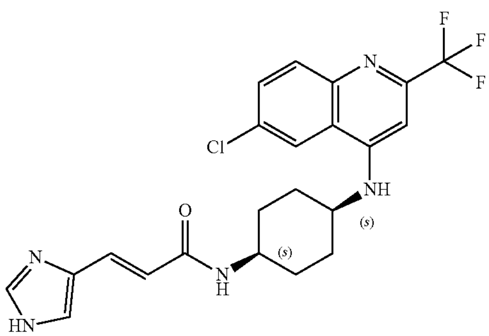 [SMILES: O=C(/C=C/c1c[nH]cn1)N[C@H]1CC[C@@H](Nc2cc(C(F)(F)F)nc3ccc(Cl)cc23)CC1] | 4-89 |
| 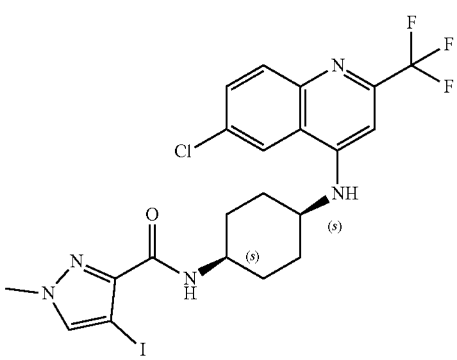 [SMILES: Cn1cc(I)c(C(=O)N[C@H]2CC[C@@H](Nc3cc(C(F)(F)F)nc4ccc(Cl)cc34)CC2)n1] | 4-90 |
| 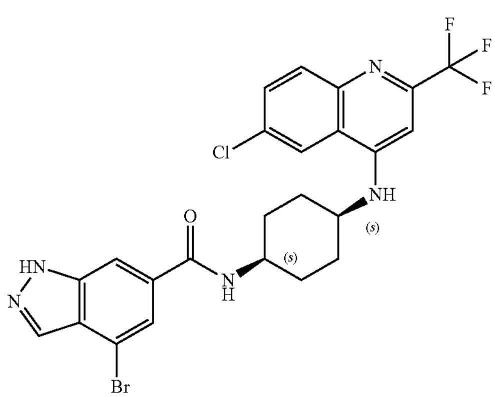 [SMILES: O=C(N[C@H]1CC[C@@H](Nc2cc(C(F)(F)F)nc3ccc(Cl)cc23)CC1)c1cc(Br)c2cn[nH]c2c1] | 4-91 |

TABLE I-continued
Representative compounds having Structure (I)
| Structure | Cpd No. |
|---|---|
| 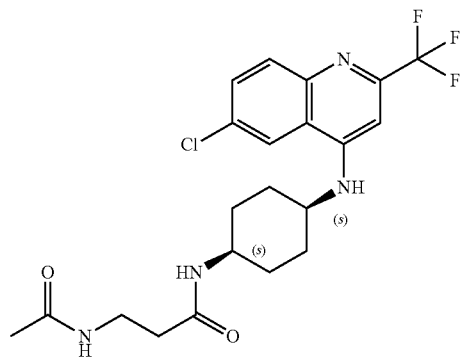 [SMILES: CC(=O)NCCC(=O)N[C@H]1CC[C@@H](Nc2cc(C(F)(F)F)nc3ccc(Cl)cc23)CC1] | 4-92 |
| 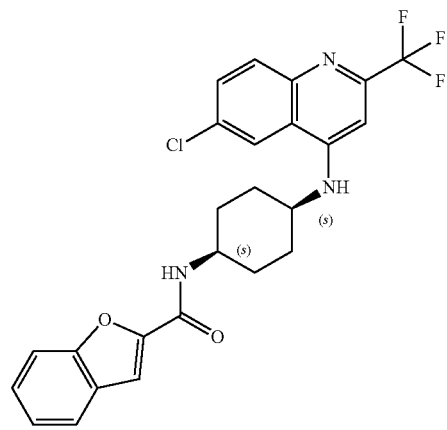 [SMILES: O=C(N[C@H]1CC[C@@H](Nc2cc(C(F)(F)F)nc3ccc(Cl)cc23)CC1)c1cc2ccccc2o1] | 4-93 |
| 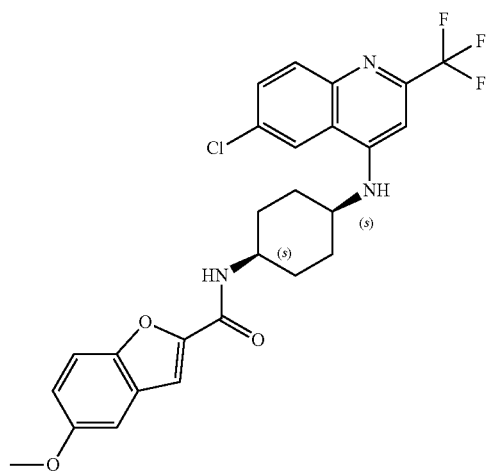 [SMILES: COc1ccc2oc(C(=O)N[C@H]3CC[C@@H](Nc4cc(C(F)(F)F)nc5ccc(Cl)cc45)CC3)cc2c1] | 4-94 |

TABLE I-continued

Representative compounds having Structure (I)

| Structure | Cpd No. |
|---|---|
| 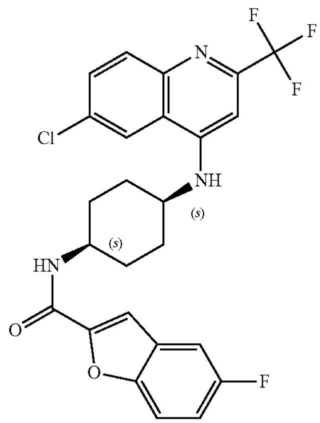 [SMILES: O=C(N[C@H]1CC[C@@H](Nc2cc(C(F)(F)F)nc3ccc(Cl)cc23)CC1)c1cc2cc(F)ccc2o1] | 4-95 |
| 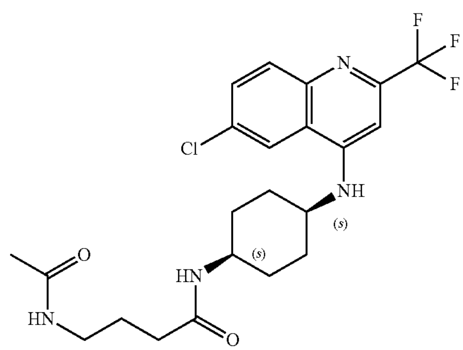 [SMILES: CC(=O)NCCCC(=O)N[C@H]1CC[C@@H](Nc2cc(C(F)(F)F)nc3ccc(Cl)cc23)CC1] | 4-96 |
| 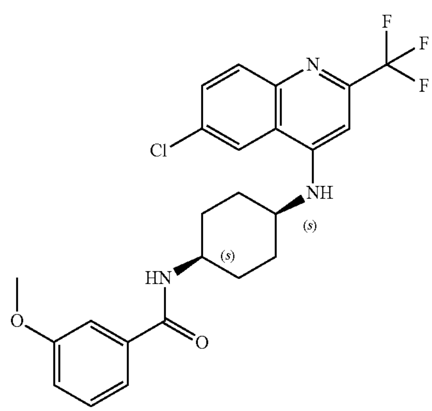 [SMILES: COc1cccc(C(=O)N[C@H]2CC[C@@H](Nc3cc(C(F)(F)F)nc4ccc(Cl)cc34)CC2)c1] | 4-97 |
| 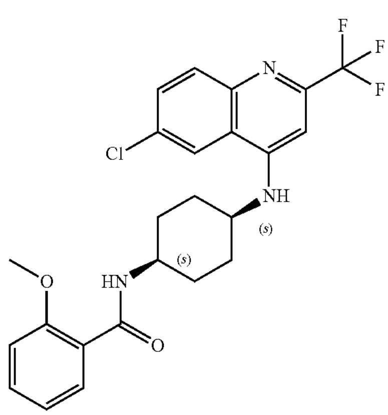 [SMILES: COc1ccccc1C(=O)N[C@H]1CC[C@@H](Nc2cc(C(F)(F)F)nc3ccc(Cl)cc23)CC1] | 4-98 |

TABLE I-continued
Representative compounds having Structure (I)
| Structure | Cpd No. |
|---|---|
| 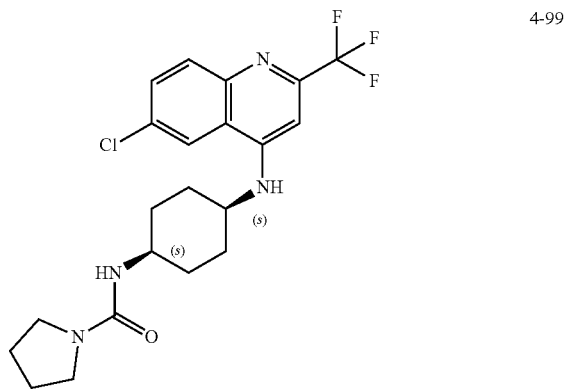 | 4-99 |
| 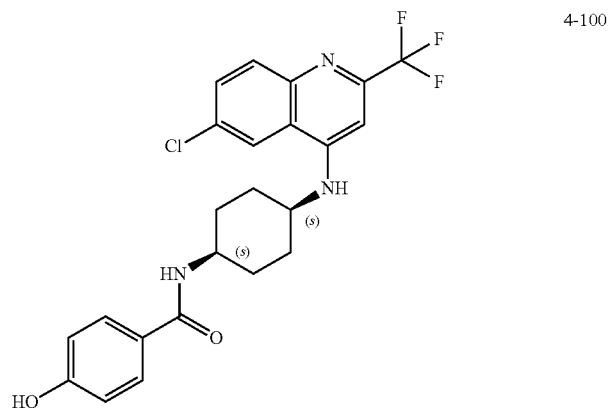 | 4-100 |
| 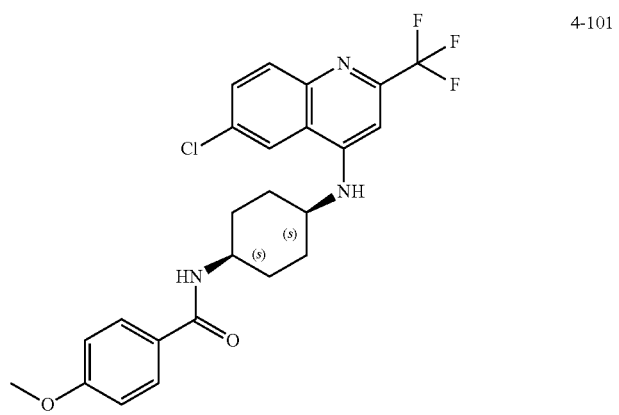 | 4-101 |

TABLE I-continued
Representative compounds having Structure (I)
| Structure | Cpd No. |
|---|---|
| 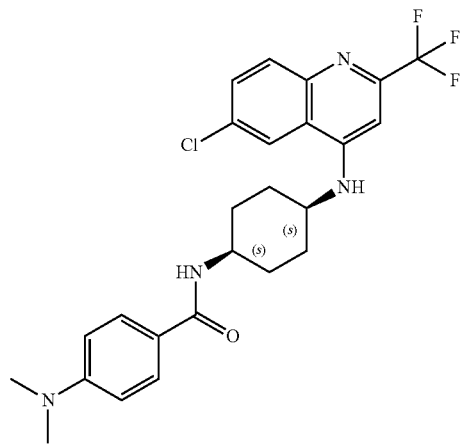 [SMILES: CN(C)c1ccc(C(=O)N[C@H]2CC[C@@H](Nc3cc(C(F)(F)F)nc4ccc(Cl)cc34)CC2)cc1] | 4-102 |
| 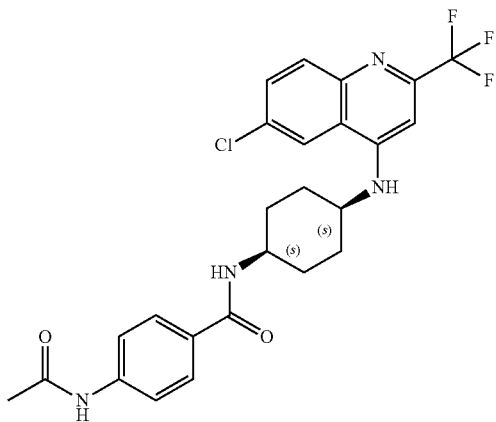 [SMILES: CC(=O)Nc1ccc(C(=O)N[C@H]2CC[C@@H](Nc3cc(C(F)(F)F)nc4ccc(Cl)cc34)CC2)cc1] | 4-103 |
| 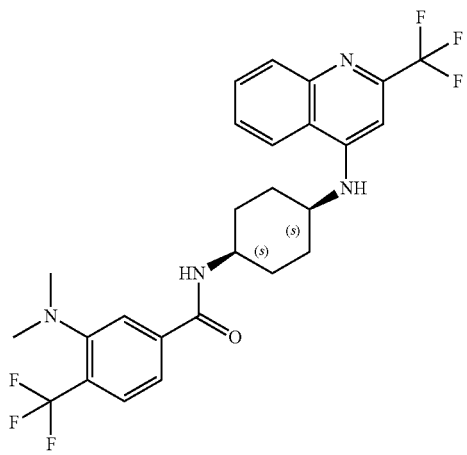 [SMILES: CN(C)c1cc(C(=O)N[C@H]2CC[C@@H](Nc3cc(C(F)(F)F)nc4ccccc34)CC2)ccc1C(F)(F)F] | 4-104 |

TABLE I-continued
Representative compounds having Structure (I)
| Structure | Cpd No. |
|---|---|
| 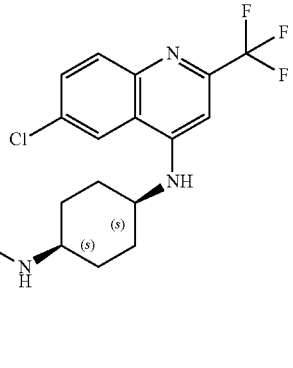 | 4-105 |
| 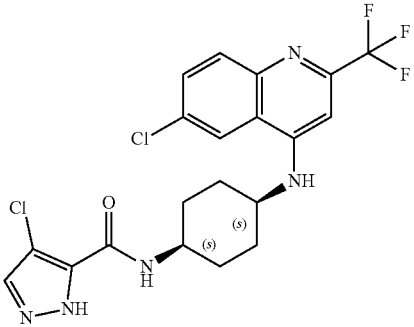 [SMILES: O=C(N[C@H]1CC[C@@H](Nc2cc(C(F)(F)F)nc3ccc(Cl)cc23)CC1)c1[nH]ncc1Cl] | 4-106 |
| 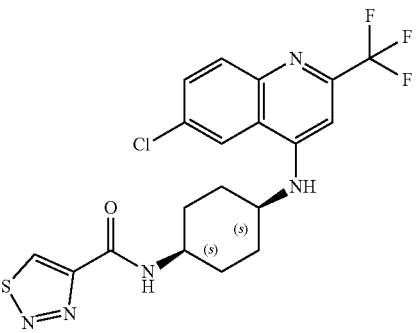 [SMILES: O=C(N[C@H]1CC[C@@H](Nc2cc(C(F)(F)F)nc3ccc(Cl)cc23)CC1)c1csnn1] | 4-107 |
| 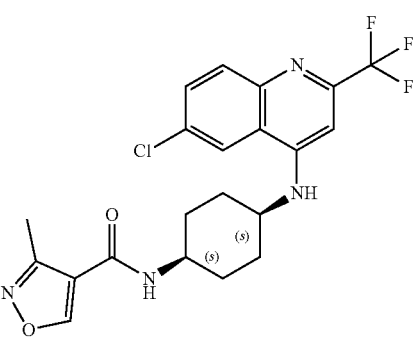 [SMILES: Cc1nocc1C(=O)N[C@H]1CC[C@@H](Nc2cc(C(F)(F)F)nc3ccc(Cl)cc23)CC1] | 4-108 |

TABLE I-continued

Representative compounds having Structure (I)

| Structure | Cpd No. |
|---|---|
| 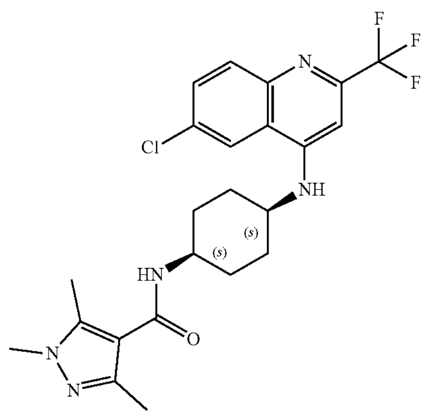 [SMILES: Cc1nn(C)c(C)c1C(=O)N[C@H]1CC[C@@H](Nc2cc(C(F)(F)F)nc3ccc(Cl)cc23)CC1] | 4-109 |
| 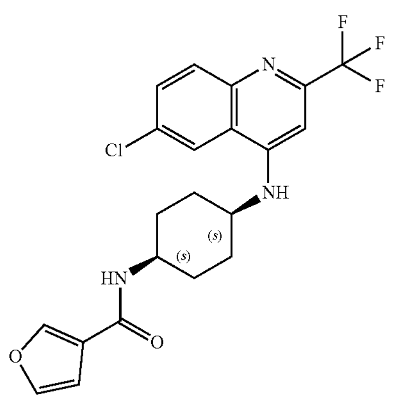 [SMILES: O=C(N[C@H]1CC[C@@H](Nc2cc(C(F)(F)F)nc3ccc(Cl)cc23)CC1)c1ccoc1] | 4-110 |
| 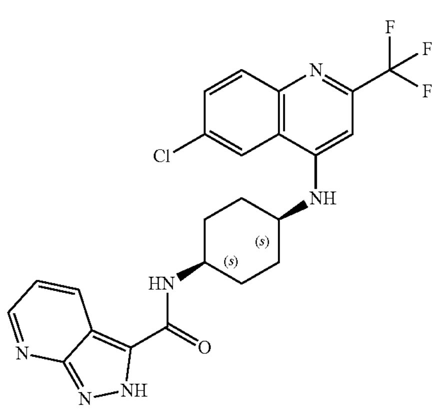 [SMILES: O=C(N[C@H]1CC[C@@H](Nc2cc(C(F)(F)F)nc3ccc(Cl)cc23)CC1)c1[nH]nc2ncccc12] | 4-111 |

TABLE I-continued
Representative compounds having Structure (I)
| Structure | Cpd No. |
|---|---|
| 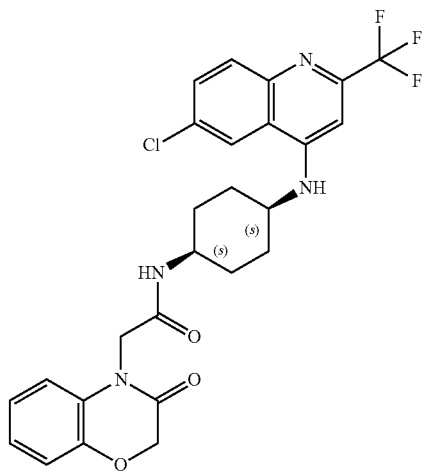 [SMILES: O=C(CN1C(=O)COc2ccccc21)N[C@H]1CC[C@@H](Nc2cc(C(F)(F)F)nc3ccc(Cl)cc23)CC1] | 4-112 |
| 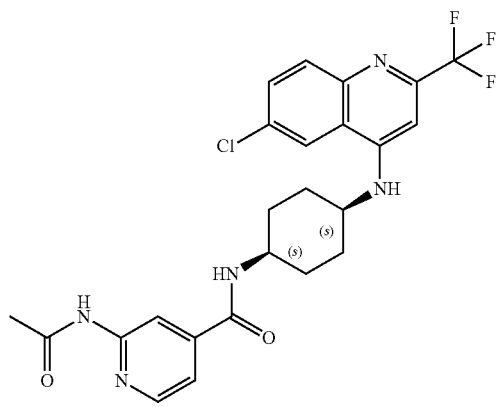 [SMILES: CC(=O)Nc1cc(C(=O)N[C@H]2CC[C@@H](Nc3cc(C(F)(F)F)nc4ccc(Cl)cc34)CC2)ccn1] | 4-113 |
| 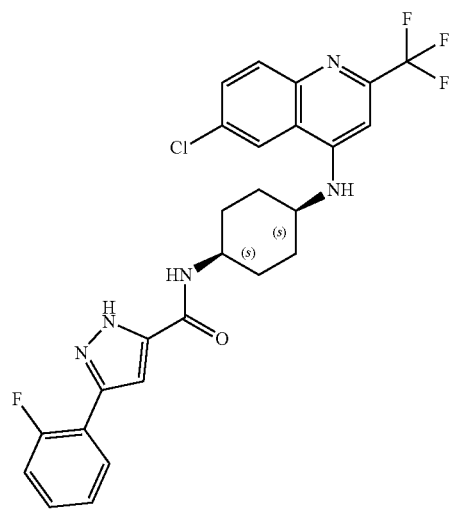 [SMILES: O=C(N[C@H]1CC[C@@H](Nc2cc(C(F)(F)F)nc3ccc(Cl)cc23)CC1)c1cc(-c2ccccc2F)n[nH]1] | 4-114 |

TABLE I-continued

Representative compounds having Structure (I)

| Structure | Cpd No. |
|---|---|
| 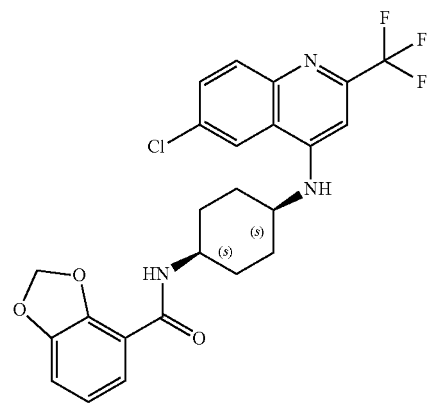 [SMILES: O=C(N[C@H]1CC[C@@H](Nc2cc(C(F)(F)F)nc3ccc(Cl)cc23)CC1)c1cccc2c1OCO2] | 4-115 |
| 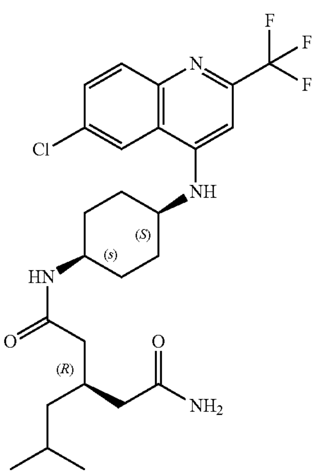 | 4-116 |
| 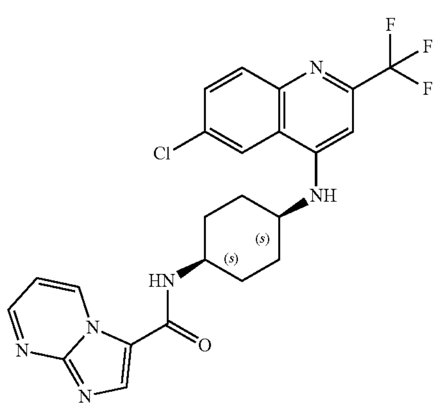 [SMILES: O=C(N[C@H]1CC[C@@H](Nc2cc(C(F)(F)F)nc3ccc(Cl)cc23)CC1)c1cnc2ncccn12] | 4-117 |

TABLE I-continued

Representative compounds having Structure (I)

| Structure | Cpd No. |
|---|---|
| 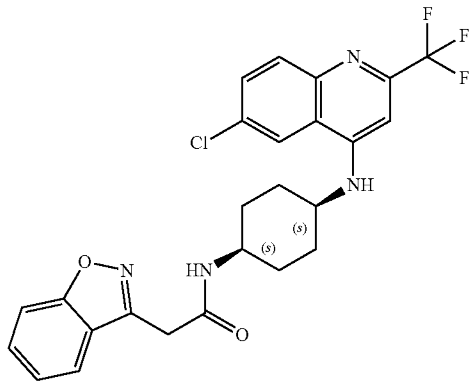 [SMILES: O=C(Cc1noc2ccccc12)N[C@H]1CC[C@@H](Nc2cc(C(F)(F)F)nc3ccc(Cl)cc23)CC1] | 4-118 |
| 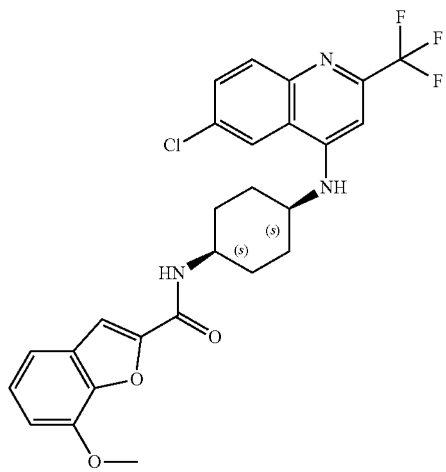 [SMILES: COc1cccc2cc(C(=O)N[C@H]3CC[C@@H](Nc4cc(C(F)(F)F)nc5ccc(Cl)cc45)CC3)oc12] | 4-119 |
| 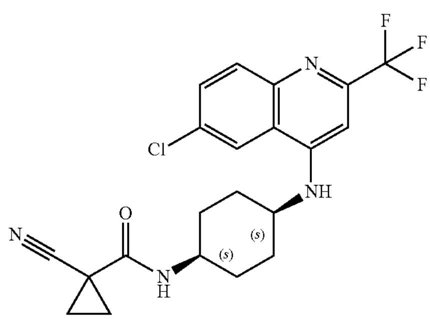 [SMILES: N#CC1(C(=O)N[C@H]2CC[C@@H](Nc3cc(C(F)(F)F)nc4ccc(Cl)cc34)CC2)CC1] | 4-120 |
| 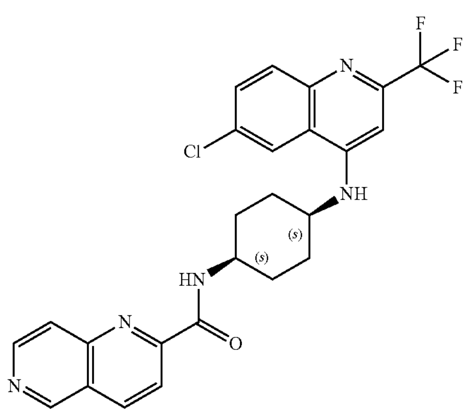 [SMILES: O=C(N[C@H]1CC[C@@H](Nc2cc(C(F)(F)F)nc3ccc(Cl)cc23)CC1)c1ccc2cnccc2n1] | 4-121 |

TABLE I-continued

Representative compounds having Structure (I)

| Structure | Cpd No. |
|---|---|
| 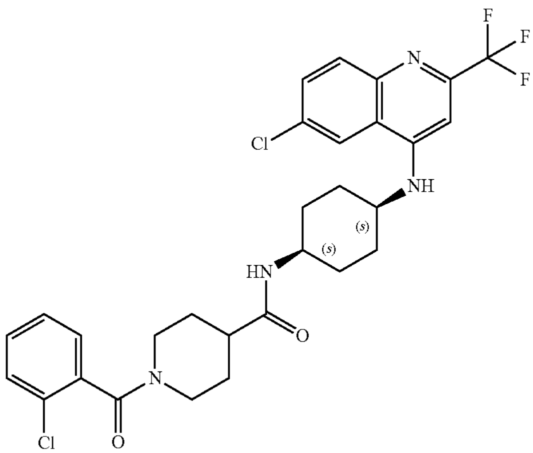 [SMILES: O=C(N[C@H]1CC[C@@H](Nc2cc(C(F)(F)F)nc3ccc(Cl)cc23)CC1)C1CCN(C(=O)c2ccccc2Cl)CC1] | 4-122 |
| 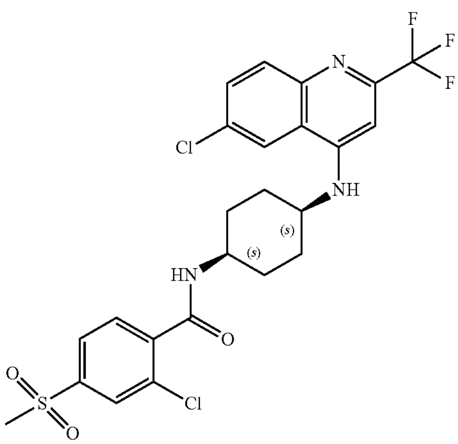 [SMILES: CS(=O)(=O)c1ccc(C(=O)N[C@H]2CC[C@@H](Nc3cc(C(F)(F)F)nc4ccc(Cl)cc34)CC2)c(Cl)c1] | 4-123 |
| 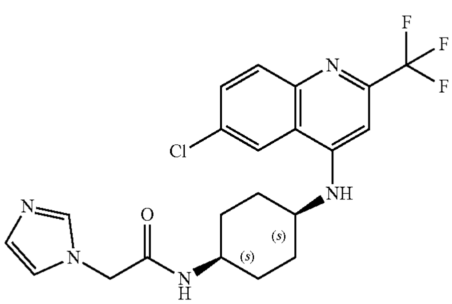 [SMILES: O=C(Cn1ccnc1)N[C@H]1CC[C@@H](Nc2cc(C(F)(F)F)nc3ccc(Cl)cc23)CC1] | 4-124 |
| 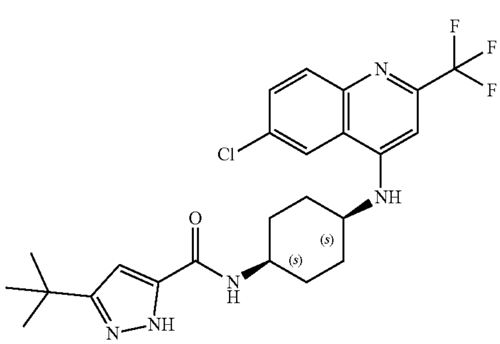 [SMILES: CC(C)(C)c1cc(C(=O)N[C@H]2CC[C@@H](Nc3cc(C(F)(F)F)nc4ccc(Cl)cc34)CC2)[nH]n1] | 4-125 |

TABLE I-continued

Representative compounds having Structure (I)

| Structure | Cpd No. |
|---|---|
| 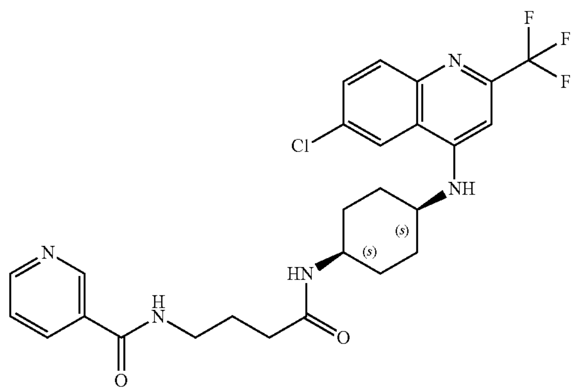 [SMILES: O=C(CCCNC(=O)c1cccnc1)N[C@H]1CC[C@@H](Nc2cc(C(F)(F)F)nc3ccc(Cl)cc23)CC1] | 4-126 |
| 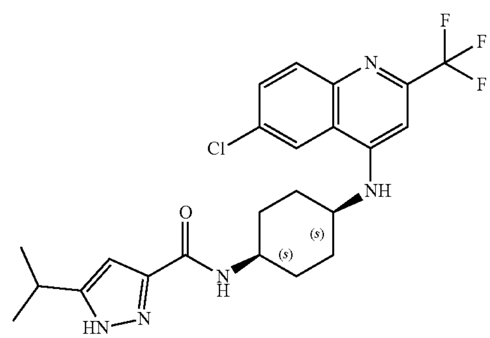 [SMILES: CC(C)c1cc(C(=O)N[C@H]2CC[C@@H](Nc3cc(C(F)(F)F)nc4ccc(Cl)cc34)CC2)n[nH]1] | 4-127 |
| 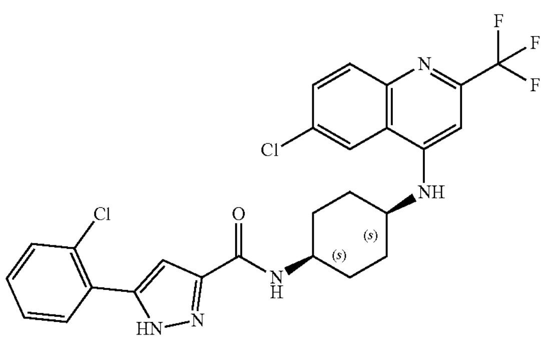 [SMILES: O=C(N[C@H]1CC[C@@H](Nc2cc(C(F)(F)F)nc3ccc(Cl)cc23)CC1)c1cc(-c2ccccc2Cl)[nH]n1] | 4-128 |
| 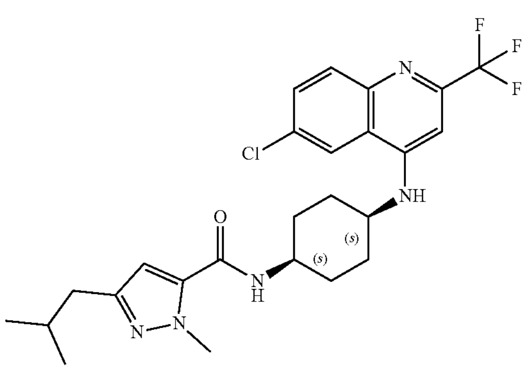 [SMILES: CC(C)Cc1cc(C(=O)N[C@H]2CC[C@@H](Nc3cc(C(F)(F)F)nc4ccc(Cl)cc34)CC2)n(C)n1] | 4-129 |

TABLE I-continued

Representative compounds having Structure (I)

| Structure | Cpd No. |
|---|---|
| 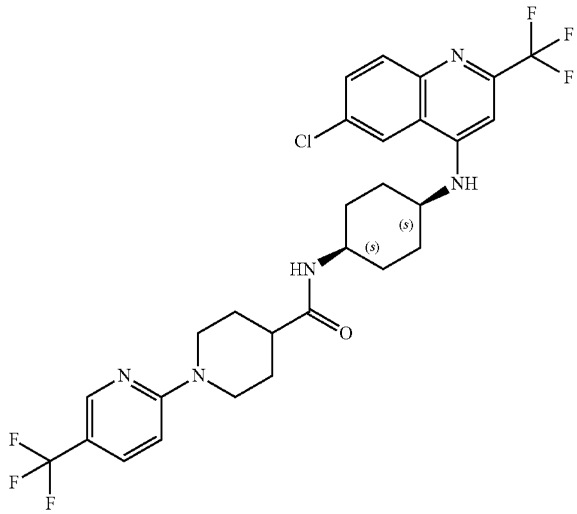 [SMILES: O=C(N[C@H]1CC[C@@H](Nc2cc(C(F)(F)F)nc3ccc(Cl)cc23)CC1)C1CCN(c2ccc(C(F)(F)F)cn2)CC1] | 4-130 |
| 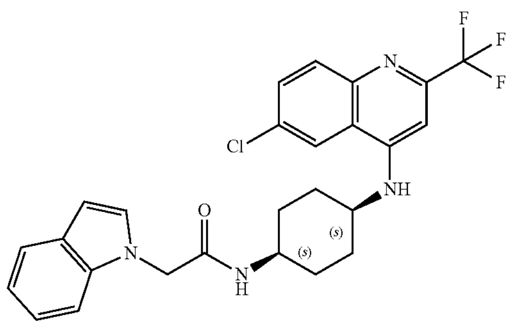 [SMILES: O=C(Cn1ccc2ccccc21)N[C@H]1CC[C@@H](Nc2cc(C(F)(F)F)nc3ccc(Cl)cc23)CC1] | 4-131 |
| 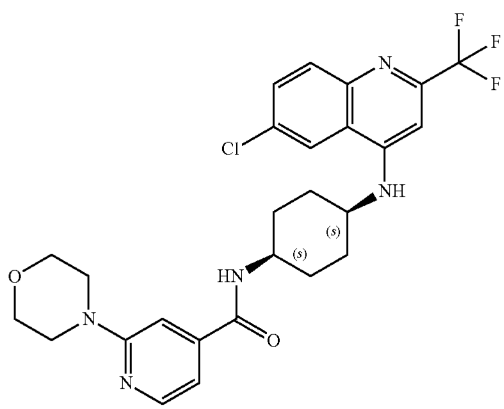 [SMILES: O=C(N[C@H]1CC[C@@H](Nc2cc(C(F)(F)F)nc3ccc(Cl)cc23)CC1)c1ccnc(N2CCOCC2)c1] | 4-132 |
| 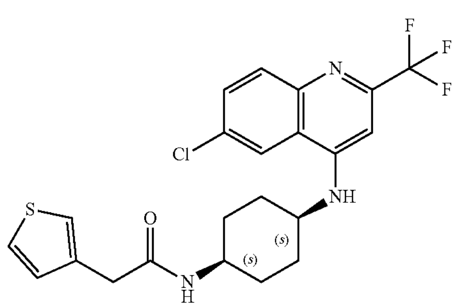 [SMILES: O=C(Cc1ccsc1)N[C@H]1CC[C@@H](Nc2cc(C(F)(F)F)nc3ccc(Cl)cc23)CC1] | 4-133 |

TABLE I-continued

Representative compounds having Structure (I)

| Structure | Cpd No. |
|---|---|
| 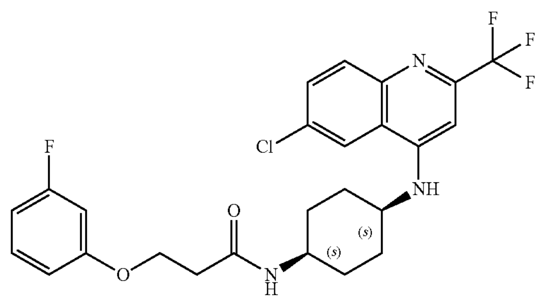 [SMILES: O=C(CCOc1cccc(F)c1)N[C@H]1CC[C@@H](Nc2cc(C(F)(F)F)nc3ccc(Cl)cc23)CC1] | 4-134 |
| 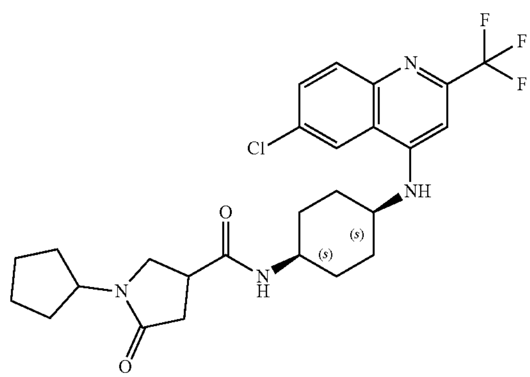 [SMILES: O=C(N[C@H]1CC[C@@H](Nc2cc(C(F)(F)F)nc3ccc(Cl)cc23)CC1)C1CC(=O)N(C2CCCC2)C1] | 4-135 |
| 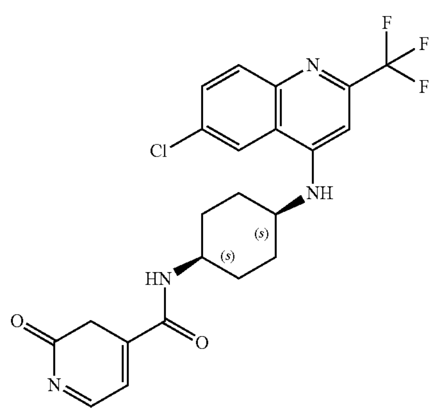 [SMILES: O=C1CC(C(=O)N[C@H]2CC[C@@H](Nc3cc(C(F)(F)F)nc4ccc(Cl)cc34)CC2)=CC=N1] | 4-136 |
| 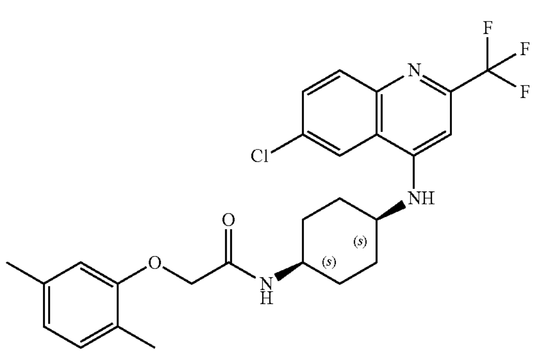 [SMILES: Cc1ccc(C)c(OCC(=O)N[C@H]2CC[C@@H](Nc3cc(C(F)(F)F)nc4ccc(Cl)cc34)CC2)c1] | 4-137 |

TABLE I-continued
Representative compounds having Structure (I)
| Structure | Cpd No. |
|---|---|
| 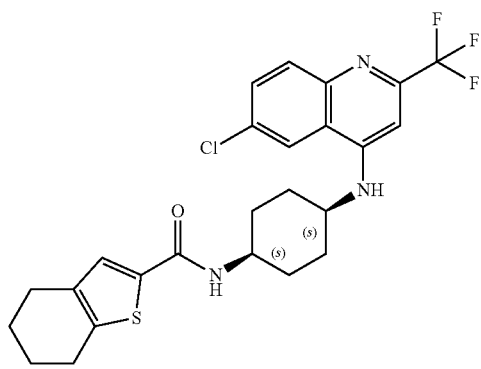 [SMILES: O=C(N[C@H]1CC[C@@H](Nc2cc(C(F)(F)F)nc3ccc(Cl)cc23)CC1)c1cc2c(s1)CCCC2] | 4-138 |
| 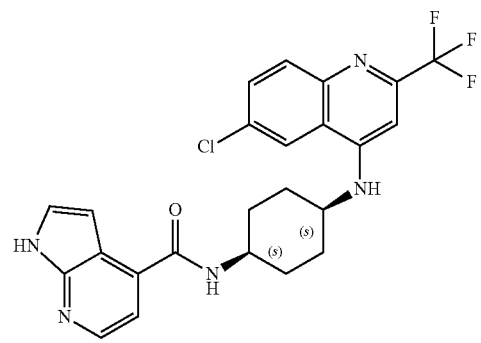 [SMILES: O=C(N[C@H]1CC[C@@H](Nc2cc(C(F)(F)F)nc3ccc(Cl)cc23)CC1)c1ccnc2[nH]ccc12] | 4-139 |
| 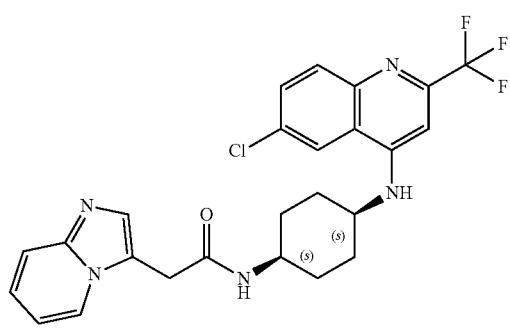 [SMILES: O=C(Cc1cnc2ccccn12)N[C@H]1CC[C@@H](Nc2cc(C(F)(F)F)nc3ccc(Cl)cc23)CC1] | 4-140 |
| 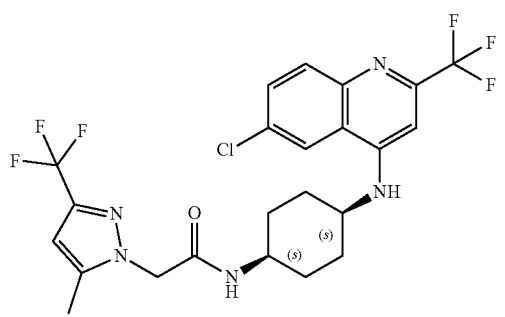 [SMILES: Cc1cc(C(F)(F)F)nn1CC(=O)N[C@H]1CC[C@@H](Nc2cc(C(F)(F)F)nc3ccc(Cl)cc23)CC1] | 4-141 |

TABLE I-continued

Representative compounds having Structure (I)

| Structure | Cpd No. |
|---|---|
| 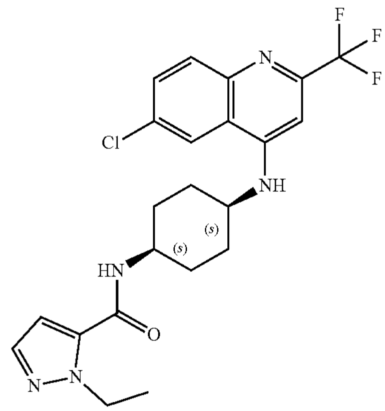 [SMILES: CCn1nccc1C(=O)N[C@H]1CC[C@@H](Nc2cc(C(F)(F)F)nc3ccc(Cl)cc23)CC1] | 4-142 |
| 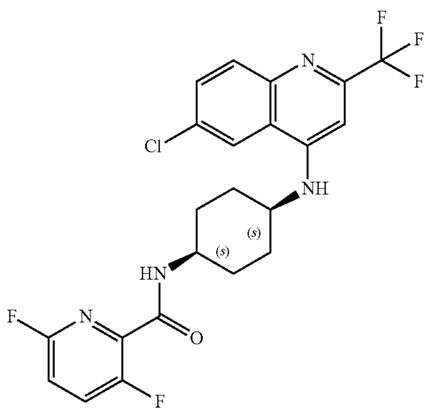 [SMILES: O=C(N[C@H]1CC[C@@H](Nc2cc(C(F)(F)F)nc3ccc(Cl)cc23)CC1)c1nc(F)ccc1F] | 4-143 |
| 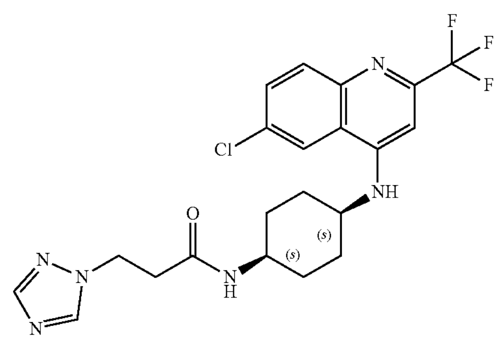 [SMILES: O=C(CCn1cncn1)N[C@H]1CC[C@@H](Nc2cc(C(F)(F)F)nc3ccc(Cl)cc23)CC1] | 4-144 |
| 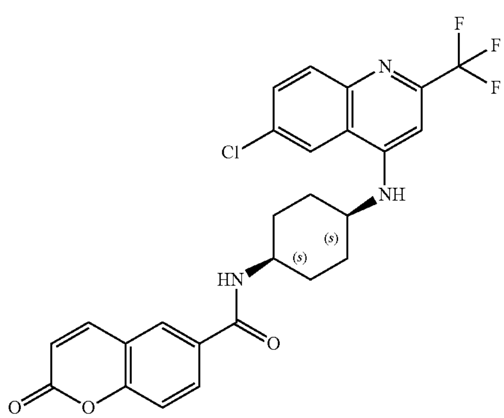 [SMILES: O=C(N[C@H]1CC[C@@H](Nc2cc(C(F)(F)F)nc3ccc(Cl)cc23)CC1)c1ccc2oc(=O)ccc2c1] | 4-145 |

TABLE I-continued

Representative compounds having Structure (I)

| Structure | Cpd No. |
|---|---|
| 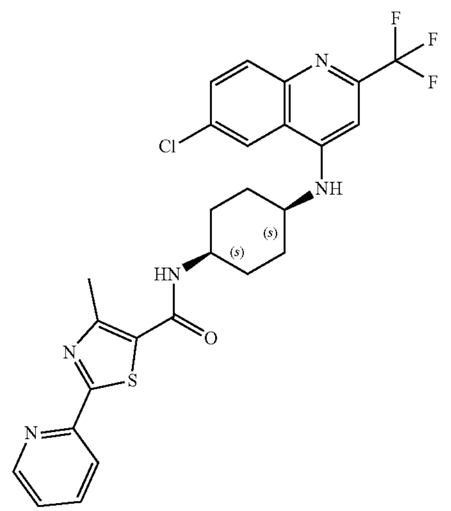 [SMILES: Cc1nc(-c2ccccn2)sc1C(=O)N[C@H]1CC[C@@H](Nc2cc(C(F)(F)F)nc3ccc(Cl)cc23)CC1] | 4-146 |
| 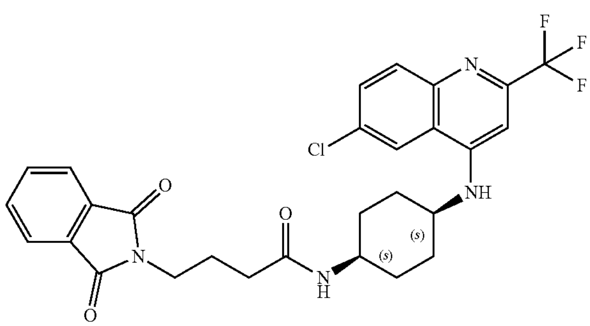 [SMILES: O=C(CCCN1C(=O)c2ccccc2C1=O)N[C@H]1CC[C@@H](Nc2cc(C(F)(F)F)nc3ccc(Cl)cc23)CC1] | 4-147 |
| 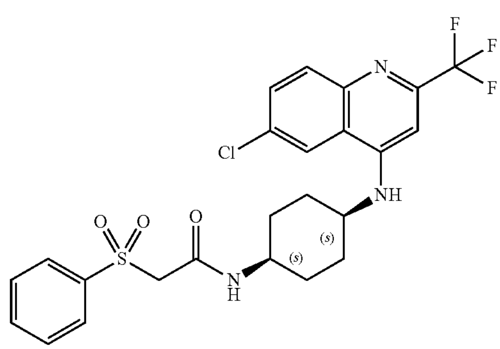 [SMILES: O=C(CS(=O)(=O)c1ccccc1)N[C@H]1CC[C@@H](Nc2cc(C(F)(F)F)nc3ccc(Cl)cc23)CC1] | 4-148 |
| 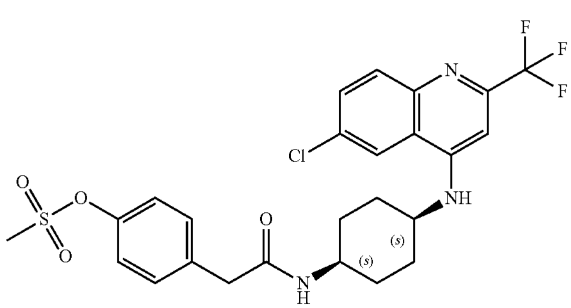 [SMILES: CS(=O)(=O)Oc1ccc(CC(=O)N[C@H]2CC[C@@H](Nc3cc(C(F)(F)F)nc4ccc(Cl)cc34)CC2)cc1] | 4-149 |

TABLE I-continued
Representative compounds having Structure (I)
| Structure | Cpd No. |
|---|---|
| 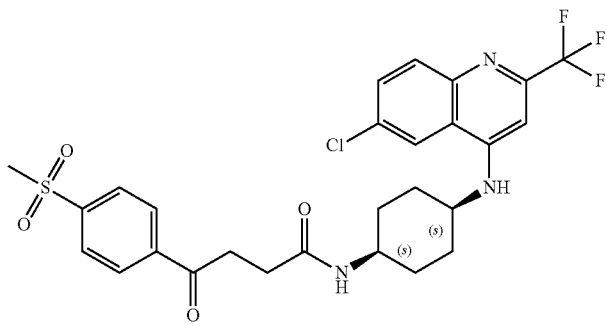 [SMILES: CS(=O)(=O)c1ccc(C(=O)CCC(=O)N[C@H]2CC[C@@H](Nc3cc(C(F)(F)F)nc4ccc(Cl)cc34)CC2)cc1] | 4-150 |
| 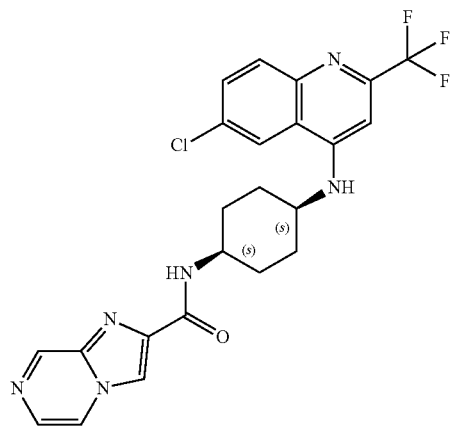 [SMILES: O=C(N[C@H]1CC[C@@H](Nc2cc(C(F)(F)F)nc3ccc(Cl)cc23)CC1)c1cn2ccncc2n1] | 4-151 |
| 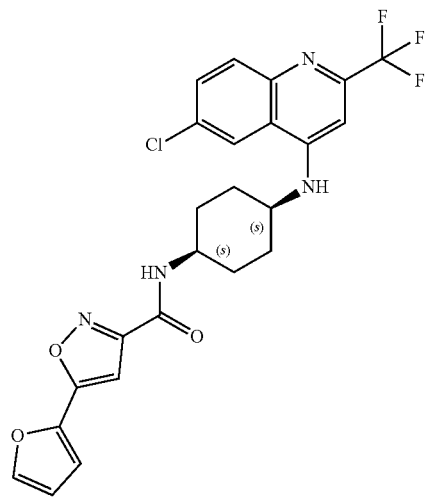 [SMILES: O=C(N[C@H]1CC[C@@H](Nc2cc(C(F)(F)F)nc3ccc(Cl)cc23)CC1)c1cc(-c2ccco2)on1] | 4-152 |

TABLE I-continued
Representative compounds having Structure (I)
| Structure | Cpd No. |
|---|---|
| 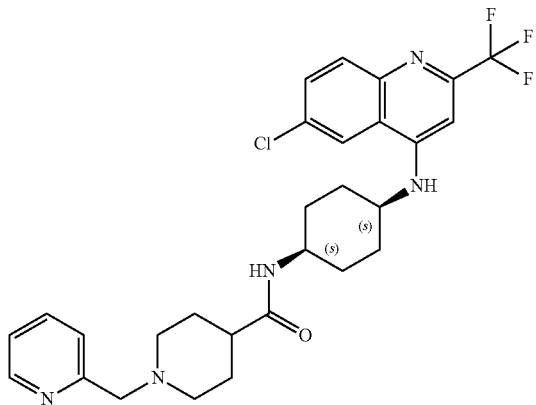 [SMILES: O=C(N[C@H]1CC[C@@H](Nc2cc(C(F)(F)F)nc3ccc(Cl)cc23)CC1)C1CCN(Cc2ccccn2)CC1] | 4-153 |
| 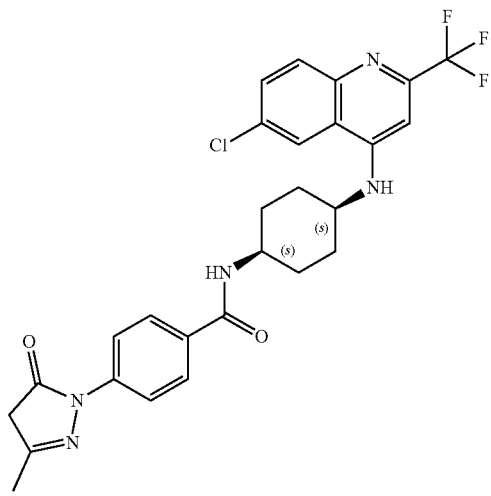 [SMILES: CC1=NN(c2ccc(C(=O)N[C@H]3CC[C@@H](Nc4cc(C(F)(F)F)nc5ccc(Cl)cc45)CC3)cc2)C(=O)C1] | 4-154 |
| 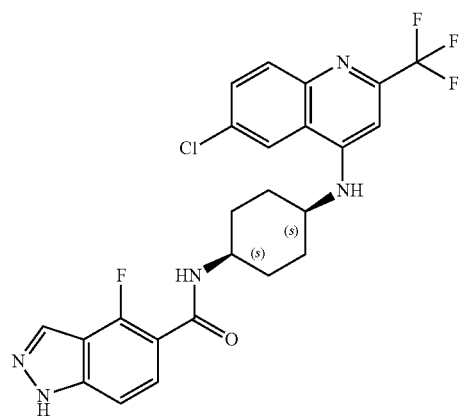 [SMILES: O=C(N[C@H]1CC[C@@H](Nc2cc(C(F)(F)F)nc3ccc(Cl)cc23)CC1)c1ccc2[nH]ncc2c1F] | 4-155 |

TABLE I-continued

Representative compounds having Structure (I)

| Structure | Cpd No. |
|---|---|
| 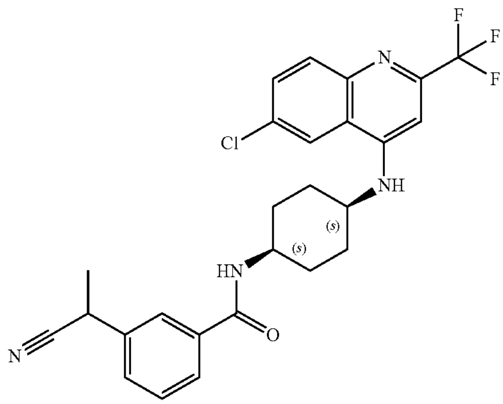 [SMILES: CC(C#N)c1cccc(C(=O)N[C@H]2CC[C@@H](Nc3cc(C(F)(F)F)nc4ccc(Cl)cc34)CC2)c1] | 4-156 |
| 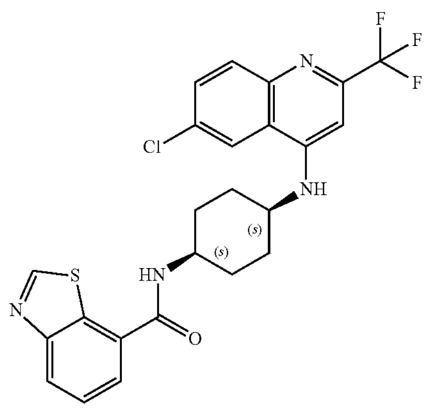 [SMILES: O=C(N[C@H]1CC[C@@H](Nc2cc(C(F)(F)F)nc3ccc(Cl)cc23)CC1)c1cccc2ncsc12] | 4-157 |
| 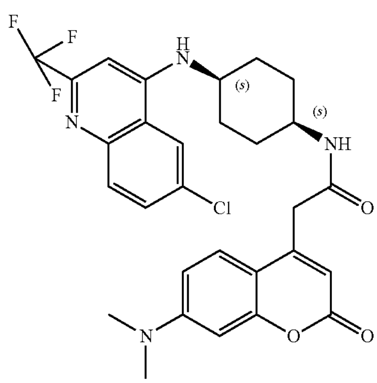 [SMILES: CN(C)c1ccc2c(CC(=O)N[C@H]3CC[C@@H](Nc4cc(C(F)(F)F)nc5ccc(Cl)cc45)CC3)cc(=O)oc2c1] | 4-158 |
| 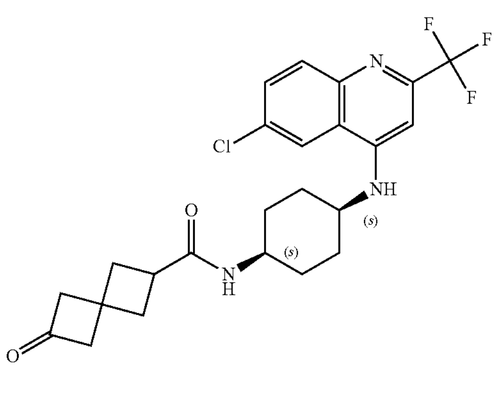 [SMILES: O=C1CC2(C1)CC(C(=O)N[C@H]1CC[C@@H](Nc3cc(C(F)(F)F)nc4ccc(Cl)cc34)CC1)C2] | 4-159 |

TABLE I-continued
Representative compounds having Structure (I)
| Structure | Cpd No. |
|---|---|
| 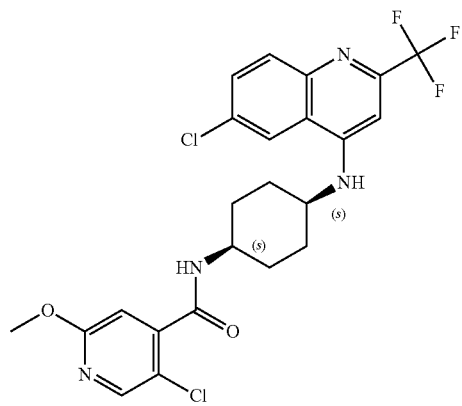 [SMILES: COc1cc(C(=O)N[C@H]2CC[C@@H](Nc3cc(C(F)(F)F)nc4ccc(Cl)cc34)CC2)c(Cl)cn1] | 4-160 |
| 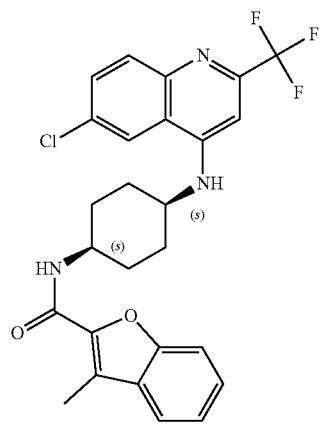 [SMILES: Cc1c(C(=O)N[C@H]2CC[C@@H](Nc3cc(C(F)(F)F)nc4ccc(Cl)cc34)CC2)oc2ccccc12] | 4-161 |
| 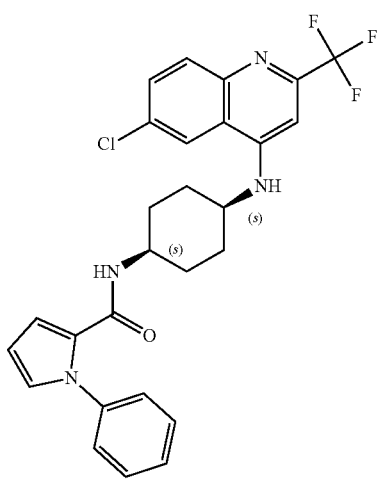 [SMILES: O=C(N[C@H]1CC[C@@H](Nc2cc(C(F)(F)F)nc3ccc(Cl)cc23)CC1)c1cccn1-c1ccccc1] | 4-162 |

TABLE I-continued
Representative compounds having Structure (I)
| Structure | Cpd No. |
|---|---|
| 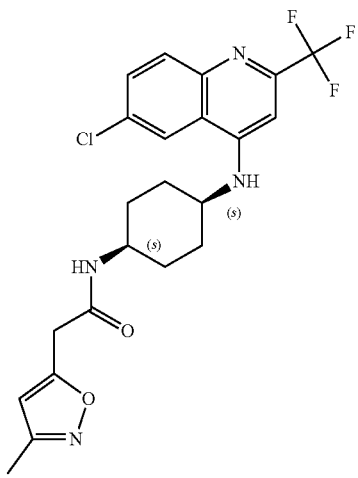 [SMILES: Cc1cc(CC(=O)N[C@H]2CC[C@@H](Nc3cc(C(F)(F)F)nc4ccc(Cl)cc34)CC2)on1] | 4-163 |
| 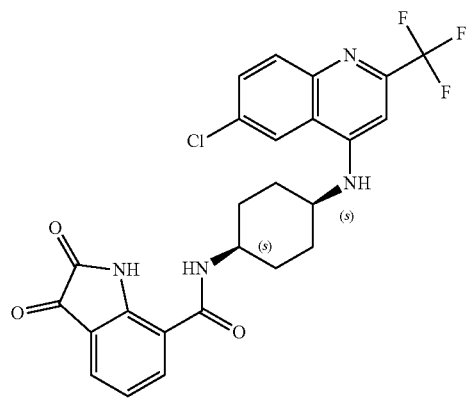 [SMILES: O=C1Nc2c(C(=O)N[C@H]3CC[C@@H](Nc4cc(C(F)(F)F)nc5ccc(Cl)cc45)CC3)cccc2C1=O] | 4-164 |
| 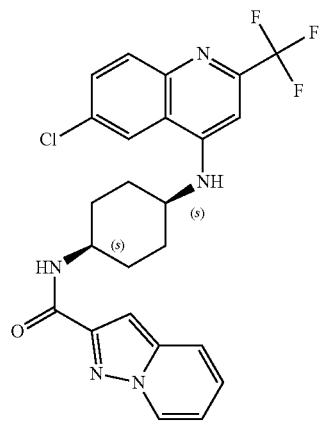 [SMILES: O=C(N[C@H]1CC[C@@H](Nc2cc(C(F)(F)F)nc3ccc(Cl)cc23)CC1)c1cc2ccccn2n1] | 4-165 |

TABLE I-continued
Representative compounds having Structure (I)
| Structure | Cpd No. |
|---|---|
| 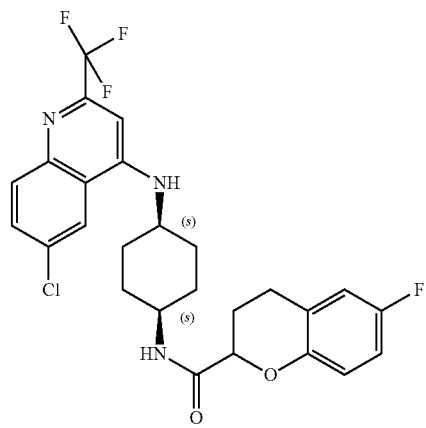 [SMILES: O=C(N[C@H]1CC[C@@H](Nc2cc(C(F)(F)F)nc3ccc(Cl)cc23)CC1)C1CCc2cc(F)ccc2O1] | 4-166 |
| 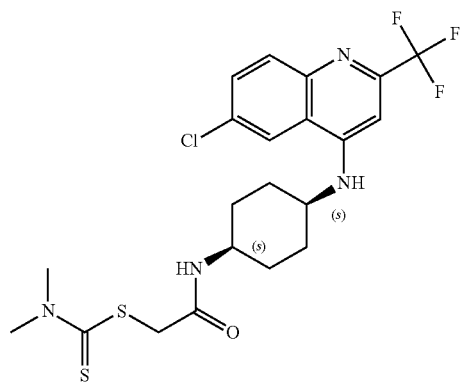 [SMILES: CN(C)C(=S)SCC(=O)N[C@H]1CC[C@@H](Nc2cc(C(F)(F)F)nc3ccc(Cl)cc23)CC1] | 4-167 |
| 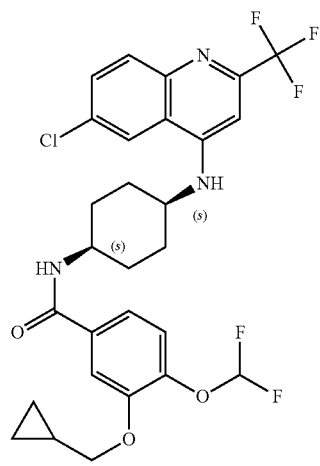 [SMILES: O=C(N[C@H]1CC[C@@H](Nc2cc(C(F)(F)F)nc3ccc(Cl)cc23)CC1)c1ccc(OC(F)F)c(OCC2CC2)c1] | 4-168 |

TABLE I-continued
| Representative compounds having Structure (I) | |
|---|---|
| Structure | Cpd No. |
| 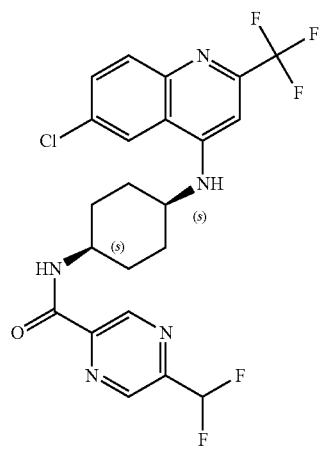 [SMILES: O=C(N[C@H]1CC[C@@H](Nc2cc(C(F)(F)F)nc3ccc(Cl)cc23)CC1)c1cnc(C(F)F)cn1] | 4-169 |
| 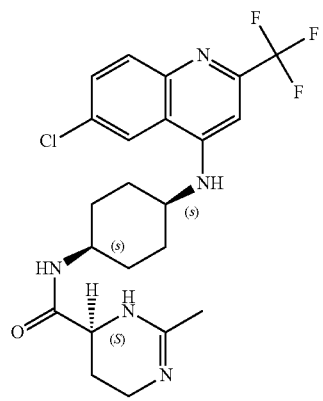 | 4-170 |
| 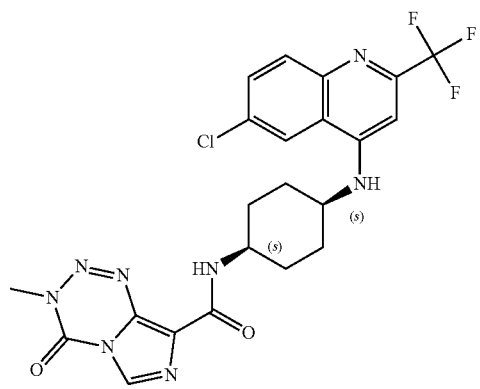 [SMILES: Cn1nnc2c(C(=O)N[C@H]3CC[C@@H](Nc4cc(C(F)(F)F)nc5ccc(Cl)cc45)CC3)ncn2c1=O] | 4-171 |

TABLE I-continued

Representative compounds having Structure (I)

| Structure | Cpd No. |
|---|---|
|  | 4-172 |
|  | 4-173 |
|  | 4-174 |
|  | 4-175 |

TABLE I-continued
Representative compounds having Structure (I)
| Structure | Cpd No. |
|---|---|
| 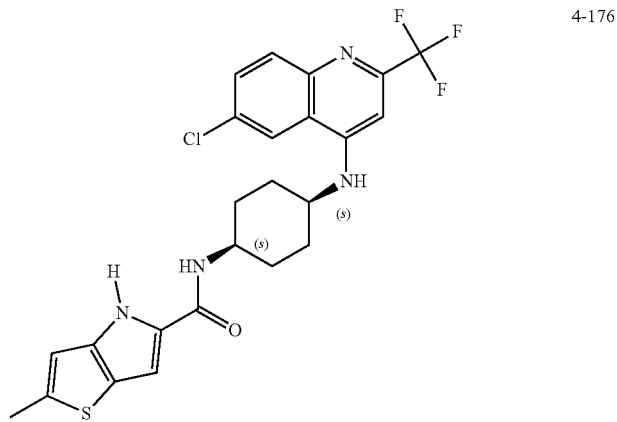 | 4-176 |
| 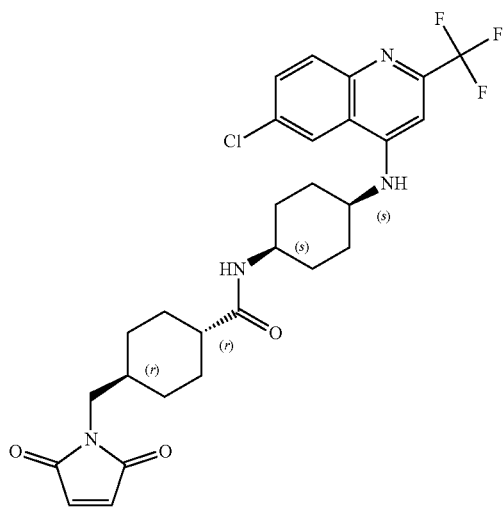 [SMILES: O=C1C=CC(=O)N1C[C@H]1CC[C@H](C(=O)N[C@H]2CC[C@@H](Nc3cc(C(F)(F)F)nc4ccc(Cl)cc34)CC2)CC1] | 4-177 |
| 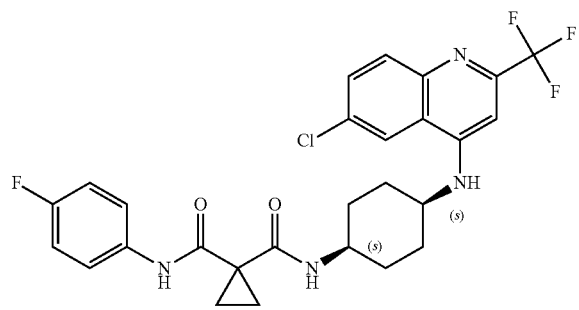 [SMILES: O=C(Nc1ccc(F)cc1)C1(C(=O)N[C@H]2CC[C@@H](Nc3cc(C(F)(F)F)nc4ccc(Cl)cc34)CC2)CC1] | 4-178 |

TABLE I-continued

Representative compounds having Structure (I)

| Structure | Cpd No. |
|---|---|
| 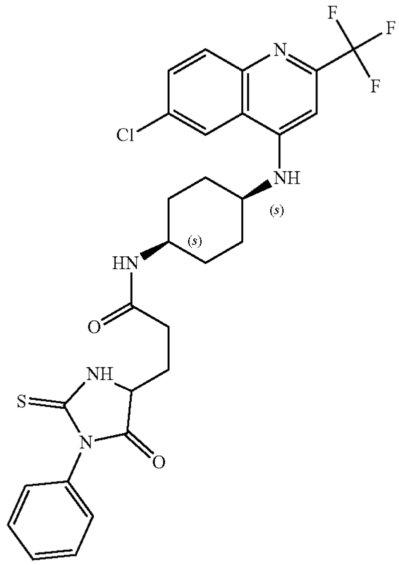 [SMILES: O=C(CCC1NC(=S)N(c2ccccc2)C1=O)N[C@H]1CC[C@@H](Nc2cc(C(F)(F)F)nc3ccc(Cl)cc23)CC1] | 4-179 |
| 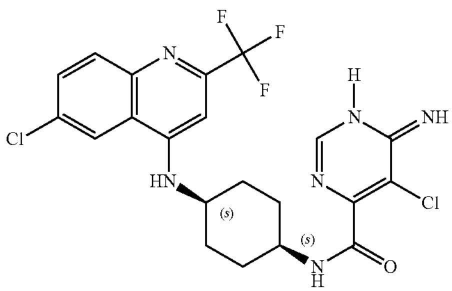 [SMILES: N=c1[nH]cnc(C(=O)N[C@H]2CC[C@@H](Nc3cc(C(F)(F)F)nc4ccc(Cl)cc34)CC2)c1Cl] | 4-180 |
| 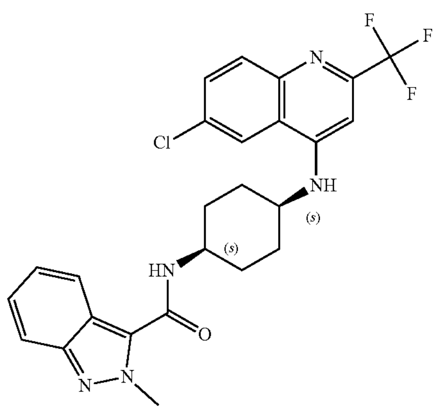 [SMILES: Cn1nc2ccccc2c1C(=O)N[C@H]1CC[C@@H](Nc2cc(C(F)(F)F)nc3ccc(Cl)cc23)CC1] | 4-181 |
| 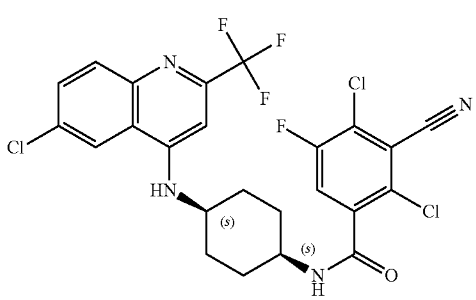 [SMILES: N#Cc1c(Cl)c(F)cc(C(=O)N[C@H]2CC[C@@H](Nc3cc(C(F)(F)F)nc4ccc(Cl)cc34)CC2)c1Cl] | 4-182 |

TABLE I-continued

Representative compounds having Structure (I)

| Structure | Cpd No. |
|---|---|
| 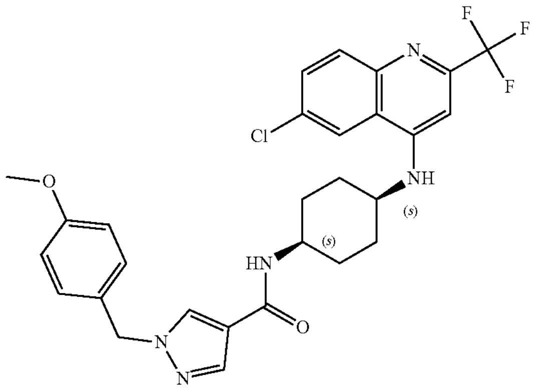 [SMILES: COc1ccc(Cn2cc(C(=O)N[C@H]3CC[C@@H](Nc4cc(C(F)(F)F)nc5ccc(Cl)cc45)CC3)cn2)cc1] | 4-183 |
| 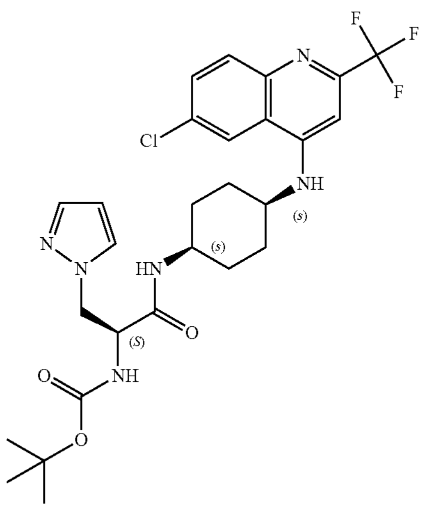 | 4-184 |
| 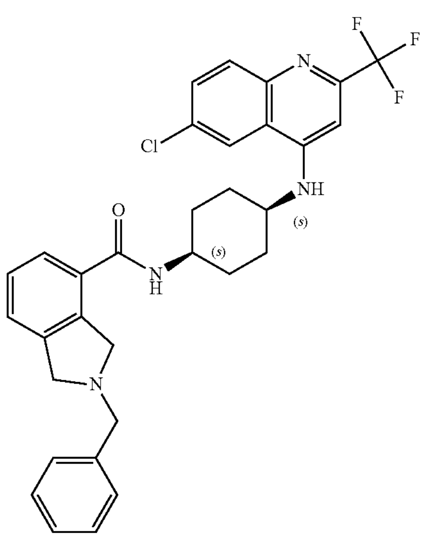 [SMILES: O=C(N[C@H]1CC[C@@H](Nc2cc(C(F)(F)F)nc3ccc(Cl)cc23)CC1)c1cccc2c1CN(Cc1ccccc1)C2] | 4-185 |

TABLE I-continued
Representative compounds having Structure (I)
| Structure | Cpd No. |
|---|---|
| 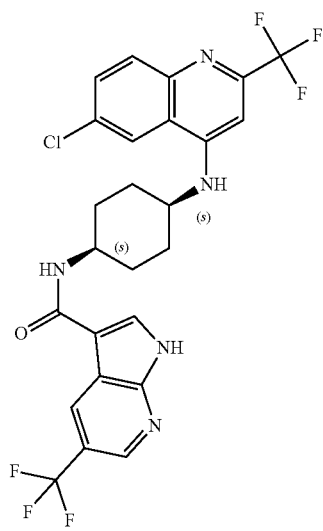 [SMILES: O=C(N[C@H]1CC[C@@H](Nc2cc(C(F)(F)F)nc3ccc(Cl)cc23)CC1)c1c[nH]c2ncc(C(F)(F)F)cc12] | 4-186 |
| 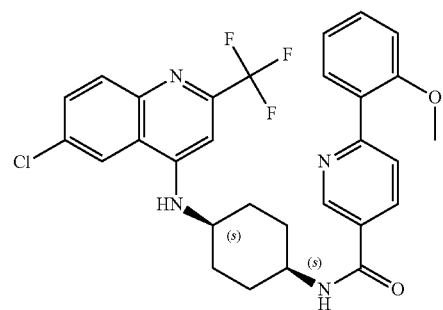 [SMILES: COc1ccccc1-c1ccc(C(=O)N[C@H]2CC[C@@H](Nc3cc(C(F)(F)F)nc4ccc(Cl)cc34)CC2)cn1] | 4-187 |
| 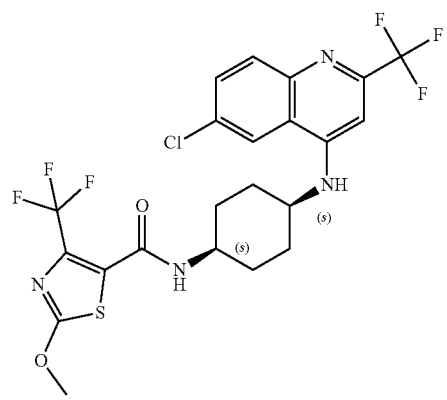 [SMILES: COc1nc(C(F)(F)F)c(C(=O)N[C@H]2CC[C@@H](Nc3cc(C(F)(F)F)nc4ccc(Cl)cc34)CC2)s1] | 4-188 |

TABLE I-continued

Representative compounds having Structure (I)

| Structure | Cpd No. |
|---|---|
| 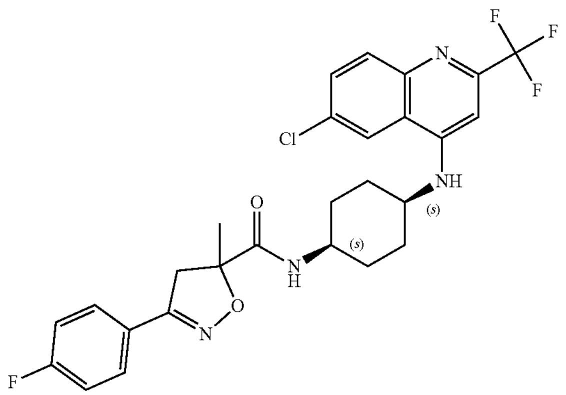 [SMILES: CC1(C(=O)N[C@H]2CC[C@@H](Nc3cc(C(F)(F)F)nc4ccc(Cl)cc34)CC2)CC(c2ccc(F)cc2)=NO1] | 4-189 |
| 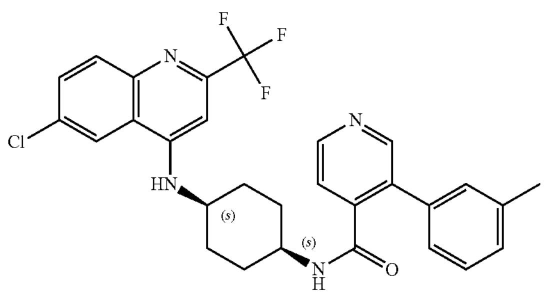 [SMILES: Cc1cccc(-c2cnccc2C(=O)N[C@H]2CC[C@@H](Nc3cc(C(F)(F)F)nc4ccc(Cl)cc34)CC2)c1] | 4-190 |
| 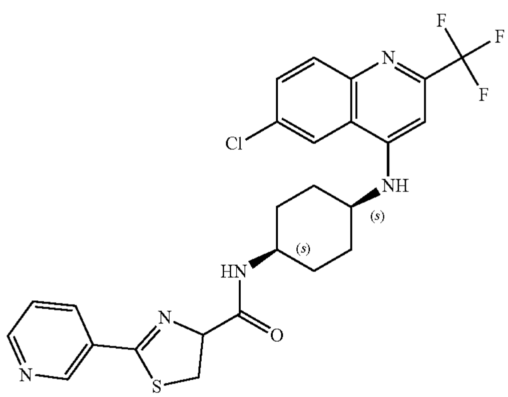 [SMILES: O=C(N[C@H]1CC[C@@H](Nc2cc(C(F)(F)F)nc3ccc(Cl)cc23)CC1)C1CSC(c2cccnc2)=N1] | 4-191 |
| 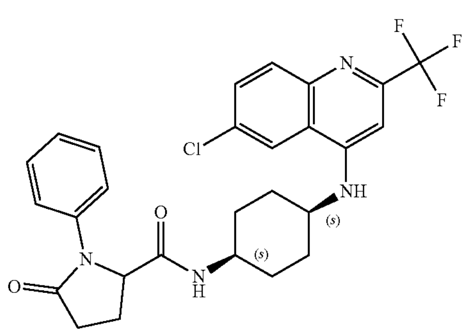 [SMILES: O=C(N[C@H]1CC[C@@H](Nc2cc(C(F)(F)F)nc3ccc(Cl)cc23)CC1)C1CCC(=O)N1c1ccccc1] | 4-192 |

TABLE I-continued

Representative compounds having Structure (I)

| Structure | Cpd No. |
|---|---|
| 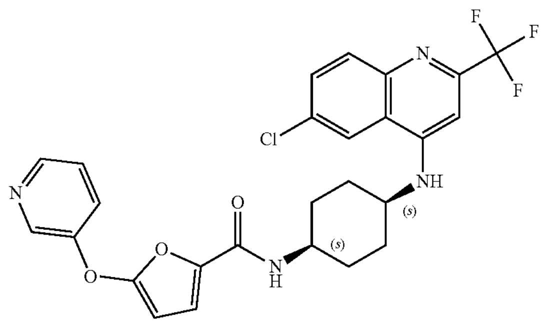 [SMILES: O=C(N[C@H]1CC[C@@H](Nc2cc(C(F)(F)F)nc3ccc(Cl)cc23)CC1)c1ccc(Oc2cccnc2)o1] | 4-193 |
| 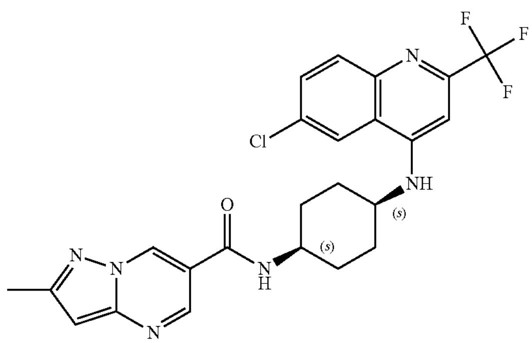 [SMILES: Cc1cc2ncc(C(=O)N[C@H]3CC[C@@H](Nc4cc(C(F)(F)F)nc5ccc(Cl)cc45)CC3)cn2n1] | 4-194 |
| 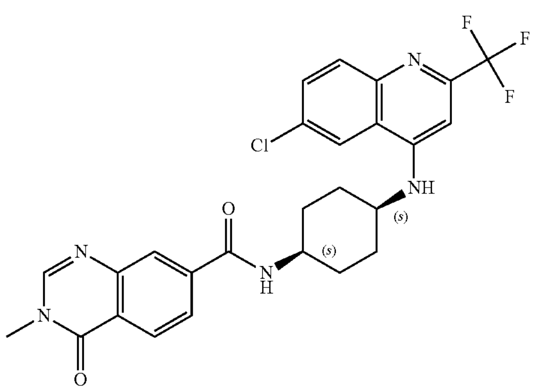 [SMILES: Cn1cnc2cc(C(=O)N[C@H]3CC[C@@H](Nc4cc(C(F)(F)F)nc5ccc(Cl)cc45)CC3)ccc2c1=O] | 4-195 |
| 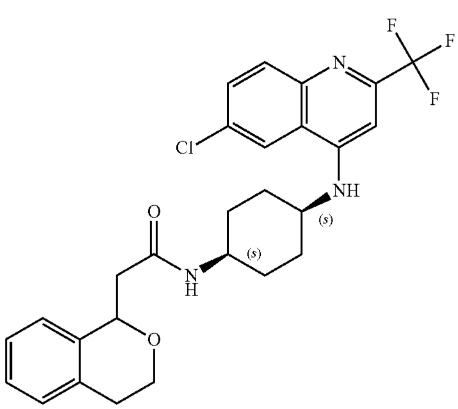 [SMILES: O=C(CC1OCCc2ccccc21)N[C@H]1CC[C@@H](Nc2cc(C(F)(F)F)nc3ccc(Cl)cc23)CC1] | 4-196 |

TABLE I-continued
Representative compounds having Structure (I)
| Structure | Cpd No. |
|---|---|
| 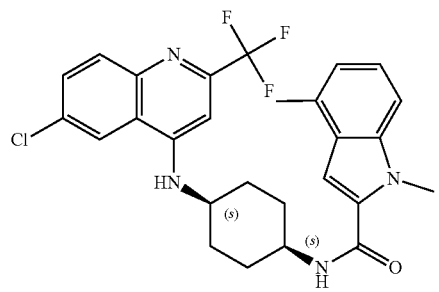 [SMILES: Cc1cccc2c1cc(C(=O)N[C@H]1CC[C@@H](Nc3cc(C(F)(F)F)nc4ccc(Cl)cc34)CC1)n2C] | 4-197 |
| 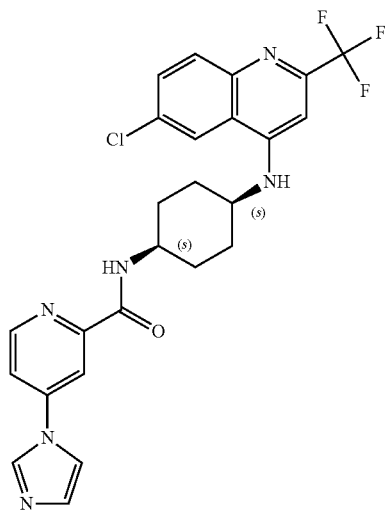 [SMILES: O=C(N[C@H]1CC[C@@H](Nc2cc(C(F)(F)F)nc3ccc(Cl)cc23)CC1)c1cc(-n2ccnc2)ccn1] | 4-198 |
| 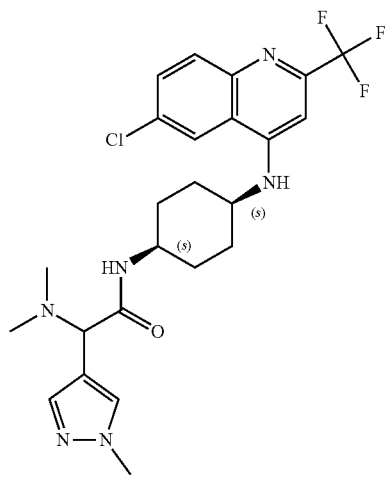 [SMILES: CN(C)C(C(=O)N[C@H]1CC[C@@H](Nc2cc(C(F)(F)F)nc3ccc(Cl)cc23)CC1)c1cnn(C)c1] | 4-199 |

TABLE I-continued

Representative compounds having Structure (I)

| Structure | Cpd No. |
|---|---|
| 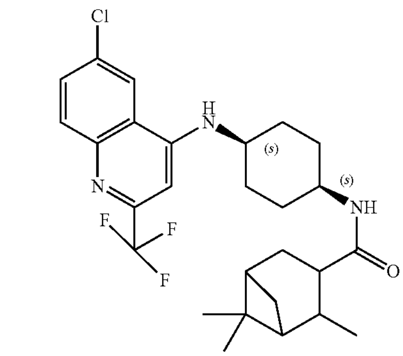 [SMILES: CC1C(C(=O)N[C@H]2CC[C@@H](Nc3cc(C(F)(F)F)nc4ccc(Cl)cc34)CC2)CC2CC1C2(C)C] | 4-200 |
| 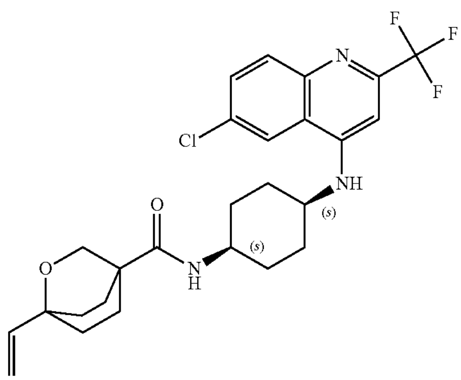 [SMILES: C=CC12CCC(C(=O)N[C@H]3CC[C@@H](Nc4cc(C(F)(F)F)nc5ccc(Cl)cc45)CC3)(CC1)CO2] | 4-201 |
| 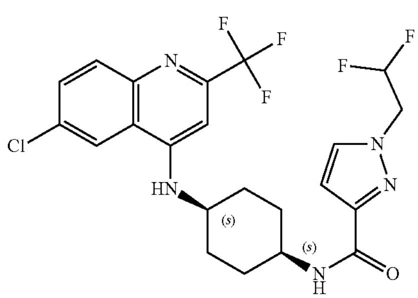 [SMILES: O=C(N[C@H]1CC[C@@H](Nc2cc(C(F)(F)F)nc3ccc(Cl)cc23)CC1)c1ccn(CC(F)F)n1] | 4-202 |
| 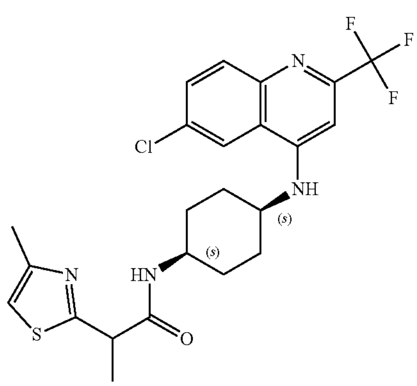 [SMILES: Cc1csc(C(C)C(=O)N[C@H]2CC[C@@H](Nc3cc(C(F)(F)F)nc4ccc(Cl)cc34)CC2)n1] | 4-203 |

TABLE I-continued
Representative compounds having Structure (I)
| Structure | Cpd No. |
|---|---|
| 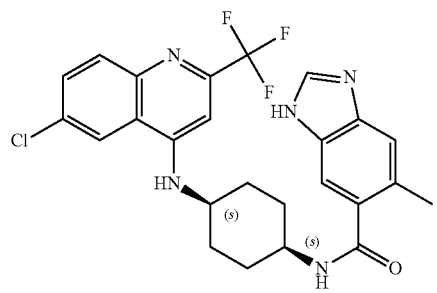 [SMILES: Cc1cc2nc[nH]c2cc1C(=O)N[C@H]1CC[C@@H](Nc2cc(C(F)(F)F)nc3ccc(Cl)cc23)CC1] | 4-204 |
| 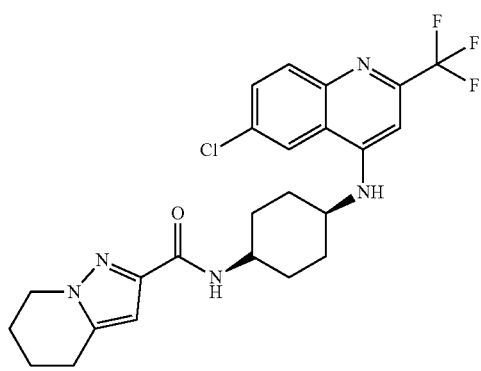 | 4-205 |
| 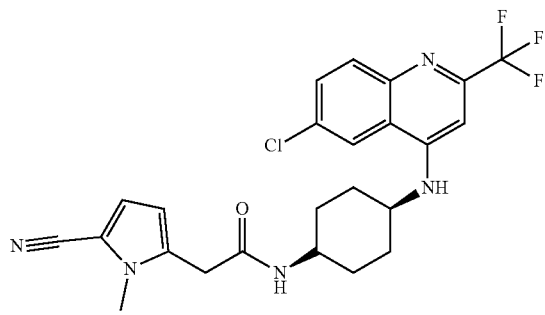 | 4-206 |
| 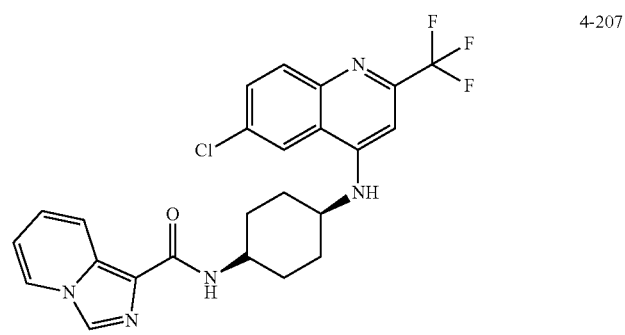 | 4-207 |

TABLE I-continued

Representative compounds having Structure (I)

| Structure | Cpd No. |
|---|---|
| 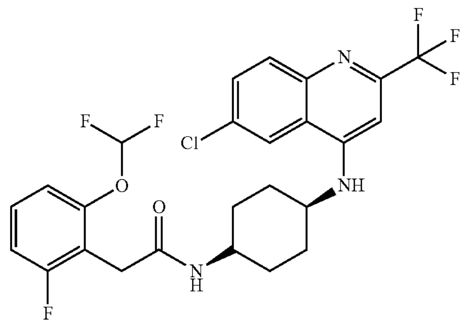 | 4-208 |
| 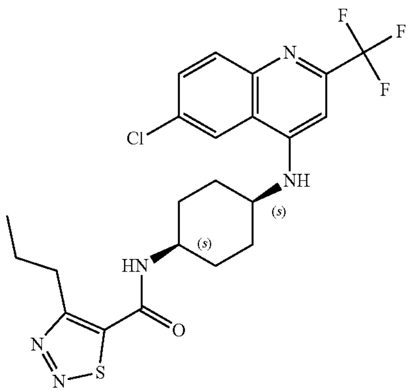 [SMILES: CCCc1nnsc1C(=O)N[C@H]1CC[C@@H](Nc2cc(C(F)(F)F)nc3ccc(Cl)cc23)CC1] | 4-209 |
| 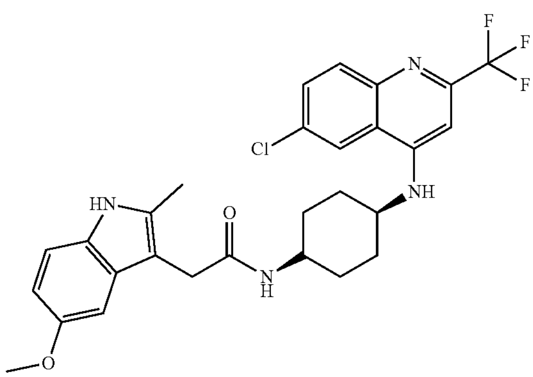 | 4-210 |
| 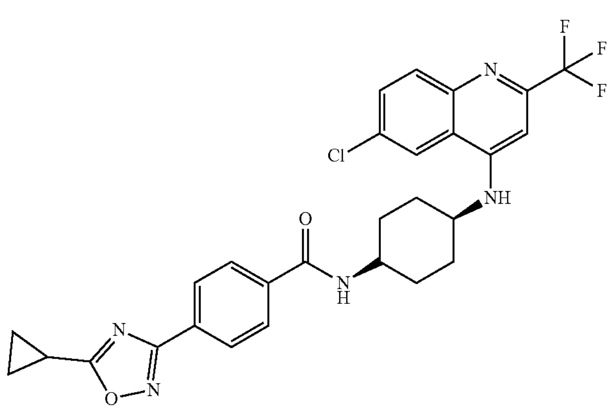 | 4-211 |

TABLE I-continued
Representative compounds having Structure (I)
| Structure | Cpd No. |
|---|---|
| 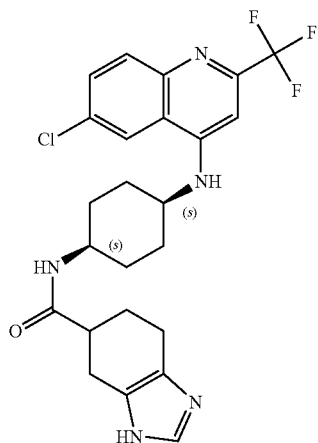 [SMILES: O=C(N[C@H]1CC[C@@H](Nc2cc(C(F)(F)F)nc3ccc(Cl)cc23)CC1)C1CCc2nc[nH]c2C1] | 4-212 |
| 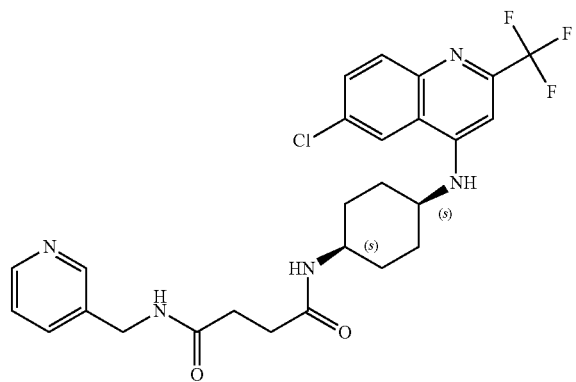 [SMILES: O=C(CCC(=O)N[C@H]1CC[C@@H](Nc2cc(C(F)(F)F)nc3ccc(Cl)cc23)CC1)NCc1cccnc1] | 4-213 |
| 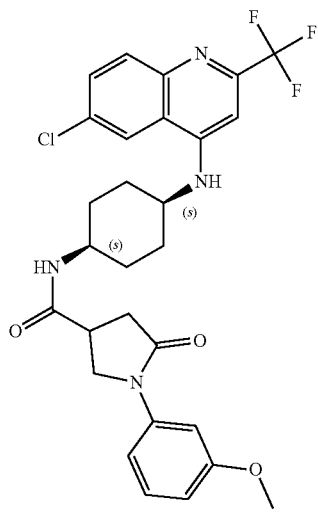 [SMILES: COc1cccc(N2CC(C(=O)N[C@H]3CC[C@@H](Nc4cc(C(F)(F)F)nc5ccc(Cl)cc45)CC3)CC2=O)c1] | 4-214 |

TABLE I-continued
Representative compounds having Structure (I)
| Structure | Cpd No. |
|---|---|
| 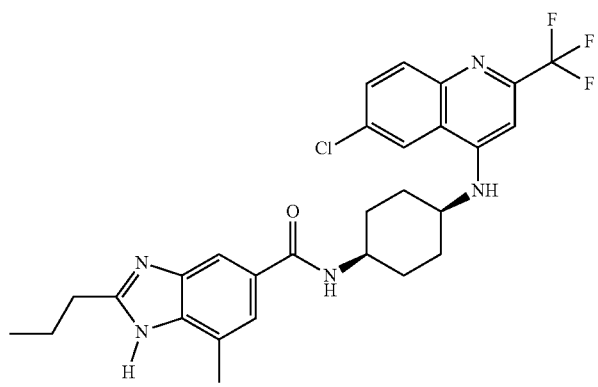 [SMILES: CCCc1nc2cc(C(=O)N[C@H]3CC[C@@H](Nc4cc(C(F)(F)F)nc5ccc(Cl)cc45)CC3)cc(C)c2[nH]1] | 4-215 |
| 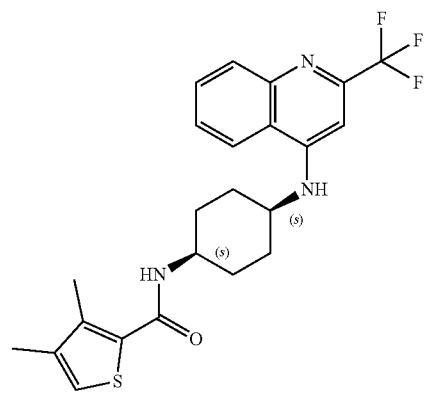 [SMILES: Cc1csc(C(=O)N[C@H]2CC[C@@H](Nc3cc(C(F)(F)F)nc4ccccc34)CC2)c1C] | 4-216 |
| 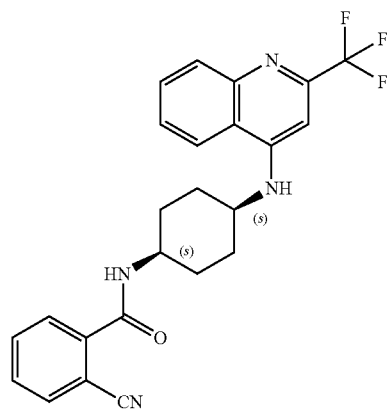 [SMILES: N#Cc1ccccc1C(=O)N[C@H]1CC[C@@H](Nc2cc(C(F)(F)F)nc3ccccc23)CC1] | 4-217 |

TABLE I-continued
Representative compounds having Structure (I)
| Structure | Cpd No. |
|---|---|
| 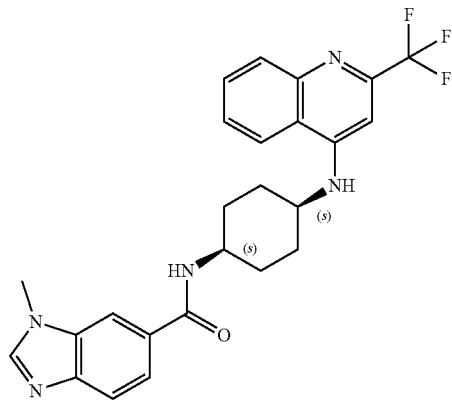 [SMILES: Cn1cnc2ccc(C(=O)N[C@H]3CC[C@@H](Nc4cc(C(F)(F)F)nc5ccccc45)CC3)cc21] | 4-218 |
| 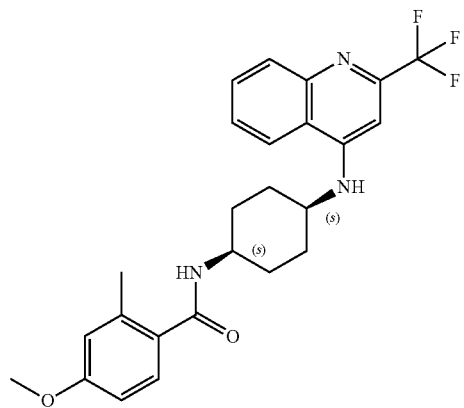 [SMILES: COc1ccc(C(=O)N[C@H]2CC[C@@H](Nc3cc(C(F)(F)F)nc4ccccc34)CC2)c(C)c1] | 4-219 |
| 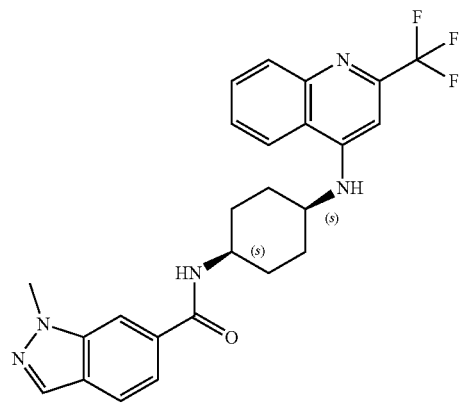 [SMILES: Cn1ncc2ccc(C(=O)N[C@H]3CC[C@@H](Nc4cc(C(F)(F)F)nc5ccccc45)CC3)cc21] | 4-220 |

TABLE I-continued
Representative compounds having Structure (I)
| Structure | Cpd No. |
|---|---|
| 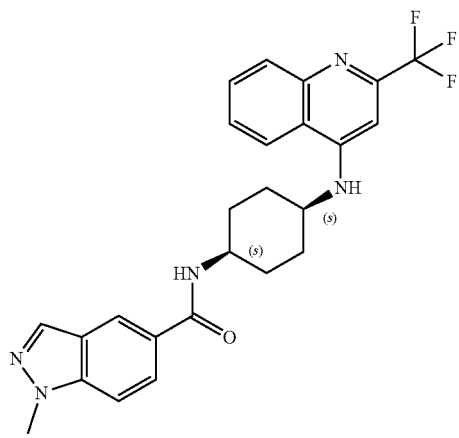 [SMILES: Cn1ncc2cc(C(=O)N[C@H]3CC[C@@H](Nc4cc(C(F)(F)F)nc5ccccc45)CC3)ccc21] | 4-221 |
| 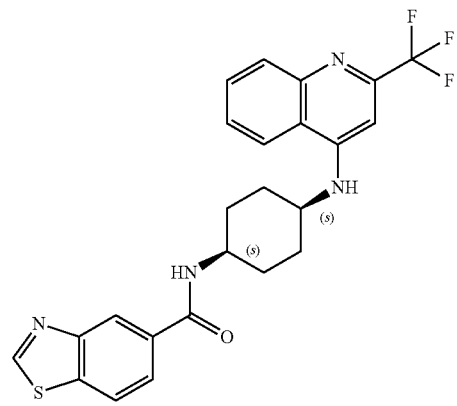 [SMILES: O=C(N[C@H]1CC[C@@H](Nc2cc(C(F)(F)F)nc3ccccc23)CC1)c1ccc2scnc2c1] | 4-222 |
| 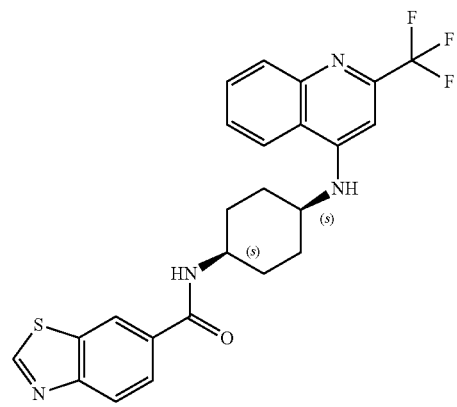 [SMILES: O=C(N[C@H]1CC[C@@H](Nc2cc(C(F)(F)F)nc3ccccc23)CC1)c1ccc2ncsc2c1] | 4-223 |

TABLE I-continued
| Representative compounds having Structure (I) | |
|---|---|
| Structure | Cpd No. |
| 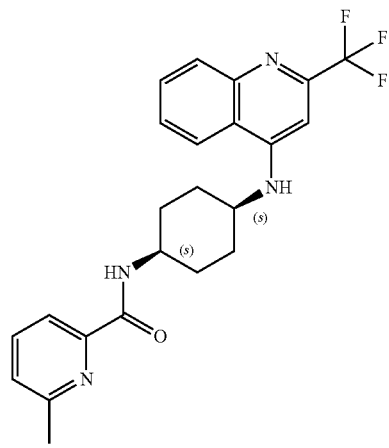 [SMILES: Cc1cccc(C(=O)N[C@H]2CC[C@@H](Nc3cc(C(F)(F)F)nc4ccccc34)CC2)n1] | 4-224 |
| 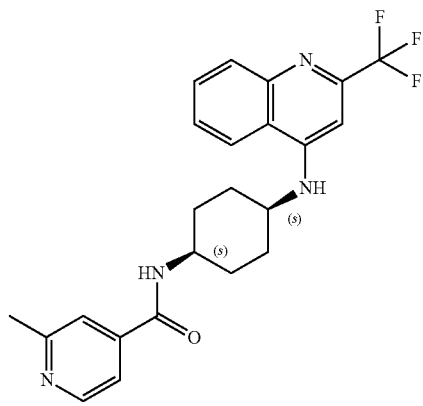 [SMILES: Cc1cc(C(=O)N[C@H]2CC[C@@H](Nc3cc(C(F)(F)F)nc4ccccc34)CC2)ccn1] | 4-225 |
| 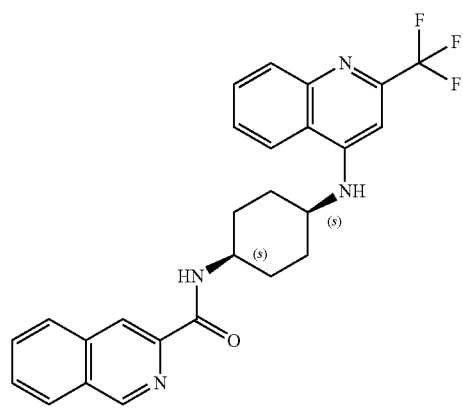 [SMILES: O=C(N[C@H]1CC[C@@H](Nc2cc(C(F)(F)F)nc3ccccc23)CC1)c1cc2ccccc2cn1] | 4-226 |

TABLE I-continued
Representative compounds having Structure (I)
| Structure | Cpd No. |
|---|---|
| 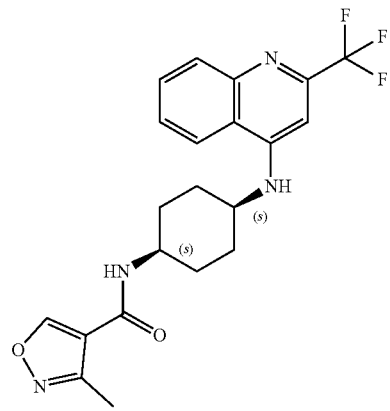 [SMILES: Cc1nocc1C(=O)N[C@H]1CC[C@@H](Nc2cc(C(F)(F)F)nc3ccccc23)CC1] | 4-227 |
| 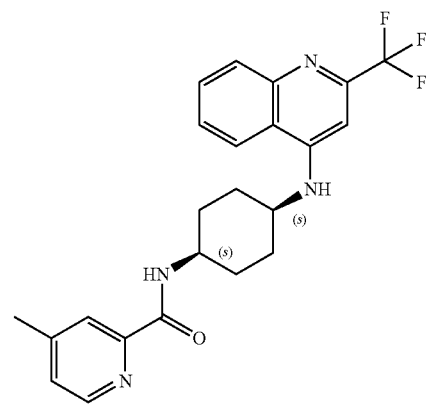 [SMILES: Cc1ccnc(C(=O)N[C@H]2CC[C@@H](Nc3cc(C(F)(F)F)nc4ccccc34)CC2)c1] | 4-228 |
| 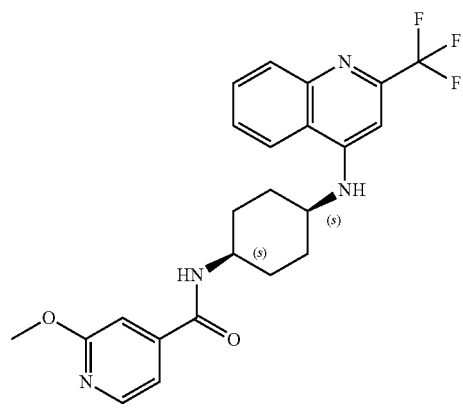 [SMILES: COc1cc(C(=O)N[C@H]2CC[C@@H](Nc3cc(C(F)(F)F)nc4ccccc34)CC2)ccn1] | 4-229 |

TABLE I-continued
| Representative compounds having Structure (I) | |
|---|---|
| Structure | Cpd No. |
| 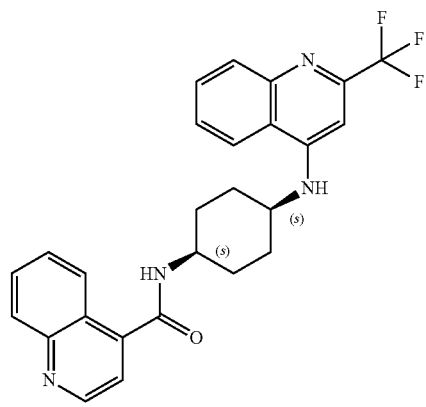 [SMILES: O=C(N[C@H]1CC[C@@H](Nc2cc(C(F)(F)F)nc3ccccc23)CC1)c1ccnc2ccccc12] | 4-230 |
| 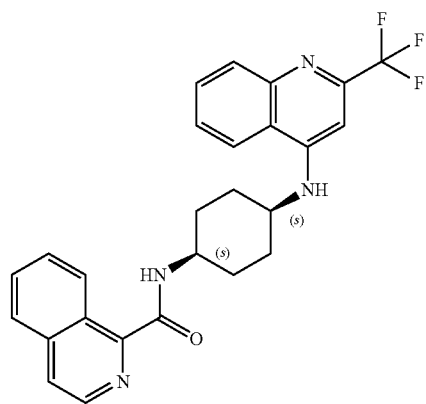 [SMILES: O=C(N[C@H]1CC[C@@H](Nc2cc(C(F)(F)F)nc3ccccc23)CC1)c1nccc2ccccc12] | 4-231 |
| 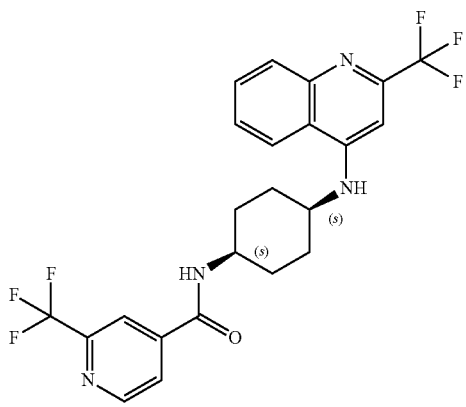 [SMILES: O=C(N[C@H]1CC[C@@H](Nc2cc(C(F)(F)F)nc3ccccc23)CC1)c1ccnc(C(F)(F)F)c1] | 4-232 |

TABLE I-continued
Representative compounds having Structure (I)
| Structure | Cpd No. |
|---|---|
| 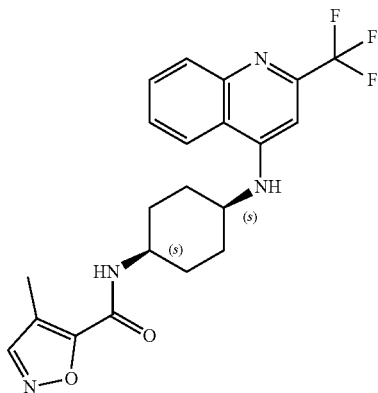 [SMILES: Cc1cnoc1C(=O)N[C@H]1CC[C@@H](Nc2cc(C(F)(F)F)nc3ccccc23)CC1] | 4-233 |
| 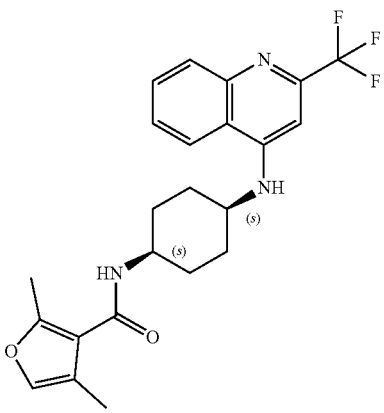 [SMILES: Cc1coc(C)c1C(=O)N[C@H]1CC[C@@H](Nc2cc(C(F)(F)F)nc3ccccc23)CC1] | 4-234 |
| 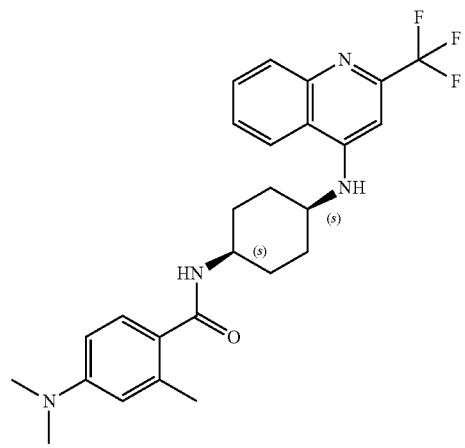 [SMILES: Cc1cc(N(C)C)ccc1C(=O)N[C@H]1CC[C@@H](Nc2cc(C(F)(F)F)nc3ccccc23)CC1] | 4-235 |

TABLE I-continued
Representative compounds having Structure (I)
| Structure | Cpd No. |
|---|---|
| 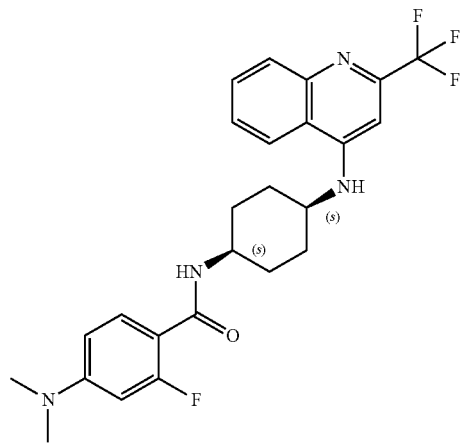 [SMILES: CN(C)c1ccc(C(=O)N[C@H]2CC[C@@H](Nc3cc(C(F)(F)F)nc4ccccc34)CC2)c(F)c1] | 4-236 |
| 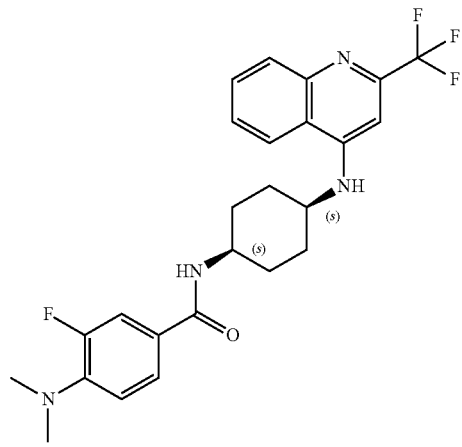 [SMILES: CN(C)c1ccc(C(=O)N[C@H]2CC[C@@H](Nc3cc(C(F)(F)F)nc4ccccc34)CC2)cc1F] | 4-237 |
| 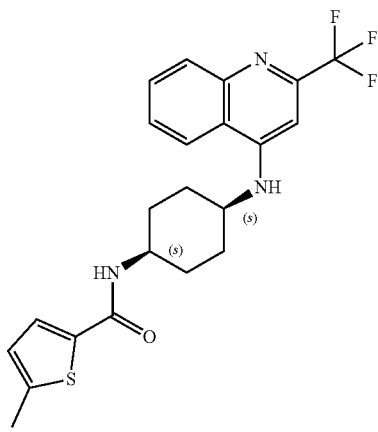 [SMILES: Cc1ccc(C(=O)N[C@H]2CC[C@@H](Nc3cc(C(F)(F)F)nc4ccccc34)CC2)s1] | 4-238 |

TABLE I-continued
Representative compounds having Structure (I)
| Structure | Cpd No. |
|---|---|
| 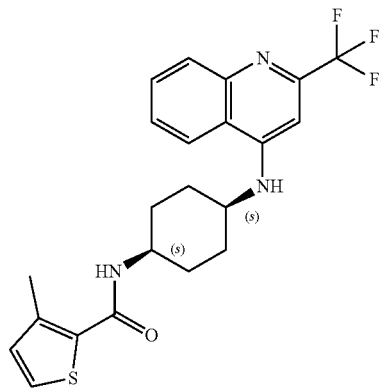 | 4-239 |
| 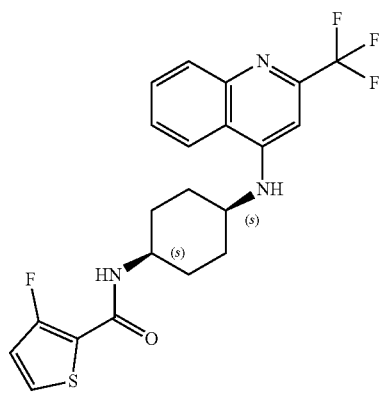 [SMILES: Cc1ccsc1C(=O)N[C@H]1CC[C@@H](Nc2cc(C(F)(F)F)nc3ccccc23)CC1] | 4-240 |
| 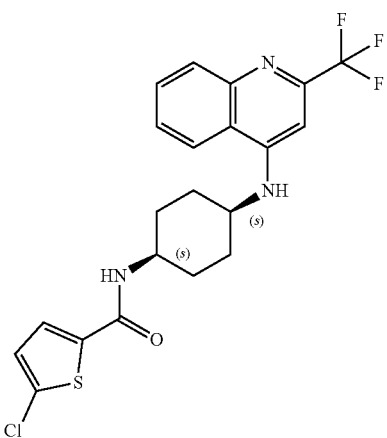 [SMILES: O=C(N[C@H]1CC[C@@H](Nc2cc(C(F)(F)F)nc3ccccc23)CC1)c1ccc(Cl)s1] | 4-241 |

TABLE I-continued
Representative compounds having Structure (I)
| Structure | Cpd No. |
|---|---|
| 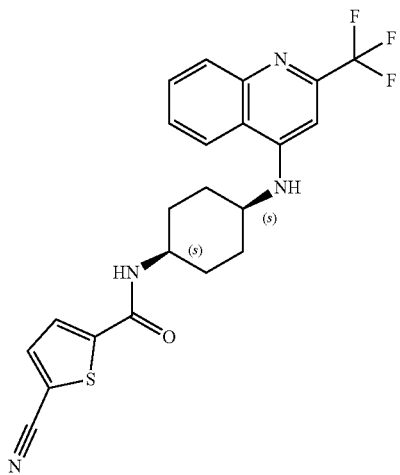 [SMILES: N#Cc1ccc(C(=O)N[C@H]2CC[C@@H](Nc3cc(C(F)(F)F)nc4ccccc34)CC2)s1] | 4-242 |
| 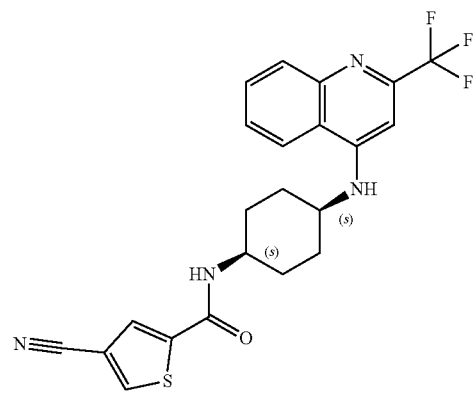 [SMILES: N#Cc1csc(C(=O)N[C@H]2CC[C@@H](Nc3cc(C(F)(F)F)nc4ccccc34)CC2)c1] | 4-243 |
| 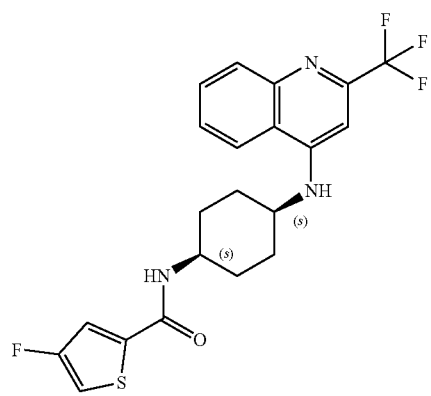 [SMILES: O=C(N[C@H]1CC[C@@H](Nc2cc(C(F)(F)F)nc3ccccc23)CC1)c1cc(F)cs1] | 4-244 |

TABLE I-continued
Representative compounds having Structure (I)
| Structure | Cpd No. |
|---|---|
| 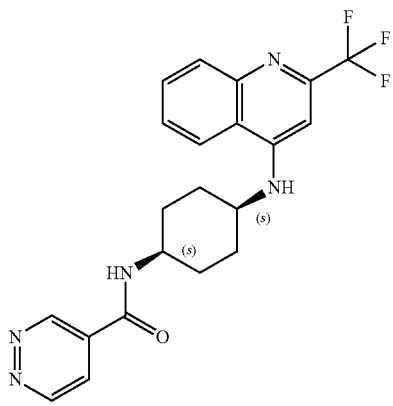 [SMILES: O=C(N[C@H]1CC[C@@H](Nc2cc(C(F)(F)F)nc3ccccc23)CC1)c1ccnnc1] | 4-245 |
| 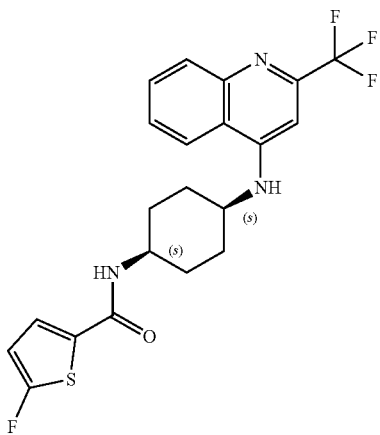 [SMILES: O=C(N[C@H]1CC[C@@H](Nc2cc(C(F)(F)F)nc3ccccc23)CC1)c1ccc(F)s1] | 4-246 |
| 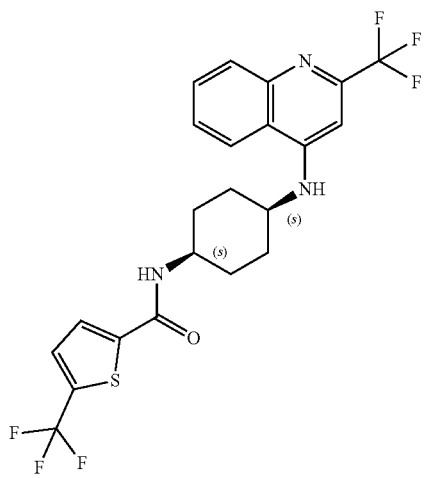 [SMILES: O=C(N[C@H]1CC[C@@H](Nc2cc(C(F)(F)F)nc3ccccc23)CC1)c1ccc(C(F)(F)F)s1] | 4-247 |

TABLE I-continued
Representative compounds having Structure (I)
| Structure | Cpd No. |
|---|---|
| 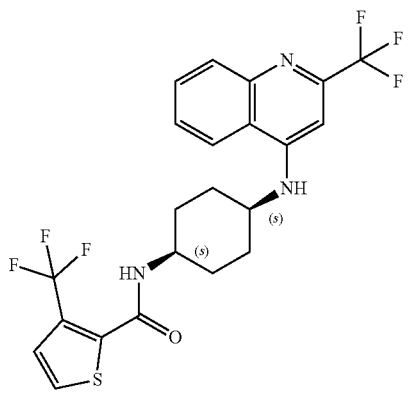 [SMILES: O=C(N[C@H]1CC[C@@H](Nc2cc(C(F)(F)F)nc3ccccc23)CC1)c1sccc1C(F)(F)F] | 4-248 |
| 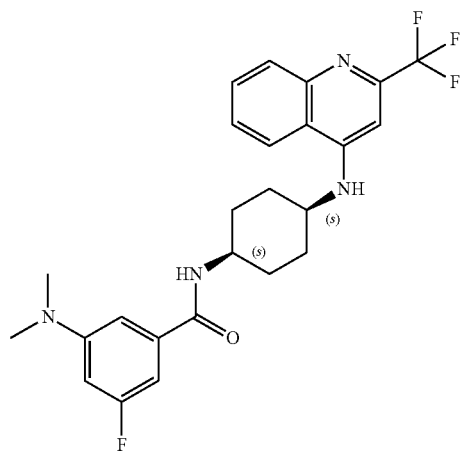 [SMILES: CN(C)c1cc(F)cc(C(=O)N[C@H]2CC[C@@H](Nc3cc(C(F)(F)F)nc4ccccc34)CC2)c1] | 4-249 |
| 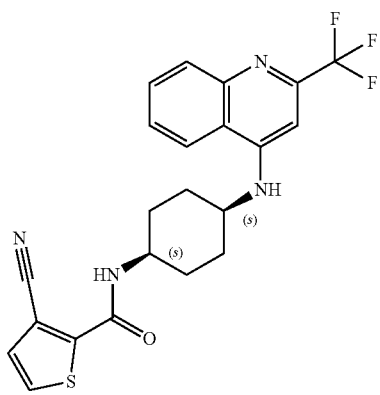 [SMILES: N#Cc1ccsc1C(=O)N[C@H]1CC[C@@H](Nc2cc(C(F)(F)F)nc3ccccc23)CC1] | 4-250 |

TABLE I-continued
Representative compounds having Structure (I)
| Structure | Cpd No. |
|---|---|
| 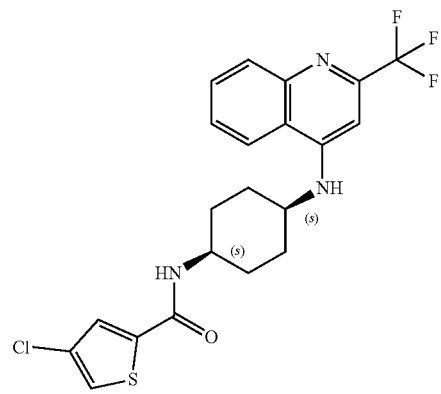 [SMILES: O=C(N[C@H]1CC[C@@H](Nc2cc(C(F)(F)F)nc3ccccc23)CC1)c1cc(Cl)cs1] | 4-251 |
| 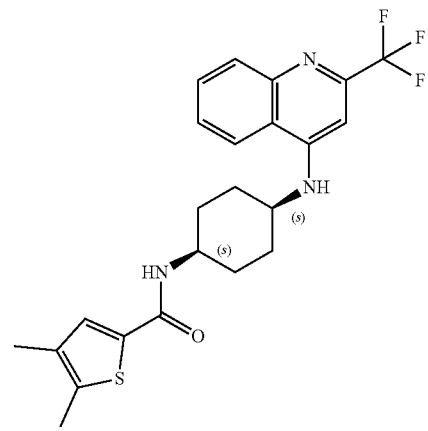 [SMILES: Cc1cc(C(=O)N[C@H]2CC[C@@H](Nc3cc(C(F)(F)F)nc4ccccc34)CC2)sc1C] | 4-252 |
| 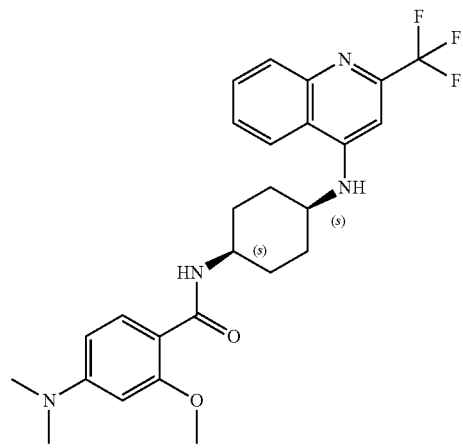 [SMILES: COc1cc(N(C)C)ccc1C(=O)N[C@H]1CC[C@@H](Nc2cc(C(F)(F)F)nc3ccccc23)CC1] | 4-253 |

TABLE I-continued
Representative compounds having Structure (I)
| Structure | Cpd No. |
|---|---|
| 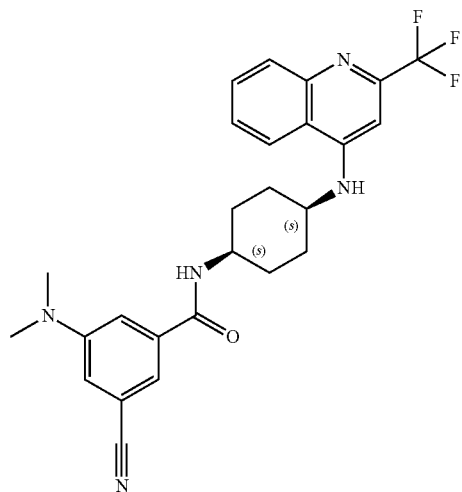 [SMILES: CN(C)c1cc(C#N)cc(C(=O)N[C@H]2CC[C@@H](Nc3cc(C(F)(F)F)nc4ccccc34)CC2)c1] | 4-254 |
| 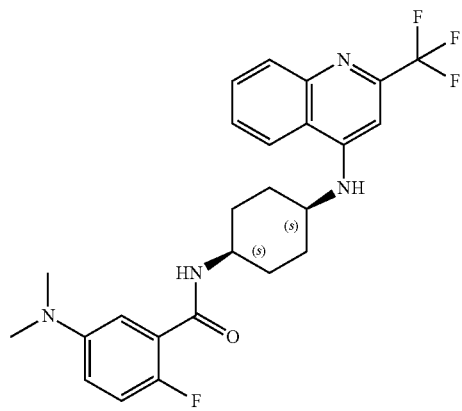 [SMILES: CN(C)c1ccc(F)c(C(=O)N[C@H]2CC[C@@H](Nc3cc(C(F)(F)F)nc4ccccc34)CC2)c1] | 4-255 |
| 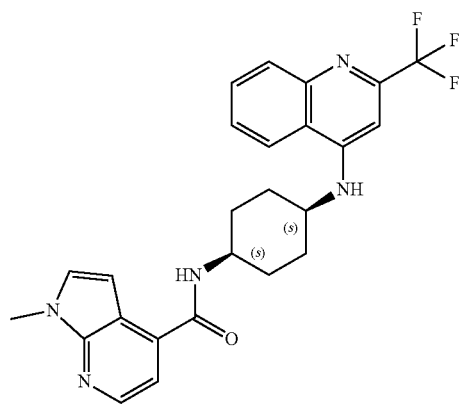 [SMILES: Cn1ccc2c(C(=O)N[C@H]3CC[C@@H](Nc4cc(C(F)(F)F)nc5ccccc45)CC3)ccnc21] | 4-256 |

TABLE I-continued

Representative compounds having Structure (I)

| Structure | Cpd No. |
|---|---|
| 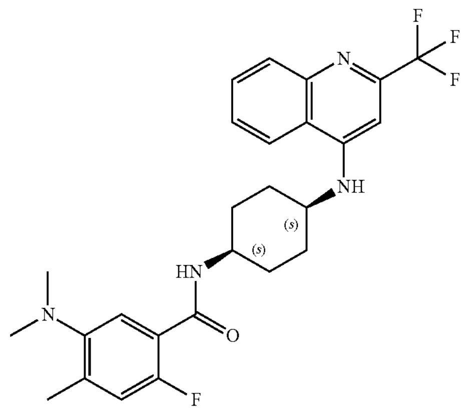 [SMILES: Cc1cc(F)c(C(=O)N[C@H]2CC[C@@H](Nc3cc(C(F)(F)F)nc4ccccc34)CC2)cc1N(C)C] | 4-257 |
| 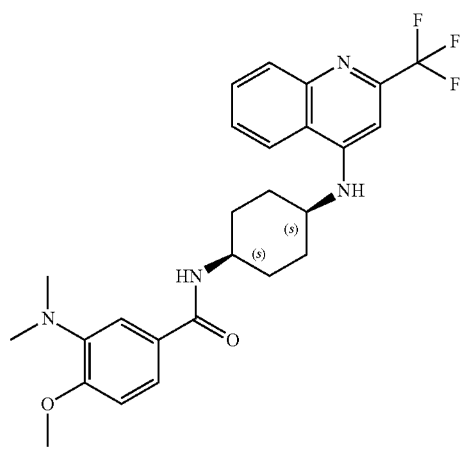 [SMILES: COc1ccc(C(=O)N[C@H]2CC[C@@H](Nc3cc(C(F)(F)F)nc4ccccc34)CC2)cc1N(C)C] | 4-258 |
| 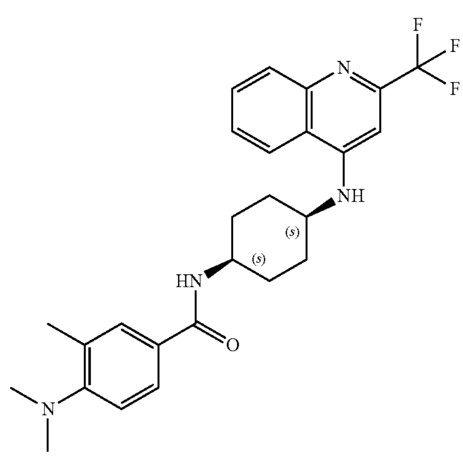 [SMILES: Cc1cc(C(=O)N[C@H]2CC[C@@H](Nc3cc(C(F)(F)F)nc4ccccc34)CC2)ccc1N(C)C] | 4-259 |

TABLE I-continued

Representative compounds having Structure (I)

| Structure | Cpd No. |
|---|---|
| 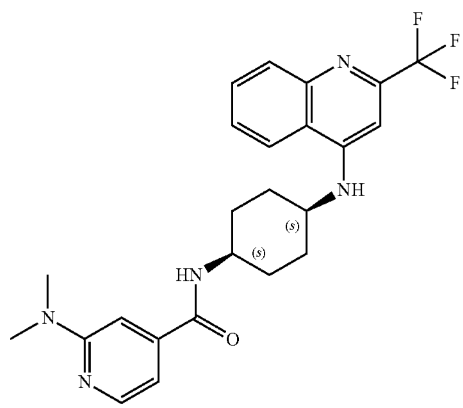 [SMILES: CN(C)c1cc(C(=O)N[C@H]2CC[C@@H](Nc3cc(C(F)(F)F)nc4ccccc34)CC2)ccn1] | 4-260 |
| 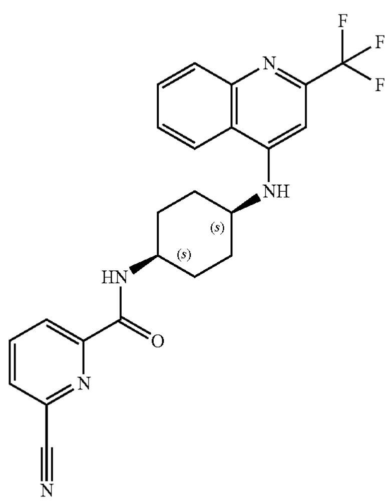 [SMILES: N#Cc1cccc(C(=O)N[C@H]2CC[C@@H](Nc3cc(C(F)(F)F)nc4ccccc34)CC2)n1] | 4-261 |
| 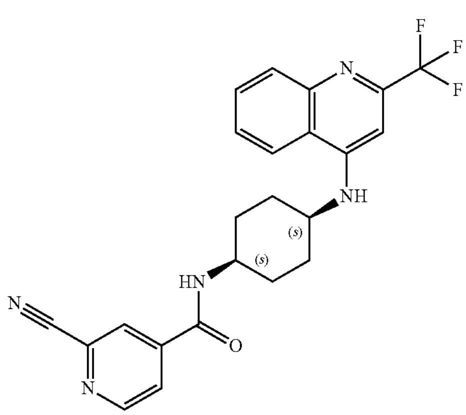 [SMILES: N#Cc1cc(C(=O)N[C@H]2CC[C@@H](Nc3cc(C(F)(F)F)nc4ccccc34)CC2)ccn1] | 4-262 |

TABLE I-continued
| Representative compounds having Structure (I) | |
|---|---|
| Structure | Cpd No. |
4-263
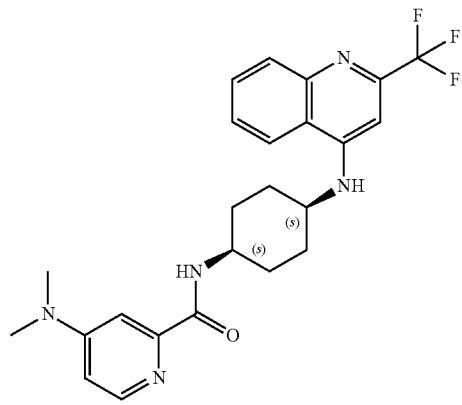 [SMILES: CN(C)c1ccnc(C(=O)N[C@H]2CC[C@@H](Nc3cc(C(F)(F)F)nc4ccccc34)CC2)c1]
4-264
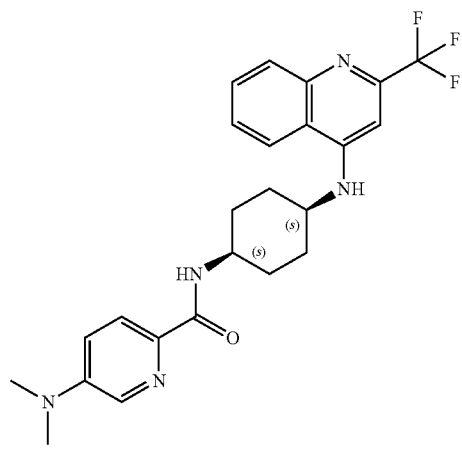 [SMILES: CN(C)c1ccc(C(=O)N[C@H]2CC[C@@H](Nc3cc(C(F)(F)F)nc4ccccc34)CC2)nc1]
4-265
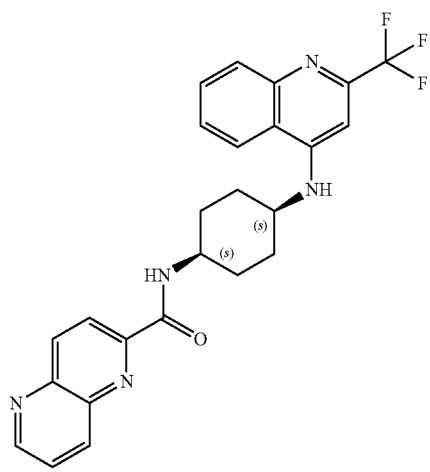 [SMILES: O=C(N[C@H]1CC[C@@H](Nc2cc(C(F)(F)F)nc3ccccc23)CC1)c1ccc2ncccc2n1]

TABLE I-continued
Representative compounds having Structure (I)
| Structure | Cpd No. |
|---|---|
| 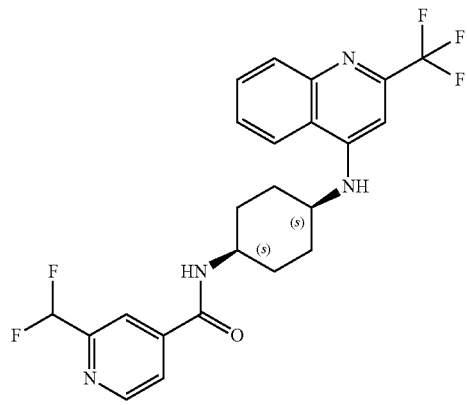 [SMILES: O=C(N[C@H]1CC[C@@H](Nc2cc(C(F)(F)F)nc3ccccc23)CC1)c1ccnc(C(F)F)c1] | 4-266 |
| 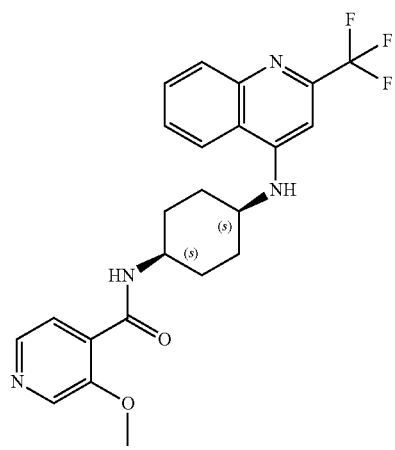 [SMILES: COc1cnccc1C(=O)N[C@H]1CC[C@@H](Nc2cc(C(F)(F)F)nc3ccccc23)CC1] | 4-267 |
| 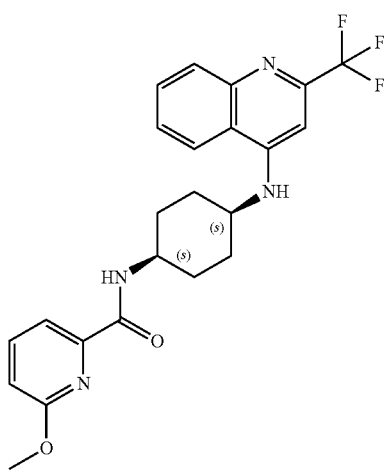 [SMILES: COc1cccc(C(=O)N[C@H]2CC[C@@H](Nc3cc(C(F)(F)F)nc4ccccc34)CC2)n1] | 4-268 |

TABLE I-continued
| Representative compounds having Structure (I) | |
|---|---|
| Structure | Cpd No. |
| 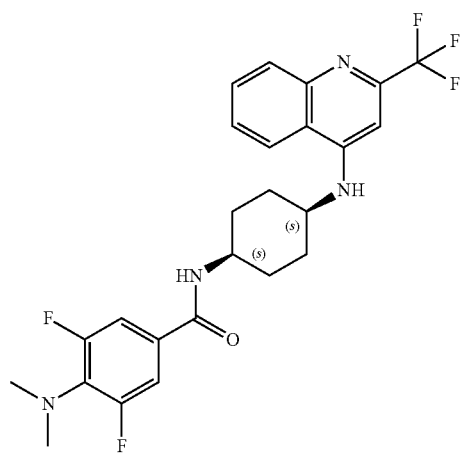 [SMILES: CN(C)c1c(F)cc(C(=O)N[C@H]2CC[C@@H](Nc3cc(C(F)(F)F)nc4ccccc34)CC2)cc1F] | 4-269 |
| 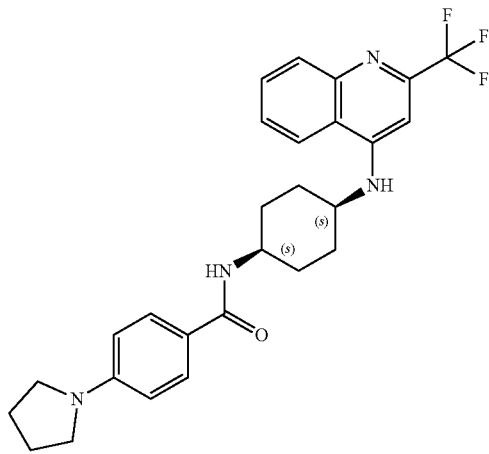 [SMILES: O=C(N[C@H]1CC[C@@H](Nc2cc(C(F)(F)F)nc3ccccc23)CC1)c1ccc(N2CCCC2)cc1] | 4-270 |
| 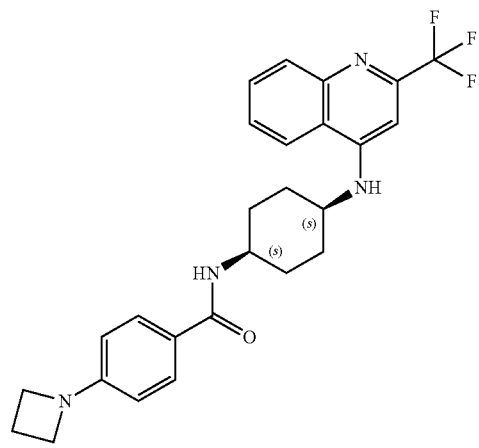 [SMILES: O=C(N[C@H]1CC[C@@H](Nc2cc(C(F)(F)F)nc3ccccc23)CC1)c1ccc(N2CCC2)cc1] | 4-271 |

TABLE I-continued

Representative compounds having Structure (I)

| Structure | Cpd No. |
|---|---|
| 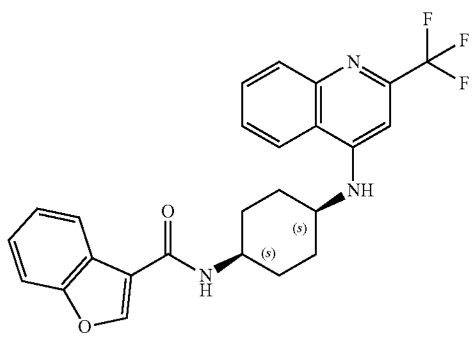 [SMILES: O=C(N[C@H]1CC[C@@H](Nc2cc(C(F)(F)F)nc3ccccc23)CC1)c1coc2ccccc12] | 4-272 |
| 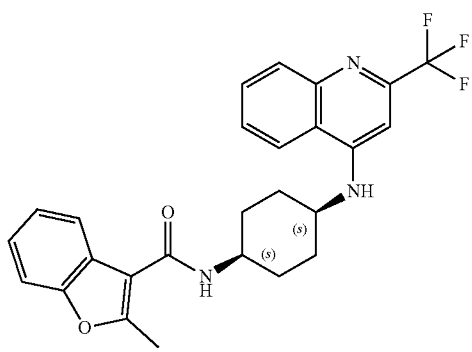 [SMILES: Cc1oc2ccccc2c1C(=O)N[C@H]1CC[C@@H](Nc2cc(C(F)(F)F)nc3ccccc23)CC1] | 4-273 |
| 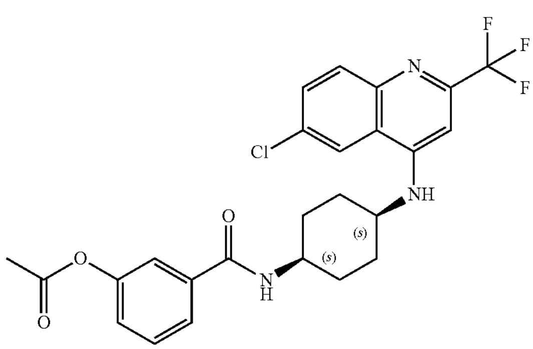 [SMILES: CC(=O)Oc1cccc(C(=O)N[C@H]2CC[C@@H](Nc3cc(C(F)(F)F)nc4ccc(Cl)cc34)CC2)c1] | 4-274 |
| 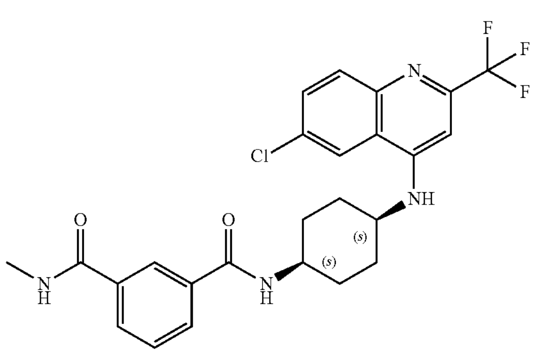 [SMILES: CNC(=O)c1cccc(C(=O)N[C@H]2CC[C@@H](Nc3cc(C(F)(F)F)nc4ccc(Cl)cc34)CC2)c1] | 4-275 |

TABLE I-continued

Representative compounds having Structure (I)

| Structure | Cpd No. |
|---|---|
| 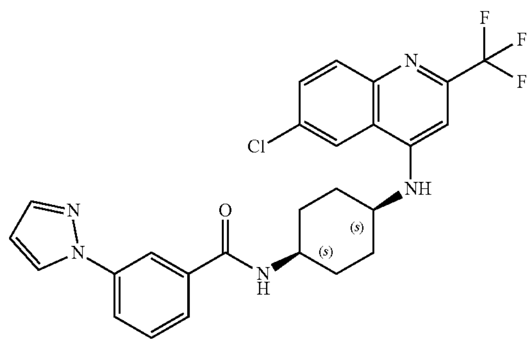 [SMILES: O=C(N[C@H]1CC[C@@H](Nc2cc(C(F)(F)F)nc3ccc(Cl)cc23)CC1)c1cccc(-n2cccn2)c1] | 4-276 |
| 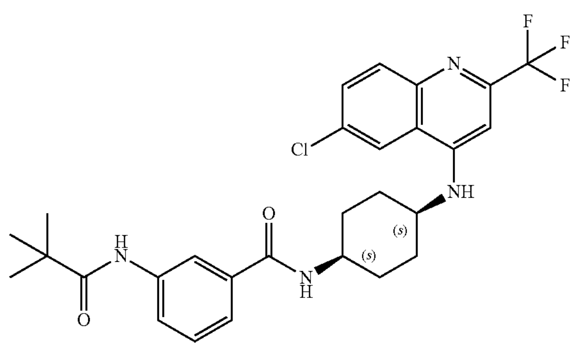 [SMILES: CC(C)(C)C(=O)Nc1cccc(C(=O)N[C@H]2CC[C@@H](Nc3cc(C(F)(F)F)nc4ccc(Cl)cc34)CC2)c1] | 4-277 |
| 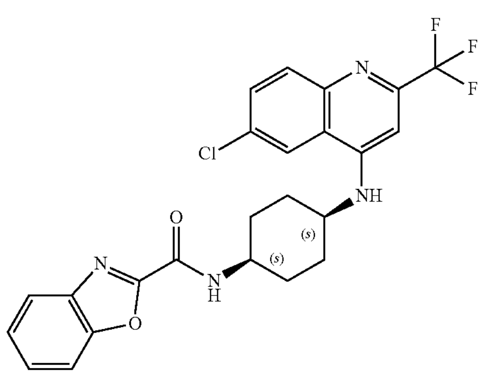 [SMILES: O=C(N[C@H]1CC[C@@H](Nc2cc(C(F)(F)F)nc3ccc(Cl)cc23)CC1)c1nc2ccccc2o1] | 4-278 |
| 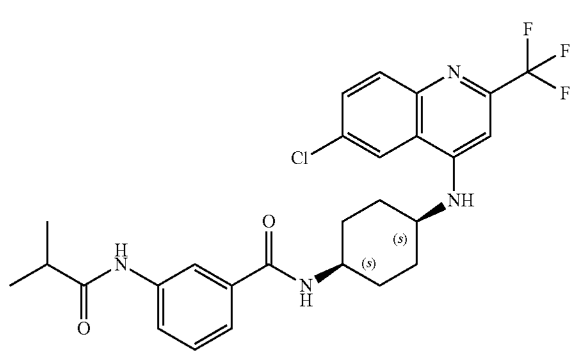 [SMILES: CC(C)C(=O)Nc1cccc(C(=O)N[C@H]2CC[C@@H](Nc3cc(C(F)(F)F)nc4ccc(Cl)cc34)CC2)c1] | 4-279 |

TABLE I-continued

Representative compounds having Structure (I)

| Structure | Cpd No. |
|---|---|
| 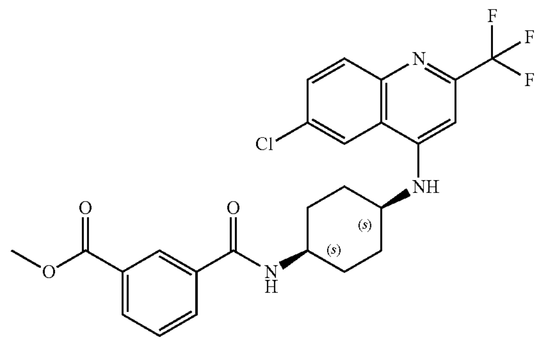 [SMILES: COC(=O)c1cccc(C(=O)N[C@H]2CC[C@@H](Nc3cc(C(F)(F)F)nc4ccc(Cl)cc34)CC2)c1] | 4-280 |
| 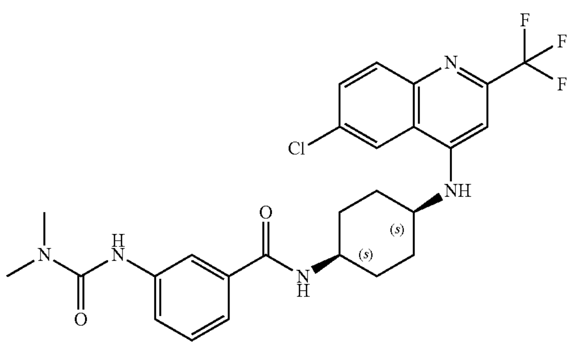 [SMILES: CN(C)C(=O)Nc1cccc(C(=O)N[C@H]2CC[C@@H](Nc3cc(C(F)(F)F)nc4ccc(Cl)cc34)CC2)c1] | 4-281 |
| 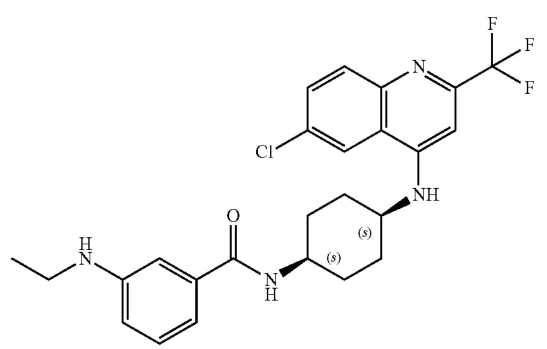 [SMILES: CCNc1cccc(C(=O)N[C@H]2CC[C@@H](Nc3cc(C(F)(F)F)nc4ccc(Cl)cc34)CC2)c1] | 4-282 |
| 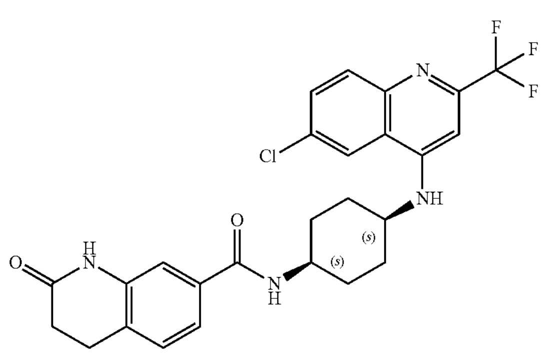 [SMILES: O=C1CCc2ccc(C(=O)N[C@H]3CC[C@@H](Nc4cc(C(F)(F)F)nc5ccc(Cl)cc45)CC3)cc2N1] | 4-283 |

TABLE I-continued
Representative compounds having Structure (I)
| Structure | Cpd No. |
|---|---|
| 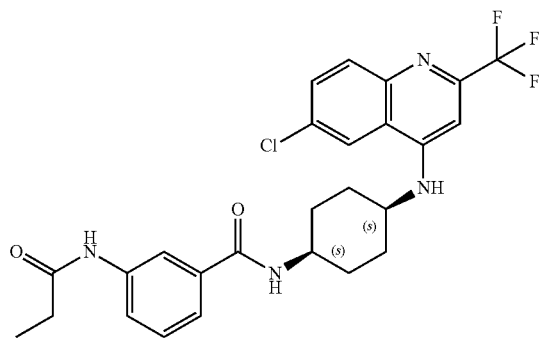 [SMILES: CCC(=O)Nc1cccc(C(=O)N[C@H]2CC[C@@H](Nc3cc(C(F)(F)F)nc4ccc(Cl)cc34)CC2)c1] | 4-284 |
| 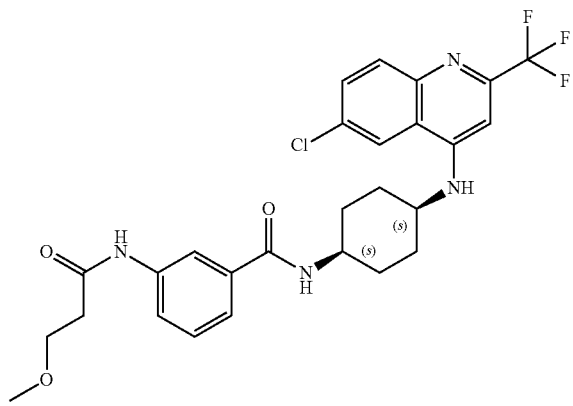 [SMILES: COCCC(=O)Nc1cccc(C(=O)N[C@H]2CC[C@@H](Nc3cc(C(F)(F)F)nc4ccc(Cl)cc34)CC2)c1] | 4-285 |
| 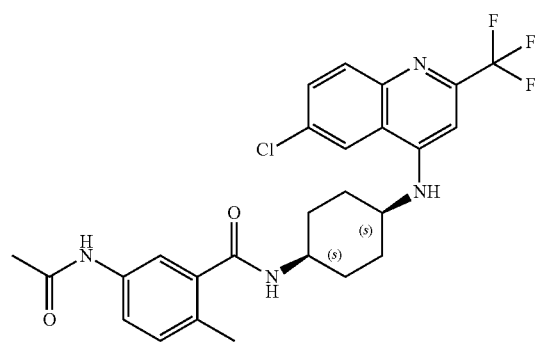 [SMILES: CC(=O)Nc1ccc(C)c(C(=O)N[C@H]2CC[C@@H](Nc3cc(C(F)(F)F)nc4ccc(Cl)cc34)CC2)c1] | 4-286 |

TABLE I-continued
| Representative compounds having Structure (I) | |
|---|---|
| Structure | Cpd No. |
| 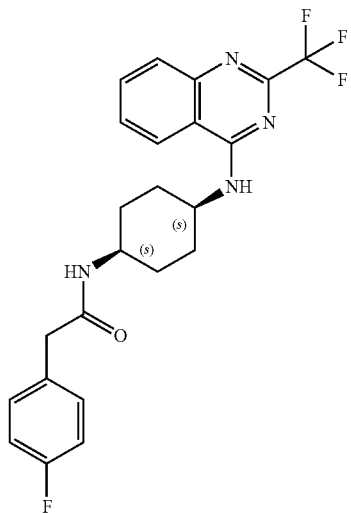 [SMILES: O=C(Cc1ccc(F)cc1)N[C@H]1CC[C@@H](Nc2nc(C(F)(F)F)nc3ccccc23)CC1] | 4-287 |
| 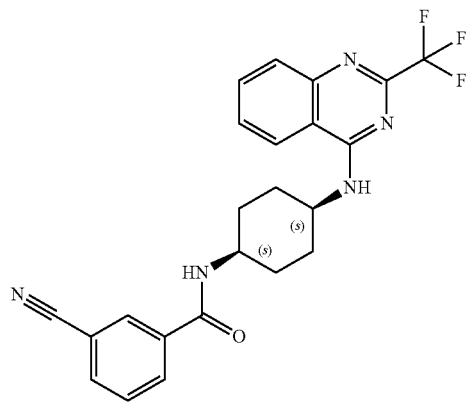 [SMILES: N#Cc1cccc(C(=O)N[C@H]2CC[C@@H](Nc3nc(C(F)(F)F)nc4ccccc34)CC2)c1] | 4-288 |
| 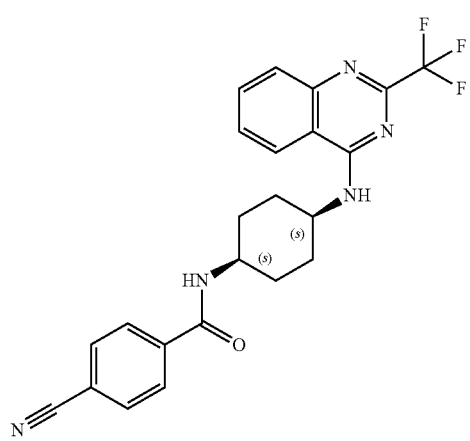 [SMILES: N#Cc1ccc(C(=O)N[C@H]2CC[C@@H](Nc3nc(C(F)(F)F)nc4ccccc34)CC2)cc1] | 4-289 |

TABLE I-continued
Representative compounds having Structure (I)
| Structure | Cpd No. |
|---|---|
| 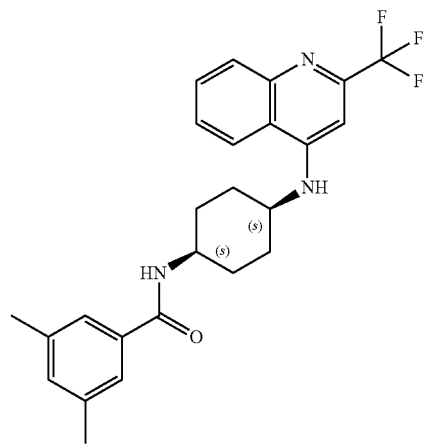 [SMILES: Cc1cc(C)cc(C(=O)N[C@H]2CC[C@@H](Nc3cc(C(F)(F)F)nc4ccccc34)CC2)c1] | 4-290 |
| 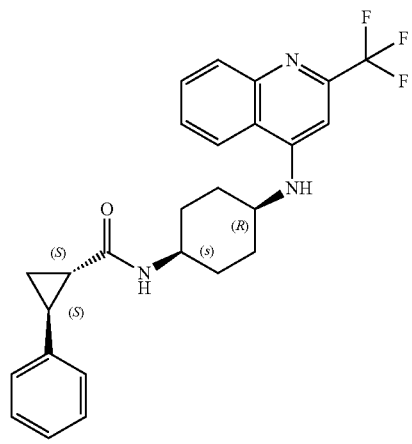 | 4-291 |
| 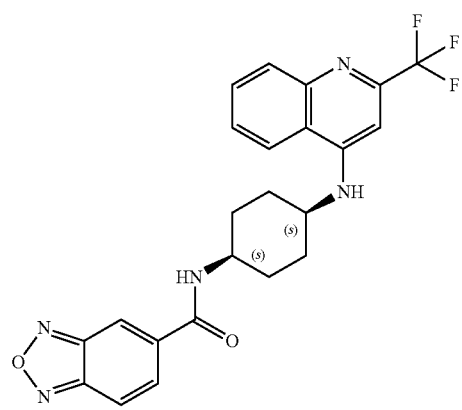 [SMILES: O=C(N[C@H]1CC[C@@H](Nc2cc(C(F)(F)F)nc3ccccc23)CC1)c1ccc2nonc2c1] | 4-292 |

231 232
TABLE I-continued
Representative compounds having Structure (I)
| Structure | Cpd No. |
|---|---|
| 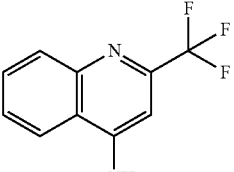 | 4-293 |
| 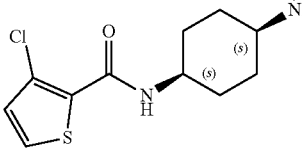 | 4-294 |
| 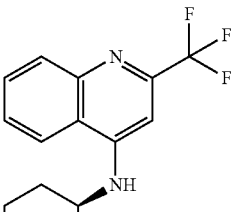 | 4-295 |
| 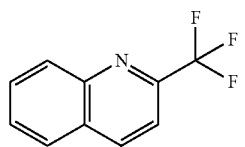 | 4-296 |

TABLE I-continued

Representative compounds having Structure (I)

| Structure | Cpd No. |
|---|---|
| 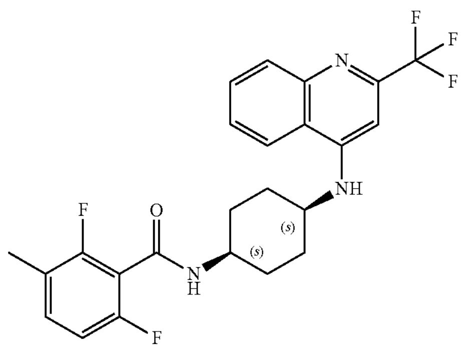 [SMILES: Cc1ccc(F)c(C(=O)N[C@H]2CC[C@@H](Nc3cc(C(F)(F)F)nc4ccccc34)CC2)c1F] | 4-297 |
| 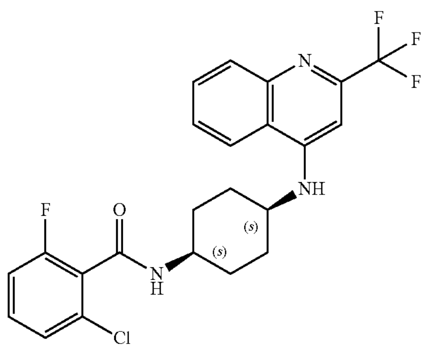 [SMILES: O=C(N[C@H]1CC[C@@H](Nc2cc(C(F)(F)F)nc3ccccc23)CC1)c1c(F)cccc1Cl] | 4-298 |
| 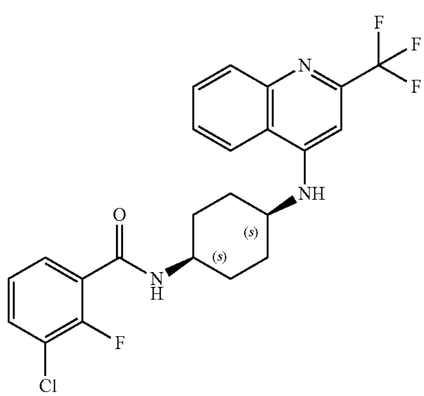 [SMILES: O=C(N[C@H]1CC[C@@H](Nc2cc(C(F)(F)F)nc3ccccc23)CC1)c1cccc(Cl)c1F] | 4-299 |
| 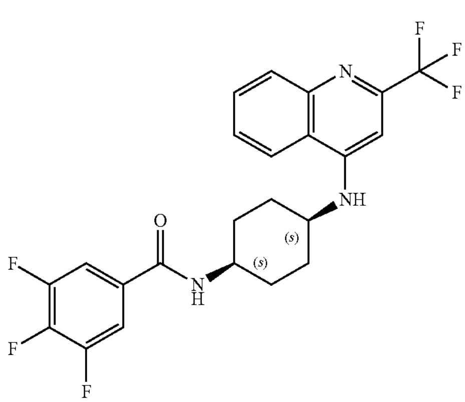 [SMILES: O=C(N[C@H]1CC[C@@H](Nc2cc(C(F)(F)F)nc3ccccc23)CC1)c1cc(F)c(F)c(F)c1] | 4-300 |

TABLE I-continued
Representative compounds having Structure (I)
| Structure | Cpd No. |
|---|---|
| 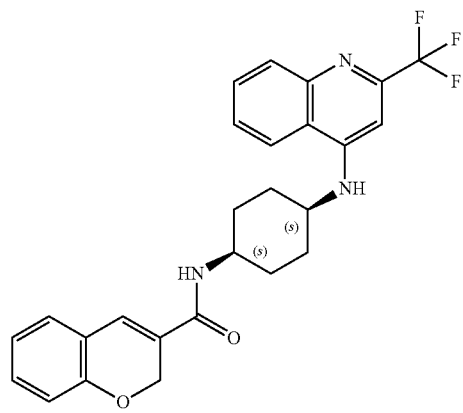 [SMILES: O=C(N[C@H]1CC[C@@H](Nc2cc(C(F)(F)F)nc3ccccc23)CC1)C1=Cc2ccccc2OC1] | 4-301 |
| 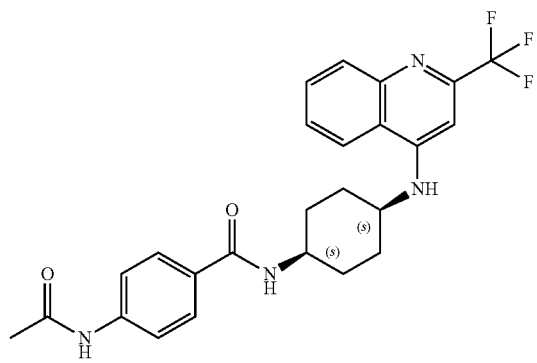 [SMILES: CC(=O)Nc1ccc(C(=O)N[C@H]2CC[C@@H](Nc3cc(C(F)(F)F)nc4ccccc34)CC2)cc1] | 4-302 |
| 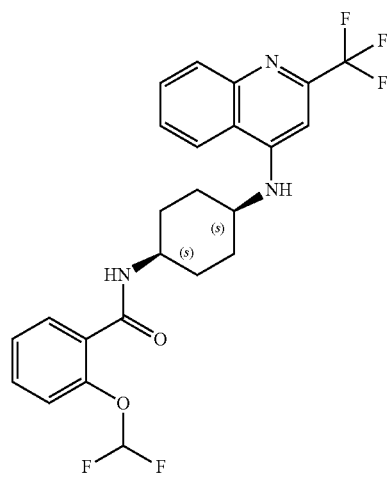 [SMILES: O=C(N[C@H]1CC[C@@H](Nc2cc(C(F)(F)F)nc3ccccc23)CC1)c1ccccc1OC(F)F] | 4-303 |

TABLE I-continued
| Representative compounds having Structure (I) | |
|---|---|
| Structure | Cpd No. |
| 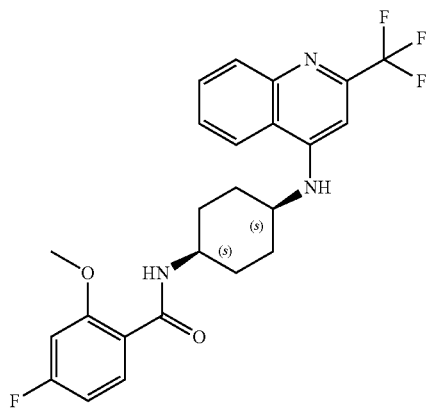 [SMILES: COc1cc(F)ccc1C(=O)N[C@H]1CC[C@@H](Nc2cc(C(F)(F)F)nc3ccccc23)CC1] | 4-304 |
| 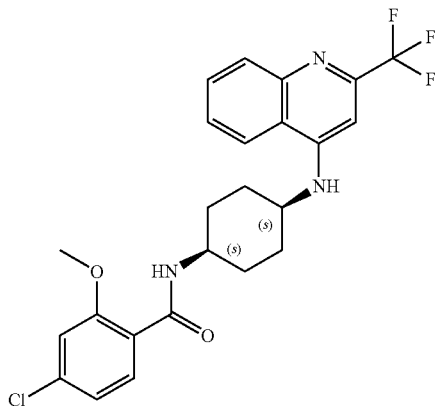 [SMILES: COc1cc(Cl)ccc1C(=O)N[C@H]1CC[C@@H](Nc2cc(C(F)(F)F)nc3ccccc23)CC1] | 4-305 |
| 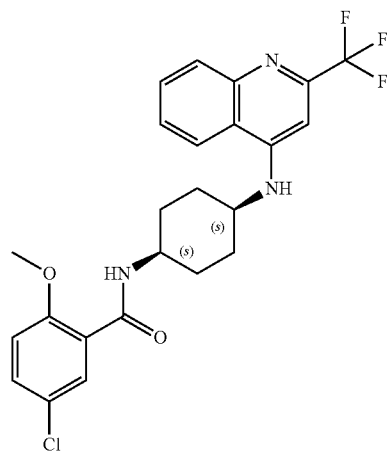 [SMILES: COc1ccc(Cl)cc1C(=O)N[C@H]1CC[C@@H](Nc2cc(C(F)(F)F)nc3ccccc23)CC1] | 4-306 |

TABLE I-continued
Representative compounds having Structure (I)
| Structure | Cpd No. |
|---|---|
| 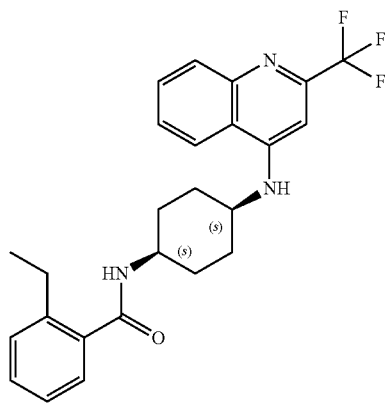 [SMILES: CCc1ccccc1C(=O)N[C@H]1CC[C@@H](Nc2cc(C(F)(F)F)nc3ccccc23)CC1] | 4-307 |
| 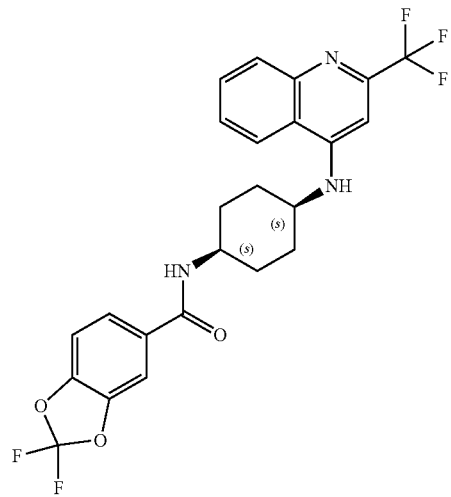 [SMILES: O=C(N[C@H]1CC[C@@H](Nc2cc(C(F)(F)F)nc3ccccc23)CC1)c1ccc2c(c1)OC(F)(F)O2] | 4-308 |
| 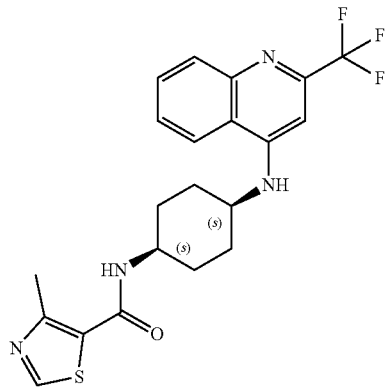 [SMILES: Cc1ncsc1C(=O)N[C@H]1CC[C@@H](Nc2cc(C(F)(F)F)nc3ccccc23)CC1] | 4-309 |

TABLE I-continued
Representative compounds having Structure (I)
| Structure | Cpd No. |
|---|---|
| 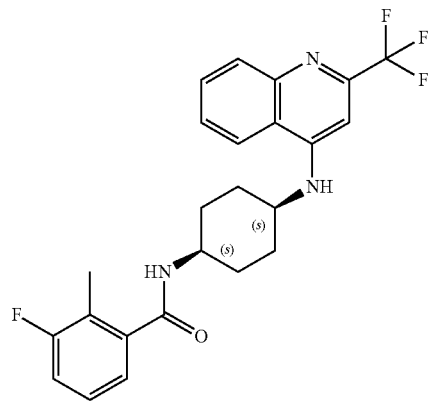 [SMILES: Cc1c(F)cccc1C(=O)N[C@H]1CC[C@@H](Nc2cc(C(F)(F)F)nc3ccccc23)CC1] | 4-310 |
| 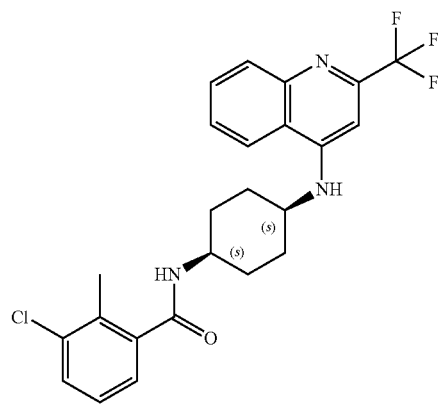 [SMILES: Cc1c(Cl)cccc1C(=O)N[C@H]1CC[C@@H](Nc2cc(C(F)(F)F)nc3ccccc23)CC1] | 4-311 |
| 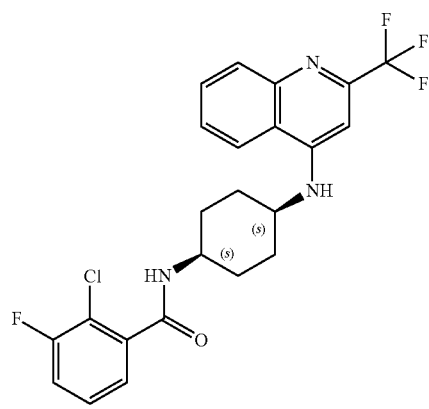 [SMILES: O=C(N[C@H]1CC[C@@H](Nc2cc(C(F)(F)F)nc3ccccc23)CC1)c1cccc(F)c1Cl] | 4-312 |

TABLE I-continued
Representative compounds having Structure (I)
| Structure | Cpd No. |
|---|---|
| 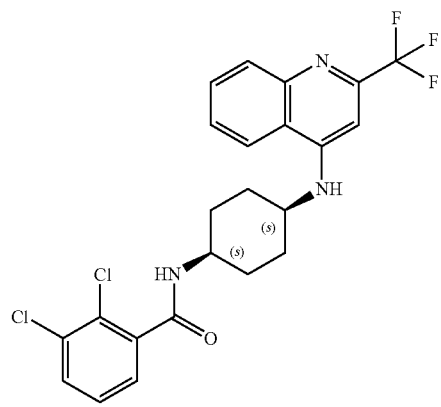 [SMILES: O=C(N[C@H]1CC[C@@H](Nc2cc(C(F)(F)F)nc3ccccc23)CC1)c1cccc(Cl)c1Cl] | 4-313 |
| 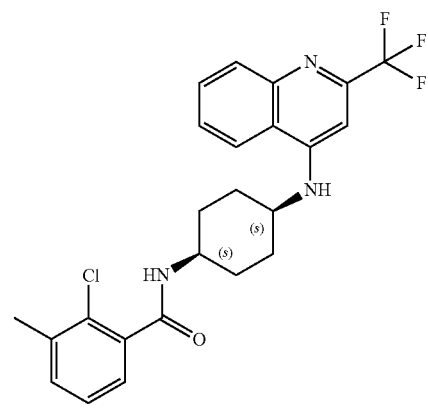 [SMILES: Cc1cccc(C(=O)N[C@H]2CC[C@@H](Nc3cc(C(F)(F)F)nc4ccccc34)CC2)c1Cl] | 4-314 |
| 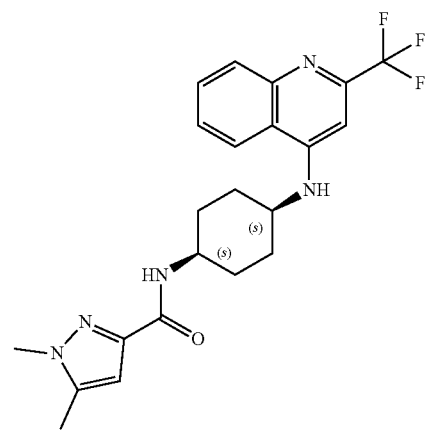 [SMILES: Cc1cc(C(=O)N[C@H]2CC[C@@H](Nc3cc(C(F)(F)F)nc4ccccc34)CC2)nn1C] | 4-315 |

TABLE I-continued

Representative compounds having Structure (I)

| Structure | Cpd No. |
|---|---|
| 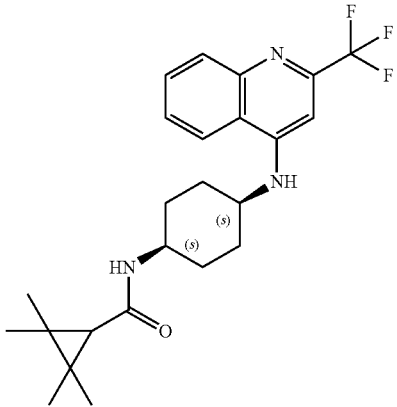 [SMILES: CC1(C)C(C(=O)N[C@H]2CC[C@@H](Nc3cc(C(F)(F)F)nc4ccccc34)CC2)C1(C)C] | 4-316 |

Representative compounds of structure (1), as well as formulas (IA) through (1C) as applicable, include, but not limited to, any one of the compounds listed below in their IUPAC names as well as a pharmaceutically acceptable salt, isomer, hydrate, solvate or isotope thereof.

4-fluoro-N-[(1s,4s)-4-{[2-(difluoromethyl)-6-fluoroquinolin-4-yl]amino}cyclohexyl]benzamide;
4-fluoro-N-[(1s,4s)-4-{[6-ethyl-2-(trifluoromethyl)quinolin-4-yl]amino}cyclohexyl]benzamide;
4-fluoro-N-[(1s,4s)-4-{[6-chloro-2-(difluoromethyl)quinolin-4-yl]amino}cyclohexyl]benzamide;
4-fluoro-N-[(1s,4s)-4-{[6-fluoro-2-(trifluoromethyl)quinolin-4-yl]amino}cyclohexyl]benzamide;
4-fluoro-N-[(1s,4s)-4-{[6-chloro-2-(trifluoromethyl)quinolin-4-yl]amino}cyclohexyl]benzamide;
4-fluoro-N-[(1s,4s)-4-{[6-methyl-2-(trifluoromethyl)quinolin-4-yl]amino}cyclohexyl]benzamide;
4-fluoro-N-[(1s,4s)-4-{[2-(trifluoromethyl)quinazolin-4-yl]amino}cyclohexyl]benzamide;
4-fluoro-N-[(1s,4s)-4-{[6-fluoro-2-(trifluoromethyl)quinazolin-4-yl]amino}cyclohexyl]benzamide;
4-fluoro-N-[(1s,4s)-4-{[2-(difluoromethyl)quinazolin-4-yl]amino}cyclohexyl]benzamide;
4-fluoro-N-[(1s,4s)-4-{[6-chloro-2-(trifluoromethyl)quinazolin-4-yl]amino}cyclohexyl]benzamide;
4-fluoro-N-[(1s,4s)-4-{[2-(difluoromethyl)-6-fluoroquinazolin-4-yl]amino}cyclohexyl]benzamide;
4-fluoro-N-[(1s,4s)-4-{[2-(trifluoromethyl)quinolin-4-yl]amino}cyclohexyl]benzamide;
4-chloro-N-[(1s,4s)-4-{[2-(trifluoromethyl)quinolin-4-yl]amino}cyclohexyl]benzamide;
N-[(1s,4s)-4-{[2-(trifluoromethyl)quinolin-4-yl]amino}cyclohexyl]cyclopropanecarboxamide;
2-chloro-N-[(1s,4s)-4-{[2-(trifluoromethyl)quinolin-4-yl]amino}cyclohexyl]benzamide; 3-chloro-N-[(1s,4s)-4-{[2-(trifluoromethyl)quinolin-4-yl]amino}cyclohexyl]benzamide;
2,3-difluoro-N-[(1s,4s)-4-{[2-(trifluoromethyl)quinolin-4-yl]amino}cyclohexyl]benzamide;
2,5-difluoro-N-[(1s,4s)-4-{[2-(trifluoromethyl)quinolin-4-yl]amino}cyclohexyl]benzamide;
3,4-difluoro-N-[(1s,4s)-4-{[2-(trifluoromethyl)quinolin-4-yl]amino}cyclohexyl]benzamide;
3,5-difluoro-N-[(1s,4s)-4-{[2-(trifluoromethyl)quinolin-4-yl]amino}cyclohexyl]benzamide;
2,4-difluoro-N-[(1s,4s)-4-{[2-(trifluoromethyl)quinolin-4-yl]amino}cyclohexyl]benzamide;
N-[(1s,4s)-4-{[2-(trifluoromethyl)quinolin-4-yl]amino}cyclohexyl]pyridine-4-carboxamide;
N-[(1s,4s)-4-{[2-(trifluoromethyl)quinolin-4-yl]amino}cyclohexyl]cyclohexanecarboxamide;
N-[(1s,4s)-4-{[2-(trifluoromethyl)quinolin-4-yl]amino}cyclohexyl]pyridine-3-carboxamide;
N-[(1s,4s)-4-{[2-(trifluoromethyl)quinolin-4-yl]amino}cyclohexyl]pyridine-2-carboxamide;
2-methyl-N-[(1s,4s)-4-{[2-(trifluoromethyl)quinolin-4-yl]amino}cyclohexyl]propanamide;
N-[(1s,4s)-4-{[2-(trifluoromethyl)quinolin-4-yl]amino}cyclohexyl]-1-benzofuran-2-carboxamide;
2-phenyl-N-[(1s,4s)-4-{[2-(trifluoromethyl)quinolin-4-yl]amino}cyclohexyl]butanamide;
4-(dimethylamino)-N-[(1s,4s)-4-{[2-(trifluoromethyl)quinolin-4-yl]amino}cyclohexyl]benzamide;
3-(dimethylamino)-N-[(1s,4s)-4-{[2-(trifluoromethyl)quinolin-4-yl]amino}cyclohexyl]benzamide;
3-fluoro-4-methoxy-N-[(1s,4s)-4-{[2-(trifluoromethyl)quinolin-4-yl]amino}cyclohexyl]benzamide;
1-acetyl-N-[(1s,4s)-4-{[2-(trifluoromethyl)quinolin-4-yl]amino}cyclohexyl]piperidine-4-carboxamide;
4-methyl-N-[(1s,4s)-4-{[2-(trifluoromethyl)quinolin-4-yl]amino}cyclohexyl]pentanamide;
2-methyl-N-[(1s,4s)-4-{[2-(trifluoromethyl)quinolin-4-yl]amino}cyclohexyl]benzamide;
N-[(1s,4s)-4-{[2-(trifluoromethyl)quinolin-4-yl]amino}cyclohexyl]benzamide;
3-methyl-N-[(1s,4s)-4-{[2-(trifluoromethyl)quinolin-4-yl]amino}cyclohexyl]furan-2-carboxamide;
N-[(1s,4s)-4-{[2-(trifluoromethyl)quinolin-4-yl]amino}cyclohexyl]-2H-1,3-benzodioxole-5-carboxamide;
N-[(1s,4s)-4-{[2-(trifluoromethyl)quinolin-4-yl]amino}cyclohexyl]furan-2-carboxamide;
2-(4-chlorophenyl)-N-[(1s,4s)-4-{[2-(trifluoromethyl)quinolin-4-yl]amino}cyclohexyl]acetamide;
5-chloro-2-fluoro-N-[(1s,4s)-4-{[2-(trifluoromethyl)quinolin-4-yl]amino}cyclohexyl]benzamide;

N-[(1s,4s)-4-{[2-(trifluoromethyl)quinolin-4-yl]amino}cyclohexyl]thiophene-2-carboxamide;
N-[(1s,4s)-4-{[2-(trifluoromethyl)quinolin-4-yl]amino}cyclohexyl]-1-benzothiophene-2-carboxamide;
4-tert-butyl-N-[(1s,4s)-4-{[2-(trifluoromethyl)quinolin-4-yl]amino}cyclohexyl]benzamide;
2,5-dimethyl-N-[(1s,4s)-4-{[2-(trifluoromethyl)quinolin-4-yl]amino}cyclohexyl]furan-3-carboxamide;
2-phenyl-N-[(1s,4s)-4-{[2-(trifluoromethyl)quinolin-4-yl]amino}cyclohexyl]acetamide;
4-methyl-N-[(1s,4s)-4-{[2-(trifluoromethyl)quinolin-4-yl]amino}cyclohexyl]thiophene-2-carboxamide;
3-cyano-N-[(1s,4s)-4-{[2-(trifluoromethyl)quinolin-4-yl]amino}cyclohexyl]benzamide;
3-fluoro-N-[(1s,4s)-4-{[2-(trifluoromethyl)quinolin-4-yl]amino}cyclohexyl]benzamide;
2-fluoro-N-[(1s,4s)-4-{[2-(trifluoromethyl)quinolin-4-yl]amino}cyclohexyl]benzamide;
3-methoxy-N-[(1s,4s)-4-{[2-(trifluoromethyl)quinolin-4-yl]amino}cyclohexyl]benzamide;
2-methoxy-N-[(1s,4s)-4-{[2-(trifluoromethyl)quinolin-4-yl]amino}cyclohexyl]benzamide;
4-fluoro-N-(5-{[2-(trifluoromethyl)quinolin-4-yl]amino}bicyclo[2.2.1]heptan-2-yl)benzamide;
3,5-dimethyl-N-[(1s,4s)-4-{[2-(trifluoromethyl)quinolin-4-yl]amino}cyclohexyl]-1,2-oxazole-4-carboxamide;
2,3-dimethyl-N-[(1s,4s)-4-{[2-(trifluoromethyl)quinolin-4-yl]amino}cyclohexyl]benzamide;
3-phenyl-N-[(1s,4s)-4-{[2-(trifluoromethyl)quinolin-4-yl]amino}cyclohexyl]propanamide;
4-fluoro-3-methyl-N-[(1s,4s)-4-{[2-(trifluoromethyl)quinolin-4-yl]amino}cyclohexyl]benzamide;
2-(4-fluorophenyl)-N-[(1s,4s)-4-{[2-(trifluoromethyl)quinolin-4-yl]amino}cyclohexyl]acetamide;
4-(morpholin-4-yl)-N-[(1s,4s)-4-{[2-(trifluoromethyl)quinolin-4-yl]amino}cyclohexyl]benzamide;
N-(4-{[6-chloro-2-(trifluoromethyl)quinolin-4-yl]amino}cyclohexyl)-4-(morpholin-4-yl)-4-oxobutanamide;
ethyl 1-{[(1s,4s)-4-{[6-chloro-2-(trifluoromethyl)quinolin-4-yl]amino}cyclohexyl]carbamoyl}cyclobutane-1-carboxylate;
2-[3-(dimethylamino)phenoxy]-N-[(1s,4s)-4-{[6-chloro-2-(trifluoromethyl)quinolin-4-yl]amino}cyclohexyl]acetamide;
2,5-dimethyl-N-[(1s,4s)-4-{[6-chloro-2-(trifluoromethyl)quinolin-4-yl]amino}cyclohexyl]-1,3-oxazole-4-carboxamide;
N-(4-{[6-chloro-2-(trifluoromethyl)quinolin-4-yl]amino}cyclohexyl)-1-(4-chlorophenyl)-5-methyl-1H-pyrazole-4-carboxamide;
N-(4-{[6-chloro-2-(trifluoromethyl)quinolin-4-yl]amino}cyclohexyl)-3-(4-chloro-3-fluorophenyl)propanamide;
(2S)—N-(4-{[6-chloro-2-(trifluoromethyl)quinolin-4-yl]amino}cyclohexyl)-3-phenyl-2-[(pyrazin-2-yl)formamido]propanamide;
2-chloro-N-(4-{[6-chloro-2-(trifluoromethyl)quinolin-4-yl]amino}cyclohexyl)-6-fluoro-3-methoxybenzamide;
N-(4-{[6-chloro-2-(trifluoromethyl)quinolin-4-yl]amino}cyclohexyl)-4-fluoro-3-(trifluoromethoxy)benzamide;
N-(4-{[6-chloro-2-(trifluoromethyl)quinolin-4-yl]amino}cyclohexyl)-2-(4-chlorophenyl)-2-methylpropanamide;
4-(4-methylpiperazin-1-yl)-N-[(1s,4s)-4-{[2-(trifluoromethyl)quinolin-4-yl]amino}cyclohexyl]benzamide;
N-(4-{[6-chloro-2-(trifluoromethyl)quinolin-4-yl]amino}cyclohexyl)-1-methyl-4,5,6,7-tetrahydro-1H-indazole-3-carboxamide;
N-(4-{[6-chloro-2-(trifluoromethyl)quinolin-4-yl]amino}cyclohexyl)-2,2-dimethyloxane-4-carboxamide;
(1S,4S)—N-(4{[6-chloro-2-(trifluoromethyl)quinolin-4-yl]amino}cyclohexyl)-4,7,7-trimethyl-3-oxo-2-oxabicyclo[2.2.1]heptane-1-carboxamide;
N-(4-{[6-chloro-2-(trifluoromethyl)quinolin-4-yl]amino}cyclohexyl)-2-(pyridin-4-yl)-1H-1,3-benzodiazole-5-carboxamide;
N-(4-{[6-chloro-2-(trifluoromethyl)quinolin-4-yl]amino}cyclohexyl)-5-fluoro-1H-pyrrolo [2,3-b]pyridine-2-carboxamide;
(2S)-2-(2-oxopyrrolidin-1-yl)-N-[(1s,4s)-4-{[6-chloro-2-(trifluoromethyl)quinolin-4-yl]amino}cyclohexyl]butanamide;
4-(4-acetylphenoxy)-N-[(1s,4s)-4-{[6-chloro-2-(trifluoromethyl)quinolin-4-yl]amino}cyclohexyl]butanamide;
2-(2,3-dimethylphenyl)-N-[(1s,4s)-4-{[6-chloro-2-(trifluoromethyl)quinolin-4-yl]amino}cyclohexyl]acetamide;
4-[(2S)-2-acetamido-2-{[(1s,4s)-4-{[6-chloro-2-(trifluoromethyl)quinolin-4-yl]amino}cyclohexyl]carbamoyl}ethyl]phenyl acetate;
3-chloro-2-iodo-N-[(1s,4s)-4-{[6-chloro-2-(trifluoromethyl)quinolin-4-yl]amino}cyclohexyl]benzamide;
1,4-dimethyl-N-[(1s,4s)-4-{[6-chloro-2-(trifluoromethyl)quinolin-4-yl]amino}cyclohexyl]-1,2,3,4-tetrahydroquinoxaline-6-carboxamide;
7-methoxy-N-[(1s,4s)-4-{[6-chloro-2-(trifluoromethyl)quinolin-4-yl]amino}cyclohexyl]-3,4-dihydro-2H-1-benzopyran-3-carboxamide;
(2S)-2-[(tert-butylcarbamoyl)amino]-3,3-dimethyl-N-[(1s,4s)-4-{[6-chloro-2-(trifluoromethyl)quinolin-4-yl]amino}cyclohexyl]butanamide;
6-methyl-N-[(1s,4s)-4-{[6-chloro-2-(trifluoromethyl)quinolin-4-yl]amino}cyclohexyl]-1-benzothiophene-2-carboxamide;
6-chloro-3-oxo-N-[(1s,4s)-4-{[6-chloro-2-(trifluoromethyl)quinolin-4-yl]amino}cyclohexyl]-2,3-dihydro-1H-indene-1-carboxamide;
3,4-dichloro-N-[(1s,4s)-4-{[6-chloro-2-(trifluoromethyl)quinolin-4-yl]amino}cyclohexyl]-1,2-thiazole-5-carboxamide;
N-[(1s,4s)-4-{[6-chloro-2-(trifluoromethyl)quinolin-4-yl]amino}cyclohexyl]-3-(1,3-thiazol-2-yl)propanamide;
N-[(1s,4s)-4-{[6-chloro-2-(trifluoromethyl)quinolin-4-yl]amino}cyclohexyl]-3-(1H-1,2,4-triazol-1-yl)benzamide;
4-fluoro-N-[(1s,4s)-4-{[6-chloro-2-(trifluoromethyl)quinolin-4-yl]amino}cyclohexyl]-1H-indole-3-carboxamide;
2-methyl-4-(2-methylbenzamido)-N-[(1s,4s)-4-{[6-chloro-2-(trifluoromethyl)quinolin-4-yl]amino}cyclohexyl]benzamide;
N-[(1s,4s)-4-{[6-chloro-2-(trifluoromethyl)quinolin-4-yl]amino}cyclohexyl]-3,4-dihydro-2H-pyran-6-carboxamide;
2-acetamido-N-[(1s,4s)-4-{[6-chloro-2-(trifluoromethyl)quinolin-4-yl]amino}cyclohexyl]benzamide;
N-[(1,2S)-2-{[(1s,4s)-4-{[6-chloro-2-(trifluoromethyl)quinolin-4-yl]amino}cyclohexyl]carbamoyl}cyclohexyl]benzamide;
1-(pyridin-3-yl)-N-[(1s,4s)-4-{[6-chloro-2-(trifluoromethyl)quinolin-4-yl]amino}cyclohexyl]-1H-pyrazole-4-carboxamide;
3-chloro-1-(3-chloropyridin-2-yl)-N-[(1s,4s)-4-{[6-chloro-2-(trifluoromethyl)quinolin-4-yl]amino}cyclohexyl]-1H-pyrazole-5-carboxamide;

(3aS,4S,6R,6aR)-6-methoxy-2,2-dimethyl-N-[(1s,4s)-4-{[6-chloro-2-(trifluoromethyl)quinolin-4-yl]amino}cyclohexyl]-tetrahydro-2H-furo[3,4-d][1,3]dioxole-4-carboxamide;
N-(2,6-difluorophenyl)-N'-[(1s,4s)-4-{[6-chloro-2-(trifluoromethyl)quinolin-4-yl]amino}cyclohexyl]ethanediamide;
3-{[(1s,4s)-4-{[6-chloro-2-(trifluoromethyl)quinolin-4-yl]amino}cyclohexyl]carbamoyl}phenyl propanoate;
3-(5-bromo-2-fluorophenyl)-N-[(1s,4s)-4-{[6-chloro-2-(trifluoromethyl)quinolin-4-yl]amino}cyclohexyl]propanamide;
4-butanamido-3-methyl-N-[(1s,4s)-4-{[6-chloro-2-(trifluoromethyl)quinolin-4-yl]amino}cyclohexyl]benzamide;
1-(3-fluorophenyl)-N-[(1s,4s)-4-{[6-chloro-2-(trifluoromethyl)quinolin-4-yl]amino}cyclohexyl]-5-(trifluoromethyl)-1H-pyrazole-4-carboxamide;
1-tert-butyl-N-[(1s,4s)-4-{[6-chloro-2-(trifluoromethyl)quinolin-4-yl]amino}cyclohexyl]-1H-1,2,3-triazole-4-carboxamide;
2-(methylamino)-N-[(1s,4s)-4-{[6-chloro-2-(trifluoromethyl)quinolin-4-yl]amino}cyclohexyl]benzamide;
(2R,3R)-2-(2-methoxyphenyl)-5-oxo-N-[(1s,4s)-4-{[6-chloro-2-(trifluoromethyl)quinolin-4-yl]amino}cyclohexyl]oxolane-3-carboxamide;
(1R,2R)-2-(2-fluorophenyl)-N-[(1s,4s)-4-{[6-chloro-2-(trifluoromethyl)quinolin-4-yl]amino}cyclohexyl]cyclopropane-1-carboxamide;
N-[(1s,4s)-4-{[6-chloro-2-(trifluoromethyl)quinolin-4-yl]amino}cyclohexyl]-5-(thiophen-2-yl)pyridine-3-carboxamide;
2,6-dimethoxy-N-[(1s,4s)-4-{[6-chloro-2-(trifluoromethyl)quinolin-4-yl]amino}cyclohexyl]pyrimidine-4-carboxamide;
6-oxo-N-[(1s,4s)-4-{[6-chloro-2-(trifluoromethyl)quinolin-4-yl]amino}cyclohexyl]-1,4,5,6-tetrahydropyridazine-3-carboxamide;
2-(1-methyl-1H-indol-3-yl)-N-[(1s,4s)-4-{[6-chloro-2-(trifluoromethyl)quinolin-4-yl]amino}cyclohexyl]acetamide;
6-chloro-N-[(1s,4s)-4-{[6-chloro-2-(trifluoromethyl)quinolin-4-yl]amino}cyclohexyl]-2H-chromene-3-carboxamide;
2-chloro-N-[(1s,4s)-4-{[6-chloro-2-(trifluoromethyl)quinolin-4-yl]amino}cyclohexyl]-1,3-benzothiazole-6-carboxamide;
2-(3-chloro-5-fluorophenyl)-N-[(1s,4s)-4-{[6-chloro-2-(trifluoromethyl)quinolin-4-yl]amino}cyclohexyl]acetamide;
2-(4-chloro-1H-indol-3-yl)-N-[(1s,4s)-4-{[6-chloro-2-(trifluoromethyl)quinolin-4-yl]amino}cyclohexyl]acetamide;
6-methoxy-2-methyl-N-[(1s,4s)-4-{[6-chloro-2-(trifluoromethyl)quinolin-4-yl]amino}cyclohexyl]pyridine-3-carboxamide;
N-[(1s,4s)-4-{[6-chloro-2-(trifluoromethyl)quinolin-4-yl]amino}cyclohexyl]-1H,4H,6H,7H-pyrano[4,3-c]pyrazole-3-carboxamide;
N-[(1s,4s)-4-{[6-chloro-2-(trifluoromethyl)quinolin-4-yl]amino}cyclohexyl]bicyclo[2.2.1]hept-5-ene-2-carboxamide;
N-[(1s,4s)-4-{[6-chloro-2-(trifluoromethyl)quinolin-4-yl]amino}cyclohexyl]-1,3-oxazole-5-carboxamide;
2-imino-N-[(1s,4s)-4-{[6-chloro-2-(trifluoromethyl)quinolin-4-yl]amino}cyclohexyl]-1,3-thiazolidine-4-carboxamide;
(2R)-2-acetamido-3-(1H-indol-3-yl)-N-[(1s,4s)-4-{[6-chloro-2-(trifluoromethyl)quinolin-4-yl]amino}cyclohexyl]propanamide;
5-chloro-3-(difluoromethyl)-1-methyl-N-[(1s,4s)-4-{[6-chloro-2-(trifluoromethyl)quinolin-4-yl]amino}cyclohexyl]-1H-pyrazole-4-carboxamide;
2-{bicyclo[2.2.1]heptan-2-yl}-N-[(1s,4s)-4-{[6-chloro-2-(trifluoromethyl)quinolin-4-yl]amino}cyclohexyl]acetamide;
4-bromo-N-[(1s,4s)-4-{[6-chloro-2-(trifluoromethyl)quinolin-4-yl]amino}cyclohexyl]-1,3-thiazole-2-carboxamide;
benzyl N-(3-{[(1s,4s)-4-{[6-chloro-2-(trifluoromethyl)quinolin-4-yl]amino}cyclohexyl]carbamoyl}propyl)carbamate;
5-(methylsulfanyl)-N-[(1s,4s)-4-{[6-chloro-2-(trifluoromethyl)quinolin-4-yl]amino}cyclohexyl]thiophene-2-carboxamide;
3-acetamido-N-[(1s,4s)-4-{[6-chloro-2-(trifluoromethyl)quinolin-4-yl]amino}cyclohexyl]benzamide;
2-benzyl-N-[(1s,4s)-4-{[6-chloro-2-(trifluoromethyl)quinolin-4-yl]amino}cyclohexyl]prop-2-enamide;
5-bromo-2-(methylsulfanyl)-N-[(1s,4s)-4-{[6-chloro-2-(trifluoromethyl)quinolin-4-yl]amino}cyclohexyl]pyrimidine-4-carboxamide;
3-(2-oxopyrrolidin-1-yl)-N-[(1s,4s)-4-{[6-chloro-2-(trifluoromethyl)quinolin-4-yl]amino}cyclohexyl]benzamide;
6-(dimethylamino)-2-methyl-N-[(1s,4s)-4-{[2-(trifluoromethyl)quinolin-4-yl]amino}cyclohexyl]pyridine-3-carboxamide;
N-[(1s,4s)-4-{[6-chloro-2-(trifluoromethyl)quinolin-4-yl]amino}cyclohexyl]-1H-indazole-7-carboxamide;
2-chloro-4-iodo-N-[(1s,4s)-4-{[6-chloro-2-(trifluoromethyl)quinolin-4-yl]amino}cyclohexyl]pyridine-3-carboxamide;
N-[(1s,4s)-4-{[6-chloro-2-(trifluoromethyl)quinolin-4-yl]amino}cyclohexyl]-2,3-dihydro-1,4-benzodioxine-2-carboxamide;
2-methyl-5-{[(1r,4r)-4-{[6-chloro-2-(trifluoromethyl)quinolin-4-yl]amino}cyclohexyl]carbamoyl}pyrazin-1-ium-1-olate;
6-chloro-N-[(1s,4s)-4-{[6-chloro-2-(trifluoromethyl)quinolin-4-yl]amino}cyclohexyl]pyridazine-4-carboxamide;
N-[(1s,4s)-4-{[6-chloro-2-(trifluoromethyl)quinolin-4-yl]amino}cyclohexyl]-1,2,3,4-tetrahydroisoquinoline-7-carboxamide;
3-(methylamino)-N-[(1s,4s)-4-{[6-chloro-2-(trifluoromethyl)quinolin-4-yl]amino}cyclohexyl]benzamide;
4-bromo-1-methyl-N-[(1s,4s)-4-{[6-chloro-2-(trifluoromethyl)quinolin-4-yl]amino}cyclohexyl]-1H-pyrazole-5-carboxamide;
N-[(1s,4s)-4-{[6-chloro-2-(trifluoromethyl)quinolin-4-yl]amino}cyclohexyl]-3-[(trifluoromethyl)sulfanyl]benzamide;
2-(5-chloro-1H-indazol-3-yl)-N-[(1s,4s)-4-{[6-chloro-2-(trifluoromethyl)quinolin-4-yl]amino}cyclohexyl]acetamide;
(22)-2-(2-amino-1,3-thiazol-4-yl)-N-[(1s,4s)-4-{[6-chloro-2-(trifluoromethyl)quinolin-4-yl]amino}cyclohexyl]pent-2-enamide;
2-chloro-4,6-dimethyl-N-[(1s,4s)-4-{[6-chloro-2-(trifluoromethyl)quinolin-4-yl]amino}cyclohexyl]pyridine-3-carboxamide;
methyl N—(R)-phenyl({[(1s,4s)-4-{[6-chloro-2-(trifluoromethyl)quinolin-4-yl]amino}cyclohexyl]carbamoyl})methyl]carbamate;
5-bromo-N-[(1s,4s)-4-{[6-chloro-2-(trifluoromethyl)quinolin-4-yl]amino}cyclohexyl]-1H-indole-7-carboxamide;
2-(ethylamino)-N-[(1s,4s)-4-{[6-chloro-2-(trifluoromethyl)quinolin-4-yl]amino}cyclohexyl]acetamide;

tert-butyl N-(1-methyl-5-{[(1s,4s)-4-{[6-chloro-2-(trifluoromethyl)quinolin-4-yl]amino}cyclohexyl]carbamoyl}-1H-pyrrol-3-yl)carbamate;
(2E)-3-(1H-imidazol-4-yl)-N-[(1s,4s)-4-{[6-chloro-2-(trifluoromethyl)quinolin-4-yl]amino}cyclohexyl]prop-2-enamide;
4-(methylamino)-N-[(1s,4s)-4-{[6-chloro-2-(trifluoromethyl)quinolin-4-yl]amino}cyclohexyl]benzamide;
4-iodo-1-methyl-N-[(1s,4s)-4-{[6-chloro-2-(trifluoromethyl)quinolin-4-yl]amino}cyclohexyl]-1H-pyrazole-3-carboxamide;
4-bromo-N-[(1s,4s)-4-{[6-chloro-2-(trifluoromethyl)quinolin-4-yl]amino}cyclohexyl-1H-indazole-6-carboxamide;
3-acetamido-N-[(1s,4s)-4-{[6-chloro-2-(trifluoromethyl)quinolin-4-yl]amino}cyclohexyl]propanamide;
N-[(1s,4s)-4-{[6-chloro-2-(trifluoromethyl)quinolin-4-yl]amino}cyclohexyl]-1-benzofuran-2-carboxamide;
5-methoxy-N-[(1s,4s)-4-{[6-chloro-2-(trifluoromethyl)quinolin-4-yl]amino}cyclohexyl]-1-benzofuran-2-carboxamide;
5-fluoro-N-[(1s,4s)-4-{[6-chloro-2-(trifluoromethyl)quinolin-4-yl]amino}cyclohexyl]-1-benzofuran-2-carboxamide;
4-acetamido-N-[(1s,4s)-4-{[6-chloro-2-(trifluoromethyl)quinolin-4-yl]amino}cyclohexyl]butanamide;
3-methoxy-N-[(1s,4s)-4-{[6-chloro-2-(trifluoromethyl)quinolin-4-yl]amino}cyclohexyl]benzamide;
2-methoxy-N-[(1s,4s)-4-{[6-chloro-2-(trifluoromethyl)quinolin-4-yl]amino}cyclohexyl]benzamide;
N-[(1s,4s)-4-{[6-chloro-2-(trifluoromethyl)quinolin-4-yl]amino}cyclohexyl]pyrrolidine-1-carboxamide;
4-fluoro-N-[(1s,4s)-4-{[2-(difluoromethyl)quinolin-4-yl]amino}cyclohexyl]benzamide;
4-fluoro-N-[(1s,4s)-4-{[6-cyano-2-(trifluoromethyl)quinolin-4-yl]amino}cyclohexyl]benzamide;
4-(dimethylamino)-N-[(1s,4s)-4-{[6-(methylamino)-2-(trifluoromethyl)quinolin-4-yl]amino}cyclohexyl]benzamide;
4-fluoro-N-[(1s,4s)-4-{[2,6-bis(trifluoromethyl)quinazolin-4-yl]amino}cyclohexyl]benzamide;
N-[(1s,4s)-4-{[6-chloro-2-(trifluoromethyl)quinolin-4-yl]amino}cyclohexyl]benzamide;
4-cyano-N-[(1s,4s)-4-{[2-(trifluoromethyl)quinolin-4-yl]amino}cyclohexyl]benzamide;
4-methoxy-N-[(1s,4s)-4-{[2-(trifluoromethyl)quinolin-4-yl]amino}cyclohexyl]benzamide;
3-[(methylcarbamoyl)amino]-N-[(1s,4s)-4-{[6-chloro-2-(trifluoromethyl)quinolin-4-yl]amino}cyclohexyl]benzamide;
3-methanesulfonamido-N-[(1s,4s)-4-{[6-chloro-2-(trifluoromethyl)quinolin-4-yl]amino}cyclohexyl]benzamide;
3,4-dimethyl-N-[(1s,4s)-4-{[2-(trifluoromethyl)quinolin-4-yl]amino}cyclohexyl]thiophene-2-carboxamide;
4-(dimethylamino)-N-[(1s,4s)-4-{[6-acetamido-2-(trifluoromethyl)quinolin-4-yl]amino}cyclohexyl]benzamide;
N-[(1s,4s)-4-{[2-(trifluoromethyl)quinolin-4-yl]amino}cyclohexyl]-1-benzofuran-3-carboxamide;
methyl 4-[(4-{[6-chloro-2-(trifluoromethyl)quinolin-4-yl]amino}cyclohexyl)carbamoyl]benzoate;
N-[(1s,4s)-4-{[6-chloro-2-(trifluoromethyl)quinolin-4-yl]amino}cyclohexyl]-2H-pyrazolo[3,4-b]pyridine-3-carboxamide;
2-(3-oxo-3,4-dihydro-2H-1,4-benzoxazin-4-yl)-N-[(1s,4s)-4-{[6-chloro-2-(trifluoromethyl)quinolin-4-yl]amino}cyclohexyl]acetamide;
2-acetamido-N-[(1s,4s)-4-{[6-chloro-2-(trifluoromethyl)quinolin-4-yl]amino}cyclohexyl]pyridine-4-carboxamide;
3-(2-fluorophenyl)-N-[(1s,4s)-4-{[6-chloro-2-(trifluoromethyl)quinolin-4-yl]amino}cyclohexyl]-1H-pyrazole-5-carboxamide;
N-[(1s,4s)-4-{[6-chloro-2-(trifluoromethyl)quinolin-4-yl]amino}cyclohexyl]-2H-1,3-benzodioxole-4-carboxamide;
(3R)-3-(2-methylpropyl)-N'-[(1s,4s)-4-{[6-chloro-2-(trifluoromethyl)quinolin-4-yl]amino}cyclohexyl]pentanediamide;
N-[(1s,4s)-4-{[6-chloro-2-(trifluoromethyl)quinolin-4-yl]amino}cyclohexyl]imidazo[1,2-a]pyrimidine-3-carboxamide;
2-(1,2-benzoxazol-3-yl)-N-[(1s,4s)-4-{[6-chloro-2-(trifluoromethyl)quinolin-4-yl]amino}cyclohexyl]acetamide;
7-methoxy-N-[(1s,4s)-4-{[6-chloro-2-(trifluoromethyl)quinolin-4-yl]amino}cyclohexyl]-1-benzofuran-2-carboxamide;
1-cyano-N-[(1s,4s)-4-{[6-chloro-2-(trifluoromethyl)quinolin-4-yl]amino}cyclohexyl]cyclopropane-1-carboxamide;
N-[(1s,4s)-4-{[6-chloro-2-(trifluoromethyl)quinolin-4-yl]amino}cyclohexyl]-1,6-naphthyridine-2-carboxamide;
1-(2-chlorobenzoyl)-N-[(1s,4s)-4-{[6-chloro-2-(trifluoromethyl)quinolin-4-yl]amino}cyclohexyl]piperidine-4-carboxamide;
2-chloro-4-methanesulfonyl-N-[(1s,4s)-4-{[6-chloro-2-(trifluoromethyl)quinolin-4-yl]amino}cyclohexyl]benzamide;
2-(1H-imidazol-1-yl)-N-[(1s,4s)-4-{[6-chloro-2-(trifluoromethyl)quinolin-4-yl]amino}cyclohexyl]acetamide;
3-tert-butyl-N-[(1s,4s)-4-{[6-chloro-2-(trifluoromethyl)quinolin-4-yl]amino}cyclohexyl]-1H-pyrazole-5-carboxamide;
4-[(pyridin-3-yl)formamido]-N-[(1s,4s)-4-{[6-chloro-2-(trifluoromethyl)quinolin-4-yl]amino}cyclohexyl]butanamide;
5-(propan-2-yl)-N-[(1s,4s)-4-{[6-chloro-2-(trifluoromethyl)quinolin-4-yl]amino}cyclohexyl]-1H-pyrazole-3-carboxamide;
5-(2-chlorophenyl)-N-[(1s,4s)-4-{[6-chloro-2-(trifluoromethyl)quinolin-4-yl]amino}cyclohexyl]-1H-pyrazole-3-carboxamide;
1-methyl-3-(2-methylpropyl)-N-[(1s,4s)-4-{[6-chloro-2-(trifluoromethyl)quinolin-4-yl]amino}cyclohexyl]-1H-pyrazole-5-carboxamide;
N-[(1s,4s)-4{[6-chloro-2-(trifluoromethyl)quinolin-4-yl]amino}cyclohexyl]-1-[5-(trifluoromethyl)pyridin-2-yl]piperidine-4-carboxamide;
2-(1H-indol-1-yl)-N-[(1s,4s)-4-{[6-chloro-2-(trifluoromethyl)quinolin-4-yl]amino}cyclohexyl]acetamide;
2-(morpholin-4-yl)-N-[(1s,4s)-4-{[6-chloro-2-(trifluoromethyl)quinolin-4-yl]amino}cyclohexyl]pyridine-4-carboxamide;
N-[(1s,4s)-4-{[6-chloro-2-(trifluoromethyl)quinolin-4-yl]amino}cyclohexyl]-2-(thiophen-3-yl)acetamide;
3-(3-fluorophenoxy)-N-[(1s,4s)-4-{[6-chloro-2-(trifluoromethyl)quinolin-4-yl]amino}cyclohexyl]propanamide;
1-cyclopentyl-5-oxo-N-[(1s,4s)-4-{[6-chloro-2-(trifluoromethyl)quinolin-4-yl]amino}cyclohexyl]pyrrolidine-3-carboxamide;
2-oxo-N-[(1s,4s)-4-{[6-chloro-2-(trifluoromethyl)quinolin-4-yl]amino}cyclohexyl]-2,3-dihydropyridine-4-carboxamide;

2-(2,5-dimethylphenoxy)-N-[(1s,4s)-4-{[6-chloro-2-(trifluoromethyl)quinolin-4-yl]amino}cyclohexyl]acetamide;
N-[(1s,4s)-4-{[6-chloro-2-(trifluoromethyl)quinolin-4-yl]amino}cyclohexyl]-4,5,6,7-tetrahydro-1-benzothiophene-2-carboxamide;
N-[(1s,4s)-4-{[6-chloro-2-(trifluoromethyl)quinolin-4-yl]amino}cyclohexyl]-1H-pyrrolo[2,3-b]pyridine-4-carboxamide;
2-{imidazo[1,2-a]pyridin-3-yl}-N-[(1s,4s)-4-{[6-chloro-2-(trifluoromethyl)quinolin-4-yl]amino}cyclohexyl]acetamide;
2-[5-methyl-3-(trifluoromethyl)-1H-pyrazol-1-yl]-N-[(1s,4s)-4-{[6-chloro-2-(trifluoromethyl)quinolin-4-yl]amino}cyclohexyl]acetamide;
1-ethyl-N-[(1s,4s)-4-{[6-chloro-2-(trifluoromethyl)quinolin-4-yl]amino}cyclohexyl]-1H-pyrazole-5-carboxamide;
3,6-difluoro-N-[(1s,4s)-4-{[6-chloro-2-(trifluoromethyl)quinolin-4-yl]amino}cyclohexyl]pyridine-2-carboxamide;
N-[(1s,4s)-4-{[6-chloro-2-(trifluoromethyl)quinolin-4-yl]amino}cyclohexyl]-3-(1H-1,2,4-triazol-1-yl)propanamide;
2-oxo-N-[(1s,4s)-4-{[6-chloro-2-(trifluoromethyl)quinolin-4-yl]amino}cyclohexyl]-2H-chromene-6-carboxamide;
4-methyl-2-(pyridin-2-yl)-N-[(1s,4s)-4-{[6-chloro-2-(trifluoromethyl)quinolin-4-yl]amino}cyclohexyl]-1,3-thiazole-5-carboxamide;
4-(1,3-dioxo-2,3-dihydro-1H-isoindol-2-yl)-N-[(1s,4s)-4-{[6-chloro-2-(trifluoromethyl)quinolin-4-yl]amino}cyclohexyl]butanamide;
2-(benzenesulfonyl)-N-[(1s,4s)-4-{[6-chloro-2-(trifluoromethyl)quinolin-4-yl]amino}cyclohexyl]acetamide;
4-({[(1s,4s)-4-{[6-chloro-2-(trifluoromethyl)quinolin-4-yl]amino}cyclohexyl]carbamoyl}methyl)phenyl methanesulfonate;
4-(4-methanesulfonylphenyl)-4-oxo-N-[(1s,4s)-4-{[6-chloro-2-(trifluoromethyl)quinolin-4-yl]amino}cyclohexyl]butanamide;
N-[(1s,4s)-4-{[6-chloro-2-(trifluoromethyl)quinolin-4-yl]amino}cyclohexyl]imidazo[1,2-a]pyrazine-2-carboxamide;
5-(furan-2-yl)-N-[(1s,4s)-4-{[6-chloro-2-(trifluoromethyl)quinolin-4-yl]amino}cyclohexyl]-1,2-oxazole-3-carboxamide;
1-[(pyridin-2-yl)methyl]-N-[(1s,4s)-4-{[6-chloro-2-(trifluoromethyl)quinolin-4-yl]amino}cyclohexyl]piperidine-4-carboxamide;
4-(3-methyl-5-oxo-4,5-dihydro-1H-pyrazol-1-yl)-N-[(1s,4s)-4-{[6-chloro-2-(trifluoromethyl)quinolin-4-yl]amino}cyclohexyl]benzamide;
4-fluoro-N-[(1s,4s)-4-{[6-chloro-2-(trifluoromethyl)quinolin-4-yl]amino}cyclohexyl]-1H-indazole-5-carboxamide;
3-(1-cyanoethyl)-N-[(1s,4s)-4-{[6-chloro-2-(trifluoromethyl)quinolin-4-yl]amino}cyclohexyl]benzamide;
N-[(1s,4s)-4-{[6-chloro-2-(trifluoromethyl)quinolin-4-yl]amino}cyclohexyl]-1,3-benzothiazole-7-carboxamide;
2-[7-(dimethylamino)-2-oxo-2H-chromen-4-yl]-N-[(1s,4s)-4-{[6-chloro-2-(trifluoromethyl)quinolin-4-yl]amino}cyclohexyl]acetamide;
6-oxo-N-[(1s,4s)-4-{[6-chloro-2-(trifluoromethyl)quinolin-4-yl]amino}cyclohexyl]spiro[3.3]heptane-2-carboxamide;
5-chloro-2-methoxy-N-[(1s,4s)-4-{[6-chloro-2-(trifluoromethyl)quinolin-4-yl]amino}cyclohexyl]pyridine-4-carboxamide;
3-methyl-N-[(1s,4s)-4-{[6-chloro-2-(trifluoromethyl)quinolin-4-yl]amino}cyclohexyl]-1-benzofuran-2-carboxamide;
1-phenyl-N-[(1s,4s)-4-{[6-chloro-2-(trifluoromethyl)quinolin-4-yl]amino}cyclohexyl]-1H-pyrrole-2-carboxamide;
2-(3-methyl-1,2-oxazol-5-yl)-N-[(1s,4s)-4-{[6-chloro-2-(trifluoromethyl)quinolin-4-yl]amino}cyclohexyl]acetamide;
2,3-dioxo-N-[(1s,4s)-4-{[6-chloro-2-(trifluoromethyl)quinolin-4-yl]amino}cyclohexyl]-2,3-dihydro-1H-indole-7-carboxamide;
N-[(1s,4s)-4-{[6-chloro-2-(trifluoromethyl)quinolin-4-yl]amino}cyclohexyl]pyrazolo[1,5-a]pyridine-2-carboxamide;
6-fluoro-N-[(1s,4s)-4-{[6-chloro-2-(trifluoromethyl)quinolin-4-yl]amino}cyclohexyl]-3,4-dihydro-2H-1-benzopyran-2-carboxamide;
2-[(dimethylcarbamothioyl)sulfanyl]-N-[(1s,4s)-4-{[6-chloro-2-(trifluoromethyl)quinolin-4-yl]amino}cyclohexyl]acetamide;
3-(cyclopropylmethoxy)-4-(difluoromethoxy)-N-[(1s,4s)-4-{[6-chloro-2-(trifluoromethyl)quinolin-4-yl]amino}cyclohexyl]benzamide;
5-(difluoromethyl)-N-[(1s,4s)-4-{[6-chloro-2-(trifluoromethyl)quinolin-4-yl]amino}cyclohexyl]pyrazine-2-carboxamide;
(4S)-2-methyl-N-[(1s,4s)-4-{[6-chloro-2-(trifluoromethyl)quinolin-4-yl]amino}cyclohexyl]-3,4,5,6-tetrahydropyrimidine-4-carboxamide;
3-methyl-4-oxo-N-[(1s,4s)-4-{[6-chloro-2-(trifluoromethyl)quinolin-4-yl]amino}cyclohexyl]-3H,4H-imidazo[4,3-d][1,2,3,5]tetrazine-8-carboxamide;
4-[(quinolin-2-yl)methoxy]-N-[(1s,4s)-4-{[6-chloro-2-(trifluoromethyl)quinolin-4-yl]amino}cyclohexyl]benzamide;
2,6-difluoro-3-(propane-1-sulfonamido)-N-[(1s,4s)-4-{[6-chloro-2-(trifluoromethyl)quinolin-4-yl]amino}cyclohexyl]benzamide;
2-chloro-4-(4-methylpiperazin-1-yl)-N-[(1s,4s)-4-{[6-chloro-2-(trifluoromethyl)quinolin-4-yl]amino}cyclohexyl]benzamide;
4-oxo-N-[(1s,4s)-4-{[6-chloro-2-(trifluoromethyl)quinolin-4-yl]amino}cyclohexyl]-1,4-dihydro-1,5-naphthyridine-3-carboxamide;
2-methyl-N-[(1s,4s)-4-{[6-chloro-2-(trifluoromethyl)quinolin-4-yl]amino}cyclohexyl]-4H-thieno[3,2-b]pyrrole-5-carboxamide;
(1r,4r)-4-[(2,5-dioxo-2,5-dihydro-1H-pyrrol-1-yl)methyl]-N-[(1s,4s)-4-{[6-chloro-2-(trifluoromethyl)quinolin-4-yl]amino}cyclohexyl]cyclohexane-1-carboxamide;
N1-(4-fluorophenyl)-N'1-[(1s,4s)-4-{[6-chloro-2-(trifluoromethyl)quinolin-4-yl]amino}cyclohexyl]cyclopropane-1,1-dicarboxamide;
3-(5-oxo-1-phenyl-2-sulfanylideneimidazolidin-4-yl)-N-[(1s,4s)-4-{[6-chloro-2-(trifluoromethyl)quinolin-4-yl]amino}cyclohexyl]propanamide;
5-chloro-6-imino-N-[(1s,4s)-4-{[6-chloro-2-(trifluoromethyl)quinolin-4-yl]amino}cyclohexyl]-1,6-dihydropyrimidine-4-carboxamide;
2-methyl-N-[(1s,4s)-4-{[6-chloro-2-(trifluoromethyl)quinolin-4-yl]amino}cyclohexyl]-2H-indazole-3-carboxamide;
2,4-dichloro-3-cyano-5-fluoro-N-[(1s,4s)-4-{[6-chloro-2-(trifluoromethyl)quinolin-4-yl]amino}cyclohexyl]benzamide;
1-[(4-methoxyphenyl)methyl]-N-[(1s,4s)-4-{[6-chloro-2-(trifluoromethyl)quinolin-4-yl]amino}cyclohexyl]-1H-pyrazole-4-carboxamide;

tert-butyl N-[(1S)-2-(1H-pyrazol-1-yl)-1-{[(1s,4s)-4-{[6-chloro-2-(trifluoromethyl)quinolin-4-yl]amino}cyclohexyl]carbamoyl}ethyl]carbamate;
2-benzyl-N-[(1s,4s)-4-{[6-chloro-2-(trifluoromethyl)quinolin-4-yl]amino}cyclohexyl]-2,3-dihydro-1H-isoindole-4-carboxamide;
N-[(1s,4s)-4-{[6-chloro-2-(trifluoromethyl)quinolin-4-yl]amino}cyclohexyl]-5-(trifluoromethyl)-1H-pyrrolo[2,3-b]pyridine-3-carboxamide;
6-(2-methoxyphenyl)-N-[(1s,4s)-4-{[6-chloro-2-(trifluoromethyl)quinolin-4-yl]amino}cyclohexyl]pyridine-3-carboxamide;
2-methoxy-N-[(1s,4s)-4-{[6-chloro-2-(trifluoromethyl)quinolin-4-yl]amino}cyclohexyl]-4-(trifluoromethyl)-1,3-thiazole-5-carboxamide;
3-(4-fluorophenyl)-5-methyl-N-[(1s,4s)-4-{[6-chloro-2-(trifluoromethyl)quinolin-4-yl]amino}cyclohexyl]-4,5-dihydro-1,2-oxazole-5-carboxamide;
3-(3-methylphenyl)-N-[(1s,4s)-4-{[6-chloro-2-(trifluoromethyl)quinolin-4-yl]amino}cyclohexyl]pyridine-4-carboxamide;
2-(pyridin-3-yl)-N-[(1s,4s)-4-{[6-chloro-2-(trifluoromethyl)quinolin-4-yl]amino}cyclohexyl]-4,5-dihydro-1,3-thiazole-4-carboxamide;
5-oxo-1-phenyl-N-[(1s,4s)-4-{[6-chloro-2-(trifluoromethyl)quinolin-4-yl]amino}cyclohexyl]pyrrolidine-2-carboxamide;
5-(pyridin-3-yloxy)-N-[(1s,4s)-4-{[6-chloro-2-(trifluoromethyl)quinolin-4-yl]amino}cyclohexyl]furan-2-carboxamide;
2-methyl-N-[(1s,4s)-4-{[6-chloro-2-(trifluoromethyl)quinolin-4-yl]amino}cyclohexyl]pyrazolo[1,5-a]pyrimidine-6-carboxamide;
3-methyl-4-oxo-N-[(1s,4s)-4-{[6-chloro-2-(trifluoromethyl)quinolin-4-yl]amino}cyclohexyl]-3,4-dihydroquinazoline-7-carboxamide;
2-(3,4-dihydro-1H-2-benzopyran-1-yl)-N-[(1s,4s)-4-{[6-chloro-2-(trifluoromethyl)quinolin-4-yl]amino}cyclohexyl]acetamide;
1,4-dimethyl-N-[(1s,4s)-4-{[6-chloro-2-(trifluoromethyl)quinolin-4-yl]amino}cyclohexyl]-1H-indole-2-carboxamide;
4-(1H-imidazol-1-yl)-N-[(1s,4s)-4-{[6-chloro-2-(trifluoromethyl)quinolin-4-yl]amino}cyclohexyl]pyridine-2-carboxamide;
2-(dimethylamino)-2-(1-methyl-1H-pyrazol-4-yl)-N-[(1s,4s)-4-{[6-chloro-2-(trifluoromethyl)quinolin-4-yl]amino}cyclohexyl]acetamide;
2,6,6-trimethyl-N-[(1s,4s)-4-{[6-chloro-2-(trifluoromethyl)quinolin-4-yl]amino}cyclohexyl]bicyclo[3.1.1]heptane-3-carboxamide;
1-ethenyl-N-[(1s,4s)-4-{[6-chloro-2-(trifluoromethyl)quinolin-4-yl]amino}cyclohexyl]-2-oxabicyclo[2.2.2]octane-4-carboxamide;
1-(2,2-difluoroethyl)-N-[(1s,4s)-4-{[6-chloro-2-(trifluoromethyl)quinolin-4-yl]amino}cyclohexyl]-1H-pyrazole-3-carboxamide;
2-(4-methyl-1,3-thiazol-2-yl)-N-[(1s,4s)-4-{[6-chloro-2-(trifluoromethyl)quinolin-4-yl]amino}cyclohexyl]propanamide;
5-methyl-N-[(1s,4s)-4-{[6-chloro-2-(trifluoromethyl)quinolin-4-yl]amino}cyclohexyl]-1H-1,3-benzodiazole-6-carboxamide;
N-(4-{[6-chloro-2-(trifluoromethyl)quinolin-4-yl]amino}cyclohexyl)-4H,5H,6H,7H-pyrazolo[1,5-a]pyridine-2-carboxamide;
N-(4-{[6-chloro-2-(trifluoromethyl)quinolin-4-yl]amino}cyclohexyl)-2-(5-cyano-1-methyl-1H-pyrrol-2-yl)acetamide;
N-(4-{[6-chloro-2-(trifluoromethyl)quinolin-4-yl]amino}cyclohexyl)imidazo[1,5-a]pyridine-1-carboxamide;
N-(4-{[6-chloro-2-(trifluoromethyl)quinolin-4-yl]amino}cyclohexyl)-2-[2-(difluoromethoxy)-6-fluorophenyl]acetamide;
4-propyl-N-[(1s,4s)-4-{[6-chloro-2-(trifluoromethyl)quinolin-4-yl]amino}cyclohexyl]-1,2,3-thiadiazole-5-carboxamide;
N-(4-{[6-chloro-2-(trifluoromethyl)quinolin-4-yl]amino}cyclohexyl)-2-(5-methoxy-2-methyl-1H-indol-3-yl)acetamide;
N-(4-{[6-chloro-2-(trifluoromethyl)quinolin-4-yl]amino}cyclohexyl)-4-(5-cyclopropyl-1,2,4-oxadiazol-3-yl)benzamide;
N-[(1s,4s)-4-{[6-chloro-2-(trifluoromethyl)quinolin-4-yl]amino}cyclohexyl]-4,5,6,7-tetrahydro-1H-1,3-benzodiazole-6-carboxamide;
N'-[(pyridin-3-yl)methyl]-N-[(1s,4s)-4-{[6-chloro-2-(trifluoromethyl)quinolin-4-yl]amino}cyclohexyl]butanediamide;
1-(3-methoxyphenyl)-5-oxo-N-[(1s,4s)-4-{[6-chloro-2-(trifluoromethyl)quinolin-4-yl]amino}cyclohexyl]pyrrolidine-3-carboxamide;
7-methyl-2-propyl-N-[(1s,4s)-4-{[6-chloro-2-(trifluoromethyl)quinolin-4-yl]amino}cyclohexyl]-1H-1,3-benzodiazole-5-carboxamide;
3-(dimethylamino)-N-[(1s,4s)-4-{[2-(trifluoromethyl)quinolin-4-yl]amino}cyclohexyl]-4-(trifluoromethyl)benzamide;
2-cyano-N-[(1s,4s)-4-{[2-(trifluoromethyl)quinolin-4-yl]amino}cyclohexyl]benzamide;
1-methyl-N-[(1s,4s)-4-{[2-(trifluoromethyl)quinolin-4-yl]amino}cyclohexyl]-1H-1,3-benzodiazole-6-carboxamide;
4-methoxy-2-methyl-N-[(1s,4s)-4-{[2-(trifluoromethyl)quinolin-4-yl]amino}cyclohexyl]benzamide;
1-methyl-N-[(1s,4s)-4-{[2-(trifluoromethyl)quinolin-4-yl]amino}cyclohexyl]-1H-indazole-6-carboxamide;
1-methyl-N-[(1s,4s)-4-{[2-(trifluoromethyl)quinolin-4-yl]amino}cyclohexyl]-1H-indazole-5-carboxamide;
N-[(1s,4s)-4-{[2-(trifluoromethyl)quinolin-4-yl]amino}cyclohexyl]-1,3-benzothiazole-5-carboxamide;
N-[(1s,4s)-4-{[2-(trifluoromethyl)quinolin-4-yl]amino}cyclohexyl]-1,3-benzothiazole-6-carboxamide;
6-methyl-N-[(1s,4s)-4-{[2-(trifluoromethyl)quinolin-4-yl]amino}cyclohexyl]pyridine-2-carboxamide;
2-methyl-N-[(1s,4s)-4-{[2-(trifluoromethyl)quinolin-4-yl]amino}cyclohexyl]pyridine-4-carboxamide;
N-[(1s,4s)-4-{[2-(trifluoromethyl)quinolin-4-yl]amino}cyclohexyl]isoquinoline-3-carboxamide;
3-methyl-N-[(1s,4s)-4-{[2-(trifluoromethyl)quinolin-4-yl]amino}cyclohexyl]-1,2-oxazole-4-carboxamide;
4-methyl-N-[(1s,4s)-4-{[2-(trifluoromethyl)quinolin-4-yl]amino}cyclohexyl]pyridine-2-carboxamide;
2-methoxy-N-[(1s,4s)-4-{[2-(trifluoromethyl)quinolin-4-yl]amino}cyclohexyl]pyridine-4-carboxamide;
N-[(1s,4s)-4-{[2-(trifluoromethyl)quinolin-4-yl]amino}cyclohexyl]quinoline-4-carboxamide;
N-[(1s,4s)-4-{[2-(trifluoromethyl)quinolin-4-yl]amino}cyclohexyl]isoquinoline-1-carboxamide;
N-[(1s,4s)-4-{[2-(trifluoromethyl)quinolin-4-yl]amino}cyclohexyl]-2-(trifluoromethyl)pyridine-4-carboxamide;

4-methyl-N-[(1s,4s)-4-{[2-(trifluoromethyl)quinolin-4-yl]amino}cyclohexyl]-1,2-oxazole-5-carboxamide;

2,4-dimethyl-N-[(1s,4s)-4-{[2-(trifluoromethyl)quinolin-4-yl]amino}cyclohexyl]furan-3-carboxamide;

4-(dimethylamino)-2-methyl-N-[(1s,4s)-4-{[2-(trifluoromethyl)quinolin-4-yl]amino}cyclohexyl]benzamide;

4-(dimethylamino)-2-fluoro-N-[(1s,4s)-4-{[2-(trifluoromethyl)quinolin-4-yl]amino}cyclohexyl]benzamide;

4-(dimethylamino)-3-fluoro-N-[(1s,4s)-4-{[2-(trifluoromethyl)quinolin-4-yl]amino}cyclohexyl]benzamide;

5-methyl-N-[(1s,4s)-4-{[2-(trifluoromethyl)quinolin-4-yl]amino}cyclohexyl]thiophene-2-carboxamide;

3-methyl-N-[(1s,4s)-4-{[2-(trifluoromethyl)quinolin-4-yl]amino}cyclohexyl]thiophene-2-carboxamide;

3-fluoro-N-[(1s,4s)-4-{[2-(trifluoromethyl)quinolin-4-yl]amino}cyclohexyl]thiophene-2-carboxamide;

5-chloro-N-[(1s,4s)-4-{[2-(trifluoromethyl)quinolin-4-yl]amino}cyclohexyl]thiophene-2-carboxamide;

5-cyano-N-[(1s,4s)-4-{[2-(trifluoromethyl)quinolin-4-yl]amino}cyclohexyl]thiophene-2-carboxamide;

4-cyano-N-[(1s,4s)-4-{[2-(trifluoromethyl)quinolin-4-yl]amino}cyclohexyl]thiophene-2-carboxamide;

4-fluoro-N-[(1s,4s)-4-{[2-(trifluoromethyl)quinolin-4-yl]amino}cyclohexyl]thiophene-2-carboxamide;

N-[(1s,4s)-4-{[2-(trifluoromethyl)quinolin-4-yl]amino}cyclohexyl]pyridazine-4-carboxamide;

5-fluoro-N-[(1s,4s)-4-{[2-(trifluoromethyl)quinolin-4-yl]amino}cyclohexyl]thiophene-2-carboxamide;

N-[(1s,4s)-4-{[2-(trifluoromethyl)quinolin-4-yl]amino}cyclohexyl]-5-(trifluoromethypthiophene-2-carboxamide;

N-[(1s,4s)-4-{[2-(trifluoromethyl)quinolin-4-yl]amino}cyclohexyl]-3-(trifluoromethypthiophene-2-carboxamide;

3-(dimethylamino)-5-fluoro-N-[(1s,4s)-4-{[2-(trifluoromethyl)quinolin-4-yl]amino}cyclohexyl]benzamide;

3-cyano-N-[(1s,4s)-4-{[2-(trifluoromethyl)quinolin-4-yl]amino}cyclohexyl]thiophene-2-carboxamide;

4-chloro-N-[(1s,4s)-4-{[2-(trifluoromethyl)quinolin-4-yl]amino}cyclohexyl]thiophene-2-carboxamide;

4,5-dimethyl-N-[(1s,4s)-4-{[2-(trifluoromethyl)quinolin-4-yl]amino}cyclohexyl]thiophene-2-carboxamide;

4-(dimethylamino)-2-methoxy-N-[(1s,4s)-4-{[2-(trifluoromethyl)quinolin-4-yl]amino}cyclohexyl]benzamide;

3-cyano-5-(dimethylamino)-N-[(1s,4s)-4-{[2-(trifluoromethyl)quinolin-4-yl]amino}cyclohexyl]benzamide;

5-(dimethylamino)-2-fluoro-N-[(1s,4s)-4-{[2-(trifluoromethyl)quinolin-4-yl]amino}cyclohexyl]benzamide;

1-methyl-N-[(1s,4s)-4-{[2-(trifluoromethyl)quinolin-4-yl]amino}cyclohexyl]-1H-pyrrolo[2,3-b]pyridine-4-carboxamide;

3-(dimethylamino)-4-methyl-N-[(1s,4s)-4-{[2-(trifluoromethyl)quinolin-4-yl]amino}cyclohexyl]benzamide;

3-(dimethylamino)-4-methoxy-N-[(1s,4s)-4-{[2-(trifluoromethyl)quinolin-4-yl]amino}cyclohexyl]benzamide;

4-(dimethylamino)-3-methyl-N-[(1s,4s)-4-{[2-(trifluoromethyl)quinolin-4-yl]amino}cyclohexyl]benzamide;

2-(dimethylamino)-N-[(1s,4s)-4-{[2-(trifluoromethyl)quinolin-4-yl]amino}cyclohexyl]pyridine-4-carboxamide;

6-cyano-N-[(1s,4s)-4-{[2-(trifluoromethyl)quinolin-4-yl]amino}cyclohexyl]pyridine-2-carboxamide;

2-cyano-N-[(1s,4s)-4-{[2-(trifluoromethyl)quinolin-4-yl]amino}cyclohexyl]pyridine-4-carboxamide;

4-(dimethylamino)-N-[(1s,4s)-4-{[2-(trifluoromethyl)quinolin-4-yl]amino}cyclohexyl]pyridine-2-carboxamide;

5-(dimethylamino)-N-[(1s,4s)-4-{[2-(trifluoromethyl)quinolin-4-yl]amino}cyclohexyl]pyridine-2-carboxamide;

N-[(1s,4s)-4-{[2-(trifluoromethyl)quinolin-4-yl]amino}cyclohexyl]-1,5-naphthyridine-2-carboxamide;

2-(difluoromethyl)-N-[(1s,4s)-4-{[2-(trifluoromethyl)quinolin-4-yl]amino}cyclohexyl]pyridine-4-carboxamide;

3-methoxy-N-[(1s,4s)-4-{[2-(trifluoromethyl)quinolin-4-yl]amino}cyclohexyl]pyridine-4-carboxamide;

6-methoxy-N-[(1s,4s)-4-{[2-(trifluoromethyl)quinolin-4-yl]amino}cyclohexyl]pyridine-2-carboxamide;

4-(dimethylamino)-3,5-difluoro-N-[(1s,4s)-4-{[2-(trifluoromethyl)quinolin-4-yl]amino}cyclohexyl]benzamide;

4-(pyrrolidin-1-yl)-N-[(1s,4s)-4-{[2-(trifluoromethyl)quinolin-4-yl]amino}cyclohexyl]benzamide;

4-(azetidin-1-yl)-N-[(1s,4s)-4-{[2-(trifluoromethyl)quinolin-4-yl]amino}cyclohexyl]benzamide;

2-methyl-N-[(1s,4s)-4-{[2-(trifluoromethyl)quinolin-4-yl]amino}cyclohexyl]-1-benzofuran-3-carboxamide;

3-{[(1s,4s)-4-{[6-chloro-2-(trifluoromethyl)quinolin-4-yl]amino}cyclohexyl]carbamoyl}phenyl acetate;

N1-methyl-N3-[(1s,4s)-4-{[6-chloro-2-(trifluoromethyl)quinolin-4-yl]amino}cyclohexyl]benzene-1,3-dicarboxamide;

3-(1H-pyrazol-1-yl)-N-[(1s,4s)-4-{[6-chloro-2-(trifluoromethyl)quinolin-4-yl]amino}cyclohexyl]benzamide;

3-(2,2-dimethylpropanamido)-N-[(1s,4s)-4-{[6-chloro-2-(trifluoromethyl)quinolin-4-yl]amino}cyclohexyl]benzamide;

N-[(1s,4s)-4-{[6-chloro-2-(trifluoromethyl)quinolin-4-yl]amino}cyclohexyl]-1,3-benzoxazole-2-carboxamide;

3-(2-methylpropanamido)-N-[(1s,4s)-4-{[6-chloro-2-(trifluoromethyl)quinolin-4-yl]amino}cyclohexyl]benzamide;

methyl 3-{[(1s,4s)-4-{[6-chloro-2-(trifluoromethyl)quinolin-4-yl]amino}cyclohexyl]carbamoyl}benzoate;

3-[(dimethylcarbamoyl)amino]-N-[(1s,4s)-4-{[6-chloro-2-(trifluoromethyl)quinolin-4-yl]amino}cyclohexyl]benzamide;

3-(ethylamino)-N-[(1s,4s)-4-{[6-chloro-2-(trifluoromethyl)quinolin-4-yl]amino}cyclohexyl]benzamide;

2-oxo-N-[(1s,4s)-4-{[6-chloro-2-(trifluoromethyl)quinolin-4-yl]amino}cyclohexyl]-1,2,3,4-tetrahydroquinoline-7-carboxamide;

3-propanamido-N-[(1s,4s)-4-{[6-chloro-2-(trifluoromethyl)quinolin-4-yl]amino}cyclohexyl]benzamide;

3-(3-methoxypropanamido)-N-[(1s,4s)-4-{[6-chloro-2-(trifluoromethyl)quinolin-4-yl]amino}cyclohexyl]benzamide;

5-acetamido-2-methyl-N-[(1s,4s)-4-{[6-chloro-2-(trifluoromethyl)quinolin-4-yl]amino}cyclohexyl]benzamide;

2-(4-fluorophenyl)-N-[(1s,4s)-4-{[2-(trifluoromethyl)quinazolin-4-yl]amino}cyclohexyl]acetamide;

3-cyano-N-[(1s,4s)-4-{[2-(trifluoromethyl)quinazolin-4-yl]amino}cyclohexyl]benzamide;

4-cyano-N-[(1s,4s)-4-{[2-(trifluoromethyl)quinazolin-4-yl]amino}cyclohexyl]benzamide;

4-(dimethylamino)-N-[(1s,4s)-4-{[6-chloro-2-(trifluoromethyl)quinolin-4-yl]amino}cyclohexyl]benzamide;

4-acetamido-N-[(1s,4s)-4-{[6-chloro-2-(trifluoromethyl)quinolin-4-yl]amino}cyclohexyl]benzamide;

4-hydroxy-N-[(1s,4s)-4-{[6-chloro-2-(trifluoromethyl)quinolin-4-yl]amino}cyclohexyl]benzamide;

4-methoxy-N-[(1s,4s)-4-{[6-chloro-2-(trifluoromethyl)quinolin-4-yl]amino}cyclohexyl]benzamide;

3,5-dimethyl-N-[(1s,4s)-4-{[2-(trifluoromethyl)quinolin-4-yl]amino}cyclohexyl]benzamide;

(1S,2S)-2-phenyl-N-[(1s,4s)-4-{[2-(trifluoromethyl)quinolin-4-yl]amino}cyclohexyl]cyclopropane-1-carboxamide;

3-chloro-N-[(1s,4s)-4-{[2-(trifluoromethyl)quinolin-4-yl]amino}cyclohexyl]thiophene-2-carboxamide;
N-[(1s,4s)-4-{[2-(trifluoromethyl)quinolin-4-yl]amino}cyclohexyl]-2,1,3-benzoxadiazole-5-carboxamide;
4-ethoxy-N-[(1s,4s)-4-{[2-(trifluoromethyl)quinolin-4-yl]amino}cyclohexyl]benzamide;
3-ethoxy-N-[(1s,4s)-4-{[2-(trifluoromethyl)quinolin-4-yl]amino}cyclohexyl]benzamide;
2,3-difluoro-4-methyl-N-[(1s,4s)-4-{[2-(trifluoromethyl)quinolin-4-yl]amino}cyclohexyl]benzamide;
2,6-difluoro-3-methyl-N-[(1s,4s)-4-{[2-(trifluoromethyl)quinolin-4-yl]amino}cyclohexyl]benzamide;
2-chloro-6-fluoro-N-[(1s,4s)-4-{[2-(trifluoromethyl)quinolin-4-yl]amino}cyclohexyl]benzamide;
3-chloro-2-fluoro-N-[(1s,4s)-4-{[2-(trifluoromethyl)quinolin-4-yl]amino}cyclohexyl]benzamide;
3,4,5-trifluoro-N-[(1s,4s)-4-{[2-(trifluoromethyl)quinolin-4-yl]amino}cyclohexyl]benzamide;
N-[(1s,4s)-4-{[2-(trifluoromethyl)quinolin-4-yl]amino}cyclohexyl]-2H-chromene-3-carboxamide;
4-acetamido-N-[(1s,4s)-4-{[2-(trifluoromethyl)quinolin-4-yl]amino}cyclohexyl]benzamide;
2-(difluoromethoxy)-N-[(1s,4s)-4-{[2-(trifluoromethyl)quinolin-4-yl]amino}cyclohexyl]benzamide;
4-fluoro-2-methoxy-N-[(1s,4s)-4-{[2-(trifluoromethyl)quinolin-4-yl]amino}cyclohexyl]benzamide;
4-chloro-2-methoxy-N-[(1s,4s)-4-{[2-(trifluoromethyl)quinolin-4-yl]amino}cyclohexyl]benzamide;
5-chloro-2-methoxy-N-[(1s,4s)-4-{[2-(trifluoromethyl)quinolin-4-yl]amino}cyclohexyl]benzamide;
2-ethyl-N-[(1s,4s)-4-{[2-(trifluoromethyl)quinolin-4-yl]amino}cyclohexyl]benzamide;
2,2-difluoro-N-[(1s,4s)-4-{[2-(trifluoromethyl)quinolin-4-yl]amino}cyclohexyl]-2H-1,3-benzodioxole-5-carboxamide;
4-methyl-N-[(1s,4s)-4-{[2-(trifluoromethyl)quinolin-4-yl]amino}cyclohexyl]-1,3-thiazole-5-carboxamide;
3-fluoro-2-methyl-N-[(1s,4s)-4-{[2-(trifluoromethyl)quinolin-4-yl]amino}cyclohexyl]benzamide;
3-chloro-2-methyl-N-[(1s,4s)-4-{[2-(trifluoromethyl)quinolin-4-yl]amino}cyclohexyl]benzamide;
2-chloro-3-fluoro-N-[(1s,4s)-4-{[2-(trifluoromethyl)quinolin-4-yl]amino}cyclohexyl]benzamide;
2,3-dichloro-N-[(1s,4s)-4-{[2-(trifluoromethyl)quinolin-4-yl]amino}cyclohexyl]benzamide;
2-chloro-3-methyl-N-[(1s,4s)-4-{[2-(trifluoromethyl)quinolin-4-yl]amino}cyclohexyl]benzamide;
1,5-dimethyl-N-[(1s,4s)-4-{[2-(trifluoromethyl)quinolin-4-yl]amino}cyclohexyl]-1H-pyrazole-3-carboxamide;
2,2,3,3-tetramethyl-N-[(1s,4s)-4-{[2-(trifluoromethyl)quinolin-4-yl]amino}cyclohexyl]cyclopropane-1-carboxamide;
4-chloro-N-[(1s,4s)-4-{[6-chloro-2-(trifluoromethyl)quinolin-4-yl]amino}cyclohexyl]-1H-pyrazole-5-carboxamide;
N-[(1s,4s)-4-{[6-chloro-2-(trifluoromethyl)quinolin-4-yl]amino}cyclohexyl]-1,2,3-thiadiazole-4-carboxamide;
3-methyl-N-[(1s,4s)-4-{[6-chloro-2-(trifluoromethyl)quinolin-4-yl]amino}cyclohexyl]-1,2-oxazole-4-carboxamide;
1,3,5-trimethyl-N-[(1s,4s)-4-{[6-chloro-2-(trifluoromethyl)quinolin-4-yl]amino}cyclohexyl]-1H-pyrazole-4-carboxamide; and
N-[(1s,4s)-4-{[6-chloro-2-(trifluoromethyl)quinolin-4-yl]amino}cyclohexyl]furan-3-carboxamide.

In certain embodiments, the invention provides a pharmaceutical composition comprising a compound of structure (I) or any one of formulas (IA) through (1C), or a pharmaceutically acceptable salt, isomer, hydrate, solvate or isotope thereof, together with at least one pharmaceutically acceptable carrier, diluent, or excipient. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid, or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent can include any sustained release material known in the art, such as glyceryl monostearate or glyceryl distearate, alone or mixed with a wax.

As used herein, the term "pharmaceutical composition" refers to a composition containing one or more of the compounds described herein, or a pharmaceutically acceptable isomer, racemate, hydrate, solvate, isotope or salt thereof, formulated with a pharmaceutically acceptable carrier, which can also include other additives, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); for administration to a pediatric subject (e.g., solution, syrup, suspension, elixir, powder for reconstitution as suspension or solution, dispersible/effervescent tablet, chewable tablet, lollipop, freezer pops, troches, oral thin strips, orally disintegrating tablet, orally disintegrating strip, and sprinkle oral powder or granules); or in any other formulation described herein. Conventional procedures and ingredients for the selection and preparation of suitable formulations are described, for example, in Remington: The Science and Practice of Pharmacy, 21st Ed., Gennaro, Ed., Lippencott Williams & Wilkins (2005) and in The United States Pharmacopeia: The National Formulary (USP 36 NF31), published in 2013.

In some embodiments, the pharmaceutical composition comprising a compound of structure (I) or any one of formulas (IA) through (1C), or a pharmaceutically acceptable salt, isomer, hydrate, solvate or isotope thereof, with at least one pharmaceutically acceptable carrier, diluent, or excipient further comprises a second therapeutic agent.

In one embodiment, the second therapeutic agent is an antihistamine, such as an H1 receptor antagonist or an H2 receptor antagonist. In one embodiment, the second therapeutic agent is an H1 receptor antagonist antihistamine, such as levocetirizine, loratadine, fexofenadine, cetirizine, desloratadine, olopatadine, diphenhydramine, cyproheptadine or hydroxyzine pamoate. In one embodiment, the second therapeutic agent is a H2 receptor antagonist, such as cimetidine, nizatidine, ranitidine or famotidine. In one embodiment, the second therapeutic agent is a leukotriene receptor antagonist or leukotriene synthesis inhibitor, such as montelukast, zafirlukast, pranlukast, or 5-lipoxygenase inhibitor (e.g., zileuton, hypericum perforatum). In one embodiment, the second therapeutic agent is an immunomodulatory agent such as Omalizumab or immunoglobulin therapy. In one embodiment, the second therapeutic agent is a corticosteroid, such as hydrocortisone, cortisone, ethamethasoneb, triamcinolone, prednisone, prednisolone, or fludrocortisone. In one embodiment, the second therapeutic agent is a tricylic antidepressant that can relieve itch such as doxepin, amitriptyline or nortriptyline. In one embodiment, the second therapeutic agent is an anti-inflammatory drug such as dapsone, sulfasalazine, hydroxycholoroquine or colchicine. In one embodiment, the second therapeutic agent is an immunosuppressant such as cyclosporine, methotrexate, mycophenolic acid or tacromilus.

In one embodiment, the second therapeutic agent is an H1 receptor antagonist antihistamine, such as levocetirizine, loratadine, fexofenadine, cetirizine, desloratadine, olopatadine, diphenhydramine, cyproheptadine or hydroxyzine pamoate. In one embodiment, the second therapeutic agent is a H2 receptor antagonist, such as cimetidine, nizatidine, ranitidine or famotidine. In one embodiment, the second therapeutic agent is a leukotriene receptor antagonist or leukotriene synthesis inhibitor, such as montelukast, zafirlukast, pranlukast, or 5-lipoxygenase inhibitor (e.g., zileuton, hypericum perforatum). In one embodiment, the second therapeutic agent is an immunomodulatory agent such as Omalizumab or immunoglobulin therapy. In one embodiment, the second therapeutic agent is a corticosteroid, such as hydrocortisone, cortisone, ethamethasoneb, triamcinolone, prednisone, prednisolone, or fludrocortisone. In one embodiment, the second therapeutic agent is a tricylic antidepressant that can relieve itch such as doxepin, amitriptyline or nortriptyline. In one embodiment, the second therapeutic agent is an anti-inflammatory drug such as dapsone, sulfasalazine, hydroxycholoroquine or colchicine. In one embodiment, the second therapeutic agent is an immunosuppressant such as cyclosporine, methotrexate, mycophenolic acid or tacromilus.

As used herein, the term "pharmaceutically acceptable carrier" refers to any ingredient other than the disclosed compounds, or a pharmaceutically acceptable isomer, racemate, hydrate, solvate, isotope or salt thereof (e.g., a carrier capable of suspending or dissolving the active compound) and having the properties of being nontoxic and noninflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents, or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal, or parenteral, including intravenous, subcutaneous and/or intramuscular. In one embodiment, the route of administration is oral. In another embodiment, the route of administration is topical.

Dosage forms can be administered once a day, or more than once a day, such as twice or thrice daily. Alternatively, dosage forms can be administered less frequently than daily, such as every other day, or weekly, if found to be advisable by a prescribing physician or drug's prescribing information. Dosing regimens include, for example, dose titration to the extent necessary or useful for the indication to be treated, thus allowing the patient's body to adapt to the treatment, to minimize or avoid unwanted side effects associated with the treatment, and/or to maximize the therapeutic effect of the present compounds. Other dosage forms include delayed or controlled-release forms. Suitable dosage regimens and/or forms include those set out, for example, in the latest edition of the Physicians' Desk Reference, incorporated herein by reference.

Proper dosages for pediatric patients can be determined using known methods, including weight, age, body surface area, and models such as Simcyp® Pediatric Simulation modeling (CERTARA, Princeton, N.J.) which can be used to establish a pharmacokinetic approach for dosing that takes into account patient age, ontogeny of the clearance pathways to eliminate a compound of any one of formulas (IA) through (1C), and body surface area (BSA). In one embodiment, the dosage form is formulated to provide a pediatric dose from about 30% to about 100% of an adult dose, or about 35%, 40%, 45%, 50%, 55%, 60%, 65%, 70%, 75%, 80%, 85%, 90%, 95%, or 100% of an adult dose.

In one embodiment, the invention provides an oral pharmaceutical composition comprising a compound of structure (I) or any one of formulas (IA) through (1C), or a pharmaceutically acceptable salt, isomer, hydrate, solvate or isotope thereof, together with at least one pharmaceutically acceptable oral carrier, diluent, or excipient. In another embodiment, the invention provides a topical pharmaceutical composition comprising a compound of structure (I) or any one of formulas (IA) through (1C), or a pharmaceutically acceptable salt, isomer, hydrate, solvate or isotope thereof, together with at least one pharmaceutically acceptable topical carrier, diluent, or excipient. For example, the oral pharmaceutical composition is provided to treat cholestatic pruritus, wherein the dosage regimen is, for example, once a day. In one embodiment, the topical pharmaceutical composition is provided to treat atopic dermatitis.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation. In some embodiments, the composition is formulated into a pediatric dosage form suitable for treating a pediatric subject.

In certain embodiments, the invention provides a compound having structure (I) or any one of formulas (IA) through (1C), or a pharmaceutically acceptable salt, isomer, hydrate, solvate or isotope thereof. Such compounds can be synthesized using standard synthetic techniques known to those skilled in the art. For example, compounds of the present invention can be synthesized using appropriately modified synthetic procedures set forth in the following Examples and Reaction Schemes.

To this end, the reactions, processes, and synthetic methods described herein are not limited to the specific conditions described in the following experimental section, but rather are intended as a guide to one with suitable skill in this field. For example, reactions may be carried out in any suitable solvent, or other reagents to perform the transformation[s] necessary. Generally, suitable solvents are protic or aprotic solvents which are substantially non-reactive with the reactants, the intermediates or products at the temperatures at which the reactions are carried out (i.e., temperatures which may range from the freezing to boiling temperatures). A given reaction may be carried out in one solvent or a mixture of more than one solvent. Depending on the particular reaction, suitable solvents for a particular work-up following the reaction may be employed.

All reagents, for which the synthesis is not described in the experimental part, are either commercially available, or are known compounds or may be formed from known compounds by known methods by a person skilled in the art. The compounds and intermediates produced according to the methods of the invention may require purification. Purification of organic compounds is well known to a person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using purpose-made or prepacked silica gel cartridges and eluents such as gradients of solvents such as heptane, ether, ethyl acetate, acetonitrile, ethanol and the like. In some cases, the compounds may be purified by preparative HPLC using methods as described.

Purification methods as described herein may provide compounds of the present invention which possess a sufficiently basic or acidic functionality in the form of a salt, such as, in the case of a compound of the present invention which is sufficiently basic, a trifluoroacetate or formate salt, or, in the case of a compound of the present invention which is sufficiently acidic, an ammonium salt. A salt of this type can either be transformed into its free base or free acid form, respectively, by various methods known to a person skilled in the art, or be used as salts in subsequent biological assays. It is to be understood that the specific form of a compound of the present invention as isolated and as described herein is not necessarily the only form in which said compound can be applied to a biological assay in order to quantify the specific biological activity.

Chemical names were generated using the ChemDraw naming software (Version 17.0.0.206) by PerkinElmer Informatics, Inc. In some cases, generally accepted names of commercially available reagents were used in place of names generated by the naming software.

EXAMPLES

General Methods $^1$H NMR (400 MHz) spectra were obtained in solution of deuterochloroform ($CDCl_3$), deuteromethanol ($CD_3OD$) or dimethyl sulfoxide-D6 (DMSO). HPLC retention times, purities, and mass spectra (LCMS) were obtained using one of the following methods:

Method 1: Shimadzu LCMS-2020 System equipped with a Kinetex EVO C18 2.1×30 mm, (5 um particles), using H2O with 0.0375% Trifluoroacetic Acid as the mobile phase A, and MeCN with 0.01875% Trifluoroacetic Acid as the mobile phase B. An ESI detector in positive mode was used. The gradient was 5% B at 0.00 min and 5-90% B at 0.00-0.80 min, 90-95% B at 0.80-0.12 min, and then 95-5% B in 0.01 min, hold on 5% B for 0.34 min, the flow rate was 1.5 ml/min.

Method 2: Agilent 1200 System equipped with a Kinetex C18 50×2.1 mm, (5 um particles), using H2O with 0.037% Trifluoroacetic Acid as the mobile phase A, and MeCN with 0.018% Trifluoroacetic Acid as the mobile phase B. An ESI detector in positive mode was used. The gradient was 5% B at 0.00 min and 5-90% B at 0.00-0.80 min, 90-95% B at 0.80-0.12 min, and then 95-5% B in 0.01 min, hold on 5% B for 0.34 min, the flow rate was 1.5 ml/min.

Method 3: Agilent 1260 Infinity II System equipped with an Agilent Poroshell 120 EC-18, 2.7 μm, 4.6×100 mm column at 30° C., using $H_2O$ with 0.1% formic acid as the mobile phase A, and MeCN with 0.1% formic acid as the mobile phase B. An ESI detector in positive mode was used. The gradient was 5-95% mobile phase B over 12 min then held at 95% for 1.8 min, then return to 10% mobile phase B over 0.2 min. The flow rate was 1 mL/min.

Method 4: Agilent 1290 Infinity II System equipped with an Agilent Poroshell 120 EC-18, 1.9 μm, 2.1×50 mm column at 35° C., using H2O with 0.1% formic acid as the mobile phase A, and MeCN with 0.1% formic acid as the mobile phase B. An ESI detector in positive mode was used. The gradient was 20-95% mobile phase B over 0.8 min then held at 95% for 0.7 mins, then return to 20% mobile phase B over 0.7 min. The flow rate was 0.7 mL/min.

Method 5: Agilent 1290 Infinity II System equipped with an Agilent Poroshell 120 EC-18, 2.7 μm, 4.61×100 mm column at 35° C., using H2O with 0.1% formic acid as the mobile phase A, and MeCN with 0.1% formic acid as the mobile phase B. An ESI detector in positive mode was used. The gradient was 5-95% mobile phase B over 8.0 min then held at 95% for 1.8 mins, then return to 20% mobile phase B over 0.2 min. The flow rate was 0.7 mL/min.

Method 6: Agilent 1260 Infinity II System equipped with an Agilent Poroshell 120 EC-18, 2.7 μm, 4.6×100 mm column at 30° C., using H2O with 0.1% formic acid as the mobile phase A, and MeCN with 0.1% formic acid as the mobile phase B. An ESI detector in positive mode was used. The gradient was 5-95% mobile phase B over 5 min then held at 95% for 1.8 min, then return to 20% mobile phase B over 0.2 min. The flow rate was 1 mL/min.

Method 7: Shimadzu LCMS-2020 System equipped with a Kinetex EVO C18 2.1×30 mm, (Sum particles), using H2O with 0.0375% Trifluoroacetic Acid as the mobile phase A, and MeCN with 0.01875% Trifluoroacetic Acid as the mobile phase B. An ESI detector in positive mode was used. The gradient was 5% B at 0.00 min and 5-95% B at 0.00-0.8 min, 95-95% B at 0.80-1.09 min, and then 95-5% B in 0.01 min, hold on 5% B for 0.1 min, the flow rate was 1.5 ml/min. LCMS-5-95AB_1.2 min·lcm Method 8: Agilent 1200 System equipped with an Xbridge Shield RP18 2.1*50 mm column (Sum particles), using H2O with 10 mM NH4HCO3 as the mobile phase A, and MeCN as the mobile phase B. An ESI detector in positive mode was used. The gradient was 5-95% B in 0.30 min and 30-95% B at 0.30-0.80 min, hold on 95% B for 0.4 min, and then 95-5% B in 0.01 min, the flow rate was 1.5 ml/min.

The pyridine, dichloromethane (DCM), tetrahydrofuran (THF), and toluene used in the procedures were from Aldrich Sure-Seal bottles kept under nitrogen ($N_2$). Other solvents were used as is. All reactions were stirred magnetically, and temperatures are external reaction temperatures. Chromatographies were typically carried out using a Combiflash Rf flash purification system (Teledyne Isco) equipped with Redisep (Teledyne Isco) Rf Gold Normal-Phase silica gel ($SiO_2$) columns or by using a similar system.

Preparative HPLC purifications were typically performed using one of the following systems: 1) Waters System equipped with a Waters 2489 uv/vis detector, an Aquity QDA detector, a Waters xBridge Prep C18 5 μm OBD, 30×150 mm column, and eluting with various gradients of $H_2O$/MeCN (0.1% formic acid) at a 30 mL/min flow rate, 2) Teledyne Isco ACCQPrep® HP150 UV system equipped with a Waters xBridge Prep C18 5 μm OBD, 30×150 mm column, and eluting with various gradients of $H_2O$/MeCN (0.1% formic acid) at a 42.5 mL/min flow rate, or 3) column: Phenomenex Synergi C18 150×30 mm-4 μm; mobile phase: [$H_2O$ (0.225% formic acid)-MeCN]; B %: 55%-85%, 12 min) and were typically concentrated using a Genevac EZ-2.

The following additional abbreviations are used: ethyl acetate (EA), triethylamine (TEA), water (H2O, sodium chloride (NaCl), Hydrochloridric acid (HCl), methanol (MeOH), dimethyl sulfoxide (DMSO), silica gel ($SiO_2$), diisobutylaluminium hydride (DIBAL), trifluoroacetic acid (TFA), 4-dimethylaminopyridine (DMAP), diphenylphosphoryl azide (DPPA), benzoyl peroxide (BPO), 1,1'-bis(diphenylphosphino)ferrocene (dppf), bis(pinacolato)diboron ($B_2pin_2$), tetrahydrofuran (THF), 1,4-diazabicyclo[2.2.2]octane bis(sulfur dioxide) adduct (DABSO), hexafluorophosphate azabenzotriazole tetramethyl uronium (HATU), hydroxybenzotriazole (H OBt), N-methyl morpholine (NMM), N-Bromosuccinimide (NBS), diisopropylethyl amine (DIPEA or DIEA), diethyl azodicarboxylate (DEAD), diisopropyl azodicarboxylate (DIAD), 2-[2-(dicyclohexylphosphino)phenyl]-N-methylindole (CM-Phos), triflic acid (TfOH), I-ethyl-3-(3-dimethylaminopropyl) carbodiimide hydrochloride (EDC), isopropanol (IPA), dimethylformamide (DMF), dimethyl acetamide (DMA), dichloromethane (DCM), 1,2-dichloroethane (DCE), acetonitrile (MeCN or ACN), 1,1'-thiocarbonyldiimidazole (TCDI), petroleum ether (PE), not determined (ND), retention time (RT), molecular weight (mw), room temperature (rt), hour (h), and not applicable (N/A).

Example 1

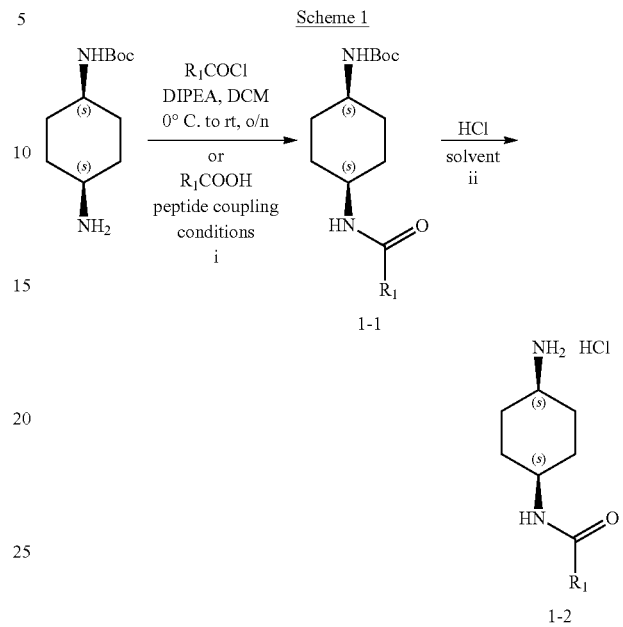

Reagents: i. R1COCl, DIPEA, solvent (DCM) or R1COOH, peptide coupling reagent (HATU), base (DIPEA), solvent (DMF); ii. HCl, solvent (1,4-dioxane)

Example 1A cis-N-(4-aminocyclohexyl)-4-fluoro-benzamide

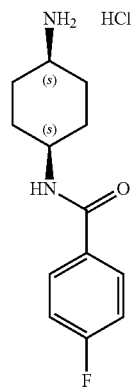 [SMILES: Cl ; N[C@H]1CC[C@@H](NC(=O)c2ccc(F)cc2)CC1]

Synthesis of tert-butyl N-[4-[(4-fluorobenzoyl)amino]cyclohexyl]carbamate

To a mixture of tert-butyl cis-N-(4-aminocyclohexyl) carbamate (1.35 g, 6.31 mmol, 1 eq) and TEA (1.28 g, 12.61 mmol, 1.76 mL, 2 eq) in DCM (20 mL) was added 4-fluorobenzoyl chloride (1 g, 6.31 mmol, 757.58 uL, 1 eq) at 0° C., then the reaction mixture was stirred at 25° C. for 0.5 hr. The reaction mixture was concentrated to give a residue that was purified by silica on column chromatography eluted by PE/EtOAc=10:1 to 1:1. Tert-butyl N-[4-[(4-fluorobenzoyl)amino]cyclohexyl]carbamate (2 g, 5.95 mmol, 94.27% yield) was obtained.

Synthesis of cis-N-(4-aminocyclohexyl)-4-fluoro-benzamide·HCl

A mixture of tert-butyl N-[4-[(4-fluorobenzoyl)amino]cyclohexyl]carbamate (2 g, 5.95 mmol, 1 eq) in HCl/EtOAc (4 M, 5 mL, 3.36 eq) was stirred at 25° C. for 1 hr. The reaction mixture was concentrated to give N-(4-aminocyclohexyl)-4-fluoro-benzamide (1.5 g, 5.50 mmol, 92.50% yield, HCl). It was used in the next step directly.

Example 1B cis-N-(4-aminocyclohexyl)-4-methoxy-benzamide

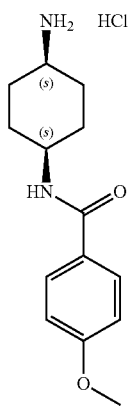 [SMILES: Cl ; COc1ccc(C(=O)N[C@H]2CC[C@@H](N)CC2)cc1]

Synthesis of tert-butyl cis-N-[4-[(4-methoxybenzoyl)amino]cyclohexyl]carbamate

To a mixture of tert-butyl N-(4-aminocyclohexyl)carbamate (5 g, 23.33 mmol, 1 eq), 4-methoxybenzoic acid (3.55 g, 23.33 mmol, 1 eq) and DIPEA (9.05 g, 69.99 mmol, 12.19 mL, 3 eq) in DMF (50 mL) was added HATU (13.31 g, 35.00 mmol, 1.5 eq), then the brown solution was stirred at 25° C. for 12 hr. The reaction mixture was poured into water (100 mL) and extracted by ethyl acetate (2×100 mL). The combined organic phase was dried and concentrated under vacuo to give a residue that was purified by silica on column chromatography eluted by petroleum ether/ethyl acetate=1:1. Tert-butyl N-[4-[(4-methoxybenzoyl)amino]cyclohexyl]carbamate (7.6 g, 21.81 mmol, 93.49% yield) was obtained.

LCMS-ESI (m/z) calculated: 348.4 found 349.2 [M+H]$^+$, RT=0.895 min (Method 1).

Synthesis of cis-N-(4-aminocyclohexyl)-4-methoxy-benzamide·HCl

A mixture of tert-butyl N-[4-[(4-methoxybenzoyl)amino]cyclohexyl]carbamate (7.6 g, 21.81 mmol, 1 eq) in HCl/dioxane (4 M, 54.53 mL, 10 eq) was stirred at 30° C. for 1 hr. The reaction mixture was concentrated under vacuo to give a residue. The residue was dissolved in MeOH (200 mL) and neutralized by basic resin by stirring for 1 hr. After filtration of the resin, the filtrate was concentrated and lyophilized to give N-(4-aminocyclohexyl)-4-methoxy-benzamide (5 g, 20.14 mmol, 92.31% yield).

LCMS-ESI (m/z) calculated: 248.3 found 249.2 [M+H]$^+$, RT=0.756 min (Method 1)

Example 2

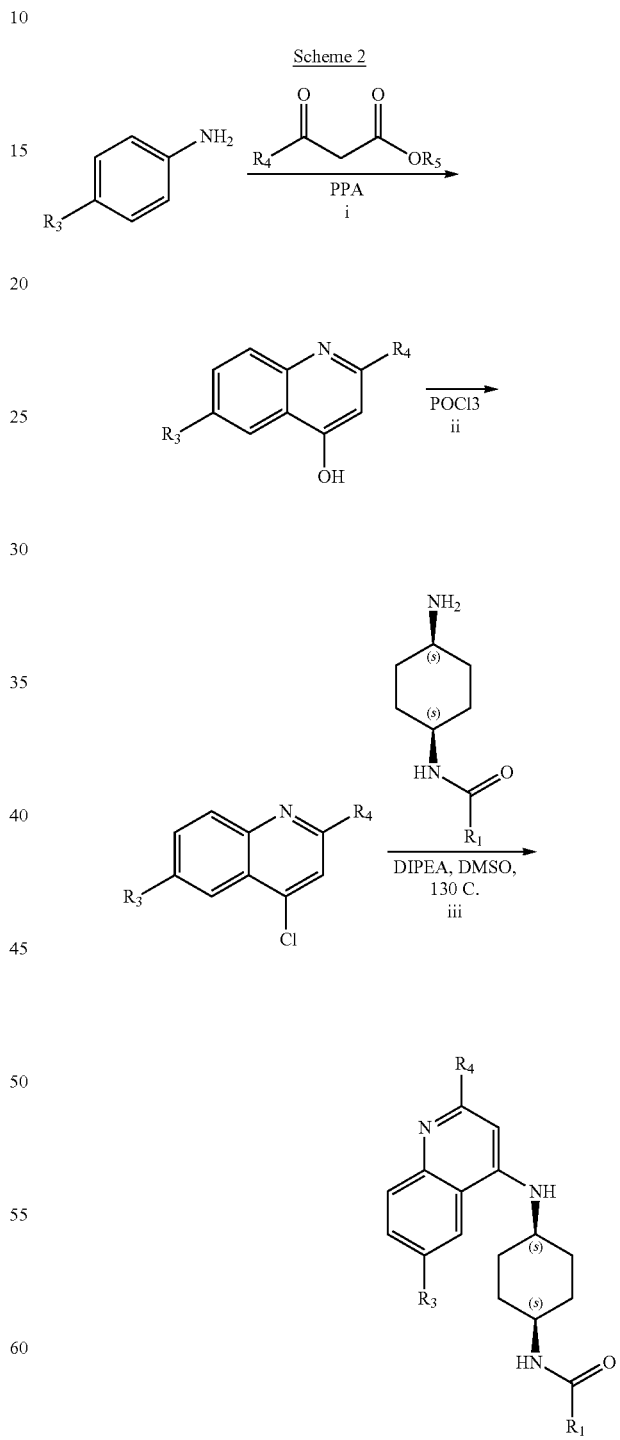

Reagents: i. PPA, heat (R5: Me, Et); ii. POCl3, solvent (DCE); iii. DIPEA, solvent (DMSO, NMP), heat

Example 2A 4-fluoro-N-[(1s,4s)-4-{[2-(difluoromethyl)quinolin-4-yl]amino}cyclohexyl]benzamide

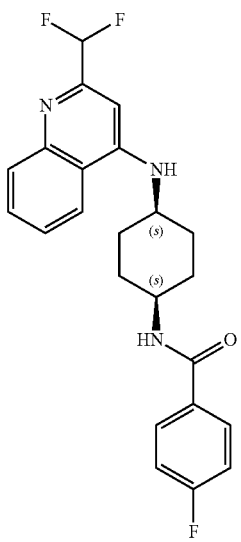 [SMILES: O=C(N[C@H]1CC[C@@H](Nc2cc(C(F)F)nc3ccccc23)CC1)c1ccc(F)cc1]

Synthesis of 2-(difluoromethyl)quinolin-4-ol

To PPA (26.85 mmol, 10 mL, 5.00 eq) was added aniline (0.5 g, 5.37 mmol, 490.20 uL, 1 eq) and ethyl 4,4-difluoro-3-oxobutanoate (891.92 mg, 5.37 mmol, 1 eq) at 140° C. The reaction mixture was stirred at 140° C. for 12 hr. The reaction mixture was poured into water (50 mL) and extracted by ethyl acetate (4×50 mL). The combined organic layers were dried and concentrated under vacuo to give a residue. The residue was mixed with petroleum ether/ethyl acetate=5:1(50 mL) and stirred for 1 h, then the mixture was filtered and washed by petroleum ether (20 mL). The filter cake was dried under vacuo to give 2-(difluoromethyl)quinolin-4-ol (470 mg, 2.41 mmol, 44.85% yield).

$^1$H NMR (400 MHz, DMSO-d6) δ ppm 8.11 (d, J=8.19 Hz, 1H) 7.68-7.83 (m, 2H) 7.43 (br t, J=7.03 Hz, 1H) 6.89-7.19 (m, 1H) 6.47 (br s, 1H).

Synthesis of 4-chloro-2-(difluoromethyl)quinoline

To a solution of 2-(difluoromethyl)quinolin-4-ol (200 mg, 1.02 mmol, 1 eq) in DCE (4 mL) was added POCl3 (785.65 mg, 5.12 mmol, 476.15 uL, 5 eq) dropwise at 0° C. for 5 min. Then the mixture was stirred at 80° C. for 3 hr. The reaction mixture was concentrated under reduced pressure to give a residue that was dissolved in ethyl acetate (20 mL) and washed by water (2×10 mL). The organic phase was dried and concentrated under vacuo to afford 4-chloro-2-(difluoromethyl)quinoline (200 mg, 936.28 umol, 91.36% yield).

LCMS-ESI (m/z) calculated: 213.61 found 214.1 [M+H]$^+$, RT=0.938 min (Method 1).

Synthesis of 4-fluoro-N-[(1S,4S)-4-{[2-(difluoromethyl)quinolin-4-yl]amino}cyclohexyl]benzamide A solution of 4-chloro-2-(difluoromethyl)quinoline (100 mg, 468.14 umol, 1 eq), cis-N-(4-aminocyclohexyl)-4-fluoro-benzamide (127.68 mg, 468.14 umol, 1 eq, HCl) and DIPEA (302.52 mg, 2.34 mmol, 407.71 uL, 5 eq) in DMSO (4 mL) was stirred at 130° C. for 12 hr. The reaction mixture was poured into water (10 mL) and extracted by ethyl acetate (2×10 mL), the combined organic layer was dried and concentrated under reduced pressure to give a residue. The residue was purified by prep-HPLC (column: Zhongpu RD-C18 150×25 mm×3 um; mobile phase: [water (0.225% FA)-ACN]; B %: 18%-48%, 10 min) to give 4-fluoro-N-[(1s,4s)-4-{[2-(difluoromethyl)quinolin-4-yl]amino}cyclohexyl]benzamide (5.5 mg, 13.30 umol, 2.84% yield, 100% purity).

LCMS-ESI (m/z) calculated: 413.4 found 414.2 [M+H]$^+$, RT=0.97 min (Method 8)

$^1$H NMR (400 MHz, METHANOL-d4) δ ppm 8.23 (dd, J=8.44, 0.81 Hz, 1H) 7.87-7.94 (m, 3H) 7.72 (ddd, J=8.38, 6.94, 1.31 Hz, 1H) 7.54 (ddd, J=8.32, 7.00, 1.19 Hz, 1H) 7.16-7.23 (m, 2H) 6.53-6.83 (m, 2H) 4.10 (br d, J=4.38 Hz, 1H) 3.85-3.95 (m, 1H) 1.87-2.08 (m, 8H)

Example 2B

N-[4-[[6-cyano-2-(trifluoromethyl)-4-quinolyl]amino]cyclohexyl]-4-fluoro-benzamide

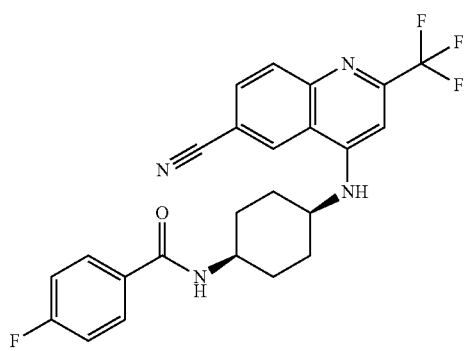 [SMILES: N#Cc1ccc2nc(C(F)(F)F)cc(N[C@H]3CC[C@@H](NC(=O)c4ccc(F)cc4)CC3)c2c1]

Synthesis of 6-bromo-2-(trifluoromethyl)quinolin-4-ol

To a solution of PPA (100 g, 1.00 eq) at 140° C. was added 4-bromoaniline (5 g, 29.07 mmol, 1 eq) and ethyl 4,4,4-trifluoro-3-oxo-butanoate (5.35 g, 29.07 mmol, 4.25 mL, 1 eq). The mixture was stirred at 140° C. for 2 hr. The reaction mixture was diluted with water (400 mL) and extracted with ethyl acetate (2×800 mL). The combined organic layers were dried over anhydrous sodium sulfate, filtered, and concentrated under reduced pressure to give a residue. The crude product 6-bromo-2-(trifluoromethyl)quinolin-4-ol (6.5 g, 19.14 mmol, 65.85% yield, 86% purity) was used into the next step without further purification.

$^1$H NMR (400 MHz, DMSO-d6) δ=12.14 (s, 1H), 8.27 (s, 1H), 7.89 (s, 2H), 7.05 (s, 1H).

Synthesis of 4-hydroxy-2-(trifluoromethyl)quinoline-6-carbonitrile

To a solution of 6-bromo-2-(trifluoromethyl)quinolin-4-ol (100 mg, 342.41 umol, 1 eq) in DMF (5 mL) was added Pd(PPh3)4 (17.01 mg, 14.72 umol, 0.05 eq), DPPF (32.65 mg, 58.89 umol, 0.2 eq), Zn(CN)$_2$ (34.58 mg, 294.47 umol, 18.69 uL, 1 eq) and Zn (1.93 mg, 29.45 umol, 0.1 eq). The flask was purged with nitrogen and the mixture stirred at 100° C. for 12 hr. The reaction mixture was diluted with water (50 mL) and extracted with dichloromethane (2×50 mL). The combined organic layers were dried over anhydrous sodium sulfate, filtered, and concentrated under reduced pressure to give a residue. The crude product was triturated with ethyl acetate at 25° C. for 20 min. Compound 4-hydroxy-2-(trifluoromethyl)quinoline-6-carbonitrile (100 mg, crude) was obtained.

LCMS-ESI (m/z) calculated: 238.17 found 239.1 [M+H]$^+$, RT=0.94 min (Method 2)

$^1$H NMR (400 MHz, DMSO-d6) δ=8.62 (s, 1H), 8.09-7.94 (m, 3H), 7.24 (s, 1H).

Synthesis of 4-chloro-2-(trifluoromethyl)quinoline-6-carbonitrile

To a solution of 4-hydroxy-2-(trifluoromethyl)quinoline-6-carbonitrile (100 mg, 335.90 umol, 1 eq) in DCE (3 mL) was added POCl3 (412.04 mg, 2.69 mmol, 249.72 uL, 8 eq) at 0° C. The mixture was stirred at 80° C. for 12 h. The reaction mixture was diluted with ice water (20 mL) and extracted with dichloromethane (2×20 mL). The combined organic layers were dried over anhydrous sodium sulfate, filtered, and concentrated under reduced pressure to give a residue. The crude product 4-chloro-2-(trifluoromethyl)quinoline-6-carbonitrile (100 mg, 292.27 umol, 87.01% yield, 75% purity) was used into the next step without further purification.

Synthesis of 4-fluoro-N-[(1S,4S)-4-{[6-cyano-2-(trifluoromethyl)quinolin-4-yl]amino}cyclohexyl]benzamide To a solution of 4-chloro-2-(trifluoromethyl)quinoline-6-carbonitrile (80 mg, 233.82 umol, 75% purity, 1 eq) and cis-N-(4-aminocyclohexyl)-4-fluoro-benzamide (63.77 mg, 233.82 umol, 1 eq, HCl) in DMSO (2 mL) was added DIEA (151.10 mg, 1.17 mmol, 203.63 uL, 5 eq). The mixture was stirred at 130° C. for 12 h. After return to rt, the mixture reaction was filtered and the filtrate was purified by prep-HPLC (column: Phenomenex Luna C18 200×40 mm×10 um; mobile phase: [water (0.2% FA)-ACN]; B %: 40%-70%, 8 min) to give desired 4-fluoro-N-[(1s,4s)-4-{[6-cyano-2-(trifluoromethyl)quinolin-4-yl]amino} cyclohexyl] benzamide (26.1 mg, 57.18 umol, 24.46% yield, 100% purity).

LCMS-ESI (m/z) calculated: 456.44 found 457.2 [M+H]$^+$, RT=1.019 min (Method 2)

$^1$H NMR (400 MHz, DMSO-d6) δ=9.16 (d, J=0.8 Hz, 1H), 8.20 (d, J=6 Hz, 1H), 8.04-8.01 (m, 2H), 7.99-7.94 (m, 2H), 7.65 (d, J=6 Hz, 1H), 7.32-7.27 (m, 2H), 6.93 (s, 1H), 3.96-3.91 (m, 2H), 1.96-1.92 (m, 4H), 1.82-1.73 (m, 4H).

Example 2C

4-(dimethylamino)-N-[(1s,4s)-4-{[6-(methylamino)-2-(trifluoromethyl)quinolin-4-yl]amino}cyclohexyl]benzamide

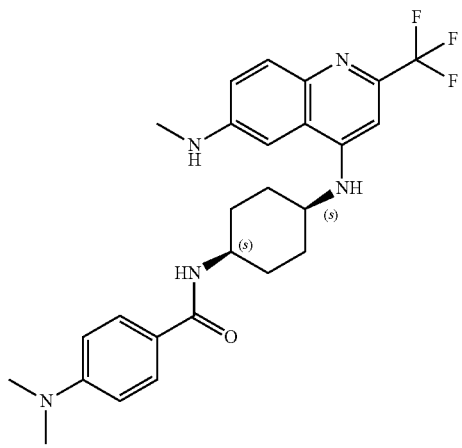 [SMILES: CNc1ccc2nc(C(F)(F)F)cc(N[C@H]3CC[C@@H](NC(=O)c4ccc(N(C)C)cc4)CC3)c2c1]

Synthesis of N-[[(1S,4S)-4-[[6-bromo-2-(trifluoromethyl)-4-quinolyl]amino]cyclohexyl]-4-(dimethylamino) benzamide To a solution of 6-bromo-4-chloro-2-(trifluoromethyl)quinoline (900 mg, 2.90 mmol, 1 eq) and cis-N-(4-aminocyclohexyl)-4-(dimethylamino)benzamide (1.73 g, 5.80 mmol, 2 eq, HCl) in NMP (10 mL) was added DIPEA (1.87 g, 14.49 mmol, 2.52 mL, 5 eq), then the reaction mixture was stirred at 130° C. for 12 hr. The mixture was poured into water (50 mL) and extracted with ethyl acetate (3×30 mL). The combined organic layers were dried over Na2SO4, filtered, and concentrated under reduced pressure. The crude product was purified by column chromatography (SiO2, Petroleum ether/Ethyl acetate=2/1 to 1/1) to afford N-[[(1S,4S)-4-[[6-bromo-2-(trifluoromethyl)-4-quinolyl]amino]cyclohexyl]-4-(dimethylamino)benzamide (1.2 g, 2.24 mmol, 77.32% yield).

LCMS-ESI (m/z) calculated: 535.4 found 535.2/537.2 [M+H]$^+$, RT=0.927 min (Method 1).

Synthesis of 4-(dimethylamino)-N-[[(1S,4S)-4-[[6-[(4-methoxyphenyl)methyl-methyl-amino]-2-(trifluoromethyl)-4-quinolyl]amino]cyclohexyl]benzamide A mixture of N-[4-[[6-bromo-2-(trifluoromethyl)-4-quinolyl]amino]cyclohexyl]-4-(dimethylamino) benzamide (100 mg, 186.78 umol, 1 eq), 1-(4-methoxyphenyl)-N-methyl-methanamine (56.48 mg, 373.56 umol, 54.84 uL, 2 eq), Cs2CO3 (121.71 mg, 373.56 umol, 2 eq) and RuPhos Pd G3 (15.62 mg, 18.68 umol, 0.1 eq) in Dioxane (2 mL) was stirred at 100° C. for 12 hr under N2 atmosphere. The reaction mixture was poured into water (10 mL) and extracted by ethyl acetate (3×10 mL). The combined organic layers were dried and concentrated under vacuo to give a residue that residue was purified by prep-TLC (petroleum ether/ethyl acetate=1:1) to give 4-(dimethylamino)-N-[4-[[6-[(4-methoxyphenyl)methyl-methyl-amino]-2-(trifluoromethyl)-4-quinolyl]amino]cyclohexyl]benzamide (100 mg, 165.10 umol, 88.39% yield)

LCMS-ESI (m/z) calculated: 605.69; found 606.5 [M+H]+, RT=0.917 min (Method 1).

Synthesis of 4-(dimethylamino)-N-[(1S,4S)-4-{[6-(methylamino)-2-(trifluoromethyl)quinolin-4-yl]amino} cyclohexyl]benzamide A mixture of 4-(dimethylamino)-N-[[(1S,4S)-4-[[6-[(4-methoxyphenyl)methyl-methyl-amino]-2-(trifluoromethyl)-4-quinolyl]amino]cyclohexyl]benzamide (80 mg, 132.08 umol, 1 eq) in TFA (0.5 mL) was stirred at 80° C. for 12 hr. The reaction mixture was poured into water (10 mL) and extracted by ethyl acetate (3×10 mL). The combined organic layers were dried and concentrated under vacuo to give a residue. The residue was purified by prep-TLC (ethyl acetate) to give 4-(dimethyl amino)-N-[(1s,4s)-4-{[6-(methylamino)-2-(trifluoromethyl)quinolin-4-yl]amino} cyclohexyl]benzamide (14.1 mg, 27.65 umol, 20.93% yield).

LCMS-ESI (m/z) calculated: 485.55; found 486.3 M+H]+, RT=0.9994 min (Method 8).

$^1$H NMR (400 MHz, DMSO-d6) δ ppm 7.76 (d, J=9.01 Hz, 2H) 7.71 (d, J=6.25 Hz, 1H) 7.61 (d, J=9.13 Hz, 1H) 7.14 (dd, J=9.13, 2.38 Hz, 1H) 6.92 (d, J=2.13 Hz, 1H) 6.69 (d, J=9.01 Hz, 2H) 6.63 (s, 1H) 6.54 (d, J=6.38 Hz, 1H) 6.21 (q, J=4.79 Hz, 1H) 3.91-4.01 (m, 1H) 3.67-3.76 (m, 1H) 2.96 (s, 6H) 2.86 (d, J=5.00 Hz, 3H) 1.85-2.00 (m, 4H) 1.64-1.84 (m, 4H).

The compounds in Table 1 were prepared following the procedures described for Example 2A.

TABLE 1

| Structure | Cpd No. | Purity RT | MW | m/z | Ion | Purity Method |
|---|---|---|---|---|---|---|
| 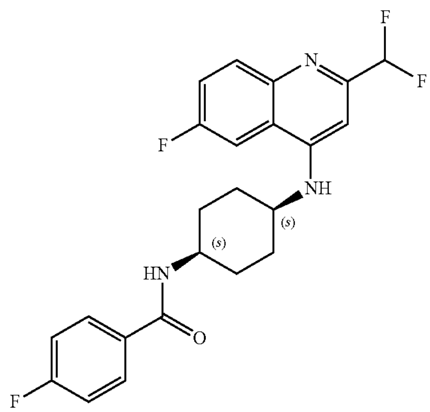 | 1-1 | 1.005 | 431.435 | 432.1 | [M + H]+ | Method 8 |
| 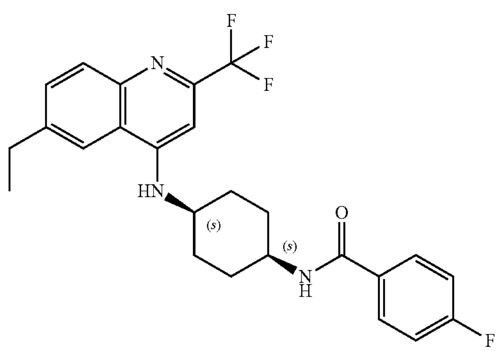 | 1-2 | 0.931 | 459.489 | 460.2 | [M + H]+ | Method 2 |
| 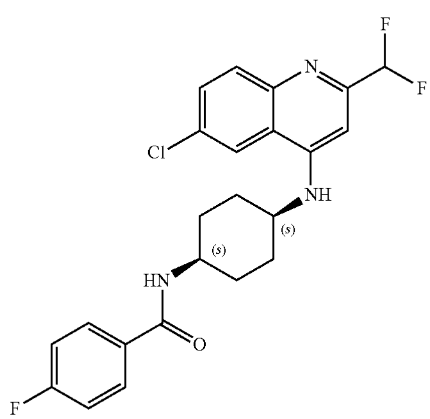 [SMILES: O=C(N[C@H]1CC[C@@H](Nc2cc(C(F)F)nc3ccc(F)cc23)CC1)c1ccc(F)cc1] | 1-3 | 1.047 | 447.89 | 448.1 | [M + H]+ | Method 8 |

TABLE 1-continued

| Structure | Cpd No. | Purity RT | MW | m/z | Ion | Purity Method |
|---|---|---|---|---|---|---|
| 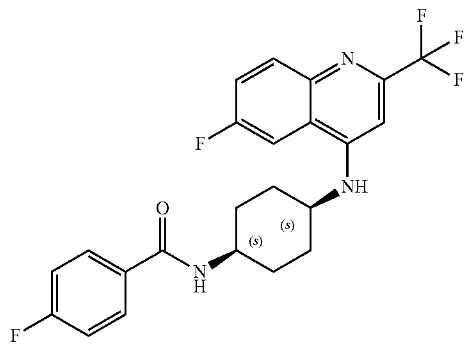 [SMILES: O=C(N[C@H]1CC[C@@H](Nc2cc(C(F)(F)F)nc3ccc(F)cc23)CC1)c1ccc(F)cc1] | 1-4 | 9.743 | 449.43 | 450.2 | [M + H]⁺ | Method 3 |
| 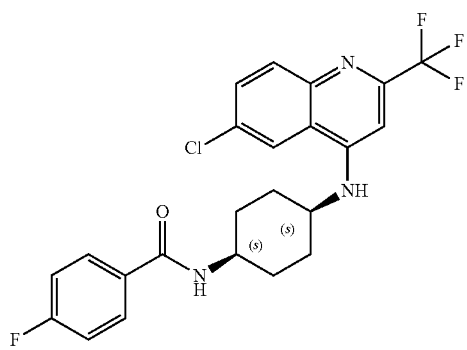 [SMILES: O=C(N[C@H]1CC[C@@H](Nc2cc(C(F)(F)F)nc3ccc(Cl)cc23)CC1)c1ccc(F)cc1] | 1-5 | 10.449 | 465.88 | 466.1 | [M + H]⁺ | Method 3 |
| 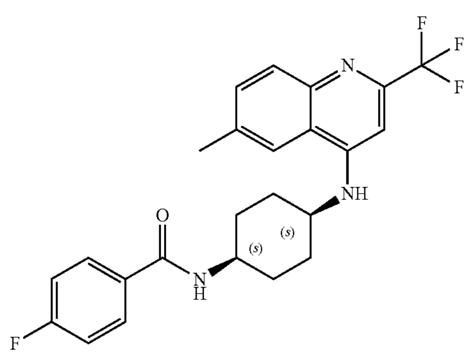 [SMILES: Cc1ccc2nc(C(F)(F)F)cc(N[C@H]3CC[C@@H](NC(=O)c4ccc(F)cc4)CC3)c2c1] | 1-6 | 8.762 | 445.46 | 446.2 | [M + H]⁺ | Method 3 |
| 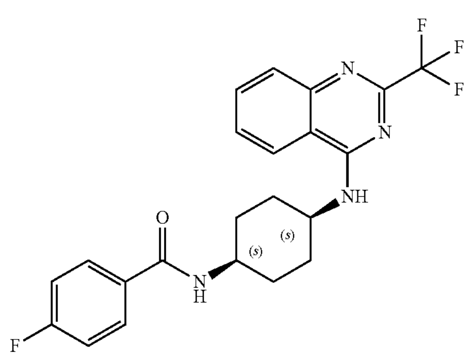 [SMILES: O=C(N[C@H]1CC[C@@H](Nc2nc(C(F)(F)F)nc3ccccc23)CC1)c1ccc(F)cc1] | 1-7 | 9.474 | 432.42 | 433.1 | [M + H]⁺ | Method 3 |

TABLE 1-continued
| Structure | Cpd No. | Purity RT | MW | m/z | Ion | Purity Method |
|---|---|---|---|---|---|---|
| 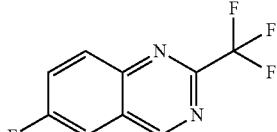 | 1-8 | 9.818 | 450.41 | 451.1 | [M + H]+ | Method 3 |
| 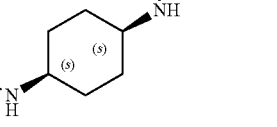 | 1-9 | 7.992 | 414.43 | 415.2 | [M + H]+ | Method 3 |
Example 3
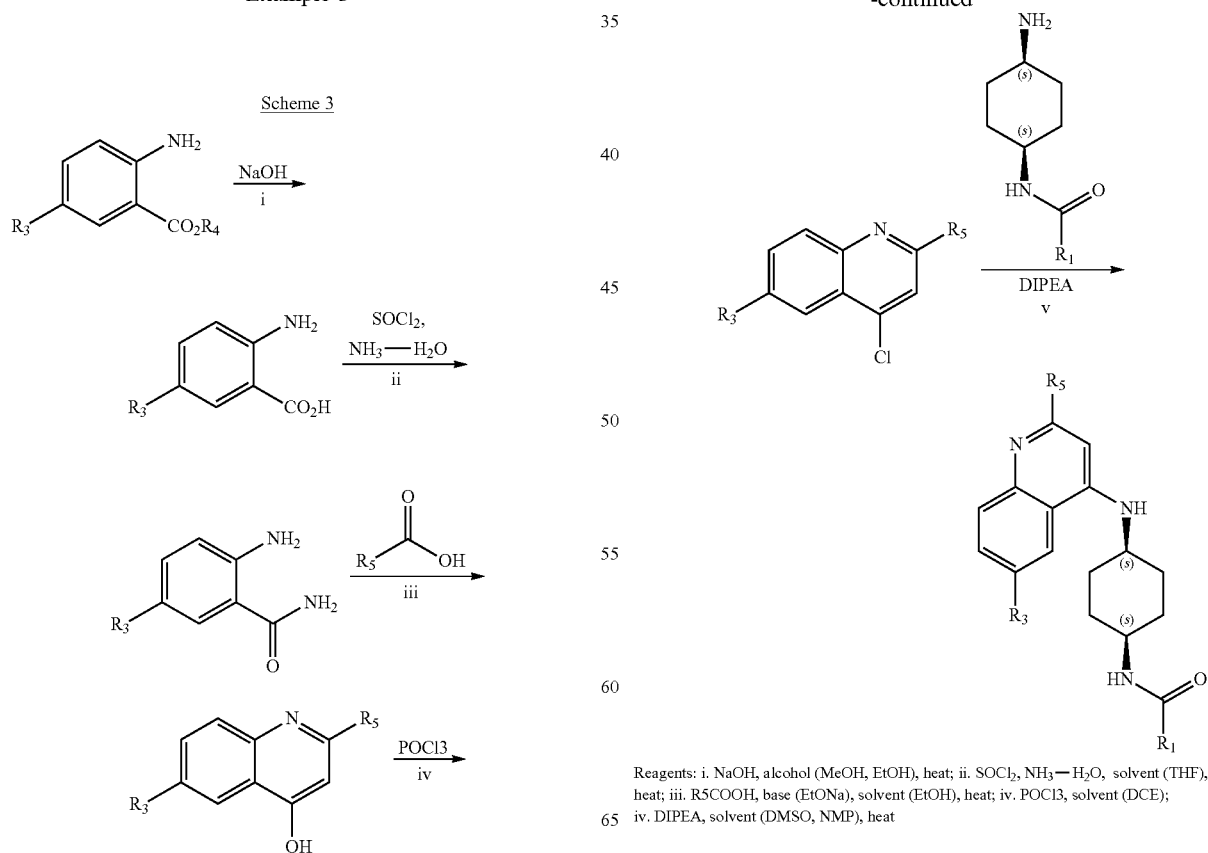
Reagents: i. NaOH, alcohol (MeOH, EtOH), heat; ii. SOCl$_2$, NH$_3$—H$_2$O, solvent (THF), heat; iii. R5COOH, base (EtONa), solvent (EtOH), heat; iv. POCl3, solvent (DCE); iv. DIPEA, solvent (DMSO, NMP), heat

Example 3A 4-fluoro-N-[(1s,4s)-4-{[2,6-bis(trifluoromethyl)quinazolin-4-yl]amino}cyclohexyl]benzamide

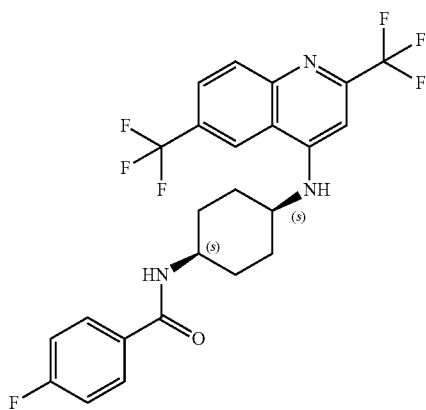 [SMILES: O=C(N[C@H]1CC[C@@H](Nc2cc(C(F)(F)F)nc3ccc(C(F)(F)F)cc23)CC1)c1ccc(F)cc1]

Synthesis of 2-amino-5-(trifluoromethyl)benzoic acid

A mixture of methyl 2-amino-5-(trifluoromethyl)benzoate (500 mg, 2.28 mmol, 1 eq) and NaOH (7 M, 650.05 uL, 1.99 eq) in MeOH (5 mL) was stirred at 40° C. at 2 h. The mixture was cooled to 10° C. and acidified to pH=5~6. The precipitate was collected by filtration. The solid (465 mg, 2.27 mmol, 99.36% yield) was used without purification in the next step.

$^1$H NMR (400 MHz, DMSO-d6) δ=7.92 (bs, 1H), 7.49 (d, J=20.2 Hz, 1H), 6.82 (d, J=20.2 Hz, 1H).

Synthesis of 2-amino-5-(trifluoromethyl)benzamide

A mixture of 2-amino-5-(trifluoromethyl)benzoic acid (450 mg, 2.19 mmol, 1 eq) in SOCl2 (5.22 g, 43.87 mmol, 3.18 mL, 20 eq) was stirred at 80° C. for 1 h. The mixture was concentrated, diluted with THF (50 mL) and the mixture was slowly poured into NH3·H2O (100 mL, 33% purity). The mixture was extracted with EtOAc (100 mL) and concentrated. The crude (430 mg, 2.11 mmol, 96.02% yield) was directly used into next step without further purification.

$^1$H NMR (400 MHz, DMSO-d6) δ ppm 6.78-6.84 (m, 1H) 7.13-7.22 (m, 2H) 7.22-7.31 (m, 1H) 7.37-7.44 (m, 1H) 7.86-7.90 (m, 1H) 7.92-8.08 (m, 1H).

Synthesis of 2,6-bis(trifluoromethyl)quinazolin-4-ol

A mixture of 2-amino-5-(trifluoromethyl)benzamide (300 mg, 1.47 mmol, 1 eq) and EtONa (400 mg, 5.88 mmol, 4 eq) in EtOH (12 mL) was stirred at 80° C. for 1 h. Then ethyl 2,2,2-trifluoroacetate (420.00 mg, 2.96 mmol, 407.77 uL, 2.01 eq) was added and the mixture was stirred for 3 h. EtONa (400 mg, 5.88 mmol, 4 eq) was added to the mixture and stirred at 80° C. for 16 h. The mixture was concentrated, water (50 mL) was added. The solution was acidified to pH=3 with 1N HCl and a solid precipitated out. The solid was collected by filtration. The crude (320 mg, 998.08 umol, 67.92% yield) was used without further purification in the next step.

LCMS-ESI (m/z) calculated: 282.14; found 283.1 [M+H]$^+$, RT=0.873 min (Method 1).

Synthesis of 4-chloro-2,6-bis(trifluoromethyl)quinazoline

A mixture of 2,6-bis(trifluoromethyl)quinazolin-4-ol (320 mg, 1.13 mmol, 1 eq), POCl3 (1.74 g, 11.34 mmol, 1.05 mL, 10 eq) in ACN (3 mL) was stirred at 80° C. for 2 h. The mixture was cooled to 20° C., quenched with water (20 mL), extracted with EtOAc (3×30 mL). The combined organic layers were concentrated and the crude (280 mg, 899.84 umol, 79.34% yield) used as is in the next step.

Synthesis of 4-fluoro-N-[(1S,4S)-4-{[2,6-bis(trifluoromethyl)quinazolin-4-yl]amino}cyclohexyl]benzamide A mixture of 4-chloro-2,6-bis(trifluoromethyl)quinazoline (100 mg, 332.68 umol, 1 eq), N-((1S,4S)-4-aminocyclohexyl)-4-fluorobenzamide (96.18 mg, 352.64 umol, 1.06 eq, HCl) and DIEA (128.70 mg, 995.81 umol, 173.45 uL, 2.99 eq) in NMP (1 mL) was stirred at 130° C. for 16 h. The mixture was cooled to 20° C. and filtered. The filtrate was purified by pre-HPLC (column: Waters Xbridge 150×25 mm×5 um; mobile phase: [water (10 mM NH4HCO3)-ACN]; B %: 50%-80%, 9 min) to afford 4-fluoro-N-[(1s,4s)-4-{[2,6-bis(trifluoromethyl)quinazolin-4-yl]amino}cyclohexyl]benzamide (45 mg, 89.93 umol, 27.03% yield).

LCMS-ESI (m/z) calculated: 500.41; found 501.3 [M+H]$^+$, Rt=1.048 min (Method 1).

$^1$H NMR (400 MHz, CHLOROFORM-d) δ=8.14-8.08 (m, 2H), 8.06-8.01 (m, 1H), 7.87-7.79 (m, 2H), 7.18 (br s, 1H), 6.20-6.09 (m, 2H), 4.59-4.51 (m, 1H), 4.30-4.22 (m, 1H), 2.13-2.00 (m, 1H), 2.15-2.00 (m, 3H), 1.99-1.85 (m, 4H).

The compounds listed in Table 2 were made using the procedures for Example 3A:

TABLE 2

| Structure | Cpd No. | Purity RT | MW | m/z | Ion | Purity Method |
|---|---|---|---|---|---|---|
| 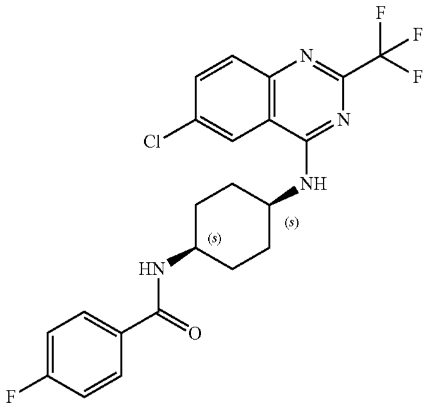 [SMILES: O=C(N[C@H]1CC[C@@H](Nc2nc(C(F)(F)F)nc3ccc(Cl)cc23)CC1)c1ccc(F)cc1] | 2-1 | 1.029 | 466.86 | 467.3 | [M + H]+ | Method 1 |
| 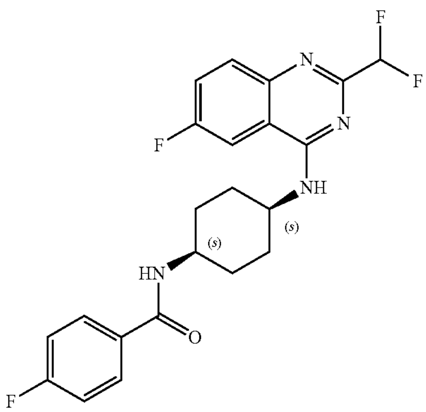 [SMILES: O=C(N[C@H]1CC[C@@H](Nc2nc(C(F)F)nc3ccc(F)cc23)CC1)c1ccc(F)cc1] | 2-2 | 0.916 | 432.423 | 432.9 | [M + H]+ | Method 2 |

Example 4

Scheme 4

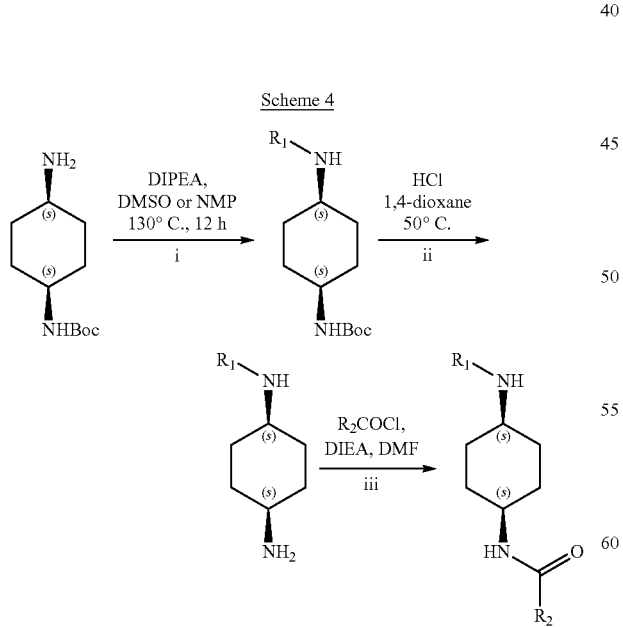

Reagents: i. DIPEA, solvent (DMSO, NMP), heat; ii. HCl, solvent (1,4-dioxane), heat; iii. R₂COCl, base (DIEA), solvent (DMF)

Example 4A

N-((1S,4S)-4-((6-chloro-2-(trifluoromethyl)quinolin-4-yl)amino) cyclohexyl) benzamide

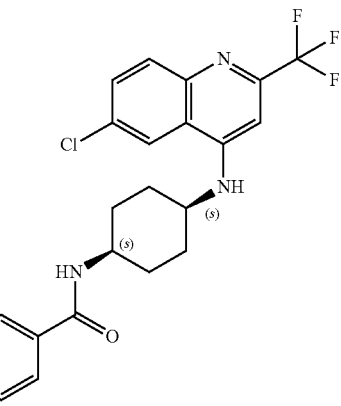

Synthesis of 6-chloro-2-(trifluoromethyl)quinolin-4-ol

The mixture of 4-chloroaniline (10 g, 78.39 mmol, 1 eq) and ethyl 4,4,4-trifluoro-3-oxo-butanoate (17.32 g, 94.06 mmol, 13.74 mL, 1.2 eq) in PPA (100 mL) was stirred at 130° C. for 2 h. The reaction mixture was poured into water (500 mL) slowly. The white precipitate was filtered to give 6-chloro-2-(trifluoromethyl)quinolin-4-ol (16 g, 64.62 mmol, 82.44% yield).

$^1$H NMR (400 MHz, DMSO-d6) δ=13.37-11.29 (br s, 1H), 8.15 (br s, 1H), 8.01 (br d, J=5.0 Hz, 1H), 7.84 (dd, J=2.1, 9.0 Hz, 1H), 7.32-6.94 (s, 1H).

Synthesis of 4,6-dichloro-2-(trifluoromethyl)quinoline

To a mixture of 6-chloro-2-(trifluoromethyl)quinolin-4-ol (16 g, 64.62 mmol, 1 eq) was added POCl3 (188.26 g, 1.23 mol, 114.10 mL, 19 eq) in portions at 20° C. under N2. The mixture was stirred at 90° C. for 2 hours. The reaction mixture was concentrated. The residue was poured into water (500 mL) dropwise then extracted with EtOAc (3×100 mL). The combined organic layers were dried over Na2SO4, filtered and concentrated under reduced pressure to give 4,6-dichloro-2-(trifluoromethyl)quinoline (17 g, 63.90 mmol, 98.88% yield). It was used as is in the next step.

$^1$H NMR (400 MHz, DMSO-d6) δ=8.34 (s, 1H), 8.28 (d, J=2.2 Hz, 1H), 8.25 (d, J=9.0 Hz, 1H), 8.03 (dd, J=2.3, 9.0 Hz, 1H).

Synthesis of tert-butyl ((1S,4S)-4-((6-chloro-2-(trifluoromethyl)quinolin-4-yl)amino)cyclohexyl) carbamate To a mixture of 4,6-dichloro-2-(trifluoromethyl)quinoline (6.9 g, 25.94 mmol, 1 eq) and tert-butyl cis-N-(4-aminocyclohexyl)carbamate (6.11 g, 28.53 mmol, 1.1 eq) in DMSO (50 mL) was added DIPEA (6.70 g, 51.87 mmol, 9.03 mL, 2 eq) in one portion at 20° C. The mixture was stirred at 130° C. for 16 hours then quenched with water (100 mL) at rt. The crude was diluted with water (200 mL) and extracted with EtOAc (3×100 mL). The combined organic layers were washed with brine (3×100 mL), dried over Na2SO4, filtered and concentrated under reduced pressure to give tert-butyl N-[4-[[6-chloro-2-(trifluoromethyl)-4-quinolyl]amino]cyclohexyl]carbamate (13.68 g, crude). It was used without further purification in the next step.

LCMS-ESI (m/z) calculated: 443.9; found 446.4 [M+H]$^+$, Rt=1.031 min (Method 1).

Synthesis of (1S,4S)—N1-[6-chloro-2-(trifluoromethyl)-4-quinolyl]cyclohexane-1,4-diamine·HCl To tert-butyl tert-butyl N-[4-[[6-chloro-2-(trifluoromethyl)-4-quinolyl]amino]cyclohexyl]carbamate (13.68 g, 30.82 mmol, 1 eq) was added HCl/dioxane (50 mL) in one portion at 20° C. The mixture was stirred at 20° C. for 30 mins then concentrated under reduced pressure to give a residue. The crude product was triturated with EtOAC (100 mL) at 25° C. for 30 min, filtered. The filtrate was concentrated under reduced pressure to yield N4-[6-chloro-2-(trifluoromethyl)-4-quinolyl]cyclohexane-1,4-diamine (9 g, 25.89 mmol, 84.01% yield).

LCMS-ESI (m/z) calculated: 343.9; found 344.2 [M+H]$^+$, Rt=0.755 min (Method 1)

$^1$H NMR (400 MHz, DMSO-d6) δ=8.73-8.67 (m, 1H), 8.10-7.99 (m, 2H), 7.97-7.89 (m, 1H), 7.81-7.74 (m, 1H), 7.36 (br d, J=5.1 Hz, 1H), 6.83-6.78 (m, 1H), 3.93-3.86 (m, 1H), 3.24-3.16 (m, 1H), 2.03-1.94 (m, 2H), 1.85-1.72 (m, 6H).

Synthesis of N-((1S,4S)-4-((6-chloro-2-(trifluoromethyl)quinolin-4-yl)amino)cyclohexyl) benzamide To a stirred solution of (1S,4S)—N1-(6-chloro-2-(trifluoromethyl)quinolin-4-yl)cyclohexane-1,3-diamine hydrochloride (75 mg, 1 Eq, 0.20 mmol) in DMF (2 mL) was added DIPEA (0.10 g, 0.14 mL, 4 Eq, 0.79 mmol), followed by benzoyl chloride (29 mg, 24 µL, 1.05 Eq, 0.21 mmol). The resulting mixture was stirred at room temperature overnight. The reaction mixture was filtered and the filtrate was directly purified by prep HPLC (ISCO ACCQPrep 150) to afford N-((1S,4S)-4-((6-chloro-2-(trifluoromethyl)quinolin-4-yl)amino)cyclohexyl)benzamide (34 mg, 76 µmol, 38%).

$^1$H NMR (400 MHz, DMSO-d$_6$) δ 8.66 (s, 1H), 8.16 (d, J=6.3 Hz, 1H), 7.95-7.84 (m, 3H), 7.76 (d, J=9.1 Hz, 1H), 7.55-7.43 (m, 3H), 7.36 (d, J=6.2 Hz, 1H), 6.83 (s, 1H), 4.01-3.93 (m, 1H), 3.88-3.80 (m, 1H), 2.02-1.88 (m, 4H), 1.83-1.68 (m, 4H).

Example 4B 4-cyano-N-((1S,4S)-4-((2-(trifluoromethyl)quinolin-4-yl)amino)cyclohexyl) benzamide

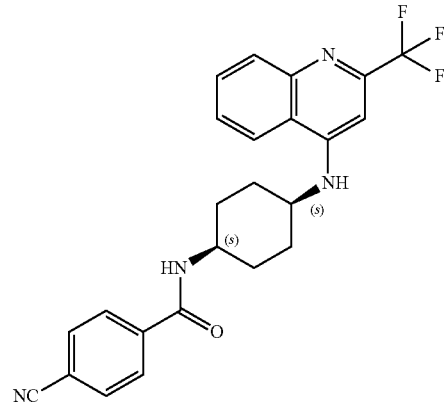 [SMILES: N#Cc1ccc(C(=O)N[C@H]2CC[C@@H](Nc3cc(C(F)(F)F)nc4ccccc34)CC2)cc1]

Synthesis of tert-butyl ((1S,4S)-4-((2-(trifluoromethyl)quinolin-4-yl)amino)cyclohexyl)carbamate To a solution of 4-chloro-2-(trifluoromethyl)quinoline (1.00 g, 1 Eq, 4.32 mmol) and tert-butyl ((1S,4S)-4-aminocyclohexyl)carbamate (925 mg, 1 Eq, 4.32 mmol) in DMSO (12 mL) was added DIPEA (2.23 g, 3.0 mL, 4 Eq, 17.3 mmol). The solution was stirred at 130° C. After stirring for 20 hours, the reaction mixture was cooled to room temperature, diluted with water and extracted with EtOAc (3×20 mL). The organic layers were combined, washed with brine and concentrated under reduced pressure. The residue was purified by flash column chromatography (ISCO Gold 80 g, 0-80% EtOAc/hexanes, 11 CV ramp, EtOAc/hexanes) to yield tert-butyl ((1S,4S)-4-((2-(trifluoromethyl)quinolin-4-yl)amino)cyclohexyl)carbamate (1.079 g, 2.635 mmol, 61.0%). The product was used as is in the next step without further purification.

LCMS-ESI (m/z) calculated: 409.45; found 410.2 [M+H]$^+$, Rt=5.275 min (Method 6).

Synthesis of (1S,4S)—N1-(2-(trifluoromethyl)quinolin-4-yl)cyclohexane-1,3-diamine hydrochloride To a solution of tert-butyl ((1S,4S)-4-((2-(trifluoromethyl)quinolin-4-yl)amino)cyclohexyl) carbamate (1.079 g, 1 Eq, 2.635 mmol) in 1,4-Dioxane (15 mL) was added 4M hydrogen chloride in 1,4-dioxane (960.8 mg, 6.588 mL, 4.00 molar, 10 Eq, 26.35 mmol). The resulting mixture was stirred at room temperature. After stirring for 20 hrs, the reaction mixture was filtered, and the filter cake was washed with diethyl ether and dried under high vacuum to yield (1S,4S)—N1-(2-(trifluoromethyl)quinolin-4-yl)cyclohexane-1,4-diamine hydrochloride.

LCMS-ESI (m/z) calculated: 309.45; found 310.2 [M+H]$^+$, Rt=2.794 min (Method 6)

Synthesis of 4-cyano-N-((1S,4S)-4-((2-(trifluoromethyl)quinolin-4-yl)amino) cyclohexyl) benzamide To a solution of (1S,4S)—N1-(2-(trifluoromethyl)quinolin-4-yl)cyclohexane-1,3-diamine hydrochloride (50 mg, 1 Eq, 0.14 mmol) in DMF (2 mL) was added DIPEA (75 mg, 0.10 mL, 4 Eq, 0.58 mmol), followed by 4-cyanobenzoyl chloride (24 mg, 1 Eq, 0.14 mmol). The resulting mixture was stirred at room temperature for 1 hour. The reaction mixture was filtered and the filtrate purified by prep HPLC (ISCO ACCQPrep 150) to yield 4-cyano-N-((1S,4S)-4-((2-(trifluoromethyl)quinolin-4-yl)amino)cyclohexyl) benzamide (35.3 mg, 80.5 μmol, 56% yield).

LCMS-ESI (m/z) calculated: 438.45; found 439.2 $[M+H]^+$, Rt=7.958 min (Method 3)

$^1$H NMR (400 MHz, DMSO-$d_6$) δ 8.53-8.35 (m, 2H), 8.03 (d, J=8.1 Hz, 2H), 7.97 (d, J=8.1 Hz, 2H), 7.90 (d, J=8.4 Hz, 1H), 7.75 (t, J=7.6 Hz, 1H), 7.58 (t, J=7.6 Hz, 1H), 7.21 (d, J=6.4 Hz, 1H), 6.80 (s, 1H), 4.04-3.93 (m, 1H), 3.89-3.78 (m, 1H), 2.03-1.88 (m, 4H), 1.86-1.68 (m, 4H).

Example 4C 4-methoxy-N-((1S,4S)-4-((2-(trifluoromethyl)quinolin-4-yl)amino)cyclohexyl) benzamide

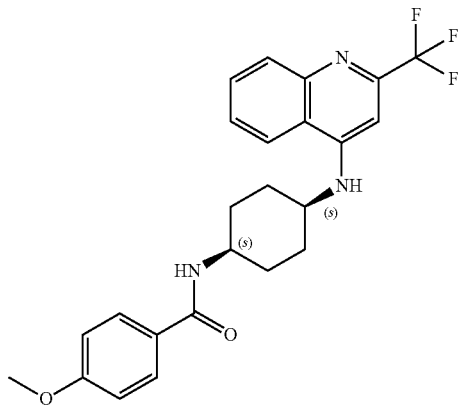 [SMILES: COc1ccc(C(=O)N[C@H]2CC[C@@H](Nc3cc(C(F)(F)F)nc4ccccc34)CC2)cc1]

Synthesis of 4-methoxy-N-((1S,4S)-4-((2-(trifluoromethyl)quinolin-4-yl)amino)cyclohexyl) benzamide To a solution of (1S,4S)—N1-(2-(trifluoromethyl)quinolin-4-yl)cyclohexane-1,3-diamine hydrochloride (50 mg, 1 Eq, 0.14 mmol) in DMF (2 mL) was added with DIPEA (75 mg, 0.10 mL, 4 Eq, 0.58 mmol), followed by 4-methoxybenzoyl chloride (25 mg, 20 μL, 1 Eq, 0.14 mmol). The resulting mixture was stirred at room temperature. After stirring for 1 hour, the reaction mixture was filtered, and the filtrate purified by prep HPLC (ISCO ACCQPrep 150) to yield 4-methoxy-N-((1S,4S)-4-((2-(trifluoromethyl)quinolin-4-yl)amino) cyclohexyl)benzamide (37.6 mg, 84.8 μmol, 59% yield).

LCMS-ESI (m/z) calculated: 443.47; found 444.2 $[M+H]^+$, Rt=7.961 min (Method 3)

$^1$H NMR (400 MHz, DMSO-$d_6$) δ 8.46 (d, J=8.5 Hz, 1H), 7.95 (d, J=6.4 Hz, 1H), 7.92-7.82 (m, 3H), 7.75 (t, J=7.6 Hz, 1H), 7.58 (t, J=7.6 Hz, 1H), 7.19 (d, J=6.4 Hz, 1H), 7.03-6.94 (m, 2H), 6.79 (s, 1H), 4.00-3.92 (m, 1H), 3.89-3.82 (m, 1H), 3.81 (s, 3H), 2.01-1.87 (m, 4H), 1.82-1.66 (m, 4H).

The compounds listed in Table 3 were prepared using the procedures for Example 4A:

TABLE 3

| Structure | Cpd No. | Purity RT | MW | m/z | Ion | Purity Method |
|---|---|---|---|---|---|---|
| 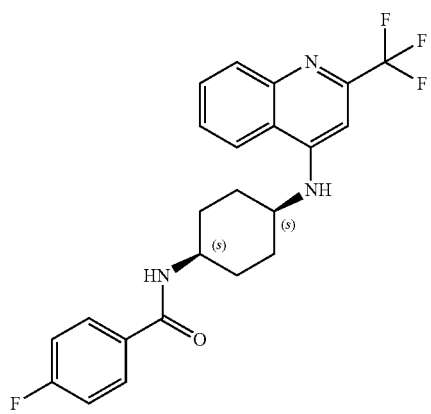 [SMILES: O=C(N[C@H]1CC[C@@H](Nc2cc(C(F)(F)F)nc3ccccc23)CC1)c1ccc(F)cc1] | 3-1 | 0.797 | 431.435 | 432.2 | $[M + H]^+$ | Method 1 |

TABLE 3-continued

| Structure | Cpd No. | Purity RT | MW | m/z | Ion | Purity Method |
|---|---|---|---|---|---|---|
| 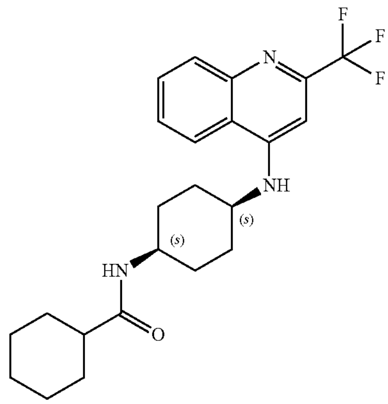 [SMILES: O=C(N[C@H]1CC[C@@H](Nc2cc(C(F)(F)F)nc3ccccc23)CC1)C1CCCCC1] | 3-2 | 0.891 | 419.492 | 420.2 | [M + H]⁺ | Method 2 |
| 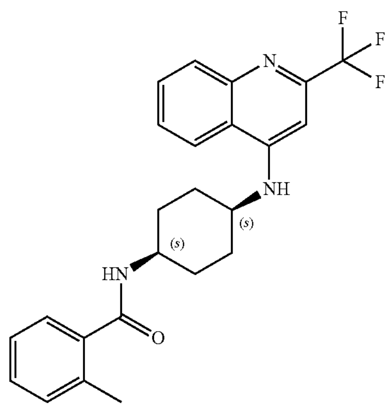 [SMILES: Cc1ccccc1C(=O)N[C@H]1CC[C@@H](Nc2cc(C(F)(F)F)nc3ccccc23)CC1] | 3-3 | 0.866 | 427.471 | 428.2 | [M + H]⁺ | Method 2 |
| 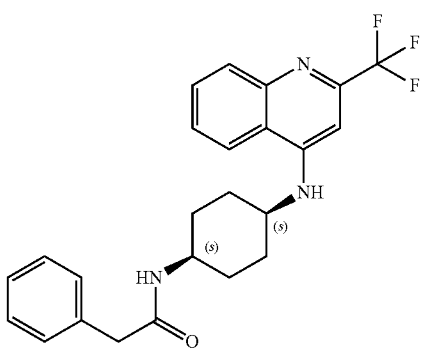 [SMILES: O=C(Cc1ccccc1)N[C@H]1CC[C@@H](Nc2cc(C(F)(F)F)nc3ccccc23)CC1] | 3-4 | 0.879 | 427.471 | 428.2 | [M + H]⁺ | Method 2 |
| 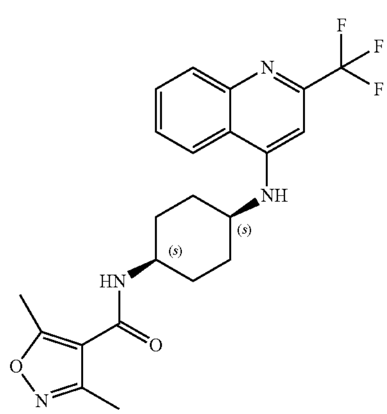 [SMILES: Cc1noc(C)c1C(=O)N[C@H]1CC[C@@H](Nc2cc(C(F)(F)F)nc3ccccc23)CC1] | 3-5 | 0.827 | 432.447 | 433.3 | [M + H]⁺ | Method 2 |

TABLE 3-continued

| Structure | Cpd No. | Purity RT | MW | m/z | Ion | Purity Method |
|---|---|---|---|---|---|---|
| 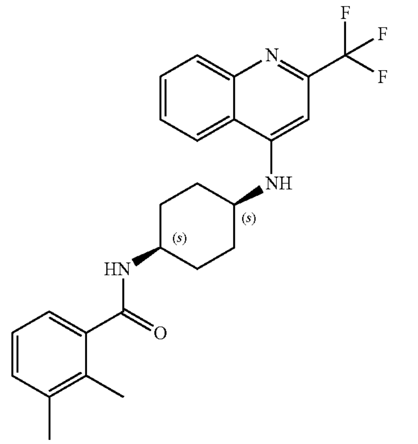 [SMILES: Cc1cccc(C(=O)N[C@H]2CC[C@@H](Nc3cc(C(F)(F)F)nc4ccccc34)CC2)c1C] | 3-6 | 0.897 | 441.498 | 442.2 | [M + H]⁺ | Method 2 |
| 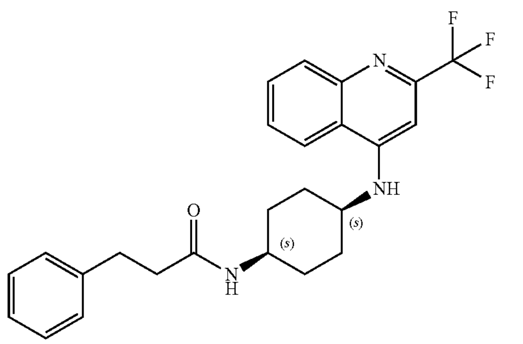 [SMILES: O=C(CCc1ccccc1)N[C@H]1CC[C@@H](Nc2cc(C(F)(F)F)nc3ccccc23)CC1] | 3-7 | 0.882 | 441.498 | 442.2 | [M + H]⁺ | Method 2 |
| 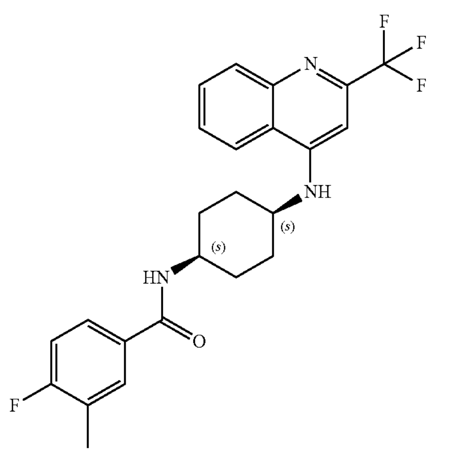 [SMILES: Cc1cc(C(=O)N[C@H]2CC[C@@H](Nc3cc(C(F)(F)F)nc4ccccc34)CC2)ccc1F] | 3-8 | 0.914 | 445.462 | 446.2 | [M + H]⁺ | Method 2 |
| 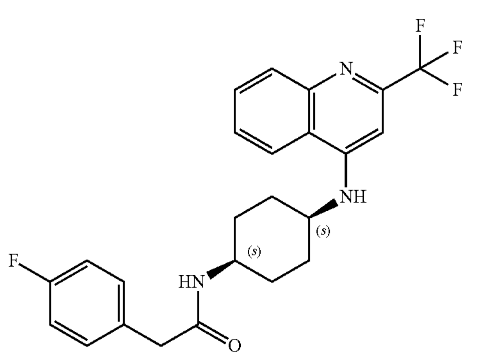 [SMILES: O=C(Cc1ccc(F)cc1)N[C@H]1CC[C@@H](Nc2cc(C(F)(F)F)nc3ccccc23)CC1] | 3-9 | 0.781 | 445.462 | 446.1 | [M + H]⁺ | Method 2 |

TABLE 3-continued

| Structure | Cpd No. | Purity RT | MW | m/z | Ion | Purity Method |
|---|---|---|---|---|---|---|
| 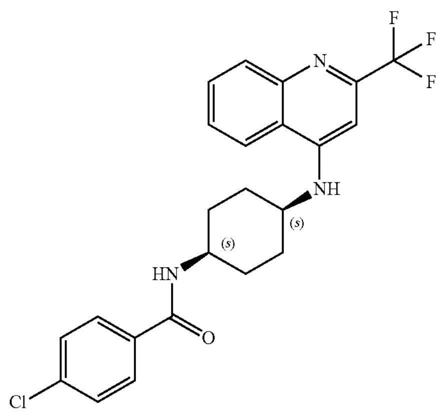 [SMILES: O=C(N[C@H]1CC[C@@H](Nc2cc(C(F)(F)F)nc3ccccc23)CC1)c1ccc(Cl)cc1] | 3-10 | 0.916 | 447.89 | 448.1 | [M + H]⁺ | Method 2 |
| 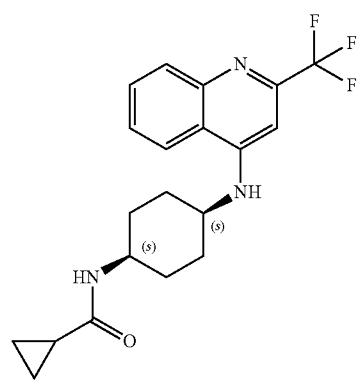 [SMILES: O=C(N[C@H]1CC[C@@H](Nc2cc(C(F)(F)F)nc3ccccc23)CC1)C1CC1] | 3-11 | 0.693 | 377.411 | 378.1 | [M + H]⁺ | Method 2 |
| 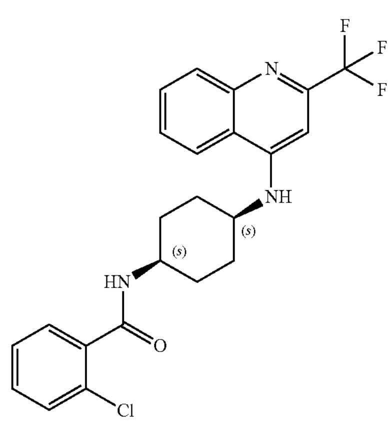 [SMILES: O=C(N[C@H]1CC[C@@H](Nc2cc(C(F)(F)F)nc3ccccc23)CC1)c1ccccc1Cl] | 3-12 | 0.889 | 447.89 | 448.2 | [M + H]⁺ | Method 2 |

TABLE 3-continued
| Structure | Cpd No. | Purity RT | MW | m/z | Ion | Purity Method |
|---|---|---|---|---|---|---|
| 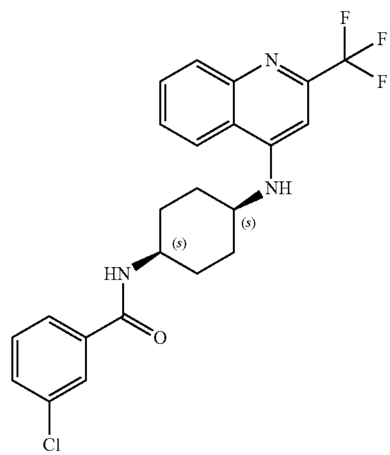 [SMILES: O=C(N[C@H]1CC[C@@H](Nc2cc(C(F)(F)F)nc3ccccc23)CC1)c1cccc(Cl)c1] | 3-13 | 0.935 | 447.89 | 448.2 | [M + H]+ | Method 2 |
| 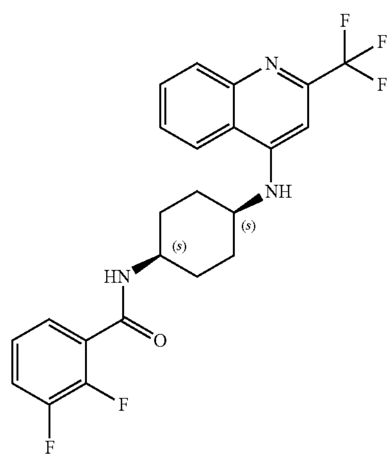 [SMILES: O=C(N[C@H]1CC[C@@H](Nc2cc(C(F)(F)F)nc3ccccc23)CC1)c1cccc(F)c1F] | 3-14 | 0.804 | 449.425 | 450.1 | [M + H]+ | Method 2 |
| 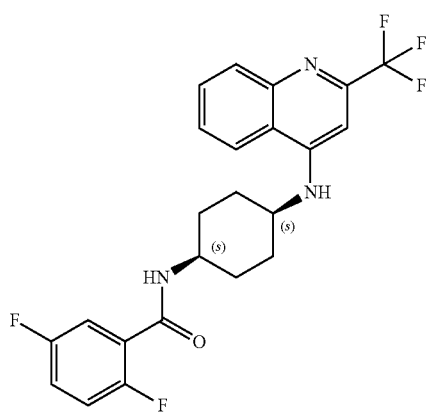 [SMILES: O=C(N[C@H]1CC[C@@H](Nc2cc(C(F)(F)F)nc3ccccc23)CC1)c1cc(F)ccc1F] | 3-15 | 0.803 | 449.425 | 450.1 | [M + H]+ | Method 2 |

TABLE 3-continued
| Structure | Cpd No. | Purity RT | MW | m/z | Ion | Purity Method |
|---|---|---|---|---|---|---|
| 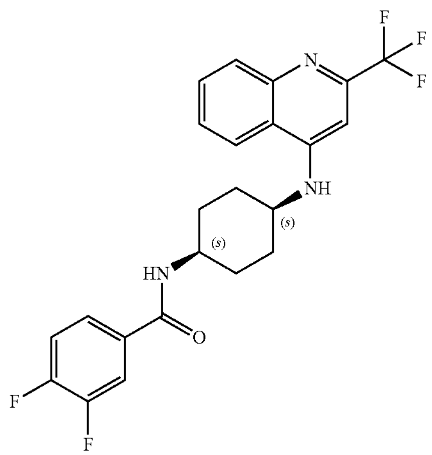 [SMILES: O=C(N[C@H]1CC[C@@H](Nc2cc(C(F)(F)F)nc3ccccc23)CC1)c1ccc(F)c(F)c1] | 3-16 | 0.811 | 449.425 | 450.1 | [M + H]+ | Method 2 |
| 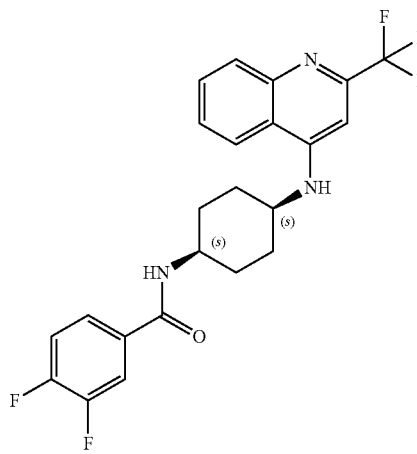 | | | | | | |
| 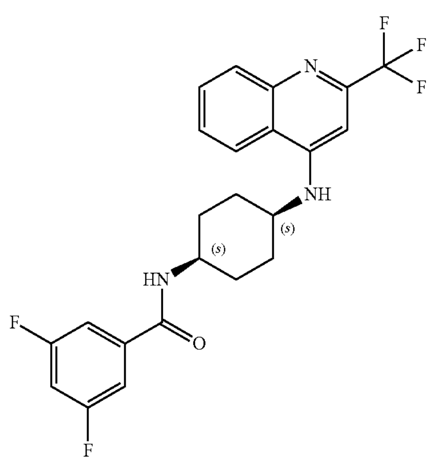 [SMILES: O=C(N[C@H]1CC[C@@H](Nc2cc(C(F)(F)F)nc3ccccc23)CC1)c1cc(F)cc(F)c1] | 3-17 | 0.819 | 449.425 | 450.1 | [M + H]+ | Method 2 |
| 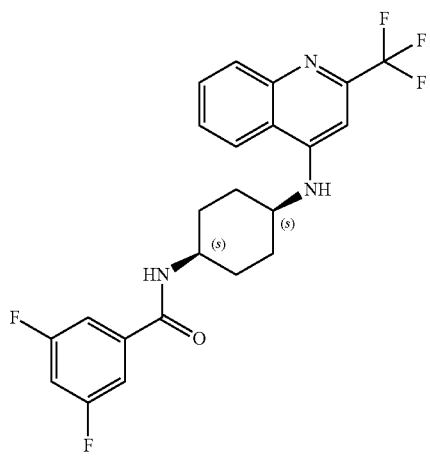 | | | | | | |
| 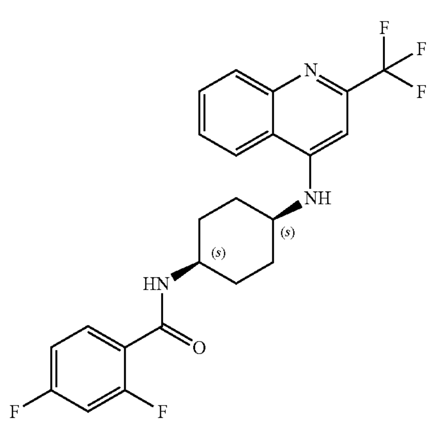 [SMILES: O=C(N[C@H]1CC[C@@H](Nc2cc(C(F)(F)F)nc3ccccc23)CC1)c1ccc(F)cc1F] | 3-18 | 0.911 | 449.425 | 450.2 | [M + H]+ | Method 2 |
| 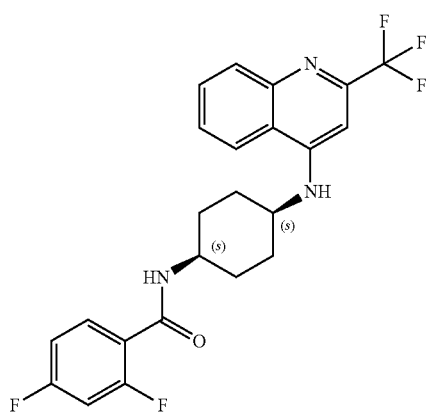 | | | | | | |

TABLE 3-continued

| Structure | Cpd No. | Purity RT | MW | m/z | Ion | Purity Method |
|---|---|---|---|---|---|---|
| 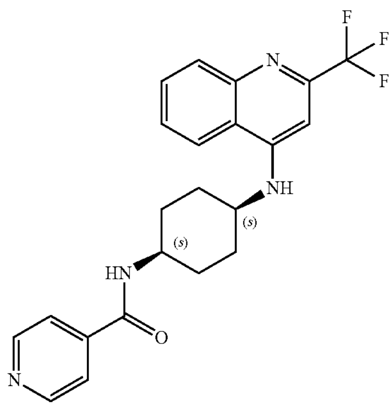 [SMILES: O=C(N[C@H]1CC[C@@H](Nc2cc(C(F)(F)F)nc3ccccc23)CC1)c1ccncc1] | 3-19 | 0.74 | 414.432 | 415.2 | [M + H]⁺ | Method 2 |
| 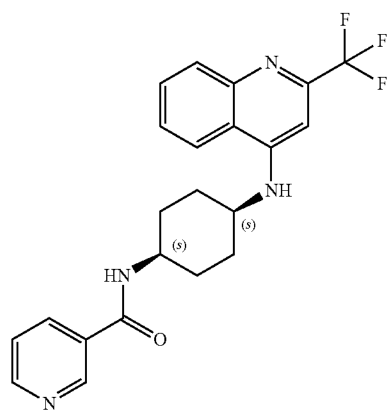 [SMILES: O=C(N[C@H]1CC[C@@H](Nc2cc(C(F)(F)F)nc3ccccc23)CC1)c1cccnc1] | 3-20 | 0.746 | 414.432 | 415.2 | [M + H]⁺ | Method 2 |
| 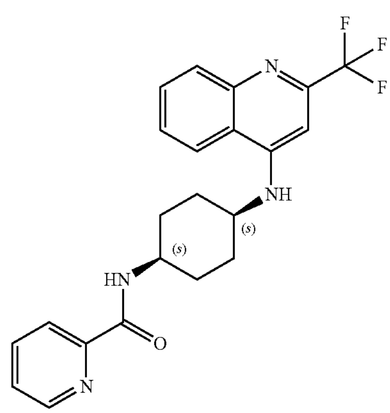 [SMILES: O=C(N[C@H]1CC[C@@H](Nc2cc(C(F)(F)F)nc3ccccc23)CC1)c1ccccn1] | 3-21 | 0.756 | 414.432 | 415.1 | [M + H]⁺ | Method 2 |

TABLE 3-continued

| Structure | Cpd No. | Purity RT | MW | m/z | Ion | Purity Method |
|---|---|---|---|---|---|---|
| 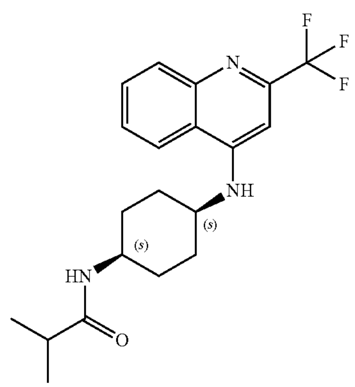 [SMILES: CC(C)C(=O)N[C@H]1CC[C@@H](Nc2cc(C(F)(F)F)nc3ccccc23)CC1] | 3-22 | 0.704 | 379.427 | 380.1 | [M + H]+ | Method 2 |
| 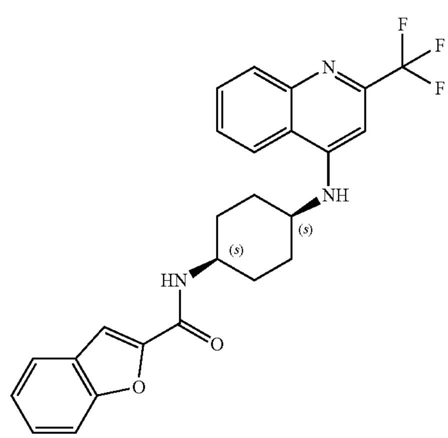 [SMILES: O=C(N[C@H]1CC[C@@H](Nc2cc(C(F)(F)F)nc3ccccc23)CC1)c1cc2ccccc2o1] | 3-23 | 0.925 | 453.465 | 454.2 | [M + H]+ | Method 2 |
| 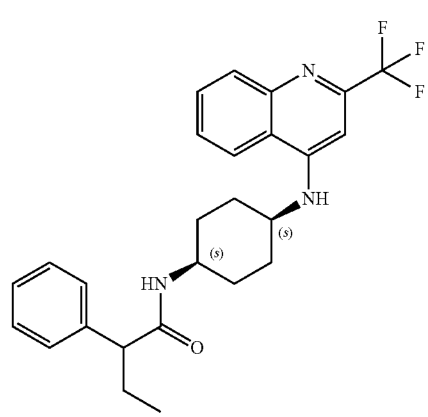 [SMILES: CCC(C(=O)N[C@H]1CC[C@@H](Nc2cc(C(F)(F)F)nc3ccccc23)CC1)c1ccccc1] | 3-24 | 0.924 | 455.525 | 456.2 | [M + H]+ | Method 2 |

TABLE 3-continued
| Structure | Cpd No. | Purity RT | MW | m/z | Ion | Purity Method |
|---|---|---|---|---|---|---|
| 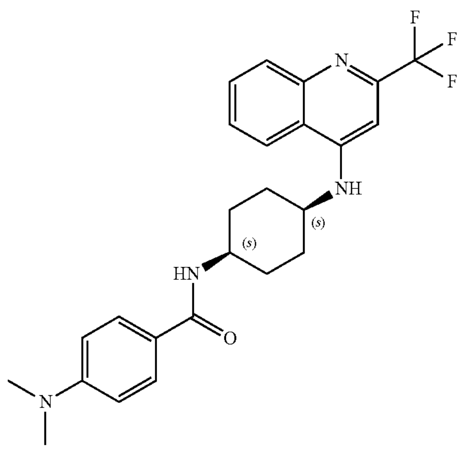 [SMILES: CN(C)c1ccc(C(=O)N[C@H]2CC[C@@H](Nc3cc(C(F)(F)F)nc4ccccc34)CC2)cc1] | 3-25 | 0.858 | 456.513 | 457.2 | [M + H]⁺ | Method 2 |
| 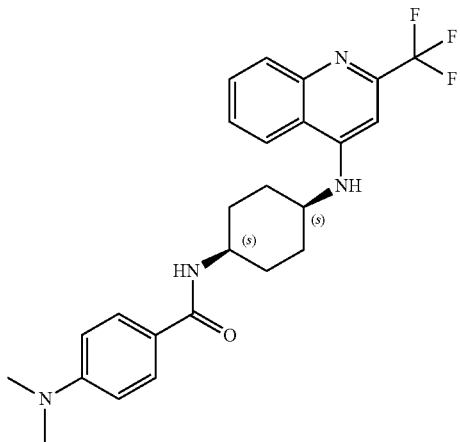 | | | | | | |
| 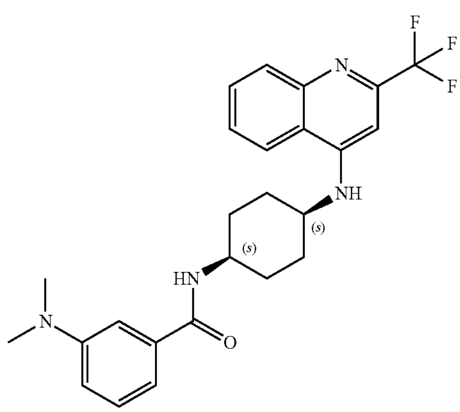 [SMILES: CN(C)c1cccc(C(=O)N[C@H]2CC[C@@H](Nc3cc(C(F)(F)F)nc4ccccc34)CC2)c1] | 3-26 | 0.806 | 456.513 | 457.2 | [M + H]⁺ | Method 2 |
| 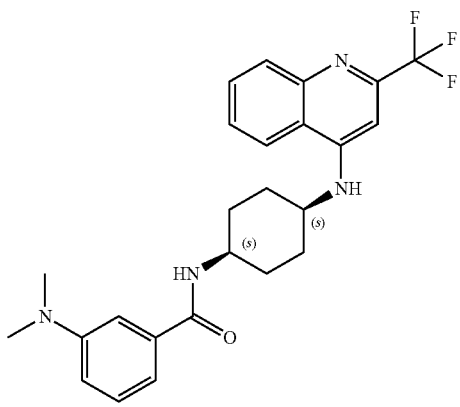 | | | | | | |
| 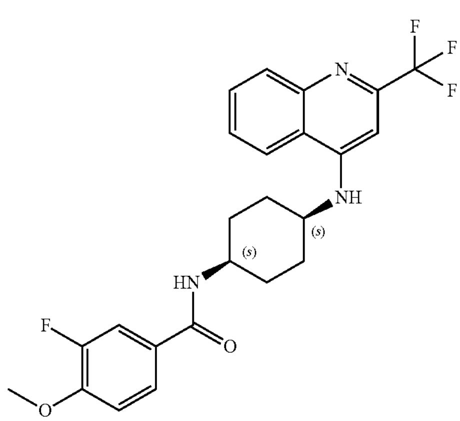 [SMILES: COc1ccc(C(=O)N[C@H]2CC[C@@H](Nc3cc(C(F)(F)F)nc4ccccc34)CC2)cc1F] | 3-27 | 0.894 | 461.461 | 462.2 | [M + H]⁺ | Method 2 |
| 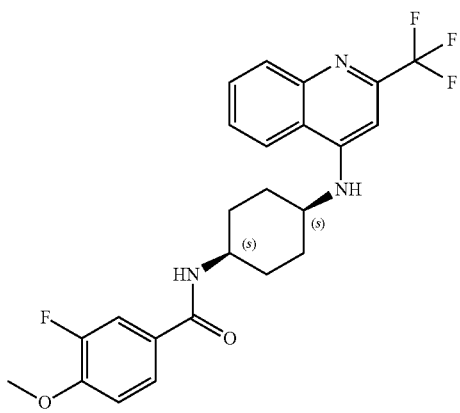 | | | | | | |

TABLE 3-continued

| Structure | Cpd No. | Purity RT | MW | m/z | Ion | Purity Method |
|---|---|---|---|---|---|---|
| 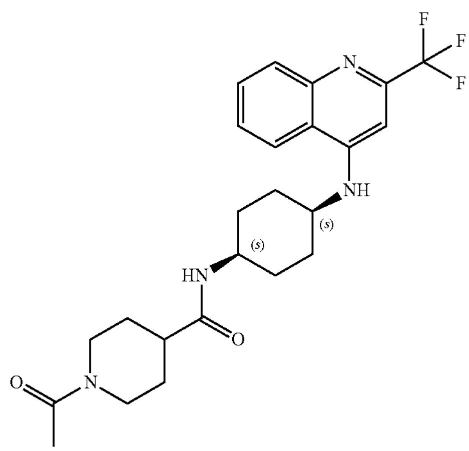 [SMILES: CC(=O)N1CCC(C(=O)N[C@H]2CC[C@@H](Nc3cc(C(F)(F)F)nc4ccccc34)CC2)CC1] | 3-28 | 0.765 | 462.517 | 463.2 | [M + H]⁺ | Method 2 |
| 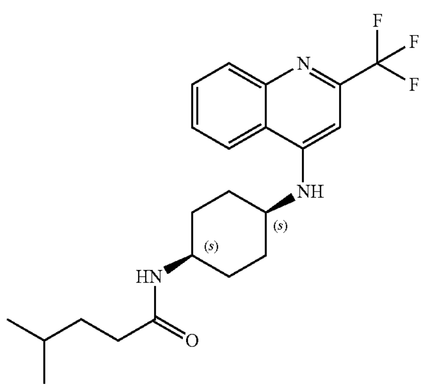 [SMILES: CC(C)CCC(=O)N[C@H]1CC[C@@H](Nc2cc(C(F)(F)F)nc3ccccc23)CC1] | 3-29 | 0.787 | 407.481 | 408.2 | [M + H]⁺ | Method 2 |
| 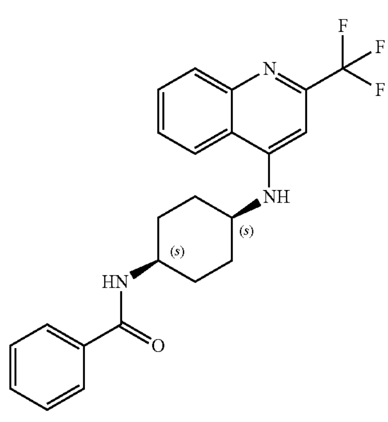 [SMILES: O=C(N[C@H]1CC[C@@H](Nc2cc(C(F)(F)F)nc3ccccc23)CC1)c1ccccc1] | 3-30 | 0.881 | 413.444 | 414.2 | [M + H]⁺ | Method 2 |

TABLE 3-continued

| Structure | Cpd No. | Purity RT | MW | m/z | Ion | Purity Method |
|---|---|---|---|---|---|---|
| 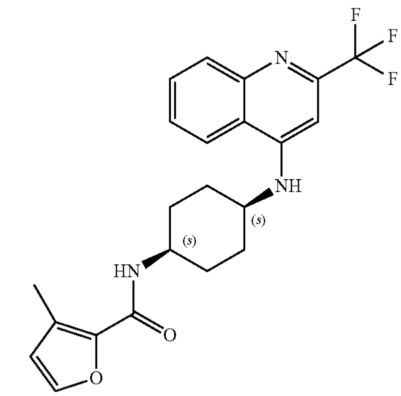 [SMILES: Cc1ccoc1C(=O)N[C@H]1CC[C@@H](Nc2cc(C(F)(F)F)nc3ccccc23)CC1] | 3-31 | 0.883 | 417.432 | 418 | [M + H]⁺ | Method 2 |
| 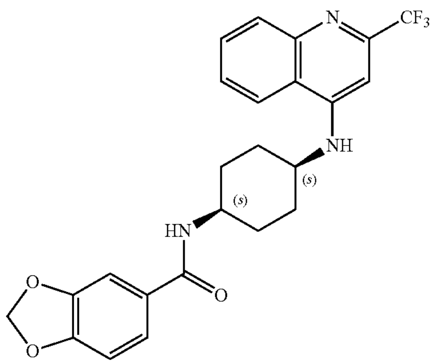 [SMILES: O=C(N[C@H]1CC[C@@H](Nc2cc(C(F)(F)F)nc3ccccc23)CC1)c1ccc2c(c1)OCO2] | 3-32 | 0.811 | 457.45 | 458.1 | [M + H]⁺ | Method 1 |
| 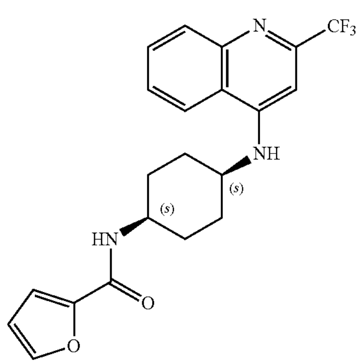 [SMILES: O=C(N[C@H]1CC[C@@H](Nc2cc(C(F)(F)F)nc3ccccc23)CC1)c1ccco1] | 3-33 | 0.775 | 403.41 | 404.1 | [M + H]⁺ | Method 1 |
| 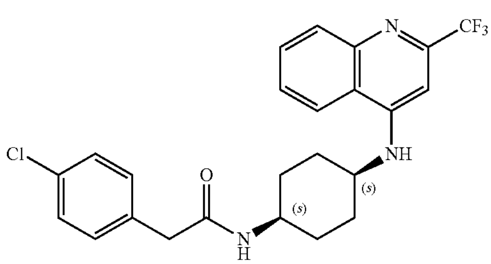 [SMILES: O=C(Cc1ccc(Cl)cc1)N[C@H]1CC[C@@H](Nc2cc(C(F)(F)F)nc3ccccc23)CC1] | 3-34 | 0.844 | 461.91 | 462.1 | [M + H]⁺ | Method 1 |

TABLE 3-continued

| Structure | Cpd No. | Purity RT | MW | m/z | Ion | Purity Method |
|---|---|---|---|---|---|---|
| 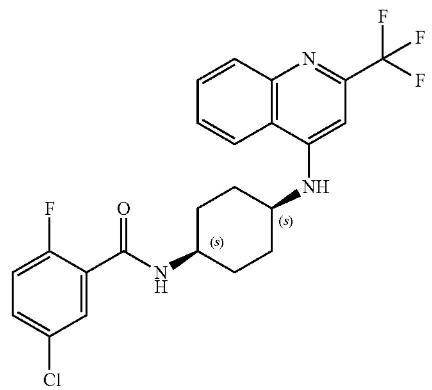 [SMILES: O=C(N[C@H]1CC[C@@H](Nc2cc(C(F)(F)F)nc3ccccc23)CC1)c1cc(Cl)ccc1F] | 3-35 | 0.851 | 465.88 | 466.1 | [M + H]⁺ | Method 1 |
| 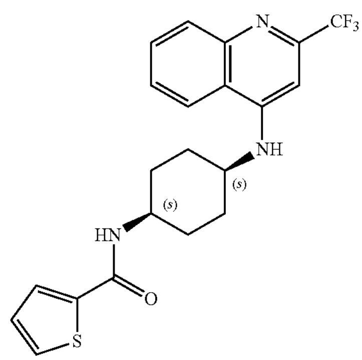 [SMILES: O=C(N[C@H]1CC[C@@H](Nc2cc(C(F)(F)F)nc3ccccc23)CC1)c1cccs1] | 3-36 | 0.799 | 419.47 | 420 | [M + H]⁺ | Method 1 |
| 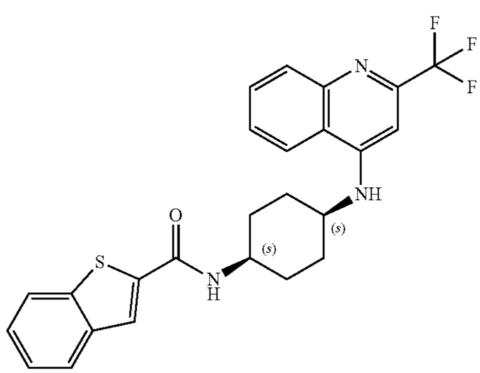 [SMILES: O=C(N[C@H]1CC[C@@H](Nc2cc(C(F)(F)F)nc3ccccc23)CC1)c1cc2ccccc2s1] | 3-37 | 0.873 | 469.53 | 470.1 | [M + H]⁺ | Method 1 |
| 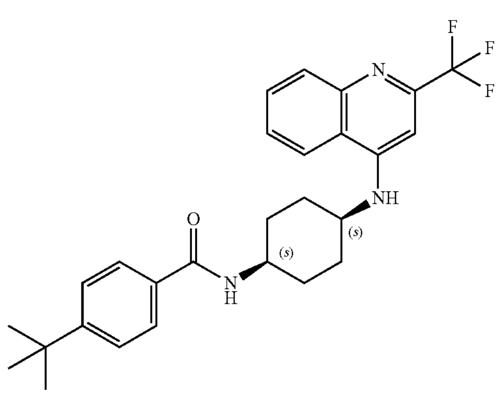 [SMILES: CC(C)(C)c1ccc(C(=O)N[C@H]2CC[C@@H](Nc3cc(C(F)(F)F)nc4ccccc34)CC2)cc1] | 3-38 | 0.895 | 469.55 | 470.2 | [M + H]⁺ | Method 1 |

TABLE 3-continued

| Structure | Cpd No. | Purity RT | MW | m/z | Ion | Purity Method |
|---|---|---|---|---|---|---|
| 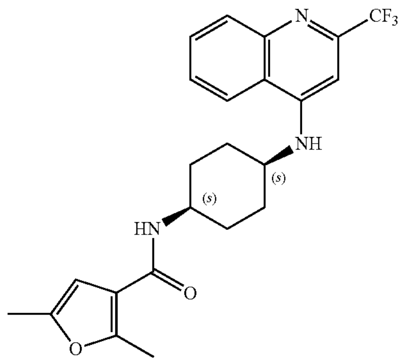 [SMILES: Cc1cc(C(=O)N[C@H]2CC[C@@H](Nc3cc(C(F)(F)F)nc4ccccc34)CC2)c(C)o1] | 3-39 | 0.825 | 431.46 | 432.1 | [M + H]⁺ | Method 1 |
| 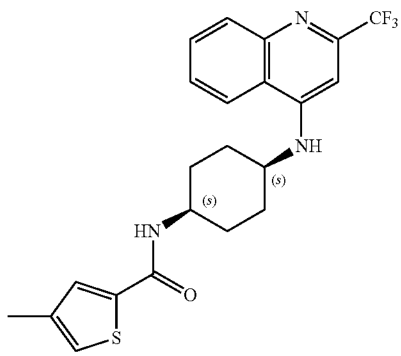 [SMILES: Cc1csc(C(=O)N[C@H]2CC[C@@H](Nc3cc(C(F)(F)F)nc4ccccc34)CC2)c1] | 3-40 | 0.829 | 433.49 | 434.1 | [M + H]⁺ | Method 1 |
| 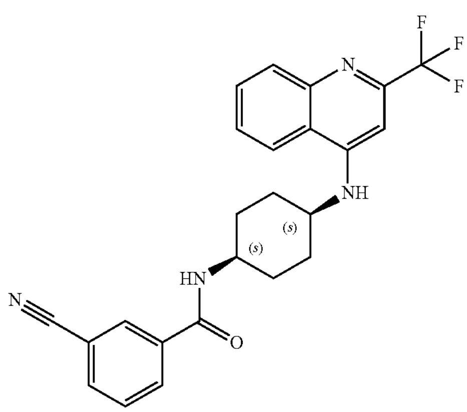 [SMILES: N#Cc1cccc(C(=O)N[C@H]2CC[C@@H](Nc3cc(C(F)(F)F)nc4ccccc34)CC2)c1] | 3-41 | 8.096 | 438.45 | 439.2 | [M + H]⁺ | Method 3 |
| 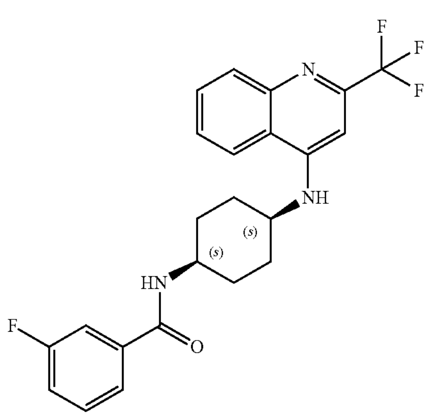 [SMILES: O=C(N[C@H]1CC[C@@H](Nc2cc(C(F)(F)F)nc3ccccc23)CC1)c1cccc(F)c1] | 3-42 | 8.432 | 431.44 | 432.2 | [M + H]⁺ | Method 3 |

TABLE 3-continued

| Structure | Cpd No. | Purity RT | MW | m/z | Ion | Purity Method |
|---|---|---|---|---|---|---|
| 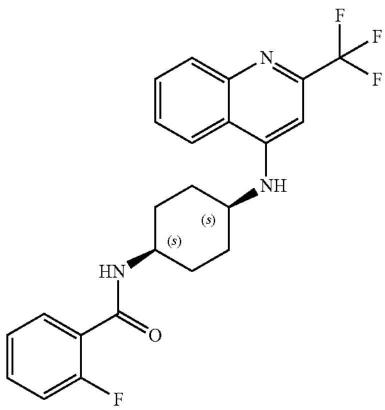 [SMILES: O=C(N[C@H]1CC[C@@H](Nc2cc(C(F)(F)F)nc3ccccc23)CC1)c1ccccc1F] | 3-43 | 8.294 | 431.44 | 432.2 | [M + H]+ | Method 3 |
| 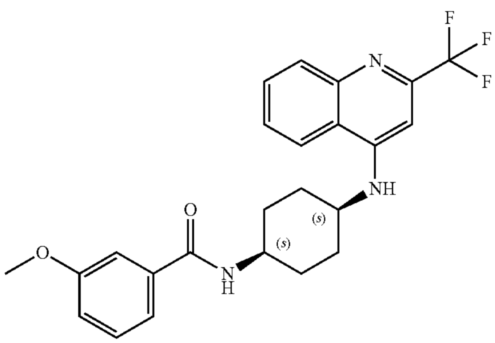 [SMILES: COc1cccc(C(=O)N[C@H]2CC[C@@H](Nc3cc(C(F)(F)F)nc4ccccc34)CC2)c1] | 3-44 | 8.250 | 443.47 | 444.2 | [M + H]+ | Method 3 |
| 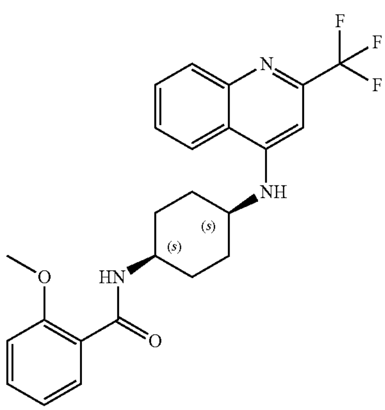 [SMILES: COc1ccccc1C(=O)N[C@H]1CC[C@@H](Nc2cc(C(F)(F)F)nc3ccccc23)CC1] | 3-45 | 8.449 | 443.47 | 444.2 | [M + H]+ | Method 3 |
| 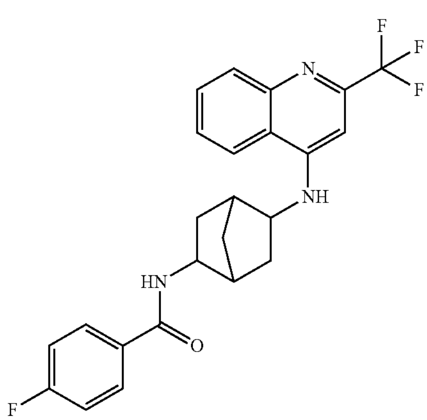 [SMILES: O=C(NC1CC2CC1CC2Nc1cc(C(F)(F)F)nc2ccccc12)c1ccc(F)cc1] | 3-46 | 8.802 | 443.45 | 444.2 | [M + H]+ | Method 3 |

Example 5

Scheme 5

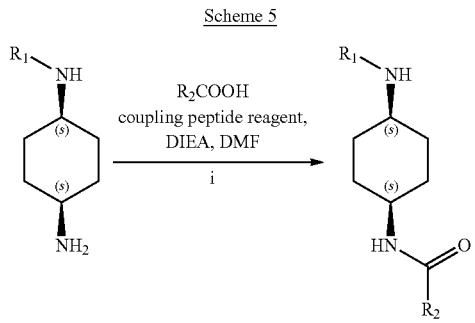

Reagents: i. R2COOH, Coupling peptide reagent (HATU), base (DIPEA), Solvent (DMF)

Example 5A

N-((1s,4s)-3-((6-chloro-2-(trifluoromethyl)quinolin-3-yl)amino)cyclohexyl)-3-(3-methylureido)benzamide

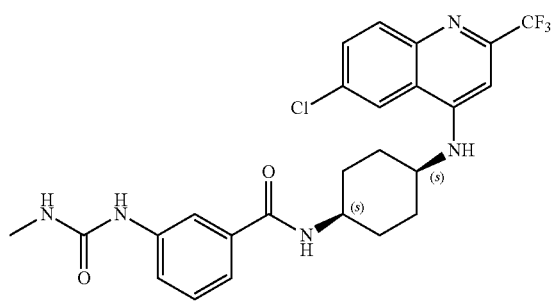 [SMILES: CNC(=O)Nc1cccc(C(=O)N[C@H]2CC[C@@H](Nc3cc(C(F)(F)F)nc4ccc(Cl)cc34)CC2)c1]

To a stirring solution of (1S,3R)—N1-(6-chloro-2-(trifluoromethyl)quinolin-3-yl)cyclohexane-1,3-diamine hydrochloride (30 mg, 1 Eq, 87 μmol) in DMF (1.5 mL) was added 3-(3-methylureido)benzoic acid (17 mg, 1 Eq, 87 μmol) HATU (36 mg, 1.1 Eq, 96 μmol) and N-ethyl-N-isopropylpropan-2-amine (DIPEA) (34 mg, 46 μL, 3 Eq, 0.26 mmol). The reaction mixture was stirred at room temperature overnight. The reaction mixture was filtered and purified by reversed phase prep HPLC (35→55% 0.1% formic acid in MeCN and 0.1% formic acid in H₂O) to afford N-((1S,4S)-3-((6-chloro-2-(trifluoromethyl)quinolin-3-yl)amino)cyclohexyl)-3-(3-methylureido) benzamide (24.7 mg, 47.5 μmol, 54%).

LCMS-ESI (m/z) calculated: 519.95; found 520.2 [M+H]$^+$, Rt=8.243 min (Method 3).

$^1$H NMR (400 MHz, DMSO-d6) δ 8.65 (d, J=10.5 Hz, 2H), 8.06 (d, J=7.2 Hz, 1H), 7.91 (d, J=7.9 Hz, 1H), 7.79-7.74 (m, 2H), 7.62 (d, J=8.5 Hz, 1H), 7.41-7.27 (m, 3H), 6.83 (s, 1H), 6.05-6.00 (m, 1H), 4.00-3.96 (m, 1H), 3.89-3.81 (m, 1H), 2.65 (app d, J=4.6 Hz, 3H), 1.82-1.67 (m, 4H).

Example 5B

N-((1S,4S)-3-((6-chloro-2-(trifluoromethyl)quinolin-3-yl)amino)cyclohexyl)-3-(methylsulfonamido)benzamide To a stirring solution of (1S,3R)—N1-(6-chloro-2-(trifluoromethyl)quinolin-3-yl)cyclohexane-1,3-diamine hydrochloride (30 mg, 1 Eq, 87 μmol) in DMF (1.5 mL) was added 3-(methylsulfonamido)benzoic acid (19 mg, 1 Eq, 87 μmol) HATU (36 mg, 1.1 Eq, 96 μmol) and N-ethyl-N-isopropylpropan-2-amine (DIPEA) (34 mg, 46 μL, 3 Eq, 0.26 mmol). The reaction mixture was stirred at room temperature overnight. The reaction mixture was filtered and purified by reversed phase prep HPLC (35→55% 0.1% formic acid in MeCN and 0.1% formic acid in H2O) to afford N-((1S,4S)-3-((6-chloro-2-(trifluoromethyl)quinolin-3-yl)amino)cyclohexyl)-3-(methylsulfonamido) benzamide (19.1 mg, 35.3 μmol, 40%).

LCMS-ESI (m/z) calculated: 540-99; found 541.1 [M+H]$^+$, Rt=8.941 min (Method 3)

$^1$H NMR (400 MHz, DMSO-d6) δ 9.87 (br s, 1H), 8.68 (s, 1H), 8.19 (d, J=7.4 Hz, 1H), 7.76 (d, J=9.1 Hz, 1H), 7.67 (s, 1H), 7.62 (d, J=7.4 Hz, 1H), 7.43 (t, J=7.8 Hz, 1H), 7.39-7.33 (m, 2H), 6.83 (s, 1H), 4.01-3.93 (m, 1H), 3.89-3.81 (m, 1H), 3.00 (s, 3H), 2.02-1.88 (m, 4H), 1.83-1.68 (m, 4H).

Compounds in Table 4 were prepared using procedures described for Example 5A.

TABLE 4

| Structure | Cpd No. | Purity RT | MW | m/z | Ion | Purity Method |
|---|---|---|---|---|---|---|
| 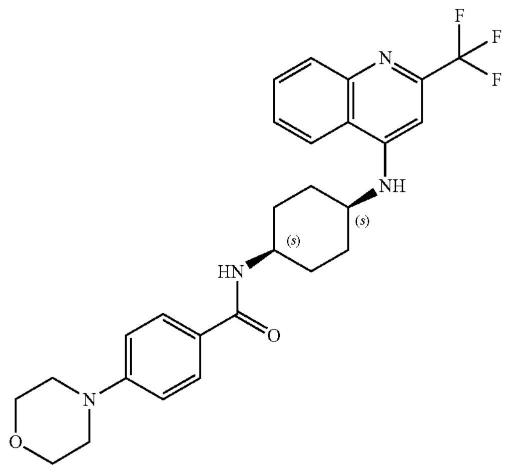 [SMILES: O=C(N[C@H]1CC[C@@H](Nc2cc(C(F)(F)F)nc3ccccc23)CC1)c1ccc(N2CCOCC2)cc1] | 4-1 | 0.829 | 498.55 | 499.2 | [M + H]⁺ | Method 1 |
| 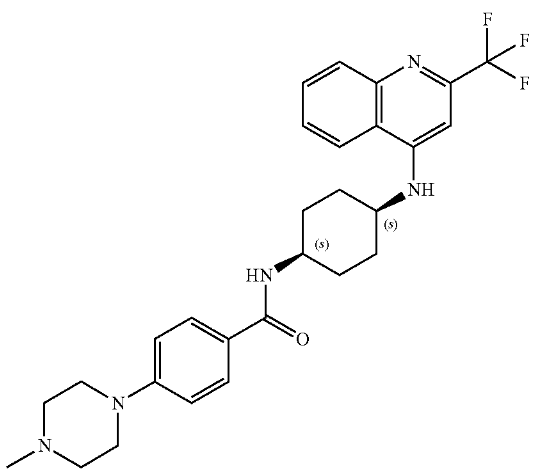 [SMILES: CN1CCN(c2ccc(C(=O)N[C@H]3CC[C@@H](Nc4cc(C(F)(F)F)nc5ccccc45)CC3)cc2)CC1] | 4-2 | 0.739 | 511.593 | 512.2 | [M + H]⁺ | Method 1 |
| 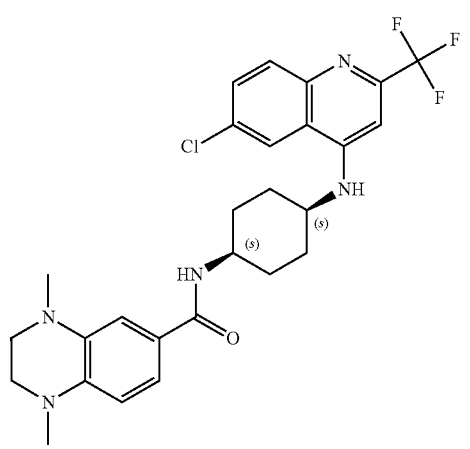 [SMILES: CN1CCN(C)c2cc(C(=O)N[C@H]3CC[C@@H](Nc4cc(C(F)(F)F)nc5ccc(Cl)cc45)CC3)ccc21] | 4-3 | 0.927 | 532.01 | 532.1 | [M + H]⁺ | Method 2 |

TABLE 4-continued

| Structure | Cpd No. | Purity RT | MW | m/z | Ion | Purity Method |
|---|---|---|---|---|---|---|
| 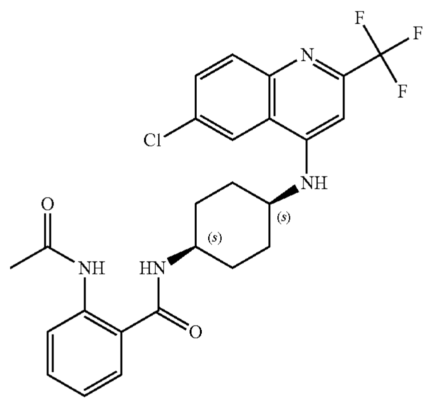 [SMILES: CC(=O)Nc1ccccc1C(=O)N[C@H]1CC[C@@H](Nc2cc(C(F)(F)F)nc3ccc(Cl)cc23)CC1] | 4-4 | 0.842 | 504.94 | 505.2 | [M + H]⁺ | Method 8 |
| 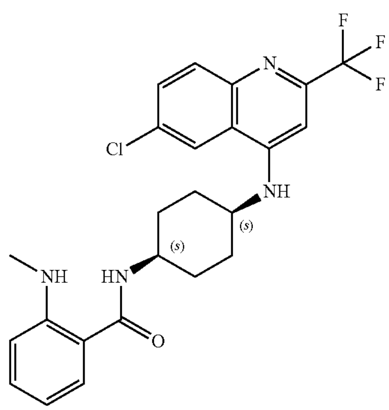 [SMILES: CNc1ccccc1C(=O)N[C@H]1CC[C@@H](Nc2cc(C(F)(F)F)nc3ccc(Cl)cc23)CC1] | 4-5 | 0.915 | 476.93 | 477.1 | [M + H]⁺ | Method 1 |
| 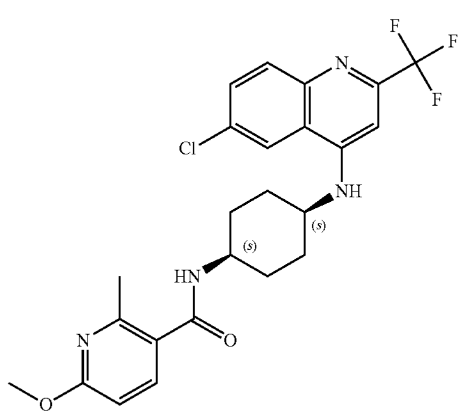 [SMILES: COc1ccc(C(=O)N[C@H]2CC[C@@H](Nc3cc(C(F)(F)F)nc4ccc(Cl)cc34)CC2)c(C)n1] | 4-6 | 0.886 | 492.93 | 493.1 | [M + H]⁺ | Method 1 |

TABLE 4-continued

| Structure | Cpd No. | Purity RT | MW | m/z | Ion | Purity Method |
|---|---|---|---|---|---|---|
| 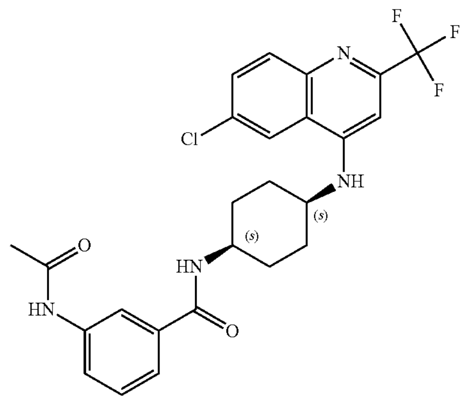 [SMILES: CC(=O)Nc1cccc(C(=O)N[C@H]2CC[C@@H](Nc3cc(C(F)(F)F)nc4ccc(Cl)cc34)CC2)c1] | 4-7 | 0.865 | 504.94 | 505.1 | [M + H]⁺ | Method 1 |
| 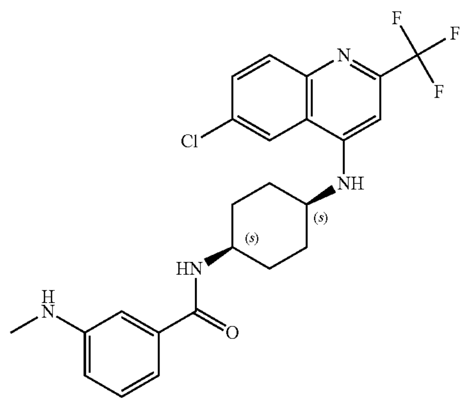 [SMILES: CNc1cccc(C(=O)N[C@H]2CC[C@@H](Nc3cc(C(F)(F)F)nc4ccc(Cl)cc34)CC2)c1] | 4-8 | 0.842 | 476.93 | 477.1 | [M + H]⁺ | Method 1 |
| 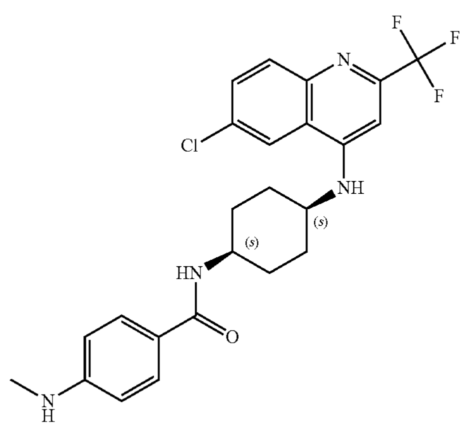 [SMILES: CNc1ccc(C(=O)N[C@H]2CC[C@@H](Nc3cc(C(F)(F)F)nc4ccc(Cl)cc34)CC2)cc1] | 4-9 | 0.882 | 476.93 | 477.1 | [M + H]⁺ | Method 1 |
| 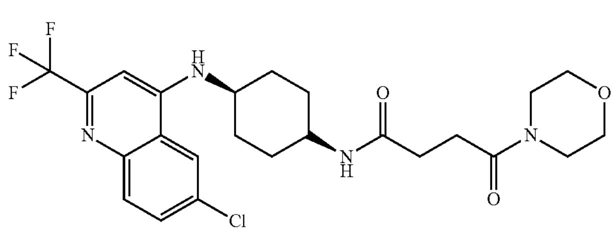 | 4-10 | .861 | 512.96 | 513 | [M + H]⁺ | Method 2 |

TABLE 4-continued

| Structure | Cpd No. | Purity RT | MW | m/z | Ion | Purity Method |
|---|---|---|---|---|---|---|
| 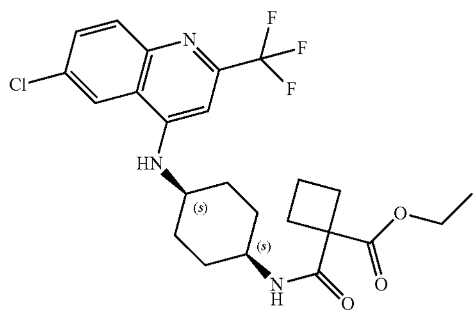 [SMILES: CCOC(=O)C1(C(=O)N[C@H]2CC[C@@H](Nc3cc(C(F)(F)F)nc4ccc(Cl)cc34)CC2)CCC1] | 4-11 | .941 | 497.94 | 498.1 | [M + H]⁺ | Method 2 |
| 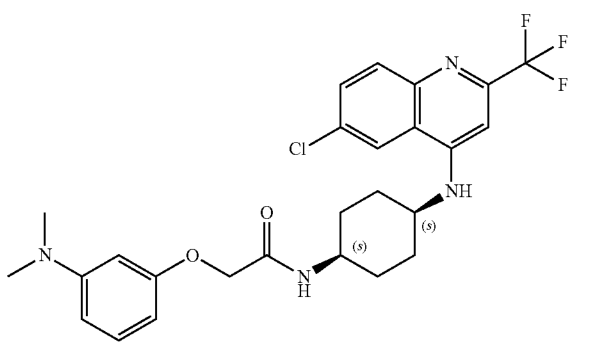 [SMILES: CN(C)c1cccc(OCC(=O)N[C@H]2CC[C@@H](Nc3cc(C(F)(F)F)nc4ccc(Cl)cc34)CC2)c1] | 4-12 | .865 | 520.98 | 521.1 | [M + H]⁺ | Method 2 |
| 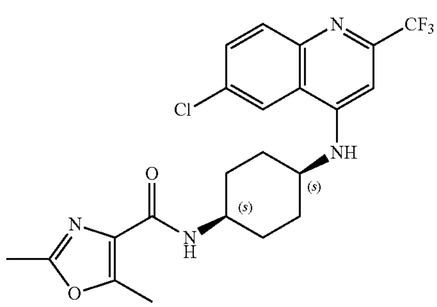 [SMILES: Cc1nc(C(=O)N[C@H]2CC[C@@H](Nc3cc(C(F)(F)F)nc4ccc(Cl)cc34)CC2)c(C)o1] | 4-13 | .85 | 466.89 | 467 | [M + H]⁺ | Method 2 |
| 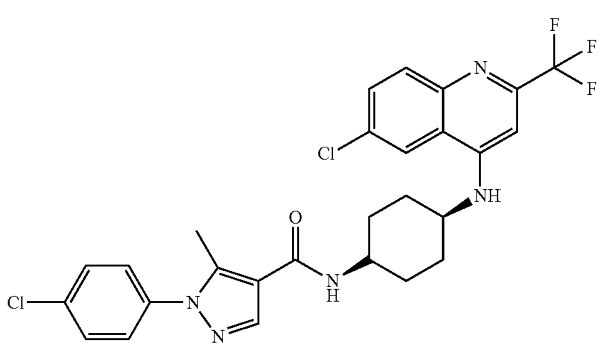 | 4-14 | 1.001 | 562.42 | 561.9 | [M + H]⁺ | Method 2 |

TABLE 4-continued

| Structure | Cpd No. | Purity RT | MW | m/z | Ion | Purity Method |
|---|---|---|---|---|---|---|
| 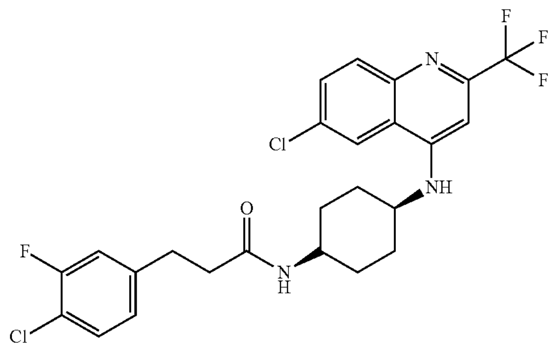 | 4-15 | 1.001 | 528.37 | 529.9 | [M + H]⁺ | Method 2 |
| 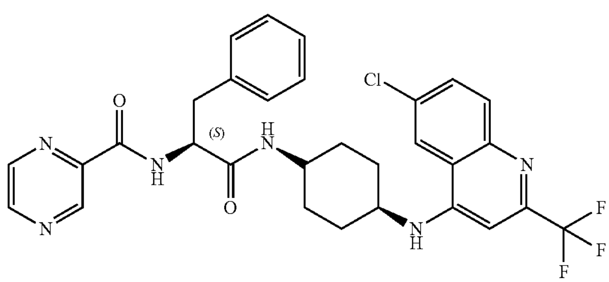 | 4-16 | .953 | 597.04 | 597 | [M + H]⁺ | Method 2 |
| 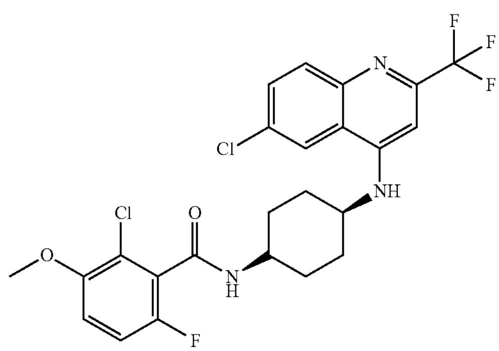 | 4-17 | .957 | 530.34 | 529.8 | [M + H]⁺ | Method 2 |
| 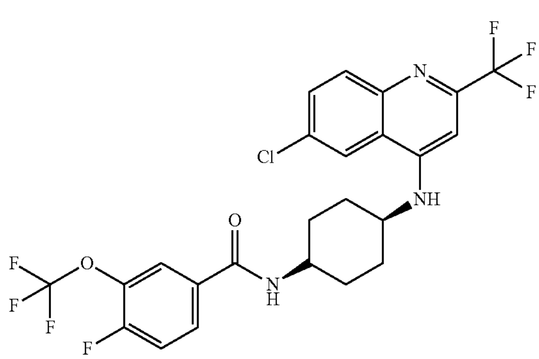 | 4-18 | 1.041 | 549.87 | 549.9 | [M + H]⁺ | Method 2 |

TABLE 4-continued

| Structure | Cpd No. | Purity RT | MW | m/z | Ion | Purity Method |
|---|---|---|---|---|---|---|
| 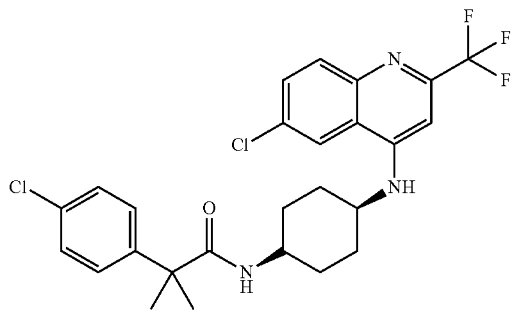 | 4-19 | 1.05 | 524.41 | 523.9 | [M + H]+ | Method 2 |
| 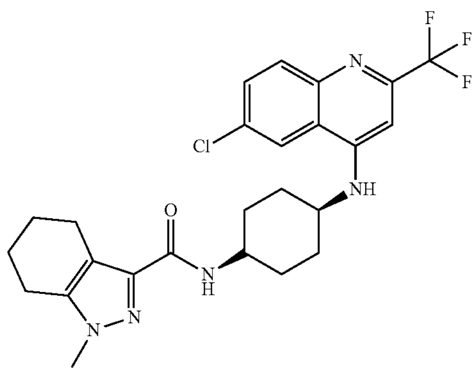 | 4-20 | .986 | 505.97 | 505.9 | [M + H]+ | Method 2 |
| 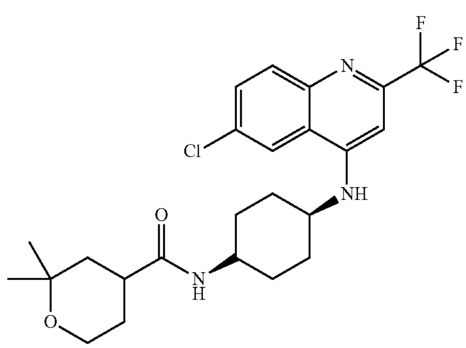 | 4-21 | .925 | 483.96 | 483.9 | [M + H]+ | Method 2 |
| 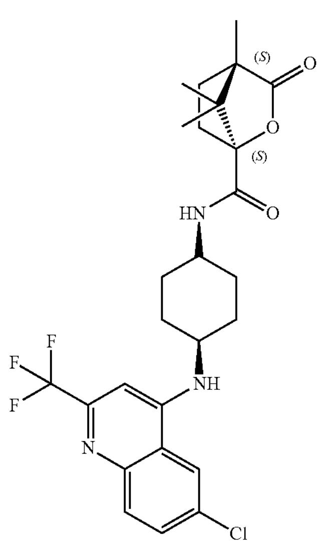 | 4-22 | .885 | 523.98 | 524.1 | [M + H]+ | Method 2 |

TABLE 4-continued

| Structure | Cpd No. | Purity RT | MW | m/z | Ion | Purity Method |
|---|---|---|---|---|---|---|
| 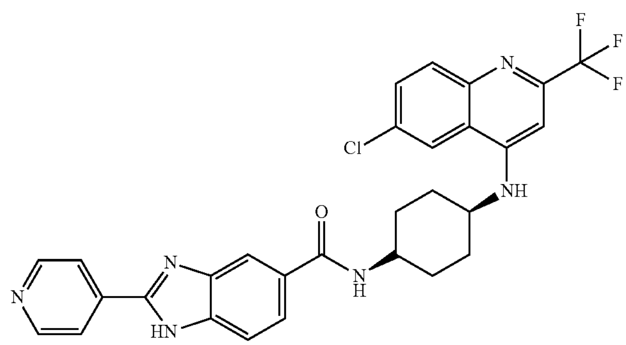 | 4-23 | .859 | 565 | 565 | [M + H]⁺ | Method 2 |
| 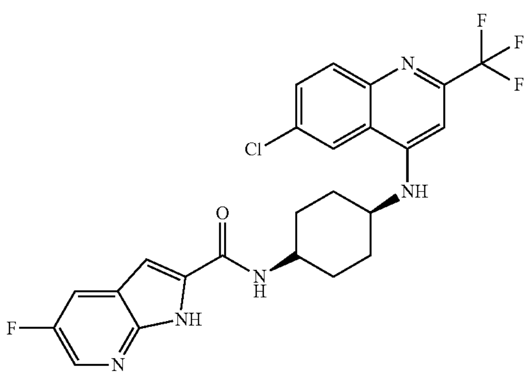 | 4-24 | .953 | 505.9 | 505.9 | [M + H]⁺ | Method 2 |
| 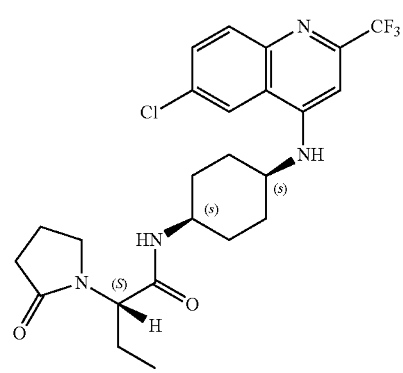 | 4-25 | .906 | 496.96 | 497.3 | [M + H]⁺ | Method 2 |

TABLE 4-continued

| Structure | Cpd No. | Purity RT | MW | m/z | Ion | Purity Method |
|---|---|---|---|---|---|---|
| 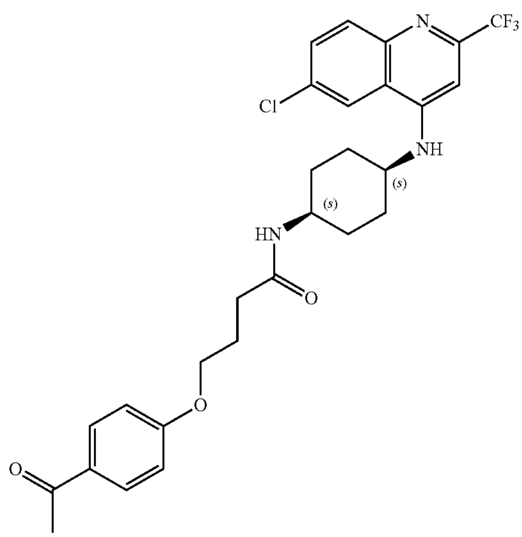 [SMILES: CC(=O)c1ccc(OCCCC(=O)N[C@H]2CC[C@@H](Nc3cc(C(F)(F)F)nc4ccc(Cl)cc34)CC2)cc1] | 4-26 | .95 | 548 | 548.4 | [M + H]⁺ | Method 2 |
| 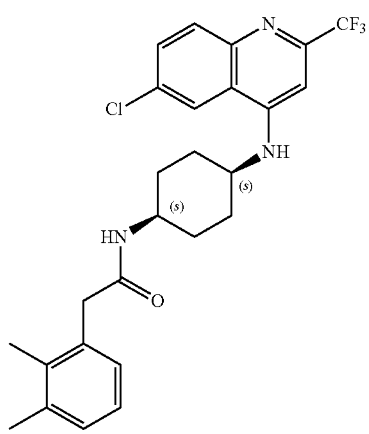 [SMILES: Cc1cccc(CC(=O)N[C@H]2CC[C@@H](Nc3cc(C(F)(F)F)nc4ccc(Cl)cc34)CC2)c1C] | 4-27 | 1.001 | 489.97 | 490.3 | [M + H]⁺ | Method 2 |
| 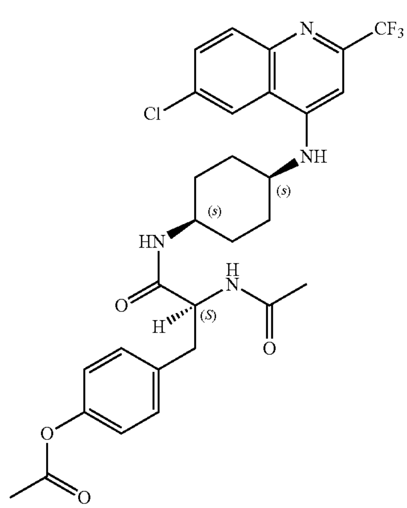 | 4-28 | .925 | 591.03 | 591.4 | [M + H]⁺ | Method 2 |

TABLE 4-continued

| Structure | Cpd No. | Purity RT | MW | m/z | Ion | Purity Method |
|---|---|---|---|---|---|---|
| 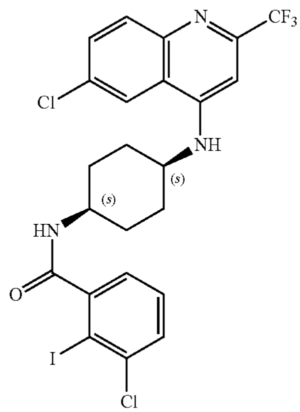 [SMILES: O=C(N[C@H]1CC[C@@H](Nc2cc(C(F)(F)F)nc3ccc(Cl)cc23)CC1)c1cccc(Cl)c1I] | 4-29 | 1.01 | 608.22 | 607.8 | [M + H]+ | Method 2 |
| 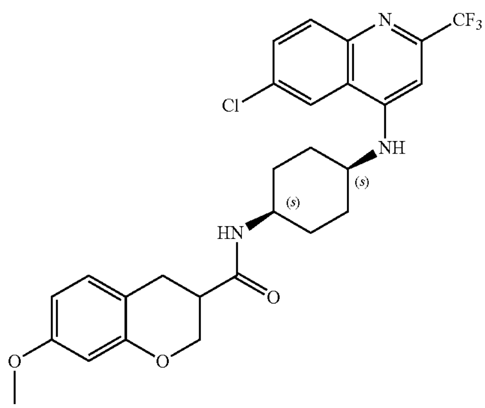 [SMILES: COc1ccc2c(c1)OCC(C(=O)N[C@H]1CC[C@@H](Nc3cc(C(F)(F)F)nc4ccc(Cl)cc34)CC1)C2] | 4-30 | .993 | 533.98 | 534.2 | [M + H]+ | Method 2 |
| 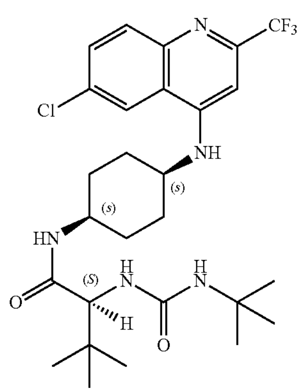 | 4-31 | .989 | 556.07 | 556.2 | [M + H]+ | Method 2 |
| 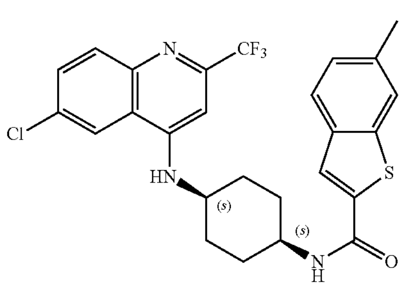 [SMILES: Cc1ccc2cc(C(=O)N[C@H]3CC[C@@H](Nc4cc(C(F)(F)F)nc5ccc(Cl)cc45)CC3)sc2c1] | 4-32 | 1.052 | 518 | 518 | [M + H]+ | Method 2 |

TABLE 4-continued

| Structure | Cpd No. | Purity RT | MW | m/z | Ion | Purity Method |
|---|---|---|---|---|---|---|
| 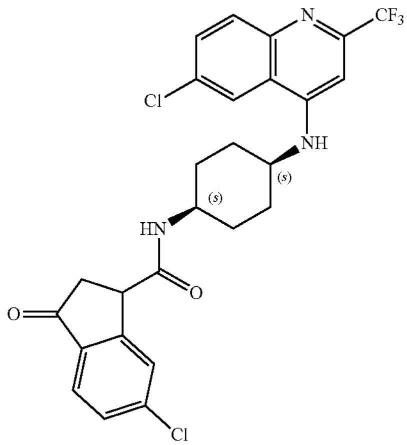 [SMILES: O=C1CC(C(=O)N[C@H]2CC[C@@H](Nc3cc(C(F)(F)F)nc4ccc(Cl)cc34)CC2)c2cc(Cl)ccc21] | 4-33 | .961 | 536.38 | 536.1 | [M + H]⁺ | Method 2 |
| 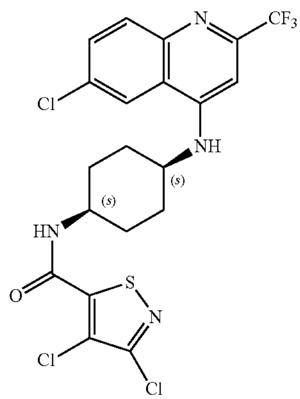 [SMILES: O=C(N[C@H]1CC[C@@H](Nc2cc(C(F)(F)F)nc3ccc(Cl)cc23)CC1)c1snc(Cl)c1Cl] | 4-34 | 1.028 | 523.78 | 525 | [M + H]⁺ | Method 2 |
| 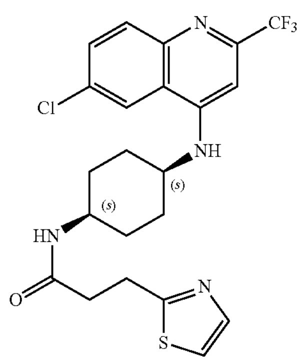 [SMILES: O=C(CCc1nccs1)N[C@H]1CC[C@@H](Nc2cc(C(F)(F)F)nc3ccc(Cl)cc23)CC1] | 4-35 | .887 | 482.95 | 483.1 | [M + H]⁺ | Method 2 |
| 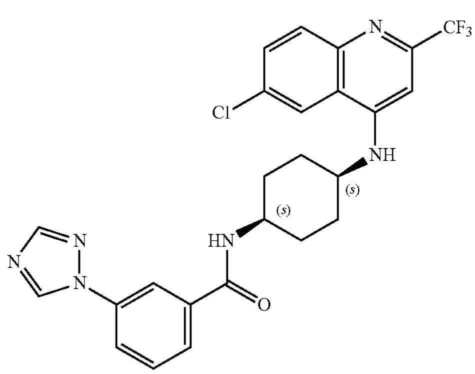 [SMILES: O=C(N[C@H]1CC[C@@H](Nc2cc(C(F)(F)F)nc3ccc(Cl)cc23)CC1)c1cccc(-n2cncn2)c1] | 4-36 | .934 | 514.94 | 515.1 | [M + H]⁺ | Method 2 |

TABLE 4-continued

| Structure | Cpd No. | Purity RT | MW | m/z | Ion | Purity Method |
|---|---|---|---|---|---|---|
| 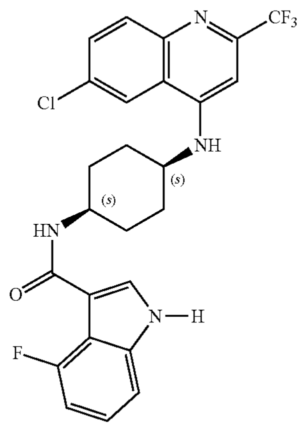 [SMILES: O=C(N[C@H]1CC[C@@H](Nc2cc(C(F)(F)F)nc3ccc(Cl)cc23)CC1)c1c[nH]c2cccc(F)c12] | 4-37 | .966 | 504.91 | 505.1 | [M + H]⁺ | Method 2 |
| 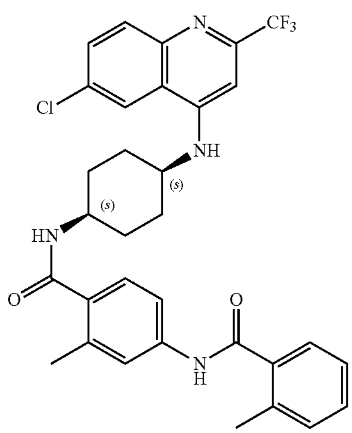 [SMILES: Cc1ccccc1C(=O)Nc1ccc(C(=O)N[C@H]2CC[C@@H](Nc3cc(C(F)(F)F)nc4ccc(Cl)cc34)CC2)c(C)c1] | 4-38 | .989 | 595.06 | 595.1 | [M + H]⁺ | Method 2 |
| 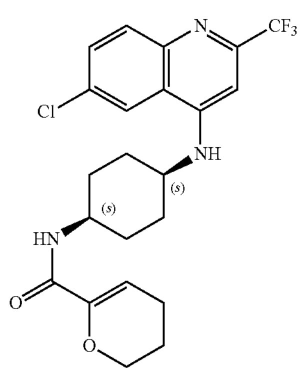 [SMILES: O=C(N[C@H]1CC[C@@H](Nc2cc(C(F)(F)F)nc3ccc(Cl)cc23)CC1)C1=CCCCO1] | 4-39 | .953 | 453.89 | 453.9 | [M + H]⁺ | Method 2 |

TABLE 4-continued

| Structure | Cpd No. | Purity RT | MW | m/z | Ion | Purity Method |
|---|---|---|---|---|---|---|
| 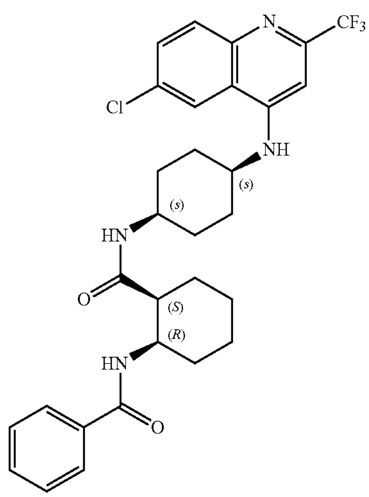 | 4-40 | .982 | 573.06 | 573.1 | [M + H]+ | Method 2 |
| 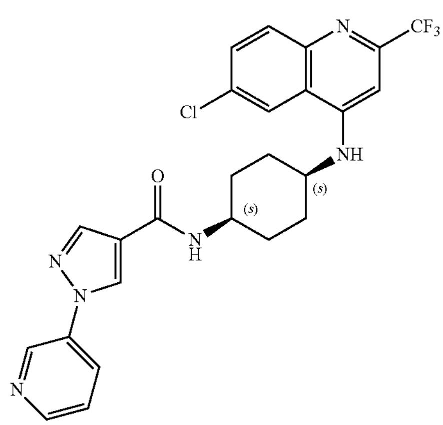 [SMILES: O=C(N[C@H]1CC[C@@H](Nc2cc(C(F)(F)F)nc3ccc(Cl)cc23)CC1)c1cnn(-c2cccnc2)c1] | 4-41 | .819 | 514.94 | 515.2 | [M + H]+ | Method 2 |
| 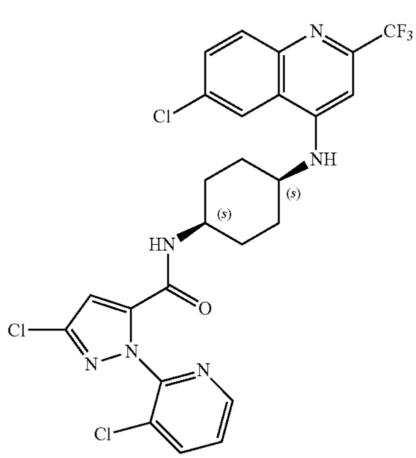 [SMILES: O=C(N[C@H]1CC[C@@H](Nc2cc(C(F)(F)F)nc3ccc(Cl)cc23)CC1)c1cc(Cl)nn1-c1ncccc1Cl] | 4-42 | .922 | 583.82 | 585 | [M + H]+ | Method 2 |

TABLE 4-continued

| Structure | Cpd No. | Purity RT | MW | m/z | Ion | Purity Method |
|---|---|---|---|---|---|---|
| 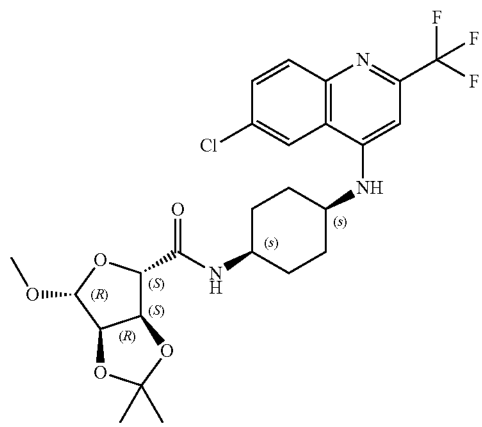 | 4-43 | .951 | 543.97 | 544.1 | [M + H]+ | Method 2 |
| 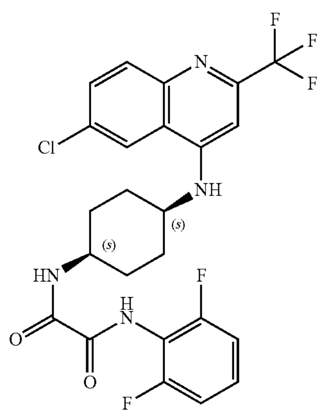 [SMILES: O=C(Nc1c(F)cccc1F)C(=O)N[C@H]1CC[C@@H](Nc2cc(C(F)(F)F)nc3ccc(Cl)cc23)CC1] | 4-44 | .938 | 526.89 | 527.1 | [M + H]+ | Method 2 |
| 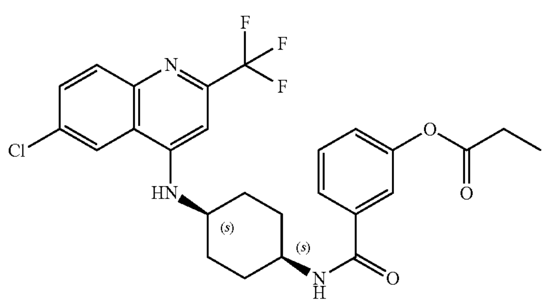 [SMILES: CCC(=O)Oc1cccc(C(=O)N[C@H]2CC[C@@H](Nc3cc(C(F)(F)F)nc4ccc(Cl)cc34)CC2)c1] | 4-45 | .953 | 519.95 | 520.1 | [M + H]+ | Method 2 |
| 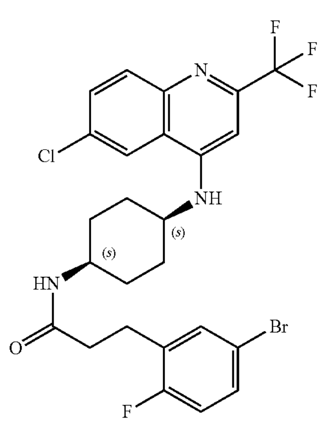 [SMILES: O=C(CCc1cc(Br)ccc1F)N[C@H]1CC[C@@H](Nc2cc(C(F)(F)F)nc3ccc(Cl)cc23)CC1] | 4-46 | .976 | 572.83 | 574 | [M + H]+ | Method 2 |

TABLE 4-continued

| Structure | Cpd No. | Purity RT | MW | m/z | Ion | Purity Method |
|---|---|---|---|---|---|---|
| 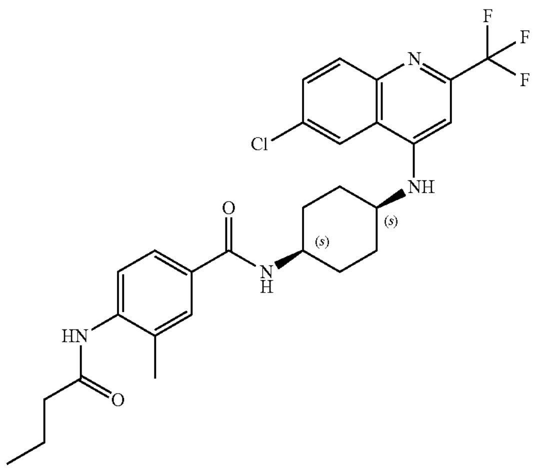 | 4-47 | .924 | 547.02 | 547.2 | [M + H]+ | Method 2 |
| 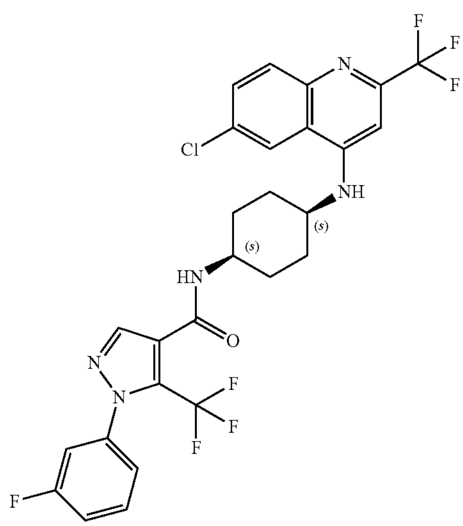 [SMILES: O=C(N[C@H]1CC[C@@H](Nc2cc(C(F)(F)F)nc3ccc(Cl)cc23)CC1)c1cnn(-c2cccc(F)c2)c1C(F)(F)F] | 4-48 | .982 | 599.94 | 600.1 | [M + H]+ | Method 2 |
| 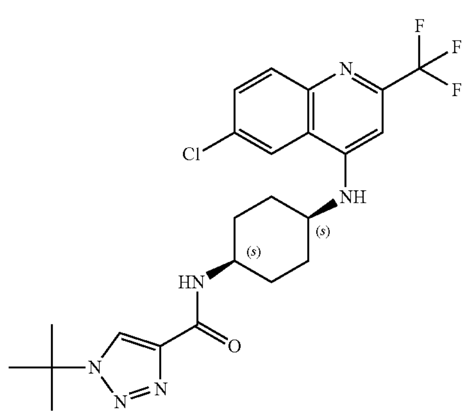 [SMILES: CC(C)(C)n1cc(C(=O)N[C@H]2CC[C@@H](Nc3cc(C(F)(F)F)nc4ccc(Cl)cc34)CC2)nn1] | 4-49 | .937 | 494.95 | 495.1 | [M + H]+ | Method 2 |

TABLE 4-continued

| Structure | Cpd No. | Purity RT | MW | m/z | Ion | Purity Method |
|---|---|---|---|---|---|---|
| 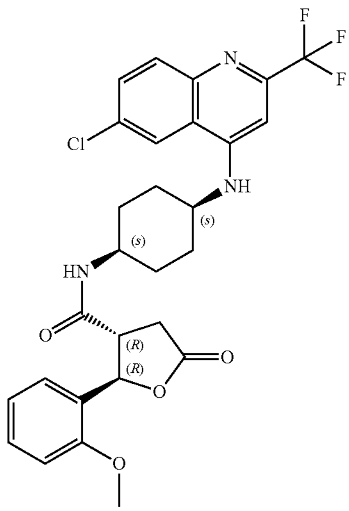 | 4-50 | .92 | 561.99 | 562.1 | [M + H]+ | Method 2 |
| 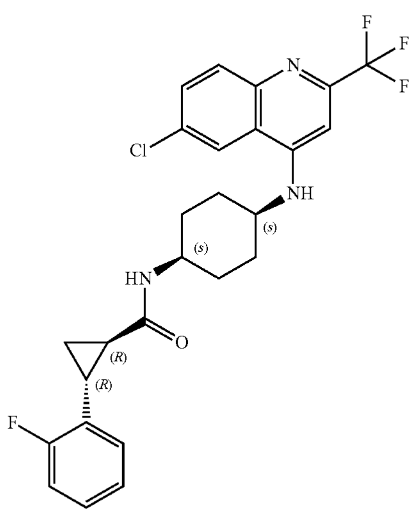 | 4-51 | .963 | 505.94 | 506.1 | [M + H]+ | Method 2 |
| 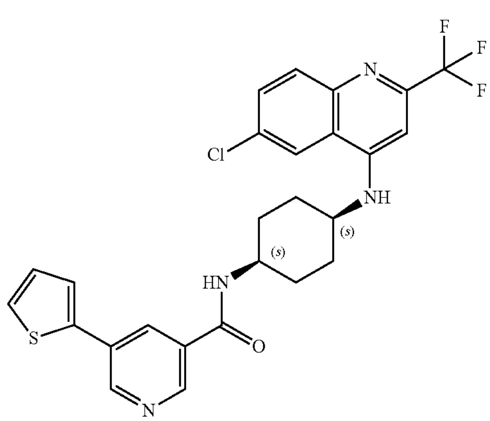 [SMILES: O=C(N[C@H]1CC[C@@H](Nc2cc(C(F)(F)F)nc3ccc(Cl)cc23)CC1)c1cncc(-c2cccs2)c1] | 4-52 | .936 | 530.99 | 531.1 | [M + H]+ | Method 2 |

TABLE 4-continued

| Structure | Cpd No. | Purity RT | MW | m/z | Ion | Purity Method |
|---|---|---|---|---|---|---|
| 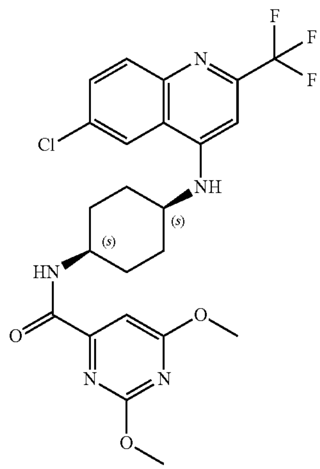 [SMILES: COc1cc(C(=O)N[C@H]2CC[C@@H](Nc3cc(C(F)(F)F)nc4ccc(Cl)cc34)CC2)nc(OC)n1] | 4-53 | 1 | 509.91 | 510.3 | [M + H]⁺ | Method 1 |
| 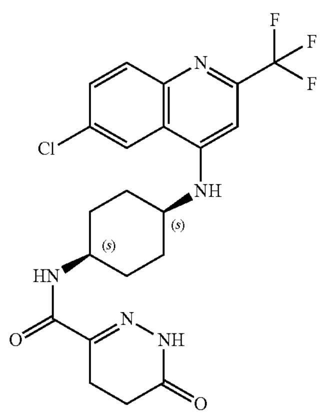 [SMILES: O=C1CCC(C(=O)N[C@H]2CC[C@@H](Nc3cc(C(F)(F)F)nc4ccc(Cl)cc34)CC2)=NN1] | 4-54 | 0.842 | 467.88 | 468.1 | [M + H]⁺ | Method 1 |
| 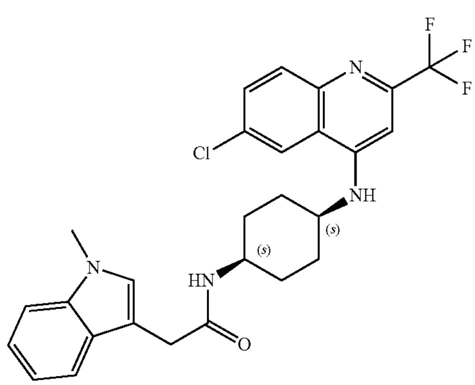 [SMILES: Cn1cc(CC(=O)N[C@H]2CC[C@@H](Nc3cc(C(F)(F)F)nc4ccc(Cl)cc34)CC2)c2ccccc21] | 4-55 | 0.978 | 514.98 | 515.3 | [M + H]⁺ | Method 1 |

TABLE 4-continued
| Structure | Cpd No. | Purity RT | MW | m/z | Ion | Purity Method |
|---|---|---|---|---|---|---|
| 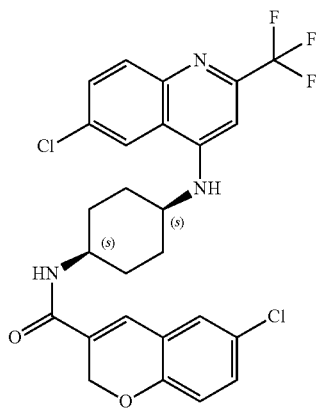 [SMILES: O=C(N[C@H]1CC[C@@H](Nc2cc(C(F)(F)F)nc3ccc(Cl)cc23)CC1)C1=Cc2cc(Cl)ccc2OC1] | 4-56 | 1 | 536.38 | 536.1 | [M + H]⁺ | Method 1 |
| 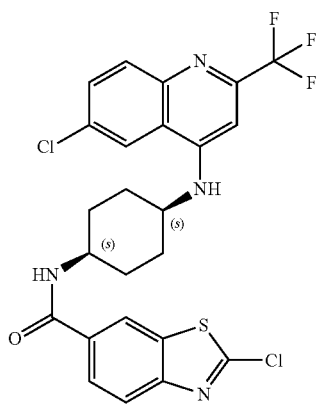 [SMILES: O=C(N[C@H]1CC[C@@H](Nc2cc(C(F)(F)F)nc3ccc(Cl)cc23)CC1)c1ccc2nc(Cl)sc2c1] | 4-57 | 0.973 | 539.4 | 539 | [M + H]⁺ | Method 1 |
| 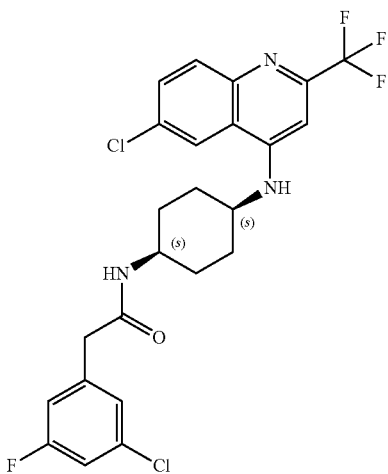 [SMILES: O=C(Cc1cc(F)cc(Cl)c1)N[C@H]1CC[C@@H](Nc2cc(C(F)(F)F)nc3ccc(Cl)cc23)CC1] | 4-58 | 0.83 | 514.35 | 514 | [M + H]⁺ | Method 1 |

TABLE 4-continued

| Structure | Cpd No. | Purity RT | MW | m/z | Ion | Purity Method |
|---|---|---|---|---|---|---|
| 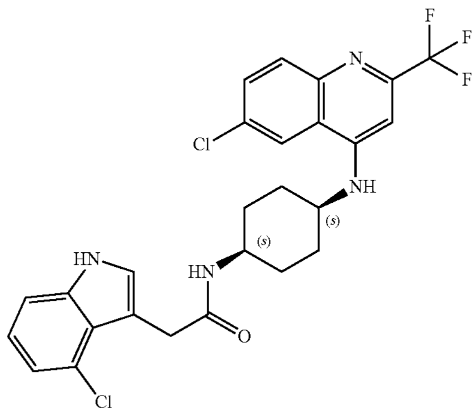 [SMILES: O=C(Cc1c[nH]c2cccc(Cl)c12)N[C@H]1CC[C@@H](Nc2cc(C(F)(F)F)nc3ccc(Cl)cc23)CC1] | 4-59 | 0.966 | 535.39 | 535.3 | [M + H]⁺ | Method 1 |
| 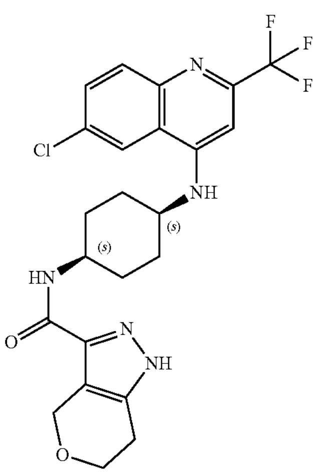 [SMILES: O=C(N[C@H]1CC[C@@H](Nc2cc(C(F)(F)F)nc3ccc(Cl)cc23)CC1)c1n[nH]c2c1COCC2] | 4-60 | 0.879 | 493.92 | 494.3 | [M + H]⁺ | Method 1 |
| 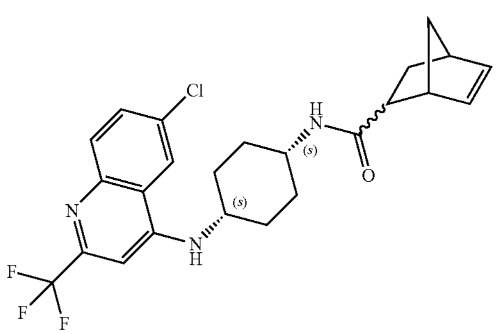 [SMILES: O=C(N[C@H]1CC[C@@H](Nc2cc(C(F)(F)F)nc3ccc(Cl)cc23)CC1)C1CC2C=CC1C2] | 4-61 | 0.963 | 463.93 | 464.3 | [M + H]⁺ | Method 1 |

TABLE 4-continued

| Structure | Cpd No. | Purity RT | MW | m/z | Ion | Purity Method |
|---|---|---|---|---|---|---|
| 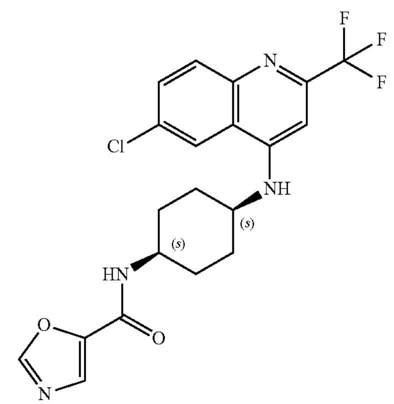 [SMILES: O=C(N[C@H]1CC[C@@H](Nc2cc(C(F)(F)F)nc3ccc(Cl)cc23)CC1)c1cnco1] | 4-62 | 0.872 | 438.84 | 439.2 | [M + H]+ | Method 1 |
| 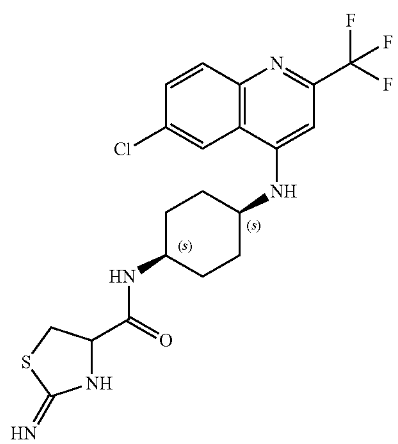 [SMILES: N=C1NC(C(=O)N[C@H]2CC[C@@H](Nc3cc(C(F)(F)F)nc4ccc(Cl)cc34)CC2)CS1] | 4-63 | 0.885 | 471.93 | 472.1 | [M + H]+ | Method 8 |
| 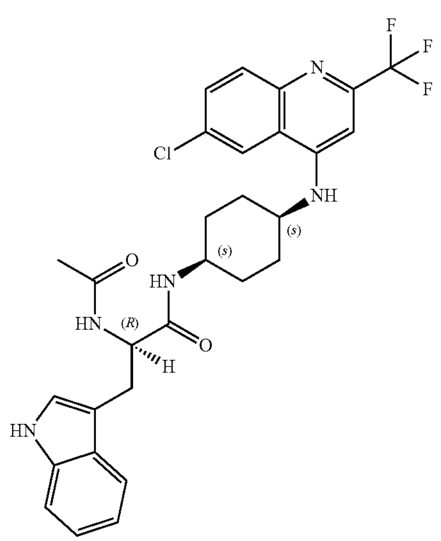 | 4-64 | 0.88 | 572.03 | 572.2 | [M + H]+ | Method 1 |

TABLE 4-continued

| Structure | Cpd No. | Purity RT | MW | m/z | Ion | Purity Method |
|---|---|---|---|---|---|---|
| 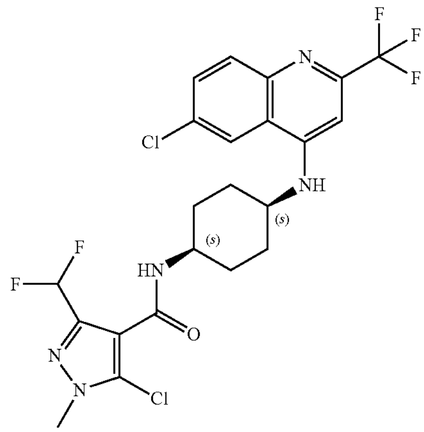 [SMILES: Cn1nc(C(F)F)c(C(=O)N[C@H]2CC[C@@H](Nc3cc(C(F)(F)F)nc4ccc(Cl)cc34)CC2)c1Cl] | 4-65 | 0.913 | 536.33 | 536.1 | [M + H]+ | Method 1 |
| 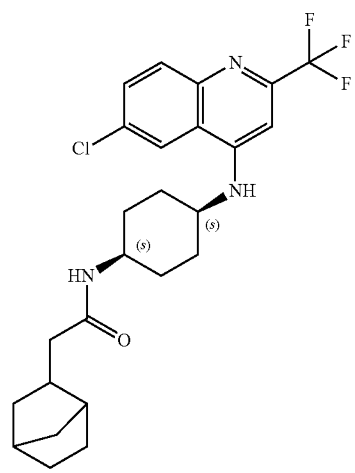 [SMILES: O=C(CC1CC2CCC1C2)N[C@H]1CC[C@@H](Nc2cc(C(F)(F)F)nc3ccc(Cl)cc23)CC1] | 4-66 | 0.959 | 479.97 | 480.2 | [M + H]+ | Method 1 |
| 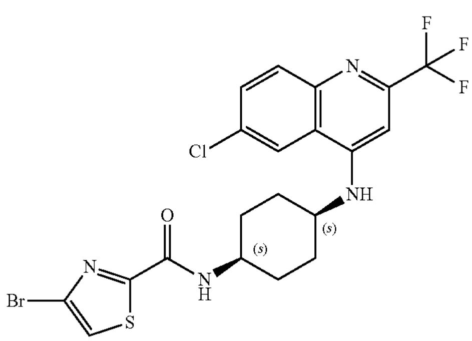 [SMILES: O=C(N[C@H]1CC[C@@H](Nc2cc(C(F)(F)F)nc3ccc(Cl)cc23)CC1)c1nc(Br)cs1] | 4-67 | 0.905 | 533.79 | 532.9 | [M + H]+ | Method 1 |
| 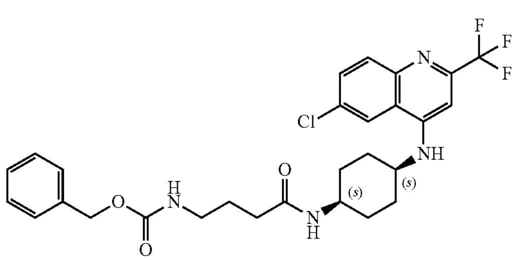 [SMILES: O=C(CCCNC(=O)OCc1ccccc1)N[C@H]1CC[C@@H](Nc2cc(C(F)(F)F)nc3ccc(Cl)cc23)CC1] | 4-68 | 0.856 | 563.02 | 563 | [M + H]+ | Method 1 |

TABLE 4-continued

| Structure | Cpd No. | Purity RT | MW | m/z | Ion | Purity Method |
|---|---|---|---|---|---|---|
| 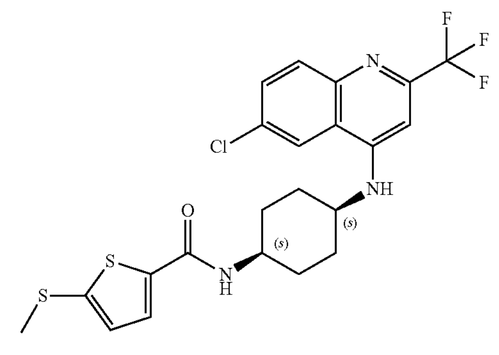 [SMILES: CSc1ccc(C(=O)N[C@H]2CC[C@@H](Nc3cc(C(F)(F)F)nc4ccc(Cl)cc34)CC2)s1] | 4-69 | 0.888 | 500 | 500.1 | [M + H]+ | Method 1 |
| 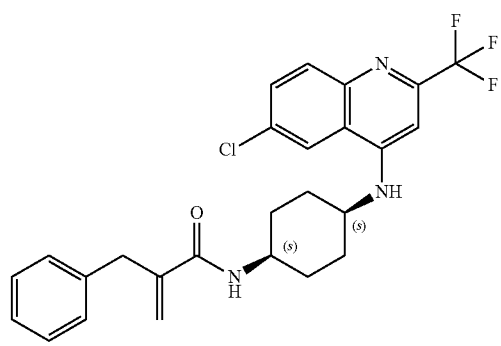 [SMILES: C=C(Cc1ccccc1)C(=O)N[C@H]1CC[C@@H](Nc2cc(C(F)(F)F)nc3ccc(Cl)cc23)CC1] | 4-70 | 0.902 | 487.95 | 488.2 | [M + H]+ | Method 1 |
| 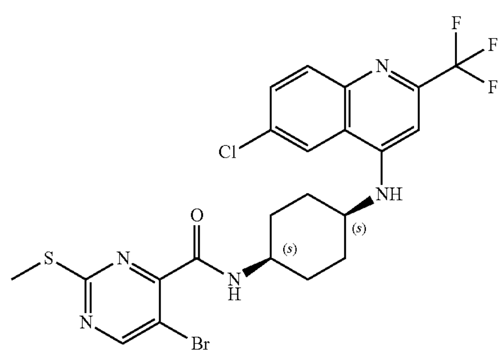 [SMILES: CSc1ncc(Br)c(C(=O)N[C@H]2CC[C@@H](Nc3cc(C(F)(F)F)nc4ccc(Cl)cc34)CC2)n1] | 4-71 | 0.892 | 574.85 | 573.9 | [M + H]+ | Method 1 |
| 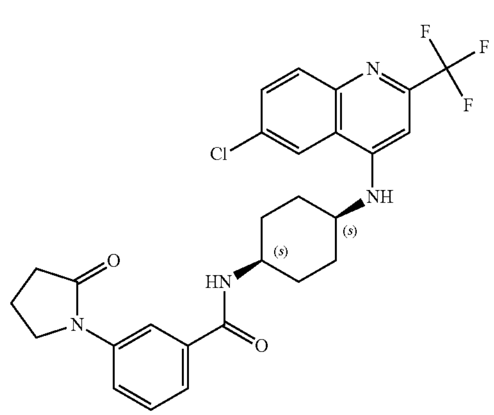 [SMILES: O=C(N[C@H]1CC[C@@H](Nc2cc(C(F)(F)F)nc3ccc(Cl)cc23)CC1)c1cccc(N2CCCC2=O)c1] | 4-72 | 0.933 | 530.98 | 531.1 | [M + H]+ | Method 2 |

TABLE 4-continued

| Structure | Cpd No. | Purity RT | MW | m/z | Ion | Purity Method |
|---|---|---|---|---|---|---|
| 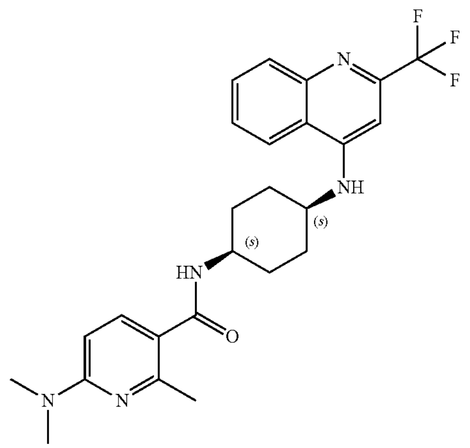 [SMILES: Cc1nc(N(C)C)ccc1C(=O)N[C@H]1CC[C@@H](Nc2cc(C(F)(F)F)nc3ccccc23)CC1] | 4-73 | 0.748 | 471.528 | 472.2 | [M + H]⁺ | Method 1 |
| 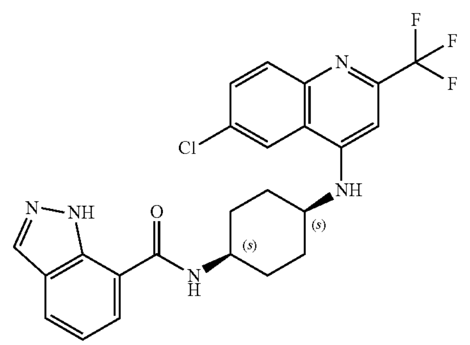 [SMILES: O=C(N[C@H]1CC[C@@H](Nc2cc(C(F)(F)F)nc3ccc(Cl)cc23)CC1)c1cccc2cn[nH]c12] | 4-74 | 0.849 | 487.91 | 488 | [M + H]⁺ | Method 1 |
| 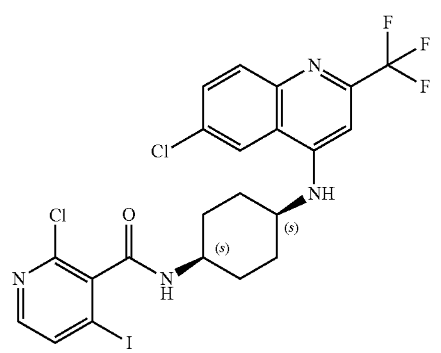 [SMILES: O=C(N[C@H]1CC[C@@H](Nc2cc(C(F)(F)F)nc3ccc(Cl)cc23)CC1)c1c(I)ccnc1Cl] | 4-75 | 0.919 | 609.21 | 609 | [M + H]⁺ | Method 1 |
| 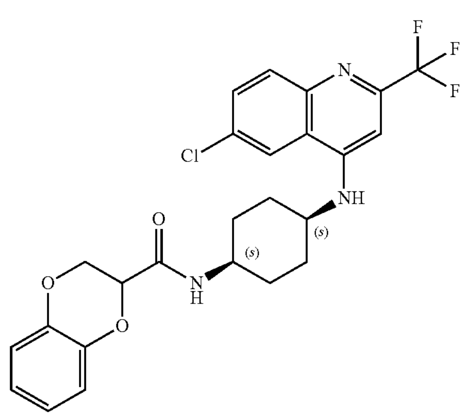 [SMILES: O=C(N[C@H]1CC[C@@H](Nc2cc(C(F)(F)F)nc3ccc(Cl)cc23)CC1)C1COc2ccccc2O1] | 4-76 | 0.913 | 505.92 | 506.2 | [M + H]⁺ | Method 1 |

TABLE 4-continued

| Structure | Cpd No. | Purity RT | MW | m/z | Ion | Purity Method |
|---|---|---|---|---|---|---|
| 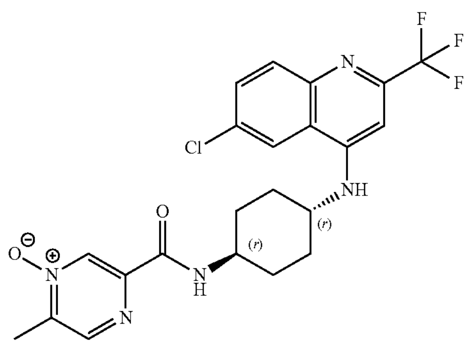 [SMILES: Cc1cnc(C(=O)N[C@H]2CC[C@H](Nc3cc(C(F)(F)F)nc4ccc(Cl)cc34)CC2)c[n+]1[O-]] | 4-77 | 0.869 | 479.89 | 480.1 | [M + H]+ | Method 1 |
| 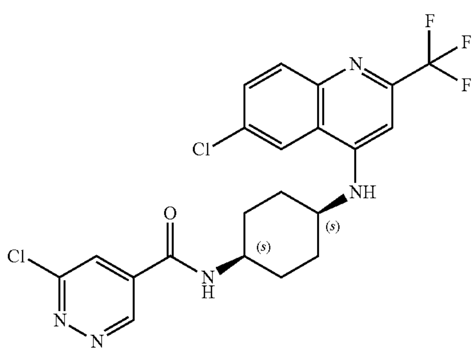 [SMILES: O=C(N[C@H]1CC[C@@H](Nc2cc(C(F)(F)F)nc3ccc(Cl)cc23)CC1)c1cnnc(Cl)c1] | 4-78 | 0.889 | 484.3 | 483.9 | [M + H]+ | Method 1 |
| 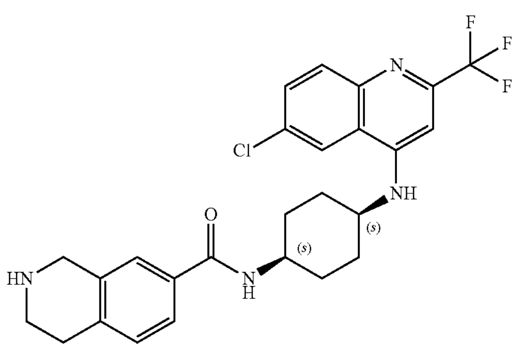 [SMILES: O=C(N[C@H]1CC[C@@H](Nc2cc(C(F)(F)F)nc3ccc(Cl)cc23)CC1)c1ccc2c(c1)CNCC2] | 4-79 | 0.747 | 502.97 | 503.1 | [M + H]+ | Method 1 |
| 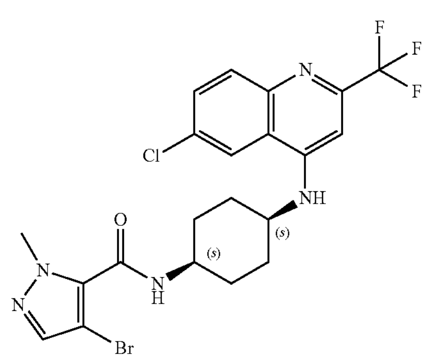 [SMILES: Cn1ncc(Br)c1C(=O)N[C@H]1CC[C@@H](Nc2cc(C(F)(F)F)nc3ccc(Cl)cc23)CC1] | 4-80 | 0.869 | 530.77 | 531.9 | [M + H]+ | Method 1 |

TABLE 4-continued

| Structure | Cpd No. | Purity RT | MW | m/z | Ion | Purity Method |
|---|---|---|---|---|---|---|
| 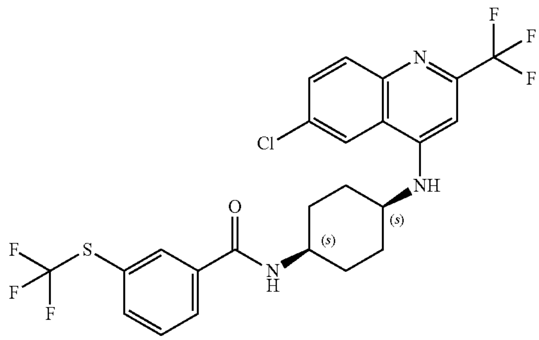 [SMILES: O=C(N[C@H]1CC[C@@H](Nc2cc(C(F)(F)F)nc3ccc(Cl)cc23)CC1)c1cccc(SC(F)(F)F)c1] | 4-81 | 1.038 | 547.94 | 548 | [M + H]+ | Method 1 |
| 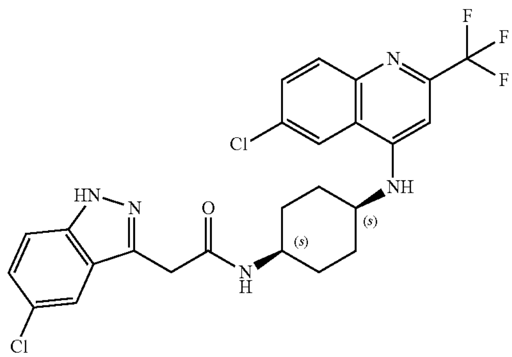 [SMILES: O=C(Cc1n[nH]c2ccc(Cl)cc12)N[C@H]1CC[C@@H](Nc2cc(C(F)(F)F)nc3ccc(Cl)cc23)CC1] | 4-82 | 0.863 | 536.38 | 536 | [M + H]+ | Method 1 |
| 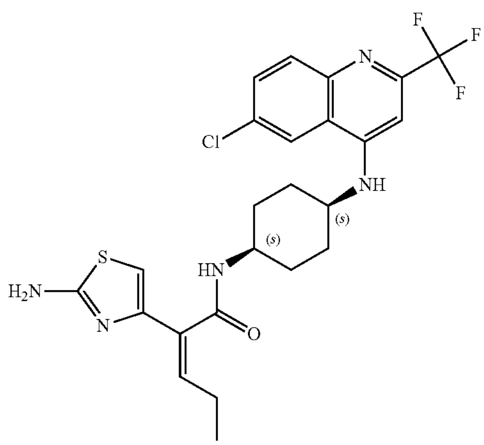 [SMILES: CC/C=C(\C(=O)N[C@H]1CC[C@@H](Nc2cc(C(F)(F)F)nc3ccc(Cl)cc23)CC1)c1csc(N)n1] | 4-83 | 0.781 | 524 | 524 | [M + H]+ | Method 1 |
| 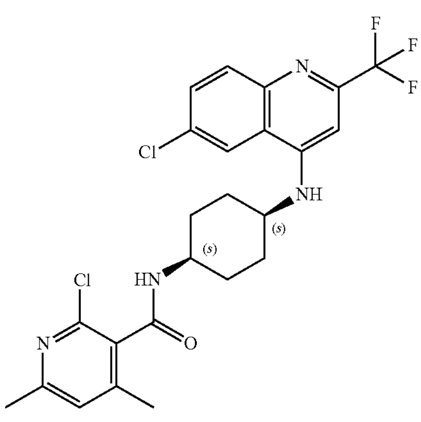 [SMILES: Cc1cc(C)c(C(=O)N[C@H]2CC[C@@H](Nc3cc(C(F)(F)F)nc4ccc(Cl)cc34)CC2)c(Cl)n1] | 4-84 | 0.954 | 511.37 | 510.9 | [M + H]+ | Method 1 |

TABLE 4-continued

| Structure | Cpd No. | Purity RT | MW | m/z | Ion | Purity Method |
|---|---|---|---|---|---|---|
| 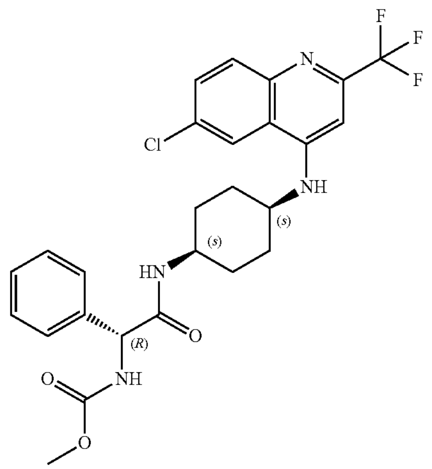 | 4-85 | 0.894 | 534.96 | 535.1 | [M + H]⁺ | Method 1 |
| 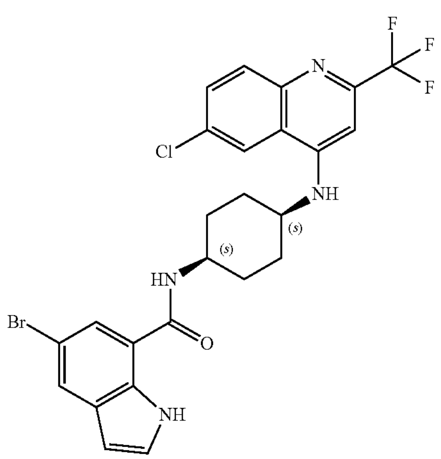 [SMILES: O=C(N[C@H]1CC[C@@H](Nc2cc(C(F)(F)F)nc3ccc(Cl)cc23)CC1)c1cc(Br)cc2cc[nH]c12] | 4-86 | 1.066 | 565.82 | 566.9 | [M + H]⁺ | Method 1 |
| 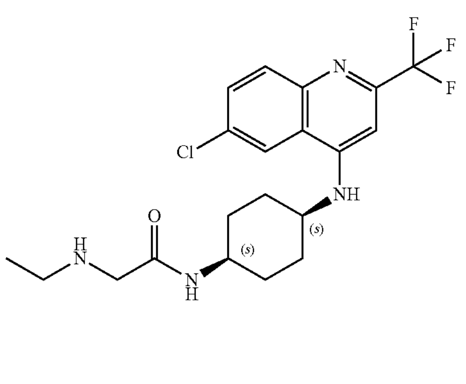 [SMILES: CCNCC(=O)N[C@H]1CC[C@@H](Nc2cc(C(F)(F)F)nc3ccc(Cl)cc23)CC1] | 4-87 | 0.756 | 428.88 | 429.1 | [M + H]⁺ | Method 1 |

TABLE 4-continued

| Structure | Cpd No. | Purity RT | MW | m/z | Ion | Purity Method |
|---|---|---|---|---|---|---|
| 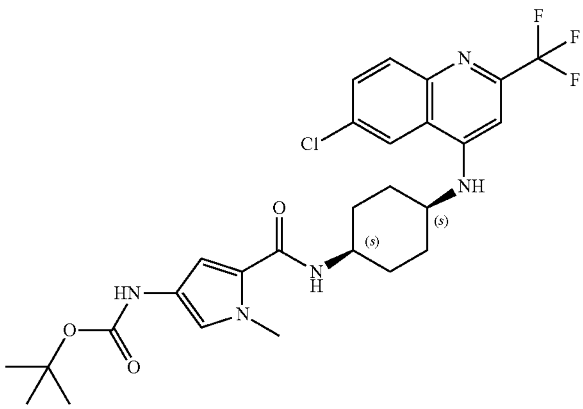 [SMILES: Cn1cc(NC(=O)OC(C)(C)C)cc1C(=O)N[C@H]1CC[C@@H](Nc2cc(C(F)(F)F)nc3ccc(Cl)cc23)CC1] | 4-88 | 0.95 | 566.02 | 566.1 | [M + H]⁺ | Method 1 |
| 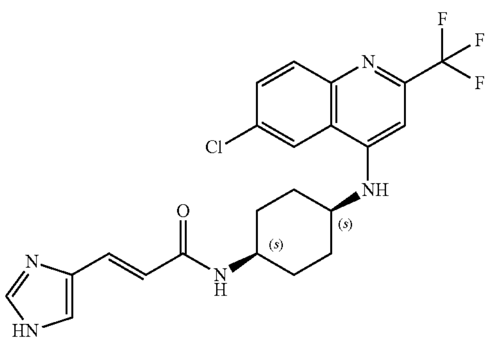 [SMILES: O=C(/C=C/c1c[nH]cn1)N[C@H]1CC[C@@H](Nc2cc(C(F)(F)F)nc3ccc(Cl)cc23)CC1] | 4-89 | 0.758 | 463.89 | 464.1 | [M + H]⁺ | Method 1 |
| 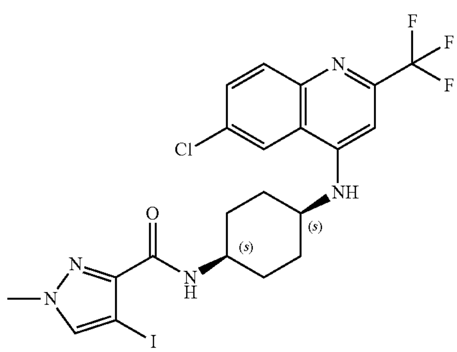 [SMILES: Cn1cc(I)c(C(=O)N[C@H]2CC[C@@H](Nc3cc(C(F)(F)F)nc4ccc(Cl)cc34)CC2)n1] | 4-90 | 0.851 | 577.77 | 577.9 | [M + H]⁺ | Method 1 |
| 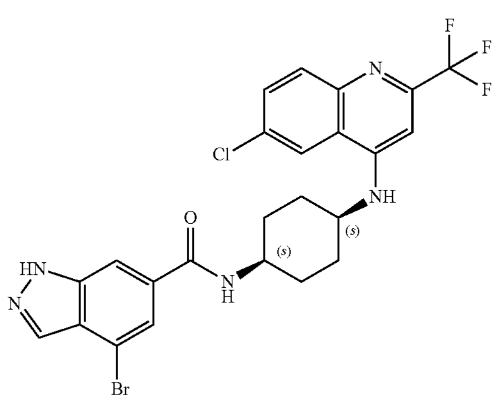 [SMILES: O=C(N[C@H]1CC[C@@H](Nc2cc(C(F)(F)F)nc3ccc(Cl)cc23)CC1)c1cc(Br)c2cn[nH]c2c1] | 4-91 | 0.892 | 566.81 | 568.1 | [M + H]⁺ | Method 1 |

TABLE 4-continued

| Structure | Cpd No. | Purity RT | MW | m/z | Ion | Purity Method |
|---|---|---|---|---|---|---|
| 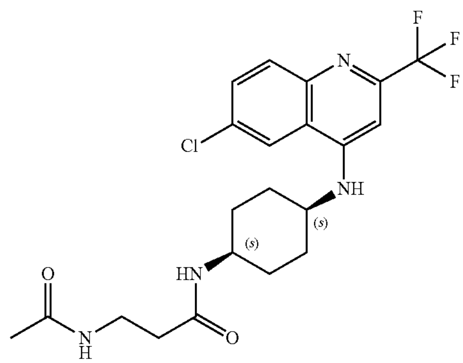 [SMILES: CC(=O)NCCC(=O)N[C@H]1CC[C@@H](Nc2cc(C(F)(F)F)nc3ccc(Cl)cc23)CC1] | 4-92 | 0.498 | 456.89 | 457.1 | [M + H]⁺ | Method 1 |
| 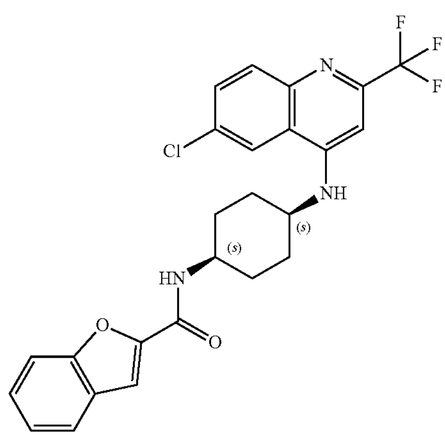 [SMILES: O=C(N[C@H]1CC[C@@H](Nc2cc(C(F)(F)F)nc3ccc(Cl)cc23)CC1)c1cc2ccccc2o1] | 4-93 | 0.775 | 487.91 | 488.3 | [M + H]⁺ | Method 1 |
| 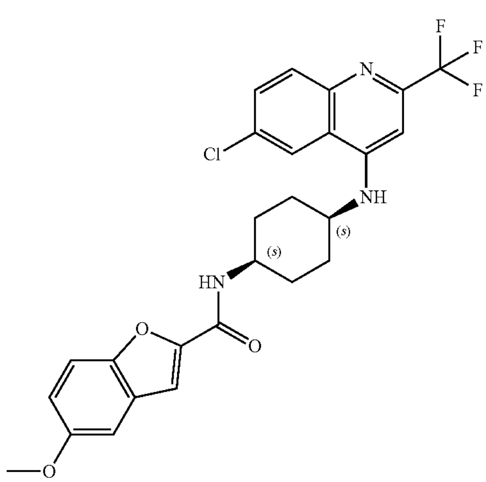 [SMILES: COc1ccc2oc(C(=O)N[C@H]3CC[C@@H](Nc4cc(C(F)(F)F)nc5ccc(Cl)cc45)CC3)cc2c1] | 4-94 | 0.706 | 517.93 | 518.2 | [M + H]⁺ | Method 1 |

TABLE 4-continued

| Structure | Cpd No. | Purity RT | MW | m/z | Ion | Purity Method |
|---|---|---|---|---|---|---|
| 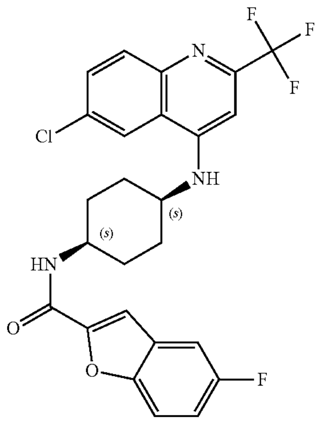 [SMILES: O=C(N[C@H]1CC[C@@H](Nc2cc(C(F)(F)F)nc3ccc(Cl)cc23)CC1)c1cc2cc(F)ccc2o1] | 4-95 | 0.785 | 505.9 | 506.1 | [M + H]⁺ | Method 1 |
| 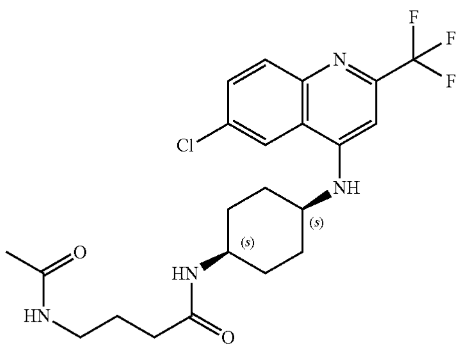 [SMILES: CC(=O)NCCCC(=O)N[C@H]1CC[C@@H](Nc2cc(C(F)(F)F)nc3ccc(Cl)cc23)CC1] | 4-96 | 0.858 | 470.92 | 471.3 | [M + H]⁺ | Method 1 |
| 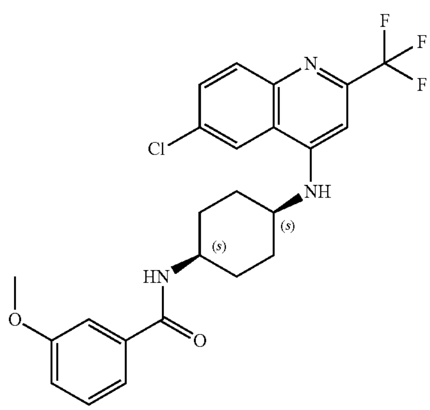 [SMILES: COc1cccc(C(=O)N[C@H]2CC[C@@H](Nc3cc(C(F)(F)F)nc4ccc(Cl)cc34)CC2)c1] | 4-97 | 0.732 | 477.91 | 478.4 | [M + H]⁺ | Method 7 |
| 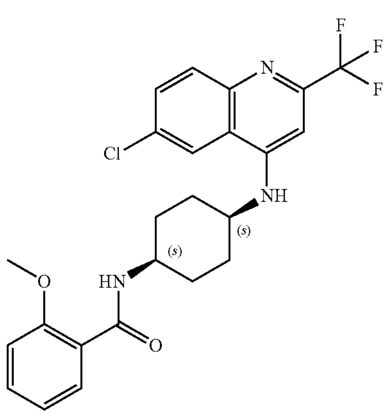 [SMILES: COc1ccccc1C(=O)N[C@H]1CC[C@@H](Nc2cc(C(F)(F)F)nc3ccc(Cl)cc23)CC1] | 4-98 | 0.681 | 477.91 | 478.1 | [M + H]⁺ | Method 7 |

TABLE 4-continued

| Structure | Cpd No. | Purity RT | MW | m/z | Ion | Purity Method |
|---|---|---|---|---|---|---|
| 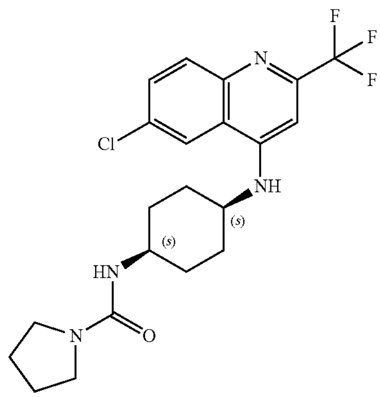 [SMILES: O=C(N[C@H]1CC[C@@H](Nc2cc(C(F)(F)F)nc3ccc(Cl)cc23)CC1)N1CCCC1] | 4-99 | 0.602 | 440.9 | 441.1 | [M + H]+ | Method 7 |
| 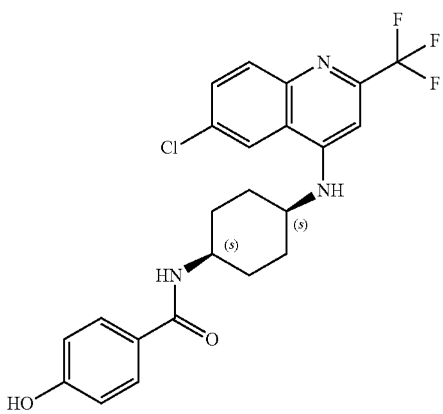 [SMILES: O=C(N[C@H]1CC[C@@H](Nc2cc(C(F)(F)F)nc3ccc(Cl)cc23)CC1)c1ccc(O)cc1] | 4-100 | 0.66 | 463.89 | 464.1 | [M + H]+ | Method 7 |
| 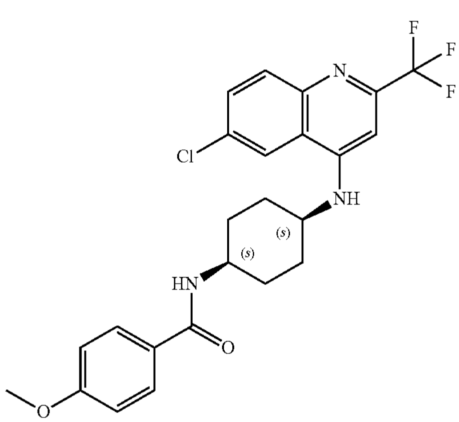 [SMILES: COc1ccc(C(=O)N[C@H]2CC[C@@H](Nc3cc(C(F)(F)F)nc4ccc(Cl)cc34)CC2)cc1] | 4-101 | 0.727 | 477.91 | 478.1 | [M + H]+ | Method 7 |

TABLE 4-continued

| Structure | Cpd No. | Purity RT | MW | m/z | Ion | Purity Method |
|---|---|---|---|---|---|---|
| 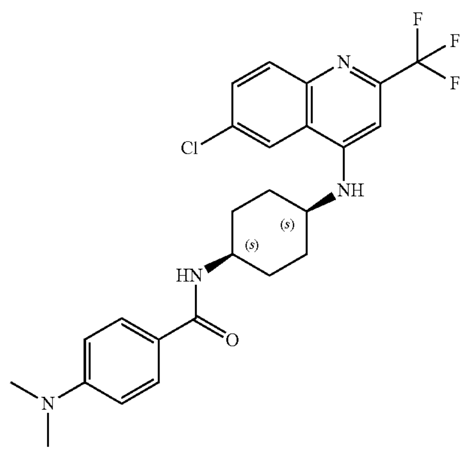 [SMILES: CN(C)c1ccc(C(=O)N[C@H]2CC[C@@H](Nc3cc(C(F)(F)F)nc4ccc(Cl)cc34)CC2)cc1] | 4-102 | 0.656 | 490.96 | 491.1 | [M + H]+ | Method 7 |
| 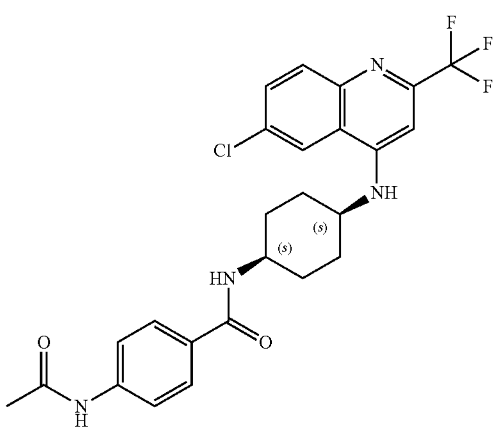 [SMILES: CC(=O)Nc1ccc(C(=O)N[C@H]2CC[C@@H](Nc3cc(C(F)(F)F)nc4ccc(Cl)cc34)CC2)cc1] | 4-103 | 0.587 | 504.94 | 505 | [M + H]+ | Method 7 |
| 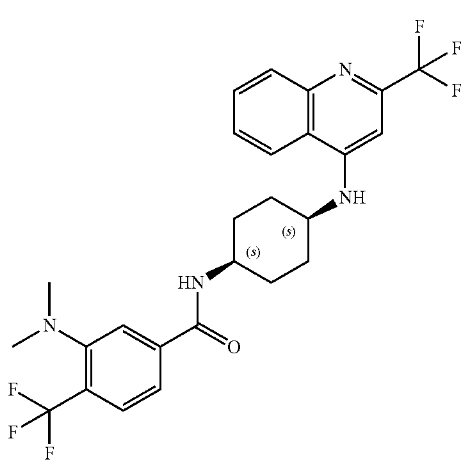 [SMILES: CN(C)c1cc(C(=O)N[C@H]2CC[C@@H](Nc3cc(C(F)(F)F)nc4ccccc34)CC2)ccc1C(F)(F)F] | 4-104 | 10.387 | 524.511 | 525.2 | [M + H]+ | Method 3 |

TABLE 4-continued

| Structure | Cpd No. | Purity RT | MW | m/z | Ion | Purity Method |
|---|---|---|---|---|---|---|
| 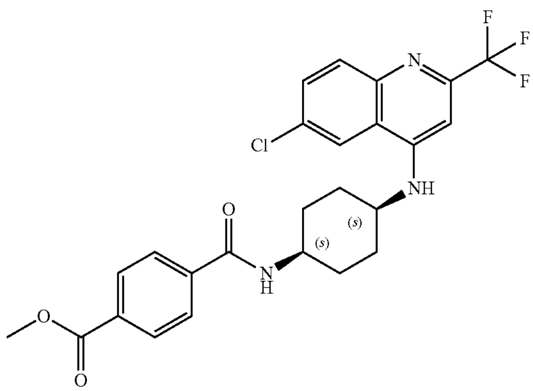 [SMILES: COC(=O)c1ccc(C(=O)N[C@H]2CC[C@@H](Nc3cc(C(F)(F)F)nc4ccc(Cl)cc34)CC2)cc1] | 4-105 | 0.966 | 505.92 | 506.1 | [M + H]⁺ | Method 2 |
| 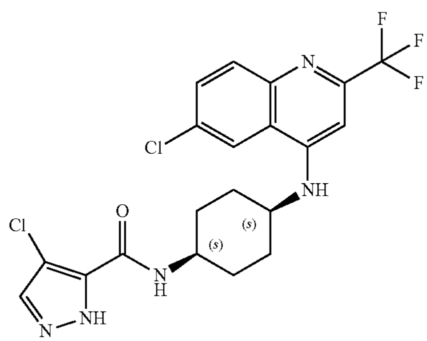 [SMILES: O=C(N[C@H]1CC[C@@H](Nc2cc(C(F)(F)F)nc3ccc(Cl)cc23)CC1)c1[nH]ncc1Cl] | 4-106 | 0.87 | 472.29 | 472 | [M + H]⁺ | Method 1 |
| 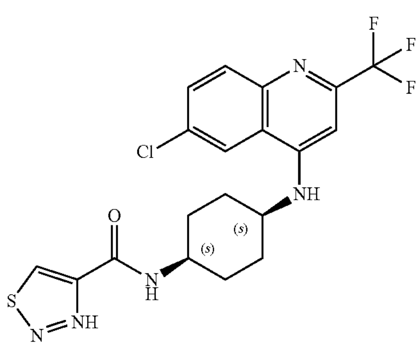 [SMILES: O=C(N[C@H]1CC[C@@H](Nc2cc(C(F)(F)F)nc3ccc(Cl)cc23)CC1)c1csnn1] | 4-107 | 0.891 | 455.88 | 456 | [M + H]⁺ | Method 1 |
| 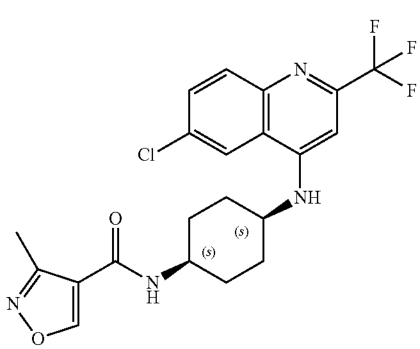 [SMILES: Cc1nocc1C(=O)N[C@H]1CC[C@@H](Nc2cc(C(F)(F)F)nc3ccc(Cl)cc23)CC1] | 4-108 | 0.884 | 452.86 | 453.1 | [M + H]⁺ | Method 1 |

TABLE 4-continued

| Structure | Cpd No. | Purity RT | MW | m/z | Ion | Purity Method |
|---|---|---|---|---|---|---|
| 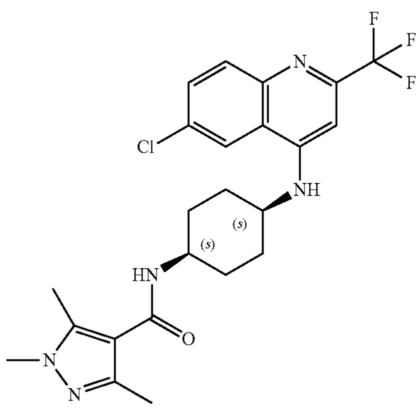 [SMILES: Cc1nn(C)c(C)c1C(=O)N[C@H]1CC[C@@H](Nc2cc(C(F)(F)F)nc3ccc(Cl)cc23)CC1] | 4-109 | 0.913 | 479.93 | 480.3 | [M + H]⁺ | Method 1 |
| 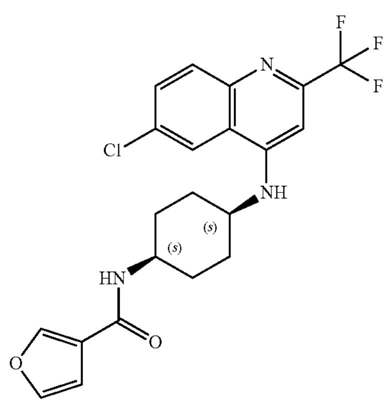 [SMILES: O=C(N[C@H]1CC[C@@H](Nc2cc(C(F)(F)F)nc3ccc(Cl)cc23)CC1)c1ccoc1] | 4-110 | 0.928 | 437.85 | 438.2 | [M + H]⁺ | Method 1 |
| 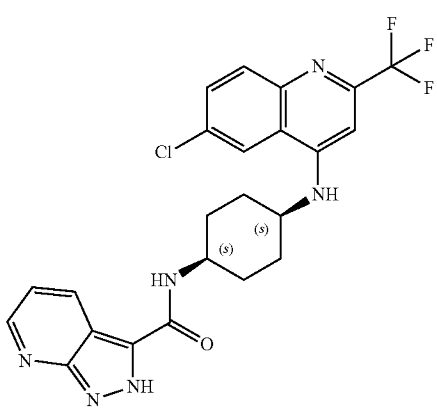 [SMILES: O=C(N[C@H]1CC[C@@H](Nc2cc(C(F)(F)F)nc3ccc(Cl)cc23)CC1)c1[nH]nc2ncccc12] | 4-111 | 0.913 | 488.9 | 489.3 | [M + H]⁺ | Method 2 |

TABLE 4-continued

| Structure | Cpd No. | Purity RT | MW | m/z | Ion | Purity Method |
|---|---|---|---|---|---|---|
| 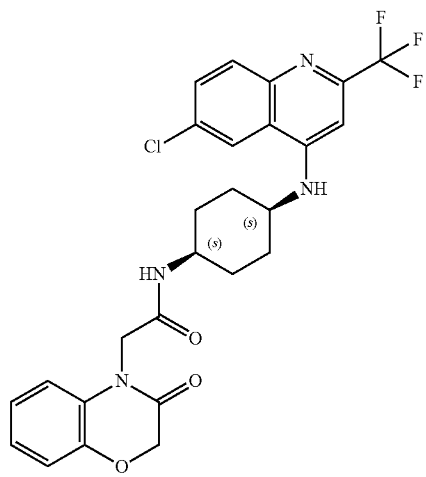 [SMILES: O=C(CN1C(=O)COc2ccccc21)N[C@H]1CC[C@@H](Nc2cc(C(F)(F)F)nc3ccc(Cl)cc23)CC1] | 4-112 | 0.933 | 532.95 | 533.1 | [M + H]⁺ | Method 2 |
| 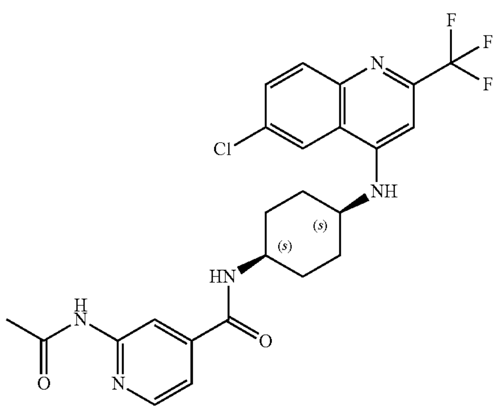 [SMILES: CC(=O)Nc1cc(C(=O)N[C@H]2CC[C@@H](Nc3cc(C(F)(F)F)nc4ccc(Cl)cc34)CC2)ccn1] | 4-113 | 0.875 | 505.93 | 506.1 | [M + H]⁺ | Method 2 |
| 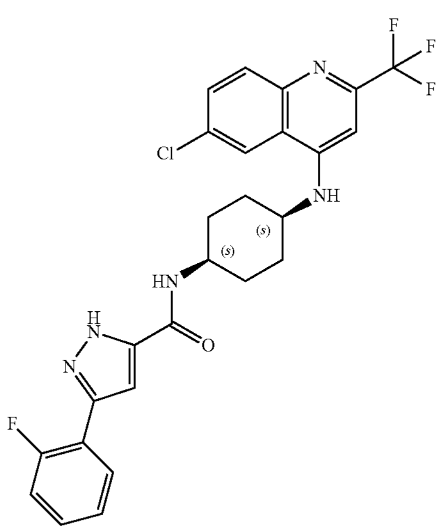 [SMILES: O=C(N[C@H]1CC[C@@H](Nc2cc(C(F)(F)F)nc3ccc(Cl)cc23)CC1)c1cc(-c2ccccc2F)n[nH]1] | 4-114 | 0.978 | 531.94 | 532.3 | [M + H]⁺ | Method 2 |

TABLE 4-continued

| Structure | Cpd No. | Purity RT | MW | m/z | Ion | Purity Method |
|---|---|---|---|---|---|---|
| 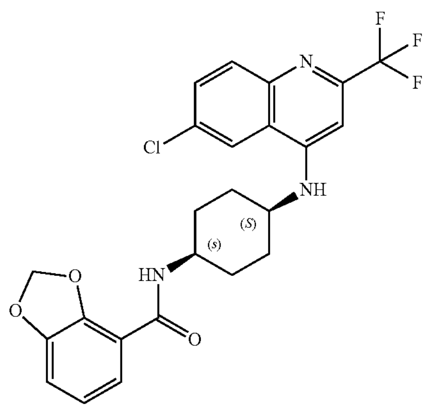 | 4-115 | 0.983 | 491.9 | 492.1 | [M + H]⁺ | Method 2 |
| 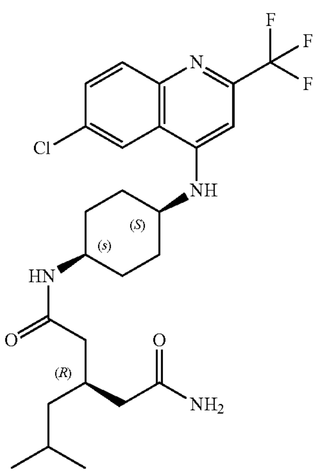 | 4-116 | 0.9 | 513 | 513.2 | [M + H]⁺ | Method 2 |
| 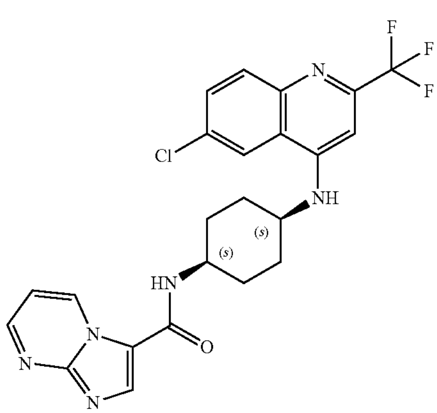 [SMILES: O=C(N[C@H]1CC[C@@H](Nc2cc(C(F)(F)F)nc3ccc(Cl)cc23)CC1)c1cnc2ncccn12] | 4-117 | 0.875 | 488.9 | 489.1 | [M + H]⁺ | Method 2 |

TABLE 4-continued

| Structure | Cpd No. | Purity RT | MW | m/z | Ion | Purity Method |
|---|---|---|---|---|---|---|
| 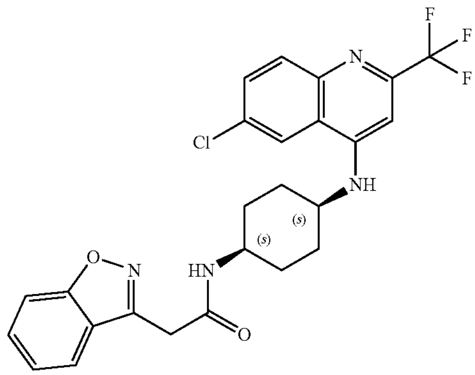 [SMILES: O=C(Cc1noc2ccccc12)N[C@H]1CC[C@@H](Nc2cc(C(F)(F)F)nc3ccc(Cl)cc23)CC1] | 4-118 | 0.95 | 502.92 | 503.1 | [M + H]+ | Method 2 |
| 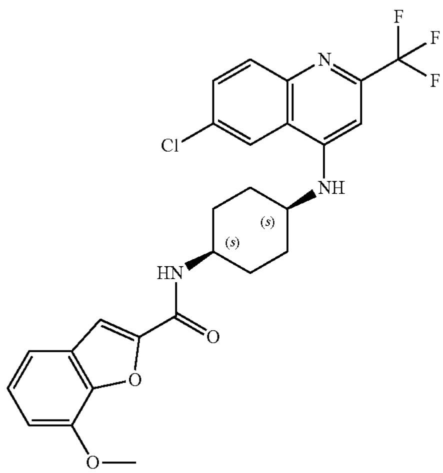 [SMILES: COc1cccc2cc(C(=O)N[C@H]3CC[C@@H](Nc4cc(C(F)(F)F)nc5ccc(Cl)cc45)CC3)oc12] | 4-119 | 1.008 | 517.93 | 518.1 | [M + H]+ | Method 2 |
| 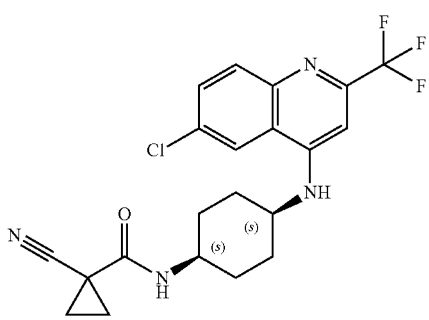 [SMILES: N#CC1(C(=O)N[C@H]2CC[C@@H](Nc3cc(C(F)(F)F)nc4ccc(Cl)cc34)CC2)CC1] | 4-120 | 0.933 | 436.86 | 437.1 | [M + H]+ | Method 2 |
| 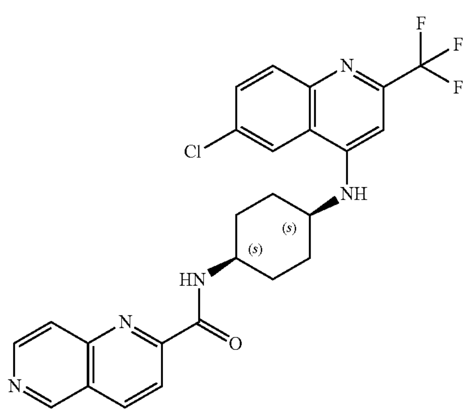 [SMILES: O=C(N[C@H]1CC[C@@H](Nc2cc(C(F)(F)F)nc3ccc(Cl)cc23)CC1)c1ccc2cnccc2n1] | 4-121 | 0.9 | 499.92 | 500.1 | [M + H]+ | Method 2 |

TABLE 4-continued

| Structure | Cpd No. | Purity RT | MW | m/z | Ion | Purity Method |
|---|---|---|---|---|---|---|
| 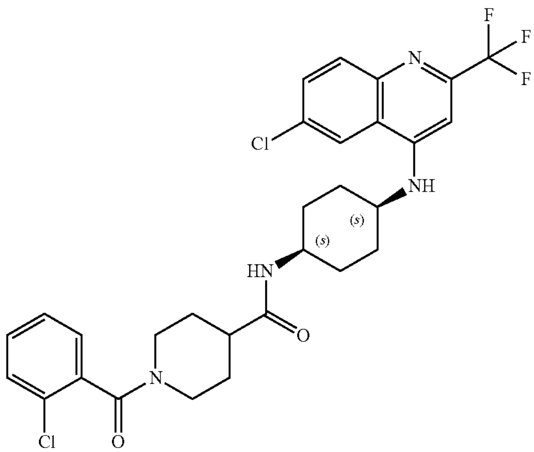 [SMILES: O=C(N[C@H]1CC[C@@H](Nc2cc(C(F)(F)F)nc3ccc(Cl)cc23)CC1)C1CCN(C(=O)c2ccccc2Cl)CC1] | 4-122 | 0.933 | 593.47 | 593.1 | [M + H]⁺ | Method 2 |
| 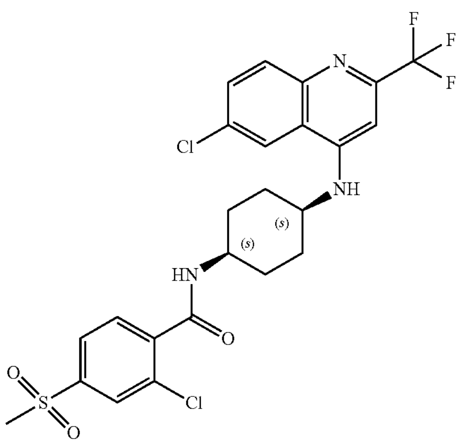 [SMILES: CS(=O)(=O)c1ccc(C(=O)N[C@H]2CC[C@@H](Nc3cc(C(F)(F)F)nc4ccc(Cl)cc34)CC2)c(Cl)c1] | 4-123 | 0.925 | 560.41 | 560.1 | [M + H]⁺ | Method 2 |
| 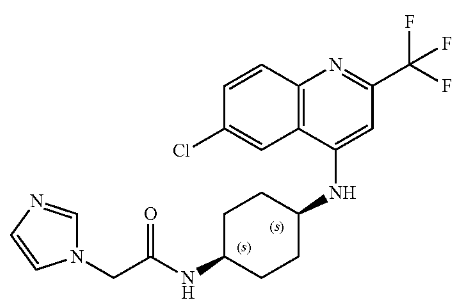 [SMILES: O=C(Cn1ccnc1)N[C@H]1CC[C@@H](Nc2cc(C(F)(F)F)nc3ccc(Cl)cc23)CC1] | 4-124 | 0.789 | 451.88 | 452.1 | [M + H]⁺ | Method 2 |
| 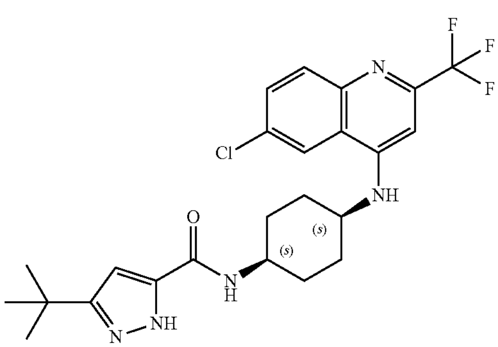 [SMILES: CC(C)(C)c1cc(C(=O)N[C@H]2CC[C@@H](Nc3cc(C(F)(F)F)nc4ccc(Cl)cc34)CC2)[nH]n1] | 4-125 | 0.947 | 493.96 | 494.2 | [M + H]⁺ | Method 2 |

TABLE 4-continued

| Structure | Cpd No. | Purity RT | MW | m/z | Ion | Purity Method |
|---|---|---|---|---|---|---|
| 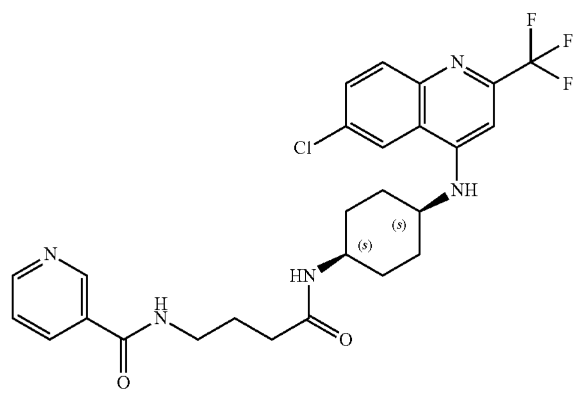 [SMILES: O=C(CCCNC(=O)c1cccnc1)N[C@H]1CC[C@@H](Nc2cc(C(F)(F)F)nc3ccc(Cl)cc23)CC1] | 4-126 | 0.822 | 533.98 | 534.2 | [M + H]+ | Method 2 |
| 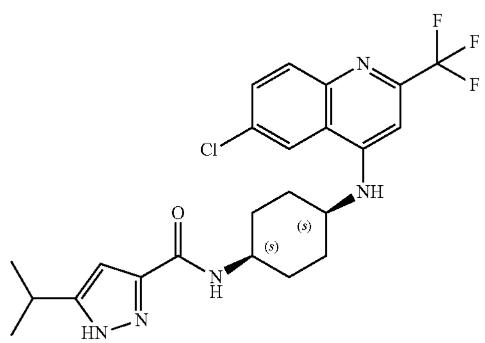 [SMILES: CC(C)c1cc(C(=O)N[C@H]2CC[C@@H](Nc3cc(C(F)(F)F)nc4ccc(Cl)cc34)CC2)n[nH]1] | 4-127 | 0.932 | 479.93 | 480.1 | [M + H]+ | Method 2 |
| 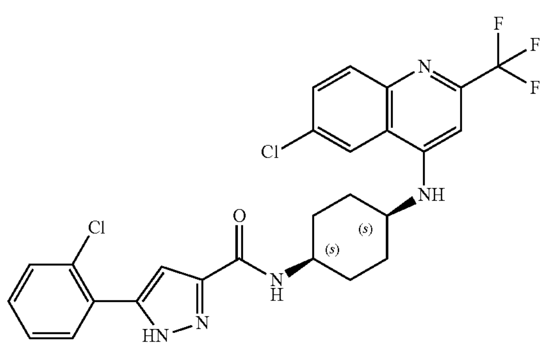 [SMILES: O=C(N[C@H]1CC[C@@H](Nc2cc(C(F)(F)F)nc3ccc(Cl)cc23)CC1)c1cc(-c2ccccc2Cl)[nH]n1] | 4-128 | 0.983 | 548.39 | 548.1 | [M + H]+ | Method 2 |
| 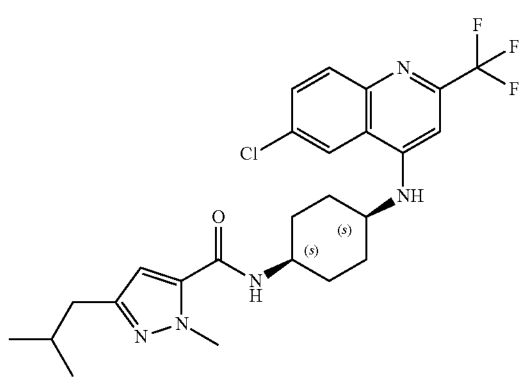 [SMILES: CC(C)Cc1cc(C(=O)N[C@H]2CC[C@@H](Nc3cc(C(F)(F)F)nc4ccc(Cl)cc34)CC2)n(C)n1] | 4-129 | 0.99 | 507.99 | 508.2 | [M + H]+ | Method 2 |

TABLE 4-continued

| Structure | Cpd No. | Purity RT | MW | m/z | Ion | Purity Method |
|---|---|---|---|---|---|---|
| 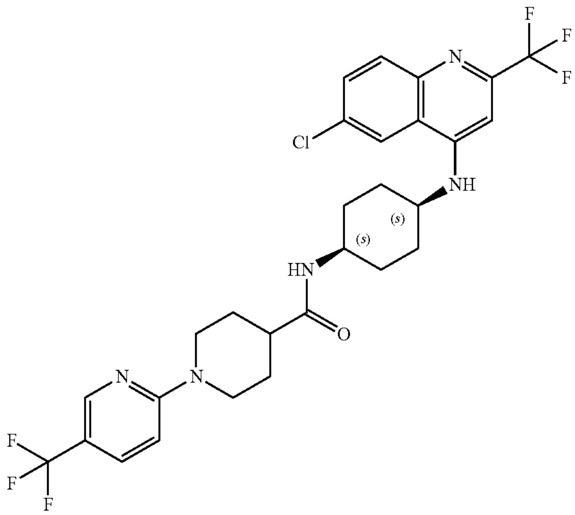 [SMILES: O=C(N[C@H]1CC[C@@H](Nc2cc(C(F)(F)F)nc3ccc(Cl)cc23)CC1)C1CCN(c2ccc(C(F)(F)F)cn2)CC1] | 4-130 | 0.958 | 600.01 | 600.2 | [M + H]+ | Method 2 |
| 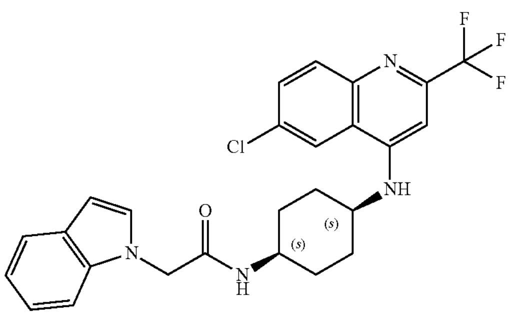 [SMILES: O=C(Cn1ccc2ccccc21)N[C@H]1CC[C@@H](Nc2cc(C(F)(F)F)nc3ccc(Cl)cc23)CC1] | 4-131 | 0.975 | 500.95 | 501.1 | [M + H]+ | Method 2 |
| 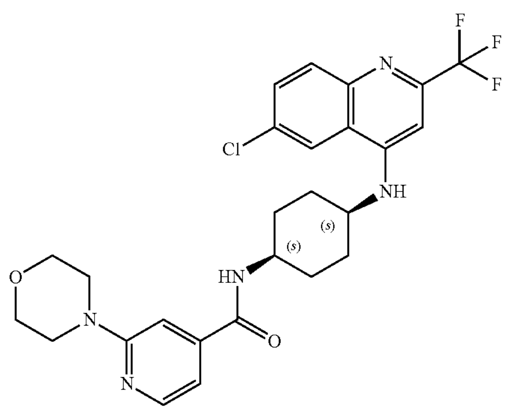 [SMILES: O=C(N[C@H]1CC[C@@H](Nc2cc(C(F)(F)F)nc3ccc(Cl)cc23)CC1)c1ccnc(N2CCOCC2)c1] | 4-132 | 0.839 | 533.98 | 534.2 | [M + H]+ | Method 2 |
| 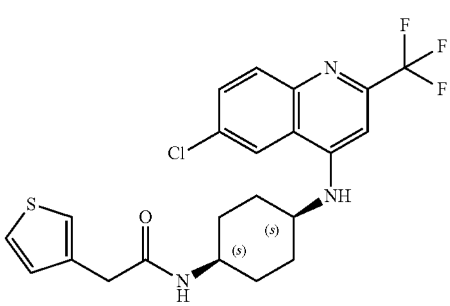 [SMILES: O=C(Cc1ccsc1)N[C@H]1CC[C@@H](Nc2cc(C(F)(F)F)nc3ccc(Cl)cc23)CC1] | 4-133 | 0.93 | 467.94 | 468.1 | [M + H]+ | Method 2 |

TABLE 4-continued

| Structure | Cpd No. | Purity RT | MW | m/z | Ion | Purity Method |
|---|---|---|---|---|---|---|
| 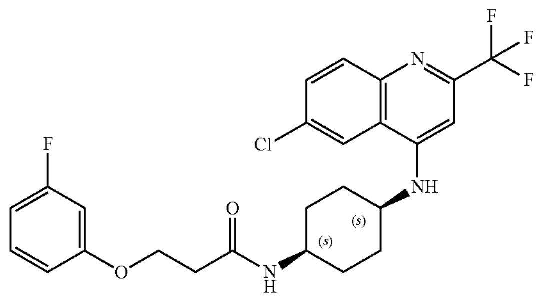 [SMILES: O=C(CCOc1cccc(F)c1)N[C@H]1CC[C@@H](Nc2cc(C(F)(F)F)nc3ccc(Cl)cc23)CC1] | 4-134 | 0.967 | 509.93 | 510.1 | [M + H]⁺ | Method 2 |
| 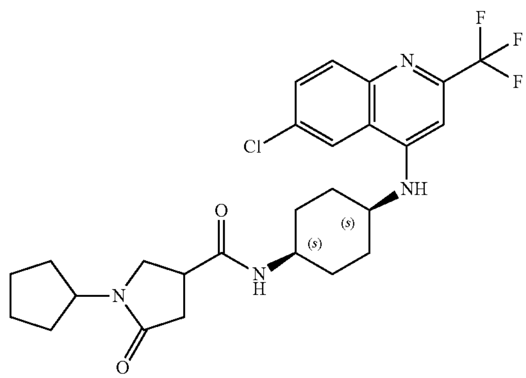 [SMILES: O=C(N[C@H]1CC[C@@H](Nc2cc(C(F)(F)F)nc3ccc(Cl)cc23)CC1)C1CC(=O)N(C2CCCC2)C1] | 4-135 | 0.912 | 523 | 523.2 | [M + H]⁺ | Method 2 |
| 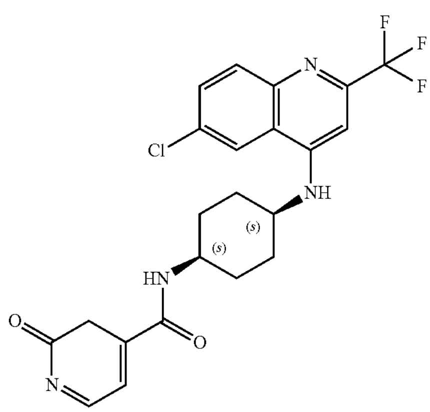 [SMILES: O=C1CC(C(=O)N[C@H]2CC[C@@H](Nc3cc(C(F)(F)F)nc4ccc(Cl)cc34)CC2)=CC=N1] | 4-136 | 0.844 | 464.87 | 465.1 | [M + H]⁺ | Method 2 |
| 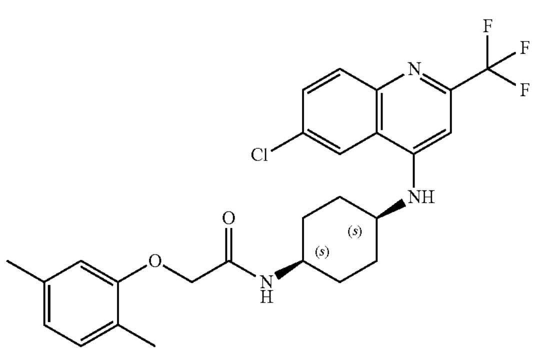 [SMILES: Cc1ccc(C)c(OCC(=O)N[C@H]2CC[C@@H](Nc3cc(C(F)(F)F)nc4ccc(Cl)cc34)CC2)c1] | 4-137 | 1.047 | 505.97 | 506.1 | [M + H]⁺ | Method 2 |

TABLE 4-continued

| Structure | Cpd No. | Purity RT | MW | m/z | Ion | Purity Method |
|---|---|---|---|---|---|---|
| 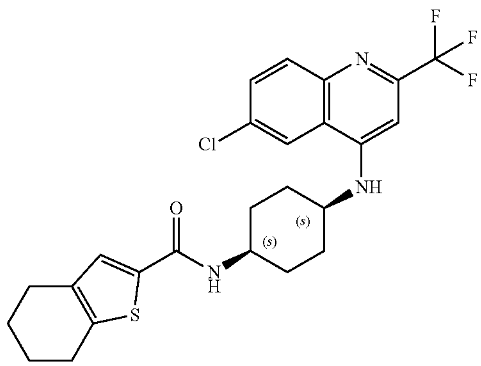 [SMILES: O=C(N[C@H]1CC[C@@H](Nc2cc(C(F)(F)F)nc3ccc(Cl)cc23)CC1)c1cc2c(s1)CCCC2] | 4-138 | 1.038 | 508 | 508.1 | [M + H]+ | Method 2 |
| 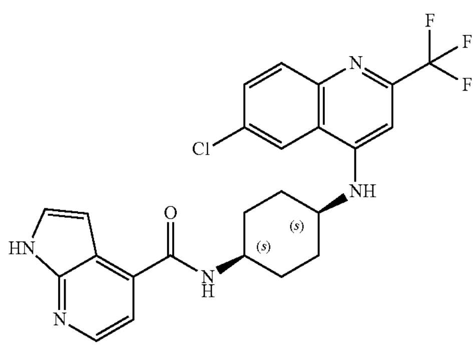 [SMILES: O=C(N[C@H]1CC[C@@H](Nc2cc(C(F)(F)F)nc3ccc(Cl)cc23)CC1)c1ccnc2[nH]ccc12] | 4-139 | 0.884 | 487.91 | 488.1 | [M + H]+ | Method 2 |
| 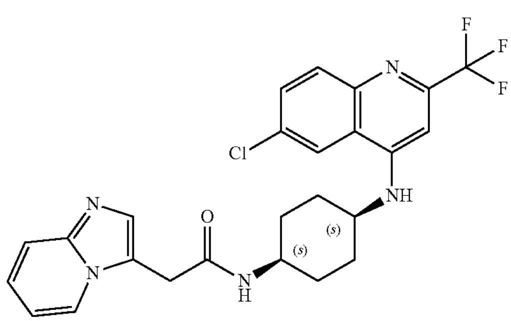 [SMILES: O=C(Cc1cnc2ccccn12)N[C@H]1CC[C@@H](Nc2cc(C(F)(F)F)nc3ccc(Cl)cc23)CC1] | 4-140 | 0.805 | 501.94 | 502.1 | [M + H]+ | Method 2 |
| 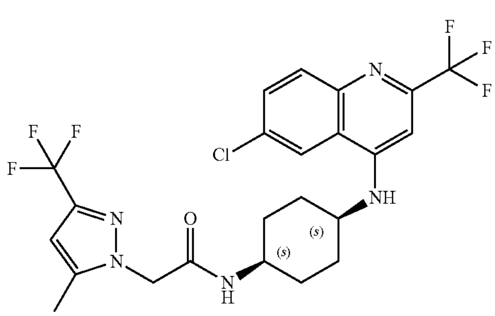 [SMILES: Cc1cc(C(F)(F)F)nn1CC(=O)N[C@H]1CC[C@@H](Nc2cc(C(F)(F)F)nc3ccc(Cl)cc23)CC1] | 4-141 | 0.967 | 533.9 | 534.1 | [M + H]+ | Method 2 |

TABLE 4-continued

| Structure | Cpd No. | Purity RT | MW | m/z | Ion | Purity Method |
|---|---|---|---|---|---|---|
| 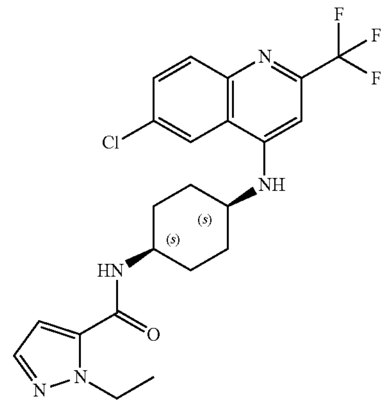 [SMILES: CCn1nccc1C(=O)N[C@H]1CC[C@@H](Nc2cc(C(F)(F)F)nc3ccc(Cl)cc23)CC1] | 4-142 | 0.831 | 465.91 | 466.1 | [M + H]+ | Method 2 |
| 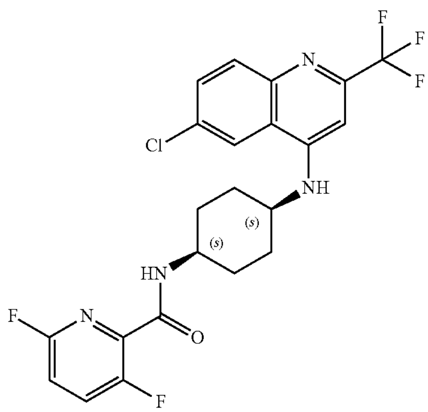 [SMILES: O=C(N[C@H]1CC[C@@H](Nc2cc(C(F)(F)F)nc3ccc(Cl)cc23)CC1)c1nc(F)ccc1F] | 4-143 | 0.843 | 484.86 | 485 | [M + H]+ | Method 2 |
| 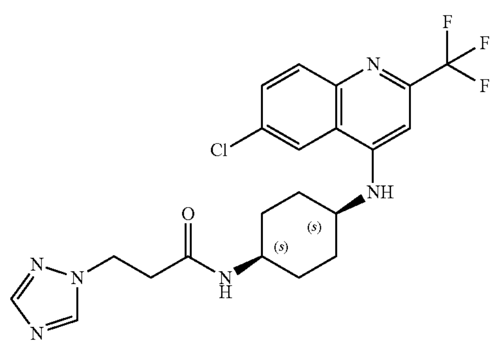 [SMILES: O=C(CCn1cncn1)N[C@H]1CC[C@@H](Nc2cc(C(F)(F)F)nc3ccc(Cl)cc23)CC1] | 4-144 | 0.739 | 466.89 | 467.1 | [M + H]+ | Method 2 |
| 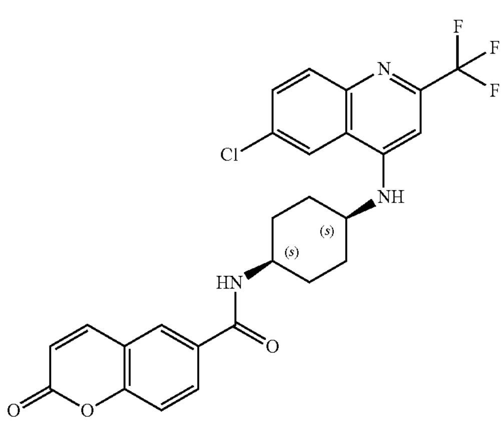 [SMILES: O=C(N[C@H]1CC[C@@H](Nc2cc(C(F)(F)F)nc3ccc(Cl)cc23)CC1)c1ccc2oc(=O)ccc2c1] | 4-145 | 0.827 | 515.92 | 516.1 | [M + H]+ | Method 2 |

TABLE 4-continued

| Structure | Cpd No. | Purity RT | MW | m/z | Ion | Purity Method |
|---|---|---|---|---|---|---|
| 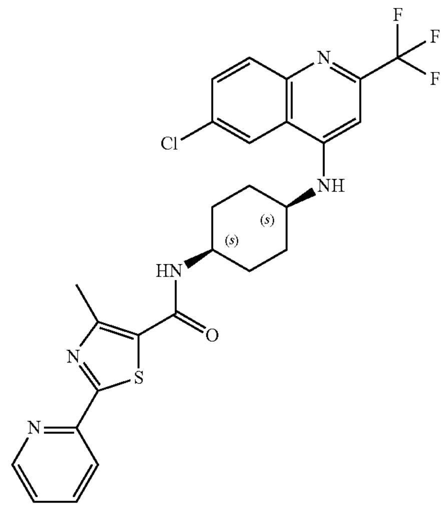 [SMILES: Cc1nc(-c2ccccn2)sc1C(=O)N[C@H]1CC[C@@H](Nc2cc(C(F)(F)F)nc3ccc(Cl)cc23)CC1] | 4-146 | 0.88 | 546.01 | 546 | [M + H]⁺ | Method 2 |
| 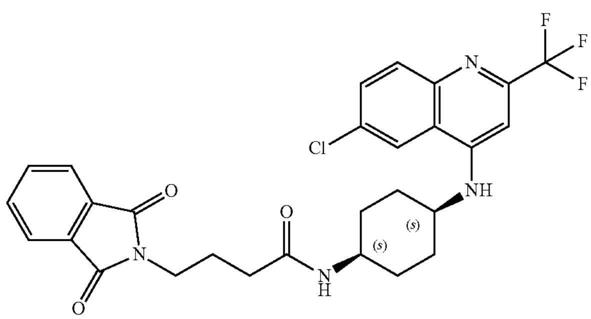 [SMILES: O=C(CCCN1C(=O)c2ccccc2C1=O)N[C@H]1CC[C@@H](Nc2cc(C(F)(F)F)nc3ccc(Cl)cc23)CC1] | 4-147 | 0.84 | 558.99 | 559.1 | [M + H]⁺ | Method 2 |
| 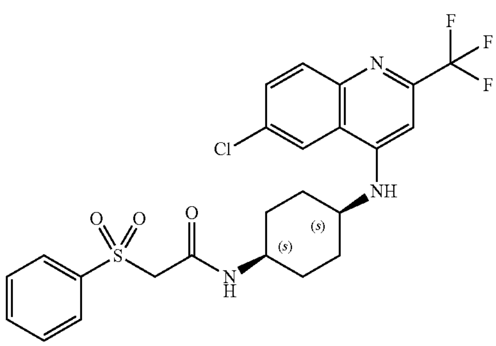 [SMILES: O=C(CS(=O)(=O)c1ccccc1)N[C@H]1CC[C@@H](Nc2cc(C(F)(F)F)nc3ccc(Cl)cc23)CC1] | 4-148 | 0.832 | 525.97 | 526 | [M + H]⁺ | Method 2 |
| 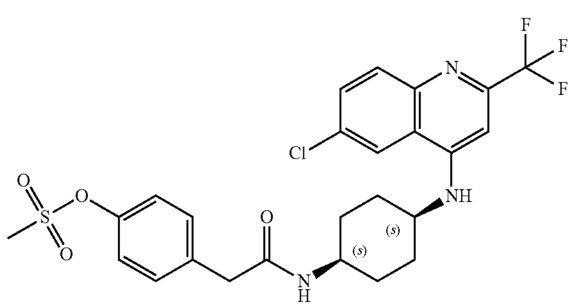 [SMILES: CS(=O)(=O)Oc1ccc(CC(=O)N[C@H]2CC[C@@H](Nc3cc(C(F)(F)F)nc4ccc(Cl)cc34)CC2)cc1] | 4-149 | 0.83 | 556 | 556 | [M + H]⁺ | Method 2 |

TABLE 4-continued

| Structure | Cpd No. | Purity RT | MW | m/z | Ion | Purity Method |
|---|---|---|---|---|---|---|
| 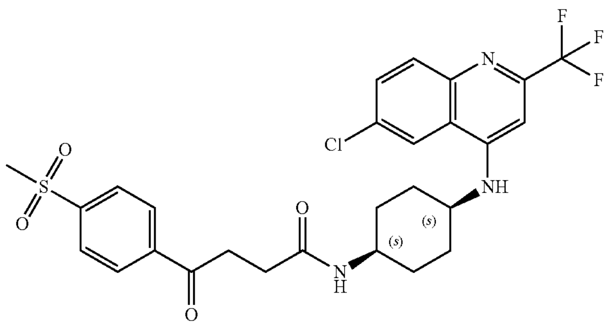 [SMILES: CS(=O)(=O)c1ccc(C(=O)CCC(=O)N[C@H]2CC[C@@H](Nc3cc(C(F)(F)F)nc4ccc(Cl)cc34)CC2)cc1] | 4-150 | 0.811 | 582.04 | 582 | [M + H]⁺ | Method 2 |
| 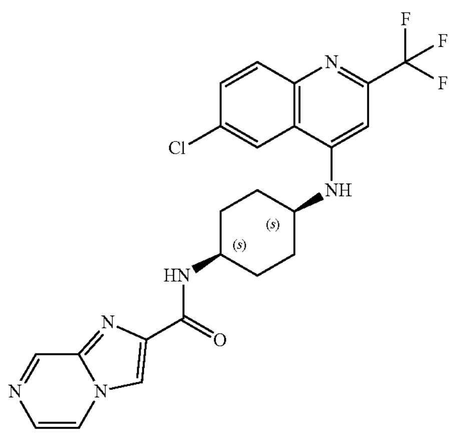 [SMILES: O=C(N[C@H]1CC[C@@H](Nc2cc(C(F)(F)F)nc3ccc(Cl)cc23)CC1)c1cn2ccncc2n1] | 4-151 | 0.798 | 488.9 | 489 | [M + H]⁺ | Method 2 |
| 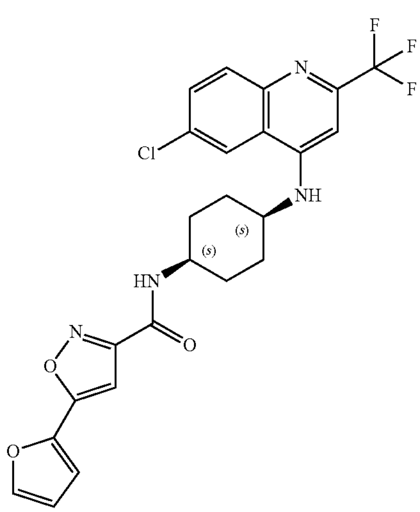 [SMILES: O=C(N[C@H]1CC[C@@H](Nc2cc(C(F)(F)F)nc3ccc(Cl)cc23)CC1)c1cc(-c2ccco2)on1] | 4-152 | 0.9 | 504.89 | 505 | [M + H]⁺ | Method 2 |

TABLE 4-continued

| Structure | Cpd No. | Purity RT | MW | m/z | Ion | Purity Method |
|---|---|---|---|---|---|---|
| 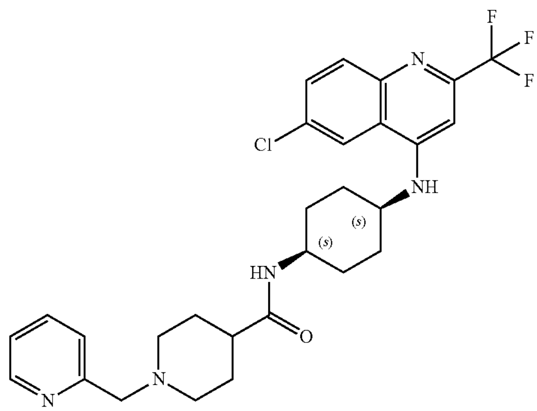 [SMILES: O=C(N[C@H]1CC[C@@H](Nc2cc(C(F)(F)F)nc3ccc(Cl)cc23)CC1)C1CCN(Cc2ccccn2)CC1] | 4-153 | 0.714 | 546.04 | 546 | [M + H]⁺ | Method 2 |
| 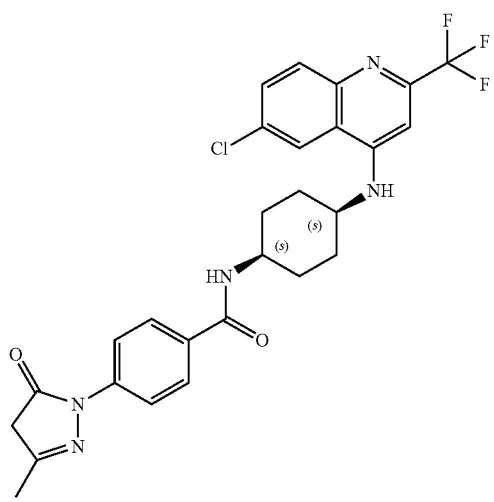 [SMILES: CC1=NN(c2ccc(C(=O)N[C@H]3CC[C@@H](Nc4cc(C(F)(F)F)nc5ccc(Cl)cc45)CC3)cc2)C(=O)C1] | 4-154 | 0.916 | 543.98 | 544.3 | [M + H]⁺ | Method 2 |
| 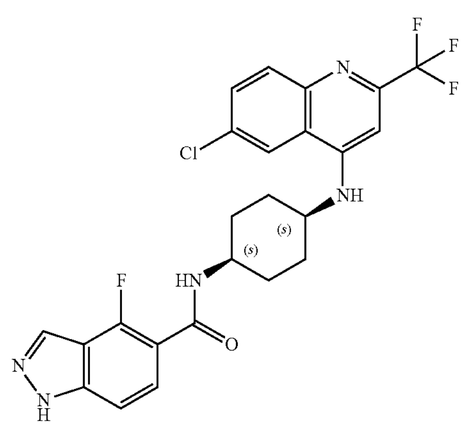 [SMILES: O=C(N[C@H]1CC[C@@H](Nc2cc(C(F)(F)F)nc3ccc(Cl)cc23)CC1)c1ccc2[nH]ncc2c1F] | 4-155 | 0.94 | 505.9 | 506.3 | [M + H]⁺ | Method 2 |

TABLE 4-continued

| Structure | Cpd No. | Purity RT | MW | m/z | Ion | Purity Method |
|---|---|---|---|---|---|---|
| 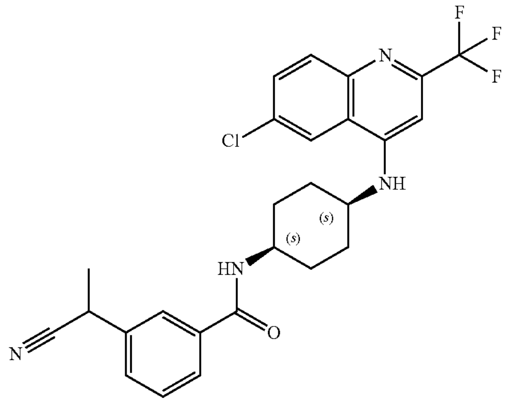 [SMILES: CC(C#N)c1cccc(C(=O)N[C@H]2CC[C@@H](Nc3cc(C(F)(F)F)nc4ccc(Cl)cc34)CC2)c1] | 4-156 | 0.966 | 500.95 | 501.3 | [M + H]⁺ | Method 2 |
| 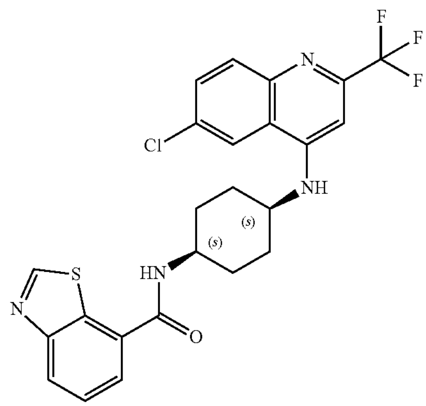 [SMILES: O=C(N[C@H]1CC[C@@H](Nc2cc(C(F)(F)F)nc3ccc(Cl)cc23)CC1)c1cccc2ncsc12] | 4-157 | 0.964 | 504.96 | 505.3 | [M + H]⁺ | Method 2 |
| 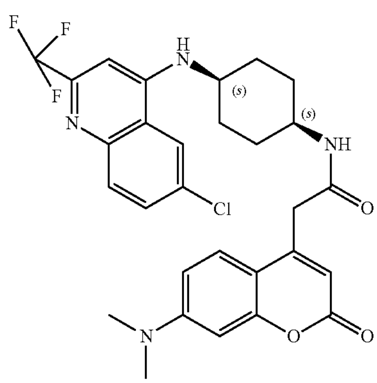 [SMILES: CN(C)c1ccc2c(CC(=O)N[C@H]3CC[C@@H](Nc4cc(C(F)(F)F)nc5ccc(Cl)cc45)CC3)cc(=O)oc2c1] | 4-158 | 0.957 | 573.01 | 573.4 | [M + H]⁺ | Method 2 |
| 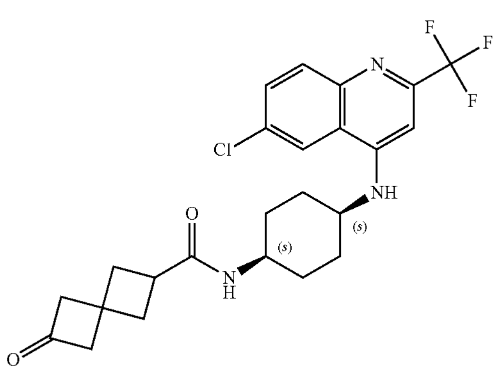 [SMILES: O=C1CC2(C1)CC(C(=O)N[C@H]1CC[C@@H](Nc3cc(C(F)(F)F)nc4ccc(Cl)cc34)CC1)C2] | 4-159 | 0.905 | 479.93 | 480.3 | [M + H]⁺ | Method 2 |

TABLE 4-continued

| Structure | Cpd No. | Purity RT | MW | m/z | Ion | Purity Method |
|---|---|---|---|---|---|---|
| 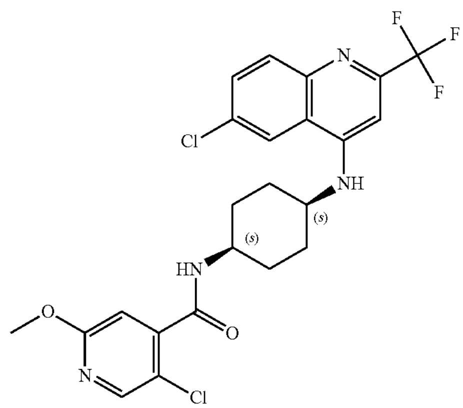 [SMILES: COc1cc(C(=O)N[C@H]2CC[C@@H](Nc3cc(C(F)(F)F)nc4ccc(Cl)cc34)CC2)c(Cl)cn1] | 4-160 | 0.963 | 513.34 | 513.3 | [M + H]⁺ | Method 2 |
| 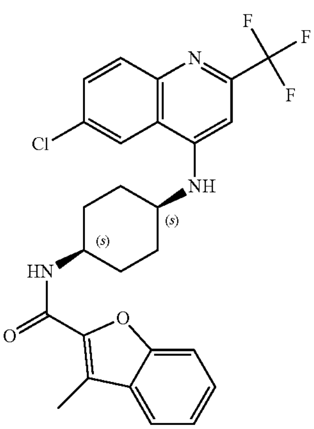 [SMILES: Cc1c(C(=O)N[C@H]2CC[C@@H](Nc3cc(C(F)(F)F)nc4ccc(Cl)cc34)CC2)oc2ccccc12] | 4-161 | 1.045 | 501.93 | 502.3 | [M + H]⁺ | Method 2 |
| 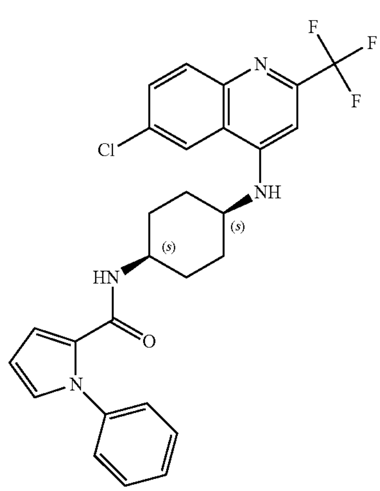 [SMILES: O=C(N[C@H]1CC[C@@H](Nc2cc(C(F)(F)F)nc3ccc(Cl)cc23)CC1)c1cccn1-c1ccccc1] | 4-162 | 0.996 | 512.96 | 513.3 | [M + H]⁺ | Method 2 |

TABLE 4-continued

| Structure | Cpd No. | Purity RT | MW | m/z | Ion | Purity Method |
|---|---|---|---|---|---|---|
| 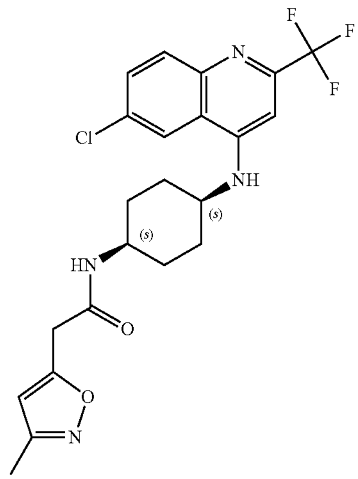 [SMILES: Cc1cc(CC(=O)N[C@H]2CC[C@@H](Nc3cc(C(F)(F)F)nc4ccc(Cl)cc34)CC2)on1] | 4-163 | 0.901 | 466.89 | 467.3 | [M + H]⁺ | Method 2 |
| 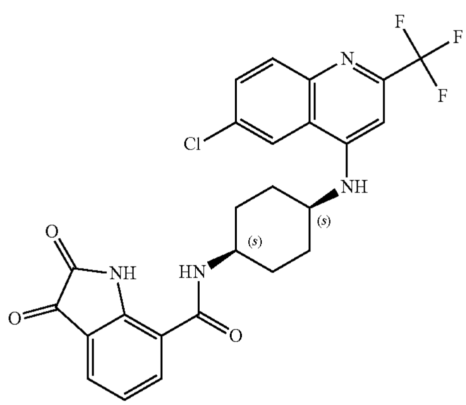 [SMILES: O=C1Nc2c(C(=O)N[C@H]3CC[C@@H](Nc4cc(C(F)(F)F)nc5ccc(Cl)cc45)CC3)cccc2C1=O] | 4-164 | 0.925 | 516.91 | 517.3 | [M + H]⁺ | Method 2 |
| 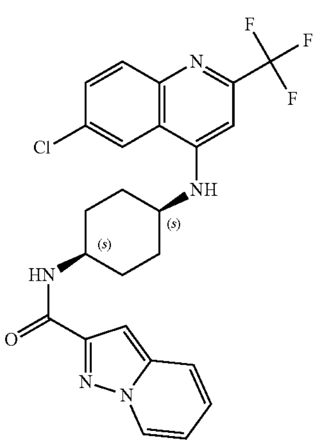 [SMILES: O=C(N[C@H]1CC[C@@H](Nc2cc(C(F)(F)F)nc3ccc(Cl)cc23)CC1)c1cc2ccccn2n1] | 4-165 | 0.959 | 487.91 | 488.2 | [M + H]⁺ | Method 2 |

TABLE 4-continued

| Structure | Cpd No. | Purity RT | MW | m/z | Ion | Purity Method |
|---|---|---|---|---|---|---|
| 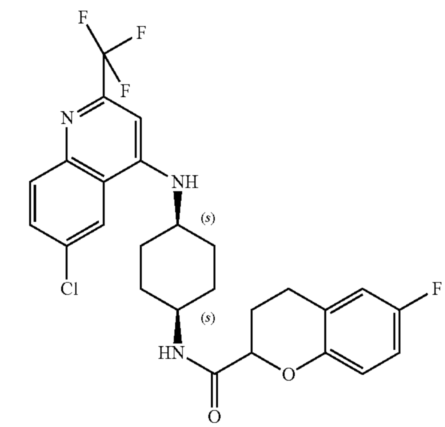 [SMILES: O=C(N[C@H]1CC[C@@H](Nc2cc(C(F)(F)F)nc3ccc(Cl)cc23)CC1)C1CCc2cc(F)ccc2O1] | 4-166 | 1.015 | 521.94 | 522.3 | [M + H]⁺ | Method 2 |
| 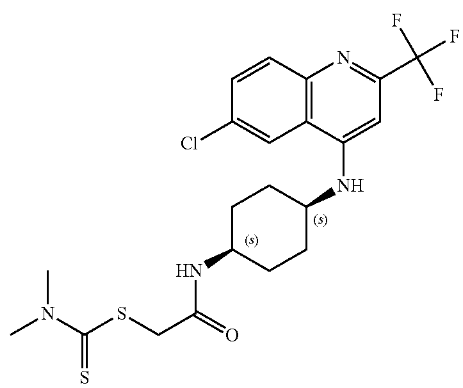 [SMILES: CN(C)C(=S)SCC(=O)N[C@H]1CC[C@@H](Nc2cc(C(F)(F)F)nc3ccc(Cl)cc23)CC1] | 4-167 | 0.942 | 505.02 | 505.3 | [M + H]⁺ | Method 2 |
| 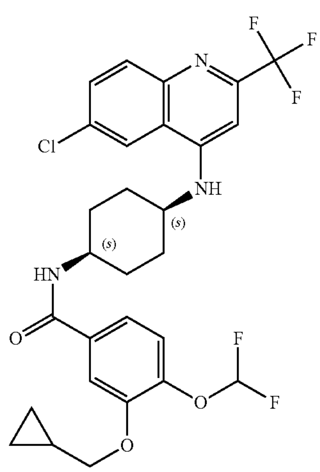 [SMILES: O=C(N[C@H]1CC[C@@H](Nc2cc(C(F)(F)F)nc3ccc(Cl)cc23)CC1)c1ccc(OC(F)F)c(OCC2CC2)c1] | 4-168 | 1.044 | 583.98 | 584.4 | [M + H]⁺ | Method 2 |

TABLE 4-continued

| Structure | Cpd No. | Purity RT | MW | m/z | Ion | Purity Method |
|---|---|---|---|---|---|---|
| 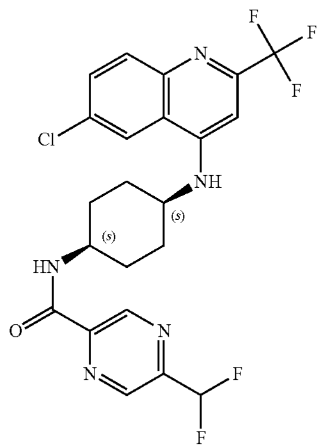 [SMILES: O=C(N[C@H]1CC[C@@H](Nc2cc(C(F)(F)F)nc3ccc(Cl)cc23)CC1)c1cnc(C(F)F)cn1] | 4-169 | 0.975 | 499.87 | 500.3 | [M + H]⁺ | Method 2 |
| 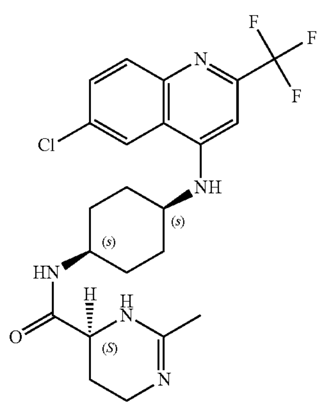 | 4-170 | 0.8 | 467.92 | 468.3 | [M + H]⁺ | Method 2 |
| 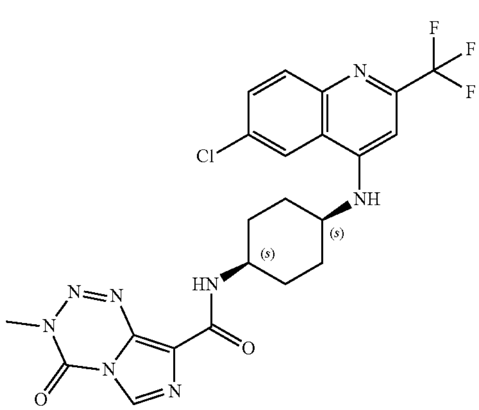 [SMILES: Cn1nnc2c(C(=O)N[C@H]3CC[C@@H](Nc4cc(C(F)(F)F)nc5ccc(Cl)cc45)CC3)ncn2c1=O] | 4-171 | 0.904 | 520.9 | 521.3 | [M + H]⁺ | Method 2 |

TABLE 4-continued

| Structure | Cpd No. | Purity RT | MW | m/z | Ion | Purity Method |
|---|---|---|---|---|---|---|
| 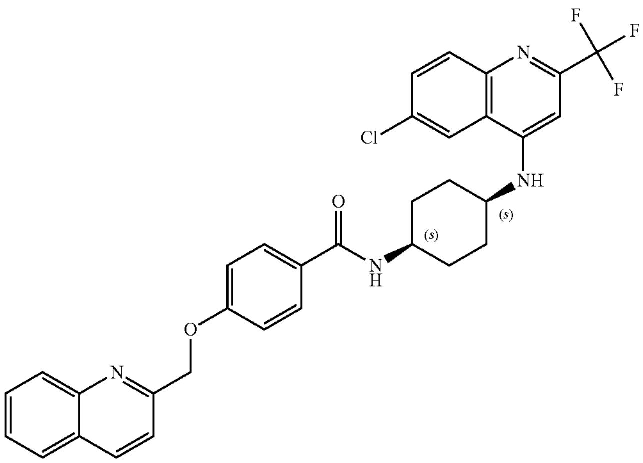 [SMILES: O=C(N[C@H]1CC[C@@H](Nc2cc(C(F)(F)F)nc3ccc(Cl)cc23)CC1)c1ccc(OCc2ccc3ccccc3n2)cc1] | 4-172 | 0.975 | 605.06 | 605.4 | [M + H]⁺ | Method 2 |
| 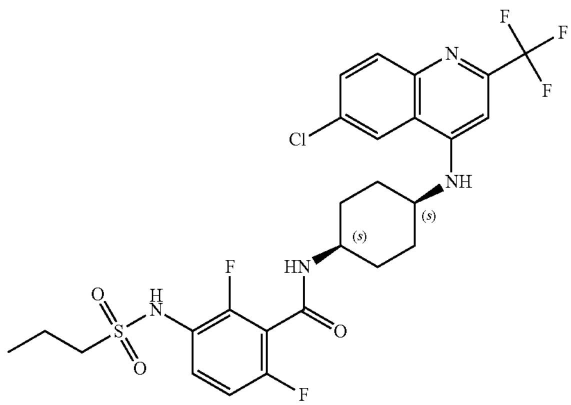 [SMILES: CCCS(=O)(=O)Nc1ccc(F)c(C(=O)N[C@H]2CC[C@@H](Nc3cc(C(F)(F)F)nc4ccc(Cl)cc34)CC2)c1F] | 4-173 | 0.963 | 605.02 | 605.3 | [M + H]⁺ | Method 2 |
| 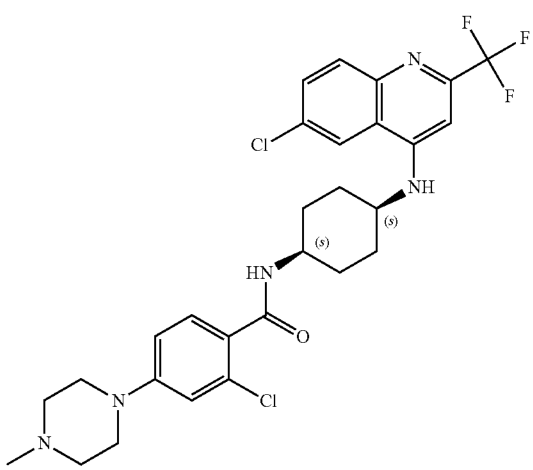 [SMILES: CN1CCN(c2ccc(C(=O)N[C@H]3CC[C@@H](Nc4cc(C(F)(F)F)nc5ccc(Cl)cc45)CC3)c(Cl)c2)CC1] | 4-174 | 0.884 | 580.48 | 580.2 | [M + H]⁺ | Method 2 |
| 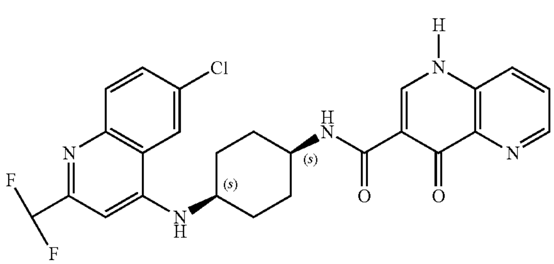 [SMILES: O=C(N[C@H]1CC[C@@H](Nc2cc(C(F)F)nc3ccc(Cl)cc23)CC1)c1c[nH]c2cccnc2c1=O] | 4-175 | 0.856 | 515.92 | 516.1 | [M + H]⁺ | Method 2 |

TABLE 4-continued

| Structure | Cpd No. | Purity RT | MW | m/z | Ion | Purity Method |
|---|---|---|---|---|---|---|
| 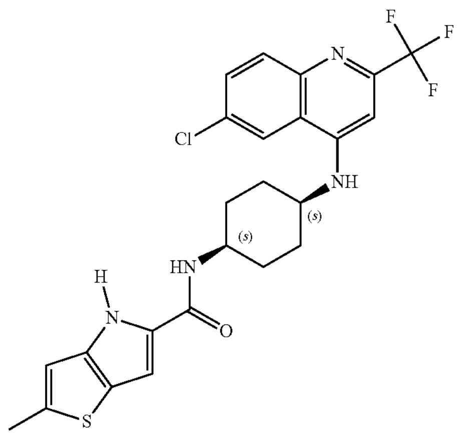 [SMILES: Cc1cc2[nH]c(C(=O)N[C@H]3CC[C@@H](Nc4cc(C(F)(F)F)nc5ccc(Cl)cc45)CC3)cc2s1] | 4-176 | 1.003 | 506.97 | 507.1 | [M + H]+ | Method 2 |
| 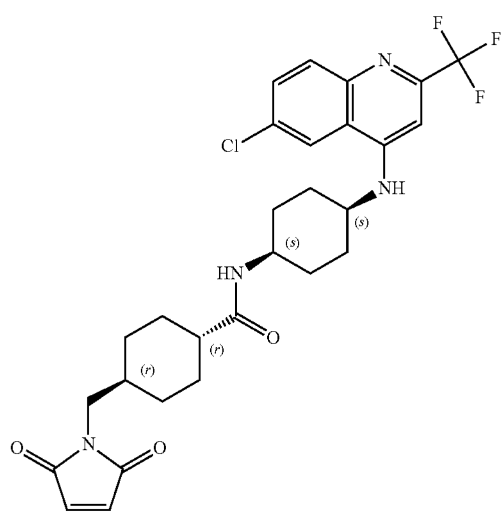 [SMILES: O=C1C=CC(=O)N1C[C@H]1CC[C@H](C(=O)N[C@H]2CC[C@@H](Nc3cc(C(F)(F)F)nc4ccc(Cl)cc34)CC2)CC1] | 4-177 | 0.956 | 563.02 | 563.2 | [M + H]+ | Method 2 |
| 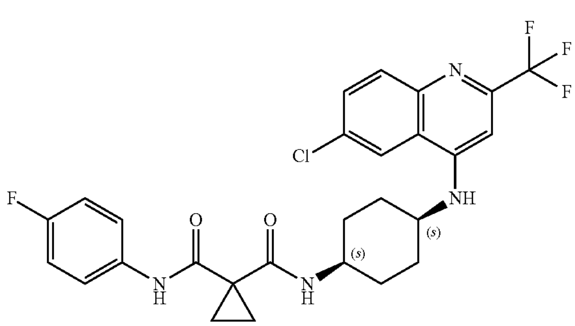 [SMILES: O=C(Nc1ccc(F)cc1)C1(C(=O)N[C@H]2CC[C@@H](Nc3cc(C(F)(F)F)nc4ccc(Cl)cc34)CC2)CC1] | 4-178 | 1.001 | 548.97 | 549.1 | [M + H]+ | Method 2 |

TABLE 4-continued

| Structure | Cpd No. | Purity RT | MW | m/z | Ion | Purity Method |
|---|---|---|---|---|---|---|
| 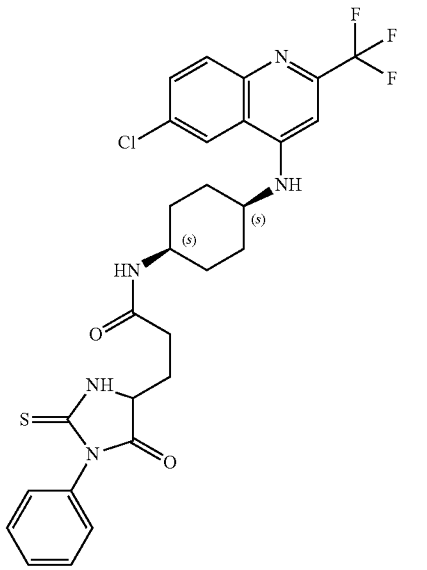 [SMILES: O=C(CCC1NC(=S)N(c2ccccc2)C1=O)N[C@H]1CC[C@@H](Nc2cc(C(F)(F)F)nc3ccc(Cl)cc23)CC1] | 4-179 | 0.943 | 590.06 | 590.1 | [M + H]+ | Method 2 |
| 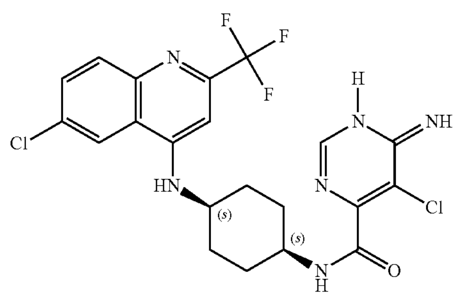 [SMILES: N=c1[nH]cnc(C(=O)N[C@H]2CC[C@@H](Nc3cc(C(F)(F)F)nc4ccc(Cl)cc34)CC2)c1Cl] | 4-180 | 0.878 | 499.32 | 499 | [M + H]+ | Method 2 |
| 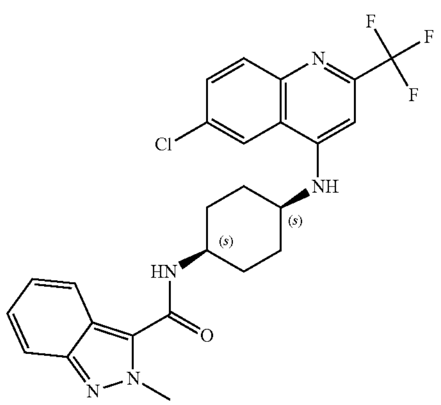 [SMILES: Cn1nc2ccccc2c1C(=O)N[C@H]1CC[C@@H](Nc2cc(C(F)(F)F)nc3ccc(Cl)cc23)CC1] | 4-181 | 0.973 | 501.94 | 502.1 | [M + H]+ | Method 2 |
| 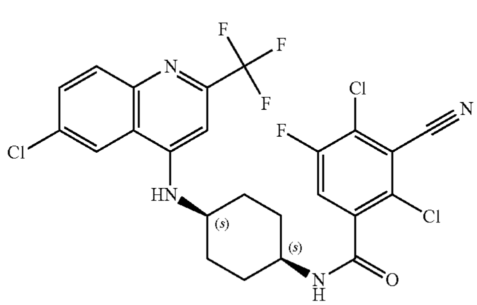 [SMILES: N#Cc1c(Cl)c(F)cc(C(=O)N[C@H]2CC[C@@H](Nc3cc(C(F)(F)F)nc4ccc(Cl)cc34)CC2)c1Cl] | 4-182 | 1.009 | 559.77 | 559.2 | [M + H]+ | Method 2 |

TABLE 4-continued

| Structure | Cpd No. | Purity RT | MW | m/z | Ion | Purity Method |
|---|---|---|---|---|---|---|
| 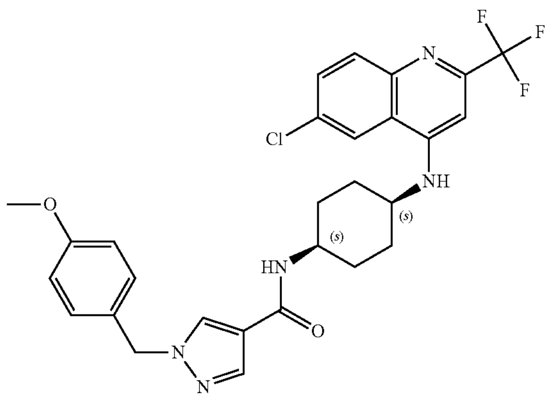 [SMILES: COc1ccc(Cn2cc(C(=O)N[C@H]3CC[C@@H](Nc4cc(C(F)(F)F)nc5ccc(Cl)cc45)CC3)cn2)cc1] | 4-183 | 0.977 | 558 | 558.3 | [M + H]+ | Method 2 |
| 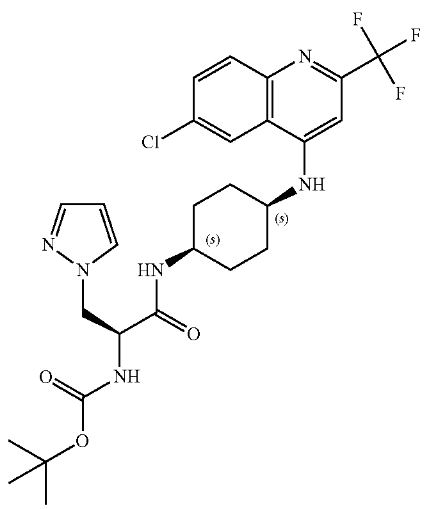 [SMILES: CC(C)(C)OC(=O)N[C@@H](Cn1cccn1)C(=O)N[C@H]1CC[C@@H](Nc2cc(C(F)(F)F)nc3ccc(Cl)cc23)CC1] | 4-184 | 0.983 | 581.04 | 581.4 | [M + H]+ | Method 2 |
| 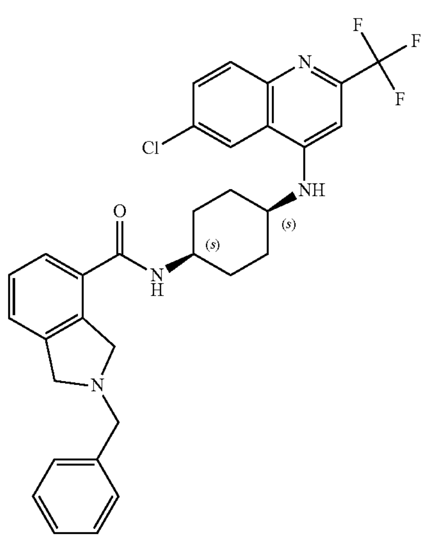 [SMILES: O=C(N[C@H]1CC[C@@H](Nc2cc(C(F)(F)F)nc3ccc(Cl)cc23)CC1)c1cccc2c1CN(Cc1ccccc1)C2] | 4-185 | 0.879 | 579.06 | 579.4 | [M + H]+ | Method 2 |

TABLE 4-continued

| Structure | Cpd No. | Purity RT | MW | m/z | Ion | Purity Method |
|---|---|---|---|---|---|---|
| 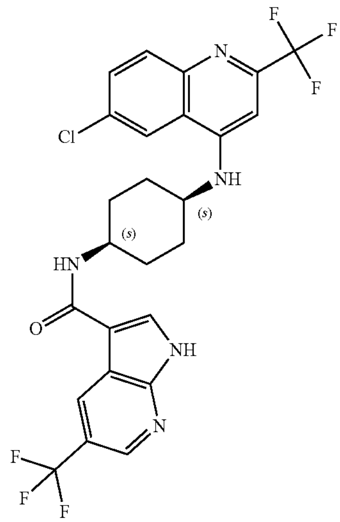 [SMILES: O=C(N[C@H]1CC[C@@H](Nc2cc(C(F)(F)F)nc3ccc(Cl)cc23)CC1)c1c[nH]c2ncc(C(F)(F)F)cc12] | 4-186 | 0.979 | 555.91 | 556.3 | [M + H]+ | Method 2 |
| 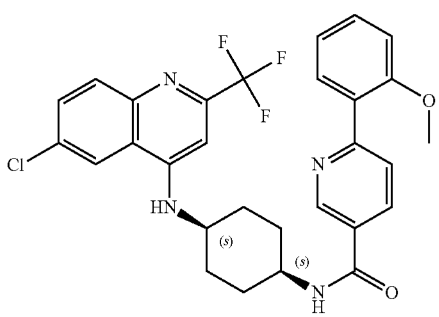 [SMILES: COc1ccccc1-c1ccc(C(=O)N[C@H]2CC[C@@H](Nc3cc(C(F)(F)F)nc4ccc(Cl)cc34)CC2)cn1] | 4-187 | 0.942 | 555 | 555.4 | [M + H]+ | Method 2 |
| 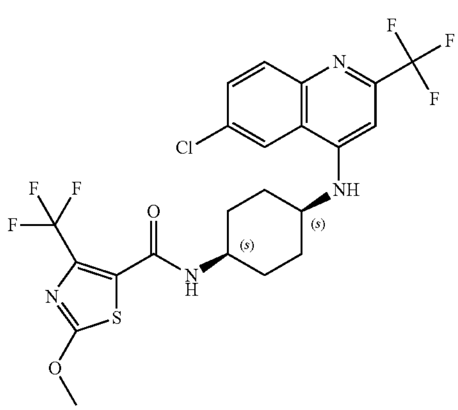 [SMILES: COc1nc(C(F)(F)F)c(C(=O)N[C@H]2CC[C@@H](Nc3cc(C(F)(F)F)nc4ccc(Cl)cc34)CC2)s1] | 4-188 | 0.996 | 552.92 | 553.3 | [M + H]+ | Method 2 |

TABLE 4-continued

| Structure | Cpd No. | Purity RT | MW | m/z | Ion | Purity Method |
|---|---|---|---|---|---|---|
| 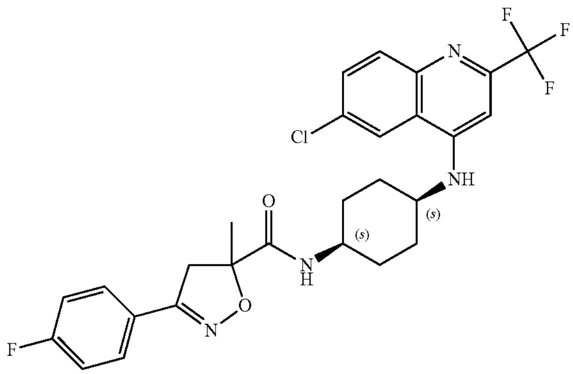 [SMILES: CC1(C(=O)N[C@H]2CC[C@@H](Nc3cc(C(F)(F)F)nc4ccc(Cl)cc34)CC2)CC(c2ccc(F)cc2)=NO1] | 4-189 | 1.016 | 548.97 | 549.3 | [M + H]⁺ | Method 2 |
| 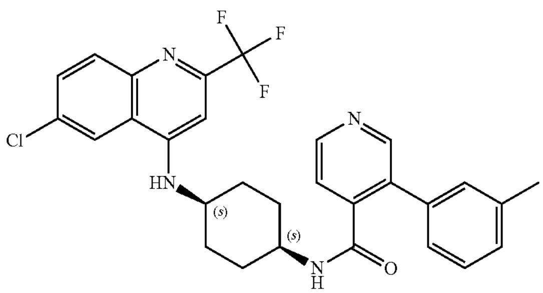 [SMILES: Cc1cccc(-c2cnccc2C(=O)N[C@H]2CC[C@@H](Nc3cc(C(F)(F)F)nc4ccc(Cl)cc34)CC2)c1] | 4-190 | 0.93 | 539 | 539.4 | [M + H]⁺ | Method 2 |
| 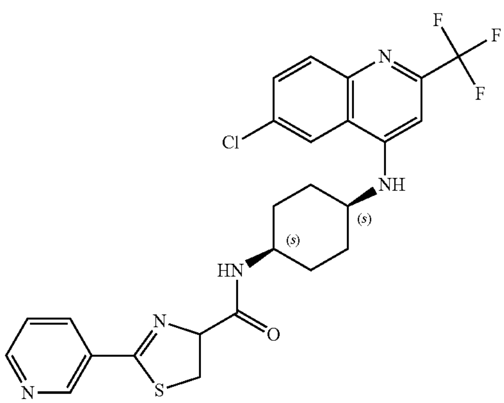 [SMILES: O=C(N[C@H]1CC[C@@H](Nc2cc(C(F)(F)F)nc3ccc(Cl)cc23)CC1)C1CSC(c2cccnc2)=N1] | 4-191 | 0.932 | 534 | 534.3 | [M + H]⁺ | Method 2 |
| 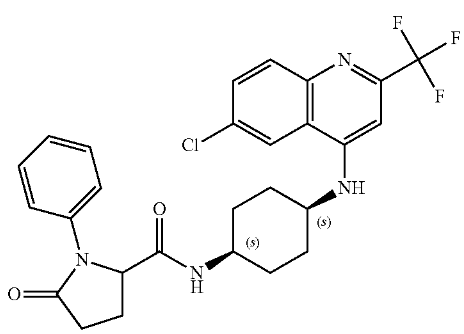 [SMILES: O=C(N[C@H]1CC[C@@H](Nc2cc(C(F)(F)F)nc3ccc(Cl)cc23)CC1)C1CCC(=O)N1c1ccccc1] | 4-192 | 0.918 | 530.98 | 531.3 | [M + H]⁺ | Method 2 |

TABLE 4-continued

| Structure | Cpd No. | Purity RT | MW | m/z | Ion | Purity Method |
|---|---|---|---|---|---|---|
| 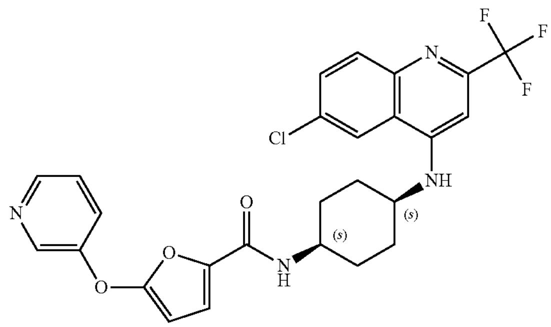 [SMILES: O=C(N[C@H]1CC[C@@H](Nc2cc(C(F)(F)F)nc3ccc(Cl)cc23)CC1)c1ccc(Oc2cccnc2)o1] | 4-193 | 0.929 | 530.93 | 531.3 | [M + H]+ | Method 2 |
| 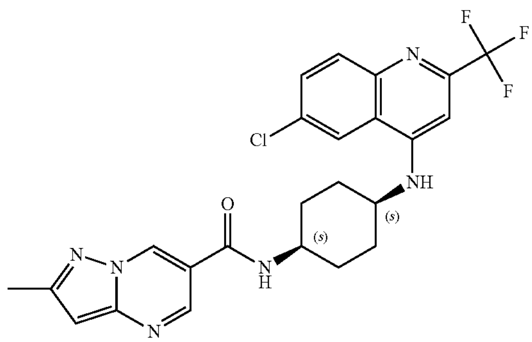 [SMILES: Cc1cc2ncc(C(=O)N[C@H]3CC[C@@H](Nc4cc(C(F)(F)F)nc5ccc(Cl)cc45)CC3)cn2n1] | 4-194 | 0.937 | 502.93 | 503.3 | [M + H]+ | Method 2 |
| 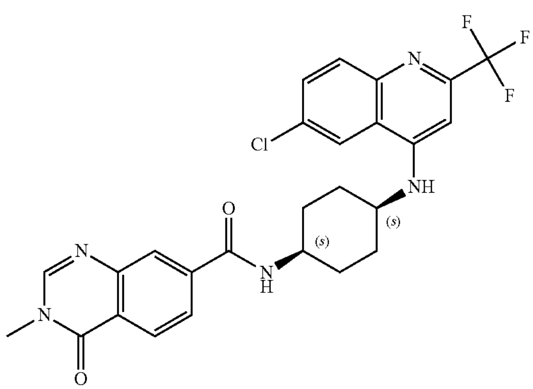 [SMILES: Cn1cnc2cc(C(=O)N[C@H]3CC[C@@H](Nc4cc(C(F)(F)F)nc5ccc(Cl)cc45)CC3)ccc2c1=O] | 4-195 | 0.909 | 529.95 | 530.3 | [M + H]+ | Method 2 |
| 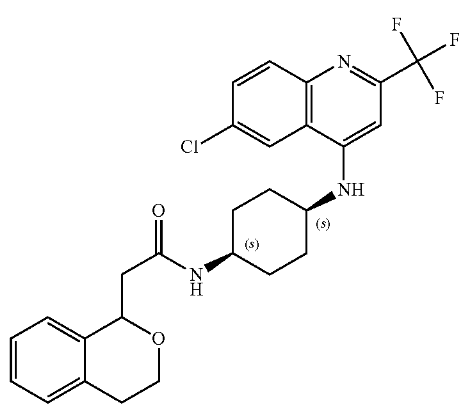 [SMILES: O=C(CC1OCCc2ccccc21)N[C@H]1CC[C@@H](Nc2cc(C(F)(F)F)nc3ccc(Cl)cc23)CC1] | 4-196 | 0.969 | 517.98 | 518.3 | [M + H]+ | Method 2 |

TABLE 4-continued

| Structure | Cpd No. | Purity RT | MW | m/z | Ion | Purity Method |
|---|---|---|---|---|---|---|
| 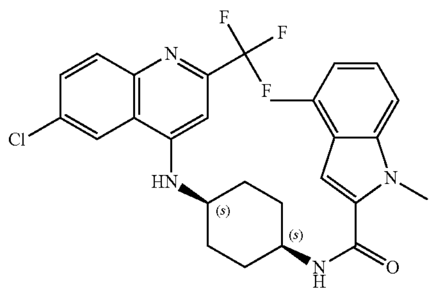 [SMILES: Cc1cccc2c1cc(C(=O)N[C@H]1CC[C@@H](Nc3cc(C(F)(F)F)nc4ccc(Cl)cc34)CC1)n2C] | 4-197 | 1.058 | 514.98 | 515.3 | [M + H]⁺ | Method 2 |
| 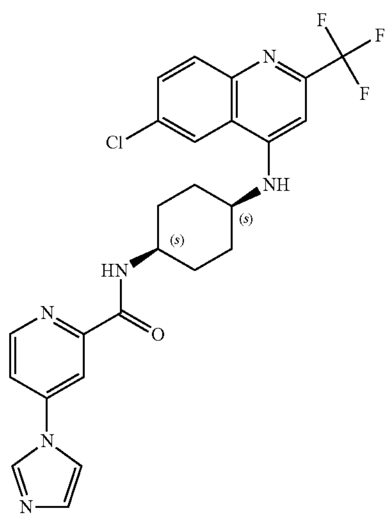 [SMILES: O=C(N[C@H]1CC[C@@H](Nc2cc(C(F)(F)F)nc3ccc(Cl)cc23)CC1)c1cc(-n2ccnc2)ccn1] | 4-198 | 0.856 | 514.94 | 515.3 | [M + H]⁺ | Method 2 |
| 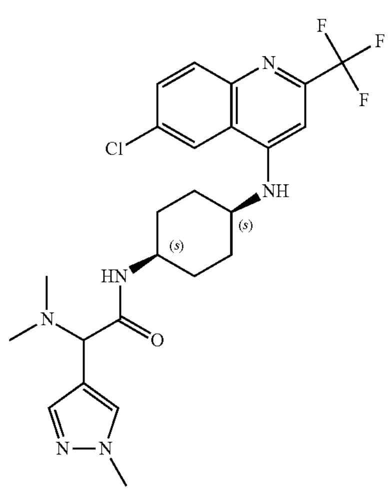 [SMILES: CN(C)C(C(=O)N[C@H]1CC[C@@H](Nc2cc(C(F)(F)F)nc3ccc(Cl)cc23)CC1)c1cnn(C)c1] | 4-199 | 0.817 | 508.97 | 509.4 | [M + H]⁺ | Method 2 |

TABLE 4-continued

| Structure | Cpd No. | Purity RT | MW | m/z | Ion | Purity Method |
|---|---|---|---|---|---|---|
| 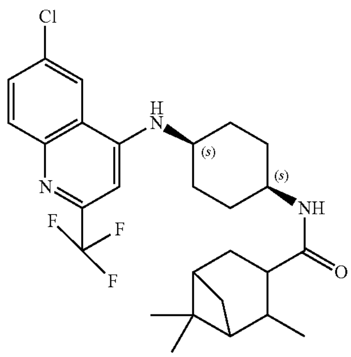 [SMILES: CC1C(C(=O)N[C@H]2CC[C@@H](Nc3cc(C(F)(F)F)nc4ccc(Cl)cc34)CC2)CC2CC1C2(C)C] | 4-200 | 1.08 | 508.03 | 508.4 | [M + H]⁺ | Method 2 |
| 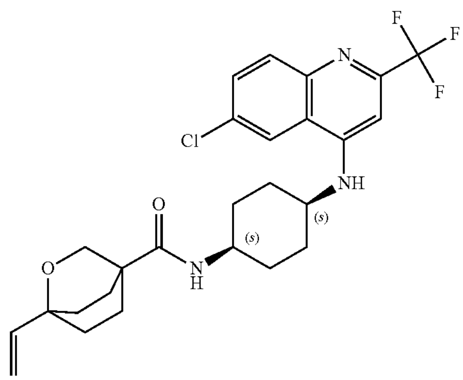 [SMILES: C=CC12CCC(C(=O)N[C@H]3CC[C@@H](Nc4cc(C(F)(F)F)nc5ccc(Cl)cc45)CC3)(CC1)CO2] | 4-201 | 0.978 | 507.98 | 508.4 | [M + H]⁺ | Method 2 |
| 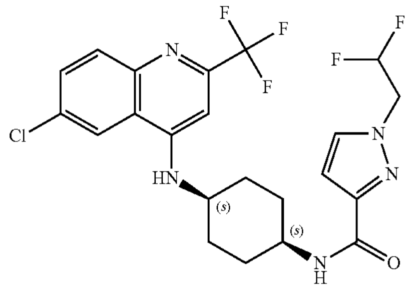 [SMILES: O=C(N[C@H]1CC[C@@H](Nc2cc(C(F)(F)F)nc3ccc(Cl)cc23)CC1)c1ccn(CC(F)F)n1] | 4-202 | 0.942 | 501.89 | 502.3 | [M + H]⁺ | Method 2 |
| 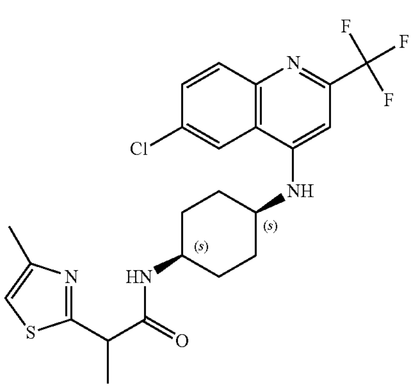 [SMILES: Cc1csc(C(C)C(=O)N[C@H]2CC[C@@H](Nc3cc(C(F)(F)F)nc4ccc(Cl)cc34)CC2)n1] | 4-203 | 0.941 | 496.98 | 497.3 | [M + H]⁺ | Method 2 |

TABLE 4-continued

| Structure | Cpd No. | Purity RT | MW | m/z | Ion | Purity Method |
|---|---|---|---|---|---|---|
| 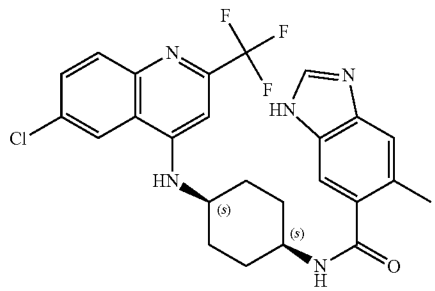 [SMILES: Cc1cc2nc[nH]c2cc1C(=O)N[C@H]1CC[C@@H](Nc2cc(C(F)(F)F)nc3ccc(Cl)cc23)CC1] | 4-204 | 0.833 | 501.94 | 502.3 | [M + H]⁺ | Method 2 |
| 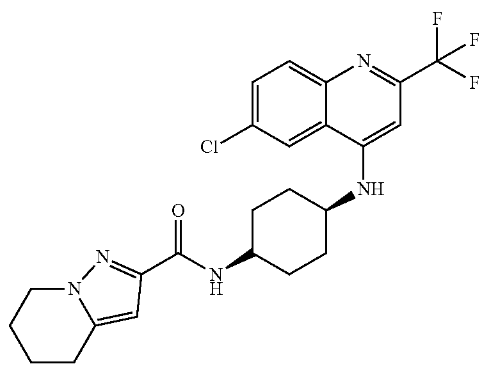 | 4-205 | 0.955 | 491.94 | 492 | [M + H]⁺ | Method 2 |
| 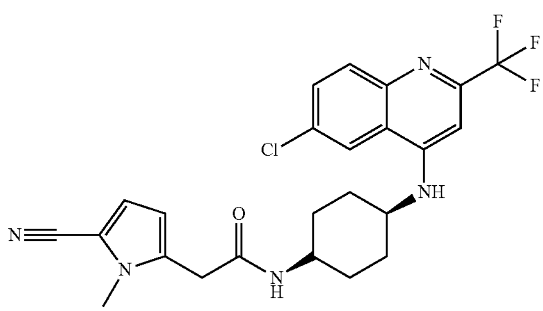 | 4-206 | 0.936 | 489.93 | 490 | [M + H]⁺ | Method 2 |
| 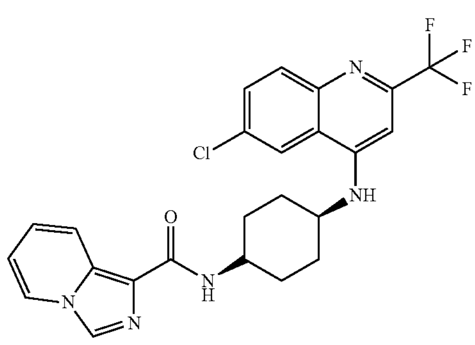 | 4-207 | 0.941 | 487.91 | 488 | [M + H]⁺ | Method 2 |

TABLE 4-continued

| Structure | Cpd No. | Purity RT | MW | m/z | Ion | Purity Method |
|---|---|---|---|---|---|---|
| 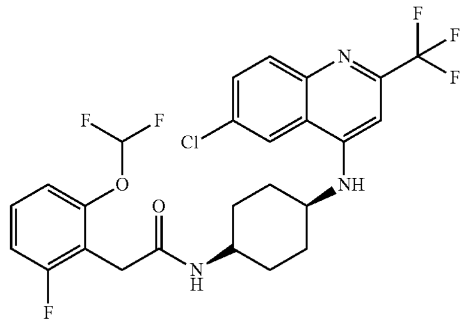 | 4-208 | 0.979 | 545.91 | 546 | [M + H]⁺ | Method 2 |
| 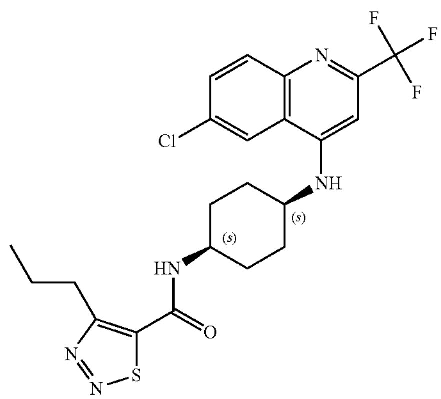 [SMILES: CCCc1nnsc1C(=O)N[C@H]1CC[C@@H](Nc2cc(C(F)(F)F)nc3ccc(Cl)cc23)CC1] | 4-209 | 0.999 | 497.97 | 498.3 | [M + H]⁺ | Method 2 |
| 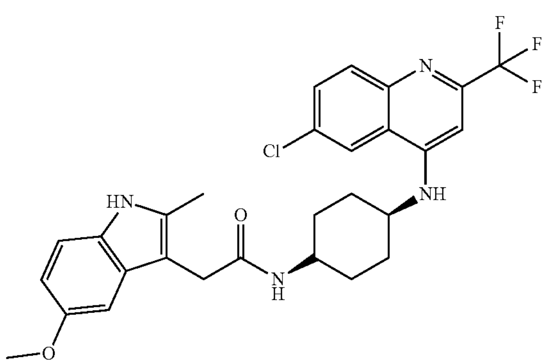 | 4-210 | 0.959 | 545 | 545 | [M + H]⁺ | Method 2 |
| 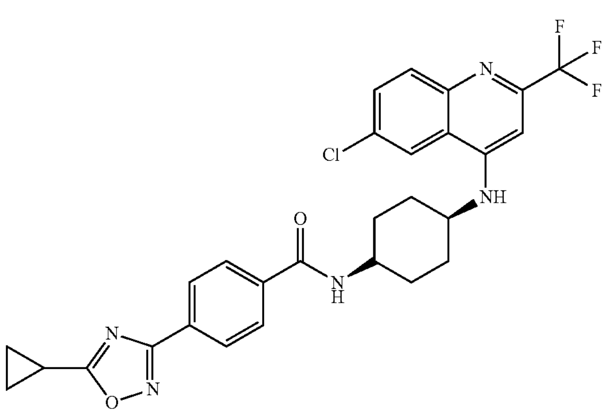 | 4-211 | 1.01 | 555.99 | 556 | [M + H]⁺ | Method 2 |

TABLE 4-continued

| Structure | Cpd No. | Purity RT | MW | m/z | Ion | Purity Method |
|---|---|---|---|---|---|---|
| 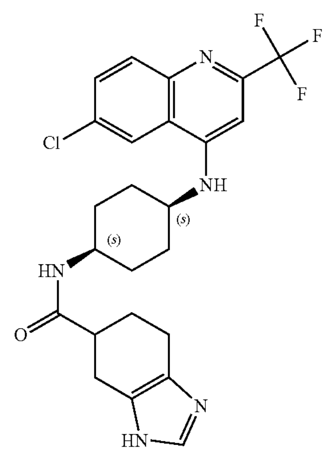 [SMILES: O=C(N[C@H]1CC[C@@H](Nc2cc(C(F)(F)F)nc3ccc(Cl)cc23)CC1)C1CCc2nc[nH]c2C1] | 4-212 | 0.812 | 491.94 | 492.3 | [M + H]⁺ | Method 2 |
| 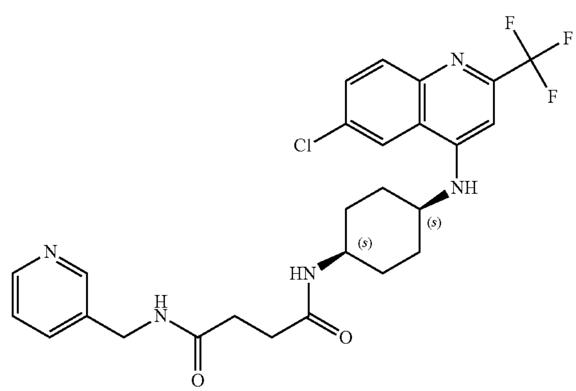 [SMILES: O=C(CCC(=O)N[C@H]1CC[C@@H](Nc2cc(C(F)(F)F)nc3ccc(Cl)cc23)CC1)NCc1cccnc1] | 4-213 | 0.793 | 533.98 | 534.2 | [M + H]⁺ | Method 2 |
| 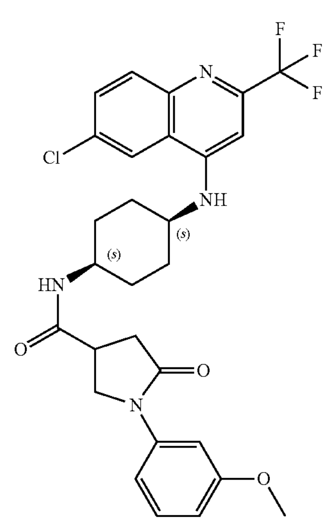 [SMILES: COc1cccc(N2CC(C(=O)N[C@H]3CC[C@@H](Nc4cc(C(F)(F)F)nc5ccc(Cl)cc45)CC3)CC2=O)c1] | 4-214 | 0.933 | 561 | 561.2 | [M + H]⁺ | Method 2 |

TABLE 4-continued

| Structure | Cpd No. | Purity RT | MW | m/z | Ion | Purity Method |
|---|---|---|---|---|---|---|
| 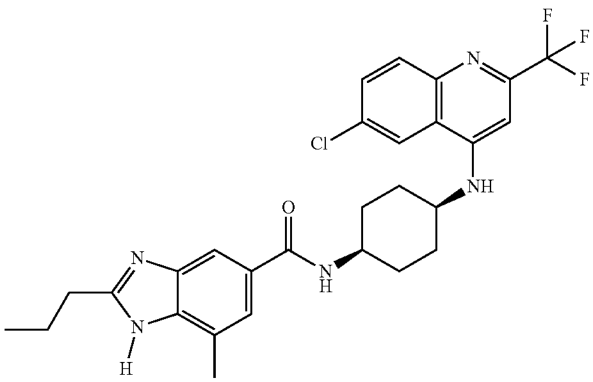 [SMILES: CCCc1nc2cc(C(=O)N[C@H]3CC[C@@H](Nc4cc(C(F)(F)F)nc5ccc(Cl)cc45)CC3)cc(C)c2[nH]1] | 4-215 | 0.857 | 544.02 | 544 | [M + H]+ | Method 2 |
| 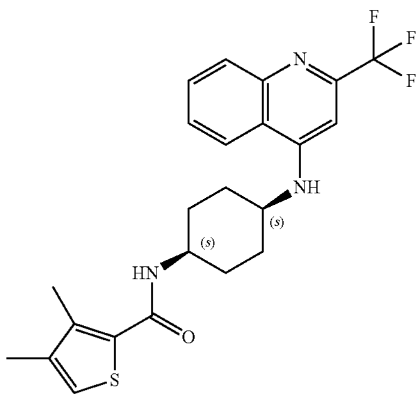 [SMILES: Cc1csc(C(=O)N[C@H]2CC[C@@H](Nc3cc(C(F)(F)F)nc4ccccc34)CC2)c1C] | 4-216 | 9.250 | 447.52 | 448.2 | [M + H]+ | Method 3 |
| 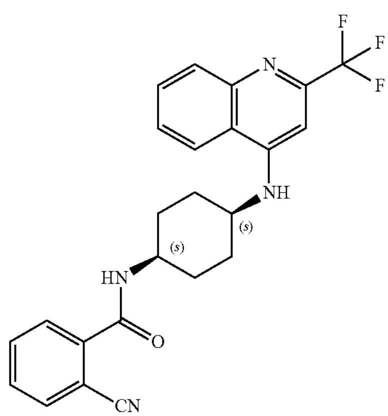 [SMILES: N#Cc1ccccc1C(=O)N[C@H]1CC[C@@H](Nc2cc(C(F)(F)F)nc3ccccc23)CC1] | 4-217 | 7.386 | 438.454 | 439.2 | [M + H]+ | Method 3 |
| 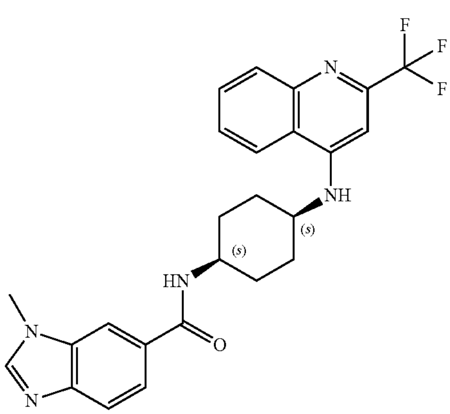 [SMILES: Cn1cnc2ccc(C(=O)N[C@H]3CC[C@@H](Nc4cc(C(F)(F)F)nc5ccccc45)CC3)cc21] | 4-218 | 4.908 | 467.496 | 468.2 | [M + H]+ | Method 3 |

TABLE 4-continued

| Structure | Cpd No. | Purity RT | MW | m/z | Ion | Purity Method |
|---|---|---|---|---|---|---|
| 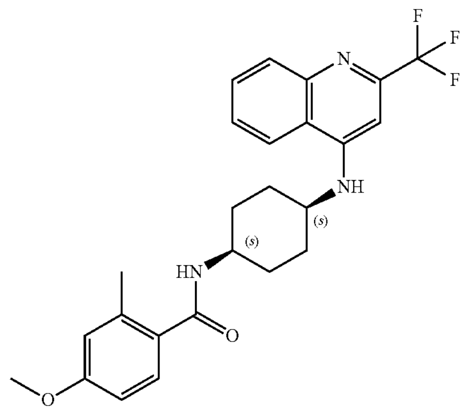 [SMILES: COc1ccc(C(=O)N[C@H]2CC[C@@H](Nc3cc(C(F)(F)F)nc4ccccc34)CC2)c(C)c1] | 4-219 | 8.256 | 457.497 | 458.2 | [M + H]+ | Method 3 |
| 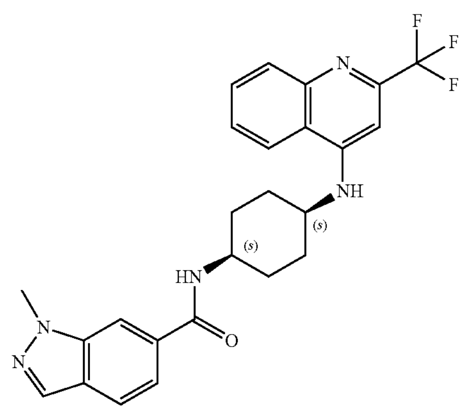 [SMILES: Cn1ncc2ccc(C(=O)N[C@H]3CC[C@@H](Nc4cc(C(F)(F)F)nc5ccccc45)CC3)cc21] | 4-220 | 7.522 | 467.496 | 468.2 | [M + H]+ | Method 3 |
| 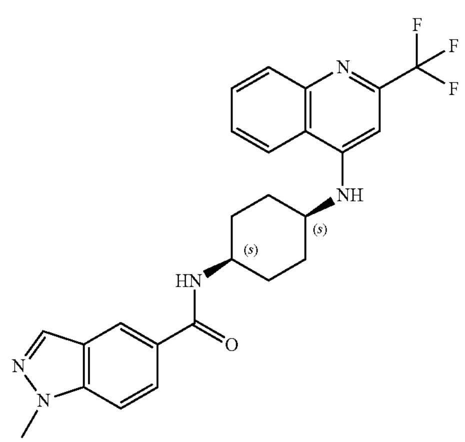 [SMILES: Cn1ncc2cc(C(=O)N[C@H]3CC[C@@H](Nc4cc(C(F)(F)F)nc5ccccc45)CC3)ccc21] | 4-221 | 7.301 | 467.496 | 468.2 | [M + H]+ | Method 3 |

TABLE 4-continued

| Structure | Cpd No. | Purity RT | MW | m/z | Ion | Purity Method |
|---|---|---|---|---|---|---|
| 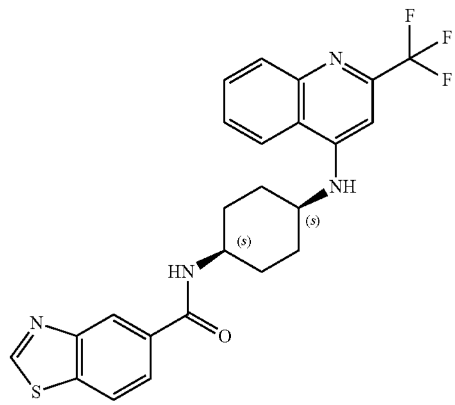 [SMILES: O=C(N[C@H]1CC[C@@H](Nc2cc(C(F)(F)F)nc3ccccc23)CC1)c1ccc2scnc2c1] | 4-222 | 7.488 | 470.51 | 471.1 | [M + H]+ | Method 3 |
| 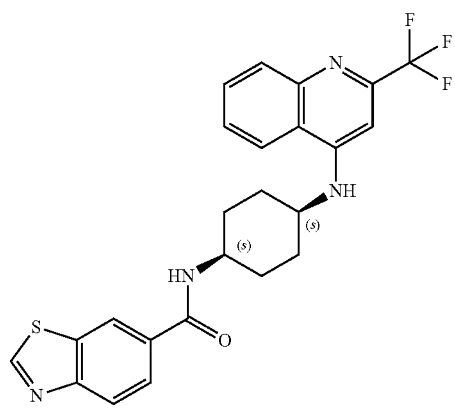 [SMILES: O=C(N[C@H]1CC[C@@H](Nc2cc(C(F)(F)F)nc3ccccc23)CC1)c1ccc2ncsc2c1] | 4-223 | 7.463 | 470.51 | 471.2 | [M + H]+ | Method 3 |
| 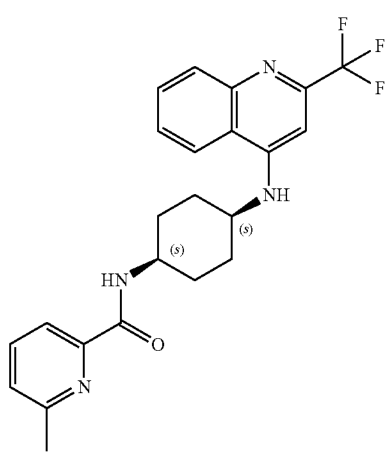 [SMILES: Cc1cccc(C(=O)N[C@H]2CC[C@@H](Nc3cc(C(F)(F)F)nc4ccccc34)CC2)n1] | 4-224 | 8.613 | 428.459 | 429.2 | [M + H]+ | Method 3 |

TABLE 4-continued
| Structure | Cpd No. | Purity RT | MW | m/z | Ion | Purity Method |
|---|---|---|---|---|---|---|
| 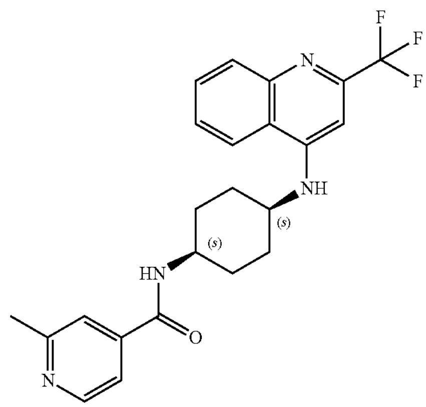 [SMILES: Cc1cc(C(=O)N[C@H]2CC[C@@H](Nc3cc(C(F)(F)F)nc4ccccc34)CC2)ccn1] | 4-225 | 5.126 | 428.459 | 429.2 | [M + H]+ | Method 3 |
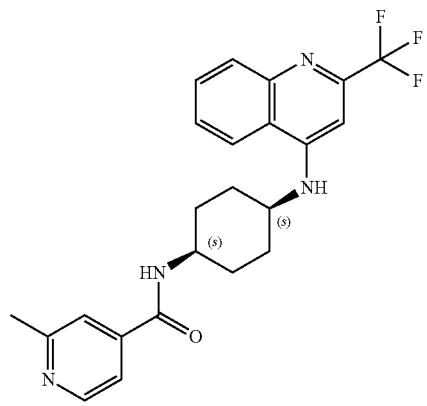
| | 4-226 | 9.377 | 464.492 | 465.2 | [M + H]+ | Method 3 |
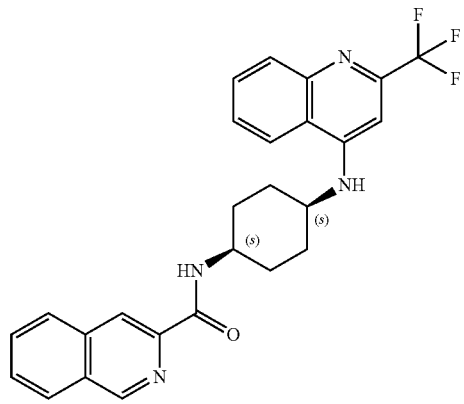 [SMILES: O=C(N[C@H]1CC[C@@H](Nc2cc(C(F)(F)F)nc3ccccc23)CC1)c1cc2ccccc2cn1]
| | 4-227 | 7.202 | 418.42 | 419.2 | [M + H]+ | Method 3 |
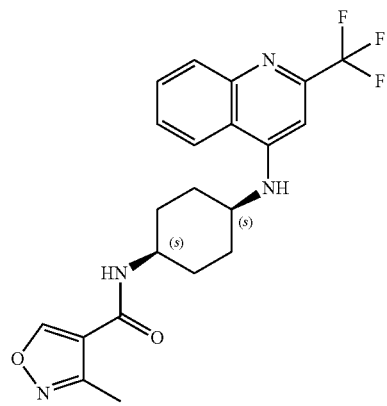 [SMILES: Cc1nocc1C(=O)N[C@H]1CC[C@@H](Nc2cc(C(F)(F)F)nc3ccccc23)CC1]

TABLE 4-continued

| Structure | Cpd No. | Purity RT | MW | m/z | Ion | Purity Method |
|---|---|---|---|---|---|---|
| 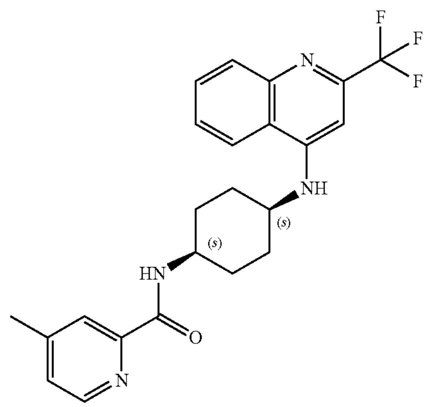 [SMILES: Cc1ccnc(C(=O)N[C@H]2CC[C@@H](Nc3cc(C(F)(F)F)nc4ccccc34)CC2)c1] | 4-228 | 8.520 | 428.459 | 429.2 | [M + H]⁺ | Method 3 |
| 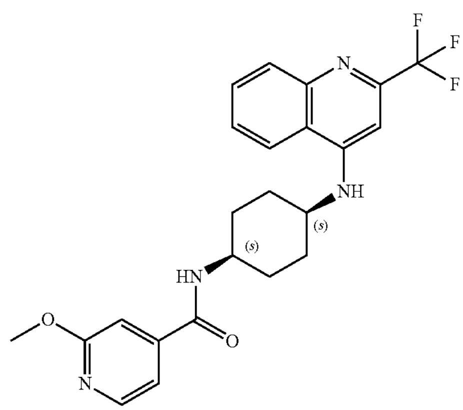 [SMILES: COc1cc(C(=O)N[C@H]2CC[C@@H](Nc3cc(C(F)(F)F)nc4ccccc34)CC2)ccn1] | 4-229 | 7.734 | 444.458 | 445.2 | [M + H]⁺ | Method 3 |
| 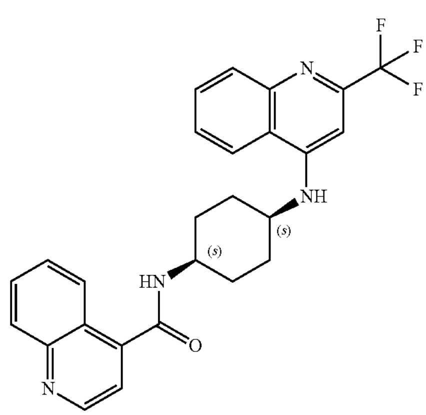 [SMILES: O=C(N[C@H]1CC[C@@H](Nc2cc(C(F)(F)F)nc3ccccc23)CC1)c1ccnc2ccccc12] | 4-230 | 6.965 | 464.492 | 465.2 | [M + H]⁺ | Method 3 |

TABLE 4-continued

| Structure | Cpd No. | Purity RT | MW | m/z | Ion | Purity Method |
|---|---|---|---|---|---|---|
| 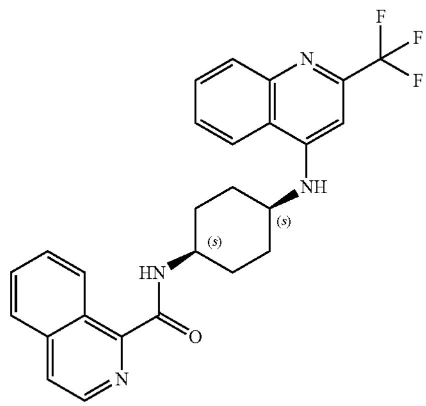 [SMILES: O=C(N[C@H]1CC[C@@H](Nc2cc(C(F)(F)F)nc3ccccc23)CC1)c1nccc2ccccc12] | 4-231 | 9.413 | 464.492 | 465.2 | [M + H]⁺ | Method 3 |
| 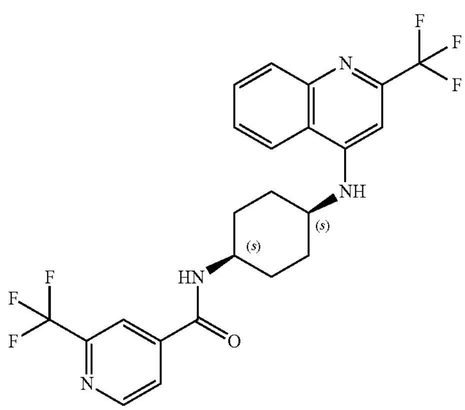 [SMILES: O=C(N[C@H]1CC[C@@H](Nc2cc(C(F)(F)F)nc3ccccc23)CC1)c1ccnc(C(F)(F)F)c1] | 4-232 | 8.852 | 482.43 | 483.2 | [M + H]⁺ | Method 3 |
| 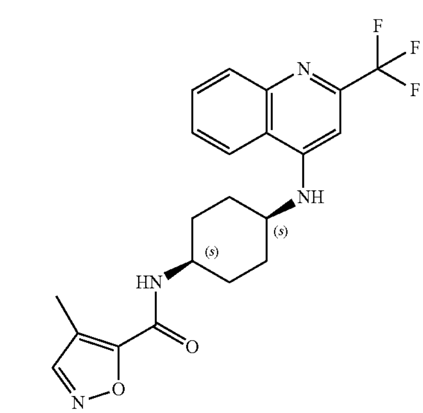 [SMILES: Cc1cnoc1C(=O)N[C@H]1CC[C@@H](Nc2cc(C(F)(F)F)nc3ccccc23)CC1] | 4-233 | 8.045 | 418.42 | 419.2 | [M + H]⁺ | Method 3 |

TABLE 4-continued
| Structure | Cpd No. | Purity RT | MW | m/z | Ion | Purity Method |
|---|---|---|---|---|---|---|
| 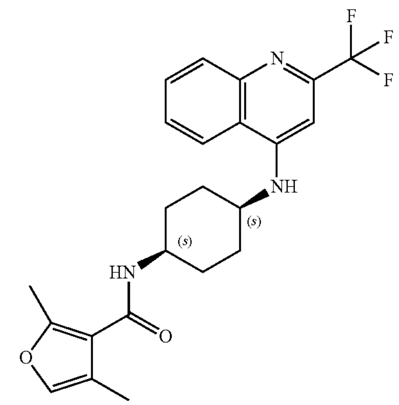 [SMILES: Cc1coc(C)c1C(=O)N[C@H]1CC[C@@H](Nc2cc(C(F)(F)F)nc3ccccc23)CC1] | 4-234 | 8.348 | 431.459 | 432.3 | [M + H]+ | Method 3 |
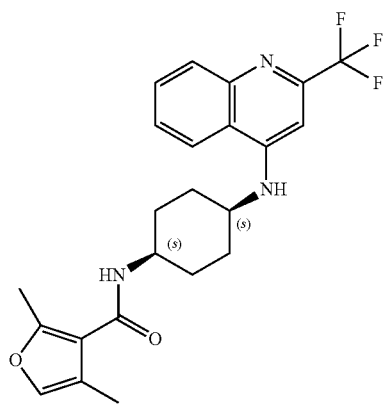
| | 4-235 | 8.099 | 470.54 | 471.2 | [M + H]+ | Method 3 |
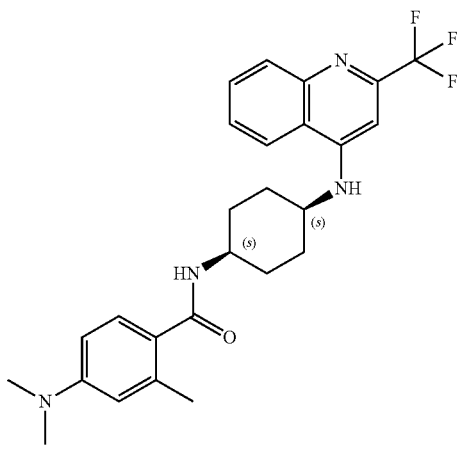 [SMILES: Cc1cc(N(C)C)ccc1C(=O)N[C@H]1CC[C@@H](Nc2cc(C(F)(F)F)nc3ccccc23)CC1]
| | 4-236 | 9.331 | 474.504 | 475.2 | [M + H]+ | Method 3 |
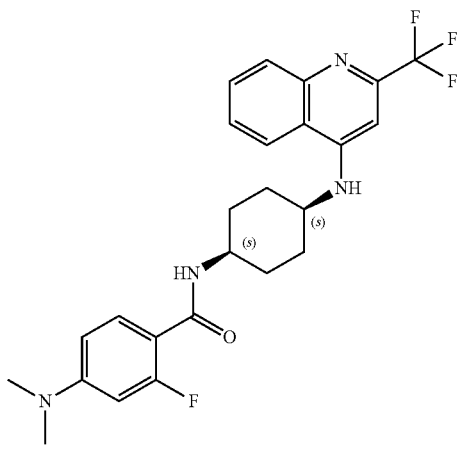 [SMILES: CN(C)c1ccc(C(=O)N[C@H]2CC[C@@H](Nc3cc(C(F)(F)F)nc4ccccc34)CC2)c(F)c1]

TABLE 4-continued
| Structure | Cpd No. | Purity RT | MW | m/z | Ion | Purity Method |
|---|---|---|---|---|---|---|
| 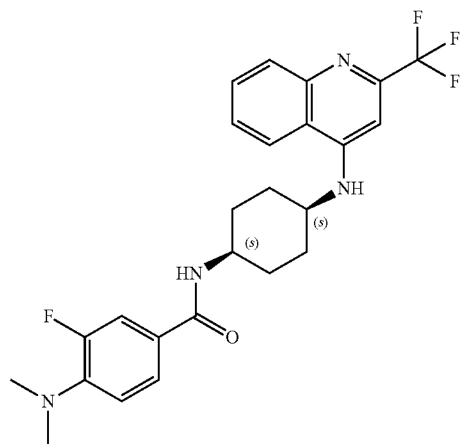 [SMILES: CN(C)c1ccc(C(=O)N[C@H]2CC[C@@H](Nc3cc(C(F)(F)F)nc4ccccc34)CC2)cc1F] | 4-237 | 8.981 | 474.504 | 475.2 | [M + H]+ | Method 3 |
| 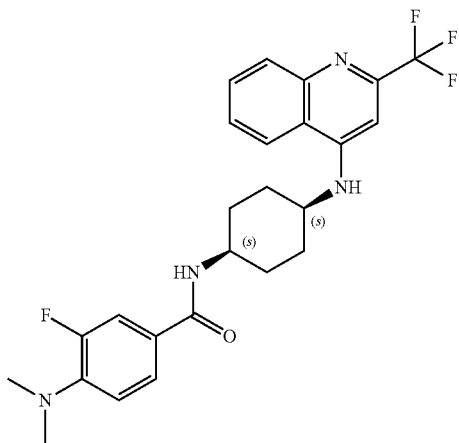 | | | | | | |
| 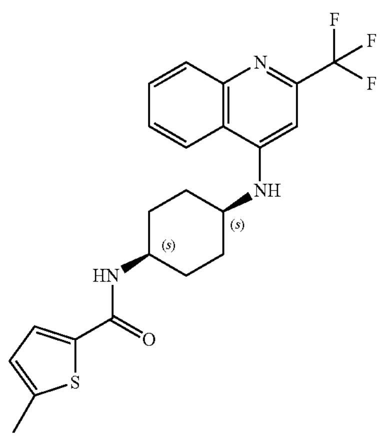 [SMILES: Cc1ccc(C(=O)N[C@H]2CC[C@@H](Nc3cc(C(F)(F)F)nc4ccccc34)CC2)s1] | 4-238 | 8.615 | 433.49 | 434.2 | [M + H]+ | Method 3 |
| 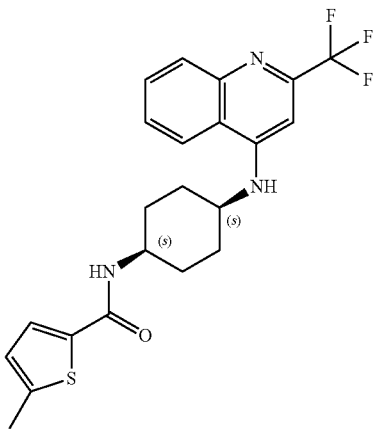 | | | | | | |
| 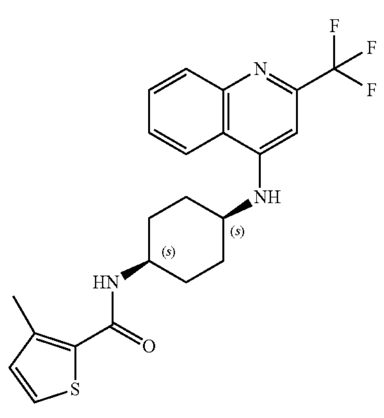 | 4-239 | 8.603 | 433.49 | 434.2 | [M + H]+ | Method 3 |
| 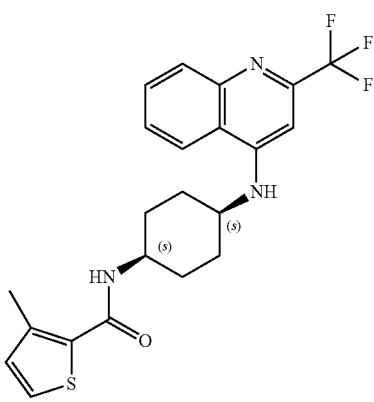 [SMILES: Cc1ccsc1C(=O)N[C@H]1CC[C@@H](Nc2cc(C(F)(F)F)nc3ccccc23)CC1] | | | | | | |

TABLE 4-continued

| Structure | Cpd No. | Purity RT | MW | m/z | Ion | Purity Method |
|---|---|---|---|---|---|---|
| 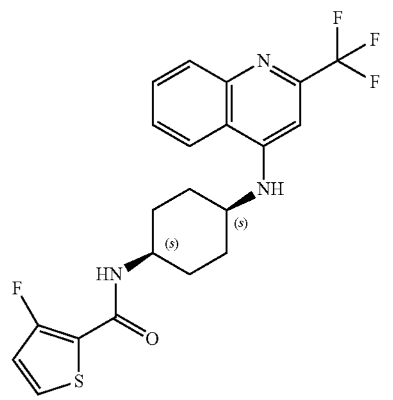 [SMILES: O=C(N[C@H]1CC[C@@H](Nc2cc(C(F)(F)F)nc3ccccc23)CC1)c1sccc1F] | 4-240 | 8.620 | 437.46 | 438.2 | [M + H]⁺ | Method 3 |
| 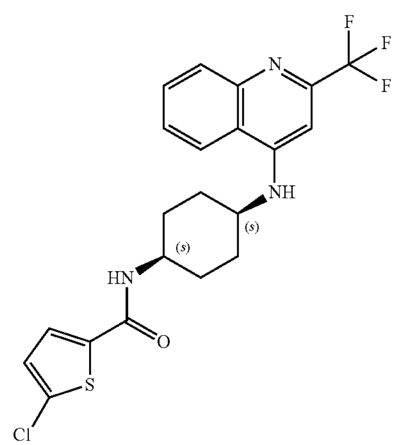 [SMILES: O=C(N[C@H]1CC[C@@H](Nc2cc(C(F)(F)F)nc3ccccc23)CC1)c1ccc(Cl)s1] | 4-241 | 9.502 | 453.91 | 454.1 | [M + H]⁺ | Method 3 |
| 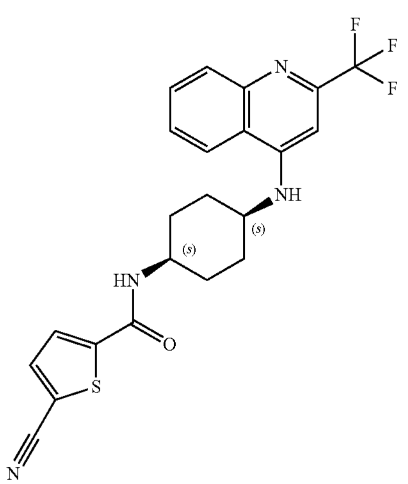 [SMILES: N#Cc1ccc(C(=O)N[C@H]2CC[C@@H](Nc3cc(C(F)(F)F)nc4ccccc34)CC2)s1] | 4-242 | 8.646 | 444.48 | 445.2 | [M + H]⁺ | Method 3 |

TABLE 4-continued
| Structure | Cpd No. | Purity RT | MW | m/z | Ion | Purity Method |
|---|---|---|---|---|---|---|
| 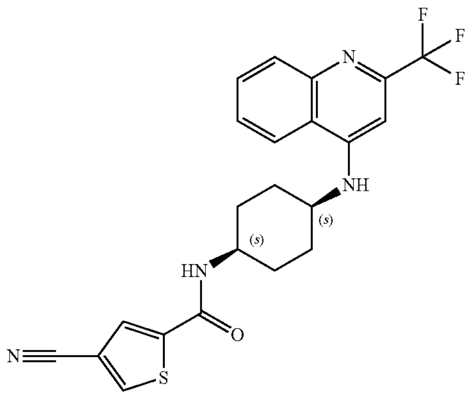 [SMILES: N#Cc1csc(C(=O)N[C@H]2CC[C@@H](Nc3cc(C(F)(F)F)nc4ccccc34)CC2)c1] | 4-243 | 8.307 | 444.48 | 445.2 | [M + H]⁺ | Method 3 |
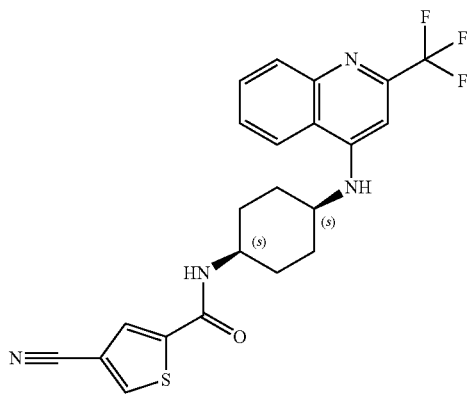
| | 4-244 | 8.635 | 437.46 | 438.2 | [M + H]⁺ | Method 3 |
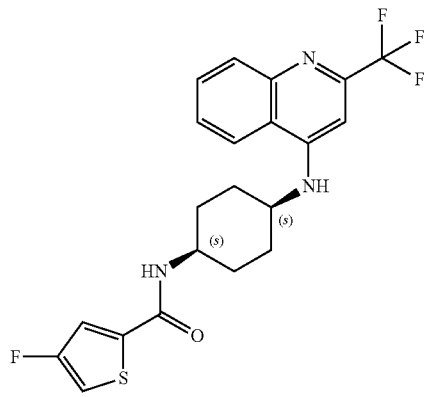 [SMILES: O=C(N[C@H]1CC[C@@H](Nc2cc(C(F)(F)F)nc3ccccc23)CC1)c1cc(F)cs1]
| | 4-245 | 5.715 | 415.42 | 416.2 | [M + H]⁺ | Method 3 |
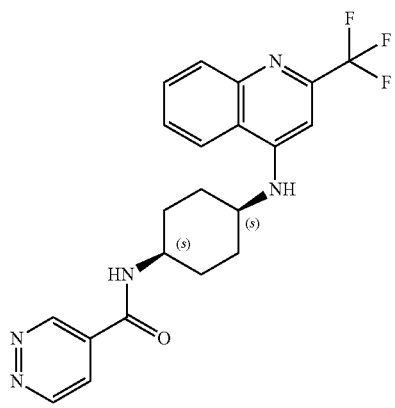 [SMILES: O=C(N[C@H]1CC[C@@H](Nc2cc(C(F)(F)F)nc3ccccc23)CC1)c1ccnnc1]

TABLE 4-continued
| Structure | Cpd No. | Purity RT | MW | m/z | Ion | Purity Method |
|---|---|---|---|---|---|---|
| 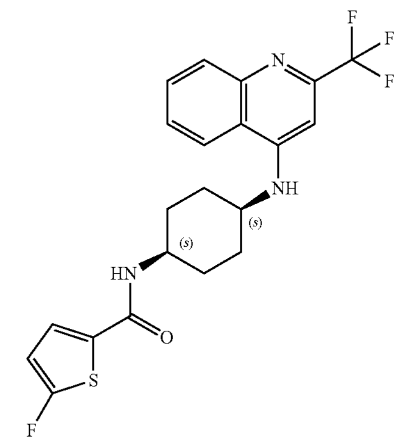 [SMILES: O=C(N[C@H]1CC[C@@H](Nc2cc(C(F)(F)F)nc3ccccc23)CC1)c1ccc(F)s1] | 4-246 | 8.814 | 437.46 | 438.1 | [M + H]+ | Method 3 |
| 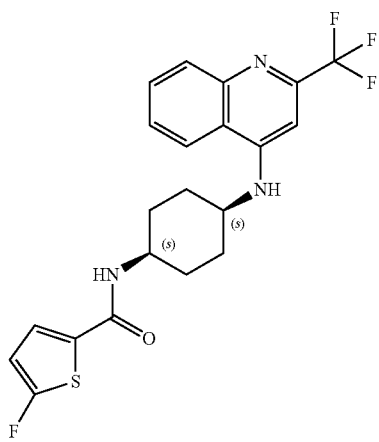 | | | | | | |
| 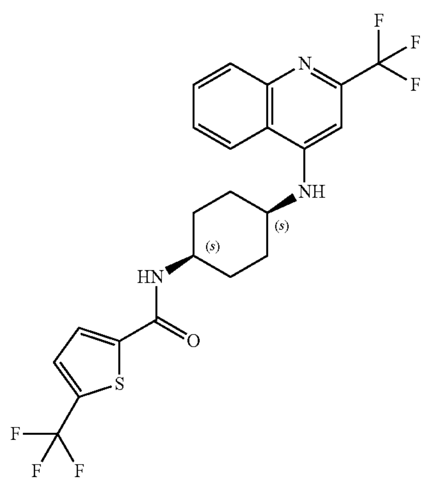 [SMILES: O=C(N[C@H]1CC[C@@H](Nc2cc(C(F)(F)F)nc3ccccc23)CC1)c1ccc(C(F)(F)F)s1] | 4-247 | 10.106 | 487.46 | 488.1 | [M + H]+ | Method 3 |
| 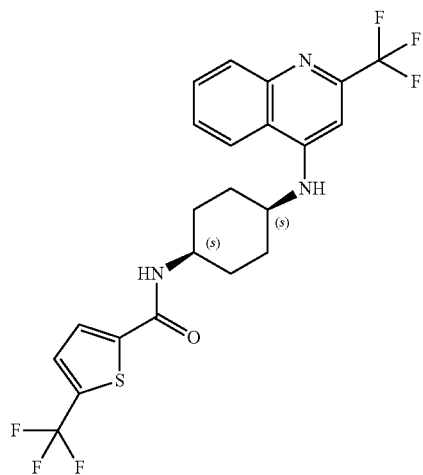 | | | | | | |
| 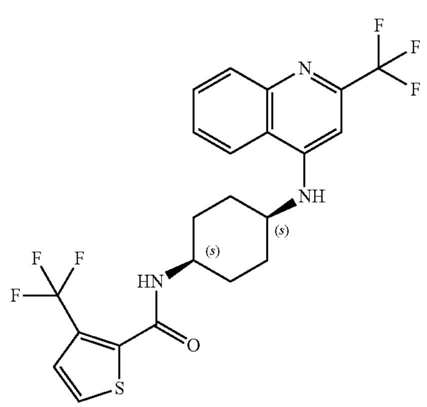 [SMILES: O=C(N[C@H]1CC[C@@H](Nc2cc(C(F)(F)F)nc3ccccc23)CC1)c1sccc1C(F)(F)F] | 4-248 | 9.151 | 487.46 | 488.1 | [M + H]+ | Method 3 |
| 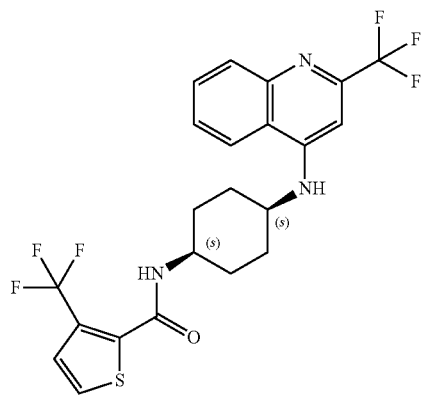 | | | | | | |

TABLE 4-continued
| Structure | Cpd No. | Purity RT | MW | m/z | Ion | Purity Method |
|---|---|---|---|---|---|---|
| 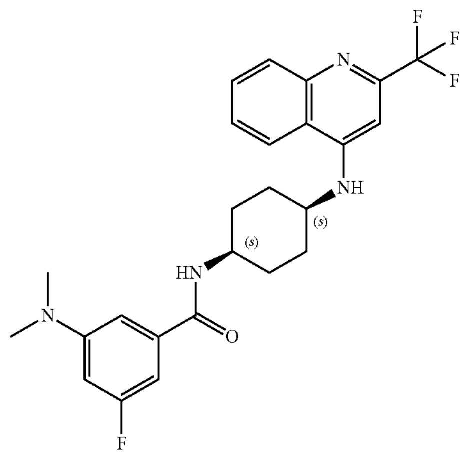 [SMILES: CN(C)c1cc(F)cc(C(=O)N[C@H]2CC[C@@H](Nc3cc(C(F)(F)F)nc4ccccc34)CC2)c1] | 4-249 | 9.334 | 474.504 | 475.2 | [M + H]⁺ | Method 3 |
| 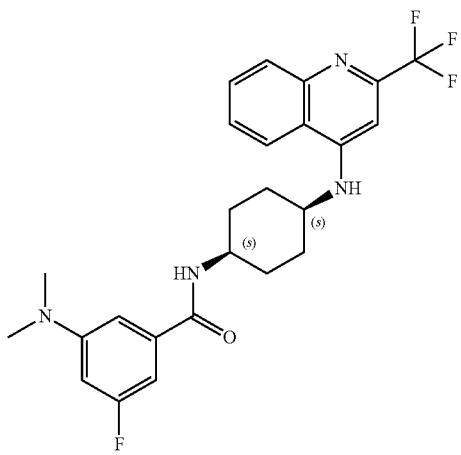 | | | | | | |
| 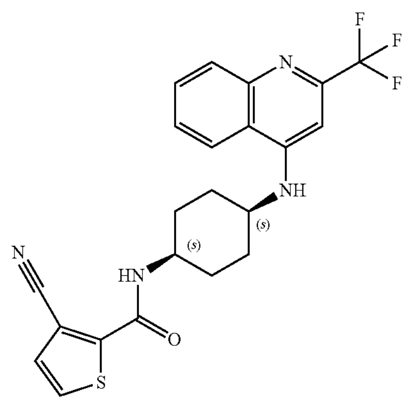 | 4-250 | 8.013 | 444.48 | 445.2 | [M + H]⁺ | Method 3 |
| 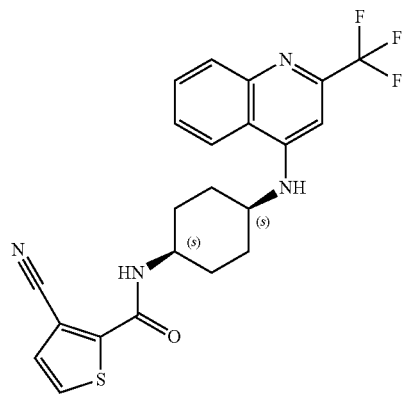 [SMILES: N#Cc1ccsc1C(=O)N[C@H]1CC[C@@H](Nc2cc(C(F)(F)F)nc3ccccc23)CC1] | | | | | | |
| 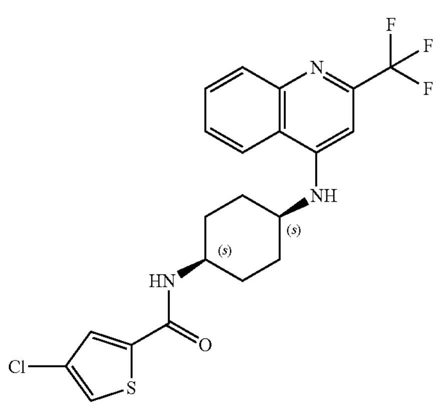 [SMILES: O=C(N[C@H]1CC[C@@H](Nc2cc(C(F)(F)F)nc3ccccc23)CC1)c1cc(Cl)cs1] | 4-251 | 9.272 | 453.91 | 454.2 | [M + H]⁺ | Method 3 |
| 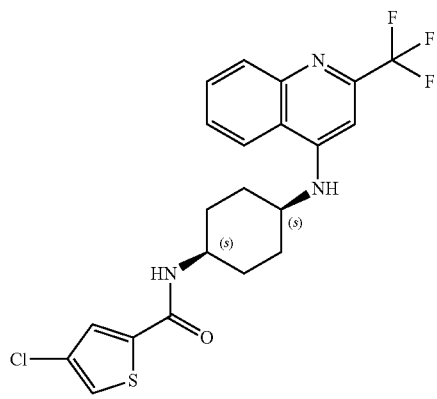 | | | | | | |

TABLE 4-continued

| Structure | Cpd No. | Purity RT | MW | m/z | Ion | Purity Method |
|---|---|---|---|---|---|---|
| 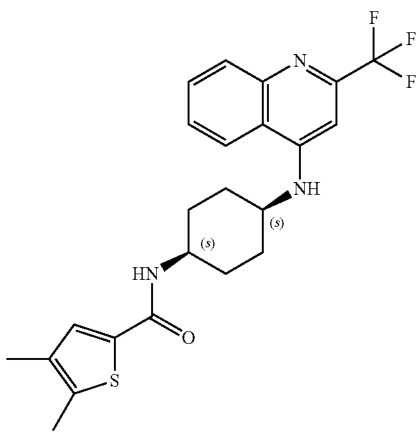 [SMILES: Cc1cc(C(=O)N[C@H]2CC[C@@H](Nc3cc(C(F)(F)F)nc4ccccc34)CC2)sc1C] | 4-252 | 9.208 | 447.52 | 448.2 | [M + H]⁺ | Method 3 |
| 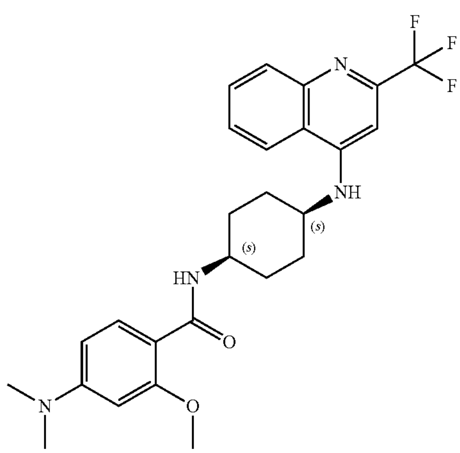 [SMILES: COc1cc(N(C)C)ccc1C(=O)N[C@H]1CC[C@@H](Nc2cc(C(F)(F)F)nc3ccccc23)CC1] | 4-253 | 8.857 | 486.539 | 487.2 | [M + H]⁺ | Method 3 |
| 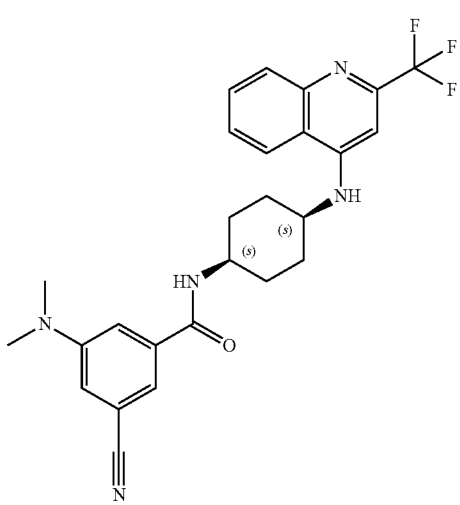 [SMILES: CN(C)c1cc(C#N)cc(C(=O)N[C@H]2CC[C@@H](Nc3cc(C(F)(F)F)nc4ccccc34)CC2)c1] | 4-254 | 9.153 | 481.523 | 482.2 | [M + H]⁺ | Method 3 |

TABLE 4-continued
| Structure | Cpd No. | Purity RT | MW | m/z | Ion | Purity Method |
|---|---|---|---|---|---|---|
| 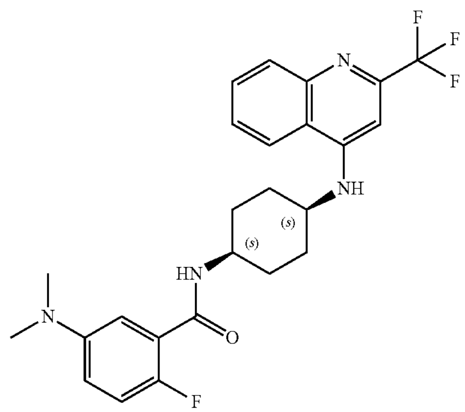 [SMILES: CN(C)c1ccc(F)c(C(=O)N[C@H]2CC[C@@H](Nc3cc(C(F)(F)F)nc4ccccc34)CC2)c1] | 4-255 | 8.717 | 474.504 | 475.2 | [M + H]+ | Method 3 |
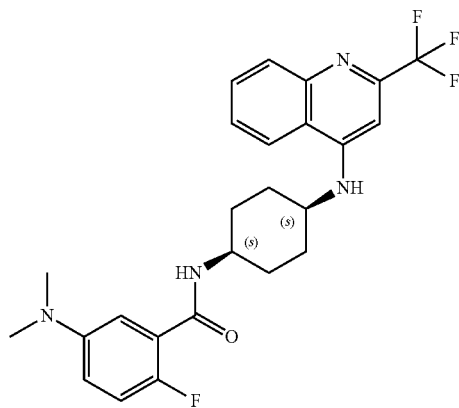
| | 4-256 | 7.352 | 467.496 | 468.2 | [M + H]+ | Method 3 |
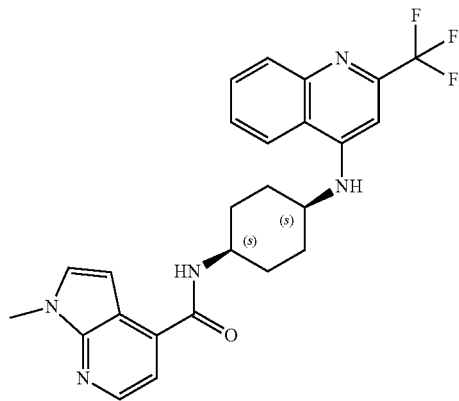 [SMILES: Cn1ccc2c(C(=O)N[C@H]3CC[C@@H](Nc4cc(C(F)(F)F)nc5ccccc45)CC3)ccnc21]
| | 4-257 | 5.696 | 470.54 | 471.2 | [M + H]+ | Method 3 |
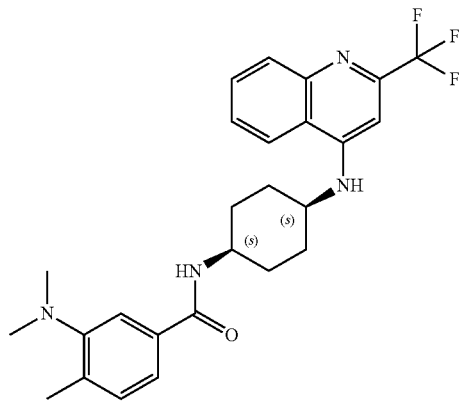 [SMILES: Cc1ccc(C(=O)N[C@H]2CC[C@@H](Nc3cc(C(F)(F)F)nc4ccccc34)CC2)cc1N(C)C]

TABLE 4-continued
| Structure | Cpd No. | Purity RT | MW | m/z | Ion | Purity Method |
|---|---|---|---|---|---|---|
| 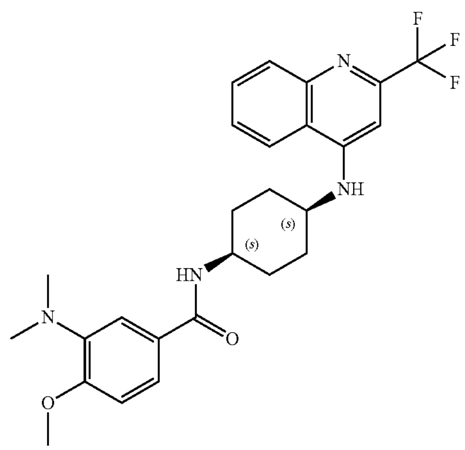 [SMILES: COc1ccc(C(=O)N[C@H]2CC[C@@H](Nc3cc(C(F)(F)F)nc4ccccc34)CC2)cc1N(C)C] | 4-258 | 4.876 | 486.539 | 487.2 | [M + H]+ | Method 3 |
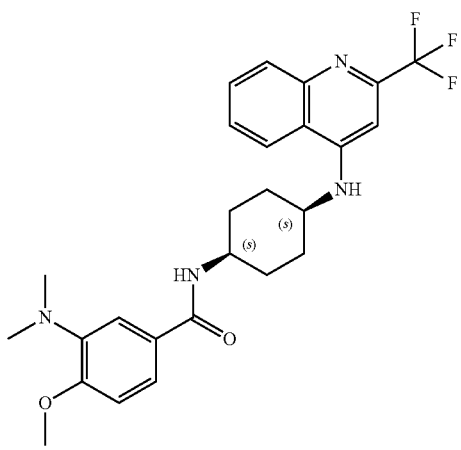
| | 4-259 | 6.297 | 470.54 | 471.3 | [M + H]+ | Method 3 |
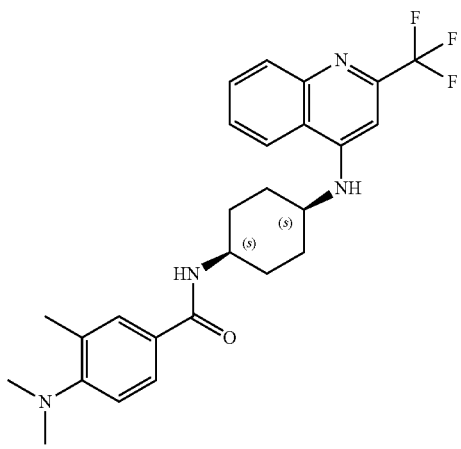 [SMILES: Cc1cc(C(=O)N[C@H]2CC[C@@H](Nc3cc(C(F)(F)F)nc4ccccc34)CC2)ccc1N(C)C]
| | 4-260 | 4.770 | 457.501 | 458.2 | [M + H]+ | Method 3 |
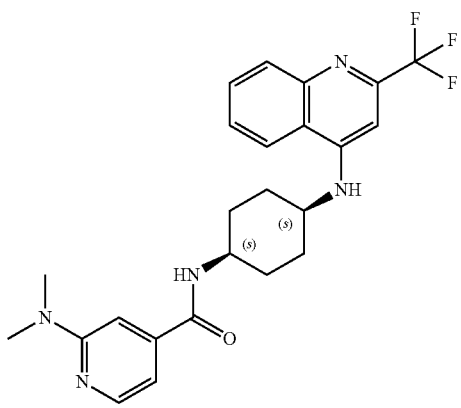 [SMILES: CN(C)c1cc(C(=O)N[C@H]2CC[C@@H](Nc3cc(C(F)(F)F)nc4ccccc34)CC2)ccn1]

TABLE 4-continued
| Structure | Cpd No. | Purity RT | MW | m/z | Ion | Purity Method |
|---|---|---|---|---|---|---|
| 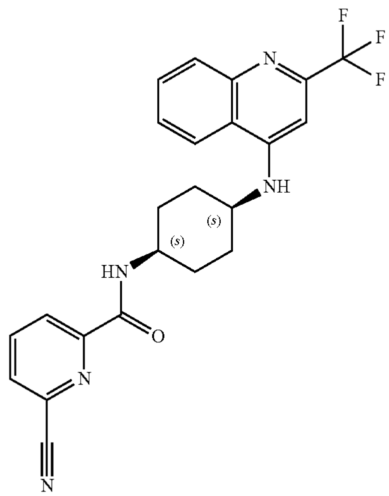 [SMILES: N#Cc1cccc(C(=O)N[C@H]2CC[C@@H](Nc3cc(C(F)(F)F)nc4ccccc34)CC2)n1] | 4-261 | 8.287 | 439.442 | 440.2 | [M + H]+ | Method 3 |
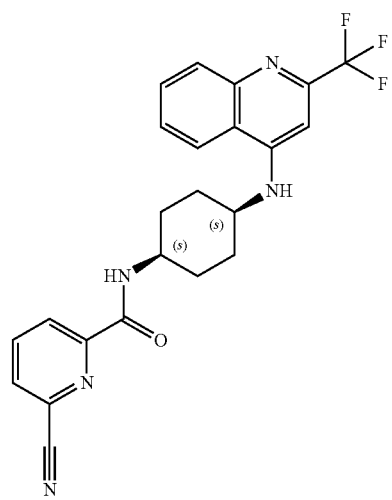
| | 4-262 | 7.460 | 439.442 | 440.2 | [M + H]+ | Method 3 |
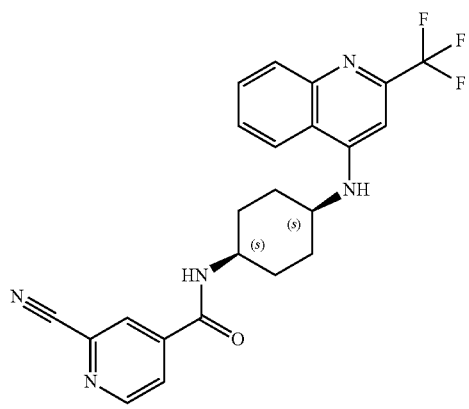 [SMILES: N#Cc1cc(C(=O)N[C@H]2CC[C@@H](Nc3cc(C(F)(F)F)nc4ccccc34)CC2)ccn1]
| | 4-263 | 4.716 | 457.501 | 458.2 | [M + H]+ | Method 3 |
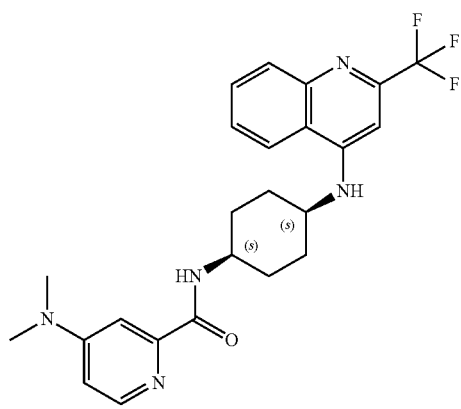 [SMILES: CN(C)c1ccnc(C(=O)N[C@H]2CC[C@@H](Nc3cc(C(F)(F)F)nc4ccccc34)CC2)c1]

TABLE 4-continued
| Structure | Cpd No. | Purity RT | MW | m/z | Ion | Purity Method |
|---|---|---|---|---|---|---|
| 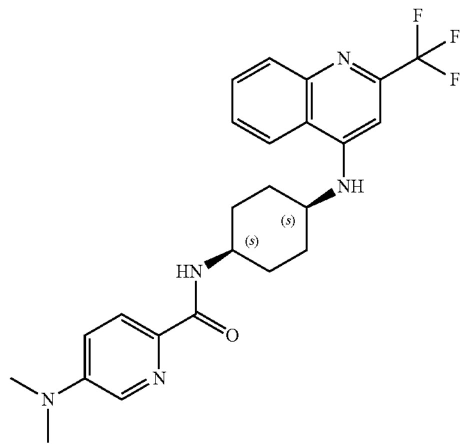 [SMILES: CN(C)c1ccc(C(=O)N[C@H]2CC[C@@H](Nc3cc(C(F)(F)F)nc4ccccc34)CC2)nc1] | 4-264 | 7.909 | 457.501 | 458.2 | [M + H]⁺ | Method 3 |
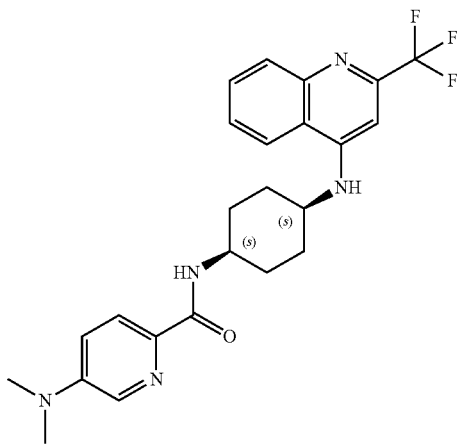
| | Cpd No. | Purity RT | MW | m/z | Ion | Purity Method |
|---|---|---|---|---|---|---|
| | 4-265 | 7.519 | 465.48 | 466.2 | [M + H]⁺ | Method 3 |
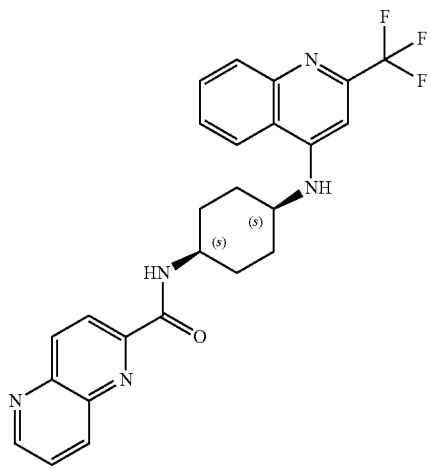 [SMILES: O=C(N[C@H]1CC[C@@H](Nc2cc(C(F)(F)F)nc3ccccc23)CC1)c1ccc2ncccc2n1]
| | Cpd No. | Purity RT | MW | m/z | Ion | Purity Method |
|---|---|---|---|---|---|---|
| | 4-266 | 7.642 | 464.44 | 465.2 | [M + H]⁺ | Method 3 |
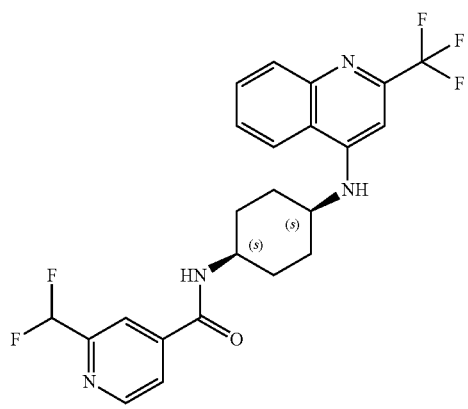 [SMILES: O=C(N[C@H]1CC[C@@H](Nc2cc(C(F)(F)F)nc3ccccc23)CC1)c1ccnc(C(F)F)c1]

TABLE 4-continued

| Structure | Cpd No. | Purity RT | MW | m/z | Ion | Purity Method |
|---|---|---|---|---|---|---|
| 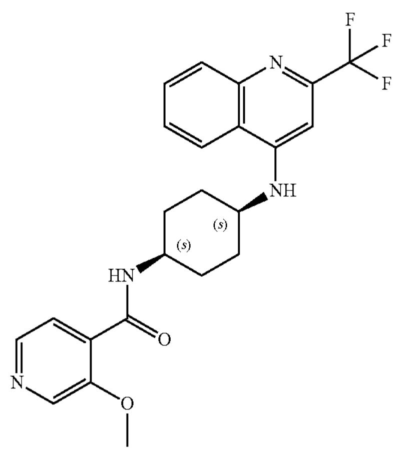 [SMILES: COc1cnccc1C(=O)N[C@H]1CC[C@@H](Nc2cc(C(F)(F)F)nc3ccccc23)CC1] | 4-267 | 6.205 | 444.458 | 445.2 | [M + H]+ | Method 3 |
| 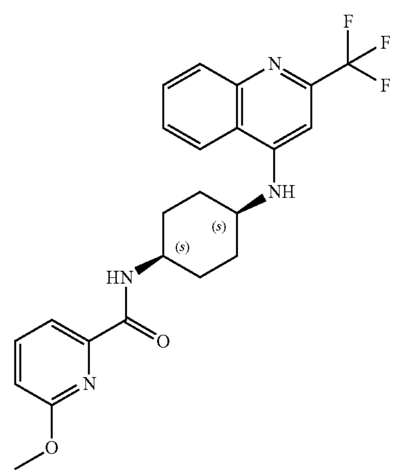 [SMILES: COc1cccc(C(=O)N[C@H]2CC[C@@H](Nc3cc(C(F)(F)F)nc4ccccc34)CC2)n1] | 4-268 | 8.701 | 444.458 | 445.2 | [M + H]+ | Method 3 |
| 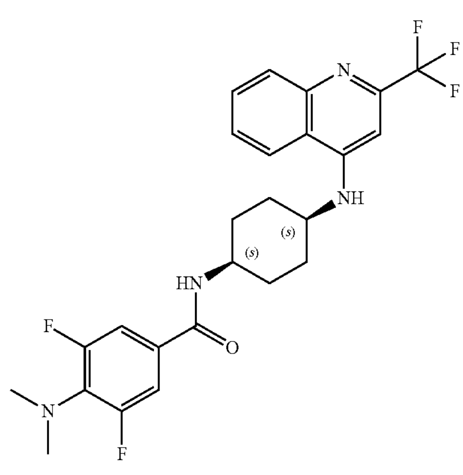 [SMILES: CN(C)c1c(F)cc(C(=O)N[C@H]2CC[C@@H](Nc3cc(C(F)(F)F)nc4ccccc34)CC2)cc1F] | 4-269 | 9.621 | 492.494 | 493.2 | [M + H]+ | Method 3 |

TABLE 4-continued

| Structure | Cpd No. | Purity RT | MW | m/z | Ion | Purity Method |
|---|---|---|---|---|---|---|
| 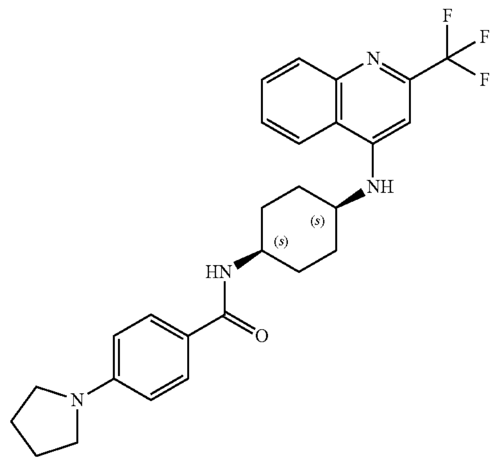 [SMILES: O=C(N[C@H]1CC[C@@H](Nc2cc(C(F)(F)F)nc3ccccc23)CC1)c1ccc(N2CCCC2)cc1] | 4-270 | 9.222 | 482.551 | 483.3 | [M + H]⁺ | Method 3 |
| 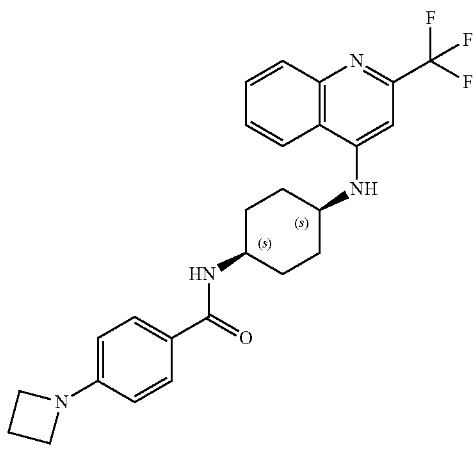 [SMILES: O=C(N[C@H]1CC[C@@H](Nc2cc(C(F)(F)F)nc3ccccc23)CC1)c1ccc(N2CCC2)cc1] | 4-271 | 8.388 | 468.524 | 469.3 | [M + H]⁺ | Method 3 |
| 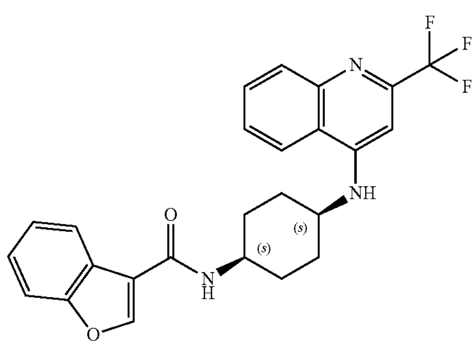 [SMILES: O=C(N[C@H]1CC[C@@H](Nc2cc(C(F)(F)F)nc3ccccc23)CC1)c1coc2ccccc12] | 4-272 | 8.85 | 453.465 | 454.2 | [M + H]⁺ | Method 3 |
| 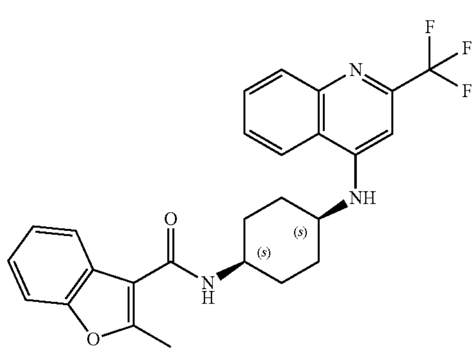 [SMILES: Cc1oc2ccccc2c1C(=O)N[C@H]1CC[C@@H](Nc2cc(C(F)(F)F)nc3ccccc23)CC1] | 4-273 | 9.249 | 467.492 | 468.2 | [M + H]⁺ | Method 3 |

TABLE 4-continued

| Structure | Cpd No. | Purity RT | MW | m/z | Ion | Purity Method |
|---|---|---|---|---|---|---|
| 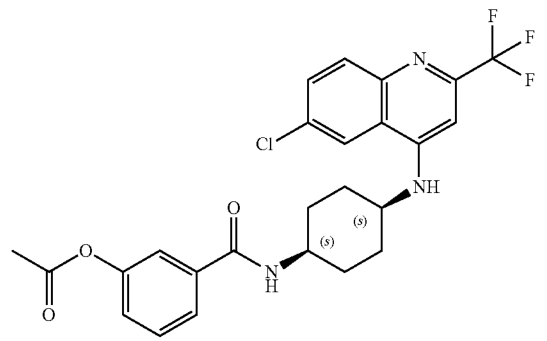 [SMILES: CC(=O)Oc1cccc(C(=O)N[C@H]2CC[C@@H](Nc3cc(C(F)(F)F)nc4ccc(Cl)cc34)CC2)c1] | 4-274 | 9.847 | 505.92 | 506.2 | [M + H]⁺ | Method 3 |
| 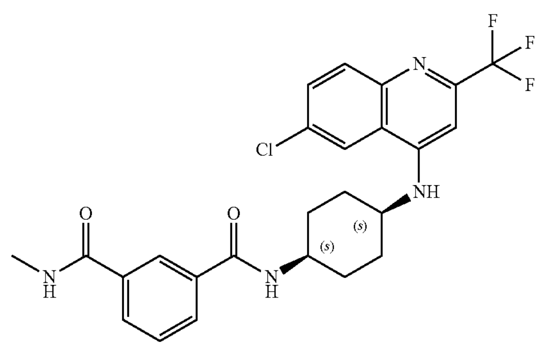 [SMILES: CNC(=O)c1cccc(C(=O)N[C@H]2CC[C@@H](Nc3cc(C(F)(F)F)nc4ccc(Cl)cc34)CC2)c1] | 4-275 | 8.283 | 504.94 | 505.2 | [M + H]⁺ | Method 3 |
| 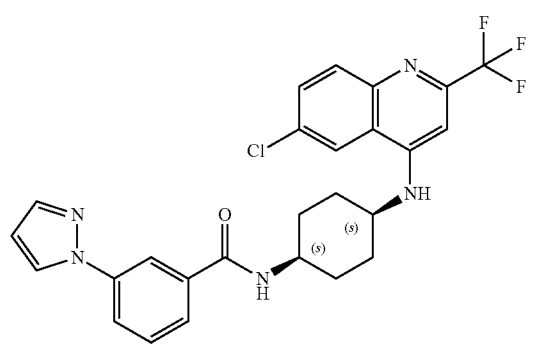 [SMILES: O=C(N[C@H]1CC[C@@H](Nc2cc(C(F)(F)F)nc3ccc(Cl)cc23)CC1)c1cccc(-n2cccn2)c1] | 4-276 | 10.099 | 513.95 | 514.2 | [M + H]⁺ | Method 3 |
| 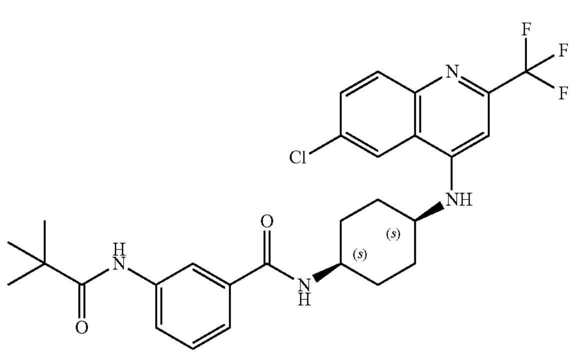 [SMILES: CC(C)(C)C(=O)Nc1cccc(C(=O)N[C@H]2CC[C@@H](Nc3cc(C(F)(F)F)nc4ccc(Cl)cc34)CC2)c1] | 4-277 | 10.156 | 547.02 | 547.2 | [M + H]⁺ | Method 3 |

TABLE 4-continued

| Structure | Cpd No. | Purity RT | MW | m/z | Ion | Purity Method |
|---|---|---|---|---|---|---|
| 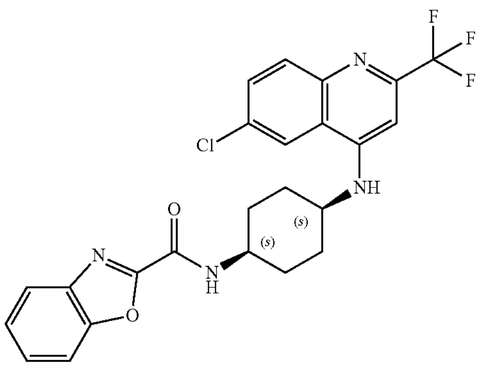 [SMILES: O=C(N[C@H]1CC[C@@H](Nc2cc(C(F)(F)F)nc3ccc(Cl)cc23)CC1)c1nc2ccccc2o1] | 4-278 | 10.645 | 488.9 | 489.2 | [M + H]+ | Method 3 |
| 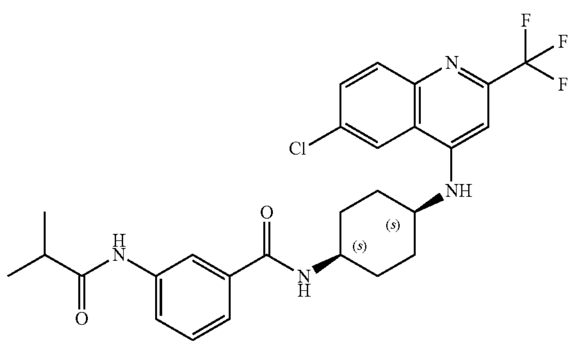 [SMILES: CC(C)C(=O)Nc1cccc(C(=O)N[C@H]2CC[C@@H](Nc3cc(C(F)(F)F)nc4ccc(Cl)cc34)CC2)c1] | 4-279 | 9.564, 9.602 | 532.99 | 533.2 | [M + H]+ | Method 3 |
| 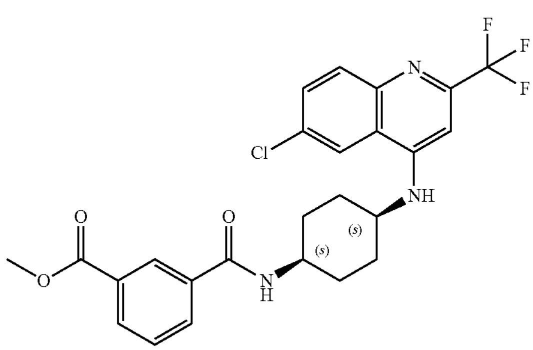 [SMILES: COC(=O)c1cccc(C(=O)N[C@H]2CC[C@@H](Nc3cc(C(F)(F)F)nc4ccc(Cl)cc34)CC2)c1] | 4-280 | 10.149 | 505.92 | 506.2 | [M + H]+ | Method 3 |
| 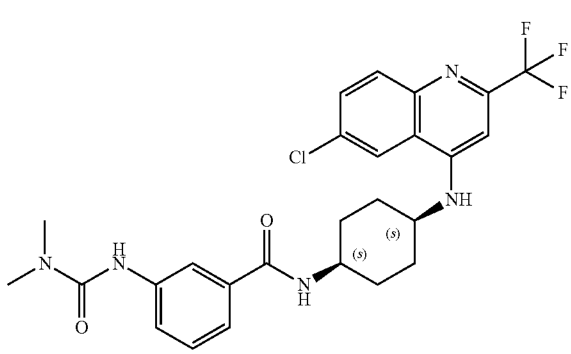 [SMILES: CN(C)C(=O)Nc1cccc(C(=O)N[C@H]2CC[C@@H](Nc3cc(C(F)(F)F)nc4ccc(Cl)cc34)CC2)c1] | 4-281 | 8.602 | 533.98 | 534.2 | [M + H]+ | Method 3 |

TABLE 4-continued

| Structure | Cpd No. | Purity RT | MW | m/z | Ion | Purity Method |
|---|---|---|---|---|---|---|
| 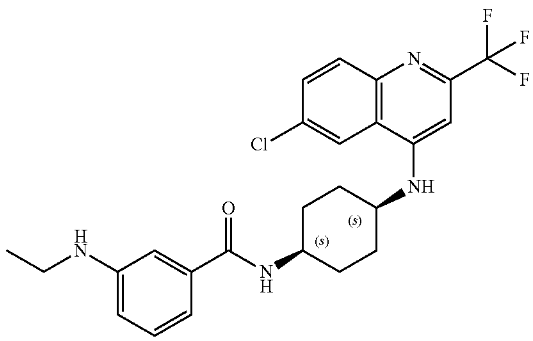 [SMILES: CCNc1cccc(C(=O)N[C@H]2CC[C@@H](Nc3cc(C(F)(F)F)nc4ccc(Cl)cc34)CC2)c1] | 4-282 | 9.38 | 490.96 | 491.2 | [M + H]⁺ | Method 3 |
| 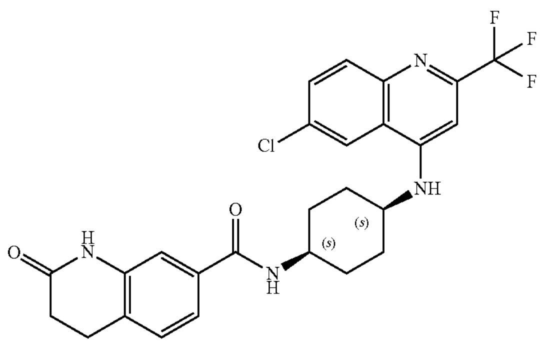 [SMILES: O=C1CCc2ccc(C(=O)N[C@H]3CC[C@@H](Nc4cc(C(F)(F)F)nc5ccc(Cl)cc45)CC3)cc2N1] | 4-283 | 8.369 | 516.95 | 517.2 | [M + H]⁺ | Method 3 |
| 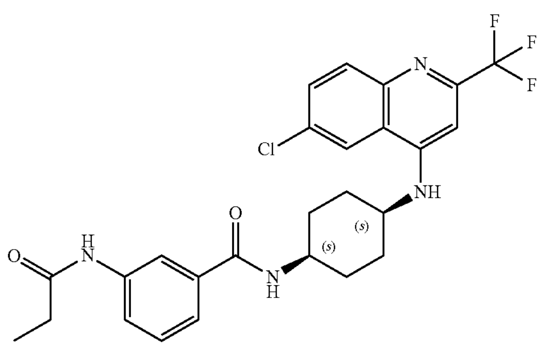 [SMILES: CCC(=O)Nc1cccc(C(=O)N[C@H]2CC[C@@H](Nc3cc(C(F)(F)F)nc4ccc(Cl)cc34)CC2)c1] | 4-284 | 9.052 | 518.97 | 519.2 | [M + H]⁺ | Method 3 |
| 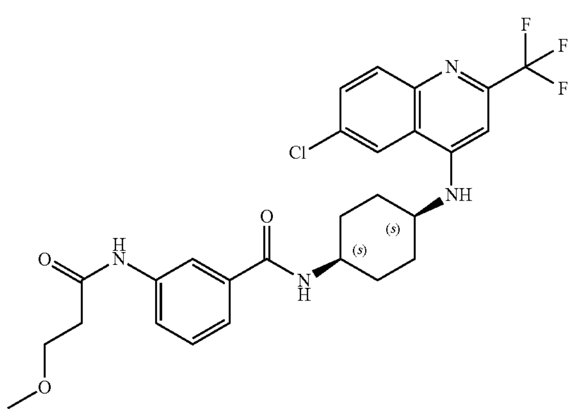 [SMILES: COCCC(=O)Nc1cccc(C(=O)N[C@H]2CC[C@@H](Nc3cc(C(F)(F)F)nc4ccc(Cl)cc34)CC2)c1] | 4-285 | 8.73 | 548.99 | 549.2 | [M + H]⁺ | Method 3 |

TABLE 4-continued
| Structure | Cpd No. | Purity RT | MW | m/z | Ion | Purity Method |
|---|---|---|---|---|---|---|
| 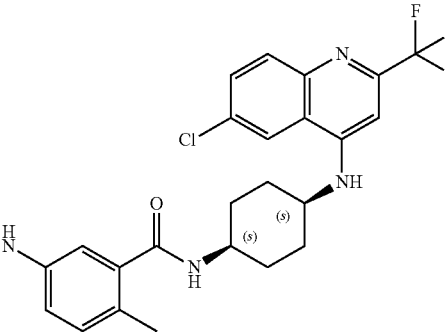 | 4-286 | 8.533 | 518.97 | 519.2 | [M + H]+ | Method 3 |
| 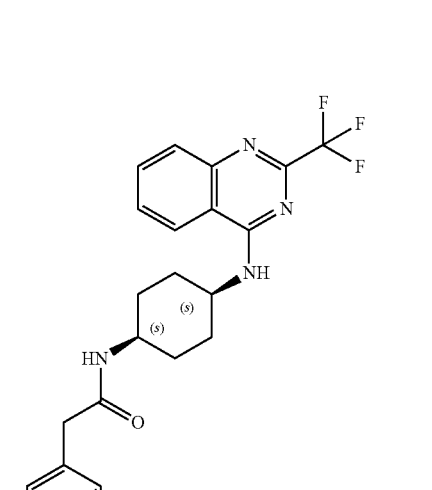 | 4-287 | 9.265 | 446.45 | 447.2 | [M + H]+ | Method 3 |
| 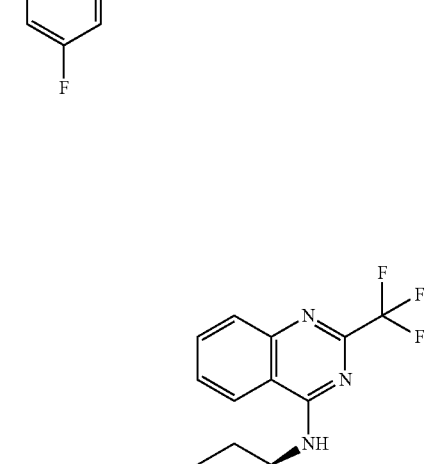 | 4-288 | 9.384 | 439.442 | 440.2 | [M + H]+ | Method 3 |

TABLE 4-continued

| Structure | Cpd No. | Purity RT | MW | m/z | Ion | Purity Method |
|---|---|---|---|---|---|---|
| 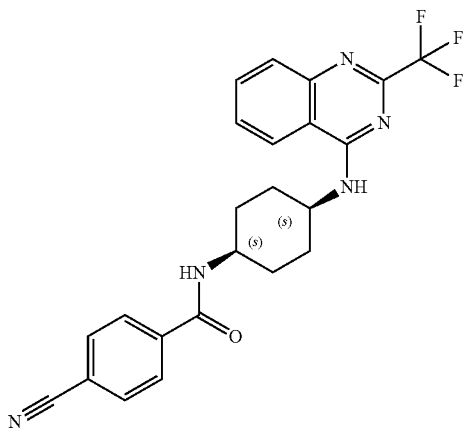 [SMILES: N#Cc1ccc(C(=O)N[C@H]2CC[C@@H](Nc3nc(C(F)(F)F)nc4ccccc34)CC2)cc1] | 4-289 | 9.283 | 439.442 | 440.2 | [M + H]+ | Method 3 |
| 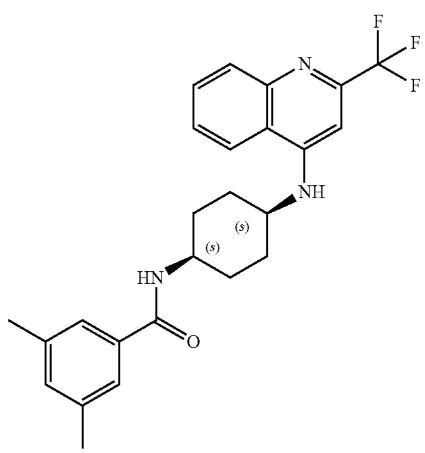 [SMILES: Cc1cc(C)cc(C(=O)N[C@H]2CC[C@@H](Nc3cc(C(F)(F)F)nc4ccccc34)CC2)c1] | 4-290 | 0.858 | 441.498 | 442.1 | [M + H]+ | Method 1 |
| 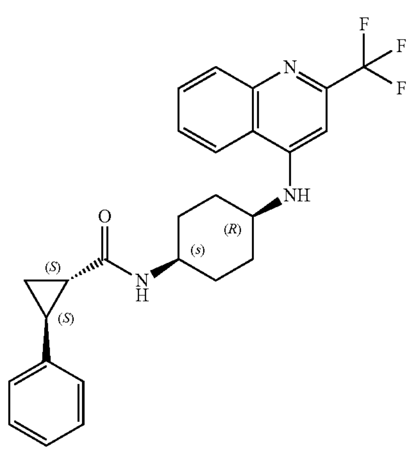 | 4-291 | 0.848 | 453.509 | 454.1 | [M + H]+ | Method 1 |

TABLE 4-continued

| Structure | Cpd No. | Purity RT | MW | m/z | Ion | Purity Method |
|---|---|---|---|---|---|---|
| 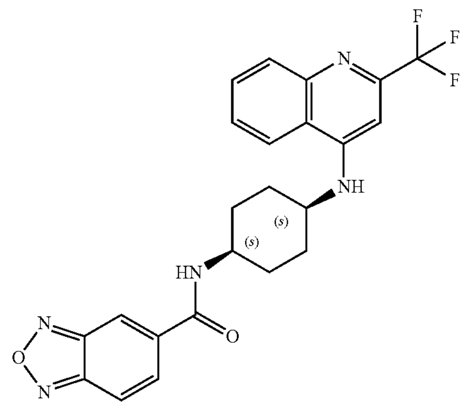 [SMILES: O=C(N[C@H]1CC[C@@H](Nc2cc(C(F)(F)F)nc3ccccc23)CC1)c1ccc2nonc2c1] | 4-292 | 0.833 | 455.441 | 456.1 | [M + H]⁺ | Method 1 |
| 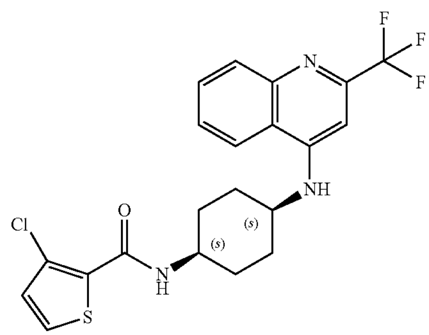 [SMILES: O=C(N[C@H]1CC[C@@H](Nc2cc(C(F)(F)F)nc3ccccc23)CC1)c1sccc1Cl] | 4-293 | 0.841 | 453.91 | 454 | [M + H]⁺ | Method 1 |
| 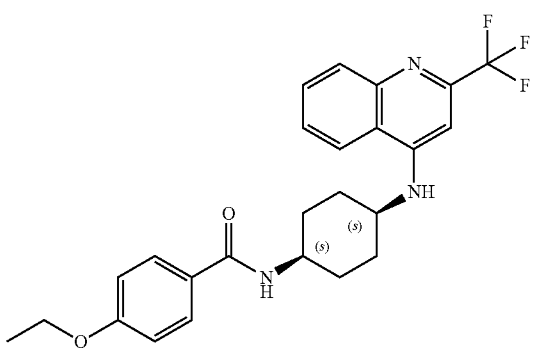 [SMILES: CCOc1ccc(C(=O)N[C@H]2CC[C@@H](Nc3cc(C(F)(F)F)nc4ccccc34)CC2)cc1] | 4-294 | 0.839 | 457.497 | 458.1 | [M + H]⁺ | Method 1 |
| 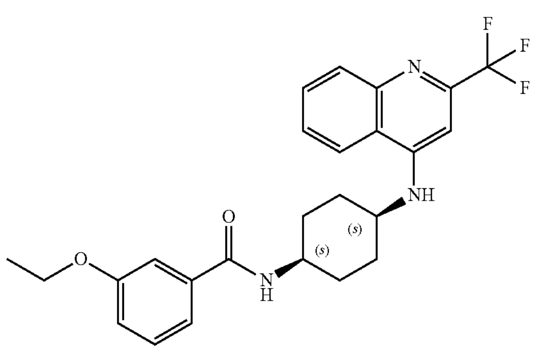 [SMILES: CCOc1cccc(C(=O)N[C@H]2CC[C@@H](Nc3cc(C(F)(F)F)nc4ccccc34)CC2)c1] | 4-295 | 0.837 | 457.497 | 458.1 | [M + H]⁺ | Method 1 |

TABLE 4-continued

| Structure | Cpd No. | Purity RT | MW | m/z | Ion | Purity Method |
|---|---|---|---|---|---|---|
| 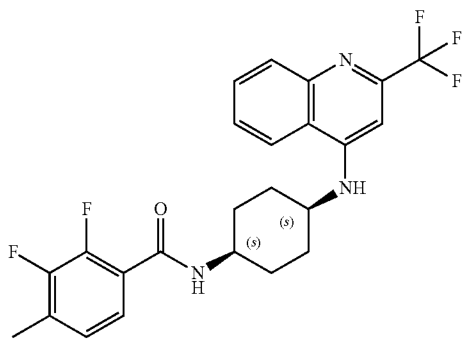 [SMILES: Cc1ccc(C(=O)N[C@H]2CC[C@@H](Nc3cc(C(F)(F)F)nc4ccccc34)CC2)c(F)c1F] | 4-296 | 0.857 | 463.452 | 464.1 | [M + H]+ | Method 1 |
| 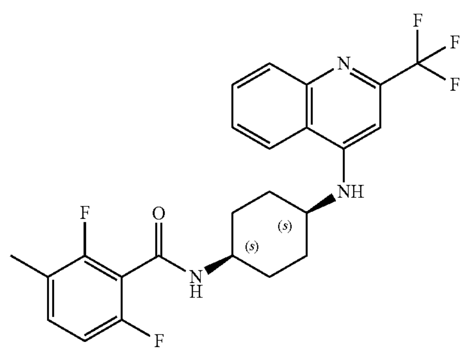 [SMILES: Cc1ccc(F)c(C(=O)N[C@H]2CC[C@@H](Nc3cc(C(F)(F)F)nc4ccccc34)CC2)c1F] | 4-297 | 0.83 | 463.452 | 464.1 | [M + H]+ | Method 1 |
| 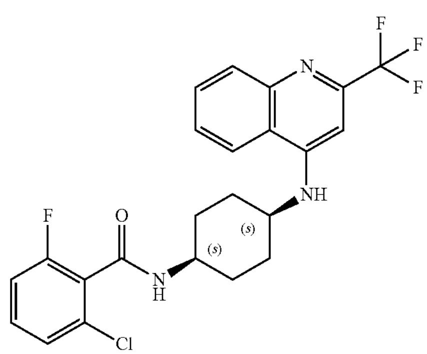 [SMILES: O=C(N[C@H]1CC[C@@H](Nc2cc(C(F)(F)F)nc3ccccc23)CC1)c1c(F)cccc1Cl] | 4-298 | 0.814 | 465.88 | 466.1 | [M + H]+ | Method 1 |
| 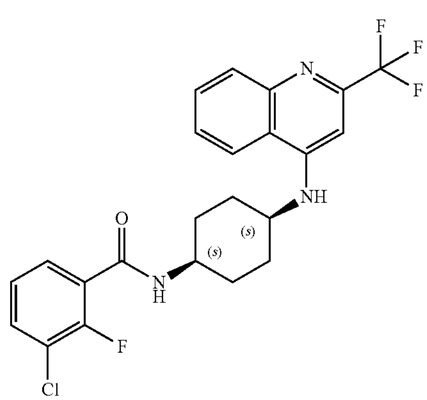 [SMILES: O=C(N[C@H]1CC[C@@H](Nc2cc(C(F)(F)F)nc3ccccc23)CC1)c1cccc(Cl)c1F] | 4-299 | 0.843 | 465.88 | 466 | [M + H]+ | Method 1 |

TABLE 4-continued

| Structure | Cpd No. | Purity RT | MW | m/z | Ion | Purity Method |
|---|---|---|---|---|---|---|
| 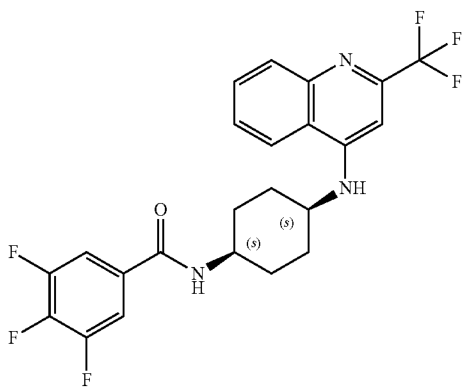 [SMILES: O=C(N[C@H]1CC[C@@H](Nc2cc(C(F)(F)F)nc3ccccc23)CC1)c1cc(F)c(F)c(F)c1] | 4-300 | 0.856 | 467.415 | 468.1 | [M + H]⁺ | Method 1 |
| 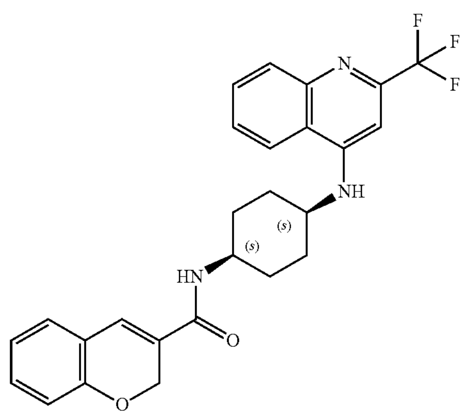 [SMILES: O=C(N[C@H]1CC[C@@H](Nc2cc(C(F)(F)F)nc3ccccc23)CC1)C1=Cc2ccccc2OC1] | 4-301 | 0.855 | 467.492 | 468.1 | [M + H]⁺ | Method 1 |
| 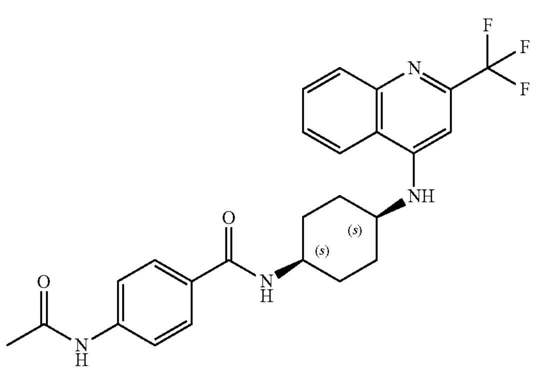 [SMILES: CC(=O)Nc1ccc(C(=O)N[C@H]2CC[C@@H](Nc3cc(C(F)(F)F)nc4ccccc34)CC2)cc1] | 4-302 | 0.776 | 470.496 | 471.1 | [M + H]⁺ | Method 1 |

TABLE 4-continued

| Structure | Cpd No. | Purity RT | MW | m/z | Ion | Purity Method |
|---|---|---|---|---|---|---|
| 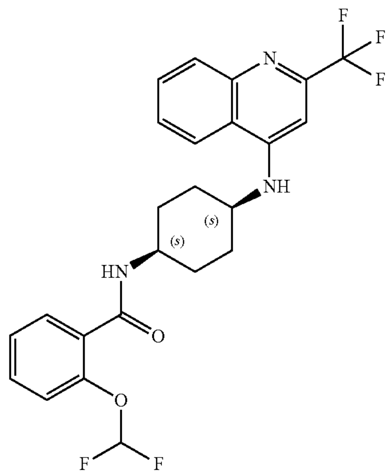 [SMILES: O=C(N[C@H]1CC[C@@H](Nc2cc(C(F)(F)F)nc3ccccc23)CC1)c1ccccc1OC(F)F] | 4-303 | 0.826 | 479.451 | 480.1 | [M + H]⁺ | Method 1 |
| 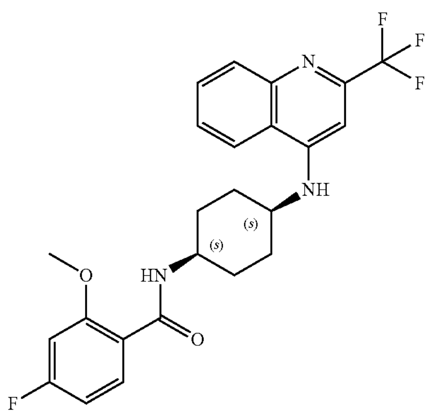 [SMILES: COc1cc(F)ccc1C(=O)N[C@H]1CC[C@@H](Nc2cc(C(F)(F)F)nc3ccccc23)CC1] | 4-304 | 0.841 | 461.461 | 462.1 | [M + H]⁺ | Method 1 |
| 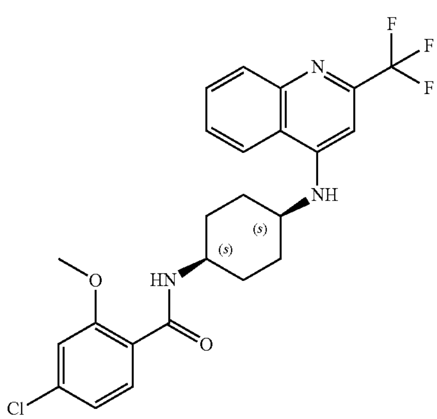 [SMILES: COc1cc(Cl)ccc1C(=O)N[C@H]1CC[C@@H](Nc2cc(C(F)(F)F)nc3ccccc23)CC1] | 4-305 | 0.858 | 477.91 | 478.1 | [M + H]⁺ | Method 1 |

TABLE 4-continued
| Structure | Cpd No. | Purity RT | MW | m/z | Ion | Purity Method |
|---|---|---|---|---|---|---|
| 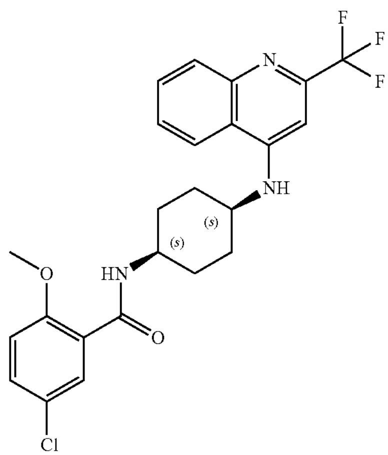 [SMILES: COc1ccc(Cl)cc1C(=O)N[C@H]1CC[C@@H](Nc2cc(C(F)(F)F)nc3ccccc23)CC1] | 4-306 | 0.862 | 477.91 | 478.1 | [M + H]⁺ | Method 1 |
| 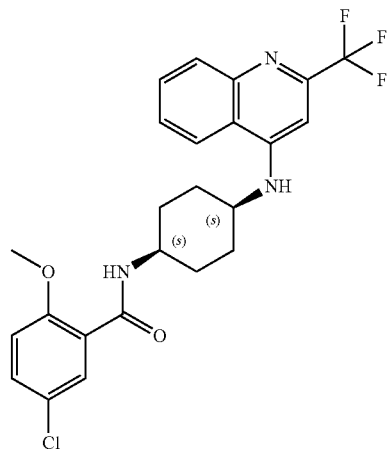 | | | | | | |
| 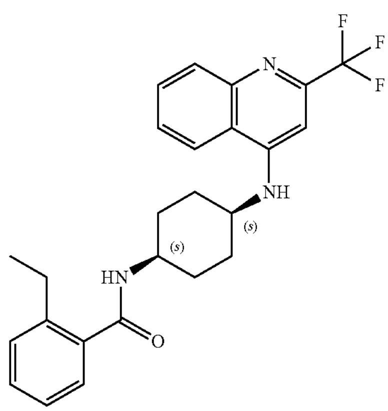 [SMILES: CCc1ccccc1C(=O)N[C@H]1CC[C@@H](Nc2cc(C(F)(F)F)nc3ccccc23)CC1] | 4-307 | 0.837 | 441.498 | 442.1 | [M + H]⁺ | Method 1 |
| 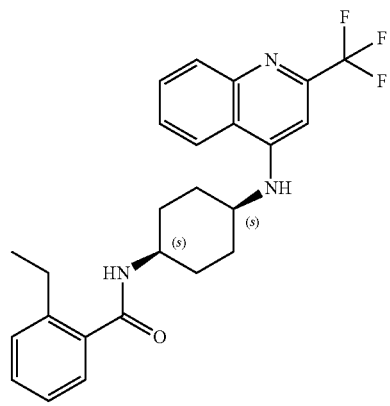 | | | | | | |
| 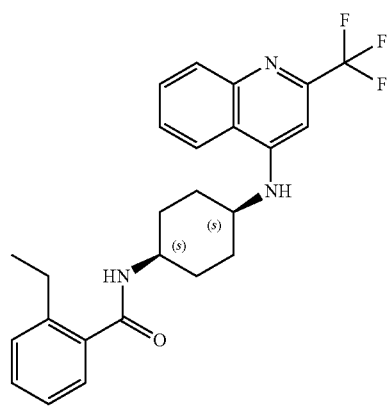 [SMILES: CCc1ccccc1C(=O)N[C@H]1CC[C@@H](Nc2cc(C(F)(F)F)nc3ccccc23)CC1] | | | | | | |

TABLE 4-continued

| Structure | Cpd No. | Purity RT | MW | m/z | Ion | Purity Method |
|---|---|---|---|---|---|---|
| 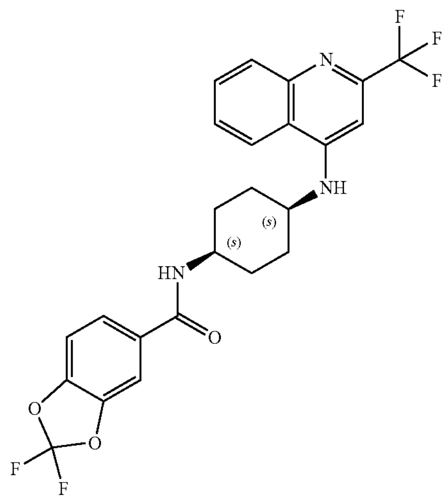 [SMILES: O=C(N[C@H]1CC[C@@H](Nc2cc(C(F)(F)F)nc3ccccc23)CC1)c1ccc2c(c1)OC(F)(F)O2] | 4-308 | 0.865 | 493.434 | 494.1 | [M + H]⁺ | Method 1 |
| 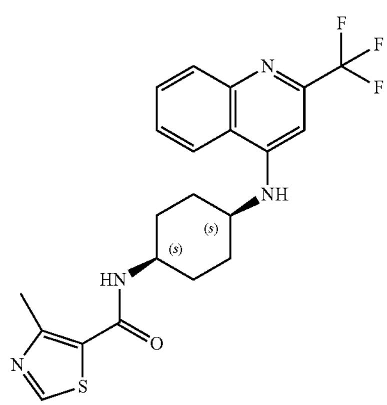 [SMILES: Cc1ncsc1C(=O)N[C@H]1CC[C@@H](Nc2cc(C(F)(F)F)nc3ccccc23)CC1] | 4-309 | 0.774 | 434.48 | 435 | [M + H]⁺ | Method 1 |
| 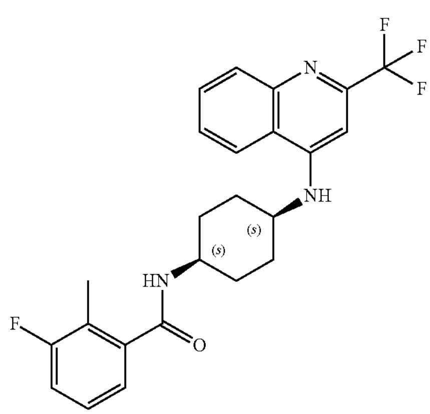 [SMILES: Cc1c(F)cccc1C(=O)N[C@H]1CC[C@@H](Nc2cc(C(F)(F)F)nc3ccccc23)CC1] | 4-310 | 0.826 | 445.462 | 446.1 | [M + H]⁺ | Method 1 |

TABLE 4-continued

| Structure | Cpd No. | Purity RT | MW | m/z | Ion | Purity Method |
|---|---|---|---|---|---|---|
| 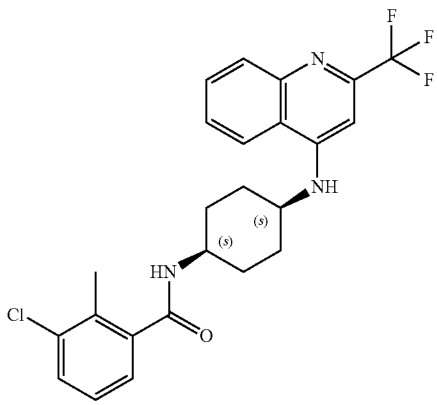 [SMILES: Cc1c(Cl)cccc1C(=O)N[C@H]1CC[C@@H](Nc2cc(C(F)(F)F)nc3ccccc23)CC1] | 4-311 | 0.847 | 461.91 | 462.1 | [M + H]⁺ | Method 1 |
| 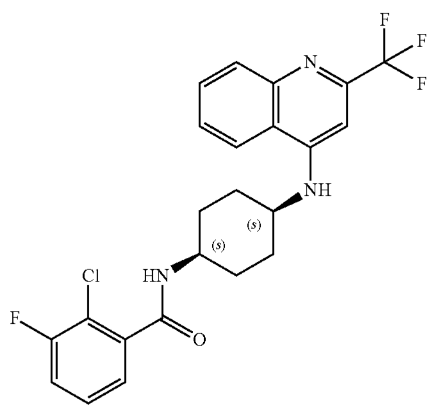 [SMILES: O=C(N[C@H]1CC[C@@H](Nc2cc(C(F)(F)F)nc3ccccc23)CC1)c1cccc(F)c1Cl] | 4-312 | 0.819 | 465.88 | 466.1 | [M + H]⁺ | Method 1 |
| 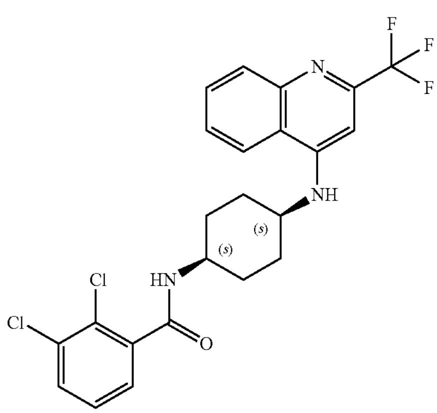 [SMILES: O=C(N[C@H]1CC[C@@H](Nc2cc(C(F)(F)F)nc3ccccc23)CC1)c1cccc(Cl)c1Cl] | 4-313 | 0.84 | 482.33 | 482 | [M + H]⁺ | Method 1 |

TABLE 4-continued

| Structure | Cpd No. | Purity RT | MW | m/z | Ion | Purity Method |
|---|---|---|---|---|---|---|
| 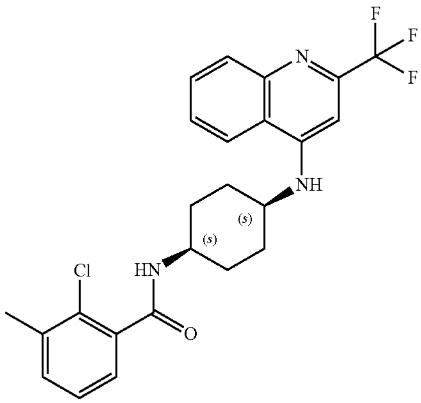 [SMILES: Cc1cccc(C(=O)N[C@H]2CC[C@@H](Nc3cc(C(F)(F)F)nc4ccccc34)CC2)c1Cl] | 4-314 | 0.832 | 461.91 | 462.1 | [M + H]⁺ | Method 1 |
| 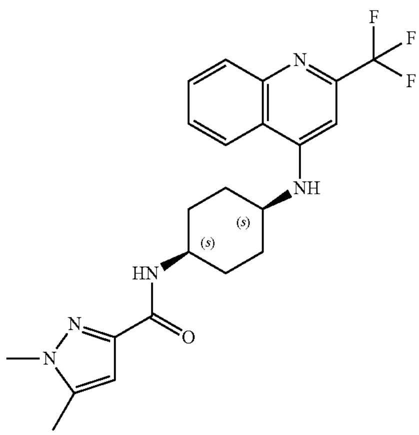 [SMILES: Cc1cc(C(=O)N[C@H]2CC[C@@H](Nc3cc(C(F)(F)F)nc4ccccc34)CC2)nn1C] | 4-315 | 0.778 | 431.463 | 432.1 | [M + H]⁺ | Method 1 |
| 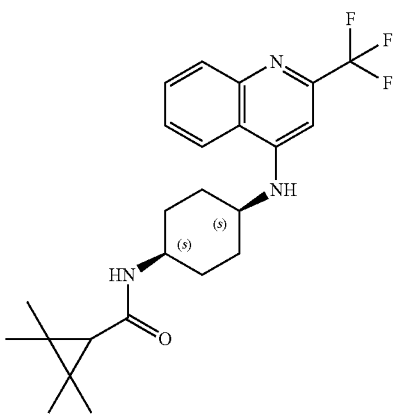 [SMILES: CC1(C)C(C(=O)N[C@H]2CC[C@@H](Nc3cc(C(F)(F)F)nc4ccccc34)CC2)C1(C)C] | 4-316 | 0.864 | 433.519 | 434.1 | [M + H]⁺ | Method 1 |

Example 6

MRGPRX2 Activity

CHO cells stably transfected to express human MRGPRX2 were maintained in an incubator at 37° C. with 5% CO2 and grown in F12 (HAM) media with 10% fetal bovine serum (FBS), 1% Glutamax, 1% penicillin/streptomycin, 800 μg/mL Geneticin (G418), and 300 μg/mL Hygromycin B.

Cells were plated in a 383-well assay plate at 20,000 cells per well in 12 μL of Opti-MEM and kept in an incubator overnight. On the day of the assay, compounds solubilized at 10 mM in DMSO were added as a 10-point curve (30 uM final top concentration with 1:3 serial dilutions) using a Tecan D300E digital dispenser. Agonists were diluted in assay buffer (final concentrations of 5.7 mM Tris-HCl, 43 mM NaCl, 50 mM LiCl, pH=8) and 2 μL of the agonist Cortistatin 14 (CPC Scientific, catalog CORT-002) are added to each well. Final concentrations of agonists were 0.3 μM Cortistatin. Final concentrations of DMSO were kept consistent across the plate. Plates were incubated in the dark for 1 h at 37° C. and then for 1 h at room temperature. IP-1 standards and HTRF detection reagents were added according to the IP-One-Gq Kit purchased from Cisbio (part number 62IPAPEJ) and incubated in the dark for 1 h at room temperature. The plate was read on a Molecular Devices SpectraMax iD5 plate reader. The HTRF ratio was calculated from the raw data and graphed using GraphPad Prism to calculate an IC50 value for each compound.

Activity data for selected MRGPRX2 antagonists (versus 0.3 uM Corstitatin agonist) are displayed in Table 5. The activity ranges are denoted as follows: "+++++" denotes antagonist activity <100 nM; "++++" denotes antagonist activity between 100 and 500 nM; "+++" denotes activity between 501 and 1000 nM; "++" denotes activity between 1001 and 2500 nM; and "+" denotes activity >2500 nM

TABLE 5

| Cpd No. | MRGPR2 Antagonist Activity | Cpd No. | MRGPR2 Antagonist Activity |
|---|---|---|---|
| Example 5A | +++++ | 1-3 | ++++ |
| Example 5B | +++++ | 4-173 | ++++ |
| 4-7 | +++++ | 3-12 | ++++ |
| 4-23 | +++++ | 4-243 | +++ |
| 4-103 | +++++ | 4-251 | +++ |
| 4-8 | ++++ | 4-57 | +++ |
| 4-164 | ++++ | 3-27 | +++ |
| 4-272 | ++++ | 3-36 | +++ |
| 4-123 | ++++ | 3-21 | +++ |
| 4-282 | ++++ | 4-107 | +++ |
| 4-283 | ++++ | 4-258 | +++ |
| 4-145 | ++++ | 4-6 | +++ |
| 3-30 | ++++ | 4-241 | +++ |
| 4-102 | ++++ | 4-60 | +++ |
| 4-279 | ++++ | 4-90 | +++ |
| 4-281 | ++++ | 4-200 | ++ |
| 3-25 | ++++ | 4-209 | ++ |
| 3-42 | ++++ | 4-230 | ++ |
| 4-242 | ++ | 4-265 | ++ |
| 4-129 | ++ | 3-24 | ++ |
| 4-141 | ++ | 4-19 | + |
| 4-162 | ++ | 4-122 | + |
| 4-291 | ++ | 4-134 | + |

Example 7

Mast Cell Beta-Hexosaminidase Release Assay

Human LAD2 cells (NIH) were maintained in an incubator at 37° C. with 5% $CO_2$ and cultured in StemPro-34 serum-free media (Gibco 10639011) supplemented with 2 mM L-glutamine, 100 U/ml penicillin, 50 mg/ml streptomycin and 100 ng/ml SCF (Invitrogen PEP0860), at a concentration of $2-5 \times 10^5$ cells/mL, with hemidepletion every 1-2 weeks.

Cells were transferred to SCF-Free medium at $2.5 \times 10^5$ cells/mL and kept in an incubator overnight. On the day of the assay, cells were washed twice in Assay Buffer (final concentrations 10 mM HEPES, 137 mM NaCl, 5.6 mM D-glucose, 2.7 mM KCl, 1 mM MgCl, 1.8 mM $CaCl_2$, 0.4 mM $Na_2HPO_4.7H_2O$, 0.04% BSA, pH=7.4) and plated in a 96-well v-bottom plate at 20,000 cells per well in 80 μL Assay Buffer. Antagonist compounds solubilized at 10 mM in DMSO were diluted in Assay Buffer to 10× final desired concentrations as a 10-point curve (10 μM final top concentration with 1:3 serial dilutions) and 10 μL added per well. Plates were then incubated for 1 hour at 37° C. Agonists were diluted in Assay Buffer to 10× desired concentrations and 10 μL of the appropriate agonist added to each well. The final concentration of Cortistatin-14 (Tocris 3374) used in antagonist assays was 500 nM. Final concentrations of DMSO were kept consistent across the plate. Plates were then incubated in a warm air oven for 30 minutes at 37° C., followed by centrifugation at 4° C. for 5 minutes at 450×g. 50 μL supernatant from each well was then transferred to a 96-well flat bottom plate containing 100 μL substrate solution per well (3.5 mg/mL p-Nitrophenyl-N-acetyl-β-D-glucosaminide (Sigma 487052) in Citrate Buffer containing a final concentration of 40 mM Citric Acid, 20 mM $Na_2HPO_4.7H_2O$, pH=4.5). To the cell pellets left in the remaining assay buffer, 150 μL 0.1% Triton-X-100 was then added to each well, resuspended by pipetting up and down, and 50 μL cell lysates transferred to a second 96-well flat bottom plate containing 100 μL substrate solution per well. Plates containing transferred supernatant and cell lysates were then incubated in a warm air oven for 90 minutes at 37° C. After incubation, 50 μL of 400 mM Glycine buffer (pH 10.7) was added into each well and the plate was read on a Molecular Devices SpectraMax iD5 plate reader (absorbance at 405 nm with reference filter at 620 nm). After background subtraction, the percentage degranulation (percent beta-hexosaminidase release) was calculated as 100× (supernatant values)/(supernatant+lysate values), followed by analysis using GraphPad Prism software to calculate an $IC_{50}$ value for each compound.

Activity data for selected MRGPRX2 antagonists in the Mast Cell Beta-Hexosaminidase Release Assay are displayed in Table 6. The activity ranges are denoted as follows: "+++++" denotes antagonist activity <100 nM; "++++" denotes antagonist activity between 100 and 500 nM; "+++" denotes activity between 501 and 1000 nM; "++" denotes activity between 1001 and 2500 nM; and "+" denotes activity >2500 nM

TABLE 6

| Cpd No. | MRGPR2 Antagonist Activity |
|---|---|
| 4-139 | +++++ |
| 4-9 | +++++ |
| Example 5B | ++++ |
| 4-7 | ++++ |
| 1-5 | ++++ |
| 3-25 | ++++ |
| 1-4 | ++++ |
| 3-10 | ++++ |
| 4-288 | +++ |
| 3-30 | +++ |
| 1-7 | +++ |

Example 8

Evans Blue Vascular Permeability Assay 8-10-week-old C57BL/6J (strain 000664; Jackson Laboratories) or MrgprX2 knockin (Mrgb2Kl; Escient Pharmaceuticals Inc.) mice were anesthetized with isoflurane and shaved on the back 4-6 days prior to the beginning of the study. On the day of the study, mice were dosed either with vehicle or test compound at 100, 30, 20, 10 or 3 mg/kg 3 hours prior to Evans blue injection. Animals were restrained and injected intravenously (IV) with 200 μl of 1% Evans Blue (cat. no. 313-13-6; Fisher Chemical) in 0.9% saline, before being placed under isoflurane. Ten minutes after IV injections animals were maintained under anesthesia and injected intradermally with 25 μl of vehicle PBS, cortistatin-14 (C-14; 300 nM; cat. no. 3374; Tocris Bioscience); Icatibant (HOE-140; 38 µM; Cat no. 3014; Tocris Bioscience) or goat anti-mouse IgE (50 µg/ml; ab9162; Abcam). Ten minutes after intradermal injection animals were photographed and sacrificed. The skin around the injection site was punctured with an 8 mm circular dermal punch and weighed and placed in 1.5 ml Eppendorf tubes. Evans blue dye was extracted from the tissue by adding 1 ml of Formamide (BP227-500; Fisher Scientific) in the tube which was then vortexed covered in foil and placed at 55° C. overnight. 200 µl of extracted dye in formamide was then placed into a 96 well plate in duplicate along with a standard curve of known Evans blue concentration standards. The plate was read at 620 nM on a plate reader and the results were expressed as g of dye per mg tissue. Statistical tests were performed with the software Graphpad Prism 8 (Graphpad Software). Data is expressed as mean and standard error of mean. Unpaired t-Tests were used to compare the statistical difference between groups.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

This application claims the benefit of priority to U.S. Provisional Application No. 63/094,864, filed Oct. 21, 2020, which application is hereby incorporated by reference in its entirety

The invention claimed is:

1. A compound having formula (IB):

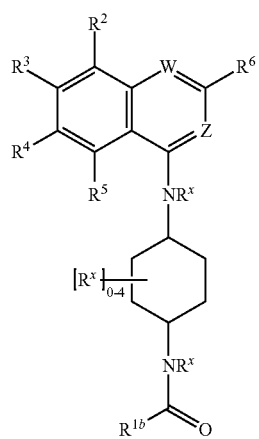

(IB)

or a pharmaceutically acceptable salt, isomer, hydrate, solvate or isotope thereof, wherein:

$R^{1b}$ is phenyl substituted with $R^q$;
each R is independently H, $C_{1-6}$ alkyl, $C_{2-6}$ alkenyl, $C_{2-6}$ alkynyl, or alkylamino;
$R^q$ is —N(R)C(O)R or —N(R)S(O)$_2$R;
$R^2$ is H;
$R^3$ is H;
$R^4$ is H or Cl;
$R^5$ is H;
$R^6$ is $CF_3$;
each $R^x$ is H;
W is N;
Z is $CR^z$; and
$R^z$ is H.

2. A compound selected from any one of the following compounds, or a pharmaceutically acceptable salt, isomer, hydrate, solvate or isotope thereof.

| Structure | Cpd No. |
| --- | --- |
| 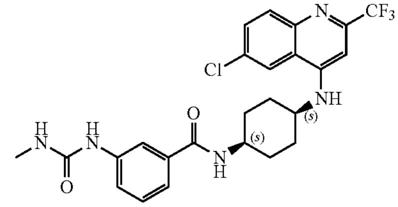 [SMILES: CNC(=O)Nc1cccc(C(=O)N[C@H]2CC[C@@H](Nc3cc(C(F)(F)F)nc4ccc(Cl)cc34)CC2)c1] | 5A |
| 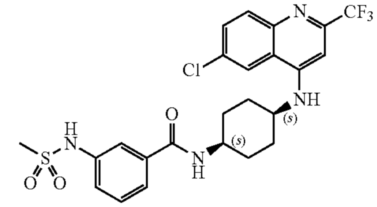 [SMILES: CS(=O)(=O)Nc1cccc(C(=O)N[C@H]2CC[C@@H](Nc3cc(C(F)(F)F)nc4ccc(Cl)cc34)CC2)c1] | 5B |
| 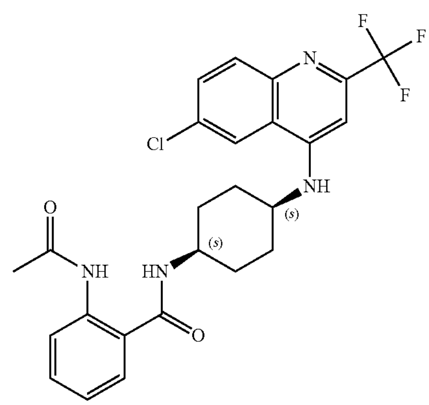 [SMILES: CC(=O)Nc1ccccc1C(=O)N[C@H]1CC[C@@H](Nc2cc(C(F)(F)F)nc3ccc(Cl)cc23)CC1] | 4-4 |
| 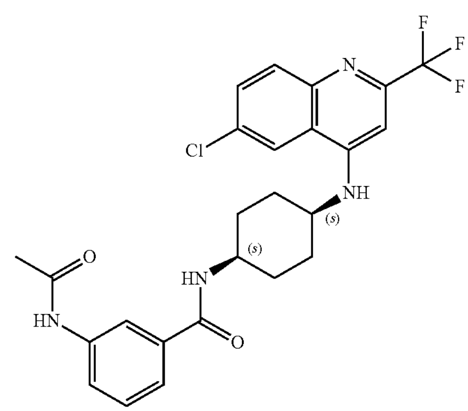 [SMILES: CC(=O)Nc1cccc(C(=O)N[C@H]2CC[C@@H](Nc3cc(C(F)(F)F)nc4ccc(Cl)cc34)CC2)c1] | 4-7 |

| Structure | Cpd No. |
|---|---|
| 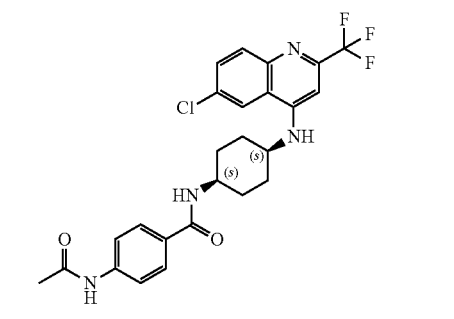 [SMILES: CC(=O)Nc1ccc(C(=O)N[C@H]2CC[C@@H](Nc3cc(C(F)(F)F)nc4ccc(Cl)cc34)CC2)cc1] | 4-103 |
| | 4-277 |
| | 4-279 |
| Structure | Cpd No. |
|---|---|
| 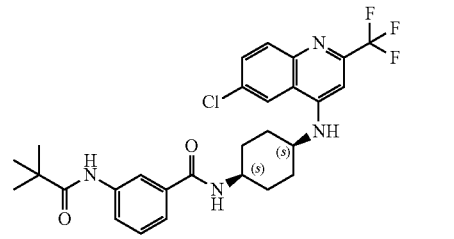 [SMILES: CC(C)(C)C(=O)Nc1cccc(C(=O)N[C@H]2CC[C@@H](Nc3cc(C(F)(F)F)nc4ccc(Cl)cc34)CC2)c1] | 4-281 |
| | 4-284 |
| | 4-302 |
3. A pharmaceutical composition comprising a compound of claim 1 and a carrier or excipient.
4. A pharmaceutical composition comprising a compound of claim 2 and a carrier or excipient.
* * * * *

UNITED STATES PATENT AND TRADEMARK OFFICE
CERTIFICATE OF CORRECTION

| | |
|---|---|
| PATENT NO. | : 11,970,452 B2 |
| APPLICATION NO. | : 17/506447 |
| DATED | : April 30, 2024 |
| INVENTOR(S) | : Marion Lanier et al. |

It is certified that error appears in the above-identified patent and that said Letters Patent is hereby corrected as shown below:

In the Claims

<u>Column 503, Claim 1, Line 45:</u>
"A compound having formula (TB):"
Should read:
--A compound having formula (IB):--

Signed and Sealed this
Thirteenth Day of August, 2024

Katherine Kelly Vidal
*Director of the United States Patent and Trademark Office*